(12) United States Patent
Donner et al.

US009278922B2

(10) Patent No.: US 9,278,922 B2
(45) Date of Patent: *Mar. 8, 2016

(54) ANTI-VIRAL COMPOUNDS

(75) Inventors: Pamela L. Donner, Mundelein, IL (US); Lissa T. Nelson, Highland Park, IL (US); Tammie K. Jinkerson, Pleasant Prairie, WI (US); Ryan G. Keddy, Beach Park, IL (US); Christopher E. Motter, Oak Creek, WI (US); Mark A. Matulenko, Libertyville, IL (US); Allan C. Krueger, Gurnee, IL (US); David A. DeGoey, Salem, WI (US); Sachin V. Patel, Round Lake, IL (US); John T. Randolph, Libertyville, IL (US); Warren M. Kati, Gurnee, IL (US); Charles W. Hutchins, Green Oaks, IL (US); Todd N. Soltwedel, Chicago, IL (US)

(73) Assignee: ABBVIE INC., North Chicago, IL (US)

( * ) Notice: Subject to any disclaimer, the term of this patent is extended or adjusted under 35 U.S.C. 154(b) by 352 days.

This patent is subject to a terminal disclaimer.

(21) Appl. No.: 12/759,986

(22) Filed: Apr. 14, 2010

(65) Prior Publication Data

US 2010/0267634 A1 Oct. 21, 2010

Related U.S. Application Data

(60) Provisional application No. 61/169,449, filed on Apr. 15, 2009, provisional application No. 61/222,591, filed on Jul. 2, 2009.

(51) Int. Cl.
| | |
|---|---|
| *A61K 38/05* | (2006.01) |
| *A61K 31/4025* | (2006.01) |
| *A61K 31/4184* | (2006.01) |
| *A61K 31/5377* | (2006.01) |
| *C07K 5/02* | (2006.01) |
| *C07K 5/062* | (2006.01) |
| *A61P 31/14* | (2006.01) |
| *C07D 403/12* | (2006.01) |
| *C07D 403/14* | (2006.01) |
| *C07D 413/14* | (2006.01) |
| *C07D 207/16* | (2006.01) |
| *A61K 31/454* | (2006.01) |
| *C07D 205/04* | (2006.01) |
| *C07D 207/22* | (2006.01) |
| *C07D 209/52* | (2006.01) |
| *C07D 211/60* | (2006.01) |
| *C07D 263/06* | (2006.01) |
| *C07D 277/06* | (2006.01) |
| *C07D 401/14* | (2006.01) |
| *C07D 405/14* | (2006.01) |
| *C07D 417/14* | (2006.01) |
| *C07D 487/04* | (2006.01) |
| *C07K 5/065* | (2006.01) |
| *C07K 5/078* | (2006.01) |
| *A61K 38/00* | (2006.01) |

(52) U.S. Cl.
CPC ......... *C07D 207/16* (2013.01); *A61K 31/4025* (2013.01); *A61K 31/4184* (2013.01); *A61K 31/454* (2013.01); *A61K 31/5377* (2013.01); *C07D 205/04* (2013.01); *C07D 207/22* (2013.01); *C07D 209/52* (2013.01); *C07D 211/60* (2013.01); *C07D 263/06* (2013.01); *C07D 277/06* (2013.01); *C07D 401/14* (2013.01); *C07D 403/14* (2013.01); *C07D 405/14* (2013.01); *C07D 413/14* (2013.01); *C07D 417/14* (2013.01); *C07D 487/04* (2013.01); *C07K 5/0606* (2013.01); *C07K 5/06034* (2013.01); *C07K 5/06043* (2013.01); *C07K 5/06069* (2013.01); *C07K 5/06078* (2013.01); *C07K 5/06139* (2013.01); *A61K 38/00* (2013.01)

(58) Field of Classification Search
CPC ............ A61K 31/4025; A61K 31/454; A61K 31/5377; A61K 31/4184; C07D 205/04; C07D 207/16
See application file for complete search history.

(56) References Cited

U.S. PATENT DOCUMENTS

| | | | |
|---|---|---|---|
| 5,830,867 A | 11/1998 | Bhatnagar et al. | |
| 5,935,982 A | 8/1999 | Dykstra et al. | |
| 6,235,493 B1 | 5/2001 | Bissell et al. | |
| 6,369,091 B1 | 4/2002 | Sircar et al. | |

(Continued)

FOREIGN PATENT DOCUMENTS

| | | |
|---|---|---|
| BR | PI0401908 A | 1/2006 |
| CN | 1292697 A | 4/2001 |

(Continued)

OTHER PUBLICATIONS

Adjabeng G., et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.

(Continued)

*Primary Examiner* — Suzanne Ziska
*Assistant Examiner* — Thurman Wheeler
(74) *Attorney, Agent, or Firm* — J.A. Lindeman & Co., PLLC

(57) ABSTRACT

Compounds effective in inhibiting replication of Hepatitis C virus ("HCV") are described. This invention also relates to processes of making such compounds, compositions comprising such compounds, and methods of using such compounds to treat HCV infection.

5 Claims, No Drawings

(56) References Cited

U.S. PATENT DOCUMENTS

| | | | |
|---|---|---|---|
| 6,703,403 | B2 | 3/2004 | Norbeck et al. |
| 6,780,529 | B2 | 8/2004 | Kimura |
| 6,881,741 | B2* | 4/2005 | Chan Chun Kong et al. .. 514/91 |
| 6,919,366 | B2 | 7/2005 | Sircar et al. |
| 7,141,574 | B2 | 11/2006 | Beaulieu et al. |
| 7,183,270 | B2 | 2/2007 | Cherney et al. |
| 7,659,270 | B2 | 2/2010 | Bachand et al. |
| 7,704,992 | B2 | 4/2010 | Bachand et al. |
| 7,728,027 | B2 | 6/2010 | Pack et al. |
| 7,741,347 | B2 | 6/2010 | Bachand et al. |
| 7,745,636 | B2 | 6/2010 | Bachand et al. |
| 7,759,495 | B2 | 7/2010 | Bachand et al. |
| 7,763,731 | B2 | 7/2010 | Rockway et al. |
| 7,906,655 | B2 | 3/2011 | Belema et al. |
| 8,034,966 | B1 | 10/2011 | Lalezari |
| 8,101,643 | B2 | 1/2012 | Qiu et al. |
| 2002/0183319 | A1 | 12/2002 | Liang et al. |
| 2003/0004203 | A1 | 1/2003 | Sircar et al. |
| 2003/0100582 | A1 | 5/2003 | Sircar et al. |
| 2004/0116509 | A1* | 6/2004 | Chan Chun Kong et al. 514/447 |
| 2005/0059650 | A1 | 3/2005 | Jones et al. |
| 2005/0075343 | A1 | 4/2005 | Sircar et al. |
| 2005/0197375 | A1 | 9/2005 | Sircar et al. |
| 2006/0003942 | A1 | 1/2006 | Tung et al. |
| 2006/0058317 | A1 | 3/2006 | Gravestock et al. |
| 2006/0105997 | A1 | 5/2006 | Arrington et al. |
| 2006/0135773 | A1 | 6/2006 | Semple et al. |
| 2007/0004741 | A1 | 1/2007 | Apodaca et al. |
| 2007/0142434 | A1 | 6/2007 | Sandanayaka et al. |
| 2007/0197558 | A1 | 8/2007 | Betebenner et al. |
| 2007/0232627 | A1 | 10/2007 | Betebenner et al. |
| 2007/0232645 | A1 | 10/2007 | Rockway et al. |
| 2007/0299068 | A1 | 12/2007 | Karp et al. |
| 2008/0044379 | A1 | 2/2008 | Bachand et al. |
| 2008/0044380 | A1 | 2/2008 | Bachand et al. |
| 2008/0050336 | A1 | 2/2008 | Bachand et al. |
| 2008/0221107 | A1 | 9/2008 | Giordanetto et al. |
| 2008/0292589 | A1 | 11/2008 | Anilkumar et al. |
| 2008/0299075 | A1 | 12/2008 | Bachand et al. |
| 2008/0311075 | A1 | 12/2008 | Bachand et al. |
| 2009/0004111 | A1 | 1/2009 | Rice et al. |
| 2009/0041716 | A1 | 2/2009 | Kim et al. |
| 2009/0043107 | A1 | 2/2009 | Pack et al. |
| 2009/0047247 | A1 | 2/2009 | Qiu et al. |
| 2009/0068140 | A1 | 3/2009 | Bachand et al. |
| 2009/0093456 | A1 | 4/2009 | Arnold et al. |
| 2009/0104151 | A1 | 4/2009 | Hanson et al. |
| 2009/0202478 | A1 | 8/2009 | Bachand et al. |
| 2009/0202483 | A1 | 8/2009 | Bachand et al. |
| 2010/0055071 | A1 | 3/2010 | Leivers et al. |
| 2010/0068176 | A1 | 3/2010 | Belema et al. |
| 2010/0068197 | A1 | 3/2010 | Anderson et al. |
| 2010/0080772 | A1 | 4/2010 | Belema et al. |
| 2010/0143499 | A1 | 6/2010 | Condon |
| 2010/0158862 | A1 | 6/2010 | Kim et al. |
| 2010/0160355 | A1 | 6/2010 | DeGoey |
| 2010/0168138 | A1 | 7/2010 | DeGoey et al. |
| 2010/0215616 | A1 | 8/2010 | Romine et al. |
| 2010/0215618 | A1 | 8/2010 | Carter et al. |
| 2010/0221214 | A1 | 9/2010 | Or et al. |
| 2010/0221215 | A1 | 9/2010 | Qiu et al. |
| 2010/0221216 | A1 | 9/2010 | Or et al. |
| 2010/0226882 | A1 | 9/2010 | Or et al. |
| 2010/0226883 | A1 | 9/2010 | Qiu et al. |
| 2010/0233120 | A1 | 9/2010 | Bachand et al. |
| 2010/0233122 | A1 | 9/2010 | Qiu et al. |
| 2010/0249190 | A1 | 9/2010 | Lopez et al. |
| 2010/0260708 | A1 | 10/2010 | Belema et al. |
| 2010/0260715 | A1 | 10/2010 | Or et al. |
| 2010/0266543 | A1 | 10/2010 | Qiu et al. |
| 2010/0267634 | A1 | 10/2010 | Donner et al. |
| 2010/0303755 | A1 | 12/2010 | Lopez et al. |
| 2010/0310512 | A1 | 12/2010 | Guo et al. |
| 2010/0316607 | A1 | 12/2010 | Or et al. |
| 2010/0317568 | A1 | 12/2010 | DeGoey et al. |
| 2011/0008288 | A1 | 1/2011 | Or et al. |
| 2011/0064695 | A1 | 3/2011 | Qiu et al. |
| 2011/0064696 | A1 | 3/2011 | Or et al. |
| 2011/0064697 | A1 | 3/2011 | Qiu et al. |
| 2011/0064698 | A1 | 3/2011 | Or et al. |
| 2011/0070196 | A1 | 3/2011 | Qiu et al. |
| 2011/0070197 | A1 | 3/2011 | Or et al. |
| 2011/0077280 | A1 | 3/2011 | Bender et al. |
| 2011/0092415 | A1 | 4/2011 | Degoey et al. |
| 2011/0112100 | A1 | 5/2011 | Milbank et al. |
| 2011/0136799 | A1 | 6/2011 | Chern et al. |
| 2011/0142798 | A1 | 6/2011 | Qiu et al. |
| 2011/0150827 | A1 | 6/2011 | Dousson et al. |
| 2011/0152246 | A1 | 6/2011 | Buckman et al. |
| 2011/0172238 | A1 | 7/2011 | Henderson et al. |
| 2011/0189129 | A1 | 8/2011 | Qiu et al. |
| 2011/0195044 | A1 | 8/2011 | Romine |
| 2011/0207699 | A1 | 8/2011 | Degoey et al. |
| 2011/0217261 | A1 | 9/2011 | Or et al. |
| 2011/0218175 | A1 | 9/2011 | Or et al. |
| 2011/0223134 | A1 | 9/2011 | Nair et al. |
| 2011/0237579 | A1 | 9/2011 | Li et al. |
| 2011/0237636 | A1 | 9/2011 | Belema et al. |
| 2011/0274648 | A1 | 11/2011 | Lavoie et al. |
| 2011/0281910 | A1 | 11/2011 | Lavoie et al. |
| 2011/0286961 | A1 | 11/2011 | Belema et al. |
| 2011/0294819 | A1 | 12/2011 | Lopez et al. |
| 2011/0300104 | A1 | 12/2011 | Qiu et al. |
| 2012/0004196 | A1 | 1/2012 | Degoey et al. |
| 2012/0028978 | A1 | 2/2012 | Zhong et al. |
| 2012/0040977 | A1 | 2/2012 | Li et al. |
| 2012/0115918 | A1 | 5/2012 | DeGoey et al. |
| 2012/0172290 | A1 | 7/2012 | Krueger et al. |
| 2012/0220562 | A1 | 8/2012 | DeGoey et al. |

FOREIGN PATENT DOCUMENTS

| | | |
|---|---|---|
| CN | 1585756 A | 2/2005 |
| DE | 75755 C | 6/1894 |
| EA | 010023 B1 | 8/2006 |
| EA | 7722 B1 | 12/2006 |
| EP | 2242751 A1 | 10/2010 |
| JP | 2003282270 A | 10/2003 |
| JP | 2010126571 A | 6/2010 |
| RU | 2006106272 A | 8/2006 |
| RU | 2286343 C2 | 10/2006 |
| WO | WO9427627 A1 | 12/1994 |
| WO | WO 99/59587 A1 | 11/1999 |
| WO | WO9961020 A1 | 12/1999 |
| WO | WO0012521 A1 | 3/2000 |
| WO | WO 02/14314 A2 | 2/2002 |
| WO | WO 02/48147 A2 | 6/2002 |
| WO | WO 03/040112 A1 | 5/2003 |
| WO | WO03082186 A2 | 10/2003 |
| WO | WO2004005283 A1 | 1/2004 |
| WO | WO2004014313 A2 | 2/2004 |
| WO | WO2004014852 A2 | 2/2004 |
| WO | WO2004014852 A3 | 4/2004 |
| WO | WO 2005/007658 A2 | 1/2005 |
| WO | WO 2005/012288 A1 | 2/2005 |
| WO | 2005026129 A1 | 3/2005 |
| WO | 2005054199 A1 | 6/2005 |
| WO | WO2004014313 A3 | 12/2005 |
| WO | WO2006020951 A1 | 2/2006 |
| WO | WO2006033703 A1 | 3/2006 |
| WO | 2006079833 A1 | 8/2006 |
| WO | 2006113769 A1 | 10/2006 |
| WO | WO2006133326 A1 | 12/2006 |
| WO | WO2007070556 A2 | 6/2007 |
| WO | WO2007070600 A2 | 6/2007 |
| WO | WO2007076034 A2 | 7/2007 |
| WO | WO2007076035 A2 | 7/2007 |
| WO | WO2007082554 A1 | 7/2007 |
| WO | WO2007070556 A3 | 8/2007 |
| WO | WO2007081517 C1 | 9/2007 |
| WO | WO2007070600 A3 | 11/2007 |
| WO | WO2007131366 A1 | 11/2007 |
| WO | WO2007144174 A1 | 12/2007 |
| WO | WO2008014236 A1 | 1/2008 |

(56) References Cited

FOREIGN PATENT DOCUMENTS

| | | |
|---|---|---|
| WO | WO2008014238 A2 | 1/2008 |
| WO | 2008021388 A1 | 2/2008 |
| WO | WO2008021927 A2 | 2/2008 |
| WO | WO2008021928 A2 | 2/2008 |
| WO | WO2008021936 A2 | 2/2008 |
| WO | WO2008021928 A3 | 3/2008 |
| WO | WO2008021936 A3 | 4/2008 |
| WO | WO2008021927 A3 | 5/2008 |
| WO | WO2008064218 A2 | 5/2008 |
| WO | WO2008070447 A2 | 6/2008 |
| WO | WO2008074450 A2 | 6/2008 |
| WO | WO2008064218 A3 | 10/2008 |
| WO | WO2008128121 A1 | 10/2008 |
| WO | 2008144463 A1 | 11/2008 |
| WO | WO2008133753 A2 | 11/2008 |
| WO | WO2008144380 A1 | 11/2008 |
| WO | 2008154271 A1 | 12/2008 |
| WO | WO2009003009 A1 | 12/2008 |
| WO | WO2009020534 A2 | 2/2009 |
| WO | WO2009020825 A1 | 2/2009 |
| WO | WO2009020828 A1 | 2/2009 |
| WO | WO2008070447 A3 | 3/2009 |
| WO | WO2009093082 A1 | 7/2009 |
| WO | WO2009094224 A1 | 7/2009 |
| WO | WO2009102318 A1 | 8/2009 |
| WO | WO2009102325 A1 | 8/2009 |
| WO | WO2009102568 A1 | 8/2009 |
| WO | WO2009102633 A1 | 8/2009 |
| WO | WO2009102694 A1 | 8/2009 |
| WO | WO2009136290 A1 | 11/2009 |
| WO | WO2009143361 A1 | 11/2009 |
| WO | WO2009155709 A1 | 12/2009 |
| WO | WO2010075376 A2 | 1/2010 |
| WO | WO2010015090 A1 | 2/2010 |
| WO | WO2010017401 A1 | 2/2010 |
| WO | WO2010039793 A1 | 4/2010 |
| WO | WO2010059858 A1 | 5/2010 |
| WO | WO2010062821 A1 | 6/2010 |
| WO | WO2010065668 A1 | 6/2010 |
| WO | WO2010065674 A1 | 6/2010 |
| WO | WO2010065681 A1 | 6/2010 |
| WO | WO 2010/075380 A1 | 7/2010 |
| WO | WO2010091413 A1 | 8/2010 |
| WO | WO2010096302 A1 | 8/2010 |
| WO | WO2010096462 A1 | 8/2010 |
| WO | WO2010096777 A1 | 8/2010 |
| WO | WO2010099527 A1 | 9/2010 |
| WO | WO2010111483 A1 | 9/2010 |
| WO | WO2010111534 A1 | 9/2010 |
| WO | WO2010111673 A1 | 9/2010 |
| WO | WO2010115767 A1 | 10/2010 |
| WO | WO2010117635 A1 | 10/2010 |
| WO | WO2010117704 A1 | 10/2010 |
| WO | WO2010117977 A1 | 10/2010 |
| WO | WO2010120621 A1 | 10/2010 |
| WO | WO2010120935 A1 | 10/2010 |
| WO | WO2010122162 A1 | 10/2010 |
| WO | WO2010132538 A1 | 11/2010 |
| WO | WO2010132601 A1 | 11/2010 |
| WO | WO2010138368 A1 | 12/2010 |
| WO | WO2010138488 A1 | 12/2010 |
| WO | WO2010138790 A1 | 12/2010 |
| WO | WO2010138791 A1 | 12/2010 |
| WO | WO2010144646 A2 | 12/2010 |
| WO | WO2010148006 A1 | 12/2010 |
| WO | WO2011004276 A1 | 1/2011 |
| WO | WO2011009084 A2 | 1/2011 |
| WO | WO2011015658 A1 | 2/2011 |
| WO | WO2011026920 A1 | 3/2011 |
| WO | WO2011028596 A1 | 3/2011 |
| WO | WO2011031904 A1 | 3/2011 |
| WO | WO2011031934 A1 | 3/2011 |
| WO | WO2011050146 A1 | 4/2011 |
| WO | WO2011054834 A1 | 5/2011 |
| WO | WO2011059850 A1 | 5/2011 |
| WO | WO2011059887 A1 | 5/2011 |
| WO | WO2011060000 A1 | 5/2011 |
| WO | WO2011066241 A1 | 6/2011 |
| WO | WO2011068941 A2 | 6/2011 |
| WO | WO2011075439 A1 | 6/2011 |
| WO | WO2011075607 A1 | 6/2011 |
| WO | WO2011075615 A1 | 6/2011 |
| WO | WO2011079327 A1 | 6/2011 |
| WO | WO2011081918 A1 | 7/2011 |
| WO | WO2011082077 A1 | 7/2011 |
| WO | WO2011087740 A1 | 7/2011 |
| WO | WO2011091417 A1 | 7/2011 |
| WO | WO2011091446 A1 | 7/2011 |
| WO | WO2011091532 A1 | 8/2011 |
| WO | WO2011112429 A1 | 9/2011 |
| WO | WO2011119853 A1 | 9/2011 |
| WO | WO2011119858 A1 | 9/2011 |
| WO | WO2011119860 A1 | 9/2011 |
| WO | WO2011119870 A1 | 9/2011 |
| WO | WO2011127350 A1 | 10/2011 |
| WO | WO2011146401 A1 | 11/2011 |
| WO | WO 2011/156578 A1 | 12/2011 |
| WO | WO2011150243 A1 | 12/2011 |
| WO | WO2011156543 A2 | 12/2011 |
| WO | WO 2012/051361 A1 | 4/2012 |
| WO | WO 2012/083164 A1 | 6/2012 |
| WO | WO 2012/083170 A1 | 6/2012 |

OTHER PUBLICATIONS

Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69 (15), pp. 5082-5086.

Alesso E.N., et al., "Synthesis of Diastereoisomeric 1,2,3-Triphenylindans," Australian Journal of Chemistry, 1997, vol. 50, pp. 149-152.

Brettle R., et al., "A Highly Efficient Enzymic Route to Novel Chiral Liquid Crystals based on 3-Aryl-2-cycloalken-1-ones," Journal of the Chemical Society, Chemical Communications, 1994, pp. 2305-2306.

Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Stucture-Activity Relationships," Journal of Medicinal Chemistry, 2008, vol. 51 (17), pp. 5243-5263.

Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (11), pp. 1839-1842.

Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.

Effenberger F., et al., "Synthesis, Structure, and Spectral Behavior of Donor-Acceptor Substituted Biphenyls," The Journal of Organic Chemistry, 1983, vol. 48, pp. 4649-4658.

Fiedler., "Encyclopedia of Excipients for Pharmaceuticals, Cosmetics and related Areas," 5th Edition, Hoepfner E.M., et al., eds., Editio Cantor Verlag Aulendorf, 2002, Table of Contents.

Hartwig J.F., et al., "III.3.2 Palladium-Catalyzed Amination of Aryl Halides and Related Reactions," Handbook of Organopalladium Chemistry for Organic Synthesis, 2002, pp. 1051-1096.

International Preliminary Report on Patentability and Written Opinion for the Application No. PCT/US2010/031102, mailed on Oct. 18, 2011, 7 pages.

Jeffrey J.L., et al., "Concise Synthesis of Pauciflorol F Using a Larock Annulation," Organic Letters, 2009, vol. 11 (23), pp. 5450-5453.

Kuethe J.T., et al., "Asymmetric Synthesis of 1,2,3-Trisubstituted Cyclopentanes and Cyclohexanes as Key Components of Substance P Antagonists," The Journal of Organic Chemistry, 2002, vol. 67 (17), pp. 5993-6000.

(56) References Cited

OTHER PUBLICATIONS

Louie J., et al., "Palladium-Catalyzed Amination of Aryl Triflates and Importance of Triflate Addition Rate," Journal of Organic Chemistry, 1997, vol. 62 (5), pp. 1268-1273.

Lucas S., et al.,"In Vivo Active Aldosterone Synthase Inhibitors with Improved Aelectivity: Lead Optimization Providing a Series of Pyridine Substituted 3,4-Dihydro-1H-Quinolin-2-one Derivatives," Journal of Medicinal Chemistry, 2008, vol. 51 (24), pp. 8077-8087.

Masters K., "Spray Drying Handbook" 4th Edition, John Wiley & Sons, 1985, Table of Contents.

Matzeit A., et al., "Radical Tandem Cyclizations by Anodic Decarboxylation of Carboxylic Acids," Synthesis, 1995, pp. 1432-1444.

Muci A.R., et al., "Practical Palladium Catalysts for C—N and C—O Bond Formation," Topics in Current Chemistry, 2002, vol. 219, pp. 131-209.

Peng T., et al., "Construction of a Library of Rhodol Fluorophores for Developing New Fluorescent Probes," Organic Letters, 2010, vol. 12 (3), pp. 496-499.

Polymer Handbook, Brandrup J., et al., Eds., Interscience Publishers, 1975, Table of Contents.

Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19 (3), pp. 414-419.

Smith A.B., et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.

Sperling L. H., "Introduction to Physical Polymer Science," 2nd Edition, John Wiley & Sons, Inc., 1992, Table of Contents.

Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.

Tellinghuisen T.L., et al., "Structure of the Zinc-Binding Domain of an Essential Component of the Hepatitis C Virus Replicase," Nature, 2005, vol. 435 (7040), pp. 374-379.

Vallee R.J., et al., "Photoannelation Reactions of 3-(Alk-1-ynyl)cyclohept-2-en-1-ones," Helvetica Chimica Acta, 2010, vol. 93 (1), pp. 17-24.

Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.

Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.

Wolfe J.P., et al., "Palladium-Catalyzed Amination of Aryl Triflates," Journal of Organic Chemistry, 1997, vol. 62 (5), pp. 1264-1267.

Aldous D.J., et al. , "A Simple Enantioselective Preparation of (2S,5S)-2,5-diphenylpyrrolidine and Related Diaryl Amines," Tetrahedron Asymmetry, 2000, vol. 11, pp. 2455-2462.

Angiolini M., et al., "Synthesis of Azabicycloalkane Amino Acid Scaffolds as Reverse-Turn Inducer Dipeptide Mimics ," European Journal Organization Chemistry, 2000, pp. 2571-2581.

Boehm T., et al., "Uber Die Bildung Von Gamma-Piperidonderivaten Aus Azetessigester, Aromatischen Aldehyden und Aminen, Eine Modifikation Der Hantzschschen Pyridinsynthese," Pharmaceutical,1943, vol. 281, pp. 62-77.

Bundgaard H., "Design of Pro Drugs," 1985, pp. 1-6.

Chong J.M., et al., "Asymmetric Synthesis of trans.2,5-Diphenylpyrrolidine: A C2-Symmetric Chirai Amine," Tetrahedron Asymmetry, 1995, vol. 6 (2), pp. 409-418.

Clarke P.A., et al., "Pot, Atom and Step Economic (Pase) Synthesis of Highly Functionalized Piperidines: A Five-Component Condensation," Tetrahedron Letters , 2007, vol. 48 , pp. 5209-5212.

Clarke P.A., et al., "Pot, Atom and Step Economic (PASE) Synthesis of Highly Substituted Piperidines:A Five-Component Condensation," Synthesis, 2008, No. 28, pp. 3530-3532.

Collado I., et al , "Stereoselective Addition of Grignard-Derived Organocopper Reagents to N-Acyliminium Ions: Synthesis of Enantiopure 5- and 4,5-Substituted Prolinates ," Journal of Organic Chemistry , 1995, vol. 60, pp. 5011-5015.

Dell'Erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.

Fan X., et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.

Gordon T.D., et al , "Synthetic Approaches to the Azole Peptide Mimetics," Tetrahedron Letters, 1993, vol. 34(12), pp. 1901-1904.

Greene T.W., et al., "Protection for the Amino group," Protective Groups in Organic Synthesis, 1999, Third Edition, pp. 494-653.

Hoover J.E, Remington's Pharmaceutical Sciences, Tbl of Cont, 1975.

International Search Report and Written Opinion for Application No. PCT/US2009/038077, mailed on Jan. 21, 2011, 16 pages.

International Search Report and Written Opinion for Application No. PCT/US2009/069177, mailed on Aug. 10, 2010, 17 pages.

International Search Report for Application No. PCT/US2009/069188, mailed on Jun. 8, 2010, 4 pages.

International Search Report for the Application No. PCT/US2010/031102, mailed on Sep. 1, 2010, 4 pages.

Jacques et al., "Enantiomers, Racemates, and Resolutions," J. Wiley & Sons, Chapter 3, pp. 197-213, 1981.

Jing Q., et al., "Bulky Achiral Triarylphosphines Mimic BINAP in Ru(II)-Catalyzed Asymmetric Hydrogenation of Ketones," Advanced Synthesis & Catalysis, 2005, vol. 347, pp. 1193-1197.

Khan A.T., et al., "Effects of Substituents in the ?-Position of 1,3-Dicarbonyl Compounds in Bromodimethylsulfonium Bromide-Catalyzed Multicomponent Reactions: A Facile Access to Functionalized Piperidines," Journal of organic chemistry, 2008, vol. 73 , pp. 8398-8402.

Li Chuan-Ying., et al., "Olefination of Ketenes for the Enantioselective Synthesis of Allenes via an Ylide Route," Tetrahedron, 2007, vol. 63, pp. 8046-8053.

Lieberman L., et al., eds., Pharmaceutical Dosage Forms, vol. 1, Marcel Dekker, Inc., 1980, Table of Contents.

Masui M., et al., "A Practical Method for Asymmetric Borane Reduction of Prochiral Ketones Using Chiral Amino Alcohols and Trimethyl Borate," Synlett, 1997, pp. 273-274.

Misra M., et al., "Organocatalyzed Highly Atom Economic One Pot Synthesis of Tetrahydropyridines as Antimalarials," Bioorganic & Medicinal Chemistry, 2009, vol. 17 , pp. 625-633.

Moinet C., et al., "Novel Non-Peptide Ligands for the Somatostatin sst3 Receptor," Bioorganic & Medicinal Chemistry Letters, 2001, vol. 11 (8), pp. 991-995.

Muri E.M.F., et al., "Pseudo-Peptides Derived From Isomannide as Potential Inhibitors of Serine Proteases," Amino Acids, 2005, vol. 28 (4), pp. 413-419.

Naylor E.M., et al. , "3-Pyridylethanolamines: Potent and Selective Human 63 Adrenergic Receptor Agonists," Bioorganic & Medicinal Chemistry Letters, 1998, vol. 8 (21), pp. 3087-3092.

Nevar N.M., et al., "One Step Preparation of 1,4-Diketones from Methyl Ketones and a-Bromomethyl Ketones in the Presence of ZnCl2•t-BuOH•Et2NR as a Condensation Agent," Synthesis, 2000, vol. 9, pp. 1259-1262.

Pak V.D., et al., "Catalytic Condensation of Schiff's Base With P-Methoxybenzal Acetone," Catalytic Synthesis of Organic Nitrate Compounds, 1970, vol. 68 (Part 4), pp. 66-71.

Penning T.D., et al, "Discovery and SAR of 2-(1-Propylpiperidin-4-yl)-1H-Benzimidazole-4-Carboxamide: A Potent Inhibitor of Poly(ADP-ribose) Polymerase (PARP) for the Treatment of Cancer ," Bioorganic & Medicinal Chemistry, 2008, vol. 16(14), pp. 6965-6975.

Sato M., et al., "Efficient Preparation of Optically Pure C2-Symmetrical Cyclic Amines for Chiral Auxiliary," Synthesis, 2004, vol. 9, pp. 1434-1438.

Sawyer J.S., et al., "Synthetic and Structure/Activity Studies on Acid-Substituted 2-Arylphenols:Discovery of 2-[2-Propyl-3-[3-[2-

(56) References Cited

OTHER PUBLICATIONS ethyl-4-(4-fluorophenyl)-5-hydroxyphenoxy]-propoxy]phenoxy] benzoic Acid, a High-Affinity Leukotriene B4 Receptor Antagonist," Journal of Medicinal Chemistry, 1995, vol. 38 (22), pp. 4411-4432.
Smith D.C., et al., "Reissert Compound Chemistry. XXVI. The Syntheses of Bis-Benzylisoquinolines," Journal of Heterocyclic Chemistry, 1976, vol. 13, pp. 573-576.
Takagi S., et al., "Antimicrobial Agents From Bletilla Striata," Phyrochemisrry, 1983, vol. 22 (4), pp. 1011-1015.
Tatsumi K., et al., "Enzyme-Mediated Coupling of 3,4-Dichloroaniline and Ferulic Acid: A Model for Pollutant Binding to Humic Materials," Environmental Science & Technology, 1994, vol. 28, pp. 210-215.
Xiao D., et al., "A Practical Synthetic Pathway to Polysubstituted Tetrahydropyridines via Multicomponent Reactions Catalyzed by BF3•OEt2," Synlett, 2005, vol. 10, pp. 1531-1534.
Zhang J., et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Journal of the American Chemical Society, 2002, vol. 4(23), pp. 4029-4032.
Jun. 20, 2013, Office Action in U.S. Appl. No. 13/328,767.
Bundgaard H., "Design of prodrugs," pp. 7-9 & 21-24, 1985.
Dell'Erba et al., "Synthetic Exploitation of the Ring-Opening of 3,4-Dinitrothiophene, IX[?]Pyrrolidines, Pyrrolines and Pyrroles from 1,4-Diaryl-2,3-dinitro-1,3-butadienes via a 5-endo-trig Cyclization," Euro. J. of Org. Chem., 2000 (6), 903-912.
Lieberman et al., Pharmaceutical Dosage Forms: Tablets, vol. 3, 1990, Informa Healthcare, Tbl of Cont.
L-selectride, Retrieved from the Internet: <URL: http://en.wikipedia.org/wiki/L-selectride> (accessed Mar. 27, 2013).
International Preliminary Report on Patentability and Written Opinion for PCT/US2009/069188, dated Jun. 29, 2011, 10 pages.
International Search Report for PCT/US2009/069177, dated Aug. 10, 2010, 5 pages.
International Search Report for PCT/US2011/39769, dated Oct. 6, 2011, 3 pages.
International Preliminary Report on Patentability and Written Opinion for PCT/US2011/39769, dated Dec. 10, 2012, 7 pages.
International Search Report for PCT/US2011/056045, dated Apr. 2, 2012, 4 pages.
International Search Report for PCT/US2012/026456, dated Jun. 22, 2012, 3 pages.
International Search Report for PCT/US2011/065501, dated Apr. 3, 2012, 5 pages.
Aug. 1, 2012, Office Action in U.S. Appl. No. 12/644,432.
Jul. 17, 2012, Office Action in U.S. Appl. No. 12/644,427.
Office Action for JP application 2012-506183 dated Jun. 24, 2014.
M. Alajarin et al.: "Dimerization of Tris(o-ureidobenzyl)amines: A Novel Class of Aggregates," Chem. Commun., pp. 169-170, 2001.
Liu et al., "Discovery of a Novel CCR5 Antagonist Lead Compound Through Fragment Assembly," Molecules 13:2426-2441 (2008).
Office Action in CN Application No. 201180067764.7 dated Aug. 20, 2014.
Office Action in Chinese Application No. 201080026637.8 dated Aug. 28, 2014.
Notice of Allowance in Russian Application No. 2011156145 dated Sep. 29, 2014.
Office Action in U.S. Appl. No. 14/021,435 dated Nov. 20, 2014.
Office Action in U.S. Appl. No. 14/017,901 dated Nov. 28, 2014.

* cited by examiner

ANTI-VIRAL COMPOUNDS

This application claims the benefit from and incorporates herein by references the entire content of U.S. Provisional Application No. 61/169,449, filed Apr. 15, 2009, and U.S. Provisional Application No. 61/222,591, filed Jul. 2, 2009.

FIELD

The present invention relates to compounds effective in inhibiting replication of Hepatitis C virus ("HCV"). The present invention also relates to compositions comprising these compounds and methods of using these compounds to treat HCV infection.

BACKGROUND

HCV is an RNA virus belonging to the Hepacivirus genus in the Flaviviridae family. HCV has enveloped virions that contain a positive stranded RNA genome encoding all known virus-specific proteins in one single, uninterrupted, open reading frame. The open reading frame comprises approximately 9500 nucleotides encoding a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects and viral elimination from the body is often inadequate. Therefore, there is a need for new drugs to treat HCV infection.

SUMMARY

The present invention features compounds of Formulae I, $I_A$, $I_B$ and $I_C$, and pharmaceutically acceptable salts thereof. These compounds and salts are capable of inhibiting the replication of HCV and therefore can be used to treat HCV infection.

The present invention also features compositions comprising the compounds or salts of the present invention. The compositions can also include other therapeutic agents, such as HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

The present invention further features methods of using the compounds or salts of the present invention to inhibit HCV replication. The methods comprise contacting cells infected with HCV virus with a compound or salt of the present invention, thereby inhibiting the replication of HCV virus in the cells.

In addition, the present invention features methods of using the compounds or salts of the present invention, or compositions comprising the same, to treat HCV infection. The methods comprise administering a compound or salt of the present invention, or a pharmaceutical composition comprising the same, to a patient in need thereof, thereby reducing the blood or tissue level of HCV virus in the patient.

The present invention also features use of the compounds or salts of the present invention for the manufacture of medicaments for the treatment of HCV infection.

Furthermore, the present invention features processes of making the compounds or salts of the invention.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features compounds having Formula I, and pharmaceutically acceptable salts thereof,

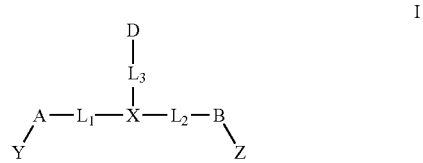

wherein:
A and B are each independently $C_3$-$C_{10}$carbocycle or 3- to 10-membered heterocycle, and are each independently optionally substituted with one or more $R_4$;
D is $C_3$-$C_{10}$carbocycle or 3- to 10-membered heterocycle, and is optionally substituted with one or more $R_4$; or D is $R_D$;
X is $C(R_C)$ or N;
$L_1$ and $L_2$ are each independently selected from a bond; or $C_1$-$C_6$alkylene, $C_2$-$C_6$alkenylene, or $C_2$-$C_6$alkynylene, each of which is independently optionally substituted at each occurrence with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano;
$L_3$ is bond or -$L_S$-K-$L_S'$-, wherein K is selected from a bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B'$)—, —N($R_B$)SO$_2$N($R_B'$)—, or —N($R_B$)S(O)N($R_B'$)—;
Y is selected from -T'-C($R_1 R_2$)N($R_5$)-T-$R_D$, -T'-C($R_3 R_4$)C($R_6 R_7$)-T-$R_D$, -$L_K$-T-$R_D$, or -$L_K$-E;
$R_1$ and $R_2$ are each independently $R_C$, and $R_5$ is $R_B$; or $R_1$ is $R_C$, and $R_2$ and $R_5$, taken together with the atoms to which they are attached, form a 3- to 8-membered heterocyclic ring which is optionally substituted with one or more $R_4$;
$R_3$, $R_4$, $R_6$, and $R_7$ are each independently $R_C$; or $R_3$ and $R_6$ are each independently $R_C$, and $R_4$ and $R_7$, taken together with the atoms to which they are attached, form a 3- to 8-membered carbocyclic or heterocyclic ring which is optionally substituted with one or more $R_4$;
Z is selected from -T'-C($R_8 R_9$)N($R_{12}$)-T-$R_D$, -T'-C($R_{10} R_{11}$)C($R_{13} R_{14}$)-T-$R_D$, -$L_K$-T-$R_D$, or -$L_K$-E;
$R_8$ and $R_9$ are each independently $R_C$, and $R_{12}$ is $R_B$; or $R_8$ is $R_C$, and $R_9$ and $R_{12}$, taken together with the atoms to which they are attached, form a 3- to 8-membered heterocyclic ring which is optionally substituted with one or more $R_A$;

$R_{10}$, $R_{11}$, $R_{13}$, and $R_{14}$ are each independently $R_C$; or $R_{10}$ and $R_{13}$ are each independently $R_C$, and $R_{11}$ and $R_{14}$, taken together with the atoms to which they are attached, form a 3- to 8-membered carbocyclic or heterocyclic ring which is optionally substituted with one or more $R_A$;

$L_K$ is independently selected at each occurrence from a bond; —N($R_B$)C(O)-$L_S$-; —C(O)N($R_B$)-$L_S$-; or $C_1$-$C_6$alkylene, $C_2$-$C_6$alkenylene, $C_2$-$C_6$alkynylene, $C_3$-$C_{10}$carbocycle or 3- to 10-membered heterocycle, each of which is independently optionally substituted at each occurrence with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano;

E is independently selected at each occurrence from $C_3$-$C_{10}$carbocycle or 3- to 10-membered heterocycle, and is independently optionally substituted at each occurrence with one or more $R_A$;

T and T' are each independently selected at each occurrence from a bond, -$L_S$-, -$L_S$-M-$L_S'$-, -$L_S$-M-$L_S'$-M'-$L_S''$-, wherein M and M' are each independently selected at each occurrence from a bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B'$)—, —N($R_B$)SO$_2$N($R_B'$)—, —N($R_B$)S(O)N($R_B'$)—, $C_3$-$C_{10}$carbocycle, or 3- to 10-membered heterocycle, and wherein said $C_3$-$C_{10}$carbocycle and 3- to 10-membered heterocycle are each independently optionally substituted at each occurrence with one or more $R_A$;

$R_A$ is independently selected at each occurrence from halogen, hydroxy, mercapto, amino, carboxy, nitro, oxo, phosphonoxy, phosphono, thioxo, formyl, cyano, -$L_A$, or -$L_S$-$R_E$, wherein two adjacent $R_A$, taken together with the atoms to which they are attached and any atoms between the atoms to which they are attached, optionally form a $C_3$-$C_{10}$carbocycle or 3- to 10-membered heterocycle;

$R_B$ and $R_B'$ are each independently selected at each occurrence from hydrogen or $R_F$;

$R_C$ is independently selected at each occurrence from hydrogen, halogen, hydroxy, mercapto, amino, carboxy, nitro, oxo, phosphonoxy, phosphono, thioxo, formyl, cyano, or $R_F$;

$R_D$ is each independently selected at each occurrence from hydrogen or $R_A$, $R_E$ is independently selected at each occurrence from —O—$R_S$, —S—$R_S$, —C(O)$R_S$, —OC(O)$R_S$, —C(O)O$R_S$, —N($R_S R_S'$), —S(O)$R_S$, —SO$_2 R_S$, —C(O)N($R_S R_S'$), —N($R_S$)C(O)$R_S'$, —N($R_S$)C(O)N($R_S' R_S''$), —N($R_S$)SO$_2 R_S'$, —SO$_2$N($R_S R_S'$), —N($R_S$)SO$_2$N($R_S' R_S''$), —N($R_S$)S(O)N($R_S' R_S''$), —OS(O)—$R_S$, —OS(O)$_2$—$R_S$, —S(O)$_2$O$R_S$, —S(O)O$R_S$, —OC(O)O$R_S$, —N($R_S$)C(O)O$R_S'$, —OC(O)N($R_S R_S'$), —N($R_S$)S(O)—$R_S'$, —S(O)N($R_S R_S'$), —C(O)N($R_S$)C(O)—$R_S'$, $C_3$-$C_{10}$carbocyclyl, or 3- to 10-membered heterocyclyl, wherein said $C_3$-$C_{10}$carbocyclyl and 3- to 10-membered heterocyclyl are each independently optionally substituted at each occurrence with one or more substituents selected from halogen, $R_T$, —O—$R_B$, —S—$R_B$, —N($R_B R_B'$), —OC(O)$R_B$, —C(O)O$R_B$, nitro, phosphonoxy, phosphono, oxo, thioxo, formyl or cyano;

$R_F$ is independently selected at each occurrence from $C_1$-$C_6$alkyl, $C_2$-$C_6$alkenyl, $C_2$-$C_6$alkynyl, $C_3$-$C_6$-carbocyclyl, $C_3$-$C_6$-carbocyclyl$C_1$-$C_6$alkyl, 3- to 6-membered heterocyclyl or (3- or 6-membered heterocyclyl)$C_1$-$C_6$alkyl, each of which is independently optionally substituted at each occurrence with one or more substituents selected from halogen, hydroxy, mercapto, amino, carboxy, nitro, oxo, phosphonoxy, phosphono, thioxo, formyl or cyano;

$L_A$ is independently selected at each occurrence from $C_1$-$C_6$alkyl, $C_2$-$C_6$alkenyl, or $C_2$-$C_6$alkynyl, each of which is independently optionally substituted at each occurrence with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano;

$L_S$, $L_S'$ and $L_S''$ are each independently selected at each occurrence from a bond; or $C_1$-$C_6$alkylene, $C_2$-$C_6$alkenylene, or $C_2$-$C_6$alkynylene, each of which is independently optionally substituted at each occurrence with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano;

$R_S$, $R_S'$ and $R_S''$ are each independently selected at each occurrence from hydrogen or $R_T$;

$R_T$ is independently selected at each occurrence from $C_1$-$C_6$alkyl, $C_2$-$C_6$alkenyl, $C_2$-$C_6$alkynyl, $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from halogen, $R_F$, —O—$R_B$, —S—$R_B$, —N($R_B R_B'$), —OC(O)$R_B$, —C(O)O$R_B$, nitro, oxo, phosphonoxy, phosphono, thioxo, formyl or cyano.

A and B preferably are independently selected from $C_5$-$C_6$carbocycle, 5- to 6-membered heterocycle, or 8- to 10-membered bicycles such as

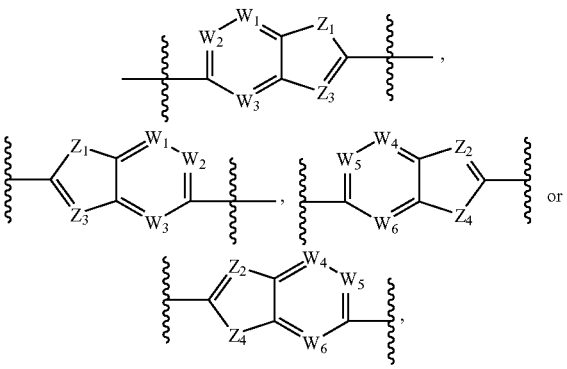

where $Z_1$ is independently selected at each occurrence from O, S, NH or $CH_2$, $Z_2$ is independently selected at each occurrence from N or CH, $Z_3$ is independently selected at each occurrence from N or CH, $Z_4$ is independently selected at each occurrence from O, S, NH or $CH_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from $C_5$-$C_6$carbocycle, 5- to 6-membered heterocycle,

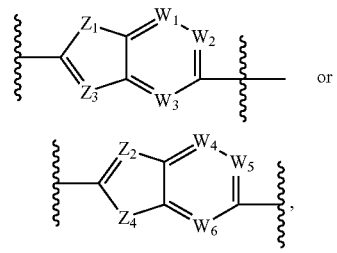 or

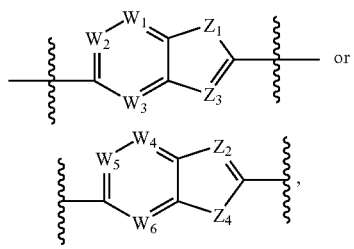, and is optionally substituted with one or more $R_A$; B is selected from $C_5$-$C_6$carbocycle, 5- to 6-membered heterocycle,

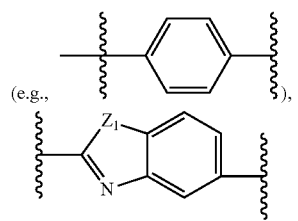 or

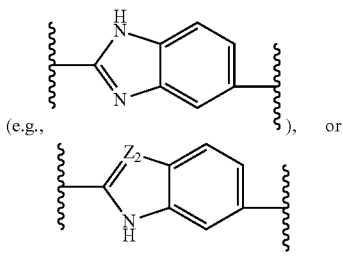, and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from phenyl (e.g., 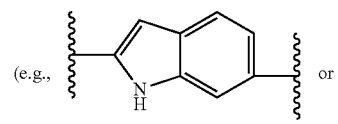),

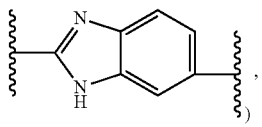

(e.g., (e.g., (e.g.,

-continued

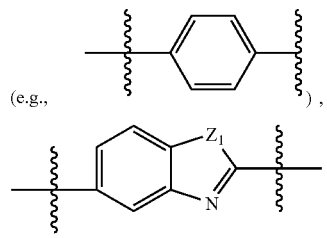), and is optionally substituted with one or more $R_A$; and B can be selected from phenyl (e.g.,

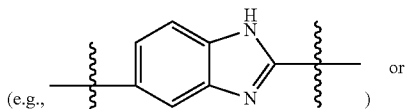),

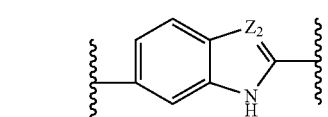

(e.g., (e.g., (e.g.,

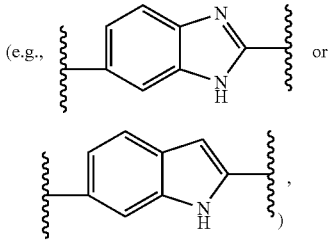)

and is optionally substituted with one or more $R_A$.

D preferably is selected from $C_5$-$C_6$carbocycle, 5- to 6-membered heterocycle, or 8- to 10-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. More preferably, D is $C_5$-$C_6$carbocycle, 5- to 6-membered heterocycle, or 6- to 10-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

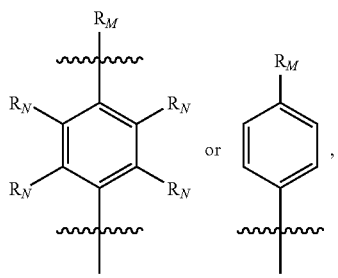

wherein $R_M$ is as defined above, and each $R_N$ is independently selected from $R_D$ and preferably is hydrogen.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

X is preferably N.

$L_1$ and $L_2$ are preferably independently $C_1$-$C_6$alkylene, and $L_3$ is preferably selected from a bond, $C_1$-$C_6$alkylene, or —C(O)—. $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. More preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—.

Y is preferably selected from -$L_S$-C($R_1 R_2$)N($R_5$)-T-$R_D$, -$L_S$-C($R_3 R_4$)C($R_6 R_7$)-T-$R_D$, -G-C($R_1 R_2$)N($R_5$)-T-$R_D$, -G-C($R_3 R_4$)C($R_6 R_7$)-T-$R_D$, —N($R_B$)C(O)C($R_1 R_2$)N($R_5$)-T-$R_D$, —N($R_B$)C(O)C($R_3 R_4$)C($R_6 R_7$)-T-$R_D$, —C(O)N($R_B$)C($R_1 R_2$)N($R_5$)-T-$R_D$, —C(O)N($R_B$)C($R_3 R_4$)C($R_6 R_7$)-T-$R_D$, —N($R_B$)C(O)-$L_S$-E, or —C(O)N($R_B$)-$L_S$-E. G is $C_5$-$C_6$carbocycle or 5- to 6-membered heterocycle, such as

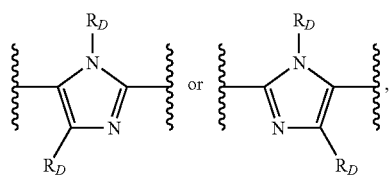

where $R_D$ is as defined above. E preferably is an 8- to 12-membered bicycle (e.g., an 8- to 10-membered bicycle such as

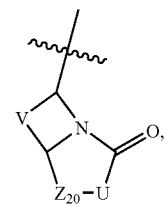

wherein U is independently selected at each occurrence from —(CH$_2$)— or —(NH)—; wherein V and $Z_{20}$ are each independently selected from $C_1$-$C_4$alkylene, $C_2$-$C_4$alkenylene or $C_2$-$C_4$alkynylene, in which at least one carbon atom is independently optionally replaced with O, S or N), and is optionally substituted with one or more $R_A$. More preferably, $R_1$ is $R_C$, and $R_2$ and $R_5$, taken together with the atoms to which they are attached, form a 5- to 6-membered heterocyclic ring or 6- to 10-membered bicycle (e.g.,

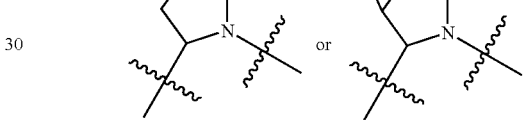

or a 6- to 8-membered bicycle; preferably

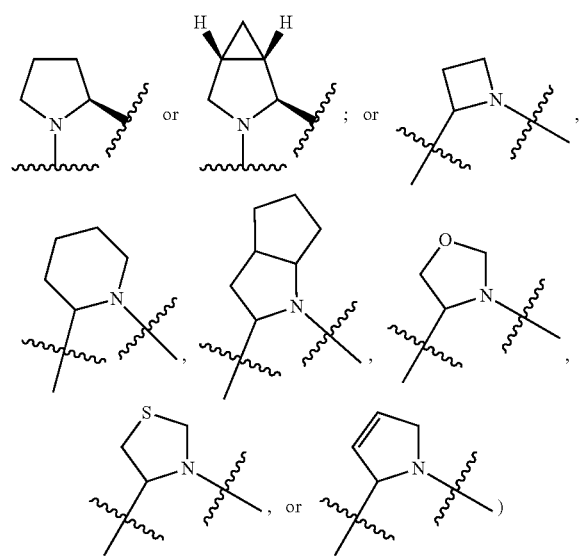

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_3$ and $R_6$ are each independently $R_C$, and $R_4$ and $R_7$, taken together with the atoms to which they are attached, form a 5- to 6-membered carbocyclic or heterocyclic ring or 6- to 10-membered bicycle (e.g.,

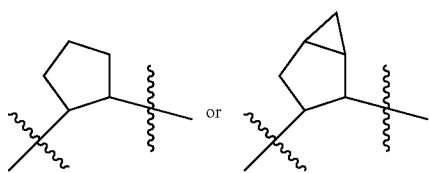 [SMILES: *C1CCCC1* ; *C1CC2CC2C1*]

or a 6- to 8-membered bicycle) which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)). Non-limiting examples of preferred Y include

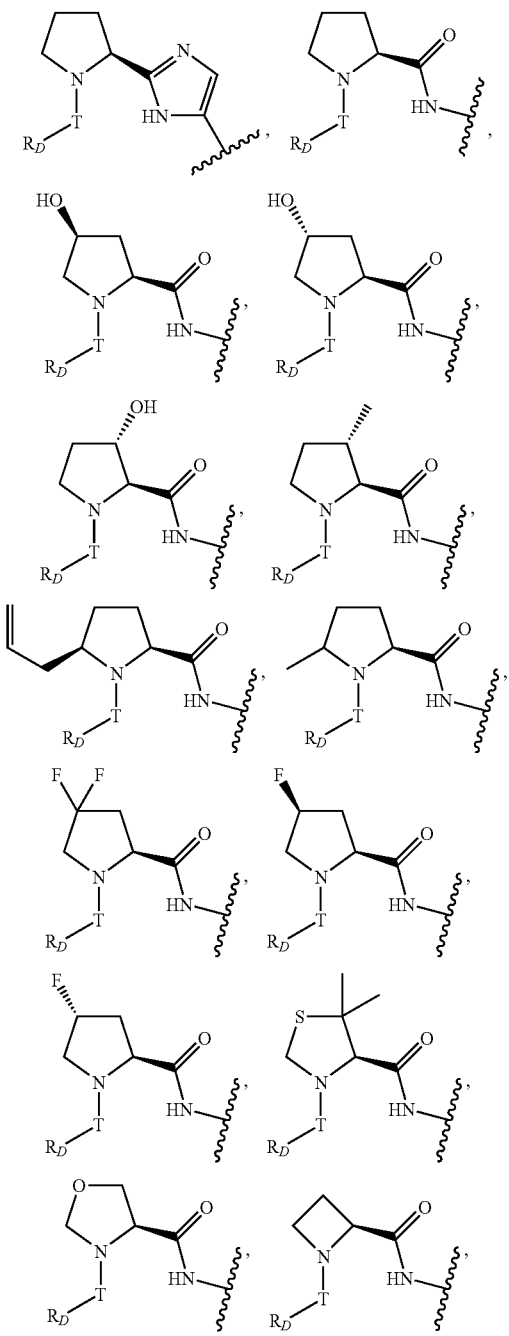

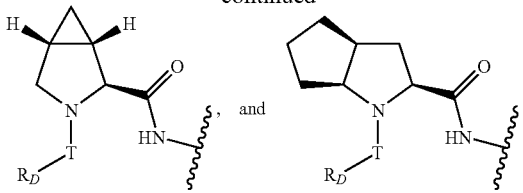

wherein T and $R_D$ are as defined hereinabove and hereinbelow.

Y can also be selected from -M-C($R_1R_2$)N($R_5$)—C(O)-$L_{Y'}$-M'-$R_D$, -M-C($R_1R_2$)N($R_5$)-$L_{Y'}$-M'-$R_D$, -$L_S$-C($R_1R_2$)N($R_5$)—C(O)-$L_{Y'}$-M'-$R_D$, -$L_S$-C($R_1R_2$)N($R_5$)-$L_{Y'}$-M'-$R_D$, -M-C($R_3R_4$)C($R_6R_7$)—C(O)-$L_{Y'}$-M'-$R_D$, -M-C($R_3R_4$)C($R_6R_7$)-$L_{Y'}$-M'-$R_D$, -$L_S$-C($R_3R_4$)C($R_6R_7$)—C(O)-$L_{Y'}$-M'-$R_D$, or -$L_S$-C($R_3R_4$)C($R_6R_7$)-$L_{Y'}$-M'-$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B$')—, —N($R_B$)S(O)— or —N($R_B$)S(O)$_2$—, and $L_{Y'}$ is $L_S'$, and preferably $L_{Y'}$ is $C_1$-$C_6$alkylene which is optionally substituted with one or more substituents selected from halogen, $R_T$, —O—$R_S$, —S—$R_S$, —N($R_SR_S'$), —OC(O)$R_S$, —C(O)O$R_S$, nitro, phosphonoxy, phosphono, oxo, thioxo, formyl or cyano. More preferably, $R_1$ is $R_C$, and $R_2$ and $R_5$, taken together with the atoms to which they are attached, form a 5- to 6-membered heterocycle or 6- to 10-membered bicycle (e.g.,

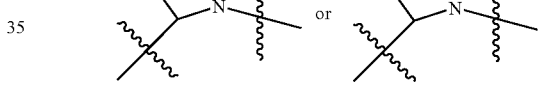

or a 6- to 8-membered bicycle) which is optionally substituted with one or more $R_4$; and $R_3$ and $R_6$ are each independently $R_C$, and $R_4$ and $R_7$, taken together with the atoms to which they are attached, form a 5- to 6-membered carbocycle/heterocycle or 6- to 10-membered bicycle (e.g.,

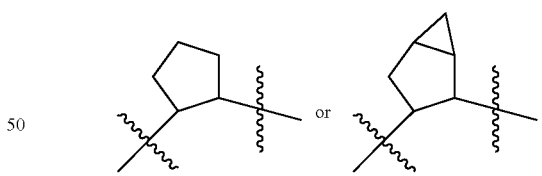

or a 6- to 8-membered bicycle) which is optionally substituted with one or more $R_A$.

Also preferably, Y is selected from —N($R_B$)CO—C($R_1R_2$)N($R_6$)—C(O)-$L_{Y'}$-N($R_B$)C(O)O—$R_D$, —N($R_B$)CO—C($R_1R_2$)N($R_5$)—C(O)-$L_{Y'}$-N($R_B$)C(O)—$R_D$, —N($R_B$)CO—C($R_1R_2$)N($R_5$)—C(O)-$L_{Y'}$-N($R_B$)S(O)$_2$—$R_D$, —N($R_B$)CO—C($R_1R_2$)N($R_5$)—C(O)-$L_{Y'}$-N($R_BR_B'$)—$R_D$, —N($R_B$)CO—C($R_1R_2$)N($R_5$)—C(O)-$L_{Y'}$—O—$R_D$, —N($R_B$)CO—C($R_1R_2$)N($R_5$)—C(O)-$L_{Y'}$-$R_D$, —N($R_B$)CO—C($R_1R_2$)N($R_5$)—$R_D$, -$L_S$-C($R_1R_2$)N($R_5$)—C(O)-$L_{Y'}$-N($R_B$)C(O)O—$R_D$, -$L_S$-C($R_1R_2$)N($R_5$)—C(O)-$L_{Y'}$-N($R_B$)C(O)—$R_D$, -$L_S$-C($R_1R_2$)N($R_5$)—C(O)-$L_{Y'}$-N($R_B$)S(O)$_2$—$R_D$, -$L_S$-C($R_1R_2$)N($R_6$)—C(O)-$L_{Y'}$-N($R_BR_B'$)—$R_D$, -$L_S$-C($R_1R_2$)N($R_5$)—C(O)-$L_{Y'}$—O—$R_D$, -$L_S$-C($R_1R_2$)N($R_5$)—C(O)-$L_{Y'}$-$R_D$, -$L_S$-C($R_1R_2$)N ($R_5$)—$R_D$, —N($R_B$)CO—C($R_3R_4$)C($R_6R_7$)—C(O)-$L_Y$'-N($R_B$)C(O)O—$R_D$, —N($R_B$)CO—C($R_3R_4$)C($R_6R_7$)—C(O)-$L_Y$'-N($R_B$)C(O)—$R_D$, —N($R_B$)CO—C($R_3R_4$)C($R_6R_7$)—C(O)-$L_Y$'-N($R_B$)S(O)$_2$—$R_D$, —N($R_B$)CO—C($R_3R_4$)C($R_6R_7$)—C(O)-$L_Y$'-N($R_BR_B$')—$R_D$, —N($R_B$)CO—C($R_3R_4$)C($R_6R_7$)—C(O)-$L_Y$'-O—$R_D$, —N($R_B$)CO—C($R_3R_4$)C($R_6R_7$)—C(O)-$L_Y$'-$R_D$, —N($R_B$)CO—C($R_3R_4$)C($R_6R_7$)—$R_D$, -$L_S$-C($R_3R_4$)C($R_6R_7$)—C(O)-$L_Y$'-N($R_B$)C(O)O—$R_D$, -$L_S$-C($R_3R_4$)C($R_6R_7$)—C(O)-$L_Y$'-N($R_B$)C(O)—$R_D$, -$L_S$-C($R_3R_4$)C($R_6R_7$)—C(O)-$L_Y$'-N($R_B$)S(O)$_2$—$R_D$, -$L_S$-C($R_3R_4$)C($R_6R_7$)—C(O)-$L_Y$'-N($R_BR_B$')—$R_D$, -$L_S$-C($R_3R_4$)C($R_6R_7$)—C(O)-$L_Y$'-O—$R_D$, -$L_S$-C($R_3R_4$)C($R_6R_7$)—C(O)-$L_Y$'-$R_D$, or -$L_S$-C($R_3R_4$)C($R_6R_7$)—$R_D$, wherein $L_Y$' is $L_S$', and preferably $L_Y$' is $C_1$-$C_6$alkylene which is optionally substituted with one or more substituents selected from halogen, $R_T$, —O—$R_S$, —S—$R_S$, —N($R_SR_S$'), —OC(O)$R_S$, —C(O)O$R_S$, nitro, phosphonoxy, phosphono, oxo, thioxo, formyl or cyano. $R_1$ may be $R_C$, and $R_2$ and $R_5$, taken together with the atoms to which they are attached, may form a 5- to 6-membered heterocycle or 6- to 10-membered bicycle (e.g.,

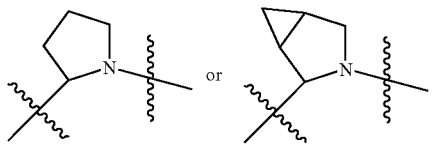 [SMILES: *C1CCCN1* ; *C1C2CC2CN1*]

or a 6- to 8-membered bicycle) which is optionally substituted with one or more $R_A$; and $R_3$ and $R_6$ may be each independently $R_C$, and $R_4$ and $R_7$, taken together with the atoms to which they are attached, may form a 5- to 6-membered carbocycle/heterocycle or 6- to 10-membered bicycle (e.g.,

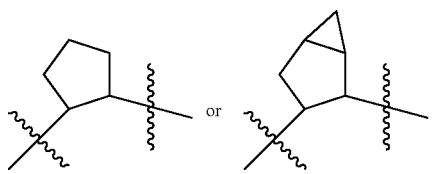 [SMILES: *C1CCCC1* ; *C1CC2CC2C1*]

or a 6- to 8-membered bicycle) which is optionally substituted with one or more $R_A$.

Highly preferably, Y is selected from —N($R_B$")CO—C($R_1R_2$)N($R_5$)—C(O)-$L_Y$-N($R_B$")C(O)-$L_S$-$R_E$ or —C($R_1R_2$)N($R_5$)—C(O)-$L_Y$-N($R_B$")C(O)-$L_S$-$R_E$, wherein $L_Y$ is $C_1$-$C_6$alkylene optionally substituted with one or more substituents selected from halogen, $R_T$, —O—$R_S$, —S—$R_S$, —N($R_SR_S$'), —OC(O)$R_S$, —C(O)O$R_S$, nitro, phosphonoxy, phosphono, oxo, thioxo, formyl or cyano; and wherein $R_B$" is each independently $R_B$. $R_B$" and $R_1$ are each preferably hydrogen or $C_1$-$C_6$alkyl, and $R_2$ and $R_5$, taken together with the atoms to which they are attached, preferably form a 5- to 6-membered heterocycle or 6- to 10-membered bicycle (e.g.,

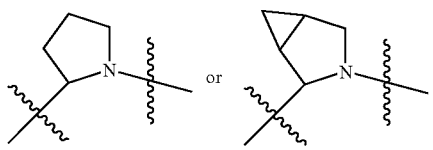 [SMILES: *C1CCCN1* ; *C1C2CC2CN1*]

or a 6- to 8-membered bicycle) which is optionally substituted with one or more $R_A$. (e.g., hydroxy, halo (e.g., fluoro), $C_1$-$C_6$alkyl (e.g., methyl), or $C_2$-$C_6$alkenyl (e.g., allyl)). Preferably, $L_Y$ is $C_1$-$C_6$alkylene substituted with one or more $R_T$ such as a $C_3$-$C_6$carbocycle or 3- to 6-membered heterocycle which is optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Z is preferably selected from -$L_S$-C($R_8R_9$)N($R_{12}$)-T-$R_D$, -$L_S$-C($R_{10}R_{11}$)C($R_{13}R_{14}$)-T-$R_D$, -G-C($R_8R_9$)N($R_{12}$)-T-$R_D$, -G-C($R_{10}R_{11}$)C($R_{13}R_{14}$)-T-$R_D$, —N($R_B$)C(O)C($R_8R_9$)N($R_{12}$)-T-$R_D$, —N($R_B$)C(O)C($R_{10}R_{11}$)C($R_{13}R_{14}$)-T-$R_D$, —C(O)N($R_B$)C($R_8R_9$)N($R_{12}$)-T-$R_D$, —C(O)N($R_B$)C($R_{10}R_{11}$)C($R_{13}R_{14}$)-T-$R_D$, —N($R_B$)C(O)-$L_S$-E, or —C(O)N($R_B$)-$L_S$-E. G is $C_5$-$C_6$carbocycle or 5- to 6-membered heterocycle, such as

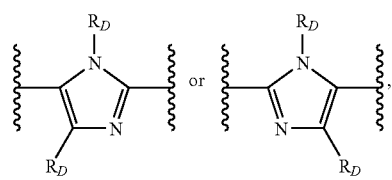

where $R_D$ is as defined above. E preferably is an 8- to 12-membered bicycle (e.g., an 8- to 10-membered bicycle such as

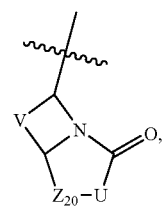

wherein U is independently selected at each occurrence from —(CH$_2$)— or —(NH)—; wherein V and $Z_{20}$ are each independently selected from $C_1$-$C_4$alkylene, $C_2$-$C_4$alkenylene or $C_2$-$C_4$alkynylene, in which at least one carbon atom is independently optionally replaced with O, S or N), and is optionally substituted with one or more $R_A$. More preferably, $R_8$ is $R_C$, and $R_9$ and $R_{12}$, taken together with the atoms to which they are attached, form a 5- to 6-membered heterocycle or 6- to 10-membered bicycle (e.g.,

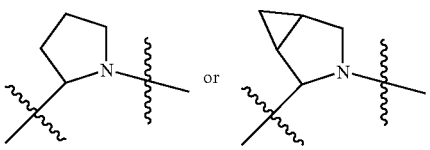 [SMILES: *C1CCCN1* ; *C1C2CC2CN1*]

or a 6- to 8-membered bicycle; preferably

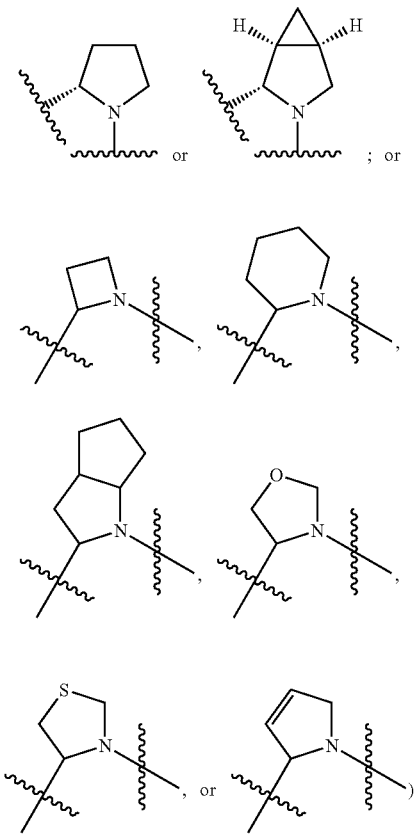

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 10-membered bicycle (e.g.,

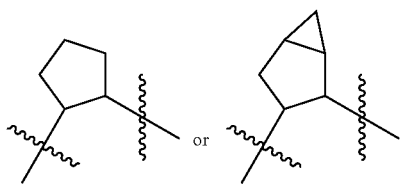 [SMILES: *C1CCCC1* ; "or" ; *C1CC2CC2C1*]

or a 6- to 8-membered bicycle) which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)). Non-limiting examples of preferred Z include

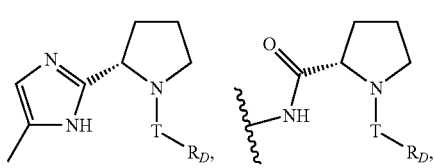

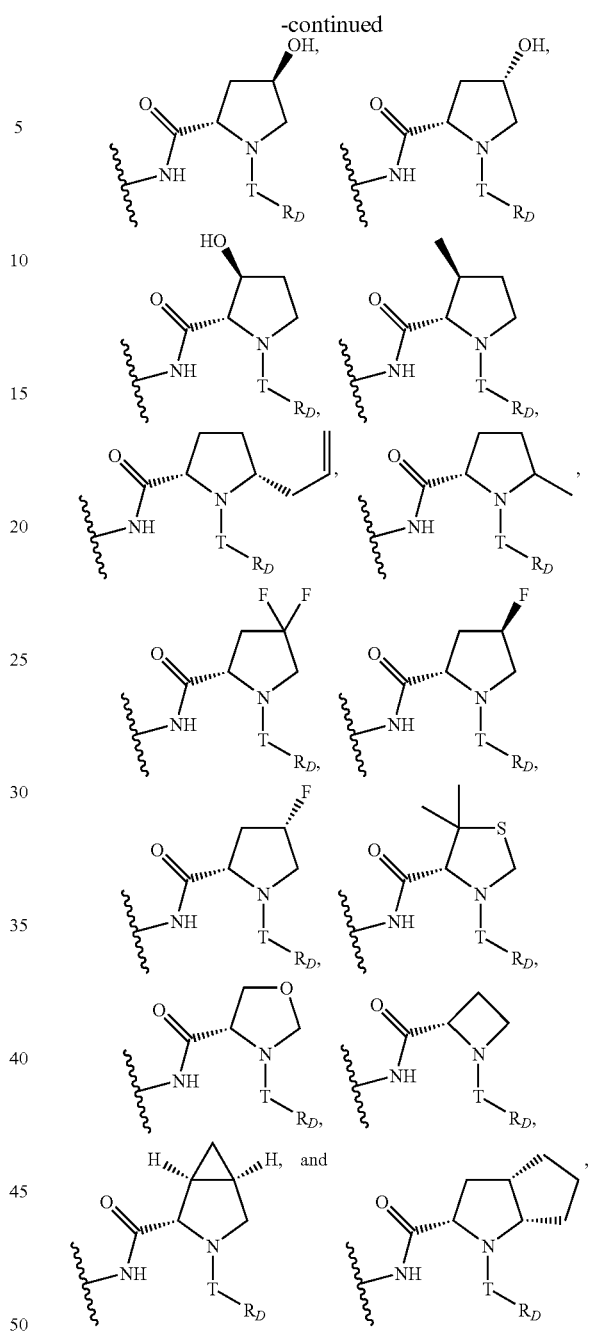

wherein T and $R_D$ are as defined hereinabove and hereinbelow.

Z can also be selected from -M-C($R_8R_9$)N($R_{12}$)—C(O)-$L_{Y'}$-M'-$R_D$, -M-C($R_8R_9$)N($R_{12}$)-$L_{Y'}$-M'-$R_D$, -$L_S$-C($R_8R_9$)N($R_{12}$)—C(O)-$L_{Y'}$-M'-$R_D$, -$L_S$-C($R_8R_9$)N($R_{12}$)-$L_{Y'}$-M'-$R_D$, -M-C($R_{10}R_{11}$)C($R_{13}R_{14}$)—C(O)-$L_{Y'}$-M-$R_D$, -M-C($R_{10}R_{11}$)C($R_{13}R_{14}$)-$L_{Y'}$-M'-$R_D$, -$L_S$-C($R_{10}R_{11}$)C($R_{13}R_{14}$)—C(O)-$L_{Y'}$-M'-$R_D$, or -$L_S$-C($R_{10}R_{11}$)C($R_{13}R_{14}$)-$L_{Y'}$-M'-$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B$'), —N($R_B$)S(O)— or —N($R_B$)S(O)$_2$—, and $L_Y'$ is $L_S'$, and preferably $L_Y'$ is $C_1$-$C_6$alkylene which is optionally substituted with one or more substituents selected from halogen, $R_T$, —O—$R_S$, —S—$R_S$, —N($R_SR_S'$), —OC(O)$R_S$, —C(O)O$R_S$, nitro, phosphonoxy, phosphono, oxo, thioxo, formyl or cyano. More preferably, $R_8$ is $R_C$, and $R_9$ and $R_{12}$, taken together with the atoms to which they are attached, form a 5- to 6-membered heterocycle or 6- to 10-membered bicycle (e.g.,

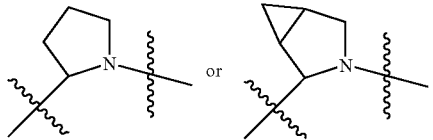 [SMILES: *C1CCCN1* ; *C1C2CC2CN1*]

or a 6- to 8-membered bicycle) which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocycle/heterocycle or 6- to 10-membered bicycle (e.g.,

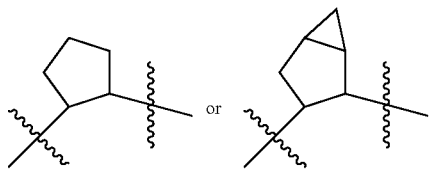 [SMILES: *C1CCCC1* ; *C1CC2CC2C1*]

or a 6- to 8-membered bicycle) which is optionally substituted with one or more $R_A$.

Also preferably, Z is selected from —N($R_B$)CO—C($R_8R_9$)N($R_{12}$)—C(O)-$L_Y$'-N($R_B$)C(O)O—$R_D$, —N($R_B$)CO—C($R_8R_9$)N($R_{12}$)—C(O)-$L_Y$'-N($R_B$)C(O)—$R_D$, —N($R_B$)CO—C($R_8R_9$)N($R_{12}$)—C(O)-$L_Y$'-N($R_B$)S(O)$_2$—$R_D$, —N($R_B$)CO—C($R_8R_9$)N($R_{12}$)—C(O)-$L_Y$'-N($R_BR_B$')—$R_D$, —N($R_B$)CO—C($R_8R_9$)N($R_{12}$)—C(O)-$L_Y$'-O—$R_D$, —N($R_B$)CO—C($R_8R_9$)N($R_{12}$)—C(O)-$L_Y$'-$R_D$, —N($R_B$)CO—C($R_8R_9$)N($R_{12}$)—$R_D$, -$L_S$-C($R_8R_9$)N($R_{12}$)—C(O)-$L_Y$'-N($R_B$)C(O)O—$R_D$, -$L_S$-C($R_8R_9$)N($R_{12}$)—C(O)-$L_Y$'-N($R_B$)C(O)—$R_D$, -$L_S$-C($R_8R_9$)N($R_{12}$)—C(O)-$L_Y$'-N($R_B$)S(O)$_2$—$R_D$, -$L_S$-C($R_8R_9$)N($R_{12}$)—C(O)-$L_Y$'-N($R_BR_B$')—$R_D$, -$L_S$-C($R_8R_9$)N($R_{12}$)—C(O)-$L_Y$'-O—$R_D$, -$L_S$-C($R_8R_9$)N($R_{12}$)—C(O)-$L_Y$'-$R_D$, -$L_S$-C($R_8R_9$)N($R_{12}$)$R_D$, —N($R_B$)CO—C($R_{10}R_{11}$)C($R_{13}R_{14}$)—C(O)-$L_Y$'-N($R_B$)C(O)O—$R_D$, —N($R_B$)CO—C($R_{10}R_{11}$)C($R_{13}R_{14}$)—C(O)-$L_Y$'-N($R_B$)C(O)—$R_D$, —N($R_B$)CO—C($R_{10}R_{11}$)C($R_{13}R_{14}$)—C(O)-$L_Y$'-N($R_B$)S(O)$_2$—$R_D$, —N($R_B$)CO—C($R_{10}R_{11}$)C($R_{13}R_{14}$)—C(O)-$L_Y$'-N($R_BR_B$')—$R_D$, —N($R_B$)CO—C($R_{10}R_{11}$)C($R_{13}R_{14}$)—C(O)-$L_Y$'-O—$R_D$, —N($R_B$)CO—C($R_{10}R_{11}$)C($R_{13}R_{14}$)—C(O)-$L_Y$'-$R_D$, —N($R_B$)CO—C($R_{10}R_{11}$)C($R_{13}R_{14}$)—$R_D$, -$L_S$-C($R_{10}R_{11}$)C($R_{13}R_{14}$)—C(O)-$L_Y$'-N($R_B$)C(O)O—$R_D$, -$L_S$-C($R_{10}R_{11}$)C($R_{13}R_{14}$)—C(O)-$L_Y$'-N($R_B$)C(O)—$R_D$, -$L_S$-C($R_{10}R_{11}$)C($R_{13}R_{14}$)—C(O)-$L_Y$'-N($R_B$)S(O)$_2$—$R_D$, -$L_S$-C($R_{10}R_{11}$)C($R_{13}R_{14}$)—C(O)-$L_Y$'N($R_BR_B$')—$R_D$, -$L_S$-C($R_{10}R_{11}$)C($R_{13}R_{14}$)—C(O)-$L_Y$'-O—$R_D$, -$L_S$-C($R_{10}R_{11}$)C($R_{13}R_{14}$)—C(O)-$L_Y$'-$R_D$, or -$L_S$-C($R_{10}R_{11}$)C($R_{13}R_{14}$)—$R_D$, wherein $L_Y$' is $L_S$', and preferably $L_Y$' is $C_1$-$C_6$alkylene which is optionally substituted with one or more substituents selected from halogen, $R_T$, —O—$R_S$, —S—$R_S$, —N($R_SR_S$'), —OC(O)$R_S$, —C(O)O$R_S$, nitro, phosphonoxy, phosphono, oxo, thioxo, formyl or cyano. $R_8$ may be $R_C$, and $R_9$ and $R_{12}$, taken together with the atoms to which they are attached, may form a 5- to 6-membered heterocycle or 6- to 10-membered bicycle (e.g.,

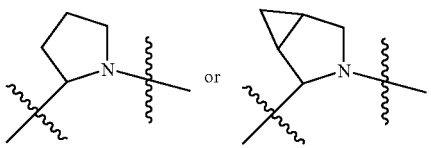 [SMILES: *C1CCCN1* ; *C1C2CC2CN1*]

or a 6- to 8-membered bicycle) which is optionally substituted with one or more $R_A$; and $R_{10}$ and $R_{13}$ may be each independently $R_C$, and $R_{11}$ and $R_{14}$, taken together with the atoms to which they are attached, may form a 5- to 6-membered carbocycle/heterocycle or 6- to 10-membered bicycle (e.g.,

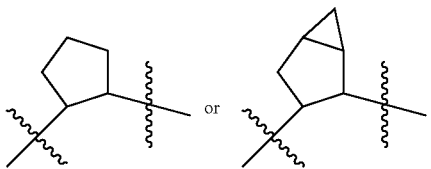 [SMILES: *C1CCCC1* ; *C1CC2CC2C1*]

or a 6- to 8-membered bicycle) which is optionally substituted with one or more $R_A$.

Highly preferably, Z is selected from —N($R_B$")CO—C($R_8R_9$)N($R_{12}$)—C(O)-$L_Y$-N($R_B$")C(O)-$L_S$-$R_E$ or —C($R_8R_9$)N($R_{12}$)—C(O)-$L_Y$-N($R_B$")C(O)-$L_S$-$R_E$, wherein $L_Y$ is $C_1$-$C_6$alkyl optionally substituted with one or more substituents selected from halogen, $R_T$, —O—$R_S$, —S—$R_S$, —N($R_SR_S$'), —OC(O)$R_S$, —C(O)O$R_S$, nitro, phosphonoxy, phosphono, oxo, thioxo, formyl or cyano; and wherein $R_B$" is each independently $R_B$. $R_B$" and $R_8$ are each preferably hydrogen or $C_1$-$C_6$alkyl, and $R_9$ and $R_{12}$, taken together with the atoms to which they are attached, preferably form a 5- to 6-membered heterocycle or 6- to 10-membered bicycle (e.g.,

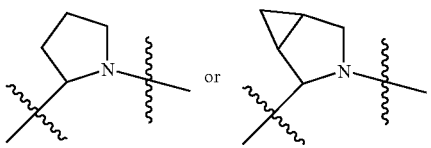 [SMILES: *C1CCCN1* ; *C1C2CC2CN1*]

or a 6- to 8-membered bicycle) which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)). Preferably, $L_Y$ is $C_1$-$C_6$alkylene substituted with one or more $R_T$ such as a $C_3$-$C_6$carbocycle or 3- to 6-membered heterocycle which is optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

T can be, without limitation, independently selected at each occurrence from —C(O)-$L_S$'-, —C(O)O-$L_S$'-, —C(O)-$L_S$'-N($R_B$)C(O)-$L_S$"-, —C(O)-$L_S$'-N($R_B$)C(O)O-$L_S$"-, —N($R_B$)C(O)-$L_S$'-N($R_B$)C(O)-$L_S$"-, —N($R_B$)C(O)-$L_S$'-N($R_B$)C(O)O-$L_S$"-, or —N($R_B$)C(O)-$L_S$'-N($R_B$)-$L_S$"-. Preferably, T is independently selected at each occurrence from —C(O)-$L_S$'-M'-$L_S$"- or —N($R_B$)C(O)-$L_S$'-M'-$L_S$"-. More preferably, T is independently selected at each occurrence from —C(O)-$L_S$'-N($R_B$)C(O)-$L_S$"- or —C(O)-$L_S$'-N($R_B$)C(O)O-$L_S$"-.

T can also be, for example, -$L_S$-M-$L_S$'-M'-$L_S$"- where $L_S$ is a bond; M is C(O); $L_S$' is $C_1$-$C_6$alkylene (e.g., 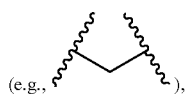), where $L_S'$ is optionally substituted with $R_T$; the optional $R_T$ is a substituent such as, but not limited to, —$C_1$-$C_6$alkyl, —$C_2$-$C_6$alkenyl, —$C_1$-$C_6$alkyl-OH, —$C_1$-$C_6$alkyl-O—$C_1$-$C_6$alkyl, 3- to 6-membered heterocycle (e.g., tetrahydrofuranyl), or $C_3$-$C_6$carbocyclyl (e.g., phenyl, cyclohexyl); M' is —NHC(O)—, —N(Et)C(O)— or —N(Me)C(O)—; and $L_S''$ is a bond. $R_D$ preferably is hydrogen, —$C_1$-$C_6$alkyl (e.g., methyl), —O—$C_1$-$C_6$alkyl (e.g., methoxy, tert-butoxy), methoxymethyl, or —N($C_1$-$C_6$alkyl), (e.g., —NMe$_2$).

T-$R_D$ can be, without limitation,

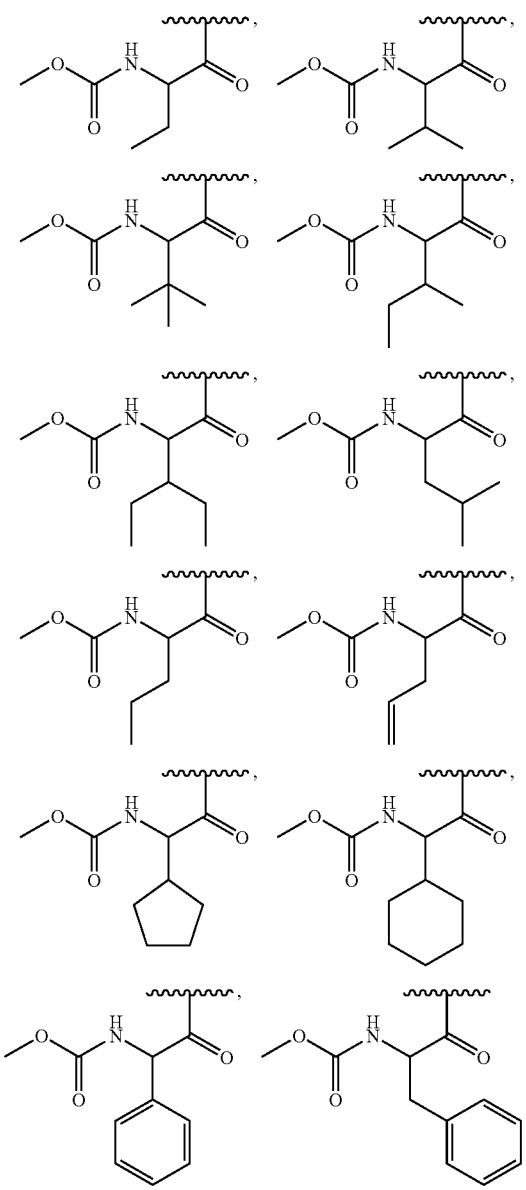

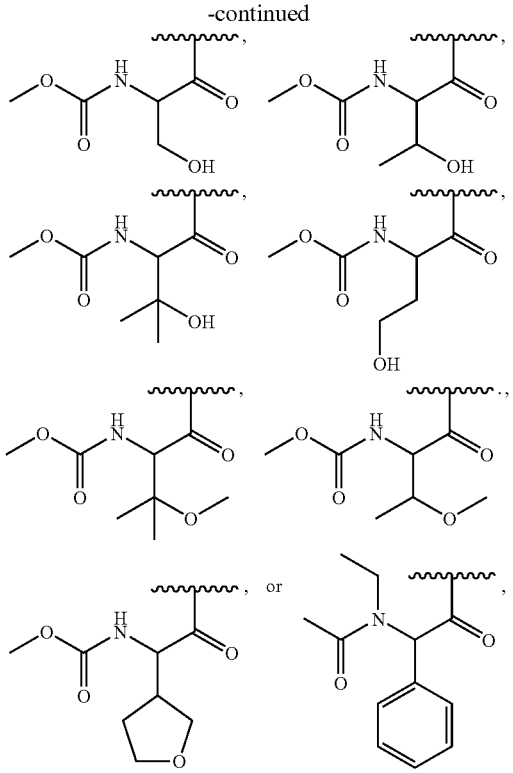

wherein the stereochemistry at a carbon within the group T-$R_D$ can be either (R) or (S).

T can also be, without limitation, -$L_S$-M-$L_S'$- where $L_S$ is a bond; M is C(O); $L_S'$ is $C_1$-$C_6$alkylene

(e.g., )

where $L_S'$ is optionally substituted with $R_T$; the optional $R_T$ is a substituent such as, but not limited to, —$C_1$-$C_6$alkyl, —$C_1$-$C_6$alkyl-OH, —$C_1$-$C_6$alkyl-O—$C_1$-$C_6$alkyl, or a $C_3$-$C_6$carbocyclyl (e.g., phenyl, cyclohexyl). $R_D$, for example is —OH; —OC(O)Me; —NH($C_1$-$C_6$alkyl) (e.g., —NHMe, —NHEt); —N($C_1$-$C_6$alkyl)$_2$ (e.g., —NMe$_2$, —NEt$_2$); a 3- to 10-membered heterocyclyl (e.g., pyrrolidinyl, imidazolidinyl, hexahydropyrimidinyl, morpholinyl, piperidinyl) optionally substituted with one or more halogen, oxo; $C_3$-$C_{10}$carbocycle (e.g., cyclopentyl) optionally substituted with —OH; —$C_1$-$C_6$alkyl (e.g., isopropyl, 3-pentyl) optionally substituted with —OH; or NHR$_T$ where $R_T$ is a 3- to 6-membered heterocyclyl (e.g., thiazolyl, pyrimidinyl). T-$R_D$ includes, but is not limited to:

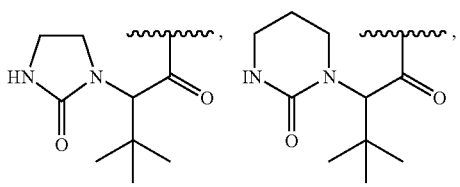

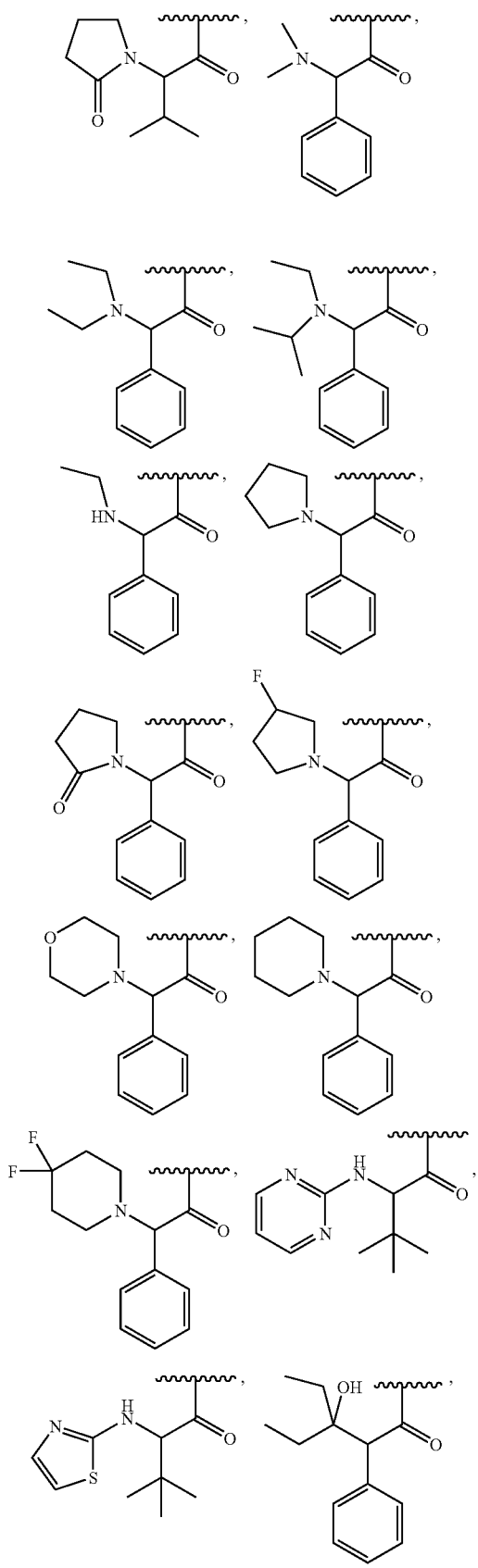
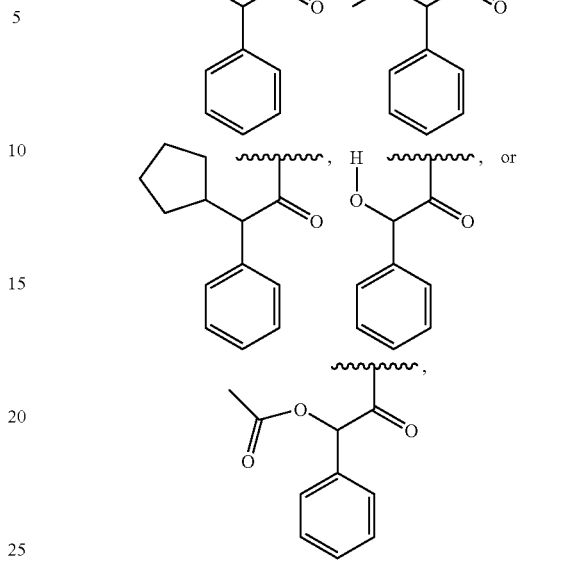

wherein the stereochemistry at a carbon within the group T-R$_D$ can be either (R) or (S).

For Formula I as well as Formulae I$_A$, I$_B$ and I$_C$ described below, including each and every embodiment described thereunder, R$_A$ preferably is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl; or -L$_A$-O—R$_S$, -L$_A$-S—R$_S$, -L$_A$-C(O)R$_S$, -L$_A$-OC(O)R$_S$, -L$_A$-C(O)OR$_S$, -L$_A$-N(R$_S$R$_S$'), -L$_A$-S(O)R$_S$, -L$_A$-SO$_2$R$_S$, -L$_A$-C(O)N(R$_S$R$_S$'), -L$_A$-N(R$_S$)C(O)R$_S$', -L$_A$-N(R$_S$)C(O)N(R$_S$'R$_S$''), -L$_A$-N(R$_S$)SO$_2$R$_S$', -L$_A$-SO$_2$N(R$_S$R$_S$'), -L$_A$-N(R$_S$)SO$_2$N(R$_S$'R$_S$''), -L$_A$-N(R$_S$)S(O)N(R$_S$'R$_S$''), -L$_A$-OS(O)—R$_S$, -L$_A$-OS(O)$_2$—R$_S$, -L$_A$-S(O)$_2$OR$_S$, -L$_A$-S(O)OR$_S$, -L$_A$-OC(O)OR$_S$, -L$_A$-N(R$_S$)C(O)OR$_S$', -L$_A$-OC(O)N(R$_S$R$_S$'), -L$_A$-N(R$_S$)S(O)—R$_S$', -L$_A$-S(O)N(R$_S$R$_S$') or -L$_A$-C(O)N(R$_S$)C(O)—R$_S$', wherein L$_A$ is bond, C$_1$-C$_6$alkylene, C$_2$-C$_6$alkenylene or C$_2$-C$_6$alkynylene.

More preferably, R$_A$ is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$, or Y and Z, or Y-A- and Z—B—, or -A-$L_1$- and -B-$L_2$-, can be the same or different. In some instances, Y-A-$L_1$- is identical to Z—B-$L_2$-. In some other instances, Y-A-$L_1$- is different from Z—B-$L_2$-.

For each compound of Formula I, $L_K$ can also be independently selected at each occurrence from a bond; -$L_S'$-$N(R_B)$C(O)-$L_S$-; -$L_S'$-C(O)$N(R_B)$-$L_S$-; or $C_1$-$C_6$alkylene, $C_2$-$C_6$alkenylene, $C_2$-$C_6$alkynylene, $C_3$-$C_{10}$carbocycle or 3- to 10-membered heterocycle, each of which is independently optionally substituted at each occurrence with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano, wherein $L_S$ and $L_S'$ are as defined above.

In one embodiment, A, B, and D are each independently phenyl, and are each independently optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. Y is -$L_S$-C($R_1 R_2$)N($R_5$)-T-$R_D$, -$_S$-C($R_3 R_4$)C($R_6 R_7$)-T-$R_D$, —N($R_B$)C(O)C($R_1 R_2$)N($R_5$)-T-$R_D$, or —N($R_B$)C(O)C($R_3 R_4$)C($R_6 R_7$)-T-$R_D$, and Z is -$L_S$-C($R_8 R_9$)N($R_{12}$)-T-$R_D$, $L_S$-C($R_{10} R_{11}$)C($R_{13} R_{14}$)-T-$R_D$, —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_2$, taken together with the atoms to which they are attached, form a 5- to 6-membered carbocyclic or heterocyclic ring which is optionally substituted with one or more $R_A$. $R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. T is preferably independently selected at each occurrence from —C(O)-$L_S'$-N($R_B$)C(O)-$L_S''$- or —C(O)-$L_S'$-N($R_B$)C(O)O-$L_S''$-, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_S'$-$L_S''$-, —C(O)-$L_S'$-O-$L_S''$-, —C(O)-$L_S'$-N($R_B$)-$L_S''$-, or —C(O)-$L_S'$-N($R_B$)S(O)$_2$-$L_S''$-. In some cases, at least one of Y and Z is, or Y and Z are independently,

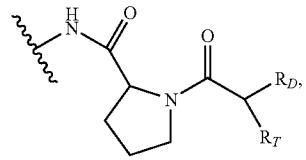

wherein $R_D$ and $R_T$ are as defined above, and non-limiting examples of $R_D$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_B$, —S—$R_B$, —N($R_B R_B'$), —OC(O)$R_B$, —C(O)O$R_B$, nitro, oxo, phosphonoxy, phosphono, thioxo, formyl or cyano.

In another embodiment, A is

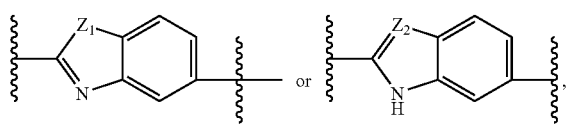

and is optionally substituted with one or more $R_A$; B is

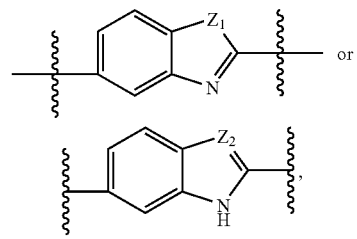

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. Y is -$L_S$-C($R_1 R_2$)N($R_5$)-T-$R_D$, -$L_S$-C($R_3 R_4$)C($R_6 R_7$)-T-$R_D$, —N($R_B$)C(O)C($R_1 R_2$)N($R_5$)-T-$R_D$, or —N($R_B$)C(O)C($R_3 R_4$)C($R_6 R_2$)-T-$R_D$, and Z is -$L_S$-C($R_8 R_9$)N($R_{12}$)-T-$R_D$, -$L_S$-C($R_{10} R_{11}$)C($R_{13} R_{14}$)-T-$R_D$, —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_A$.

$R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. T is preferably independently selected at each occurrence from —C(O)-$L_S$'-N($R_B$)C(O)-$L_S$"- or —C(O)-$L_S$'-N($R_B$)C(O)O-$L_S$"-, wherein $L_S$' preferably is $C_1$-$C_6$alkylene (e.g., —CH$_2$—) and is optionally substituted with one or more substituents selected from halogen, $R_T$, —O—$R_S$, —S—$R_S$, —N($R_S R_S$'), —OC(O)$R_S$, —C(O)O$R_S$, nitro, phosphonoxy, phosphono, oxo, thioxo, formyl or cyano. T can also be, without limitation, selected from —C(O)-$L_S$'-$L_S$"-, —C(O)-$L_S$'-O-$L_S$"-, —C(O)-$L_S$'-N($R_B$)-$L_S$"-, or —C(O)-$L_S$'-N($R_B$)S(O)$_2$-$L_S$"-. In some cases, at least one of Y and Z is, or Y and Z are independently,

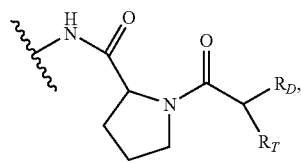

wherein $R_D$ and $R_T$ are as defined above, and non-limiting examples of $R_D$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_B$, —S—$R_B$, —N($R_B R_B$'), —OC(O)$R_B$, —C(O)O$R_B$, nitro, oxo, phosphonoxy, phosphono, thioxo, formyl or cyano.

In yet another embodiment, A is phenyl,

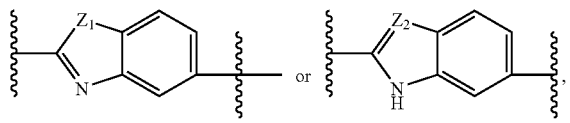

and is optionally substituted with one or more $R_A$; B is phenyl,

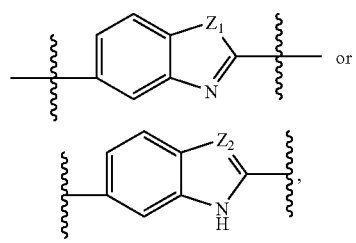

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S$'), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S$'), —OC(O)$R_S$, —C(O)O$R_S$, nitro, oxo, phosphonoxy, phosphono, thioxo, formyl or cyano; and $L_3$ is a bond or —C(O)—. Y is -$L_S$-C($R_1 R_2$)N($R_5$)-T-$R_D$, -$L_S$-C($R_3 R_4$)C($R_6 R_7$)-T-$R_D$, —N($R_B$)C(O)C($R_1 R_2$)N($R_5$)-T-$R_D$, or —N($R_B$)C(O)C($R_3 R_4$)C($R_6 R_7$)-T-$R_D$, and Z is -$L_S$-C($R_8 R_9$)N($R_{12}$)-T-$R_D$, -$L_S$-C($R_{10} R_{11}$)C($R_{13} R_{14}$)-T-$R_D$, —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_A$. $R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. T is preferably independently selected at each occurrence from —C(O)-$L_S$'-N($R_B$)C(O)-$L_S$"- or —C(O)-$L_S$'-N($R_B$)C(O)O-$L_S$"-, wherein $L_S$' preferably is $C_1$-$C_6$alkylene (e.g., —CH$_2$—) and is optionally substituted with one or more substituents selected from halogen, $R_T$, —O—$R_S$, —S—$R_S$, —N($R_S R_S$'), —OC(O)$R_S$, —C(O)O$R_S$, nitro, oxo, phosphonoxy, phosphono, thioxo, formyl or cyano. T can also be, without limitation, selected from —C(O)-$L_S$'-$L_S$"-, —C(O)-$L_S$'-O-$L_S$"-, —C(O)-$L_S$'-N($R_B$)-$L_S$"-, or —C(O)-$L_S$'-N($R_B$)S(O)$_2$-$L_S$"-. In some cases, at least one of Y and Z is, or Y and Z are independently,

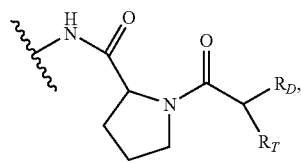

wherein non-limiting examples of $R_D$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_B$, —S—$R_B$, N($R_B R_B$'), —OC(O)$R_B$, —C(O)O$R_B$, nitro, oxo, phosphonoxy, phosphono, thioxo, formyl or cyano.

In still another embodiment, A is

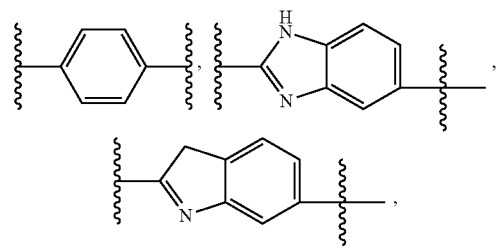

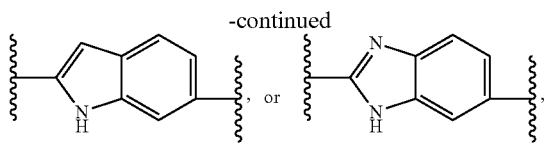

and is optionally substituted with one or more $R_A$; and B is

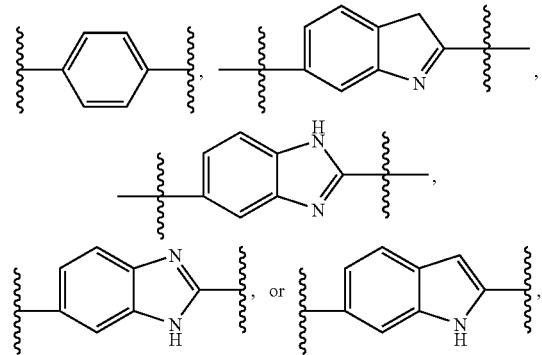

and is optionally substituted with one or more $R_A$; and D is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)OK, nitro, oxo, phosphonoxy, phosphono, thioxo, formyl or cyano; and $L_3$ is a bond or —C(O)—. Y is -$L_S$-C($R_1 R_2$)N($R_5$)-T-$R_D$, -$L_S$-C($R_3 R_4$)C($R_6 R_7$)-T-$R_D$, —N($R_B$)C(O)C($R_1 R_2$)N($R_5$)-T-$R_D$, or —N($R_B$)C(O)C($R_3 R_4$)C($R_6 R_7$)-T-$R_D$, and Z is -$L_S$-C($R_8 R_9$)N($R_{12}$)-T-$R_D$, -$L_S$-C($R_{10} R_{11}$)C($R_{13} R_{14}$)-T-$R_D$, —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_A$. $R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. T is preferably independently selected at each occurrence from —C(O)-$L_S$'-N($R_B$)C(O)-$L_S$''- or —C(O)-$L_S$'-N($R_B$)C(O)O-$L_S$''-, wherein $L_S$' preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_S$'-$L_S$'', —C(O)-$L_S$'-O-$L_8$'', —C(O)-$L_S$'-N($R_B$)-

$L_S$''-, or —C(O)-$L_S$'-N($R_B$)S(O)$_2$-$L_S$''-. In some cases, at least one of Y and Z is, or Y and Z are independently,

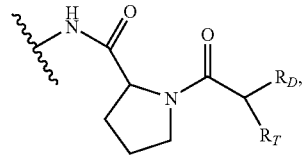

wherein non-limiting examples of $R_D$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_D$, —S—$R_D$, —N($R_B R_B'$), —OC(O)$R_B$, —C(O)O$R_B$, nitro, oxo, phosphonoxy, phosphono, thioxo, formyl or cyano.

In one embodiment, A, B, and D are each independently phenyl, and are each independently optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. Y is -G-C($R_1 R_2$)N($R_5$)T-$R_D$ or -G-C($R_3 R_4$)C($R_6 R_7$)-T-$R_D$, and Z is -G-C($R_8 R_9$)N($R_{12}$)-T-$R_D$ or -G-C($R_{10} R_{11}$)C($R_{13} R_{14}$)-T-$R_D$. G is $C_5$-$C_6$carbocycle or 5- to 6-membered heterocycle, such as

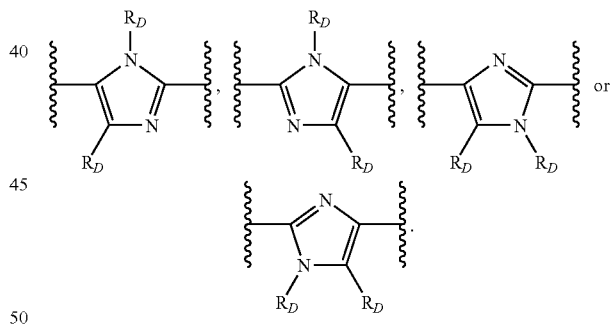

$R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_A$. $R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. $R_D$ is as defined above. T is preferably independently selected at each occurrence from —C(O)-$L_S$'-N($R_B$)C(O)-$L_S$''- or —C(O)-$L_S$'-N $(R_B)C(O)O-L_S''-$, wherein $L_S'$ preferably is $C_1$-$C_6$alkylene (e.g., $-CH_2-$) and is optionally substituted with one or more substituents selected from halogen, $R_T$, $-O-R_S$, $-S-R_S$, $-N(R_SR_S')$, $-OC(O)R_S$, $-C(O)OR_S$, nitro, phosphonoxy, phosphono, oxo, thioxo, formyl or cyano. T can also be, without limitation, selected from $-C(O)-L_S'-L_S''-$, $-C(O)-L_S'-O-L_S''-$, $-C(O)-L_S'-N(R_B)-L_S''-$, or $-C(O)-L_S'-N(R_B)S(O)_2-L_S''-$. In some cases, at least one of Y and Z is, or Y and Z are independently,

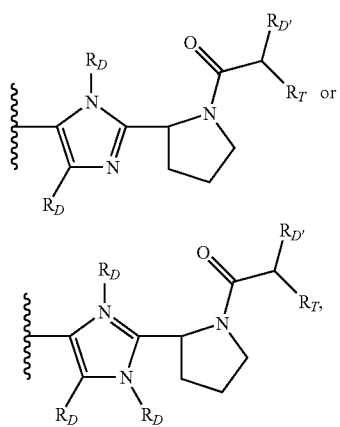

wherein $R_D$ is as defined above and preferably is hydrogen, $R_D'$ is $R_D$ and non-limiting examples of $R_D'$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, $-O-R_B$, $-S-R_B$, $-N(R_BR_B')$, $-OC(O)R_B$, $-C(O)OR_B$, nitro, oxo, phosphonoxy, phosphono, thioxo, formyl or cyano.

In another embodiment, A is

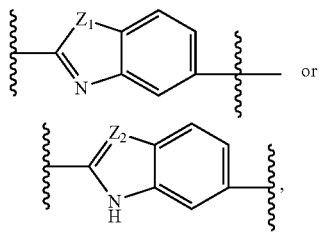

and is optionally substituted with one or more $R_A$; B is

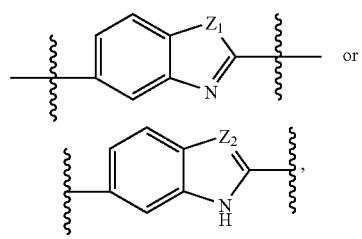

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or $CH_2$; and $Z_2$ is independently selected at each occurrence from N or CH. $L_1$ and $L_2$ are each independently $C_1$-$C_6$alkylene, $L_3$ is a bond, $C_1$-$C_6$alkylene or $-C(O)-$, and $L_1$, $L_2$, and $L_3$ are each independently optionally substituted with one or more substituents selected from halogen, $R_T$, $-O-R_S$, $-S-R_S$, $-N(R_SR_S')$, $-OC(O)R_S$, $-C(O)OR_S$, nitro, oxo, phosphonoxy, phosphono, thioxo, formyl, or cyano. Preferably, $L_1$ and $L_2$ are $-(CH_2)-$, and are each independently optionally substituted with one or more substituents selected from halogen, $R_T$, $-O-R_S$, $-S-R_S$, $-N(R_SR_S')$, $-OC(O)R_S$, $-C(O)OR_S$, nitro, oxo, phosphonoxy, phosphono, thioxo, formyl or cyano; and $L_3$ is a bond or $-C(O)-$. Y is $-G-C(R_1R_2)N(R_5)-T-R_D$ or $-G-C(R_3R_4)C(R_6R_7)-T-R_D$, and Z is $-G-C(R_8R_9)N(R_{12})-T-R_D$ or $-G-C(R_{10}R_{11})C(R_{13}R_{14})-T-R_D$. G is $C_5$-$C_6$carbocycle or 5- to 6-membered heterocycle, such as

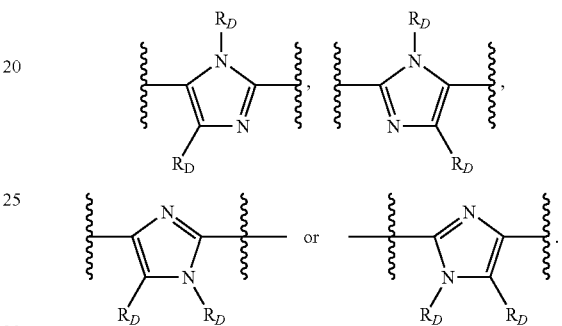

$R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_A$. $R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. $R_D$ is as defined above. T is preferably independently selected at each occurrence from $-C(O)-L_S'-N(R_B)C(O)-L_S''-$ or $-C(O)-L_S'-N(R_B)C(O)O-L_S''-$, wherein $L_S'$ preferably is $C_1$-$C_6$alkylene (e.g., $-CH_2-$) and is optionally substituted with one or more substituents selected from halogen, $R_T$, $-O-R_S$, $-S-R_S$, $-N(R_SR_S')$, $-OC(O)R_S$, $-C(O)OR_S$, nitro, phosphonoxy, phosphono, oxo, thioxo, formyl or cyano. T can also be, without limitation, selected from $-C(O)-L_S'-L_S''-$, $-C(O)-L_S'-O-L_S''-$, $-C(O)-L_S'-N(R_B)-L_S''-$, or $-C(O)-L_S'-N(R_B)S(O)_2-L_S''-$. In some cases, at least one of Y and Z is, or Y and Z are independently,

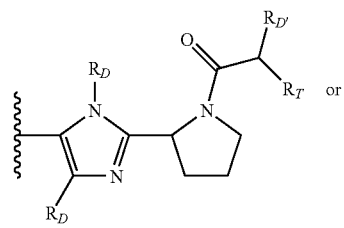

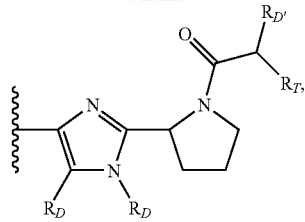

wherein $R_D$ is as defined above and preferably is hydrogen, $R_{D'}$ is $R_D$ and non-limiting examples of $R_{D'}$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_B$, —S—$R_B$, —N($R_B R_B'$), —OC(O)$R_B$, —C(O)O$R_B$, nitro, oxo, phosphonoxy, phosphono, thioxo, formyl or cyano.

In yet another embodiment, A is phenyl,

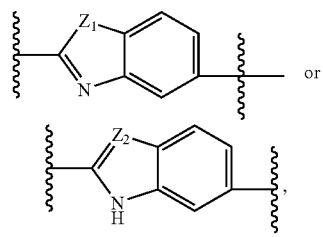

and is optionally substituted with one or more $R_A$; B is phenyl,

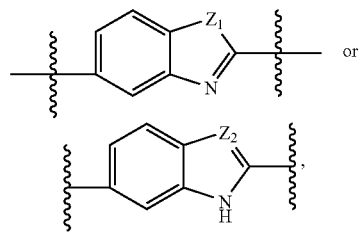

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or $CH_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —($CH_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. Y is -G-C($R_1 R_2$)N($R_5$)-T-$R_D$ or -G-C($R_3 R_4$)C($R_6 R_7$)-T-$R_D$, and Z is -G-C($R_8 R_9$)N($R_{12}$)-T-$R_D$ or -G-C($R_{10} R_{11}$)C($R_{13} R_{14}$)-T-$R_D$. G is $C_5$-$C_6$carbocycle or 5- to 6-membered heterocycle, such as

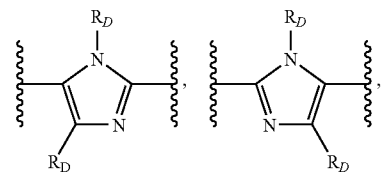

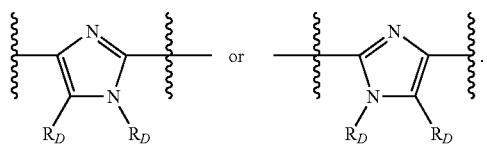

$R_1$ is $R_C$, and $R_2$ and $R_5$, taken together with the atoms to which they are attached, form a 5- to 6-membered heterocyclic ring which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_A$. $R_8$ is $R_C$, and $R_9$ and $R_{12}$, taken together with the atoms to which they are attached, form a 5- to 6-membered heterocyclic ring which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_A$. $R_D$ is as defined above. T is preferably independently selected at each occurrence from —C(O)-$L_S'$-N($R_B$)C(O)-$L_S''$- or —C(O)-$L_S'$-N($R_B$)C(O)O-$L_S''$-, wherein $L_S'$ preferably is $C_1$-$C_6$alkylene (e.g., —$CH_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_S'$-$L_S''$-, —C(O)-$L_S'$-O-$L_S''$-, —C(O)-$L_S'$-N($R_B$)-$L_S''$-, or —C(O)-$L_S'$-N($R_B$)S(O)$_2$-$L_S''$-. In some cases, at least one of Y and Z is, or Y and Z are independently,

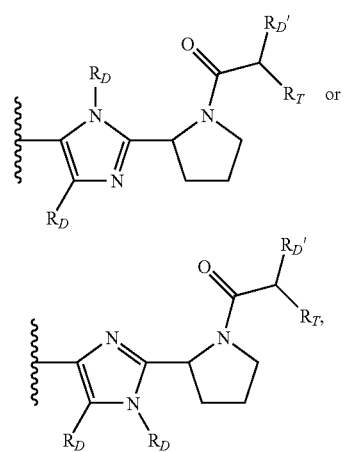

wherein $R_D$ is as defined above and preferably is hydrogen, $R_D{}'$ is $R_D$ and non-limiting examples of $R_D{}'$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_B$, —S—$R_B$, —N($R_B R_D{}'$), —OC(O)$R_B$, —C(O)O$R_B$, nitro, oxo, phosphonoxy, phosphono, thioxo, formyl or cyano.

In still another embodiment, A is

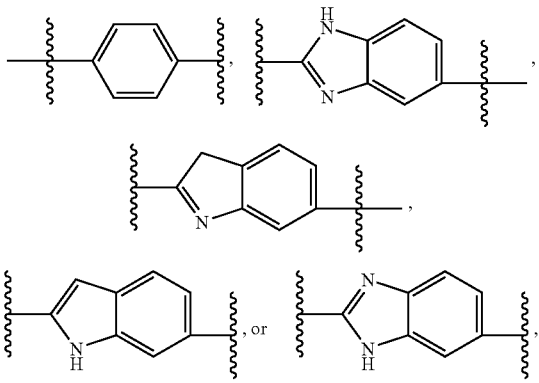

and is optionally substituted with one or more $R_4$; and B is

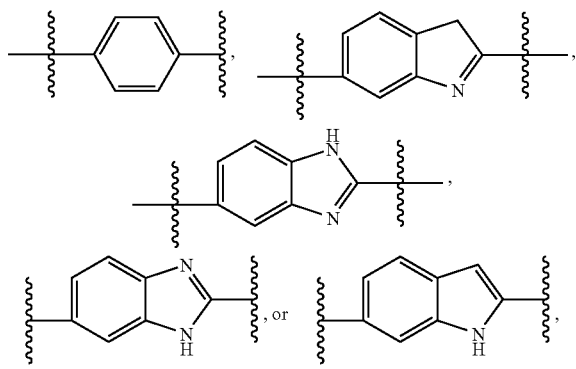

and is optionally substituted with one or more $R_4$; and D is $C_5$-$C_6$carbocycle or 5- to 6-membered heterocycle (e.g., phenyl), and is optionally substituted with one or more $R_4$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S{}'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S{}'$), —OC(O)$R_S$, —C(O)O$R_S$, nitro, oxo, phosphonoxy, phosphono, thioxo, formyl or cyano; and $L_3$ is a bond or —C(O)—. Y is -G-C($R_1 R_2$)N($R_5$)-T-$R_D$ or -G-C($R_3 R_4$)C($R_6 R_7$)-T-$R_D$, and Z is -G-C($R_8 R_9$)N($R_{12}$)-T-$R_D$ or -G-C($R_{10} R_{11}$)C($R_{13} R_{14}$)-T-$R_D$. G is $C_5$-$C_6$carbocycle or 5- to 6-membered heterocycle, such as

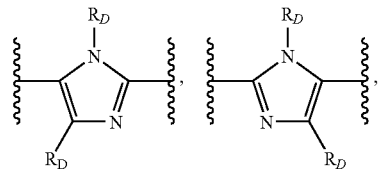

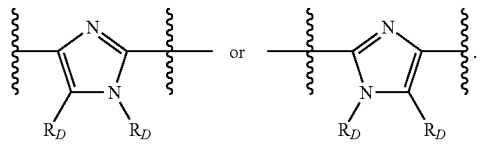

$R_1$ is $R_C$, and $R_2$ and $R_5$, taken together with the atoms to which they are attached, form a 5- to 6-membered heterocyclic ring which is optionally substituted with one or more $R_4$; $R_3$ and $R_6$ are each independently $R_C$, and $R_4$ and $R_7$, taken together with the atoms to which they are attached, form a 5- to 6-membered carbocyclic or heterocyclic ring which is optionally substituted with one or more $R_4$. $R_8$ is $R_C$, and $R_9$ and $R_{12}$, taken together with the atoms to which they are attached, form a 5- to 6-membered heterocyclic ring which is optionally substituted with one or more $R_4$; and $R_{10}$ and $R_{13}$ are each independently $R_C$, and $R_{11}$ and $R_{14}$, taken together with the atoms to which they are attached, form a 5- to 6-membered carbocyclic or heterocyclic ring which is optionally substituted with one or more $R_4$. $R_D$ is as defined above. T is preferably independently selected at each occurrence from —C(O)-$L_S{}'$-N($R_B$)C(O)-$L_S{}''$- or —C(O)-$L_S{}'$-N($R_B$)C(O)O-$L_S{}''$-, wherein $L_S{}'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S{}'$), —OC(O)$R_S$, —C(O)O$R_S$, nitro, phosphonoxy, phosphono, oxo, thioxo, formyl or cyano. T can also be, without limitation, selected from —C(O)-$L_S{}'$-$L_S{}''$-, —C(O)-$L_S{}'$-O-$L_S{}''$-, —C(O)-$L_S{}'$-N($R_B$)-$L_S{}''$-, or —C(O)-$L_S{}'$-N($R_B$)S(O)$_2$-$L_S{}''$-. In some cases, at least one of Y and Z is, or Y and Z are independently,

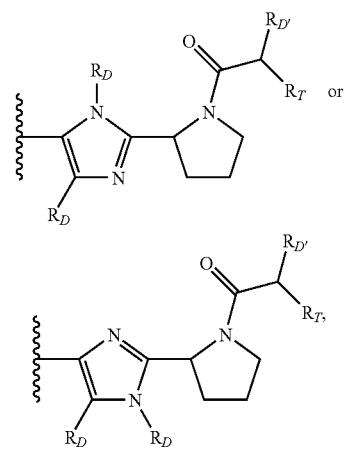

wherein $R_D$ is as defined above and preferably is hydrogen, $R_D{}'$ is $R_D$ and non-limiting examples of $R_D{}'$ include 5- or 6-membered heterocycles (e.g., pyridinyl), and non-limiting examples of $R_T$ include $C_1$-$C_6$alkyl optionally substituted at each occurrence with one or more substituents selected from halogen, $R_F$, —O—$R_B$, —S—$R_B$, —N($R_B R_B'$), —OC(O)$R_B$, —C(O)O$R_B$, nitro, oxo, phosphonoxy, phosphono, thioxo, formyl or cyano.

In one embodiment, A and B are each independently 5- or 6-membered carbocycle or heterocycle

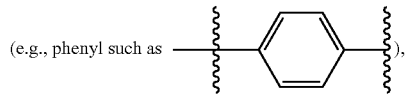 [SMILES: *c1ccc(*)cc1]

(e.g., phenyl such as )

and are each independently optionally substituted with one or more $R_A$. X preferably is N. D preferably is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano. Preferably, $L_1$ and $L_2$ are each independently $C_1$-$C_6$alkylene (e.g., —CH$_2$—) and $L_3$ is bond. Y is —N($R_B$)C(O)C($R_1 R_2$)N($R_5$)T-$R_D$, or —N($R_B$)C(O)C($R_3 R_4$)C($R_6 R_2$)T-$R_D$, and Z is —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring

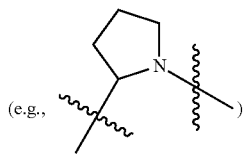

(e.g., )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

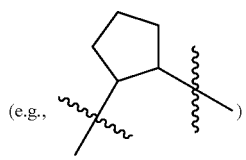

(e.g., )

which is optionally substituted with one or more $R_A$. $R_8$ is $R_C$, and $R_9$ and $R_{12}$, taken together with the atoms to which they are attached, form a 5- to 6-membered heterocyclic ring

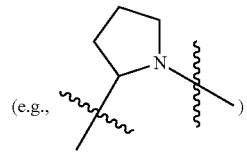

(e.g., )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

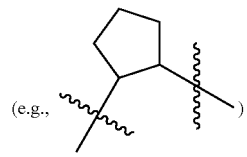

(e.g., )

which is optionally substituted with one or more $R_A$. T is preferably independently selected at each occurrence from —C(O)-$L_Y$'-N($R_B$)C(O)-$L_S$"- or —C(O)-$L_Y$'—N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, at least one of Y and Z is, or both Y and Z are independently,

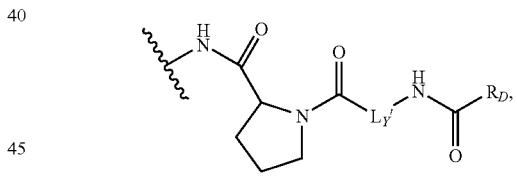

wherein non-limiting examples of $R_D$ include (1) —O—$C_1$-$C_6$alkyl, —O—$C_2$-$C_6$alkenyl, —O—$C_2$-$C_6$alkynyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In another embodiment, A is

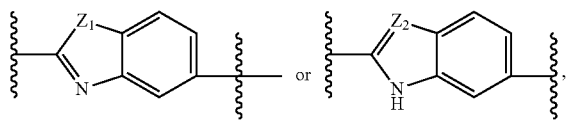

and is optionally substituted with one or more $R_A$; B is

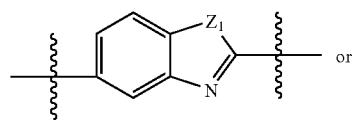

and is optionally substituted with one or more $R_A$. $Z_1$ is independently selected at each occurrence from O, S, NH or $CH_2$; and $Z_2$ is independently selected at each occurrence from N or CH. X is 5- or 6-membered carbocycle or heterocycle or 6- to 10-membered bicycle and is optionally substituted with one or more $R_A$. X preferably is N. D preferably is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. Preferably, $L_1$ and $L_2$ are each independently $C_1$-$C_6$alkylene (e.g., —$CH_2$—) and $L_3$ is bond. Y is -$L_S$-C($R_1 R_2$)N($R_5$)-T-$R_D$ or -$L_S$-C($R_3 R_4$)C($R_6 R_7$)-T-$R_D$, and Z is -$L_S$-C($R_8 R_9$)N($R_{12}$)-T-$R_D$ or -$L_S$-C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring

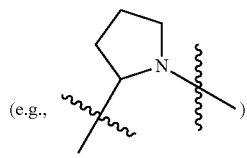 [SMILES: *C1CCCN1*]

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

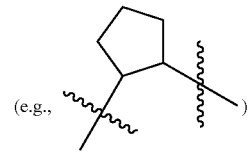

which is optionally substituted with one or more $R_A$. $R_8$ is $R_C$, and $R_9$ and $R_{12}$, taken together with the atoms to which they are attached, form a 5- to 6-membered heterocyclic ring

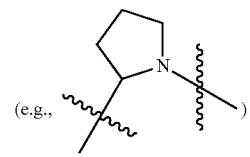

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

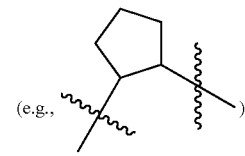

which is optionally substituted with one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is independently $C_1$-$C_6$alkylene (e.g., —$CH_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_Y'$-$L_S''$-, —C(O)-$L_Y'$-O-$L_S''$-, —C(O)-$L_Y'$-N($R_B$)-$L_S''$-, or —C(O)-$L_Y'$-N($R_B$)S(O)$_2$-$L_S''$-. In some cases, at least one of Y and Z is, or both Y and Z are independently,

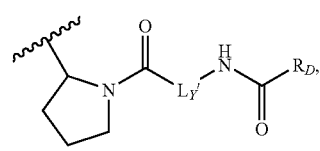

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y'$ include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In still yet another embodiment, A and B are each independently 5- or 6-membered carbocycle or heterocycle (e.g., A and B are each independently phenyl, such as

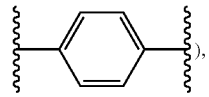), and are each independently optionally substituted with one or more $R_A$. X preferably is N. D preferably is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano. Preferably, $L_1$ and $L_2$ are each independently $C_1$-$C_6$alkylene (e.g., —CH$_2$—) and $L_3$ is bond. Y is -G-C($R_1 R_2$)N($R_5$)-T-$R_D$ or -G-C($R_3 R_4$)C($R_6 R_2$)-T-$R_D$, and Z is -G-C($R_8 R_9$)N($R_{12}$)-T-$R_D$ or -G-C($R_{10} R_{11}$)C($R_{13} R_{14}$)-T-$R_D$. G is $C_5$-$C_6$carbocycle or 5- to 6-membered heterocycle, such as

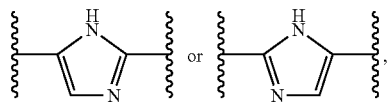

and is optionally substituted one or more $R_A$. $R_1$ is $R_C$, and $R_2$ and $R_5$, taken together with the atoms to which they are attached, form a 5- to 6-membered heterocyclic ring

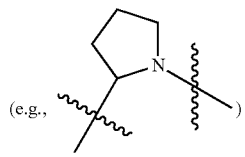

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

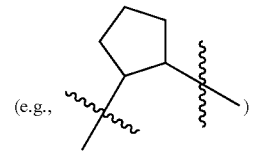

which is optionally substituted with one or more $R_A$. $R_8$ is $R_C$, and $R_9$ and $R_{12}$, taken together with the atoms to which they are attached, form a 5- to 6-membered heterocyclic ring

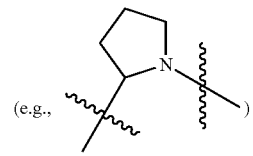

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

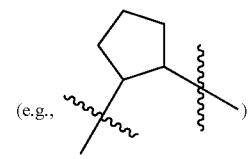

which is optionally substituted with one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —CH$_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_Y'$-$L_S''$-, —C(O)-$L_Y'$-O-$L_S''$-, —C(O)-$L_Y'$-N($R_B$)-$L_S''$-, or —C(O)-$L_Y'$-N($R_B$)S(O)$_2$-$L_S''$-. In some cases, at least one of Y and Z is, or both Y and Z are independently,

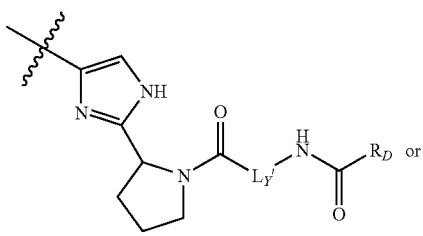 or

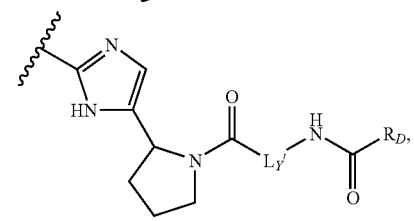, wherein non-limiting examples of $R_D$ include (1) —O—$C_1$-$C_6$alkyl, —O—$C_2$-$C_6$alkenyl, —O—$C_2$-$C_6$alkynyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y'$ include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In yet another embodiment, A and B are each independently 5- or 6-membered carbocycle or heterocycle (e.g., A and B are each independently phenyl, such as

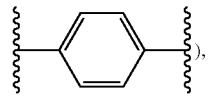), and are each independently optionally substituted with one or more $R_A$. X preferably is N. D preferably is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano. Preferably, $L_1$ and $L_2$ are each independently $C_1$-$C_6$alkylene (e.g., —$CH_2$—) and $L_3$ is bond. Y is —N($R_B$)C(O)C($R_1R_2$)N($R_5$)-T-$R_D$ or —N($R_B$)C(O)C($R_3R_4$)C($R_6R_7$)-T-$R_D$, and Z is -G-C($R_8R_9$)N($R_{12}$)-T-$R_D$ or -G-C($R_{10}R_{11}$)C($R_{13}R_{14}$)-T-$R_D$; or Y is -G-C($R_1R_2$)N($R_5$)-T-$R_D$ or -G-C($R_3R_4$)C($R_6R_7$)-T-$R_D$, and Z is —N($R_B$)C(O)C($R_8R_9$)N($R_{12}$)-T-$R_D$ or —N($R_B$)C(O)C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring (e.g., 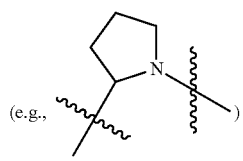)

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g., 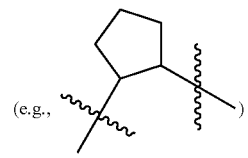)

which is optionally substituted with one or more $R_A$. $R_8$ is $R_C$, and $R_9$ and $R_{12}$, taken together with the atoms to which they are attached, form a 5- to 6-membered heterocyclic ring (e.g., 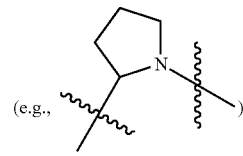)

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 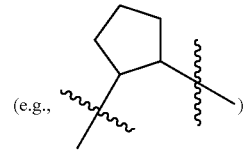)

which is optionally substituted with one or more $R_A$. G is $C_5$-$C_6$carbocycle or 5- to 6-membered heterocycle, such as

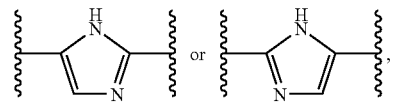

and is optionally substituted one or more $R_A$. T is preferably independently selected at each occurrence from —C(O)-$L_Y'$—N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —$CH_2$—) and optionally substituted with one or more substituents selected from halogen, $R_T$, —O—$R_S$, —S—$R_S$, —N($R_SR_S'$), —OC(O)$R_S$, —C(O)OR$_S$, nitro, phosphonoxy, phosphono, oxo, thioxo, formyl or cyano. T can also be, without limitation, selected from —C(O)-$L_Y'$-$L_S''$-, —C(O)-$L_Y'$-O-$L_S''$-, —C(O)-$L_Y'$-N($R_B$)-$L_S''$-, or —C(O)-$L_Y'$-N($R_B$)S(O)$_2$-$L_S''$-. In some cases, Y is

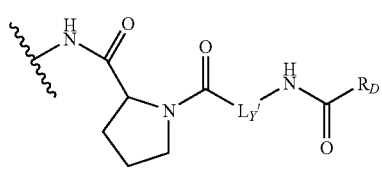

as described above, and Z is

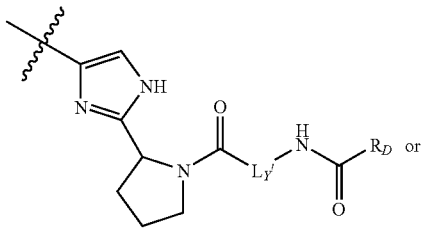

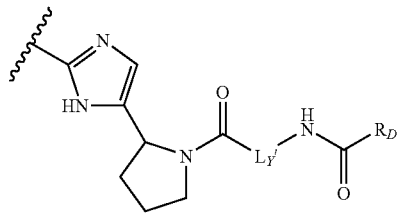

as described above. In some other cases, Y is

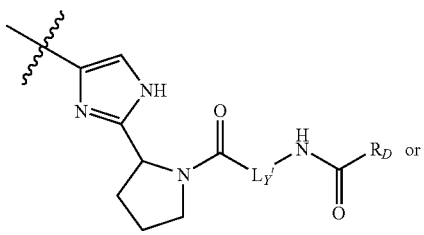

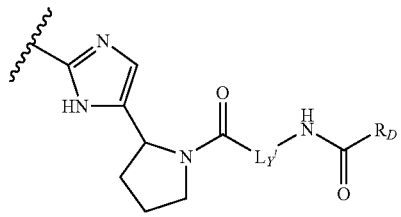

as described above, and Z is

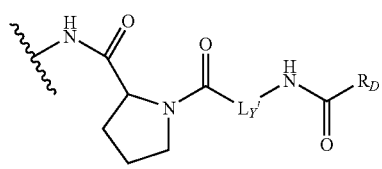

as described above.

In still another embodiment, A is 5- or 6-membered carbocycle or heterocycle

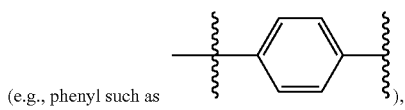 [SMILES: *c1ccc(*)cc1]

(e.g., phenyl such as ), and B is

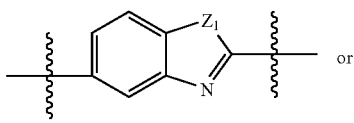 or

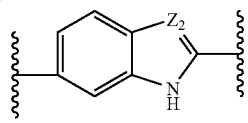

(e.g., 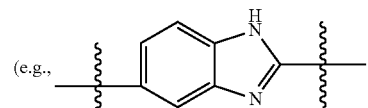

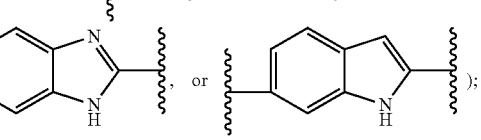 );

or A is

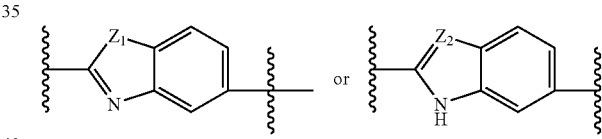 or 

(e.g., 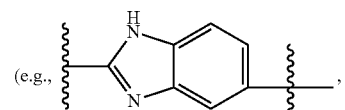

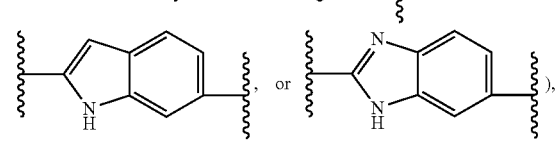 ), and B is 5- or 6-membered carbocycle or heterocycle (e.g., phenyl such as 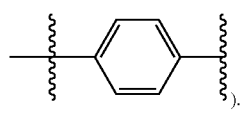 ).

A and B are each independently optionally substituted with one or more $R_A$. $Z_1$ is independently selected at each occurrence from O, S, NH or $CH_2$; and $Z_2$ is independently selected at each occurrence from N or CH. X preferably is N. D preferably is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano. Preferably, $L_1$ and $L_2$ are each independently $C_1$-$C_6$alkylene (e.g., —CH$_2$—) and $L_3$ is bond. When A is 5- or 6-membered carbocycle or heterocycle

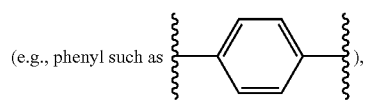

(e.g., phenyl such as            ),

Y is —N($R_B$)C(O)C($R_1 R_2$)N($R_5$)-T-$R_D$, —N($R_B$)C(O)C($R_3 R_4$)C($R_6 R_7$)-T-$R_D$, -G-C($R_1 R_2$)N($R_5$)-T-$R_D$ or -G-C($R_3 R_4$)C($R_6 R_7$)-T-$R_D$, and Z is -$L_S$-C($R_8 R_9$)N($R_{12}$)-T-$R_D$ or -$L_S$-C($R_{10}R_{11}$)C($R_{13}R_{14}$)-T-$R_D$. When B is 5- or 6-membered carbocycle or heterocycle

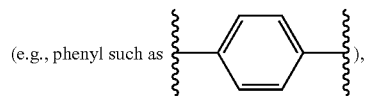

(e.g., phenyl such as            ),

Y is -$L_S$-C($R_1 R_2$)N($R_5$)-T-$R_D$ or -$L_S$-C($R_3 R_4$)C($R_6 R_7$)-T-$R_D$, and Z is —N($R_B$)C(O)C($R_8 R_9$)N($R_{12}$)-T-$R_D$, —N($R_B$)C(O)C($R_{10}R_{11}$)C($R_{13}R_{14}$)-T-$R_D$, -G-C($R_8 R_9$)N($R_{12}$)-T-$R_D$ or -G-C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring

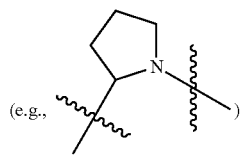

(e.g.,            )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

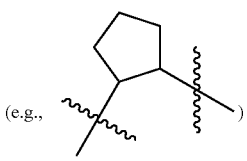

(e.g.,            )

which is optionally substituted with one or more $R_A$. $R_8$ is $R_C$, and $R_9$ and $R_{12}$, taken together with the atoms to which they are attached, form a 5- to 6-membered heterocyclic ring

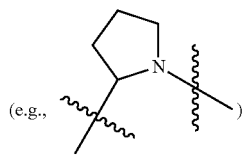

(e.g.,            )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

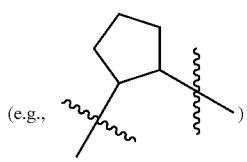

(e.g.,            )

which is optionally substituted with one or more $R_A$. G is $C_5$-$C_6$carbocycle or 5- to 6-membered heterocycle, such as

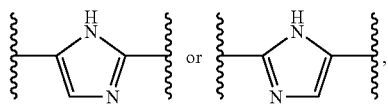

and is optionally substituted one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —CH$_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_Y'$-$L_S''$-, —C(O)-$L_Y'$-O-$L_S''$-, —C(O)-$L_Y'$-N($R_B$)-$L_S''$-, or —C(O)-$L_Y'$-N($R_B$)S(O)$_2$-$L_S''$-. In some cases when A is 5- or 6-membered carbocycle or heterocycle

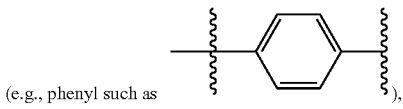 [SMILES: *c1ccc(*)cc1]

(e.g., phenyl such as            ),

Y is

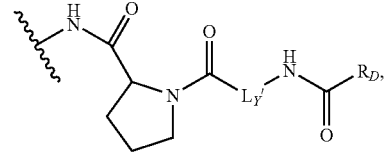

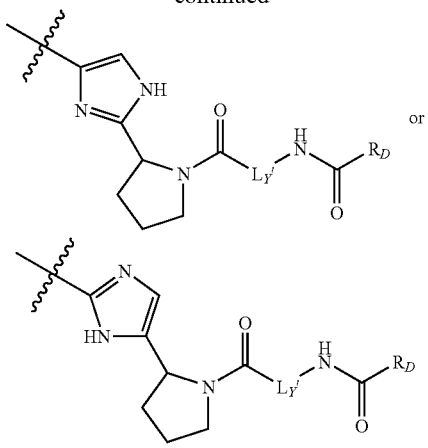

as described above, and Z is

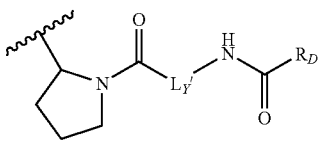

as described above. In some other cases when B is 5- or 6-membered carbocycle or heterocycle

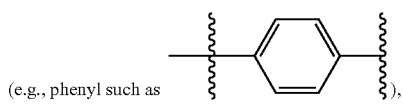

(e.g., phenyl such as ），

Y is

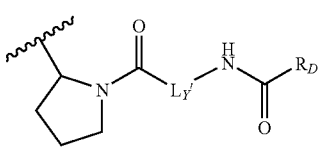

as described above, and Z is

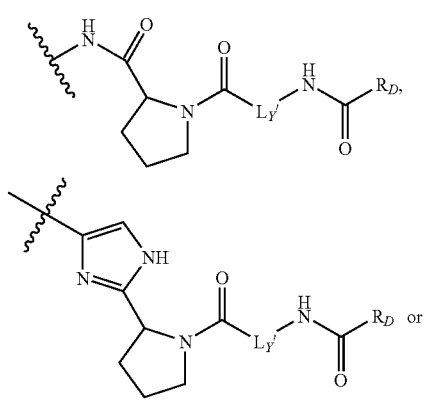

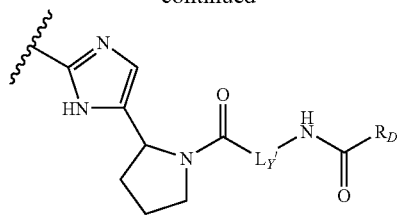

as described above.

In another aspect, the present invention features compounds of Formula $I_A$ and pharmaceutically acceptable salts thereof.

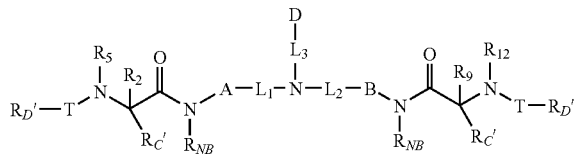

$I_A$ wherein:
$R_{NB}$ is each independently selected from $R_B$;
$R_C{'}$ is each independently selected from $R_C$;
$R_D{'}$ is each independently selected from $R_D$;
$R_2$ and $R_5$, taken together with the atoms to which they are attached, form a 3- to 8-membered heterocyclic ring which is optionally substituted with one or more $R_A$;
$R_9$ and $R_{12}$, taken together with the atoms to which they are attached, form a 3- to 8-membered heterocyclic ring which is optionally substituted with one or more $R_A$;
A, B, D, $L_1$, $L_2$, $L_3$, T, $R_A$, $R_B$, $R_C$, and $R_D$ are as described above for Formula I.

In this aspect, A and B preferably are independently selected from $C_5$-$C_6$ carbocycle, 5- to 6-membered heterocycle, or 8- to 10-membered bicycles such as

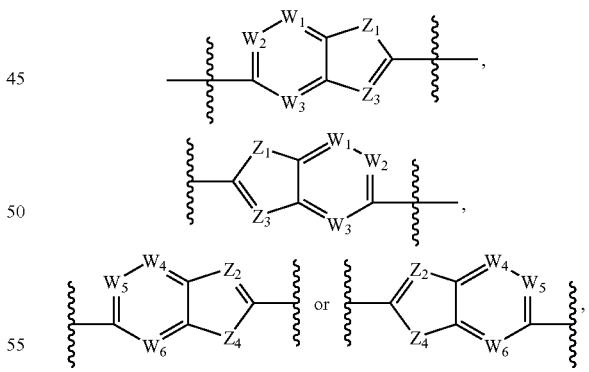

where $Z_1$ is independently selected at each occurrence from O, S, NH or $CH_2$, $Z_2$ is independently selected at each occurrence from N or CH, $Z_3$ is independently selected at each occurrence from N or CH, $Z_4$ is independently selected at each occurrence from O, S, NH or $CH_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from $C_5$-$C_6$ carbocycle, 5- to 6-membered heterocycle,

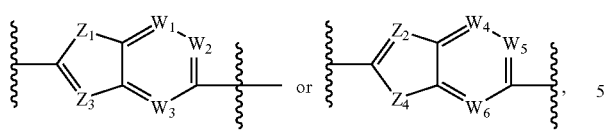

and is optionally substituted with one or more $R_A$; B is selected from $C_5$-$C_6$carbocycle, 5- to 6-membered heterocycle,

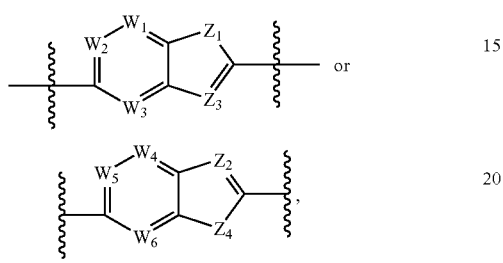

and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from phenyl (e.g., 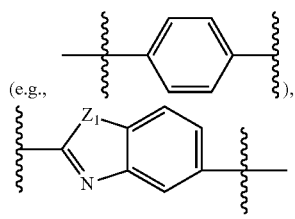),

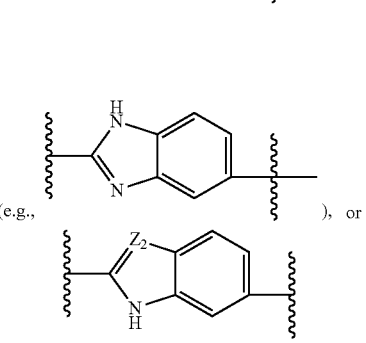

and is optionally substituted with one or more $R_A$; and B can be selected from phenyl (e.g., 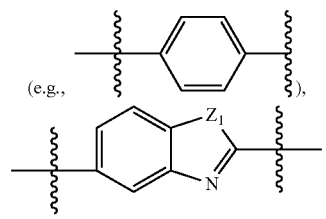), (e.g., 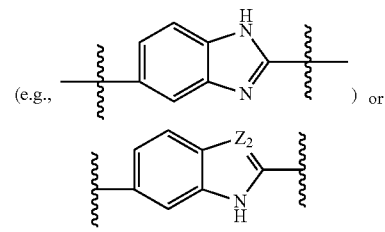) or

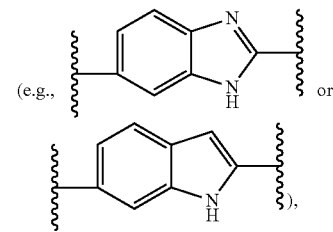

(e.g., 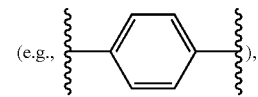), and is optionally substituted with one or more $R_A$.

Highly preferably, A and B are independently selected from $C_5$-$C_6$carbocycle or 5- to 6-membered heterocycle, and are each independently optionally substituted with one or more $R_A$. Preferably, at least one of A and B is phenyl (e.g., 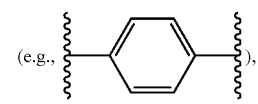), and is optionally substituted with one or more $R_A$. For instance, both A and B can be each independently phenyl (e.g., 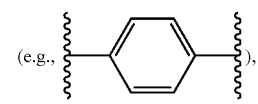), and are each independently optionally substituted with one or more $R_A$.

D preferably is selected from $C_5$-$C_6$carbocycle, 5- to 6-membered heterocycle, or 8- to 10-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. More preferably, D is $C_5$-$C_6$carbocycle, 5- to 6-membered heterocycle, or 6- to 10-membered bicycles, and is substituted with one or more $R_M$, where $R_M$ is halogen, nitro, oxo, phosphonoxy, phosphono, thioxo, cyano, or -$L_S$-$R_S$. Also preferably, D is phenyl, and is optionally substituted with one or more $R_A$. More preferably, D is phenyl, and is substituted with one or more $R_M$, wherein $R_M$ is as defined above. Highly preferably, D is

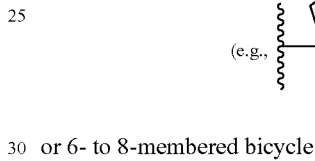

wherein $R_M$ is as defined above, and each $R_N$ is independently selected from $R_D$ and preferably is hydrogen.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

$L_1$ and $L_2$ are preferably independently $C_1$-$C_6$alkylene, and $L_3$ is preferably selected from a bond, $C_1$-$C_6$alkylene, or —C(O)—. $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)$R_S$, nitro, oxo, phosphonoxy, phosphono, thioxo, formyl, or cyano. More preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—.

$R_2$ and $R_5$, taken together with the atoms to which they are attached, preferably form a 5- to 6-membered heterocyclic ring

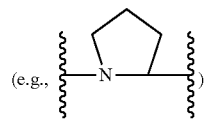

or 6- to 8-membered bicycle

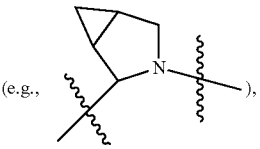

which is optionally substituted with one or more $R_A$.

$R_9$ and $R_{12}$, taken together with the atoms to which they are attached, preferably form a 5- to 6-membered heterocyclic ring

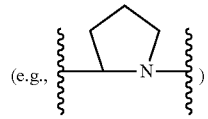 [SMILES: *C1CCCN1*]

or 6- to 8-membered bicycle

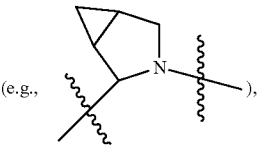 [SMILES: *C1C2CC2CN1*]

which is optionally substituted with one or more $R_A$.

-T-$R_D$' can be, without limitation, independently selected at each occurrence from —C(O)-$L_S$'-$R_D$', —C(O)O-$L_S$'-$R_D$', —C(O)-$L_S$'-N($R_B$)C(O)-$L_S$"-$R_D$', —C(O)-$L_S$'-N($R_B$)C(O)O-$L_S$"-$R_D$', —N($R_B$)C(O)-$L_S$'-N($R_B$)C(O)-$L_S$"-$R_D$', —N($R_B$)C(O)-$L_S$'-N($R_B$)C(O)O-$L_S$"-$R_D$', or —N($R_B$)C(O)-$L_S$'-N($R_B$)-$L_S$"-$R_D$'. Preferably, -T-$R_D$' is independently selected at each occurrence from —C(O)-$L_S$'-M'-$L_S$"-$R_D$' or —N($R_B$)C(O)-$L_S$'-M'-$L_S$"-$R_D$'. More preferably, -T-$R_D$' is independently selected at each occurrence from —C(O)-$L_S$'-N($R_B$)C(O)-$L_S$"-$R_D$' or —C(O)-$L_S$'-N($R_B$)C(O)O-$L_S$"-$R_D$'.

-T-$R_D$' can also be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$'-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or —N($R_B$)C(O)-$L_Y$'-N($R_B$)-$L_S$"-$R_D$', wherein $L_Y$' is each independently $L_S$' and, preferably is each independently $C_1$-$C_6$alkylene (e.g., —CH$_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'—N($R_B$)C(O)O-$L_S$"-$R_D$'. Highly preferably, -T-$R_D$' is independently selected at each occurrence from —C(O)-$L_Y$'-N($R_B$)C (O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from halogen, $R_T$, —O—$R_S$, —S—$R_S$, —N($R_S R_S$'), —OC(O)$R_S$, —C(O)O$R_S$, nitro, phosphonoxy, phosphono, oxo, thioxo, formyl or cyano.

$R_{NB}$ and $R_C$' are preferably hydrogen, and $R_D$' preferably is independently selected at each occurrence from $L_A$, or 5- or 6-membered carbocycle or heterocycle which is optionally substituted with one or more halogen, $R_T$, —O—$R_B$, —S—$R_B$, —N($R_B R_B$'), —OC(O)$R_B$, —C(O)O$R_B$, nitro, phosphonoxy, phosphono, oxo, thioxo, formyl or cyano. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

For each compound of Formula $I_A$, $L_K$ can also be independently selected at each occurrence from a bond; -$L_S$'-N($R_B$)C(O)-$L_S$-; -$L_S$'-C(O)N($R_B$)-$L_S$-; or $C_1$-$C_6$alkylene, $C_2$-$C_6$alkenylene, $C_2$-$C_6$alkynylene, $C_3$-$C_{10}$carbocycle or 3- to 10-membered heterocycle, each of which is independently optionally substituted at each occurrence with one or more substituents selected from halogen, $R_T$, —O—$R_S$, —S—$R_S$, —N($R_S R_S$'), —OC(O)$R_S$, —C(O)O$R_S$, nitro, oxo, phosphonoxy, phosphono, thioxo, formyl or cyano, wherein $L_S$ and $L_S$' are as defined above.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S$'), -$L_A$-S(O)$R_S$, $L_A$-SO$_2$$R_S$, -$L_A$-C(O)N($R_S R_S$'), -$L_A$-N($R_S$)C(O)$R_S$', -$L_A$-N($R_S$)C(O)N($R_S$'$R_S$''), -$L_A$-N($R_S$)SO$_2$$R_S$', -$L_A$-SO$_2$N($R_S R_S$'), -$L_A$-N($R_S$)SO$_2$N($R_S$'$R_S$''), -$L_A$-N($R_S$)S(O)N($R_S$'$R_S$''), -$L_A$-OS(O)—$R_S$, -$L_A$-OS(O)$_2$—$R_S$, -$L_A$-S(O)$_2$O$R_S$, -$L_A$-S(O)ON, -$L_A$-OC(O)O$R_S$, -$L_A$-N($R_S$)C(O)O$R_S$', -$L_A$-OC(O)N($R_S R_S$'), -$L_A$-N($R_S$)S(O)—$R_S$', -$L_A$-S(O)N($R_S R_S$') or -$L_A$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A, B, and D are each independently phenyl, and are each independently optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S$'), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S$'), —OC(O)$R_S$, —C(O)O$R_S$, nitro, oxo, phosphonoxy, phosphono, thioxo, formyl or cyano; and $L_3$ is a bond or —C(O)—. -T-$R_D$' is preferably independently selected at each occurrence from —C(O)-$L_S$'-N($R_B$)C(O)-$L_S$"-$R_D$' or —C(O)-$L_S$'-N($R_B$)C(O)O-$L_S$"-$R_D$', wherein $L_S$' preferably is $C_1$-$C_6$alkylene (e.g., —CH$_2$—) and is optionally substituted with one or more substituents selected from halogen, $R_T$, —O—$R_S$, —S—$R_S$, —N($R_S R_S$'), —OC(O)$R_S$, —C(O)O$R_S$, nitro, phosphonoxy, phosphono, oxo, thioxo, formyl or cyano. -T-$R_D$' can also be, without limitation, selected from —C(O)-$L_S$'-$L_S$"-$R_D$', —C(O)-$L_S$'-O-$L_S$"-$R_D$', —C(O)-$L_S$'-N($R_B$)-$L_S$"-$R_D$', or —C(O)-$L_S$'-N($R_B$)S(O)$_2$-$L_S$"-$R_D$'.

In another embodiment of this aspect, A is

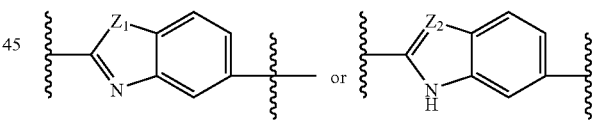

and is optionally substituted with one or more $R_A$; B is

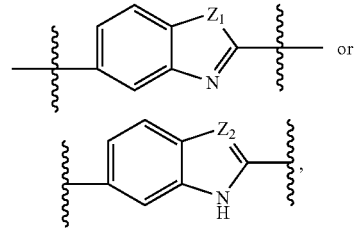

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. T can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_B$)S(O)$_2$-$L_S''$-$R_D'$.

In yet another embodiment of this aspect, A is phenyl,

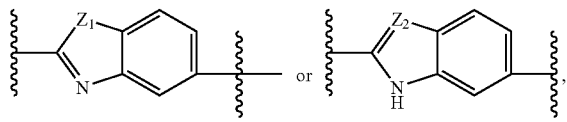

and is optionally substituted with one or more $R_A$; B is phenyl,

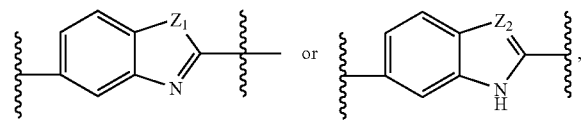

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_B$)S(O)$_2$-$L_S''$-$R_D'$.

In still another embodiment of this aspect, A is

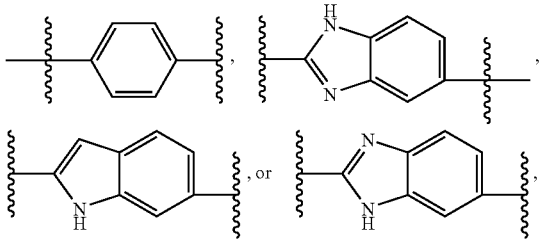

and is optionally substituted with one or more $R_A$; and B is

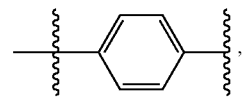

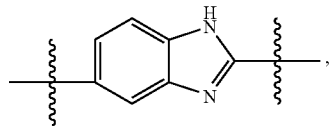

and is optionally substituted with one or more $R_A$; and D is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_B$)S(O)$_2$-$L_S''$-$R_D'$.

In a further embodiment of this aspect, A, B, and D are each independently $C_5$-$C_6$carbocycle, 5- to 6-membered heterocycle (e.g., A, B, and D are each independently phenyl), and are each independently optionally substituted with one or more $R_4$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. Preferably, $L_1$ and $L_2$ are each independently $C_1$-$C_6$alkylene (e.g., —CH$_2$—) and $L_3$ is bond. -T-$R_D'$ is independently selected at each occurrence from —C(O)-$L_Y'$-N($R_B$)C(O)-$L_S''$-$R_D'$ or —C(O)-$L_Y'$-N($R_B$)C(O)O-$L_S''$-$R_D'$, wherein $L_Y'$ is $C_1$-$C_6$alkylene (e.g., —CH$_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano, and $L_S''$ preferably is bond. -T-$R_D'$ can also be, without limitation, selected from —C(O)-$L_Y'$-$L_S''$-$R_D'$, —C(O)-$L_Y'$-O-$L_S''$-$R_D'$, —C(O)-$L_Y'$-N($R_B$)-$L_S''$-$R_D'$, or —C(O)-$L_Y'$-N($R_B$)S(O)$_2$-$L_S''$-$R_D'$.

In still another aspect, the present invention features compounds of Formula $I_B$ and pharmaceutically acceptable salts thereof:

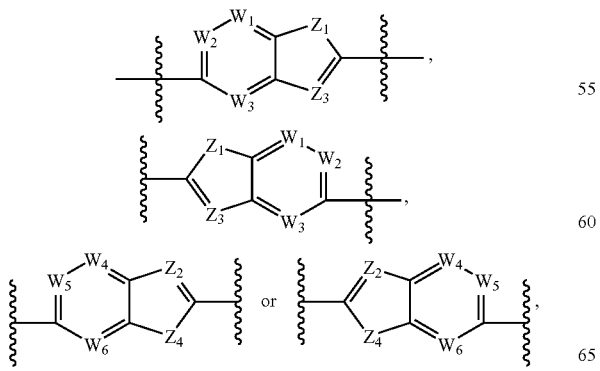

$I_B$ wherein:
$R_C'$ is each independently selected from $R_C$;
$R_D'$ is each independently selected from $R_D$;
$R_2$ and $R_5$, taken together with the atoms to which they are attached, form a 3- to 8-membered heterocyclic ring which is optionally substituted with one or more $R_4$;
$R_9$ and $R_{12}$, taken together with the atoms to which they are attached, form a 3- to 8-membered heterocyclic ring which is optionally substituted with one or more $R_4$;
A, B, D, $L_1$, $L_2$, $L_3$, T, $R_4$, $R_C$, and $R_D$ are as described above for Formula I.

In this aspect, A and B preferably are independently selected from $C_5$-$C_6$carbocycle, 5- to 6-membered heterocycle, or 8- to 10-membered bicycles such as

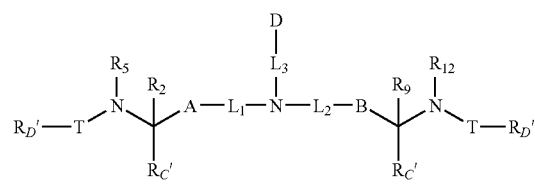

where $Z_1$ is independently selected at each occurrence from O, S, NH or CH$_2$, $Z_2$ is independently selected at each occurrence from N or CH, $Z_3$ is independently selected at each occurrence from N or CH, $Z_4$ is independently selected at each occurrence from O, S, NH or CH$_2$, and $W_1$, $W_2$, $W_3$, $W_4$, $W_5$ and $W_6$ are each independently selected at each occurrence from CH or N. A and B are each independently optionally substituted with one or more $R_4$.

More preferably, A is selected from $C_5$-$C_6$carbocycle, 5- to 6-membered heterocycle,

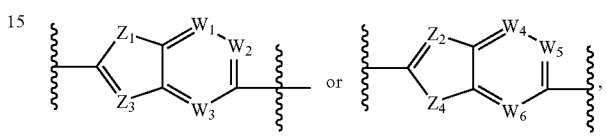

and is optionally substituted with one or more $R_4$; B is selected from $C_5$-$C_6$carbocycle, 5- to 6-membered heterocycle,

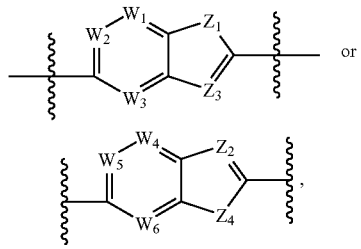

and is optionally substituted with one or more $R_4$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from phenyl (e.g., 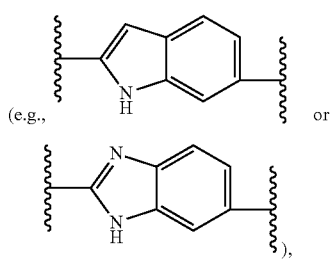), and is optionally substituted with one or more $R_A$; and B can be selected from phenyl

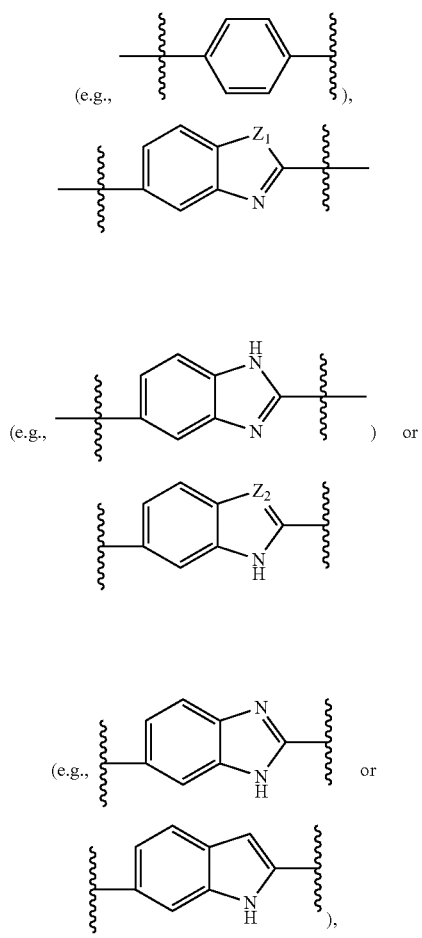

and is optionally substituted with one or more $R_A$.

Highly preferably, A is selected from

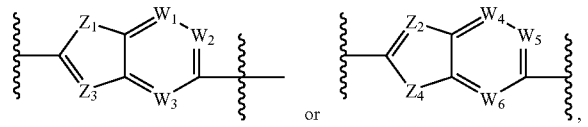

and is optionally substituted with one or more $R_A$; B is selected from

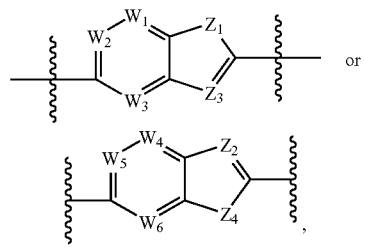 or and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from

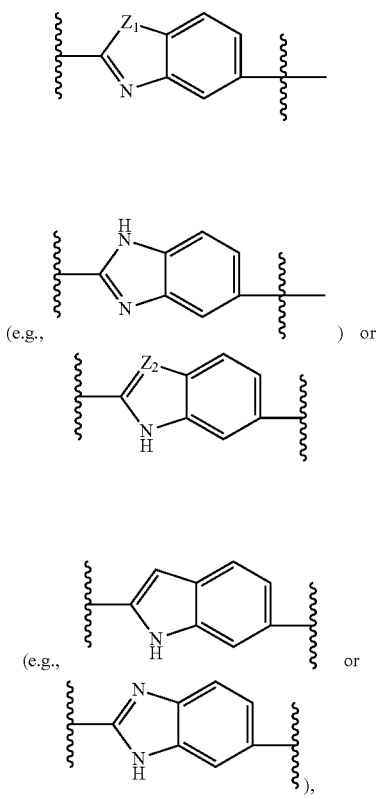

and is optionally substituted with one or more $R_A$; and B can be selected from

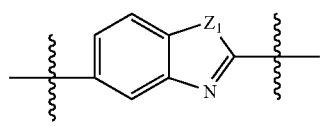

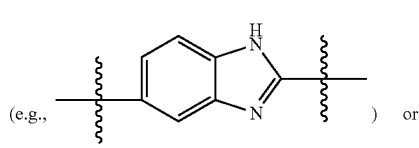

-continued

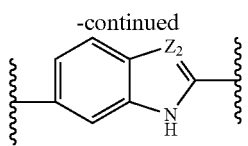

(e.g., 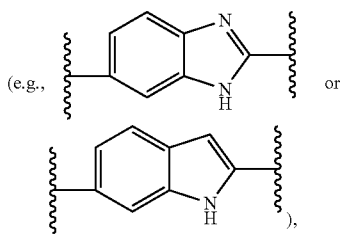 or

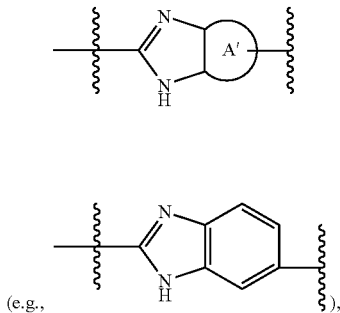), and is optionally substituted with one or more $R_A$.
Also preferably, A is

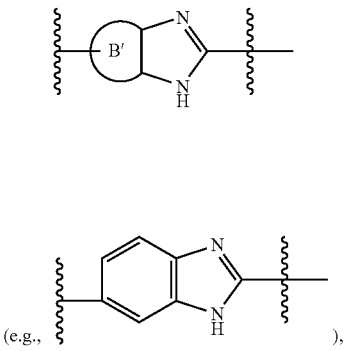

A' and B' are independently selected from $C_5$-$C_6$carbocycle or 5- to 6-membered heterocycle, and A and B are independently optionally substituted with one or more $R_A$.

D preferably is selected from $C_5$-$C_6$carbocycle, 5- to 6-membered heterocycle, or 8- to 10-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. More preferably, D is $C_5$-$C_6$carbocycle, 5- to 6-membered heterocycle, or 6- to 10-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D

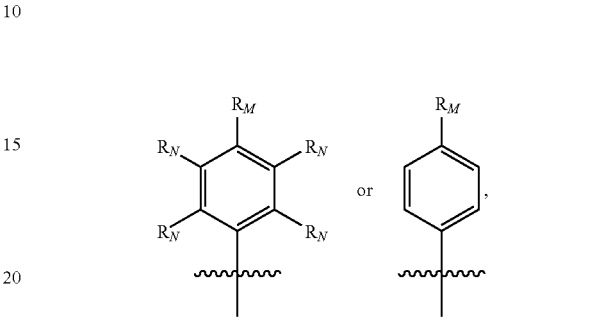

is wherein $R_M$ is as defined above, and each $R_N$ is independently selected from $R_D$ and preferably is hydrogen.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

$L_1$ and $L_2$ are preferably independently $C_1$-$C_6$alkylene, and $L_3$ is preferably selected from a bond, $C_1$-$C_6$alkylene, or —C(O)—. $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. More preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—.

$R_2$ and $R_5$, taken together with the atoms to which they are attached, preferably form a 5- to 6-membered heterocyclic ring

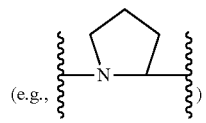 [SMILES: *C1CCCN1*]

(e.g., ) or 6- to 8-membered bicycle

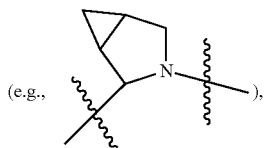 [SMILES: *C1C2CC2CN1*]

(e.g., ), which is optionally substituted with one or more $R_A$.

$R_9$ and $R_{12}$, taken together with the atoms to which they are attached, preferably form a 5- to 6-membered heterocyclic ring

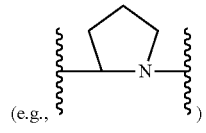 [SMILES: *C1CCCN1*]

(e.g., ) or 6- to 8-membered bicycle

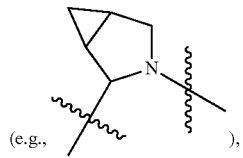 [SMILES: *C1C2CC2CN1*]

(e.g., ), which is optionally substituted with one or more $R_A$.

-T-$R_D$' can be, without limitation, independently selected at each occurrence from —C(O)-$L_S$'-$R_D$', —C(O)O-$L_S$'-$R_D$', —C(O)-$L_S$'-N($R_B$)C(O)-$L_S$''-$R_D$', —C(O)-$L_S$'-N($R_B$)C(O)O-$L_S$''-$R_D$', —N($R_B$)C(O)-$L_S$'-N($R_B$)C(O)-$L_S$''-$R_D$', —N($R_B$)C(O)-$L_S$'-N($R_B$)C(O)O-$L_S$''-$R_D$', or —N($R_B$)C(O)-$L_S$'-N($R_B$)-$L_S$''-$R_D$'. Preferably, -T-$R_D$' is independently selected at each occurrence from —C(O)-$L_S$'-M'-$L_S$''-$R_D$' or —N($R_B$)C(O)-$L_S$'-M'-$L_S$''-$R_D$'. More preferably, -T-$R_D$' is independently selected at each occurrence from —C(O)-$L_S$'-N($R_B$)C(O)-$L_S$''-$R_D$' or —C(O)-$L_S$'-N($R_B$)C(O)O-$L_S$''-$R_D$'.

-T-$R_D$' can also be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$''-$R_D$', —C(O)-$L_Y$'-N($R_B$)C(O)O-$L_S$''-$R_D$', —N($R_B$)C(O)-$L_Y$'-N($R_B$)C(O)-$L_S$''-$R_D$', —N($R_B$)C(O)-$L_Y$'-N($R_B$)C(O)O-$L_S$''-$R_D$', or —N($R_B$)C(O)-$L_Y$'-N($R_B$)-$L_S$''-$R_D$', wherein $L_Y$' is each independently $L_S$' and, preferably, is each independently $C_1$-$C_6$alkylene (e.g., —$CH_2$—) and optionally substituted with one or more substituents selected from halogen, $R_T$, —O—$R_S$, —S—$R_S$, —N($R_S$$R_S$'), —OC(O)$R_S$, —C(O)O$R_S$, nitro, phosphonoxy, phosphono, oxo, thioxo, formyl or cyano. Preferably, -T-$R_D$' is independently selected at each occurrence from —C(O)-$L_Y$'-M'-$L_S$''-$R_D$' or —N($R_B$)C(O)-$L_Y$'-M'-$L_S$''-$R_D$'. More preferably, -T-$R_D$' is independently selected at each occurrence from —C(O)-$L_Y$'-N($R_B$)C(O)-$L_S$''-$R_D$' or —C(O)-$L_Y$'—N($R_B$)C(O)O-$L_S$''-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —$CH_2$—) and optionally substituted with one or more substituents selected from halogen, $R_T$, —O—$R_S$, —S—$R_S$, —N($R_S$$R_S$'), —OC(O)$R_S$, —C(O)O$R_S$, nitro, phosphonoxy, phosphono, oxo, thioxo, formyl or cyano.

$R_C$' is preferably hydrogen, and $R_D$' preferably is independently selected at each occurrence from $L_A$, or 5- or 6-membered carbocycle or heterocycle which is optionally substituted with one or more halogen, $R_T$, —O—$R_B$, —S—$R_B$, —N($R_B$$R_B$'), —OC(O)$R_B$, —C(O)O$R_B$, nitro, phosphonoxy, phosphono, oxo, thioxo, formyl or cyano. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

For each compound of Formula $I_B$, $L_K$ can also be independently selected at each occurrence from a bond; -$L_S$'-N($R_B$)C(O)-$L_S$-; -$L_S$'-C(O)N($R_B$)-$L_S$-; or $C_1$-$C_6$alkylene, $C_2$-$C_6$alkenylene, $C_2$-$C_6$alkynylene, $C_3$-$C_{10}$carbocycle or 3- to 10-membered heterocycle, each of which is independently optionally substituted at each occurrence with one or more substituents selected from halogen, $R_T$, —O—$R_S$, —S—$R_S$, —N($R_S$$R_S$'), —OC(O)$R_S$, —C(O)O$R_S$, nitro, oxo, phosphonoxy, phosphono, thioxo, formyl or cyano, wherein $L_S$ and $L_S$' are as defined above.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S$$R_S$'), -$L_A$-S(O)$R_S$, -$L_A$-SO$_2$$R_S$, -$L_A$-C(O)N($R_S$$R_S$'), -$L_A$-N($R_S$)C(O)$R_S$', -$L_A$-N($R_S$)C(O)N($R_S$'$R_S$''), -$L_A$-N($R_S$)SO$_2$$R_S$'-$L_A$-SO$_2$N($R_S$$R_S$'), -$L_A$-N($R_S$)SO$_2$N($R_S$'$R_S$''), -$L_A$-N($R_S$)S(O)N($R_S$'$R_S$''), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S$$R_S$'), -$L_A$-N($R_S$)S(O)—$R_S$', -$L_A$-S(O)N($R_S$$R_S$') or -$L_A$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A, B, and D are each independently phenyl, and are each independently optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_B$)S(O)$_2$-$L_S''$-$R_D'$.

In another embodiment of this aspect, A is

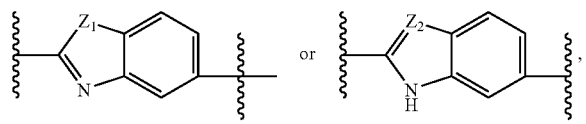

and is optionally substituted with one or more $R_A$; B is

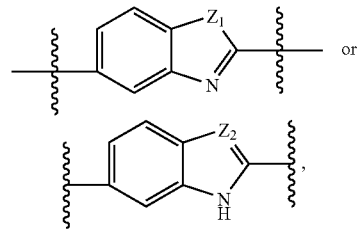

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_B$)S(O)$_2$-$L_S''$-$R_D'$. -T-$R_D'$ can also be independently selected at each occurrence from —C(O)-$L_Y'$-N($R_B$)C(O)-$L_S''$-$R_D'$ or —C(O)-$L_Y'$-N($R_B$)C(O)O-$L_S''$-$R_D'$, wherein $L_Y'$ is $C_1$-$C_6$alkylene (e.g., —CH$_2$—) and optionally substituted with one or more substituents selected from halogen, $R_T$, —O—$R_S$, —S—$R_8$, —N($R_S R_S'$), —OC(O)$R_S$, —C(O)O$R_S$, nitro, phosphonoxy, phosphono, oxo, thioxo, formyl or cyano, and $L_S''$ preferably is bond. -T-$R_D'$ can also be, without limitation, selected from —C(O)-$L_Y'$-$L_S''$-$R_D'$, —C(O)-$L_Y'$-O-$L_S''$-$R_D'$, —C(O)-$L_Y'$-N($R_B$)-$L_S''$-$R_D'$, or —C(O)-$L_Y'$-N($R_B$)S(O)$_2$-$L_S''$-$R_D'$.

In yet another embodiment of this aspect, A is phenyl,

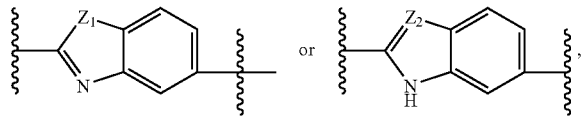

and is optionally substituted with one or more $R_A$; B is phenyl,

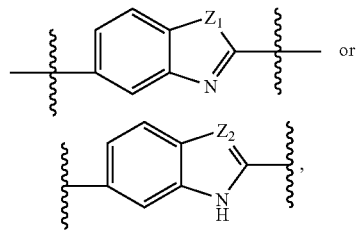

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_D$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_D$)-$L_e''$-$R_D'$, or —C(O)-$L_S'$-N($R_B$)S(O)$_2$-$L_S''$-$R_D'$.

In still another embodiment of this aspect, A is

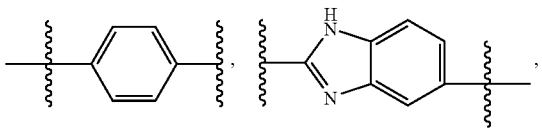

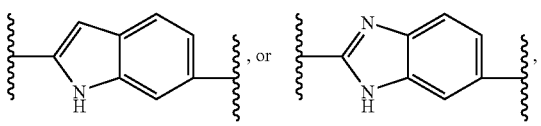

or and is optionally substituted with one or more $R_A$; and B is

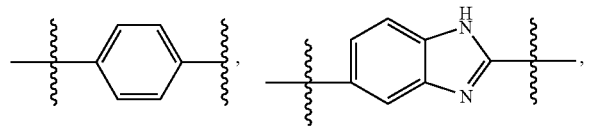

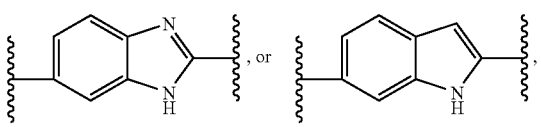

and is optionally substituted with one or more $R_A$; and D is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_B$)S(O)$_2$-$L_S''$-$R_D'$.

In yet another aspect, the present invention further features compounds of Formula $I_C$ and pharmaceutically acceptable salts thereof.

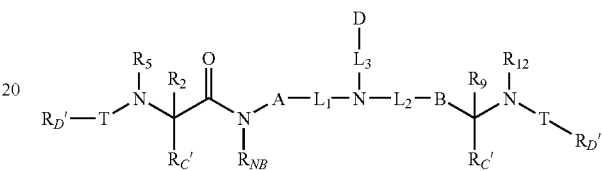

$I_C$ wherein:
$R_{NB}$ is $R_B$;
$R_C'$ is each independently selected from $R_C$;
$R_D'$ is each independently selected from $R_D$;
$R_2$ and $R_5$, taken together with the atoms to which they are attached, form a 3- to 8-membered heterocyclic ring which is optionally substituted with one or more $R_A$;
$R_9$ and $R_{12}$, taken together with the atoms to which they are attached, form a 3- to 8-membered heterocyclic ring which is optionally substituted with one or more $R_A$;
A, B, D, $L_1$, $L_2$, $L_3$, T, $R_A$, $R_B$, $R_C$, and $R_D$ are as described above in Formula I.

In this aspect, A and B preferably are independently selected from $C_5$-$C_6$carbocycle, 5- to 6-membered heterocycle, or 8- to 10-membered bicycles such as

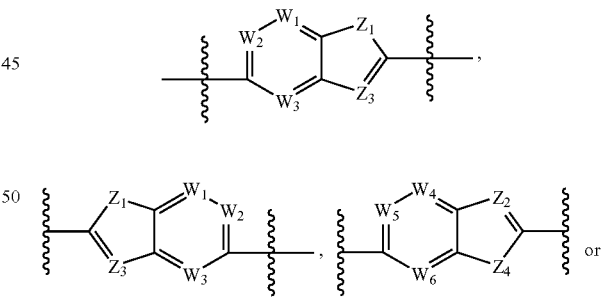

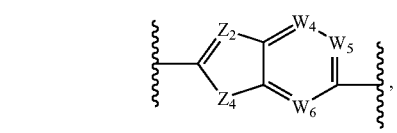

where $Z_1$ is independently selected at each occurrence from O, S, NH or CH$_2$, $Z_2$ is independently selected at each occurrence from N or CH, $Z_3$ is independently selected at each occurrence from N or CH, $Z_4$ is independently selected at each occurrence from O, S, NH or CH$_2$, and W$_1$, W$_2$, W$_3$, W$_4$, W$_5$ and W$_6$ are each independently selected at each occurrence from CH or N. A and B are each independently optionally substituted with one or more R$_A$.

More preferably, A is selected from C$_5$-C$_6$carbocycle, 5- to 6-membered heterocycle,

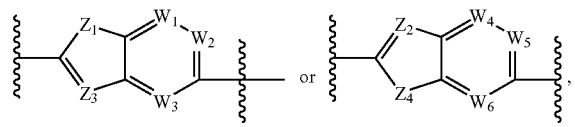

and is optionally substituted with one or more R$_A$; B is selected from C$_5$-C$_6$carbocycle, 5- to 6-membered heterocycle,

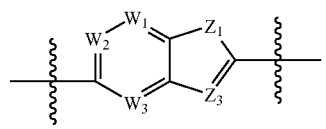

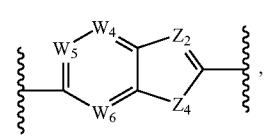

and is optionally substituted with one or more R$_A$, where Z$_1$, Z$_2$, Z$_3$, Z$_4$, W$_1$, W$_2$, W$_3$, W$_4$, W$_5$, W$_6$ are as defined above. Preferably, Z$_3$ is N and Z$_4$ is NH. For instance, A can be selected from phenyl (e.g., 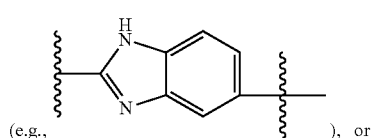),

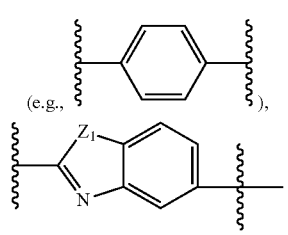

(e.g., 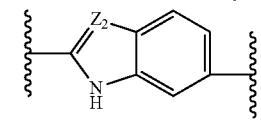), or

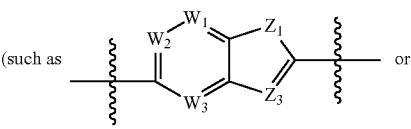

(e.g., 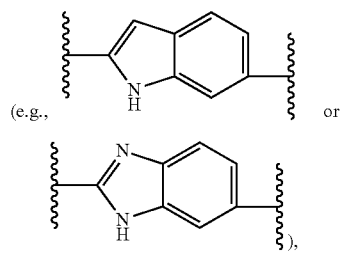 or

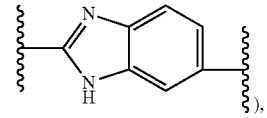), and is optionally substituted with one or more R$_A$; and B can be selected from phenyl (e.g., 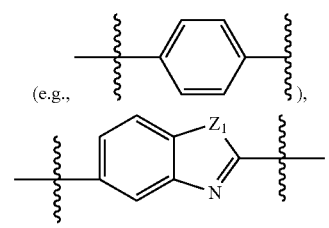),

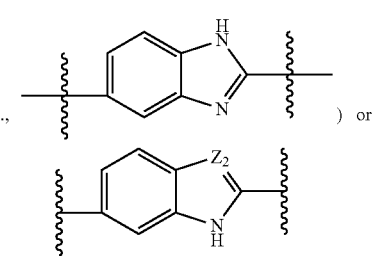

(e.g., 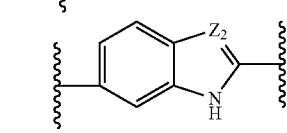) or

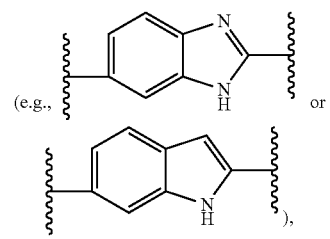

(e.g., 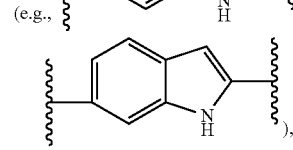 or

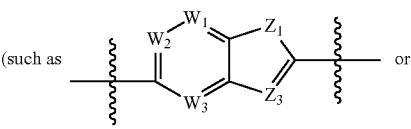), and is optionally substituted with one or more R$_A$.

Highly preferably, A is C$_5$-C$_6$carbocycle or 5- to 6-membered heterocycle, and is optionally substituted with one or more R$_A$; and B preferably is 8- to 10-membered bicycle (such as 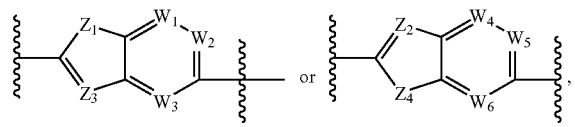 or

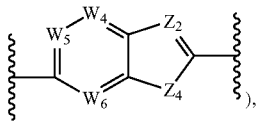

and is optionally substituted with one or more $R_A$. $Z_1$ is O, S, NH or $CH_2$; $Z_2$ is N or CH; $Z_3$ is N or CH; $Z_4$ is O, S, NH or $CH_2$; and $W_1$, $W_2$, $W_3$, $W_4$, $W_5$ and $W_6$ are each independently selected from CH or N.

More highly preferably, A is phenyl

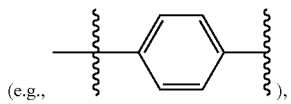

(e.g., ), and is optionally substituted with one or more $R_A$; and B is

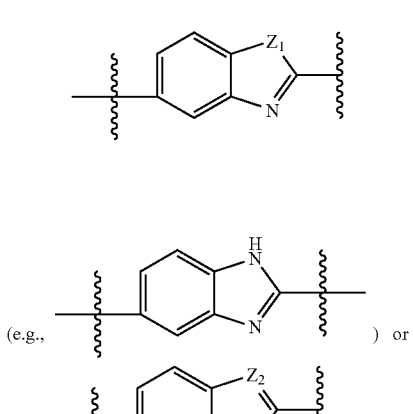

and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, B can be

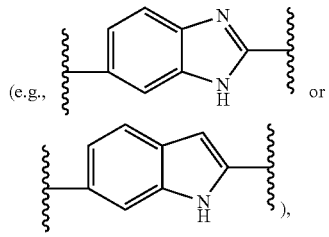

and is optionally substituted with one or more $R_A$.

Also preferably, A is $C_5$-$C_6$carbocycle (e.g., phenyl) or 5- to 6-membered heterocycle, and B is

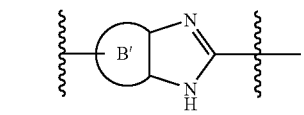

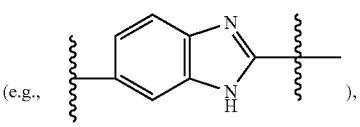

B' is selected from $C_5$-$C_6$carbocycle or 5- to 6-membered heterocycle, and A and B are independently optionally substituted with one or more $R_A$.

D preferably is selected from $C_5$-$C_6$carbocycle, 5- to 6-membered heterocycle, or 8- to 10-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, thioxo, formyl or cyano. More preferably, D is $C_5$-$C_6$carbocycle, 5- to 6-membered heterocycle, or 6- to 10-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

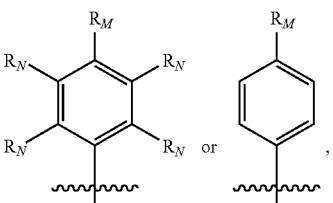

wherein $R_M$ is as defined above, and each $R_N$ is independently selected from $R_D$ and preferably is hydrogen.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

$L_1$ and $L_2$ are preferably independently $C_1$-$C_6$alkylene, and $L_3$ is preferably selected from a bond, $C_1$-$C_6$alkylene, or —C(O)—. $L_1$, $L_2$, and $L_1$ are each independently optionally substituted with one or more substituents selected from halogen, $R_T$, —O—$R_S$, —S—$R_S$, —N($R_SR_S$'), —OC(O)$R_S$, —C(O)O$R_S$, nitro, oxo, phosphonoxy, phosphono, thioxo, formyl, or cyano. More preferably, $L_1$ and $L_2$ are —(CH$_2$)—, and are each independently optionally substituted with one or more substituents selected from halogen, $R_T$, —O—$R_S$, —S—$R_S$, —N($R_SR_S$'), —OC(O)$R_S$, —C(O)O$R_S$, nitro, oxo, phosphonoxy, phosphono, thioxo, formyl or cyano; and $L_3$ is a bond or —C(O)—.

$R_2$ and $R_5$, taken together with the atoms to which they are attached, preferably form a 5- to 6-membered heterocyclic ring

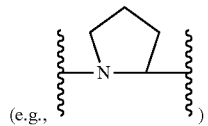 [SMILES: *C1CCCN1*]

(e.g., )

or 6- to 8-membered bicycle

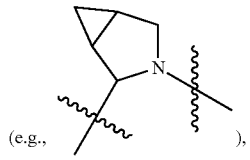 [SMILES: *C1C2CC2CN1*]

(e.g., ), which is optionally substituted with one or more $R_A$.

$R_9$ and $R_{12}$, taken together with the atoms to which they are attached, preferably form a 5- to 6-membered heterocyclic ring

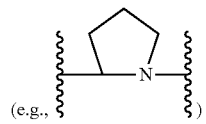 [SMILES: *C1CCCN1*]

(e.g., )

or 6- to 8-membered bicycle

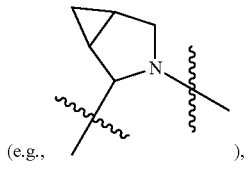

(e.g., ), which is optionally substituted with one or more $R_A$.

-T-$R_D$' can be, without limitation, independently selected at each occurrence from —C(O)-$L_S$'-$R_D$', —C(O)O-$L_S$'-$R_D$', —C(O)-$L_S$'-N($R_B$)C(O)-$L_S$"-$R_D$', —C(O)-$L_S$'-N($R_B$)C(O)O-$L_S$"-$R_D$', —N($R_B$)C(O)-$L_S$'-N($R_B$)C(O)-$L_S$"-$R_D$', —N($R_B$)C(O)-$L_S$'-N($R_B$)C(O)O-$L_S$"-$R_D$', or —N($R_B$)C(O)-$L_S$'-N($R_B$)-$L_S$"-$R_D$'. Preferably, -T-$R_D$' is independently selected at each occurrence from —C(O)-$L_S$'-M'-$L_S$"-$R_D$' or —N($R_B$)C(O)-$L_S$'-M'-$L_S$"-$R_D$'. More preferably, -T-$R_D$' is independently selected at each occurrence from —C(O)-$L_S$'-N($R_B$)C(O)-$L_S$"-$R_D$' or —C(O)-$L_S$'-N($R_B$)C(O)O-$L_S$"-$R_D$'.

-T-$R_D$' can also be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or —N($R_B$)C(O)-$L_Y$'-N($R_B$)-$L_S$"-$R_D$', wherein $L_Y$' is each independently $L_S$' and, preferably, is each independently $C_1$-$C_6$alkylene (e.g., —CH$_2$—) and optionally substituted with one or more substituents selected from halogen, $R_T$, —O—$R_S$, —S—$R_S$, —N($R_SR_S$'), —OC(O)$R_S$, —C(O)O$R_S$, nitro, phosphonoxy, phosphono, oxo, thioxo, formyl or cyano. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'—N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from halogen, $R_T$, —O—$R_S$, —S—$R_S$, —N($R_SR_S$'), —OC(O)$R_S$, —C(O)O$R_S$, nitro, phosphonoxy, phosphono, oxo, thioxo, formyl or cyano.

$R_{NB}$ and $R_C$' are preferably hydrogen, and $R_D$' preferably is independently selected at each occurrence from $L_A$, or 5- or 6-membered carbocycle or heterocycle which is optionally substituted with one or more halogen, $R_T$, —O—$R_B$, —S—$R_B$, —N($R_BR_B$'), —OC(O)$R_B$, —C(O)O$R_B$, nitro, phosphonoxy, phosphono, oxo, thioxo, formyl or cyano. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

For each compound of Formula $I_C$, $L_K$ can also be independently selected at each occurrence from a bond; -$L_S$'-N $(R_B)C(O)-L_S-$; $-L_S'-C(O)N(R_B)-L_S-$; or $C_1-C_6$alkylene, $C_2-C_6$alkenylene, $C_2-C_6$alkynylene, $C_3-C_{10}$carbocycle or 3- to 10-membered heterocycle, each of which is independently optionally substituted at each occurrence with one or more substituents selected from halogen, $R_T$, $-O-R_S$, $-S-R_S$, $-N(R_SR_S')$, $-OC(O)R_S$, $-C(O)OR_S$, nitro, oxo, phosphonoxy, phosphono, thioxo, formyl or cyano, wherein $L_S$ and $L_S'$ are as defined above.

$R_A$ preferably is halogen, hydroxy, mercapto, amino, carboxy, nitro, oxo, phosphonoxy, phosphono, thioxo, cyano; or $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3-C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl; or $-L_A-O-R_S$, $-L_A-S-R_S$, $-L_A-C(O)R_S$, $-L_A-OC(O)R_S$, $-L_A-C(O)OR_S$, $-L_A-N(R_SR_S')$, $-L_A-S(O)R_S$, $L_A-SO_2R_S$, $-L_A-C(O)N(R_SR_S')$, $-L_A-N(R_S)C(O)R_S'$, $-L_A-N(R_S)C(O)N(R_S'R_S'')$, $-L_A-N(R_S)SO_2R_S'$, $-L_A-SO_2N(R_SR_S')$, $-L_A-N(R_S)SO_2N(R_S'R_S'')$, $-L_A-N(R_S)S(O)N(R_S'R_S'')$, $-L_A-OS(O)-R_S$, $-L_A-OS(O)_2-R_S$, $-L_A-S(O)_2OR_S$, $-L_A-S(O)ON$, $-L_A-OC(O)OR_S$, $-L_A-N(R_S)C(O)OR_S'$, $-LA-OC(O)N(R_SR_S')$, $-L_A-N(R_S)S(O)-R_S'$, $-L_A-S(O)N(R_SR_S')$ or $-L_A-C(O)N(R_S)C(O)-R_S'$, wherein $L_A$ is bond, $C_1-C_6$alkylene, $C_2-C_6$alkenylene or $C_2-C_6$alkynylene.

More preferably, $R_A$ is halogen, hydroxy, mercapto, amino, carboxy, nitro, oxo, phosphonoxy, phosphono, thioxo, cyano; or $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3-C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl.

Highly preferably, $R_A$ is halogen, hydroxy, mercapto, amino, carboxy, nitro, oxo, phosphonoxy, phosphono, thioxo, cyano; or $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1-C_6$alkylene, $C_2-C_6$alkenylene or $C_2-C_6$alkynylene.

A and B can be the same or different. Likewise, $L_1$ and $L_2$ can be the same or different.

In one embodiment of this aspect, A, B, and D are each independently phenyl, and are each independently optionally substituted with one or more $R_A$. $L_1$ and $L_2$ are each independently $C_1-C_6$alkylene, $L_3$ is a bond, $C_1-C_6$alkylene or $-C(O)-$, and $L_1$, $L_2$, and $L_3$ are each independently optionally substituted with one or more substituents selected from halogen, $R_T$, $-O-R_S$, $-S-R_S$, $-N(R_SR_S')$, $-OC(O)R_S$, $-C(O)OR_S$, nitro, oxo, phosphonoxy, phosphono, thioxo, formyl, or cyano. Preferably, $L_1$ and $L_2$ are $-(CH_2)-$, and are each independently optionally substituted with one or more substituents selected from halogen, $R_T$, $-O-R_S$, $-S-R_S$, $-N(R_SR_S')$, $-OC(O)R_S$, $-C(O)OR_S$, nitro, oxo, phosphonoxy, phosphono, thioxo, formyl or cyano; and $L_3$ is a bond or $-C(O)-$. $-T-R_D'$ is preferably independently selected at each occurrence from $-C(O)-L_S'-N(R_B)C(O)-L_S''-R_D'$ or $-C(O)-L_S'-N(R_B)C(O)O-L_S''-R_D'$, wherein $L_S'$ preferably is $C_1-C_6$alkylene (e.g., $-CH_2-$) and is optionally substituted with one or more substituents selected from halogen, $R_T$, $-O-R_S$, $-S-R_S$, $-N(R_SR_S')$, $-OC(O)R_S$, $-C(O)OR_S$, nitro, phosphonoxy, phosphono, oxo, thioxo, formyl or cyano. $-T-R_D'$ can also be, without limitation, selected from $-C(O)-L_S'-L_S''-R_D'$, $-C(O)-L_S'-O-L_S''-R_D'$, $-C(O)-L_S'-N(R_B)-L_S''-R_D'$, or $-C(O)-L_S'-N(R_B)S(O)_2-L_S''-R_D'$.

In another embodiment of this aspect, A is

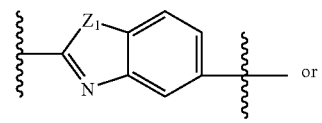

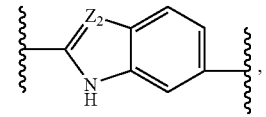

and is optionally substituted with one or more $R_A$; B is

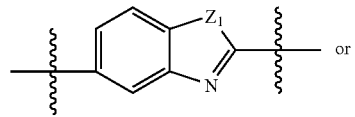

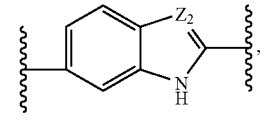

and is optionally substituted with one or more $R_A$; and D is $C_5-C_6$carbocycle or 5- to 6-membered heterocycle (e.g., phenyl), and is optionally substituted with one or more $R_A$. $Z_1$ is independently selected at each occurrence from O, S, NH or $CH_2$; and $Z_2$ is independently selected at each occurrence from N or CH. $L_1$ and $L_2$ are each independently $C_1-C_6$alkylene, $L_3$ is a bond, $C_1-C_6$alkylene or $-C(O)-$, and $L_1$, $L_2$, and $L_3$ are each independently optionally substituted with one or more substituents selected from halogen, $R_T$, $-O-R_S$, $-S-R_S$, $-N(R_SR_S')$, $-OC(O)R_S$, $-C(O)OR_S$, nitro, oxo, phosphonoxy, phosphono, thioxo, formyl, or cyano. Preferably, $L_1$ and $L_2$ are $-(CH_2)-$, and are each independently optionally substituted with one or more substituents selected from halogen, $R_T$, —S—$R_S$, —N($R_SR_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_SR_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_D$)S(O)$_2$-$L_S''$-$R_D'$.

In yet another embodiment of this aspect, A is phenyl,

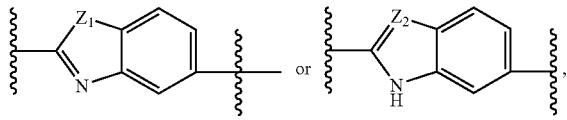

and is optionally substituted with one or more $R_A$; B is phenyl,

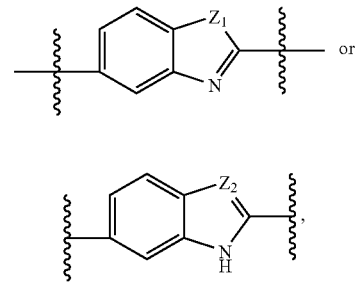

and is optionally substituted with one or more $R_A$; and D is $C_5$-$C_6$carbocycle or 5- to 6-membered heterocycle (e.g., phenyl), and is optionally substituted with one or more $R_A$. $Z_1$ is independently selected at each occurrence from O, S, NH or CH$_2$; and $Z_2$ is independently selected at each occurrence from N or CH. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_SR_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_SR_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_D$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_SR_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_D$)-$L_S''$-$R_D'$, or —C(O)-$L_S'$-N($R_B$)S(O)$_2$-$L_S''$-$R_D'$.

In still another embodiment of this aspect, A is

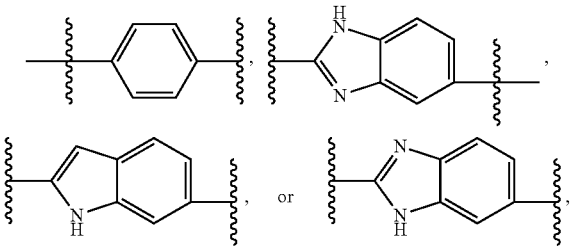

and is optionally substituted with one or more $R_A$; and B is

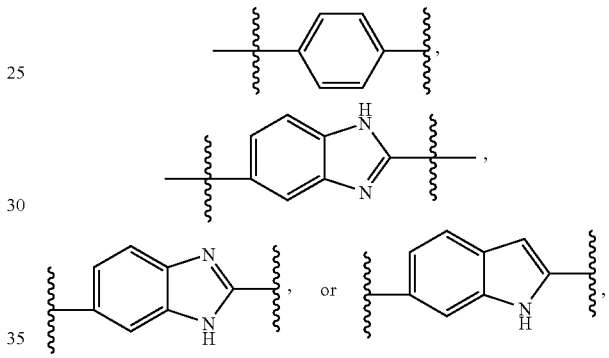

and is optionally substituted with one or more $R_A$; and D is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, $L_3$ is a bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_SR_S'$), —OC(O)$R_S$, —C(O)O$R_S$, nitro, oxo, phosphonoxy, phosphono, thioxo, formyl, or cyano. Preferably, $L_1$ and $L_2$ are —(CH$_2$)—, and are each independently optionally substituted with one or more substituents selected from halogen, $R_T$, —O—$R_S$, —S—$R_S$, —N($R_SR_S'$), —OC(O)$R_S$, —C(O)O$R_S$, nitro, oxo, phosphonoxy, phosphono, thioxo, formyl or cyano; and $L_3$ is a bond or —C(O)—. -T-$R_D'$ is preferably independently selected at each occurrence from —C(O)-$L_S'$-N($R_B$)C(O)-$L_S''$-$R_D'$ or —C(O)-$L_S'$-N($R_B$)C(O)O-$L_S''$-$R_D'$, wherein $L_S'$ preferably is $C_1$-$C_6$alkylene (e.g., —CH$_2$—) and is optionally substituted with one or more substituents selected from halogen, $R_T$, —O—$R_S$, —S—$R_S$, —N($R_SR_S'$), —OC(O)$R_S$, —C(O)O$R_S$, nitro, phosphonoxy, phosphono, oxo, thioxo, formyl or cyano. -T-$R_D'$ can also be, without limitation, selected from —C(O)-$L_S'$-$L_S''$-$R_D'$, —C(O)-$L_S'$-O-$L_S''$-$R_D'$, —C(O)-$L_S'$-N($R_B$)-$L_S''$-$R_D'$, or —C(O)-$L_S'$-N($R_S$)S(O)$_2$-$L_S''$-$R_D'$.

In a further embodiment of this aspect, A is phenyl, and is optionally substituted with one or more $R_A$; and B is

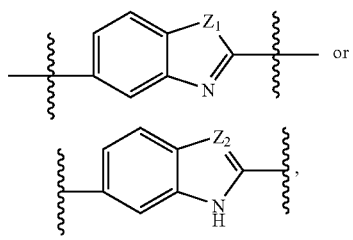

and is optionally substituted with one or more $R_A$, wherein $Z_1$ is O, S, NH or $CH_2$; and $Z_2$ is N or CH. D is $C_5$-$C_6$carbocycle or 5- to 6-membered heterocycle (e.g., phenyl), and is optionally substituted with one or more $R_A$. $L_1$ and $L_2$ are each independently $C_1$-$C_6$alkylene, and $L_3$ is bond, $C_1$-$C_6$alkylene or —C(O)—, and $L_1$, $L_2$, and $L_3$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano. Preferably, $L_1$ and $L_2$ are each independently $C_1$-$C_6$alkylene (e.g., —$CH_2$—), and $L_3$ is bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —$CH_2$—) and optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_D$)S(O)$_2$-$L_S$"-$R_D$'.

The present invention also features the compounds of Formulae I, $I_A$, $I_D$ and $I_C$ as described herein (including each embodiment described herein) or salts thereof, except that D is $C_3$-$C_{10}$carbocycle or 3- to 10-membered heterocycle which is substituted with J and optionally substituted with one or more $R_A$, where J is $C_3$-$C_{10}$carbocycle or 3- to 10-membered heterocycle and is optionally substituted with one or more $R_A$, or J is —$SF_5$. Preferably, D is $C_5$-$C_6$carbocycle, 5- to 6-membered heterocycle or 6- to 10-membered bicycle and is optionally substituted with one or more $R_A$, and J is $C_3$-$C_6$carbocycle or 3- to 6-membered heterocycle and is optionally substituted with one or more $R_A$. More preferably, D is $C_5$-$C_6$carbocycle or 5- to 6-membered heterocycle and is optionally substituted with one or more $R_A$, and J is $C_3$-$C_6$carbocycle or 3- to 6-membered heterocycle and is optionally substituted with one or more $R_A$. Highly preferably, D is phenyl substituted with J and optionally substituted with one or more $R_A$, where J is $C_3$-$C_6$carbocycle or 3- to 6-membered heterocycle and is optionally substituted with one or more $R_A$. Preferred $R_A$s are as described above. In one embodiment, D is

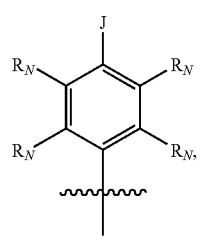

wherein each $R_N$ is independently selected from $R_D$ and preferably is hydrogen, and J is as defined above and preferably is $C_3$-$C_6$carbocycle or 3- to 6-membered heterocycle optionally substituted with one or more $R_A$. In another embodiment, D is

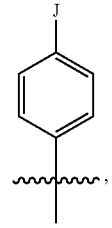

and J is $C_3$-$C_6$carbocycle or 3- to 6-membered heterocycle and is optionally substituted with one or more $R_A$.

The present invention also features the compounds of Formulae I, $I_A$, $I_B$ and $I_C$ as described herein (including each embodiment described herein) or salts thereof, except that:
  $R_1$ and $R_2$ are each independently $R_C$, and $R_5$ is $R_B$; or $R_1$ is $R_C$, and $R_2$ and $R_5$, taken together with the atoms to which they are attached, form a 3- to 10-membered heterocyclic ring which is optionally substituted with one or more $R_A$; and
  $R_3$, $R_4$, $R_6$, and $R_7$ are each independently $R_C$; or $R_3$ and $R_6$ are each independently $R_C$, and $R_4$ and $R_7$, taken together with the atoms to which they are attached, form a 3- to 10-membered carbocyclic or heterocyclic ring which is optionally substituted with one or more $R_A$;

The compounds of the present invention can be used in the form of salts. Depending on the particular compound, a salt of a compound may be advantageous due to one or more of the salt's physical properties, such as enhanced pharmaceutical stability under certain conditions or desired solubility in water or oil. In some instances, a salt of a compound may be useful for the isolation or purification of the compound.

Where a salt is intended to be administered to a patient, the salt preferably is pharmaceutically acceptable. Pharmaceutically acceptable salts include, but are not limited to, acid addition salts, base addition salts, and alkali metal salts.

Pharmaceutically acceptable acid addition salts may be prepared from inorganic or organic acids. Examples of suitable inorganic acids include, but are not limited to, hydrochloric, hydrobromic, hydroionic, nitric, carbonic, sulfuric, and phosphoric acid. Examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts include, but are not limited to, metallic salts and organic salts. Non-limiting examples of suitable metallic salts include alkali metal (group Ia) salts, alkaline earth metal (group IIa) salts, and other pharmaceutically acceptable metal salts. Such salts may be made, without limitation, from aluminum, calcium, lithium, magnesium, potassium, sodium, or zinc. Non-limiting examples of suitable organic salts can be made from tertiary amines and quaternary amine, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as alkyl halides (e.g., methyl, ethyl, propyl, butyl, decyl, lauryl, myristyl, and stearyl chlorides/bromides/iodides), dialkyl sulfates (e.g., dimethyl, diethyl, dibuytl, and diamyl sulfates), aralkyl halides (e.g., benzyl and phenethyl bromides), and others.

The compounds or salts of the present invention may exist in the form of solvates, such as with water (i.e., hydrates), or with organic solvents (e.g., with methanol, ethanol or acetonitrile to form, respectively, methanolate, ethanolate or acetonitrilate).

The compounds or salts of the present invention may also be used in the form of prodrugs. Some prodrugs are aliphatic or aromatic esters derived from acidic groups on the compounds of the invention. Others are aliphatic or aromatic esters of hydroxyl or amino groups on the compounds of the invention. Phosphate prodrugs of hydroxyl groups are preferred prodrugs.

The compounds of the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer; and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The invention encompasses each conformational isomer of these compounds and mixtures thereof.

Certain compounds of the invention may also exist in zwitterionic form and the invention encompasses each zwitterionic form of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., A, B, D, X, $L_1$, $L_2$, $L_3$, Y, Z, T, $R_A$ or $R_B$). Unless otherwise specified, each variable within such a formula is defined independently of any other variable, and any variable that occurs more than one time in a formula is defined independently at each occurrence. If moieties are described as being "independently" selected from a group, each moiety is selected independently from the other. Each moiety therefore can be identical to or different from the other moiety or moieties.

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "carbocyclylalkyl" contains two components: carbocyclyl and alkyl. Thus, for example, $C_3$-$C_6$carbocyclyl$C_1$-$C_6$alkyl refers to a $C_3$-$C_6$carbocyclyl appended to the parent molecular moiety through a $C_1$-$C_6$alkyl group.

Unless otherwise specified, when a linking element links two other elements in a depicted chemical structure, the leftmost-described component of the linking element is bound to the left element in the depicted structure, and the rightmost-described component of the linking element is bound to the right element in the depicted structure. To illustrate, if the chemical structure is -$L_S$-M-$L_S$'- and M is —N($R_B$)S(O)—, then the chemical structure is -$L_S$-N($R_B$)S(O)-$L_S$'-.

If a linking element in a depicted structure is a bond, then the element left to the linking element is joined directly to the element right to the linking element via a covalent bond. For example, if a chemical structure is depicted as -$L_S$-M-$L_S$'- and M is selected as bond, then the chemical structure will be -$L_S$-$L_S$'-. If two or more adjacent linking elements in a depicted structure are bonds, then the element left to these linking elements is joined directly to the element right to these linking elements via a covalent bond. For instance, if a chemical structure is depicted as -$L_S$-M-$L_S$'-M'-$L_S$"-, and M and $L_S$' are selected as bonds, then the chemical structure will be -$L_S$-M'-$L_S$"-. Likewise, if a chemical structure is depicted as -$L_S$-M-$L_S$'-M'-$L_S$"-, and M, $L_S$' and M' are bonds, then the chemical structure will be -$L_S$-$L_S$"-.

When a chemical formula is used to describe a moiety, the dash(s) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. To illustrate, tetrazolyl (which has only one substitutable position) will be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkenylene" refers to a divalent unsaturated hydrocarbyl chain which may be linear or branched and which has at least one carbon-carbon double bond. Non-limiting examples of alkenylene groups include —C(H)=C(H)—, —C(H)=C(H)—$CH_2$—, —C(H)C(H)—$CH_2$—$CH_2$—, —$CH_2$—C(H)=C(H)—$CH_2$—, —C(H)=C(H)—CH($CH_3$)—, and —$CH_2$—C(H)=C(H)—CH($CH_2CH_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —$CH_2$—, —$CH_2CH_2$—, —$CH_2CH_2CH_2$—, —$CH_2CH_2CH_2CH_2$—, and —$CH_2$CH($CH_3$)$CH_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynylene" refers to a divalent unsaturated hydrocarbon group which may be linear or branched and which has at least one carbon-carbon triple bonds. Representative alkynylene groups include, by way of example, —C≡C—, —C≡C—$CH_2$—, —C≡C—$CH_2$—$CH_2$—, —$CH_2$—C≡C—$CH_2$—, —C≡C—($CH_3$)—, and —$CH_2$—C≡C—CH($CH_2CH_3$)—.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom. Where a carbocycle group is a divalent moiety linking two other elements in a depicted chemical structure (such as A in Formula I), the carbocycle group can be attached to the two other elements through any two substitutable ring atoms.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group. Where a heterocycle group is a divalent moiety linking two other elements in a depicted chemical structure (such as A in Formula I), the heterocycle group can be attached to the two other elements through any two substitutable ring atoms.

A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), and tetrahydroisoquinolinyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

═ in a chemical formula refers to a single or double bond.

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS (3$^{rd}$ ed., John Wiley & Sons, NY (1999). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxy carbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Hoc) and benzyloxycarbonyl (Cbz).

The compounds of the present invention can be prepared using a variety of methods. As a non-limiting example, the compounds of the present invention can be prepared by coupling a compound of Formula II to a compound of Formula III as shown in Scheme I, where Q is halo (e.g., bromo, chloro or iodo), and A, B, D, L$_1$, L$_2$, L$_3$, Y and Z are as described above. Amino compound II may be alkylated by reaction with haloalkyl (e.g., halomethyl) compound III in the presence of a base, such as KOH, t-BuOK, sodium amide, sodium hydride, CsOH, Hunig's base, Na$_2$CO$_3$, or NaHCO$_3$, in a suitable organic solvent, such as THF or DMT, or in water (if the base is compatible with aqueous solvent) with or without an added surfactant, such as sodium dodecyl sulfate or tetrabutylammonium bromide. Formation of symmetric products (e.g., Formula I' in Scheme I, where B, Z and L$_2$ in Formula I are identical to A, Y and L$_1$, respectively) may be conducted in a single operation as shown, or the nonsymmetric products shown can be formed by sequential formation of a monoalkylated product V followed by reaction with a second haloalkyl (e.g., halomethyl) compound VI under conditions similar to those described above.

Alternatively, Q in compounds III and VI (e.g., bromo, chloro or iodo) can be replaced with 4-methylbenzesulfonate and reacted with II or V, respectively, under similar conditions. Monoalkylated compound V may also be generated by reaction of amine II with an aldehyde IV to form a Schiff base (imine), which may be reduced to the products V with a hydride reducing agent, such as sodium borohydride or sodium cyanoborohydride (with or without the addition of an acid, such as acetic acid) in a solvent such as ethanol, toluene, THF, or dichloromethane. Alternatively the Schiff based formed from II and IV can be reduced to the products V by hydrogenation in the presence of a suitable catalyst, such as a palladium or platinum catalyst or Raney nickel.

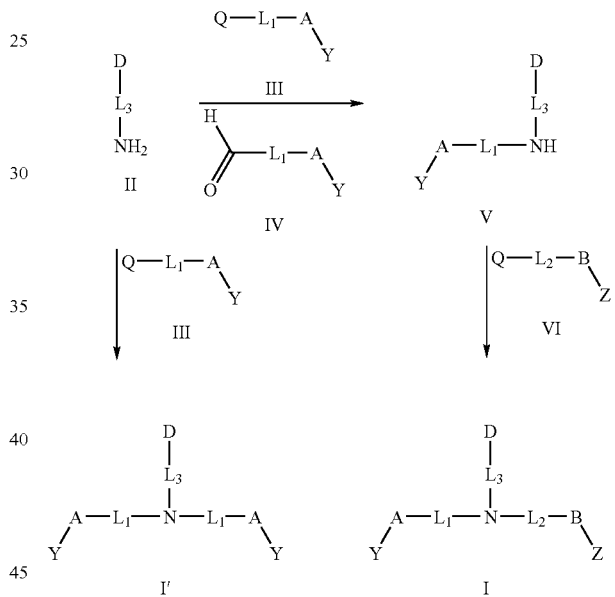

Scheme I

As another non-limiting example, the compounds of the present invention can be prepared by coupling a compound of Formula II to a compound of Formula III as shown in Scheme II, where R is -L$_S$'-M'-L$_S$"-R$_D$, and L$_S$', M', L$_S$" and R$_D$ are as described above. Amino compound II may be alkylated by reaction with 4-nitrobenzyl bromide III in the presence of a base, such as KOH, t-BuOK, sodium amide, sodium hydride, CsOH, Hunig's base, Na$_2$CO$_3$, or NaHCO$_3$, in a suitable organic solvent, such as THF or DMF, or in water (if the base is compatible with aqueous solvent) with or without an added surfactant, such as sodium dodecyl sulfate or tetrabutylammonium bromide. The dinitro compound IV may be reduced to the diamino product V with a hydride reducing agent, such as sodium borohydride (with or without the addition of a transition metal salt, such as BiCl$_3$, SbCl$_3$, NiCl$_2$, Cu$_2$Cl$_2$, or CoCl$_2$) in a solvent such as ethanol or THF. Alternatively, IV can be reduced to the product V by hydrogenation in the presence of a suitable catalyst, such as a palladium or platinum catalyst or Raney nickel. The diamine V may be reacted with a suitably protected proline acid (Boc is shown, although Cbz, Troc, or Fmoc may be substituted) in the presence of a peptide coupling reagent, such as EDAC/HOBT, PyBOP, HATU, or DEBPT, in a solvent such as THF, DMF, dichloromethane, or DMSO, with or without the addition of an amine base such as Hunig's base, pyridine, 2,6-lutidine, or triethylamine, to give VI. Removal of the Boc protecting groups to give VII may be accomplished by treatment with an acid, such as TFA, HCl, or formic acid. Compounds of the present invention may be prepared by coupling of VII with an acid of choice using the standard peptide coupling reagents and conditions described above. Likewise, compounds of Formula $I_A$, as described above, can be similarly prepared.

Cbz, Troc, or Fmoc may be substituted) in the presence of a peptide coupling reagent, such as EDAC/HOBT, PyBOP, HATU, or DEBPT, in a solvent such as THF, DMF, dichloromethane, or DMSO, with or without the addition of an amine base, such as Hunig's base, pyridine, 2,6-lutidine, or triethylamine, to give III as a mixture of the amide products. Heating III in acetic acid (50-100° C.) gives the benzimidazole compound IV. Alternatively, IV may be prepared by reaction of II with an aldehyde, followed by treatment with an oxidant, such as Cu(OAc)$_2$ or MnO$_2$. See Penning et al., BIOORG. MED. CHEM. 16:6965-6975 (2008), which is incorporated herein by reference in its entirety. The ester functionality of IV may be reduced to the alcohol V under the standard conditions, such as treatment with lithium aluminum hydride or DIBAL, in a suitable solvent, such as THF or dichlo-

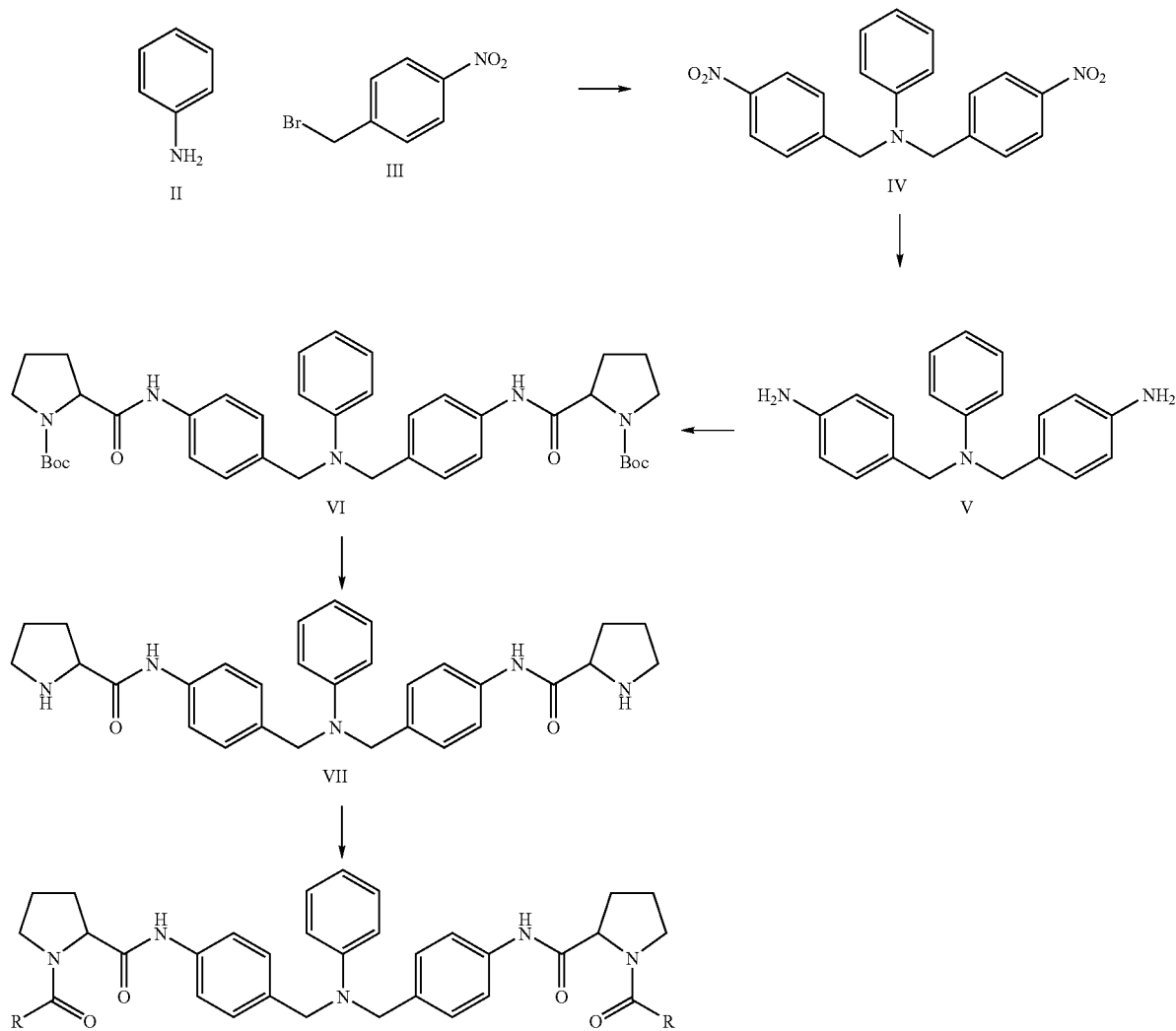

Scheme II

As yet another non-limiting example, the compounds of the present invention can be prepared by the methods shown in Scheme III, where R is -L$_S$'-M'-L$_S$''-R$_D$, and L$_S$', M', L$_S$'' and R$_D$ are as described above. The diamine II may be reacted with a suitably protected proline acid (Hoc is shown, although romethane. Alcohol V may be transformed to the bromomethyl compound VI using established conditions, such as by treatment with CBr$_4$ and triphenylphosphine or by treatment with PBr$_3$. Alternatively, V may be oxidized by a number of methods to the aldehyde VII, such as MO$_2$, PCC, PDC, Swern oxidation, or Dess-Martin periodinane. Compound VII can be used to prepare compound IX by reaction with aniline to form a Schiff base (imine), which may be reduced to IX with a hydride reducing agent, such as sodium borohydride or sodium cyanoborohydride (with or without the addition of an acid, such as acetic acid) in a solvent such as ethanol, toluene, THF, or dichloromethane. Alternatively the Schiff based formed from VII can be reduced to the products IX by hydrogenation in the presence of a suitable catalyst, such as a palladium or platinum catalyst or Raney nickel. Compound VI may be reacted with aniline in the presence of a base, such as KOH, t-BuOK, sodium amide, sodium hydride, CsOH, Hunig's base, $Na_2CO_3$, or $NaHCO_3$, in a suitable organic solvent, such as THF or DMT, or in water (if the base is compatible with aqueous solvent) with or without an added surfactant, such as sodium dodecyl sulfate or tetrabutylammonium bromide, to give symmetric compound VIII. Alternatively, VIII can also be generated by reaction of IX with VI under the alkylation conditions described above. After removal of the Boc protecting groups from VIII (accomplished by treatment with an acid, such as TFA, HCl, or formic acid), the compounds of the present invention may be prepared by coupling of the resulting diamine with an acid of choice using the standard peptide coupling reagents and conditions described above. Compound IX may also be reacted with 4-nitrobenzyl bromide under the alkylation conditions described above to give X. Reduction of the nitro group of X using the conditions described above and coupling with a suitably protected proline acid can provide XI. After removal of the Boc protecting groups from XI (accomplished by treatment with an acid, such as TFA, HCl, or formic acid), the compounds of the present invention may be prepared by coupling of the resulting diamine with an acid of choice using the standard peptide coupling reagents and conditions described above. Likewise, compounds of Formula $I_B$ can be similarly prepared, where A is

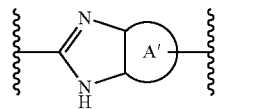

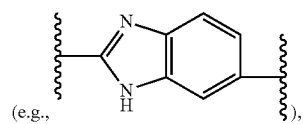

B is

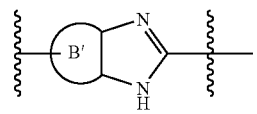

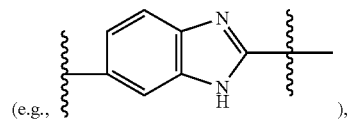 [SMILES: *c1ccc2nc(*)[nH]c2c1]

A' and B' are as described above, and A and B are independently optionally substituted with one or more $R_A$. Similarly, compounds of Formula $I_C$ can be prepared according to Scheme III.

Scheme III

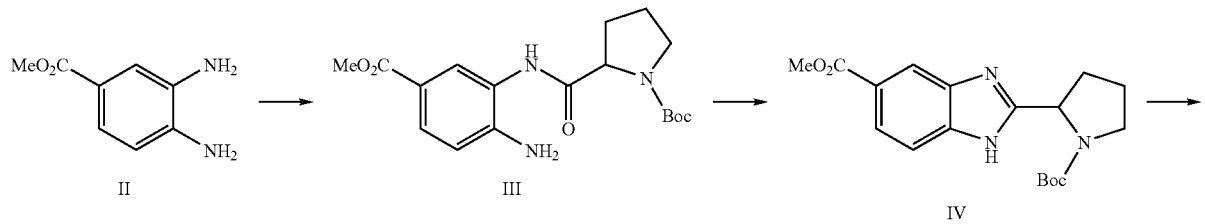

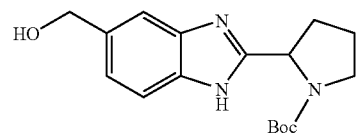

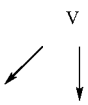

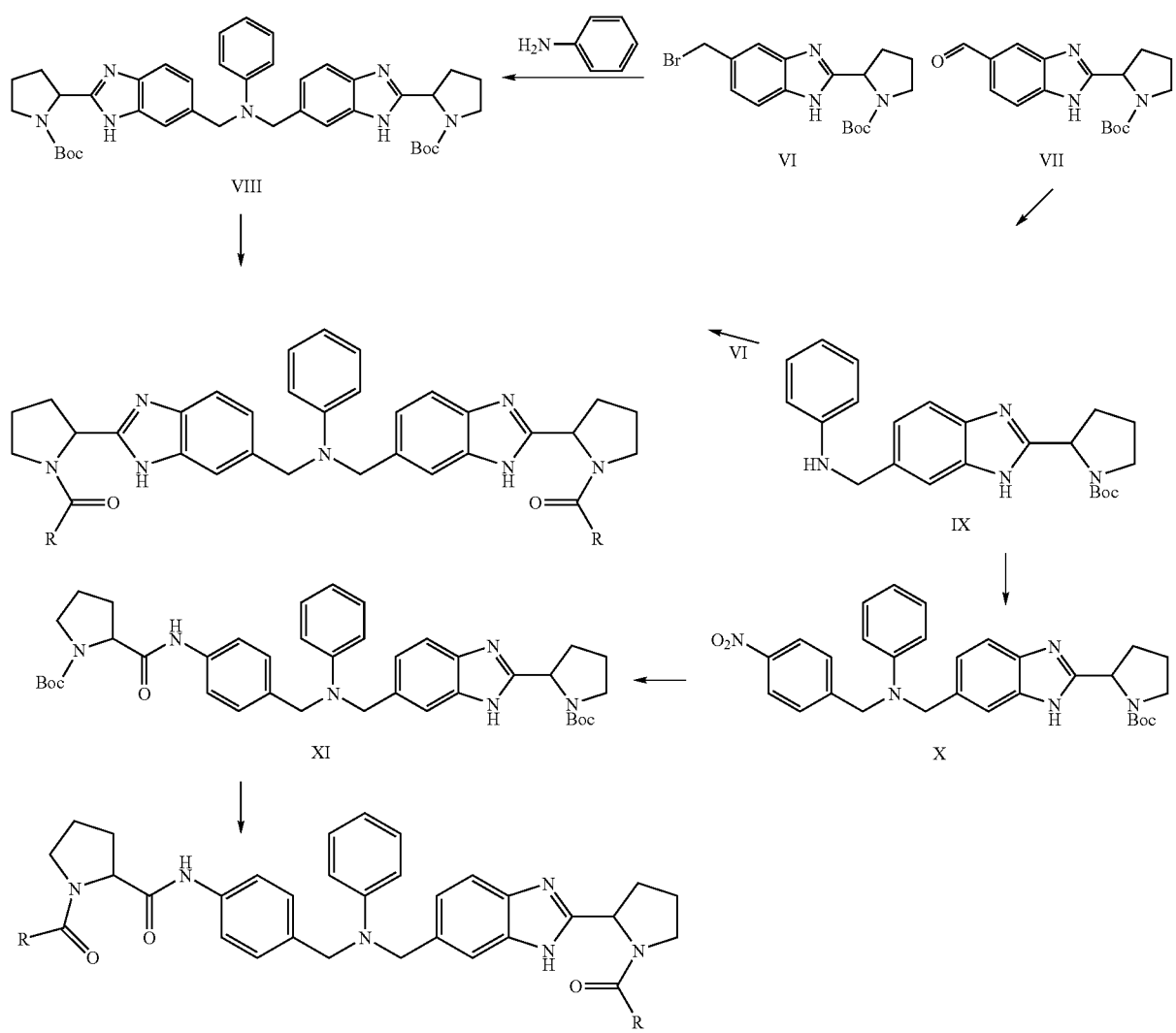

As still another non-limiting example, the compounds of the present invention can be prepared by the methods shown in Scheme IV, where R is -$L_S'$-M'-$F_S''$-$R_D$, and $L_S'$, M', $L_S''$, $R_D$, $R_1$, $R_2$, and $R_5$ are as described above. Compound II may be prepared from 4'-iodoacetophenone using known conditions, such as treatment with $Br_2$. Compound II may be reacted with the salt of an amino acid (prepared from suitably protected amino acid and a base, such as $Cs_2CO_3$, KOH, NaOH, or $Na_2CO_3$, in a solvent such as ethanol or THF) in a solvent such as THF, DMF or DMSO, to provide ester III. The ester III may be treated with an ammonia source, such as $NH_4OAc$, $NH_4Cl$, or ammonia gas, and heated in a solvent such as toluene or xylene with azeotropic removal of water to provide the imidazole IV. See Gordon et al., TET. LETT. 34:1901-1904 (1993), and Moinet et al., BIOORG. MED. CHEM. LETT. 11:991-995 (2001), both of which are incorporated herein by reference in their entireties. The iodide IV may be converted to the ester V by treatment with a palladium catalyst (such as $Pd(PPh_3)_4$ or $Pd(dppf)Cl_2$, or a Pd (II) catalyst such $Pd(OAc)_2$ or $Pd2(dba)_3$ with or without the addition of organophosphorous ligands, such as $PPh_3$ or $P(t-Bu)_3$) and carbon monoxide in the presence of a base, such as triethylamine or Hunig's base, in a solvent such as methanol or ethanol, with or without heating. The ester obtained V may be reduced to the alcohol VI and then oxidized to the aldehyde VII by the methods described above. Compound VII can be used to prepare compound VIII by reaction with aniline to form a Schiff base (imine), which may be reduced to VIII with a hydride reducing agent, such as sodium borohydride or sodium cyanoborohydride (with or without the addition of an acid, such as acetic acid) in a solvent such as ethanol, toluene, THF, or dichloromethane. Alternatively the Schiff based formed from VII can be reduced to the products VIII by hydrogenation in the presence of a suitable catalyst, such as a palladium or platinum catalyst or Raney nickel. Compound VIII may be reacted with 4-nitrobenzyl bromide under the alkylation conditions described above to give IX. Reduction of the nitro group of IX using the conditions described above and coupling with a suitably protected proline acid can provide XI. After removal of the Hoc protecting groups from XI (accomplished by treatment with an acid, such as TFA, HCl, or formic acid), the compounds of the present invention may be prepared by coupling of the resulting diamine with an acid of choice using the standard peptide coupling reagents and conditions described above. Likewise, compounds of Formula $I_C$ can be similarly prepared.

Scheme IV

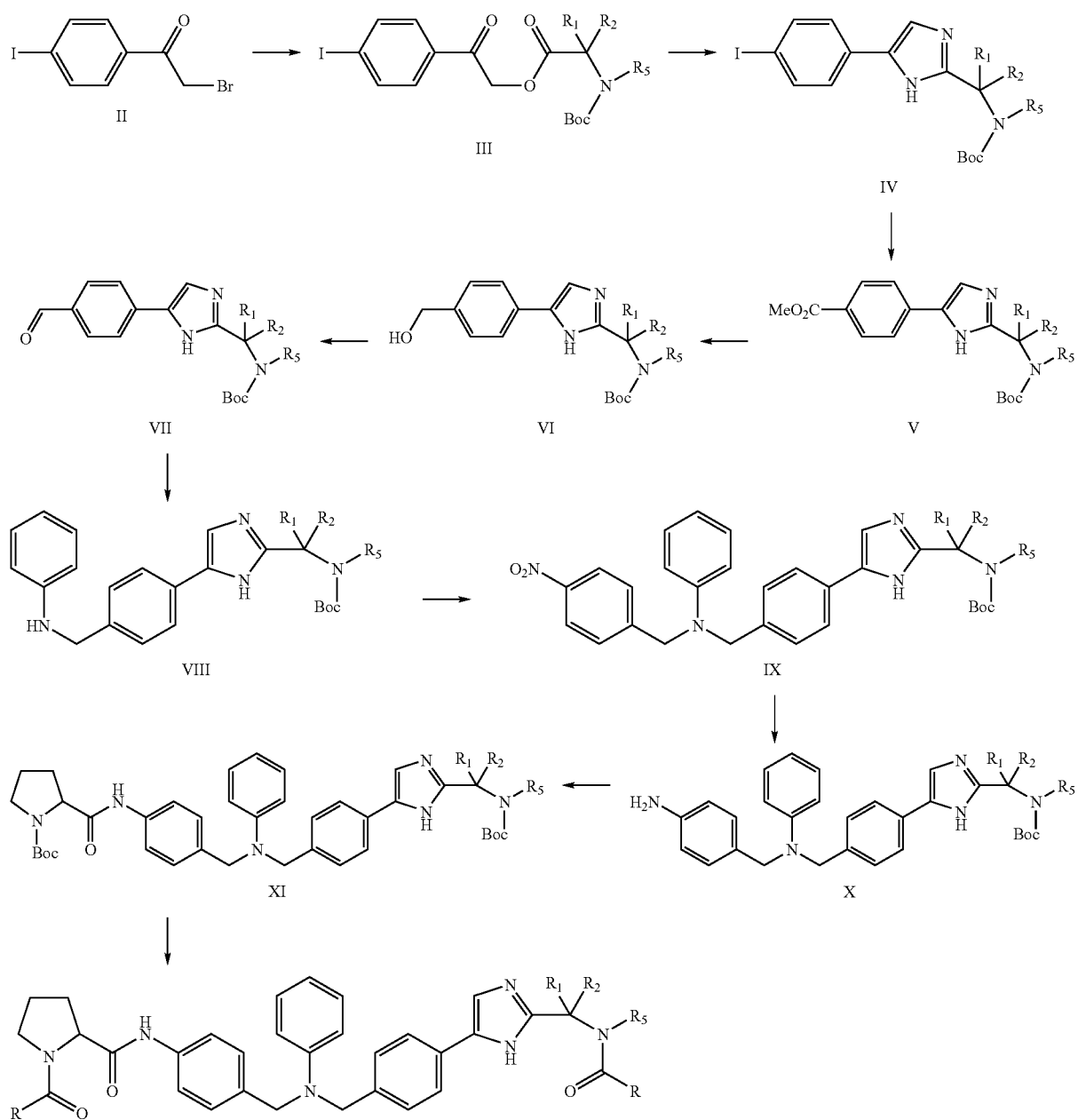

As another non-limiting example, the compounds of the present invention of general Formula I can be prepared as shown in Scheme I'. Coupling a compound of Formula (1) to a compound of Formula (2) as shown in Scheme I', where Q is halo (e.g., bromo, chloro or iodo), and A, B, D, $L_1$, $L_2$, $L_3$, Y and Z are as described above gives compounds of Formula (4). Amino compound (1) may be alkylated by reaction with haloalkyl (e.g., halomethyl) compound (2) in the presence of a base, such as KOH, t-BuOK, sodium amide, sodium hydride, CsOH, Hunig's base, $Na_2CO_3$, or $NaHCO_3$, in a suitable organic solvent, such as THF or DMT, or in water (if the base is compatible with aqueous solvent) with or without an added surfactant, such as sodium dodecyl sulfate or tetrabutylammonium bromide. Compounds of Formula (4) can be reacted with (5), where Q is halo (e.g., bromo, chloro or iodo), using the same conditions as those to react (1) with (2), to give compounds of general Formula I. Where B, Z and $L_2$ in Formula I are identical to A, Y and $L_1$, respectively then symmetric products result. The formation of symmetric products may be conducted in a single operation, or the nonsymmetric products (where any of B, Z, or $L_2$ is different from A, Y, or $L_1$, respectively) can be formed by sequential formation of a monoalkylated product (4) followed by reaction with a second haloalkyl (e.g., halomethyl) compound (5) under conditions similar to those described above. Alternatively, Q in compounds (2) and (5) (e.g., bromo, chloro or iodo) can be replaced with 4-methylbenzesulfonate and reacted with (1) or (4), respectively, under similar conditions. Monoalkylated compound (4) may also be generated by reaction of amine (1) with an aldehyde (3) to form a Schiff base (imine), which may be reduced to the products (4) with a hydride reducing agent, such as sodium borohydride or sodium cyanoborohydride (with or without the addition of an acid, such as acetic acid) in a solvent such as ethanol, toluene, THF, or dichloromethane. Alternatively the Schiff based formed from (1) and (3) can be reduced to the products (4) by hydrogenation in the presence of a suitable catalyst, such as a palladium or platinum catalyst or Raney nickel.

As still another non-limiting example, the compounds of the present invention can be prepared as shown in Scheme II'. Coupling a compound of Formula (6), wherein $R_A$ is as defined above and n is 0, 1, 2, 3, 4, or 5, to a compound of Formula (7) can give compounds of formula (8). For example, amino compound (6) may be alkylated by reaction with 4-nitrobenzyl bromide (7) in the presence of a base, such as KOH, t-BuOK, sodium amide, sodium hydride, CsOH, Hunig's base, $Na_2CO_3$, or $NaHCO_3$, in a suitable organic solvent, such as THF or DMT, or in water (if the base is compatible with aqueous solvent) with or without an added surfactant, such as sodium dodecyl sulfate or tetrabutylammonium bromide. The dinitro compound (8) may be reduced to the diamino product (9) with a hydride reducing agent, such as sodium borohydride (with or without the addition of a transition metal salt, such as $BiCl_3$, $SbCl_3$, $NiCl_2$, $Cu_2Cl_2$, or $CoCl_2$) in a solvent such as ethanol or THF. Alternatively, (8) can be reduced to the product (9) by hydrogenation in the presence of a suitable catalyst, such as a palladium or platinum catalyst or Raney nickel. The diamine (9) may be reacted with a suitably protected proline acid (Boc is shown, although Cbz, Troc, or Fmoc may be substituted) in the presence of a peptide coupling reagent, such as EDAC/HOBT, PyBOP, HATU, or DEBPT, in a solvent such as THF, DMF, dichloromethane, or DMSO, with or without the addition of an amine base such as Hunig's base, pyridine, 2,6-lutidine, or triethylamine, to give (10). Removal of the Boc protecting groups to give (11) may be accomplished by treatment with an acid, such as TFA, HCl, or formic acid. Compounds of the present invention (12), wherein $R_{20}$ is -$L_S$'-M'-$L_S$"-$R_D$, and $L_S$', M', $L_S$" and $R_D$ are as described above, may be prepared by coupling of (11) with an acid of choice using the standard peptide coupling reagents and conditions described above. Likewise, compounds of Formula $I_A$, as described above, can be similarly prepared.

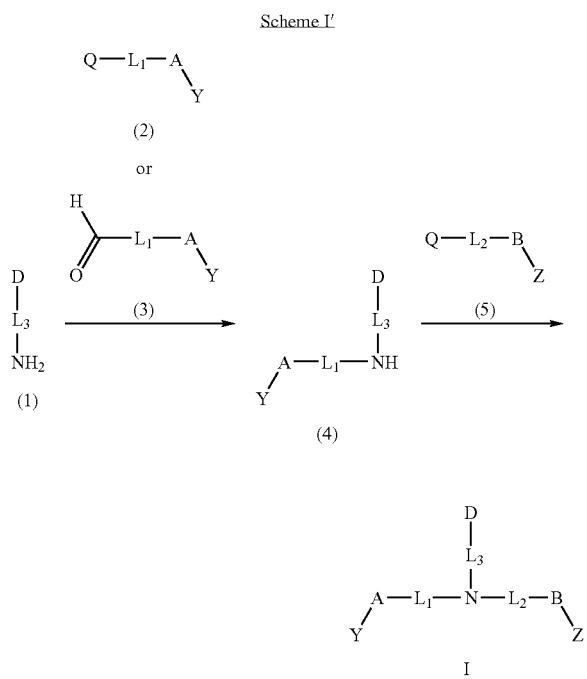

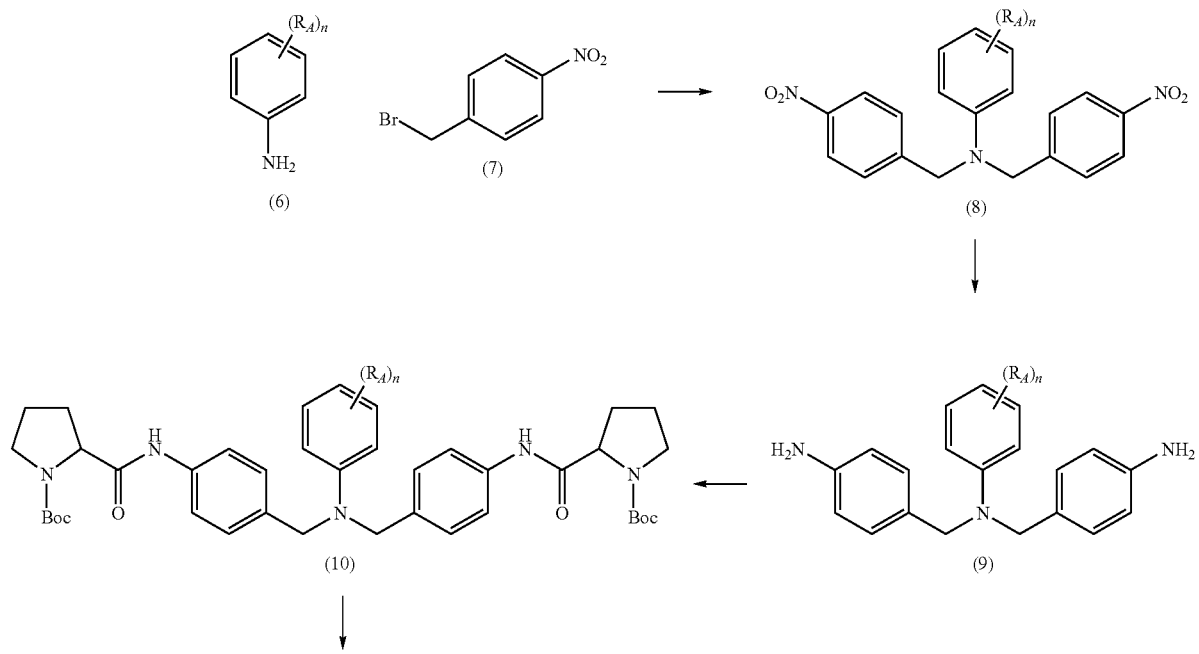

-continued

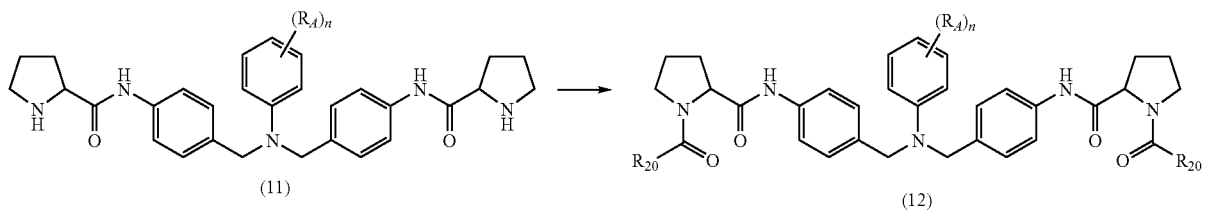

As yet another non-limiting example, the compounds of the present invention (20) and (24) can be prepared by the methods shown in Scheme III', where $R_{20}$ is $-L_S'-M'-L_S''-R_D$, and $L_S'$, M', $L_S''$, $R_D$, and $R_A$ are as described above and n is 0, 1, 2, 3, 4, or 5. The diamine (13) may be reacted with a suitably protected proline acid (Boc is shown, although Cbz, Troc, or Fmoc may be substituted) in the presence of a peptide coupling reagent, such as EDAC/HOBT, PyBOP, HATU, or DEBPT, in a solvent such as THF, DMF, dichloromethane, or DMSO, with or without the addition of an amine base, such as Hunig's base, pyridine, 2,6-lutidine, or triethylamine, to give (14) as a mixture of the amide products. Heating (14) in acetic acid (50-100° C.) gives the benzimidazole compound (15). Alternatively, (15) may be prepared by reaction of (13) with an aldehyde, followed by treatment with an oxidant, such as $Cu(OAc)_2$ or $MnO_2$. See Penning et al., BIOORG. MED. CHEM. 16:6965-6975 (2008), which is incorporated herein by reference in its entirety. The ester functionality of (15) may be reduced to the alcohol (16) under the standard conditions, such as treatment with lithium aluminum hydride or DIBAL, in a suitable solvent, such as THF or dichloromethane. Alcohol (16) may be transformed to the bromomethyl compound (17) using established conditions, such as by treatment with $CBr_4$ and triphenylphosphine or by treatment with $PBr_3$. Alternatively, (16) may be oxidized by a number of methods to the aldehyde (18), such as $MnO_2$, PCC, PDC, Swern oxidation, or Dess-Martin periodinane. Compound (18) can be used to prepare compound (21) by reaction with aniline to form a Schiff base (imine), which may be reduced to (21) with a hydride reducing agent, such as sodium borohydride or sodium cyanoborohydride (with or without the addition of an acid, such as acetic acid) in a solvent such as ethanol, toluene, THF, or dichloromethane. Alternatively the Schiff based formed from (18) can be reduced to the products (21) by hydrogenation in the presence of a suitable catalyst, such as a palladium or platinum catalyst or Raney nickel. Compound (17) may be reacted with (6) in the presence of a base, such as KOH, t-BuOK, sodium amide, sodium hydride, CsOH, Hunig's base, $Na_2CO_3$, or $NaHCO_3$, in a suitable organic solvent, such as THF or DMF, or in water (if the base is compatible with aqueous solvent) with or without an added surfactant, such as sodium dodecyl sulfate or tetrabutylammonium bromide, to give symmetric compound (19). Alternatively, (19) can also be generated by reaction of (21) with (17) under the alkylation conditions described above. After removal of the Boc protecting groups from (19) (accomplished by treatment with an acid, such as TFA, HCl, or formic acid), the compounds of the present invention (20) may be prepared by coupling of the resulting diamine with an acid of choice using the standard peptide coupling reagents and conditions described above. Compound (21) may also be reacted with 4-nitrobenzyl bromide under the alkylation conditions described above to give (22). Reduction of the nitro group of (22) using the conditions described above and coupling with a suitably protected proline acid can provide (23). After removal of the Boc protecting groups from (23) (accomplished by treatment with an acid, such as TFA, HCl, or formic acid), the compounds of the present invention (24) may be prepared by coupling of the resulting diamine with an acid of choice using the standard peptide coupling reagents and conditions described above. Likewise, compounds of Formula $I_B$ can be similarly prepared, where A is

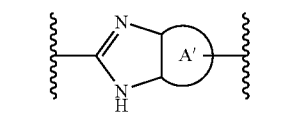

B is (e.g., 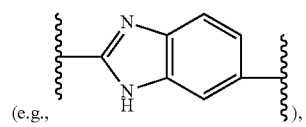),

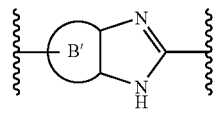

(e.g., 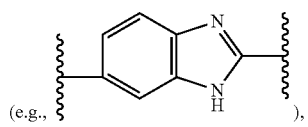),

A' and B' are as described above, and A and B are independently optionally substituted with one or more $R_A$. Similarly, compounds of Formula $I_C$ can be prepared according to Scheme III'.
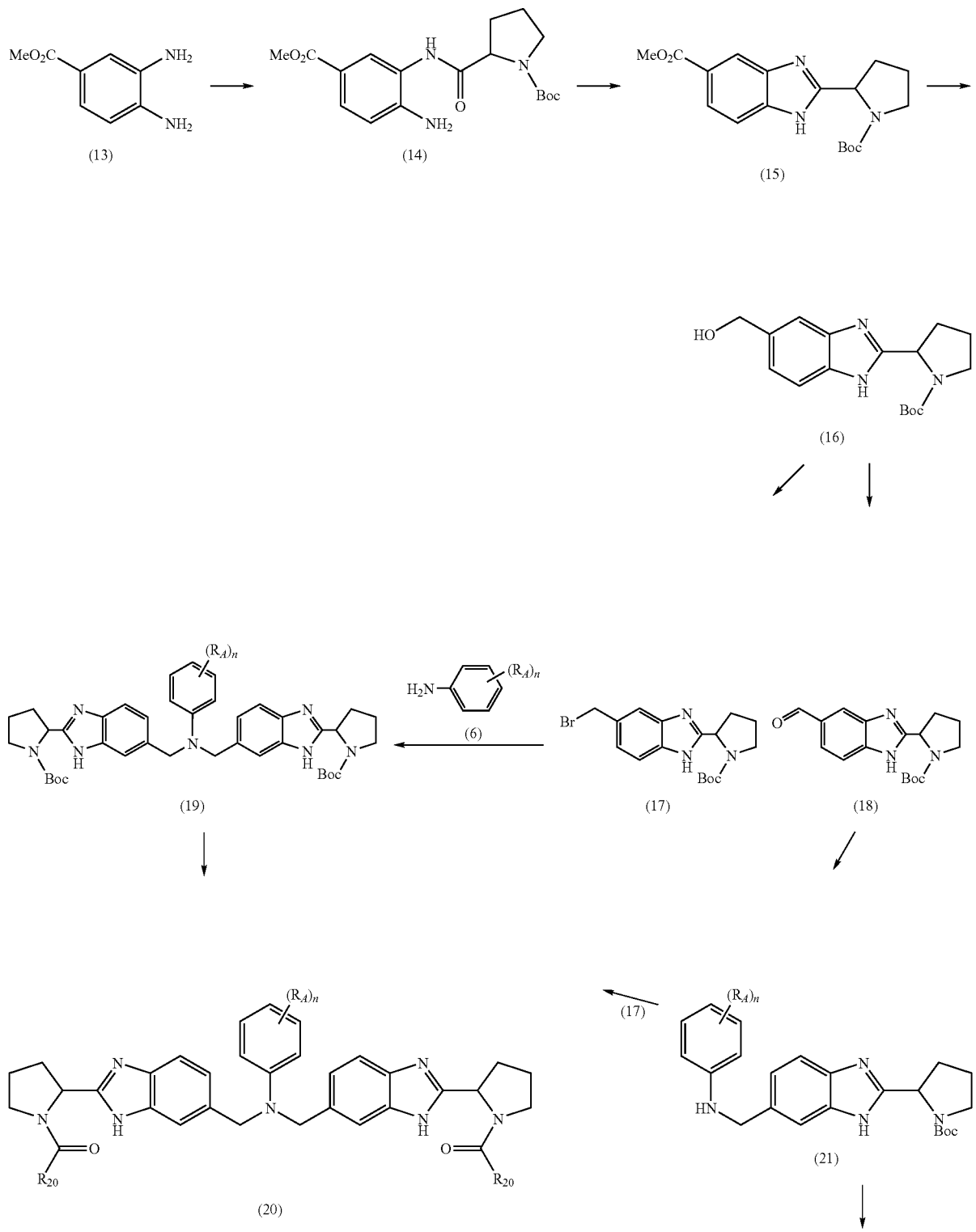

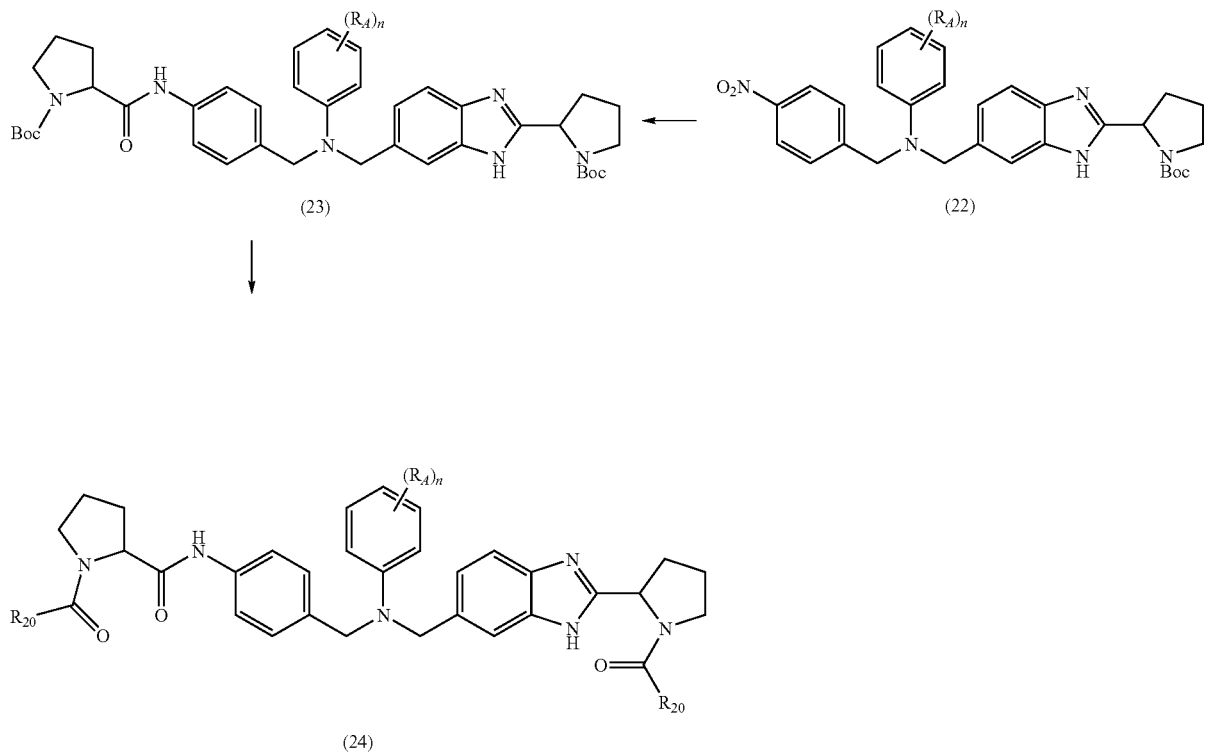

As still another non-limiting example, the compounds of the present invention (35) can be prepared by the methods shown in Scheme IV', where $R_{20}$ is $-L_S'-M'-L_S''-R_D$, and $L_S'$, M', $L_S''$, $R_D$, $R_1$, $R_2$, $R_5$, and $R_A$ are as described above, and n is 0, 1, 2, 3, 4, or 5. Compound (25) may be prepared from 4'-iodoacetophenone using known conditions, such as treatment with $Br_2$. Compound (25) may be reacted with the salt of an amino acid (prepared from suitably protected amino acid and a base, such as $Cs_2CO_3$, KOH, NaOH, or $Na_2CO_3$, in a solvent such as ethanol or THF) in a solvent such as THF, DMF or DMSO, to provide ester (26). The ester (26) may be treated with an ammonia source, such as $NH_4OAc$, $NH_4Cl$, or ammonia gas, and heated in a solvent such as toluene or xylene with azeotropic removal of water to provide the imidazole (27). See Gordon et al., TET. LETT. 34:1901-1904 (1993), and Moinet et al., BIOORG. MED. CHEM. LETT. 11:991-995 (2001), both of which are incorporated herein by reference in their entireties. The iodide (27) may be converted to the ester (28) by treatment with a palladium catalyst (such as $Pd(PPh_3)_4$ or $Pd(dppf)Cl_2$, or a Pd (II) catalyst such $Pd(OAc)_2$ or $Pd_2(dba)_3$) with or without the addition of organophosphorous ligands, such as $PPh_3$ or $P(t-Bu)_3$) and carbon monoxide in the presence of a base, such as triethylamine or Hunig's base, in a solvent such as methanol or ethanol, with or without heating. The ester obtained (28) may be reduced to the alcohol (29) and then oxidized to the aldehyde (30) by the methods described above. Compound (30) can be used to prepare compound (31) by reaction with aniline to form a Schiff base (imine), which may be reduced to (31) with a hydride reducing agent, such as sodium borohydride or sodium cyanoborohydride (with or without the addition of an acid, such as acetic acid) in a solvent such as ethanol, toluene, THF, or dichloromethane. Alternatively the Schiff based formed from (30) can be reduced to the products (31) by hydrogenation in the presence of a suitable catalyst, such as a palladium or platinum catalyst or Raney nickel. Compound (31) may be reacted with 4-nitrobenzyl bromide under the alkylation conditions described above to give (32). Reduction of the nitro group of (32) using the conditions described above and coupling with a suitably protected proline acid can provide (34). After removal of the Hoc protecting groups from (34) (accomplished by treatment with an acid, such as TFA, HCl, or formic acid), the compounds of the present invention (35) may be prepared by coupling of the resulting diamine with an acid of choice using the standard peptide coupling reagents and conditions described above. Likewise, compounds of Formula I, can be similarly prepared.

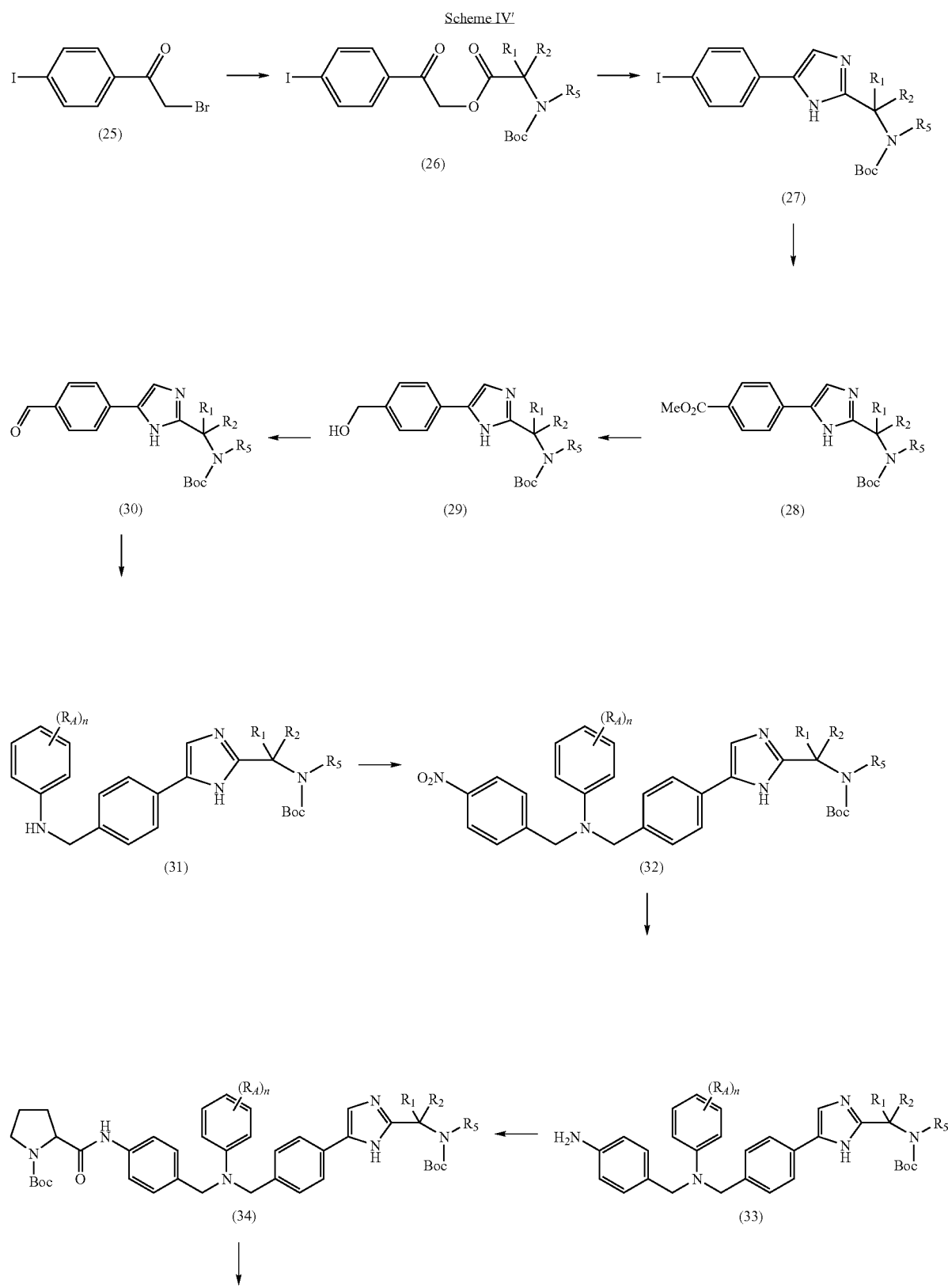

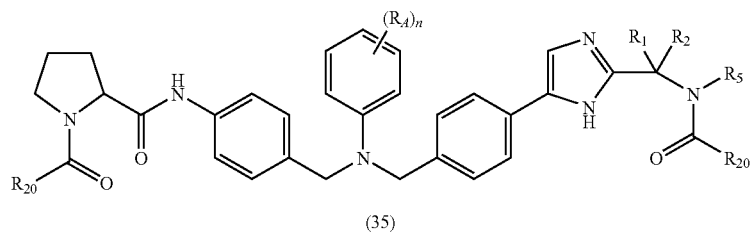

(35)

If a moiety described herein (e.g., —NH₂ or —OH) is not compatible with the synthetic methods, the moiety may be protected with a suitable protecting group that is stable to the reaction conditions used in the methods. The protecting group may be removed at a suitable point in the reaction sequence to provide a desired intermediate or target compound. Suitable protecting groups and methods for protecting or deprotecting moieties are well know in the art, examples of which can be found in Greene and Wuts, supra. Optimum reaction conditions and reaction times for each individual step may vary depending on the particular reactants employed and substituents present in the reactants used. Solvents, temperatures and other reaction conditions may be readily selected by one of ordinary skill in the art based on the present invention.

Other compounds of the invention can be similarly prepared according to the above-described schemes as well as the procedures described in the following examples, as appreciated by those skilled in the art. It should be understood that the above-described embodiments and schemes and the following examples are given by way of illustration, not limitation. Various changes and modifications within the scope of the present invention will become apparent to those skilled in the art from the present description.

Example compounds below were named using either ChemDraw version 9.0 or ACD version 10 (ACD v10). Final compounds and intermediates for Examples 1-23 were named using ChemDraw. Final compounds for Examples 24-150 were named using ACD v10. Intermediates for Examples 24-150 were named using ChemDraw, unless otherwise indicated.

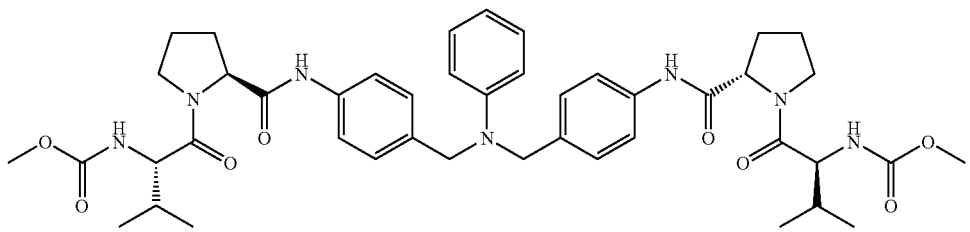

EXAMPLE 1

Dimethyl (2S,2'S)-1,1'-(2S,2'S)-2,2'-(4,4'-(phenylazanediyl)bis(methylene)bis(4,1-phenylene)bis(azanediyl))bis(oxomethylene)bis(pyrrolidine-2,1-diyl))bis(3-methyl-1-oxobutane-2,1-diyl)dicarbamate

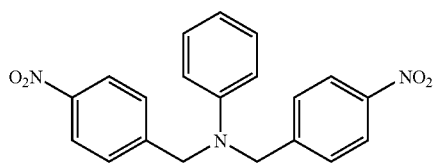 [SMILES: O=[N+]([O-])c1ccc(CN(Cc2ccc([N+](=O)[O-])cc2)c2ccccc2)cc1]

EXAMPLE 1A

N,N-bis(4-nitrobenzyl)aniline

Combined aniline (0.457 ml, 5 mmol), sodium hydrogen carbonate (0.924 g, 11.00 mmol) and sodium dodecyl sulfate (0.020 g, 0.070 mmol) in water (20 ml) and heated in an oil bath at 80° C. for about 5 minutes. Added 1-(bromomethyl)-4-nitrobenzene (2.376 g, 11.00 mmol) and continue heating at 80° C. for about 1 hr. After 1 hr, the reaction was cooled to room temperature. The product was collected by filtration, rinsed with water, and dried under vacuum. The product was recrystallized from a mixture of EtOAc and hexanes to give the product (1.67 g, 92% yield, yellow powder).

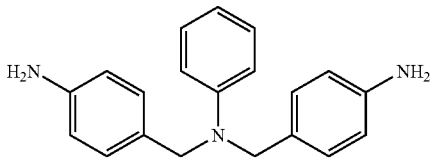

EXAMPLE 1B

N,N-bis(4-aminobenzyl)aniline

Method A. Combined the product from Example 1A (436 mg, 1.2 mmol) and bismuth(III) chloride (1.14 g, 3.60 mmol) in ethanol (12 mL) and cooled in a water bath. Added Sodium borohydride (726 mg, 19.20 mmol) portionwise (exotherm and bubbling occurred) and the reaction tuned dark black in color. Stirred at room temperature for about 1 hour. Added MeOH and filtered through celite, rinsing with MeOH. Concentrated to half volume via rotovap, diluted with 25% isopropanol/CHCl$_3$, and washed with 10% sodium bicarbonate. Dried the organic layer over Na$_2$SO$_4$, filter and concentrated to give the title compound (310.4 mg, 85% yield, yellow oil).

Method B. To the product from Example 1A (200 mg, 0.550 mmol) in THF (20 ml) in a 50 ml pressure bottle was added Ra—Ni, water wet, A-7000 (200 mg, 3.41 mmol) and the mixture was stirred for 2 hr at 30 psi at room temperature. The mixture was filtered through a nylon membrane and the solvent was evaporated to give the title compound, which was used without further purification.

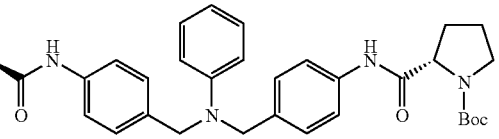

EXAMPLE 1C (2S,2'S)-tert-butyl 2,2'-(4,4'-(phenylazanediyl)bis(methylene)bis(4,1-phenylene)bis(azanediyl))bis(oxomethylene)dipyrrolidine-1-carboxylate Dissolved the product from Example 1B (310.4 mg, 1.023 mmol) in DMSO (5.115 mL) and added N-(tert-butoxycarbonyl)-L-proline (440 mg, 2.046 mmol), HATU (817 mg, 2.148 mmol) and Hunig's Base (0.715 mL, 4.09 mmol). After stirring for 48 hours, add water and filtered to collect solid. The solid was purified by chromatography on silica gel eluting with 0-4% MeOH/CH$_3$Cl$_2$ to give the title compound (339.4 mg, 47.5% yield, light yellow powder).

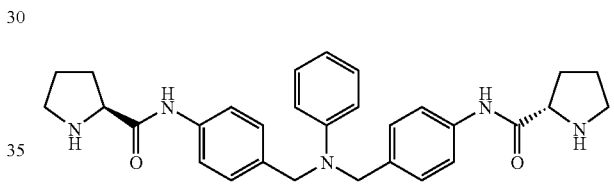

EXAMPLE 1D (2S,2'S)-N,N'-(4,4'-(phenylazanediyl)bis(methylene)bis(4,1-phenylene))dipyrrolidine-2-carboxamide To the product from Example 1C (150 mg, 0.215 mmol) in CH$_2$Cl$_2$ (537 μl) was added TFA (537 μl) and the reaction was stirred under N$_2$ atmosphere for 45 minutes and concentrated via rotovap. The residue was dissolved in 25% isopropanol/CHCl$_3$, and washed with half-saturated NaHCO$_3$. Dried organic over Na$_2$SO$_4$, filtered and concentrated to give the title compound (93.8 mg, 88% yield, light tan solid).

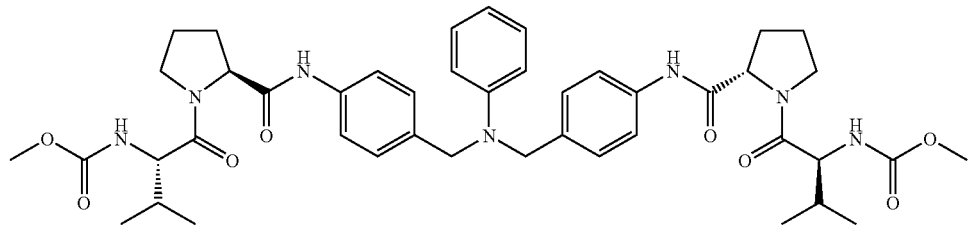

EXAMPLE 1E

Dimethyl (2S,2'S)-1,1'-((2S,2'S)-2,2'-(phenylazanediyl)bis(methylene)bis(4,1-phenylene)bis(azanediyl))bis(oxomethylene)bis(pyrrolidine-2,1-diyl))bis(3-methyl-1-oxobutane-2,1-diyl)dicarbamate To a mixture of the product from Example 1D (0.01 g, 0.020 mmol), (S)-2-(methoxycarbonylamino)-3-methylbutanoic acid (8.80 mg, 0.050 mmol), and HATU (0.019 g, 0.050 mmol) in DMSO (0.100 ml) was added Hunig's base (0.021 ml, 0.121 mmol), and the reaction was stirred at room temperature for 15 minutes. The reaction was diluted with acetonitrile and water (0.1% TFA) and purified by reversed phase chromatography (C18), eluting with 10-100% acetonitrile in water (0.1% TFA) to give the title compound (14 mg, 86% yield, white solid) as a TFA salt. $^1$H NMR (500 MHz, DMSO-D6) δ ppm 0.88 (d, J=6.71 Hz, 6 H) 0.93 (d, J=6.71 Hz, 6 H) 1.81-2.04 (m, 8 H) 2.08-2.19 (m, 2 H) 3.58-3.65 (m, 2 H) 3.77-3.85 (m, 2 H) 4.02 (t, J=8.54 Hz, 2 H) 4.42 (dd, J=8.16, 4.81 Hz, 2 H) 4.59 (s, 4 H) 6.57 (t, J=6.33 Hz, 1 H) 6.65 (d, J=7.32 Hz, 2 H) 7.07 (t, J=7.86 Hz, 2 H) 7.17 (d, J=8.70 Hz, 4 H) 7.37 (d, J=8.39 Hz, 2 H) 7.51 (d, J=8.54 Hz, 4 H) 10.01 (s, 2 H).

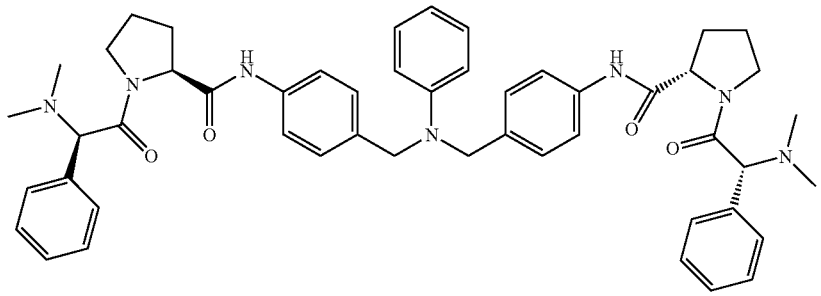

EXAMPLE 2

(R,2S,2'S)-N,N'-(4,4'-(phenylazanediyl)bis(methylene)bis(4,1-phenylene))bis(1-((R)-2-(dimethylamino)-2-phenylacetyppyrrolidine-2-carboxamide)

To a mixture of the product from Example 1D (45 mg, 0.090 mmol), (R)-2-(dimethylamino)-2-phenylacetic acid (40.5 mg, 0.226 mmol), and HATU (86 mg, 0.226 mmol) in DMSO (0.45 ml) was added Hunig's base (95 μl, 0.543 mmol), and the reaction was stirred at room temperature for 1 hour. Poured reaction into water and extract with EtOAc, followed by washing with brine. Dried organic over Na$_2$SO$_4$, filtered and concentrated. Purification by chromatography on silica gel eluting with 0-5% MeOH/CH$_2$Cl$_2$ to give the title compound (7 mg, 9.4% yield). $^1$H NMR (500 MHz, DMSO-D6) δppm 10.03 (br s, 2 H) 7.30-7.60 (m, 14 H) 7.15-7.25 (m, 4 H) 7.02-7.13 (m, 2 H) 6.62-6.73 (m, 2 H) 6.58 (t, J=7.17 Hz, 1 H) 4.61 (s, 4 H) 4.31-4.40 (m, 2 H) 3.82-3.91 (m, 2 H) 3.10-3.60 (m, 16 H) 1.74-2.12 (m, 8 H).

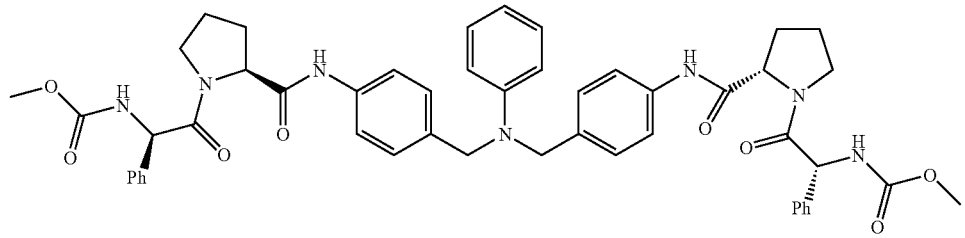

EXAMPLE 3

Dimethyl (1R,1'R)-2,2'-(2S,2'S)-2,2'-(4,4'-(phenylazanediyl)bis(methylene)bis(4,1-phenylene)bis(azanediyl))bis(oxomethylene)bis(pyrrolidine-2,1-diyl))bis(2-oxo-1-phenylethane-2,1-diyl)dicarbamate To a mixture of the product from Example 1D (47.2 mg, 0.095 mmol), (R)-2-(methoxycarbonylamino)-2-phenylacetic acid (49.6 mg, 0.237 mmol), and HATU (90 mg, 0.237 mmol) in DMSO (0.47 ml) was added Hunig's base (99 µl, 0.569 mmol), and the reaction was stirred at rt for 1 hour. Poured reaction into water and extract with EtOAc, followed by washing with brine. Dried organic over $Na_2SO_4$, filtered and concentrated. Purification by chromatography on silica gel eluting with 0-5% $MeOH/CH_2Cl_2$. Second purification by reversed phase chromatography (C18), eluting with 10-100% acetonitrile in water (0.1% TFA) to give the title compound (6.5 mg, 7.7% yield). $^1H$ NMR (500 MHz, DMSO-D6) δ ppm 9.79-10.11 (m, 2 H) 7.60-7.97 (m, 2 H) 7.46-7.62 (m, 3 H) 7.28-7.46 (m, 10 H) 7.13-7.27 (m, 4 H) 7.03-7.14 (m, 3 H) 6.63-6.74 (m, 2 H) 6.54-6.63 (m, 1 H) 5.28-5.54 (m, 2 H) 4.61 (s, 4 H) 4.34-4.50 (m, 2 H) 3.63-3.85 (m, 2 H) 3.53 (s, 6 H) 3.06-3.24 (m, 2 H) 1.70-2.09 (m, 8 H).

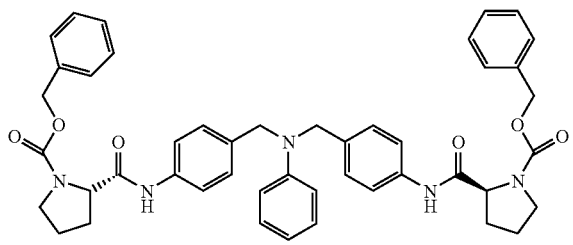

EXAMPLE 4

(2S,2'S)-benzyl 2,2'-(4,4'-(phenylazanediyl)bis(methylene)bis(4,1-phenylene)bis(azanediyl))bis(oxomethylene)dipyrrolidine-1-carboxylate The product from Example 1D (25 mg, 0.050 mmol) was combined with benzyl 2,5-dioxopyrrolidin-1-yl carbonate (27.5 mg, 0.111 mmol) and triethylamine (0.021 mL, 0.151 mmol) in DMF (0.5 mL) and the mixture was stirred at room temperature overnight. Partitioned between water (5 ml) and EtOAc (3×5 ml). Dried organic over $Na_2SO_4$, filtered and concentrated. Purification by chromatography on silica gel eluting with 10-50% EtOAc in hexanes to provide the title compound as a colorless solid (9 mg, 23.4% yield). $^1H$ NMR (500 MHz, DMSO-D6) δ ppm 9.97-10.06 (m, 2 H) 7.48-7.58 (m, 4 H) 7.35-7.41 (m, 3 H) 7.29-7.35 (m, 1 H) 7.03-7.26 (m, 12 H) 6.63-6.74 (m, J=8.32, 8.32 Hz, 2 H) 6.54-6.63 (m, 1 H) 5.02-5.12 (m, 3 H) 4.93 (d, J=13.12 Hz, 1 H) 4.58-4.67 (m, 4 H) 4.28-4.39 (m, 2 H) 3.38-3.55 (m, 4 H) 2.14-2.31 (m, 2 H) 1.77-1.98 (m, 6 H).

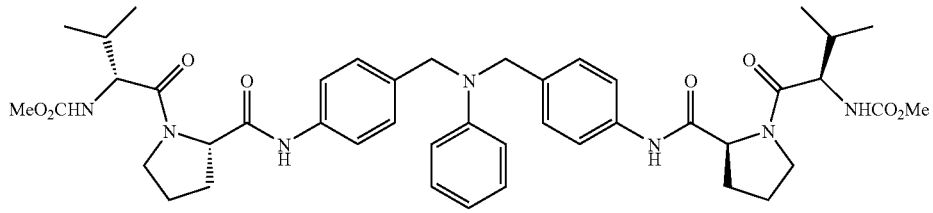

EXAMPLE 5

Dimethyl (2R,2'R)-1,1'-((2S,2'S)-2,2'-(4,4'-(phenylazanediyl)bis(methylene)bis(4,1-phenylene)bis(azanediyl))bis(oxomethylene)bis(pyrrolidine-2,1-diyl))bis(3-methyl-1-oxobutane-2,1-diyl)dicarbamate To a solution of the product from Example 1D (12 mg, 0.024 mmol), (R)-2-(methoxycarbonylamino)-3-methylbutanoic acid (8.87 mg, 0.051 mmol), and HATU (19.25 mg, 0.051 mmol) in anhydrous DMSO (0.25 ml) was added Hunig's Base (0.013 ml, 0.072 mmol), and the resulting mixture was stirred at rt for 90 min. The mixture was partitioned between water (5 ml) and EtOAc (3×5 ml) and the combined organic layers were dried over $Na_2SO_4$. The mixture was filtered and concentrated in vacuo, and the crude product was purified by chromatography on silica gel (C18) eluting with a gradient of 10-100% acetonitrile in water (0.1% TFA). Fractions containing pure product were pooled and concentrated in vacuo to give the title compound as a solid (7 mg, 31%) as a TFA salt. $^1H$ NMR (500 MHz, DMSO-D6) δ ppm 10.23 (s, 0.5 H) 9.67 (s, 1.5 H) 7.49-7.56 (m, 4 H) 7.43 (d, J=8.39 Hz, 0.5 H) 7.35 (d, J=8.24 Hz, 1.5 H) 7.14-7.22 (m, 4 H) 7.03-7.11 (m, 2 H) 6.65 (d, J=8.24 Hz, 2 H) 6.57 (t, J=7.02 Hz, 1 H) 4.98 (d, J=8.09 Hz, 0.5 H) 4.56-4.63 (m, 4 H) 4.40 (dd, J=8.55, 2.75 Hz, 1.5 H) 4.05-4.11 (m, 2 H) 3.75-3.84 (m, 2 H) 3.56-3.65 (m, 3 H) 3.51-3.56 (m, 6 H) 3.42-3.49 (m, 1 H) 2.05-2.15 (m, 2 H) 1.87-2.04 (m, 6 H) 0.83-0.93 (m, 12 H).

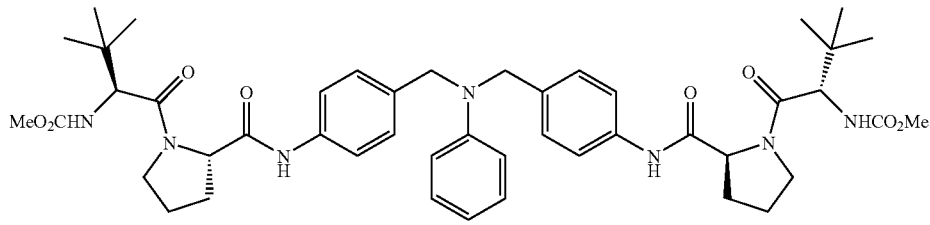

EXAMPLE 6

Dimethyl (2S,2'S)-1,1'-((2S,2'S)-2,2'-(4,4'-(phenylazanediyl)bis(methylene)bis(4,1-phenylene)bis(azanediyl))bis(oxomethylene)bis(pyrrolidine-2,1-diyl))bis(3,3-dimethyl-1-oxobutane-2,1-diyl) dicarbamate To a solution of the product from Example 1D (12 mg, 0.024 mmol) and (S)-2-(methoxycarbonylamino)-3,3-dimethylbutanoic acid (9.58 mg, 0.051 mmol) in DMSO (0.2 ml) were added HATU (19.25 mg, 0.051 mmol) and Hunig's Base (0.013 ml, 0.072 mmol). The resulting mixture was stirred at room temperature for 90 min. The mixture was partitioned between water (1 ml) and EtOAc (3×1 mL), and the combined organic layers were dried over $Na_2SO_4$. The crude product was purified by chromatography on silica gel (C18) eluting with a gradient of 10-100% acetonitrile in 0.1% aq. TFA to provide the title compound (8 mg, 34.8% yield) as a TFA salt. $^1$H NMR (500 MHz, DMSO-D6) δ ppm 9.99 (s, 2 H) 7.51 (d, J=8.54 Hz, 4 H) 7.17 (d, J=8.55 Hz, 4 H) 7.02-7.13 (m, 4 H) 6.66 (d, J=8.09 Hz, 2 H) 6.53-6.61 (m, 1 H) 4.58 (s, 4 H) 4.43 (dd, J=7.93, 5.34 Hz, 2 H) 4.21 (d, J=8.85 Hz, 2 H) 3.73-3.83 (m, 2 H) 3.64 (s, 2 H) 3.54 (s, 6 H) 2.09-2.20 (m, 2 H) 1.93-2.04 (m, 2 H) 1.79-1.92 (m, 4 H) 0.96 (s, 18 H).

EXAMPLE 7

Dimethyl (2S,2'S)-1,1'-((2S,2'S)-2,2'-(6,6'-(phenylazanediyl)bis(methylene)bis(1H-benzo[d]imidazole-6,2-diyl))bis(pyrrolidine-2,1-diyl))bis(3,3-dimethyl-1-oxobutane-2,1-diyl)dicarbamate

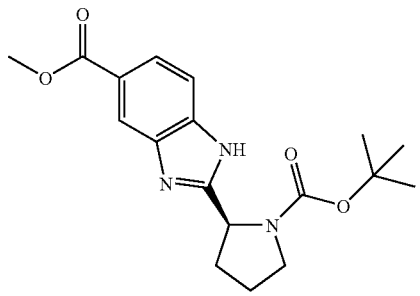

EXAMPLE 7A (S)-Methyl 2-(1-(tert-butoxycarbonyl)pyrrolidin-2-yl)-1H-benzo[d]imidazole-5-carboxylate Combined methyl 3,4-diaminobenzoate (5.0 g, 30.1 mmol) with EDAC (17.3 g, 90 mmol) and Boc-proline (6.48 g, 30.1 mmol) in a mixture of pyridine (50 mL) and DMT (50 mL),

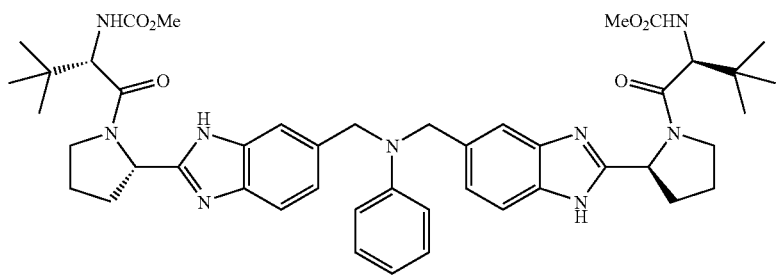

and the mixture was then allowed to stir at room temperature overnight. The mixture was evaporated, and the residue was dissolved in EtOAc and washed with water (3×200 mL), aq. 10% NaHCO3, and then brine. Dried organic over MgSO₄, filtered, and evaporated to yield 10.4 g (95%) of a light yellowish colored solid that was used without further purification.

The product from the first step (10.4 g) was dissolved in acetic acid (75 mL), and the mixture was then allowed to heat with stirring at 70° C. for 3 hours. The mixture was evaporated down to dryness, azeotroping with toluene and then dried under vacuum. The residue was purified by chromatography on silica gel eluting with 50-100% EtOAc in hexanes to give the title compound (8.96 g, yield 91%) as a faint light yellowish/white colored solid.

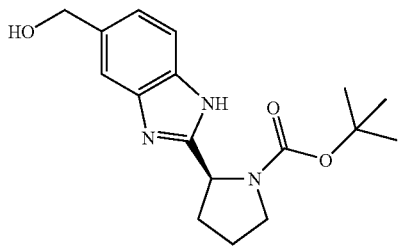 [SMILES: CC(C)(C)OC(=O)N1CCC[C@H]1c1nc2cc(CO)ccc2[nH]1]

EXAMPLE 7B (S)-tert-Butyl 245-(hydroxymethyl)-1H-benzo[d] imidazol-2-yl)pyrrolidine-1-carboxylate To a solution of the product from Example 7A (1.75 g, 5.07 mmol) in CH₂Cl₂ (40 mL) at −78° C. was added DiBAL (15.7 mL, 1 M in CH₂Cl₂) dropwise, and the mixture was allowed to stir at −78° C. for 15 minutes and was then allowed to come to room temperature and stirred for 1 hour. The reaction was then cooled in an ice bath and MeOH (2 mL) was slowly added dropwise, followed by addition of saturated MgSO₄ (60 mL), and the mixture was stirred for 30 min. EtOAc (200 mL) was added and the organic was separated, washed with brine, dried (MgSO₄), filtered and evaporated to give the title compound (1.506 g, yield 94%) as a faint yellowish colored solid.

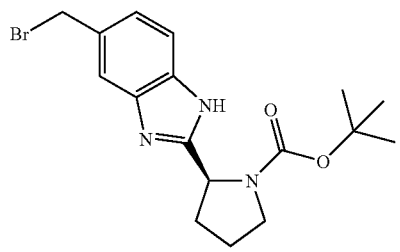 [SMILES: CC(C)(C)OC(=O)N1CCC[C@H]1c1nc2cc(CBr)ccc2[nH]1]

EXAMPLE 7C (S)-tert-Butyl 2-(5-(bromomethyl)-1H-benzo[d]imidazol-2-yl)pyrrolidine-1-carboxylate To a mixture of the product from Example 7B (0.50 g, 1.57 mmol) and polymer-bound triphenylphosphine (2.1 g, 3.15 mmol, 150-300 mesh) in THF at 0° C. was added CBr₄, and the mixture was stirred at 0° C. for 10 min., and was then allowed to stir at room temperature for 1.5 hours. The mixture was then filtered and rinsed with THF. The THF was evaporated to give the title compound (493 mg, yield 82%) as a light yellowish colored solid which was used without further purification.

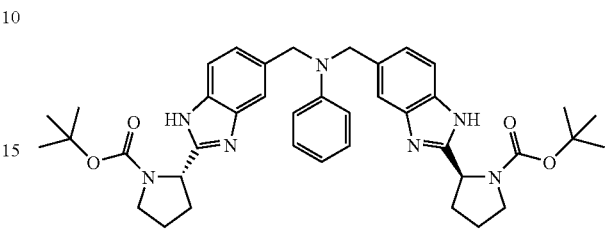

EXAMPLE 7D (2S,2'S)-tert-Butyl 2,2'-(5,5'-(phenylazanediyl)bis (methylene)bis(1H-benzo[d]imidazole-5,2-diyl)) dipyrrolidine-1-carboxylate A mixture of the product from Example 7C (0.20 g, 0.526 mmol), aniline (0.019 mL, 0.210 mmol), and K2CO₃ (0.087 g, 0.631 mmol) in DMF (1.0 mL) was allowed to stir at room temperature for 2 hours. Additional product from Example 7C (0.10 g) was added along with additional K2CO₃ (0.044 g), and the mixture was allowed to stir overnight. The mixture was poured into EtOAc and the organic was then washed with water, brine, dried (MgSO₄), filtered and evaporated. The product was purified by chromatography on silica gel eluting with 50-100% EtOAc in hexanes to give the title compound (46 mg, yield 32%) as a colorless semi-solid.

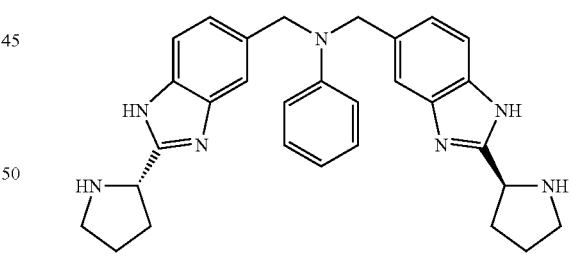

EXAMPLE 7E

N,N-bis((2-((S)-pyrrolidin-2-yl)-1H-benzo[d]imidazol-5-yl)methyl)aniline

To a solution of the product from Example 7D (46 mg, 0.066 mmol) in CH₂Cl₂ (1.0 mL) was added TFA (1.0 mL), and the mixture was stirred at room temperature for 30 min. The solvent was evaporated and the residue was used without further purification.

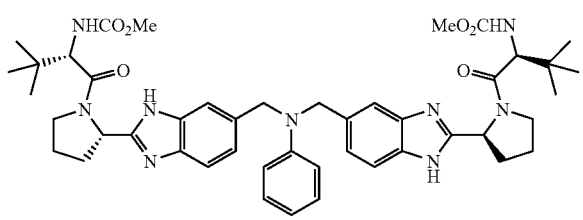

EXAMPLE 7F

Dimethyl (2S,2'S)-1,1'-(((2S,2'S)-2,2'-(6,6'-(phenylazanediyl)bis(methylene)bis(1H-benzo[d]imidazole-6,2-diyl))bis(pyrrolidine-2,1-diyl))bis(3,3-dimethyl-1-oxobutane-2,1-diyl)dicarbamate To a solution of the product from Example 7E (32.4 mg, 0.066 mmol), (S)-2-(methoxycarbonylamino)-3,3-dimethylbutanoic acid (26.2 mg, 0.139 mmol), and HATU (52.7 mg, 0.139 mmol) in anhydrous DMSO (0.5 ml) was added Hunig's Base (0.035 ml, 0.198 mmol), and the resulting mixture was stirred at rt for 90 min. The mixture was partitioned between water (5 ml) and EtOAc (3×5 ml) and the combined organic layers were dried over $Na_2SO_4$. The mixture was filtered and concentrated in vacuo, and the crude product was purified by chromatography on reverse phase chromatography (C18) eluting with a gradient of 10-100% acetonitrile in water (0.1% TFA). Fractions containing pure product were pooled and concentrated in vacuo to give the title compound as a solid (14 mg, 18%) as a TFA salt. $^1$H NMR (500 MHz, DMSO-D6) δ ppm 14.55 (br s, 2 H) 7.72 (d, J=8.39 Hz, 2 H) 7.56 (s, 2 H) 7.41 (d, J=8.09 Hz, 2 H) 7.31 (d, J=8.70 Hz, 2 H) 7.07-7.12 (m, 2 H) 6.73 (d, J=8.09 Hz, 2 H) 6.58-6.63 (m, 1 H) 5.19 (dd, J=8.16, 5.87 Hz, 2 H) 4.85-4.97 (m, 4 H) 4.21 (d, J=8.70 Hz, 2 H) 3.81-3.92 (m, 4 H) 3.57 (s, 6 H) 2.01-2.25 (m, 8 H) 0.85 (s, 18 H).

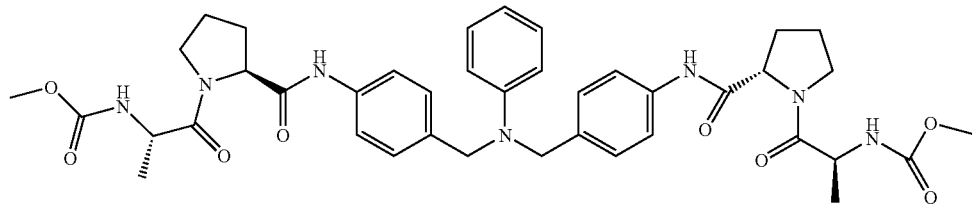

EXAMPLE 8

Dimethyl (2S,2'S)-1,1'-((2S,2'S)-2,2'-(4,4'-(phenylazanediyl)bis(methylene)bis(4,1-phenylene)bis(azanediyl))bis(oxomethylene)bis(pyrrolidine-2,1-diyl))bis(1-oxopropane-2,1-diyl)dicarbamate The product from Example 1D (0.024 g, 0.048 mmol), (S)-2-(methoxycarbonylamino)propanoic acid (0.015 g, 0.101 mmol), HATU (0.039 g, 0.101 mmol) and Hunig's base (0.025 ml, 0.145 mmol) were mixed in DMSO (0.5 ml) and stirred at room temperature for 2.5 h under nitrogen. The reaction mixture was diluted with $CH_2Cl_2$ and washed with water. The organic extract was separated, dried over $Na_2SO_4$, filtered, and evaporated. The product was purified by chromatography on silica gel eluting with 0-5% MeOH in $CH_2Cl_2$ to give the title compound (11.9 mg, 32.6% yield). $^1$H NMR (500 MHz, DMSO-D6) δ ppm 9.92 (s, 2 H) 7.50 (d, J=8.54 Hz, 4 H) 7.34 (d, J=7.48 Hz, 2 H) 7.17 (d, J=8.70 Hz, 4 H) 7.06 (dd, J=8.85, 7.32 Hz, 2 H) 6.65 (d, J=7.93 Hz, 2 H) 6.56 (t, J=7.25 Hz, 1 H) 4.59 (s, 4 H) 4.41 (dd, J=8.24, 4.42 Hz, 2 H) 4.27-4.36 (m, 2 H) 3.62-3.70 (m, 2 H) 3.54-3.61 (m, 2 H) 3.60 (s, 6 H) 2.07-2.18 (m, 2 H) 1.95-2.04 (m, 2 H) 1.81-1.96 (m, 4H) 1.18 (d, J=4.00 Hz, 6 H).

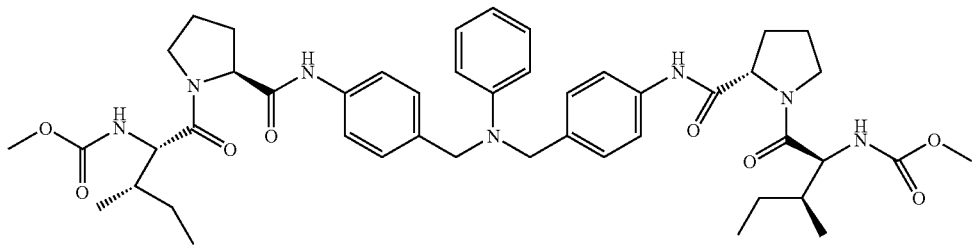

EXAMPLE 9

Dimethyl (2S,2'S,3S,3'S)-1,1'-(2S,2'S)-2,2'-(4,4'-(phenylazanediyl)bis(methylene)bis(4,1-phenylene) bis(azanediyl))bis(oxomethylene)bis(pyrrolidine-2,1-diyl))bis(3-methyl-1-oxopentane-2,1-diyl) dicarbamate The product from Example 1D (0.0179 g, 0.036 mmol), (2S,3S)-2-(methoxycarbonylamino)-3-methylpentanoic acid (0.014 g, 0.076 mmol), HATU (0.029 g, 0.076 mmol) and Hunig's base (0.019 ml, 0.108 mmol) were dissolved in DMSO (0.360 ml), and the reaction mixture was stirred at room temperature for 2 h under nitrogen. The reaction mixture was diluted with $CH_2Cl_2$ and washed with water. The organic extract was separated, dried over $Na_2SO_4$, filtered, and evaporated. The product was purified by chromatography on silica gel eluting with 0-3% MeOH in $CH_2Cl_2$ to give the title compound (12.6 mg, 41.1% yield). $^1$H NMR (500 MHz, DMSO-D6) δ ppm 9.98 (s, 2 H) 7.51 (d, J=8.55 Hz, 4 H) 7.37 (d, J=8.55 Hz, 2 H) 7.17 (d, J=8.54 Hz, 4 H) 7.07 (dd, J=8.77, 7.25 Hz, 2 H) 6.65 (d, J=8.09 Hz, 2 H) 6.56 (t, J=7.25 Hz, 1 H) 4.59 (s, 4 H) 4.43 (dd, J=8.16, 4.81 Hz, 2 H) 4.07 (t, J=8.93 Hz, 2 H) 3.79-3.86 (m, 2 H) 3.57-3.66 (m, 2 H) 3.52 (s, 6 H) 2.08-2.18 (m, 2 H) 1.95-2.05 (m, 2 H) 1.82-1.93 (m, 4 H) 1.66-1.76 (m, 2 H) 1.44-1.55 (m, 2 H) 1.06-1.15 (m, 2 H) 0.89 (d, J=6.71 Hz, 6 H) 0.78-0.84 (m, 6 H).

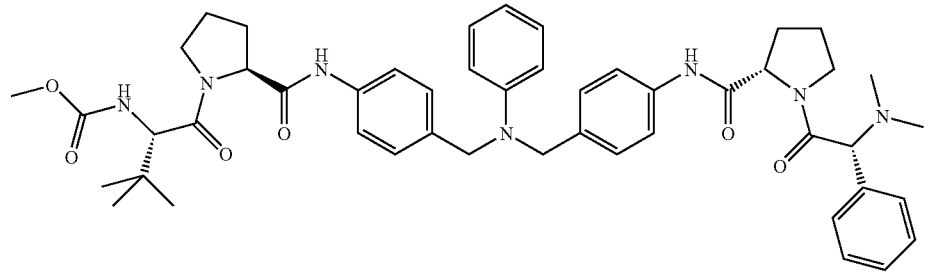

EXAMPLE 10

Methyl (S)-1-((S)-2-(4-(((4-((S)-1-((R)-2-(dimethylamino)-2-phenylacetyl)pyrrolidine-2-carboxamido) benzyl)(phenyl)amino)methyl)phenylcarbamoyl) pyrrolidin-1-yl)-3,3-dimethyl-1-oxobutan-2-ylcarbamate

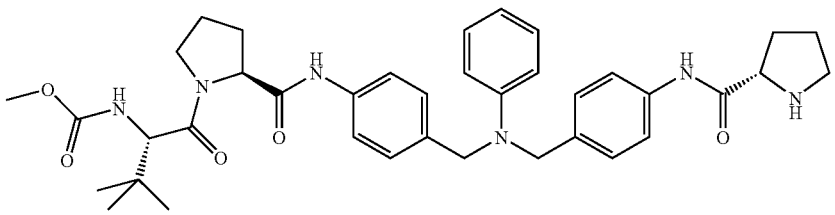 [SMILES: COC(=O)N[C@H](C(=O)N1CCC[C@H]1C(=O)Nc1ccc(CN(Cc2ccc(NC(=O)[C@@H]3CCCN3)cc2)c2ccccc2)cc1)C(C)(C)C]

EXAMPLE 10A

Methyl (S)-3,3-dimethyl-1-oxo-1-((S)-2-(4-((phenyl (4-((S)-pyrrolidine-2-carboxamido)benzyl)amino) methyl)phenylcarbamoyl)pyrrolidin-1-yl)butan-2-ylcarbamate The product from Example 1D (120 mg, 0.241 mmol) was combined with (S)-2-(methoxycarbonylamino)-3,3-dimethylbutanoic acid (45.6 mg, 0.241 mmol), HATU (92 mg, 0.241 mmol) and Hunig's base (0.126 mL, 0.723 mmol) in DMSO (3.0 mL) and the mixture was stirred at room temperature for 45 min. Diluted with water and collected the solid by filtration. The product was purified by reversed phase chromatography (C18), eluting with 10-100% acetonitrile in water (0.1% TFA) to give the title compound (32 mg, 19.8% yield).

EXAMPLE 10B

Methyl (S)-1-((S)-2-(4-(((4-((S)-1-((R)-2-(dimethylamino)-2-phenylacetyl)pyrrolidine-2-carboxamido) benzyl)(phenyl)amino)methyl)phenylcarbamoyl) pyrrolidin-1-yl)-3,3-dimethyl-1-oxobutan-2-ylcarbamate The product from Example 10A (15 mg, 0.022 mmol) was combined with (R)-2-(dimethylamino)-2-phenylacetic acid (4.82 mg, 0.027 mmol), HATU (9.38 mg, 0.025 mmol) and Hunig's base (0.014 mL, 0.078 mmol) in DMSO (0.5 mL) and the mixture was stirred at room temperature for 45 min. Diluted with water and collected the solid by filtration. The

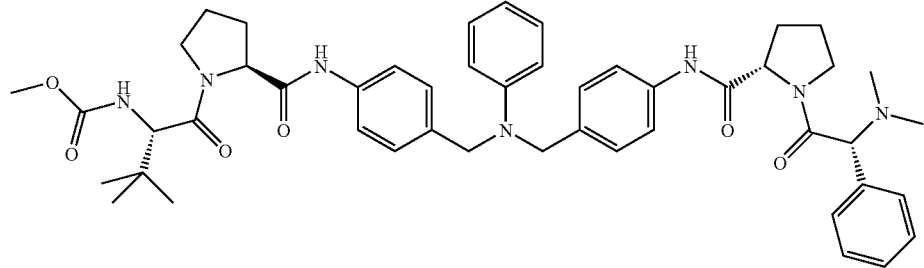

product was purified by chromatography on silica gel, eluting with 0-4% MeOH in CH$_2$Cl$_2$ to give the title compound (8 mg, 43% yield). $^1$H NMR (500 MHz, CHLOROFORM-D) δ ppm 1.02 (s, 9 H) 1.65-1.73 (m, 1 H) 1.86-1.95 (m, 2 H) 1.99-2.08 (m, 1 H) 2.13-2.20 (m, 2 H) 2.26 (s, 6 H) 2.49 (dd, J=12.21, 6.56 Hz, 1 H) 2.53-2.60 (m, 1 H) 3.32-3.39 (m, 1 H) 3.65-3.68 (m, 1 H) 3.69 (s, 3 H) 3.74-3.80 (m, 1 H) 3.81-3.87 (m, 1 H) 4.01 (s, 1 H) 4.38 (d, J=9.77 Hz, 1 H) 4.56 (s, 4 H) 4.76 (d, J=7.17 Hz, 1 H) 4.80 (dd, J=8.01, 2.52 Hz, 1 H) 5.39 (d, J=9.61 Hz, 1 H) 6.70 (t, J=7.25 Hz, 1 H) 6.73 (d, J=7.93 Hz, 2 H) 7.12-7.19 (m, 6 H) 7.36-7.43 (m, 5 H) 7.47-7.51 (m, 4 H) 9.30 (s, 1 H) 9.71 (s, 1 H).

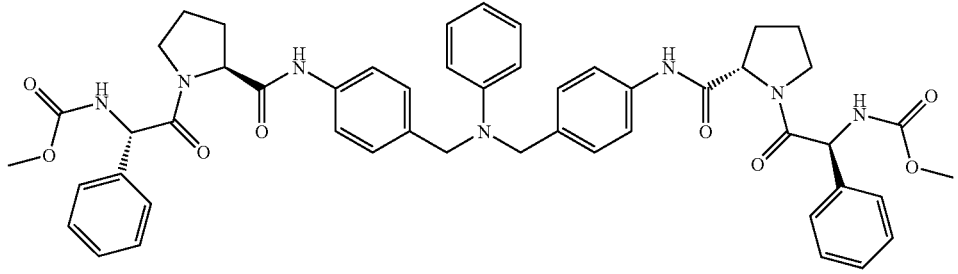

EXAMPLE 11

Dimethyl (1S,1'S)-2,2'-((2S,2'S)-2,2'-(4,4'-(phenylazanediyl)bis(methylene)bis(4,1-phenylene)bis(azanediyl))bis(oxomethylene)bis(pyrrolidine-2,1-diyl))bis(2-oxo-1-phenylethane-2,1-diyl)dicarbamate The product from Example 1D (9.0 mg, 0.018 mmol) was combined with (S)-2-(methoxycarbonylamino)-2-phenylacetic acid (7.95 mg, 0.038 mmol), HATU (14.44 mg, 0.038 mmol) and Hunig's base (0.013 mL, 0.072 mmol) in DMSO (1.0 mL) and the mixture was stirred at room temperature for 45 min. Diluted with water and collected the solid by filtration. The product was purified by chromatography on silica gel, eluting with 0-5% MeOH in $CH_2Cl_2$ to give the title compound (7.2 mg, 45.2% yield). $^1$H NMR (500 MHz, CHLOROFORM-D) δ ppm 1.78-1.87 (m, 2 H) 1.89-1.99 (m, 4 H) 2.38-2.45 (m, 2 H) 3.15-3.22 (m, 2 H) 3.52-3.67 (m, 8 H) 4.49 (s, 4 H) 4.77 (dd, J=7.86, 1.91 Hz, 2 H) 5.42 (d, J=7.78 Hz, 2 H) 5.94 (d, J=7.78 Hz, 2 H) 6.61-6.71 (m, 3 H) 7.07-7.13 (m, 6 H) 7.20-7.25 (m, 5 H) 7.30 (dd, J=7.55, 2.67 Hz, 9 H) 8.87 (s, 2 H).

EXAMPLE 12

Methyl (S)-1-((S)-2-(4-(((4-((S)-1-((R)-2-(diethylamino)-2-phenylacetyl)pyrrolidine-2-carboxamido)benzyl)(phenyl)amino)methyl)phenylcarbamoyl)pyrrolidin-1-yl)-3,3-dimethyl-1-oxobutan-2-ylcarbamate The product from Example 10A (15 mg, 0.022 mmol) was combined with (R)-2-(diethylamino)-2-phenylacetic acid (6.04 mg, 0.029 mmol), HATU (9.38 mg, 0.025 mmol) and Hunig's base (0.024 mL, 0.135 mmol) in DMSO (1.0 mL) and the mixture was stirred at room temperature for 45 min. Diluted with water and collected the solid by filtration. The

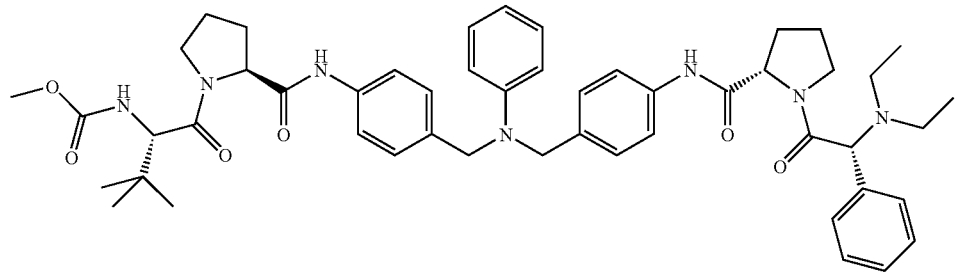 [SMILES: CCN(CC)[C@@H](C(=O)N1CCC[C@H]1C(=O)Nc1ccc(CN(Cc2ccc(NC(=O)[C@@H]3CCCN3C(=O)[C@@H](NC(=O)OC)C(C)(C)C)cc2)c2ccccc2)cc1)c1ccccc1]

product was purified by chromatography on silica gel, eluting with 0-5% MeOH in $CH_2Cl_2$ to give the title compound (11 mg, 57.2% yield). $^1$H NMR (500 MHz, CHLOROFORM-D) δ ppm 0.87 (t, J=7.10 Hz, 6 H) 0.94 (s, 9 H) 1.59-1.68 (m, 1 H) 1.78-1.86 (m, 2 H) 1.92-2.00 (m, 1 H) 2.04-2.12 (m, 2 H) 2.43-2.52 (m, 2 H) 2.55-2.67 (m, 4 H) 3.23-3.30 (m, 1 H) 3.56-3.61 (m, 2 H) 3.62 (s, 3 H) 3.71-3.78 (m, 1 H) 4.30 (d, J=9.61 Hz, 1 H) 4.48 (s, 4 H) 4.55 (s, 1 H) 4.72-4.77 (m, 2 H) 5.31 (d, J=9.77 Hz, 1 H) 6.63 (t, J=7.25 Hz, 1 H) 6.67 (d, J=7.93 Hz, 2 H) 7.06-7.12 (m, 6 H) 7.24-7.32 (m, 3 H) 7.33 (d, J=8.54 Hz, 2 H) 7.35-7.42 (m, 4 H) 9.22 (s, 1 H) 9.64 (s, 1 H).

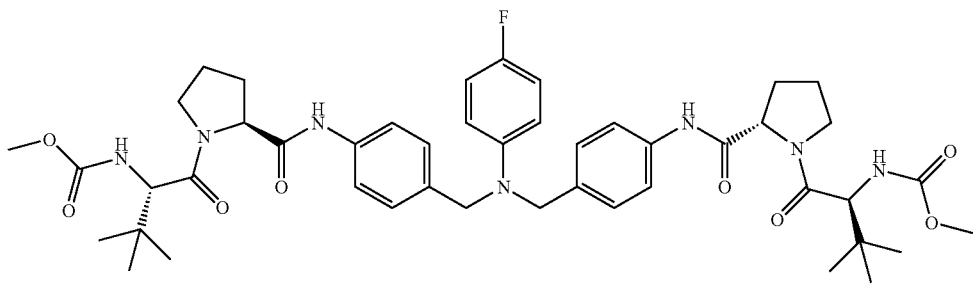

EXAMPLE 13

Dimethyl (2S,2'S)-1,1'-((2S,2'S)-2,2'-(4,4'-(4-fluorophenylazanediyl)bis(methylene)bis(4,1-phenylene)bis(azanediyl))bis(oxomethylene)bis(pyrrolidine-2,1-diyl))bis(3,3-dimethyl-1-oxobutane-2,1-diyl) dicarbamate

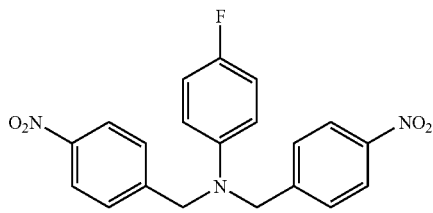 [SMILES: O=[N+]([O-])c1ccc(CN(Cc2ccc([N+](=O)[O-])cc2)c2ccc(F)cc2)cc1]

EXAMPLE 13A

4-Fluoro-N,N-bis(4-nitrobenzyl)aniline

Example 13A was prepared by the methods used to prepare Example 1A, substituting 4-fluoroaniline for aniline (4.78 g, 93% yield).

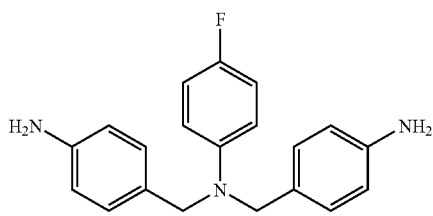

EXAMPLE 13B

N,N-bis(4-aminobenzyl)-4-fluoroaniline

Example 13B was prepared from the product from Example 13A by method A used to prepare Example 1B (0.548 g, 100% yield).

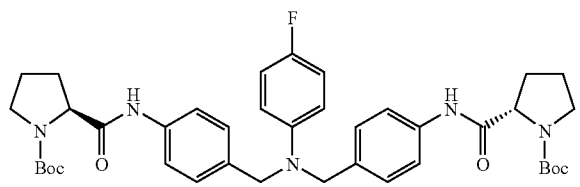 [SMILES: CC(C)(C)OC(=O)N1CCC[C@H]1C(=O)Nc1ccc(CN(Cc2ccc(NC(=O)[C@@H]3CCCN3C(=O)OC(C)(C)C)cc2)c2ccc(F)cc2)cc1]

EXAMPLE 13C (2S,2'S)-tert-Butyl 2,2'-(4,4'-(4-fluorophenylazanediyl)bis(methylene)bis(4,1-phenylene)bis(azanediyl))bis(oxomethylene)dipyrrolidine-1-carboxylate Example 13C was prepared from the product from Example 13B by the methods used to prepare Example 1C (0.650 g, 53.3% yield).

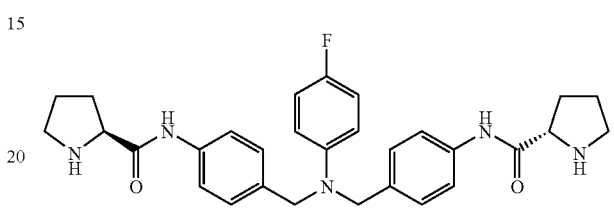

EXAMPLE 13D (2S,2'S)-N,N'-(4,4'-(4-fluorophenylazanediyl)bis(methylene)bis(4,1-phenylene))dipyrrolidine-2-carboxamide Example 13D was prepared from the product from Example 13C by the methods used to prepare Example 1D (0.650 g, 53.3% yield).

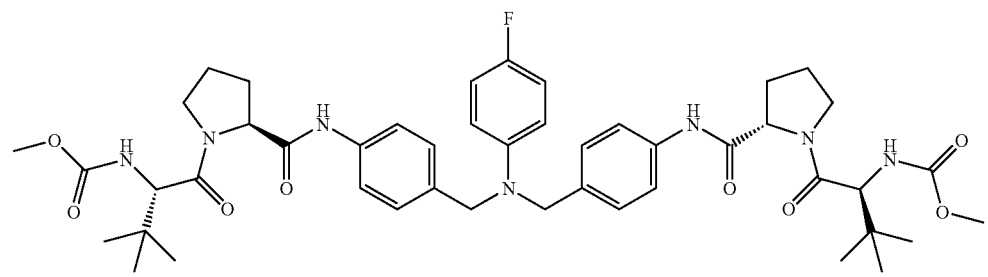

EXAMPLE 13E

Dimethyl (2S,2'S)-1,1'-(2S,2'S)-2,2'-(4,4'-(4-fluorophenylazanediyl)bis(methylene)bis(4,1-phenylene)bis(azanediyl))bis(oxomethylene)bis(pyrrolidine-2,1-diyl))bis(3,3-dimethyl-1-oxobutane-2,1-diyl) dicarbamate To a mixture of the product from Example 13D (0.100 g, 0.194 mmol), (S)-2-(methoxycarbonylamino)-3,3-dimethylbutanoic acid (0.111 g, 0.388 mmol), and HATU (0.162 g, 0.427 mmol) in DMF (2.0 ml) was added Hunig's base (0.134 ml, 0.766 mmol), and the reaction was stirred at room temperature for 30 minutes. The reaction was partitioned between water and EtOAc. The organic phase washed with brine, dried (Na$_2$SO$_4$), filtered, and concentrated. The residue was purified by chromatography on silica gel eluting with 0-3% MeOH in CH$_2$Cl$_2$) to provide the title compound (0.071 g, 42.7% yield). $^1$H NMR (500 MHz, DMSO-D6) δ ppm 0.96 (s, 18 H), 1.81-1.90 (m, 4 H), 1.94-2.02 (m, 2 H), 2.11-2.18 (m, 2 H), 3.54 (s, 6 H), 3.61-3.66 (m, 2 H), 3.75-3.81 (m, 2 H), 4.21 (d, J=8.85 Hz, 2 H), 4.43 (dd, J=8.24, 5.49 Hz, 2 H), 4.55 (s, 4 H), 6.64 (dd, J=9.31, 4.43 Hz, 2 H), 6.91 (dd, J=9.00, 9.00 Hz, 2 H), 7.09 (br d, J=8.85 Hz, 2 H), 7.15 (d, J=8.55 Hz, 4 H), 7.51 (d, J=8.54 Hz, 4 H), 9.99 (br s, 2 H).

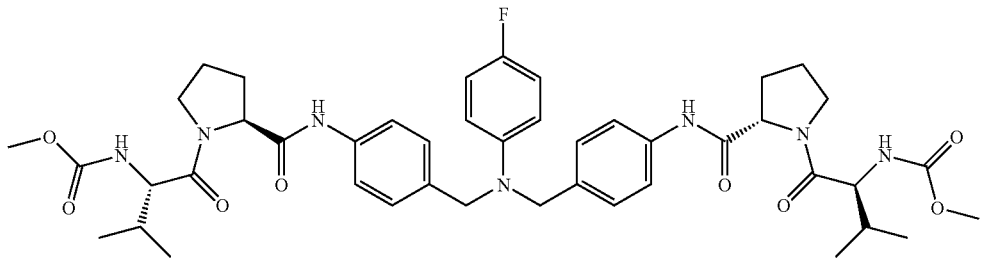

EXAMPLE 14

Dimethyl (2S,2'S)-1,1'-(2S,2'S)-2,2'-(4,4'-(4-fluorophenylazanediyl)bis(methylene)bis(4,1-phenylene) bis(azanediyl))bis(oxomethylene)bis(pyrrolidine-2, 1-diyl))bis(3-methyl-1-oxobutane-2,1-diyl) dicarbamate The product from Example 13D was reacted with (S)-2-(methoxycarbonylamino)-3-methylbutanoic acid by the methods used to prepare Example 13E to give the title compound (0.108 g, 67.1% yield). $^1$H NMR (500 MHz, DMSO-D6) δ ppm 0.87 (d, J=6.57 Hz, 6 H), 0.93 (d, J=6.72 Hz, 6 H), 1.84-2.02 (m, 8 H), 2.11-2.17 (m, 2 H), 3.52 (s, 6 H), 3.60-3.64 (m, 2 H), 3.77-3.83 (m, 2 H), 4.02 (dd, J=8.39, 8.39 Hz, 2 H), 4.43 (dd, J=8.24, 4.88 Hz, 2 H), 4.55 (s, 4 H), 6.63 (dd, J=9.31, 4.43 Hz, 2 H), 6.91 (dd, J=9.0, 9.0 Hz, 2 H), 7.16 (d, J=8.54 Hz, 4 H), 7.32 (d, J=8.40, 2 H), 7.51 (d, J=8.54 Hz, 4 H), 9.98 (s, 2 H).

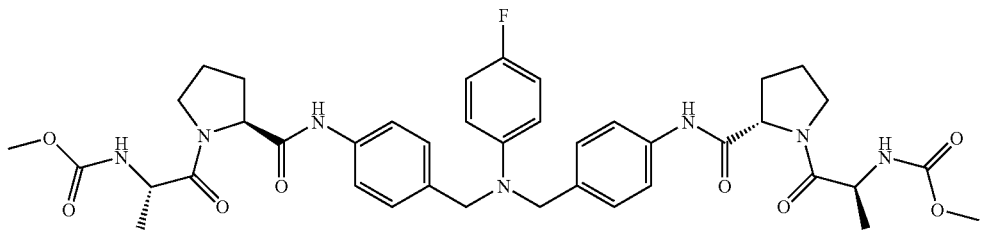

EXAMPLE 15

Dimethyl (2S,2'S)-1,1'-(2S,2'S)-2,2'-(4,4'-(4-fluorophenylazanediyl)bis(methylene)bis(4,1-phenylene)bis(azanediyl))bis(oxomethylene)bis(pyrrolidine-2,1-diyl))bis(1-oxopropane-2,1-diyl)dicarbamate The product from Example 13D was reacted with (S)-2-(methoxycarbonylamino)propanoic acid by the methods used to prepare Example 13E to give the title compound (0.083 g, 55.3% yield). $^1$H NMR (500 MHz, DMSO-D6) δ ppm 1.18 (d, J=7.48, 6 H), 1.83-1.94 (m, 4 H), 1.97-2.02 (m, 2 H), 2.09-2.15 (m, 2 H), 3.51 (s, 6 H), 3.56-3.60 (m, 2 H), 3.64-3.69 (m, 2 H), 4.28-4.34 (m, 2 H), 4.40-4.42 (dd, J=8.39, 4.57 Hz, 2 H), 4.55 (s, 4 H), 6.63 (dd, J=9.46, 4.58 Hz, 2 H), 6.91 (dd, J=9.00, 9.00 Hz, 2 H), 7.16 (d, J=8.55, 4 H), 7.35 (d, J=7.47 Hz, 2 H), 7.50 (d, J=8.55 Hz, 4 H), 9.92 (s, 2 H).

EXAMPLE 17

Dimethyl (2S,2'S)-1,1'-((2S,2'S)-2,2'-(5,5'-(phenylazanediyl)bis(methylene)bis(1H-benzo[d]imidazole-5,2-diyl))bis(pyrrolidine-2,1-diyl))bis(3-methyl-1-oxobutane-2,1-diyl)dicarbamate Combined the product from Example 7E (17.4 mg, 0.035 mmol), HATU (33.6 mg, 0.088 mmol), and (S)-2-(methoxycarbonylamino)-3-methylbutanoic acid (15.50 mg, 0.088 mmol) in DMSO (0.18 mL) and added Hunig's Base (37.1 µl,

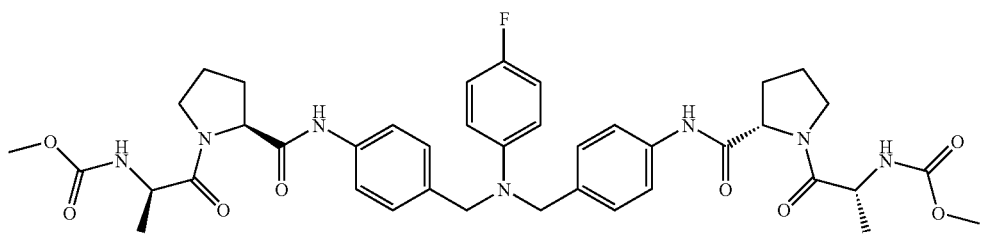

EXAMPLE 16

Dimethyl (2R,2'R)-1,1'42S fluorophenylazanediyl)bis(methylene)bis(4,1-phenylene)bis(azanediyl))bis(oxomethylene)bis(pyrrolidine-2,1-diyl))bis(1-oxopropane-2,1-diyl)dicarbamate The product from Example 13D was reacted with (R)-2-(methoxycarbonylamino)propanoic acid by the methods used to prepare Example 13E to give the title compound (0.152 g, 72.9% yield). $^1$H NMR (500 MHz, BENZENE-D6) δ ppm 0.97 (d, J=6.56 Hz, 6 H), 1.19-1.29 (m, 2 H), 1.58-1.68 (m, 2 H), 2.30-2.33 (m, 2 H), 2.49-2.53 (m, 2 H), 3.02-3.06 (m, 2 H), 3.37 (s, 6 H), 4.09 (s, 4 H), 4.14-4.17 (m, 2 H), 4.52 (br d, J=7.33 Hz, 2 H), 5.51 (br s, 2 H), 6.43 (dd, J=9.31, 4.43 Hz, 2 H), 6.77 (dd, J=8.70, 8.70 Hz, 2 H), 6.95-7.00 (m, 6 H), 7.95 (d, J=8.09 Hz, 4 H), 9.43 (br s, 2 H).

0.212 mmol). The mixture was stirred at room temperature for 1 h, poured into water, and extracted with EtOAc. Dried organic over Na$_2$SO$_4$, filtered, and evaporated. The product was purified by chromatography (C18), eluting with 10-100% acetonitrile in water (0.1% TFA) to give the title compound (14.0 mg, 49.1% yield) as a TFA salt. $^1$H NMR (500 MHz, DMSO-D6) δ ppm 14.50 (br s, 2 H) 7.70 (d, J=8.39 Hz, 2 H) 7.54 (s, 2 H) 7.39 (d, J=7.17 Hz, 2 H) 7.33 (d, J=8.55 Hz, 2 H) 7.07-7.12 (m, 2 H) 6.73 (d, J=8.09 Hz, 2 H) 6.61 (t, J=7.25 Hz, 1 H) 5.20 (dd, J=8.01, 5.42 Hz, 2 H) 4.84-4.96 (m, 4 H) 4.11 (t, J=8.01 Hz, 2 H) 3.81-3.90 (m, 4 H) 3.54 (s, 6 H) 2.15-2.22 (m, 2 H) 2.02-2.15 (m, 4 H) 1.92-2.01 (m, 2 H) 0.74-0.89 (m, 14 H).

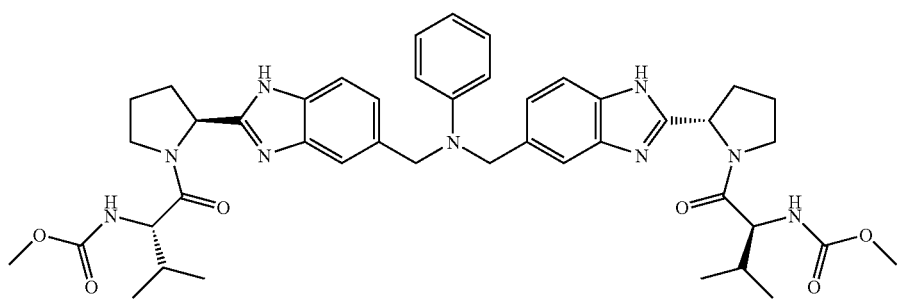

131

EXAMPLE 18

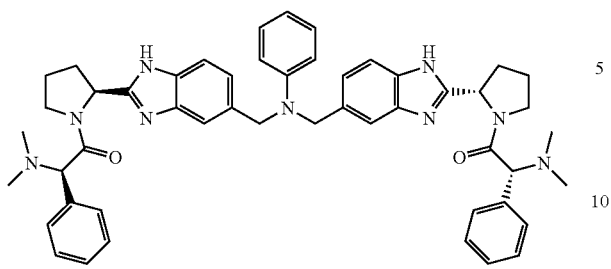

(2R,2'R)-1,1'-((2S,2'S)-2,2'-(5,5'-(phenylazanediyl)bis(methylene)bis(1H-benzo[d]imidazole-5,2-diyl))bis(pyrrolidine-2,1-diyl))bis(2-(dimethylamino)-2-phenylethanone)

The product from Example 7E was reacted with (R)-2-(dimethylamino)-2-phenylacetic acid by the methods used to prepare Example 17 to give the title compound (0.041 g, 54.2% yield) as a TFA salt. $^1$H NMR (500 MHz, DMSO-D6) δ ppm 9.90-10.40 (m, 2 H) 7.47-7.70 (m, 12 H) 6.90-7.44 (m, 4 H) 6.68-6.80 (m, 4 H) 6.56-6.66 (m, 1 H) 4.78-5.81 (m, 8 H) 4.01 (s, 12 H) 2.83-3.12 (m, 4 H) 1.87-2.28 (m, 8 H).

132

EXAMPLE 19

Dimethyl (2S,2'S)-1,1'-((2S,2'S)-2,2'-(4,4'-(4-dimethyl (2S,2'S)-1,1'-((2S,2'S)-2,2'-(4,4'-(thiazol-2-ylazanediyl)bis(methylene)bis(4,1-phenylene))bis(azanediyl)bis(oxomethylene)bis(pyrrolidine-2,1-diyl))bis(3,3-dimethyl-1-oxobutane-2,1-diyl) dicarbamate

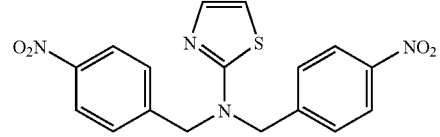

EXAMPLE 19A

N,N-bis(4-nitrobenzyl)thiazol-2-amine

Example 19A was prepared by the methods used to prepare Example 1A, substituting 2-aminothiazole for aniline (0.915 g, 42.9% yield).

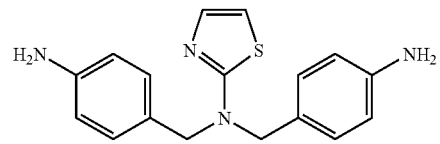

EXAMPLE 19B

N,N-bis(4-aminobenzyl)thiazol-2-amine

Example 19B was prepared from the product from Example 19A by method A used to prepare Example 1B (0.211 g, 56.2% yield).

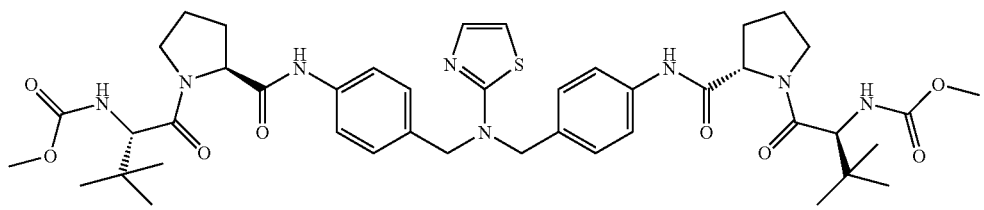

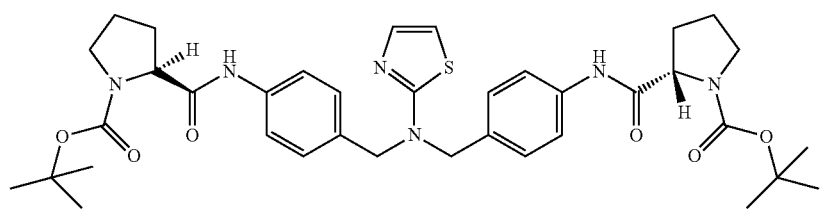

EXAMPLE 19C (2S,2'S)-tert-butyl 2,2'-(4,4'-(thiazol-2-ylazanediyl)bis(methylene)bis(4,1-phenylene))bis(azanediyl)bis(oxomethylene)dipyrrolidine-1-carboxylate Example 19C was prepared from the product from Example 19B by the methods used to prepare Example 1C (0.25 g, 52.2% yield).

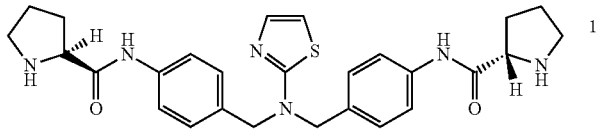

EXAMPLE 19D (2S,2'S)-N,N'-(4,4'-(thiazol-2-ylazanediyl)bis(methylene)bis(4,1-phenylene))dipyrrolidine-2-carboxamide Example 19D was prepared from the product from Example 19C by the methods used to prepare Example 1D (0.058 g, 32.5% yield).

EXAMPLE 19E

Dimethyl (2S,2'S)-1,1'-((2S,2'S)-2,2'-(4,4'-(4-dimethyl (2S,2'S)-1,1'-(2S,2'S)-2,2'-(4,4'- (thiazol-2-ylazanediyl)bis(methylene)bis(4,1-phenylene))bis(azanediyl)bis(oxomethylene)bis(pyrrolidine-2,1-diyl))bis(3,3-dimethyl-1-oxobutane-2,1-diyl) dicarbamate To a mixture of the product from Example 19D (0.0581 g, 0.115 mmol), (S)-2-(methoxycarbonylamino)-3,3-dimethylbutanoic acid (0.0529 g, 0.280 mmol), and HATU (0.100 g, 0.264 mmol) in CH$_2$Cl$_2$ (2.5 ml) was added Hunig's base (0.08 mL, 0.462 mmol), and the reaction was stirred at room temperature for 2 h. The reaction was washed with water and the organic phase dried (MgSO$_4$), filtered, and concentrated. The residue was purified by chromatography on silica gel, eluting with 0-5% MeOH in CH$_2$Cl$_2$ to provide the title compound (0.047 g, 48.3% yield). $^1$H NMR (500 MHz, BENZENE-D6) δ 1.00 (d, J=8.2, 18H), 1.75-1.10 (m, 6H), 2.13-1.98 (m, 2H), 3.25-3.14 (m, 2H), 3.40-3.31 (m, 2H), 3.42 (s, 3H), 3.44 (s, 3H), 4.20 (s, 1H), 4.31 (d, J=13.8, 1H), 4.49 (dd, J=24.6, 15.4, 4H), 4.65 (dd, J=7.6, 5.3, 1H), 4.78 (dd, J=7.8, 4.7, 1H), 5.28 (d, J=4.4, 1H), 5.52 (d, J=11.0, 1H), 5.56 (d, J=8.9, 1H), 5.79 (d, J=4.5, 1H), 6.84 (d, J=8.3, 2H), 7.66 (d, J=8.4, 2H), 7.81 (d, J=8.4, 2H), 9.77 (s, 1H), 9.88 (s, 1H).

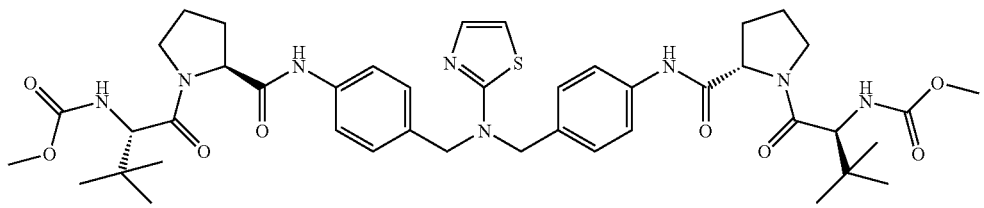

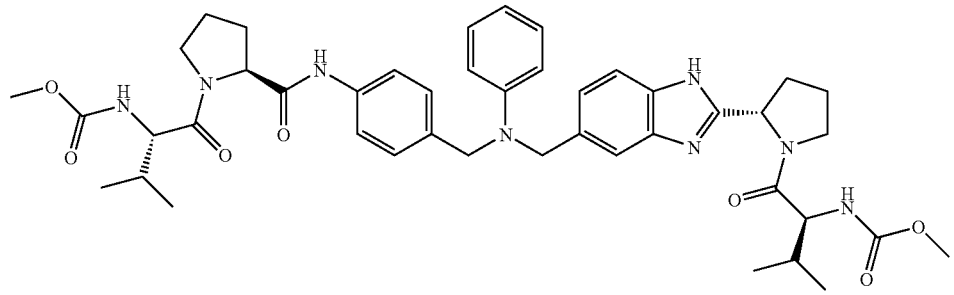

EXAMPLE 20

Methyl (S)-1-((S)-2-(5-(((4-(S)-1-((S)-2-(methoxy-carbonylamino)-3-methylbutanoyl)pyrrolidine-2-carboxamido)benzyl)(phenyl)amino)methyl)-1H-benzo[d]imidazol-2-yl)pyrrolidin-1-yl)-3-methyl-1-oxobutan-2-ylcarbamate

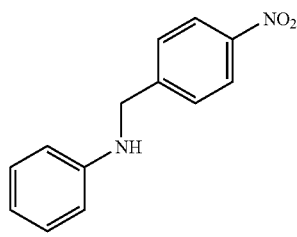 [SMILES: O=[N+]([O-])c1ccc(CNc2ccccc2)cc1]

EXAMPLE 20A

N-(4-nitrobenzyl)aniline

Combined aniline (6.16 g, 66.2 mmol) and 4-nitrobenzaldehyde (10.0 g, 66.2 mmol) in MeOH (165 mL) and toluene (165 mL), and heated to 60° C. for 3 h. Cooled the mixture to room temperature, added sodium borohydride (5.01 g, 132 mmol) portionwise, and then stirred at room temperature for 1 h. Added sat NaHCO3 and stirred for 1 h. Added water and extracted with EtOAc. Combined extracts were washed with brine, dried (MgSO$_4$) filtered, and evaporated to an amber oil that was purified by chromatography on silica gel, eluting with CH$_2$Cl$_2$ to give the title compound (9.0 g, 59.6% yield).

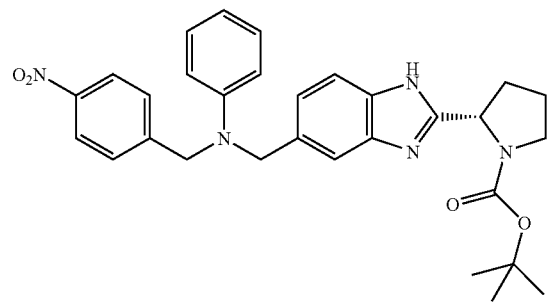 [SMILES: CC(C)(C)OC(=O)N1CCC[C@H]1c1nc2cc(CN(Cc3ccc([N+](=O)[O-])cc3)c3ccccc3)ccc2[nH]1]

EXAMPLE 20B (S)-tert-butyl 2-(5-(((4-nitrobenzyl)(phenyl)amino)methyl)-1H-benzo[d]imidazol-2-yl)pyrrolidine-1-carboxylate The product from Example 20A (0.530 g, 2.32 mmol) and K2CO$_3$ (0.802 g, 5.81 mmol) were combined in dry DMF (20 mL) at room temperature, and nitrogen was bubbled through the solution for 10 min. The product from Example 7C (1.0 g, 2.63 mmol) was added in three equal portions in 20 min. intervals, and the reaction was stirred a total of 2.5 h. The mixture was poured into water, extracted into EtOAc, washed with brine. The organic was dried (MgSO$_4$), filtered and evaporated. The product was purified by chromatography on silica gel, eluting with c 0-4% MeOH in CH$_2$Cl$_2$, and a second column eluting with 0-5% EtOAc in CH$_2$Cl$_2$ to give the title compound (0.350 g, 28.6% yield).

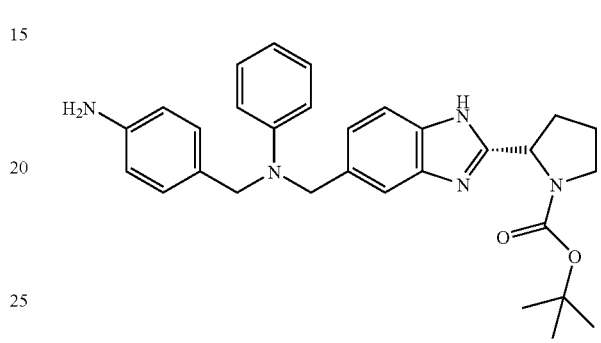

EXAMPLE 20C (S)-tert-butyl 2-(5-(((4-aminobenzyl)(phenyl)amino)methyl)-1H-benzo[d]imidazol-2-yl)pyrrolidine-1-carboxylate Example 20C was prepared from the product from Example 20B by method A used to prepare Example 1B.

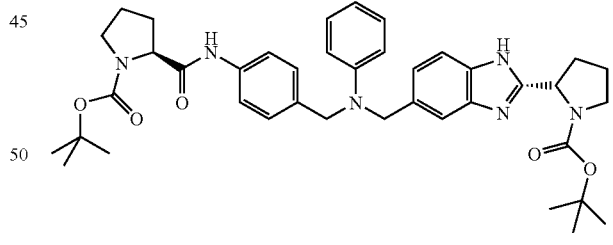

EXAMPLE 20D (S)-tert-butyl 2-(4-(((((2-((S)-1-(tert-butoxycarbonyl)pyrrolidin-2-yl)-1H-benzo[d]imidazol-5-yl)methyl)(phenyl)amino)methyl)phenylcarbamoyl)pyrrolidine-1-carboxylate Example 20D was prepared from the product from Example 20C by the methods used to prepare Example 1C (0.15 g, 38.1% yield).

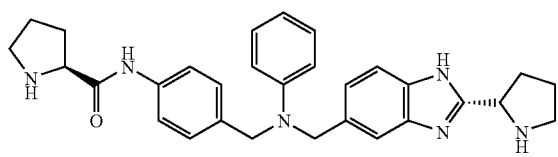

EXAMPLE 20E (S)-N-(4-((phenyl((2-((S)-pyrrolidin-2-yl)-1H-benzo[d]imidazol-5-yl)methyl)amino)methyl)phenyl)pyrrolidine-2-carboxamide Example 20E was prepared from the product from Example 20D by the methods used to prepare Example 1D (0.082 g, 77% yield).

EXAMPLE 20F

Methyl (S)-1-((S)-2-(5-(((4-(S)-1-((S)-2-(methoxycarbonylamino)-3-methylbutanoyl)pyrrolidine-2-carboxamido)benzyl)(phenyl)amino)methyl)-1H-benzo[d]imidazol-2-yl)pyrrolidin-1-yl)-3-methyl-1-oxobutan-2-ylcarbamate Example 20F was prepared from the product from Example 20E and (S)-2-(methoxycarbonylamino)-3-methylbutanoic acid by the methods used to prepare Example 10B. The title compound was purified by chromatography on silica gel, eluting with 0-5% MeOH in $CH_2Cl_2$, followed by 10-60% EtOAc in $CH_2Cl_2$ (containing 0.5% NH4OH) (0.044

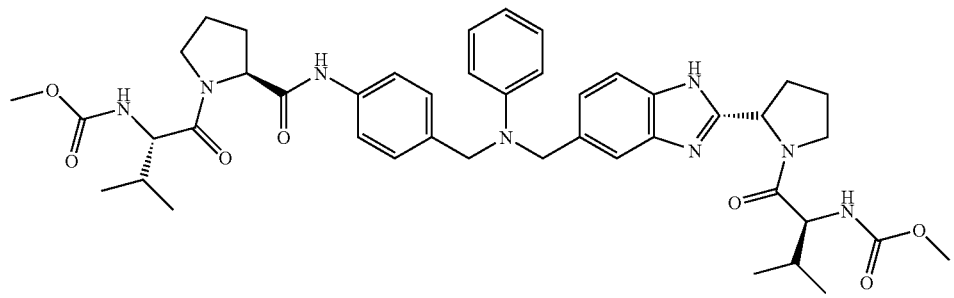

g, 32.8% yield). $^1$H NMR (500 MHz, DMSO-D6) δ ppm 0.76 (d, J=6.71 Hz, 3 H) 0.78 (dd, J=6.71, 2.75 Hz, 3 H) 0.83 (d, J=7.32 Hz, 3 H) 0.88 (d, J=6.71 Hz, 3 H) 1.23-1.53 (m, 1 H) 1.78-1.91 (m, 4 H) 1.91-1.99 (m, 2 H) 2.05-2.17 (m, 4 H) 3.48 (d, J=5.19 Hz, 6 H) 3.54-3.60 (m, 1 H) 3.72-3.79 (m, 2 H) 3.92-4.04 (m, 2 H) 4.38 (dd, J=8.09, 4.88 Hz, 1 H) 4.56 (s, 2 H) 4.68 (d, J=10.99 Hz, 2 H) 5.05-5.12 (m, 1 H) 6.51 (td, J=7.21, 4.04 Hz, 1 H) 6.64 (d, J=8.24 Hz, 2 H) 6.96-7.05 (m, 3 H) 7.14 (dd, J=8.62, 2.21 Hz, 2 H) 7.20 (s, 1 H) 7.22-7.30 (m, 2 H) 7.35 (dd, J=35.78, 8.32 Hz, 1 H) 7.46 (dd, J=8.62, 1.75 Hz, 2 H) 9.94 (s, 1 H) 11.98 (d, J=26.25 Hz, 1 H).

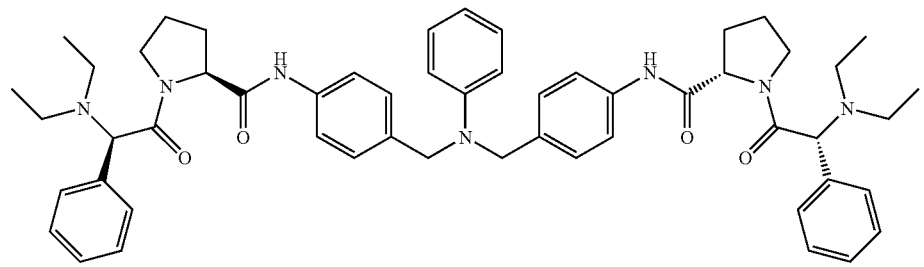 [SMILES: CCN(CC)[C@@H](C(=O)N1CCC[C@H]1C(=O)Nc1ccc(CN(Cc2ccc(NC(=O)[C@@H]3CCCN3C(=O)[C@@H](c3ccccc3)N(CC)CC)cc2)c2ccccc2)cc1)c1ccccc1]

EXAMPLE 21

(R,2S,2'S)-N,N'-(4,4'-(phenylazanediyl)bis(methylene)bis(4,1-phenylene))bis(1-((R)-2-(diethylamino)-2-phenylacetyl)pyrrolidine-2-carboxamide)

Example 21 was prepared from the product from Example 1D and (R)-2-(diethylamino)-2-phenylacetic acid by the methods used to prepare Example 10B. The title compound was purified by chromatography on silica gel, eluting with 0-5% MeOH in CH$_2$Cl$_2$ (9.0 mg, 14.6% yield). $^1$H NMR (500 MHz, DMSO-D6) δ ppm 0.96 (t, J=7.10 Hz, 12 H) 1.81-1.96 (m, 4 H) 2.00-2.07 (m, 2 H) 2.08-2.17 (m, 2 H) 2.49-2.56 (m, 4 H) 2.63-2.72 (m, 4 H) 3.42-3.47 (m, 2 H) 3.82-3.89 (m, 2 H) 4.45 (dd, J=8.16, 4.50 Hz, 2 H) 4.67 (s, 4 H) 4.74 (s, 2 H) 6.64 (t, J=7.25 Hz, 1 H) 6.74 (d, J=7.93 Hz, 2 H) 7.12-7.18 (m, 2 H) 7.26 (d, J=8.54 Hz, 4 H) 7.34 (t, J=7.17 Hz, 2 H) 7.40 (t, J=7.40 Hz, 4 H) 7.47 (d, J=7.17 Hz, 4 H) 7.59 (d, J=8.54 Hz, 4 H) 10.03 (s, 2 H).

EXAMPLE 22 dimethyl (2S,2'S,3S,3'S)-1,1'-((2S,2'S)-2,2'-(5,5'-(phenylazanediyl)bis(methylene)bis(1H-benzo[d]imidazole-5,2-diyl))bis(pyrrolidine-2,1-diyl))bis(3-methyl-1-oxopentane-2,1-diyl)dicarbamate To a solution of the product from Example 7E (12 mg, 0.024 mmol), (2S,3S)-2-(methoxycarbonylamino)-3-methylpentanoic acid (9.70 mg, 0.051 mmol), and HATU (19.49 mg, 0.051 mmol) in anhydrous DMSO (0.2 ml) was added Hunig's Base (0.013 ml, 0.073 mmol), and the resulting mixture was stirred at rt for 90 min. The mixture was partitioned between water (2 ml) and EtOAc (3×2 ml) and the combined organic layers were dried over Na$_2$SO$_4$. The mixture was filtered and concentrated in vacuo, and the crude product was

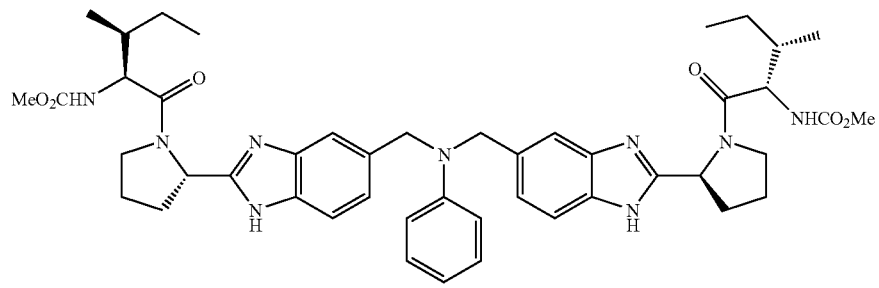

purified by chromatography on silica gel (C18) eluting with a gradient of 10-100% ACN in water (0.1% TFA). Fractions containing pure product were pooled and concentrated in vacuo to give the title compound as a solid (9 mg, 31.4%) as a TFA salt. $^1$H NMR (500 MHz, DMSO-D6) δ ppm 14.70 (br s, 2 H) 7.73 (d, J=8.39 Hz, 2 H) 7.56 (s, 2 H) 7.43 (d, J=8.39 Hz, 2 H) 7.38 (d, J=8.70 Hz, 2 H) 7.07-7.12 (m, 2 H) 6.73 (d, J=8.09 Hz, 2 H) 6.61 (t, J=7.25 Hz, 1 H) 5.21 (dd, J=8.16, 5.57 Hz, 2 H) 4.91 (s, 4 H) 4.11-4.18 (m, 2 H) 3.82-3.94 (m, 4H) 3.54 (s, 6 H) 2.01-2.26 (m, 8 H) 1.64-1.77 (m, 2 H) 1.27-1.37 (m, 2 H) 0.96-1.10 (m, 2 H) 0.71-0.90 (m, 12 H).

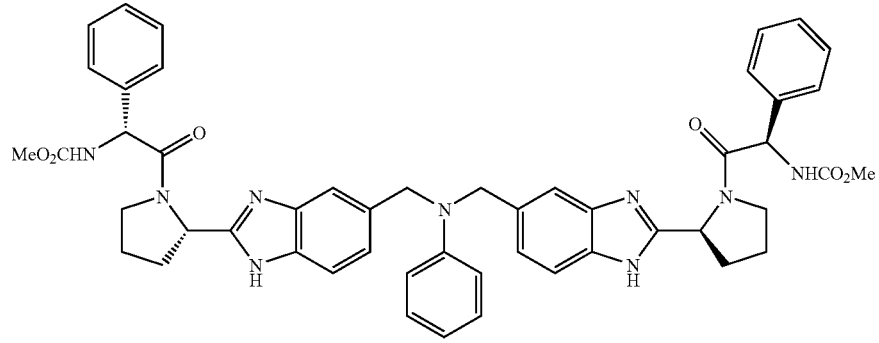

EXAMPLE 23 dimethyl (1R,1R)-2,2'-((2S,2'S)-2,2'-(5,5'-(phenyla-zanediyl)bis(methylene)bis(1H-benzo[d]imidazole-5,2-diyl))bis(pyrrolidine-2,1-diyl))bis(2-oxo-1-phenylethane-2,1-diyl)dicarbamate To a mixture of the product from Example 7E (12 mg, 0.024 mmol), (R)-2-(methoxycarbonylamino)-2-phenylacetic acid (10.72 mg, 0.051 mmol), and HATU (19.49 mg, 0.051 mmol) in anhydrous DMSO (0.2 ml) was added Hunig's Base (0.013 ml, 0.073 mmol), and the resulting mixture was stirred at rt for 90 min. Partitioned between water (2 mL) and EtOAc (2×2 mL) and dried the combined organic layers over Na$_2$SO$_4$. Filtered and conc. in vacuo. The crude product was purified by chromatography on silica gel (C18) eluting with a gradient of 10-100% acetonitrile in water (0.1% TFA). Pure fractions were pooled and concentrated in vacuo to give the title compound as a solid (13 mg, 43.8%) as a TFA salt. $^1$H NMR (500 MHz, DMSO-D6) δ ppm 14.50 (br s, 2 H) 6.87-7.88 (m, 18 H) 6.56-6.79 (m, 3 H) 5.36-5.58 (m, 2 H) 5.22-5.35 (m, 2 H) 4.94 (s, 4 H) 3.69-3.99 (m, 4 H) 3.46-3.56 (m, 6 H) 3.13-3.26 (m, 2 H) 1.86-2.34 (m, 8 H).

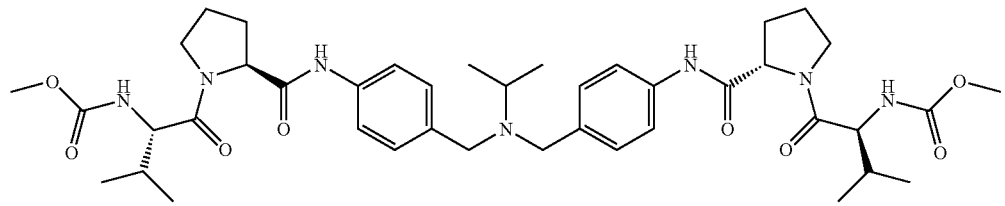

EXAMPLE 24 dimethyl ([(1-methylethyl)imino]bis{methanediylbenzene-4,1-diylcarbamoyl(2S)pyrrolidine-2,1-diyl[(2S)-3-methyl-1-oxobutane-1,2-diyl]})biscarbamate

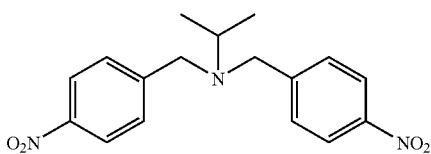

EXAMPLE 24A

N,N-bis(4-nitrobenzyl)propan-2-amine

A mixture of bis(4-nitrobenzyl)amine (50 mg, 0.174 mmol) and acetone (51.1 µL, 0.696 mmol) in methanol (752 µL)/acetic acid (39.6 µL)/CH$_2$Cl$_2$ (79 µL) was stirred at room temperature for 1 hour. The reaction was cooled to 0° C. and sodium cyanoborohydride (32.8 mg, 0.522 mmol) was added. The mixture was stirred at 0° C. for 1 hour, and allowed to warm to rt and stirred overnight. The reaction was concentrated and the residue was partitioned between EtOAc and saturated aqueous NaHCO$_3$. The organic layer was washed with brine, dried (Na$_2$SO$_4$), filtered and concentrated in vacuo. Purification by flash chromatography (silica gel, 50% EtOAc/hexane) afforded the title product (42.8 mg, 75%). MS (ESI) m/z 329.9 (M+H)$^+$.

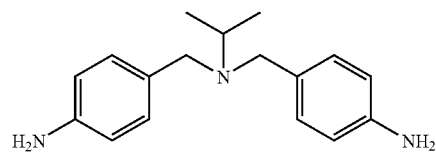 [SMILES: CC(C)N(Cc1ccc([N+](=O)[O-])cc1)Cc1ccc([N+](=O)[O-])cc1]

EXAMPLE 24B 4-(((4-aminobenzyl)(isopropyl)amino)methyl)aniline

To a solution of the product from Example 24A (42.8 mg, 0.130 mmol) in ethanol (1.3 mL) under a N$_2$ atmosphere was added bismuth trichloride (0.026 mL, 0.39 mmol). The mixture was cooled in a cold-water bath, and sodium borohydride (79 mg, 2.079 mmol) was slowly added portion-wise over several minutes. When the addition was complete, the resulting mixture was stirred at rt for 1 hour, and then filtered through celite and rinsed with methanol. The filtrate was concentrated to ~½ volume, diluted with 1:3 isopropyl alcohol:CH$_2$Cl$_2$, and washed with saturated aqueous NaHCO$_3$. The organic layer was dried (Na$_2$SO$_4$), filtered and concentrated in vacuo to give the title compound (31.9 mg). MS (APCI) m/s 270.5 (M+H)$^+$.

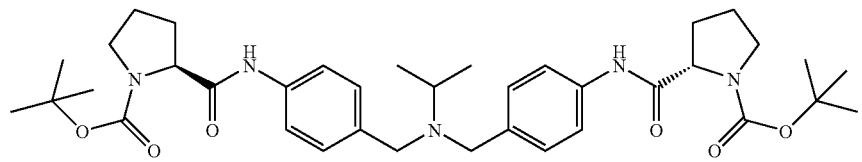 [SMILES: CC(C)N(Cc1ccc(NC(=O)[C@@H]2CCCN2C(=O)OC(C)(C)C)cc1)Cc1ccc(NC(=O)[C@@H]2CCCN2C(=O)OC(C)(C)C)cc1]

EXAMPLE 24C (2S,2'S)-tert-butyl 2,2'-(4,4'-(isopropylazanediyl)bis(methylene)bis(4,1-phenylene)bis(azanediyl))bis(oxomethylene)dipyrrolidine-1-carboxylate To a solution of the product from Example 24B (31.9 mg, 0.118 mmol) in anhydrous DMSO (592 µL) was added N-(tert-butoxycarbonyl)-L-proline (51 mg, 0.237 mmol), HATU (95 mg, 0.249 mmol) and Hünig's Base (83 µL, 0.474 mmol). The resulting mixture was stirred at rt for 2 hours, and was then partitioned between water and ethyl acetate. The organic layer was washed with brine, dried (Na$_2$SO$_4$), filtered and concentrated in vacuo. Purification by flash chromatography (silica gel, 50% EtOAc/hexane) afforded the title compound (24.3 mg, 31%). MS (ESI) m/z 664.4 (M+H)$^+$.

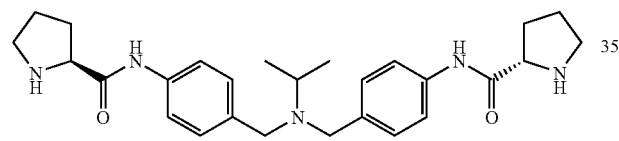

EXAMPLE 24D (2S,2'S)-N,N'-(4,4'-(isopropylazanediyl)bis(methylene)bis(4,1-phenylene))dipyrrolidine-2-carboxamide To a solution of the product from Example 24C (24.3 mg, 0.037 mmol) in CH$_2$Cl$_2$ (0.2 mL) was added trifluoroacetic acid (0.100 mL). The resulting mixture was stirred at rt for 1 hour, and was concentrated in vacuo. The residue was dissolved in a 1:3 mixture of isopropyl alcohol:CH$_2$Cl$_2$ and washed with aqueous saturated NaHCO$_3$, dried (Na$_2$SO$_4$), filtered, and concentrated in vacuo to give the title compound (10.4 mg, 61%). MS (ESI) m/z 464.2 (M+H)$^+$.

EXAMPLE 24E dimethyl ([(1-methylethyl)imino]bis{methanediylbenzene-4,1-diylcarbamoyl(2S)pyrrolidine-2,1-diyl[(2S)-3-methyl-1-oxobutane-1,2-diyl]})biscarbamate To a solution of the product from Example 24D (10.4 mg, 0.022 mmol) in anhydrous DMSO (0.15 mL) was added (S)-2-(methoxycarbonylamino)-3-methylbutanoic acid (10.61 mg, 0.056 mmol), HATU (21.3 mg, 0.056 mmol) and Hünig's Base (23.5 µL, 0.135 mmol). The resulting mixture was stirred at rt for 1 hour, and was then partitioned between water and ethyl acetate. The organic layer was washed with brine, dried (Na$_2$SO$_4$), filtered and concentrated in vacuo. Purification by C18-reverse-phase HPLC (10-90% CH$_3$CN/0.1% TFA in water) afforded the title compound as a TFA salt (7.5 mg). $^1$H NMR (500 MHz, DMSO-D6) δ ppm 0.87 (t, J=7.5 Hz, 7 H), 0.93 (d, J=6.7 Hz, 5 H), 1.34 (d, J=6.6 Hz, 6 H), 1.84-1.94 (m, 6 H), 1.95-2.04 (m, 3 H), 2.17 (td, J=7.2, 4.8 Hz, 2 H), 2.37-2.42 (m, 3 H), 3.60-3.69 (m, 6 H), 3.82 (d, J=9.5 Hz, 2 H), 4.03 (t, J=8.5 Hz, 3 H), 4.34 (d, J=13.4 Hz, 2 H), 4.42-4.46 (m, 2 H), 7.31 (d, J=8.4 Hz, 2 H), 7.40 (t, J=9.2 Hz, 4 H), 7.64 (dd, J=8.7, 2.0 Hz, 4 H), 9.10 (s, 1 H), 10.21 (s, 2 H); MS (ESI) m/z 778.4 (M–H)$^+$.

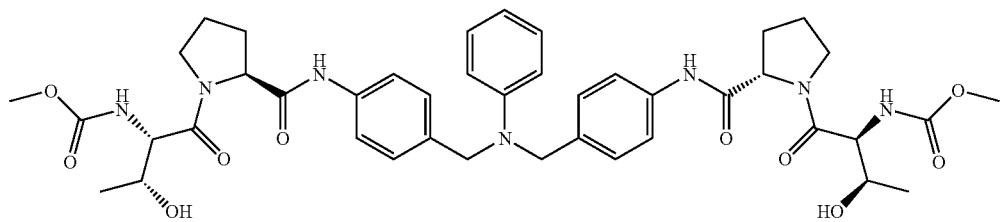

EXAMPLE 25 dimethyl[(phenylimino)bis{methanediylbenzene-4,1-diylcarbamoyl(2S)pyrrolidine-2,1-diyl[(2S,3R)-3-hydroxy-1-oxobutane-1,2-diyl]}]biscarbamate

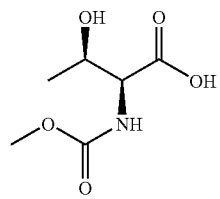

EXAMPLE 25A (2S,3R)-3-hydroxy-2-(methoxycarbonylamino)butanoic acid

L-Threonine (0.50 g, 4.2 mmol) and sodium bicarbonate (1.13 g, 13.4 mmol) were dissolved into water (20 mL) then cooled in an ice bath. Methyl chloroformate (0.36 mL, 4.62 mmol) was dissolved in diethyl ether (2 mL) and added dropwise with vigorous stirring. The solution was stirred at ambient temperature for 5 hours then adjusted to pH 3 with concentrated hydrochloric acid and extracted into ethyl acetate. The organic solution was dried over sodium sulfate, filtered, and concentrated to give 0.12 g of the title compound as a waxy solid.

EXAMPLE 25B dimethyl[(phenylimino)bis{methanediylbenzene-4,
1-diylcarbamoyl(2S)pyrrolidine-2,1-diyl[(2S,3R)-3-
hydroxy-1-oxobutane-1,2-diyl]}]biscarbamate The product from Example 25A (0.027 g, 0.16 mmol) and the product from Example 1D (0.035 g, 0.07 mmol) were combined in dimethylsulfoxide (1.5 mL) at ambient temperature and treated with diisopropylethylamine (0.061 mL, 0.35 mmol) followed by HATU (0.056 g, 0.15 mmol) and stirred for 45 min. The solution was diluted with water and the solid product was filtered off then purified by combi-flash 4 g silica column, eluting with 0-10% methanol in dichlomethane to give 0.025 g of the title compound as a yellow solid. $^1$H NMR (500 MHz, DMSO-D6) δ ppm 1.12 (d, J=6.41 Hz, 6 H) 1.82-1.91 (m, 4 H) 1.92-2.01 (m, 2 H) 2.09-2.17 (m, 2 H) 3.52 (s, 6 H) 3.65-3.74 (m, 2 H) 3.76-3.84 (m, 4 H) 4.20 (t, J=7.40 Hz, 2 H) 4.42 (dd, J=8.39, 4.88 Hz, 2 H) 4.57 (s, 4 H) 4.81 (d, J=5.80 Hz, 2 H) 6.55 (t, J=7.25 Hz, 1 H) 6.64 (d, J=7.93 Hz, 2 H) 7.02-7.11 (m, 4 H) 7.16 (d, J=8.54 Hz, 4 H) 7.49 (d, J=8.70 Hz, 4 H) 9.83 (s, 2 H); MS (TFA,ELSD+) m/z 816 (M+H)+.

EXAMPLE 26 dimethyl[(phenylimino)bis{methanediylbenzene-4,
1-diylcarbamoyl(2S)pyrrolidine-2,1-diyl[(2S)-3-
hydroxy-1-oxopropane-1,2-diyl]}]biscarbamate

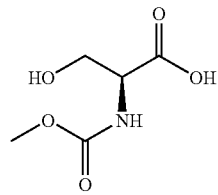

EXAMPLE 26A (S)-3-hydroxy-2-(methoxycarbonylamino)propanoic acid

L-serine (1.0 g, 9.52 mmol) was processed as in Example 25A to give 0.125 g (8%) of the title compound as a waxy solid.

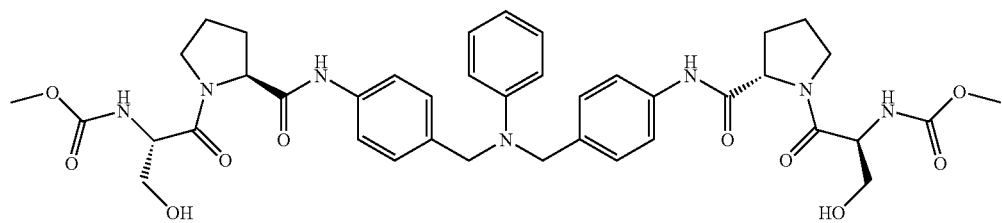

EXAMPLE 26B dimethyl [(phenylimino)bis{methanediylbenzene-4,
1-diylcarbamoyl(2S)pyrrolidine-2,1-diyl[(2S)-3-
hydroxy-1-oxopropane-1,2-diyl]}]biscarbamate The product from Example 26A (0.025 mg, 0.16 mmol) and the product from Example 1D (0.035 g, 0.07 mmol) were processed as in Example 25B to give 0.012 g (22%) of the title compound as a yellow solid. $^1$H NMR (500 MHz, DMSO-D6) δ ppm 1.87-1.97 (m, 6 H) 2.09-2.17 (m, 2 H) 3.19-3.25 (m, J=10.99 Hz, 2 H) 3.52 (s, 6 H) 3.55-3.63 (m, 2 H) 3.66-3.76 (m, 2 H) 4.08 (q, J=5.29 Hz, 2 H) 4.37-4.47 (m, 4 H) 4.57 (s, 4 H) 5.10 (s, 2 H) 6.55 (t, J=7.32 Hz, 1 H) 6.63 (d, J=8.09 Hz, 2 H) 7.02-7.08 (m, 2 H) 7.15 (d, J=8.54 Hz, 4 H) 7.31 (d, J=7.78 Hz, 2 H) 7.48 (d, J=8.54 Hz, 4 H) 9.67 (s, 2 H); MS (TFA,ELSD+) m/z 788 (M+H)+.

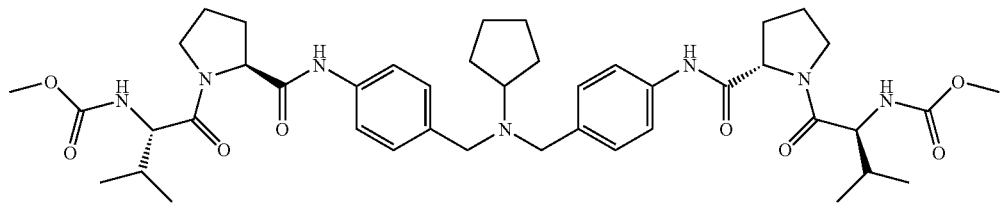

EXAMPLE 27 dimethyl[(cyclopentylimino)
bis{methanediylbenzene-4,1-diylcarbamoyl(2S)pyr-
rolidine-2,1-diyl[(2S)-3-methyl-1-oxobutane-1,2-
diyl]}]biscarbamate

EXAMPLE 27A

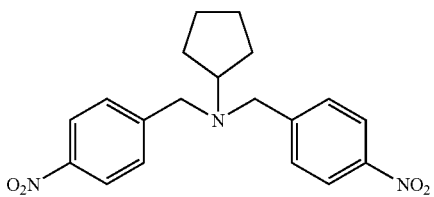 [SMILES: O=[N+]([O-])c1ccc(CN(Cc2ccc([N+](=O)[O-])cc2)C2CCCC2)cc1]

N,N-bis(4-nitrobenzyl)cyclopentanamine

To a solution of cyclopentylamine (0.148 mL, 1.5 mmol) in N,N-dimethylformamide (2 mL) was added potassium carbonate (622 mg, 4.50 mmol) followed by 1-(bromomethyl)-4-nitrobenzene (648 mg, 3.00 mmol). The resulting mixture was stirred at rt for 16 hours, more 1-(bromomethyl)-4-nitrobenzene was added (324 mg, 1.5 mmol), and stirring was continued for an additional 2 hours. The mixture was diluted with water, extracted with $CH_2Cl_2$, and the organic layer was dried ($Na_2SO_4$), filtered and concentrated. The crude product was purified by precipitation from methanol to afford the title compound (554 mg, quant.). MS (ESI) m/z 356.0 $(M+H)^+$.

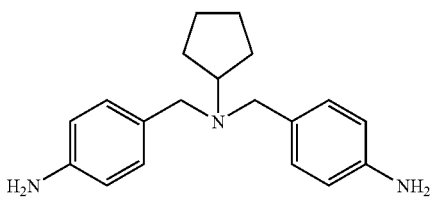

EXAMPLE 27B 4-(((4-aminobenzyl)(cyclopentyl)amino)methyl)
aniline

The product of Example 27A (231 mg, 0.65 mmol) was subjected to the method described in Example 24B to give the title compound (360 mg). MS (APCI) m/z 295.9 $(M+H)^+$.

EXAMPLE 27C (2S,2'S)-tert-butyl 2,2'-(4,4'-(cyclopentylazanediyl)
bis(methylene)bis(4,1-phenylene)bis(azanediyl))bis
(oxomethylene)dipyrrolidine-1-carboxylate The product of Example 27B (360.3 mg, 1.220 mmol) was subjected to the procedure described in Example 24C to give the title compound (427 mg, 50%). MS (ESI) m/z 690.5 $(M+H)^+$.

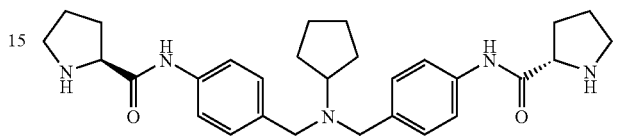

EXAMPLE 27D (2S,2'S)-N,N-(4,4'-(cyclopentylazanediyl)bis(methylene)bis(4,1-phenylene))dipyrrolidine-2-carboxamide The product of Example 27C (427.4 mg, 0.620 mmol) was subjected to the procedure described in Example 24D to give the title compound (255 mg, 84%). MS (ESI) m/z 490.2 $(M+H)^+$.

EXAMPLE 27E dimethyl[(cyclopentylimino)
bis{methanediylbenzene-4,1-diylcarbamoyl(2S)pyr-
rolidine-2,1-diyl[(2S)-3-methyl-1-oxobutane-1,2-
diyl]}]biscarbamate The product of Example 27D (50 mg, 0.102 mmol) was subjected to the procedure described in Example 24E to give the title compound as a TFA salt (11 mg). $^1H$ NMR (500 MHz, DMSO-D6) δ ppm −0.00 (s, 1 H), 0.85-0.91 (m, 8 H), 0.94 (t, J=6.0 Hz, 6 H), 1.21-1.30 (m, 1 H), 1.48-1.57 (m, 3 H), 1.71 (s, 2 H), 1.85-1.94 (m, 8 H), 1.97-2.02 (m, 4 H), 2.13-2.22 (m, 2 H), 3.77-3.87 (m, 3H), 4.03 (t, J=8.5 Hz, 2 H), 4.14 (dd, J=13.4, 5.3 Hz, 2 H), 4.26 (s, 2 H), 4.44 (dd, J=7.8, 5.2 Hz, 2 H), 7.32 (d, J=8.2 Hz, 2 H), 7.40 (t, J=8.9 Hz, 4 H), 7.62-7.67 (m, 4 H), 9.52 (s, 1 H), 10.22 (s, 2 H); MS (ESI) m/z 804.4 $(M+H)^+$.

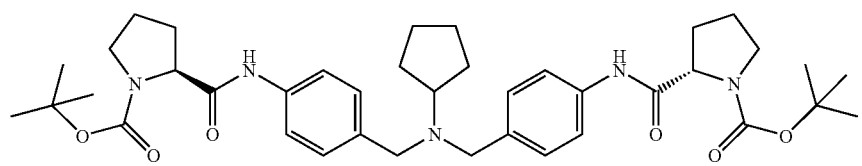 [SMILES: CC(C)(C)OC(=O)N1CCC[C@H]1C(=O)Nc1ccc(CN(Cc2ccc(NC(=O)[C@@H]3CCCN3C(=O)OC(C)(C)C)cc2)C2CCCC2)cc1]

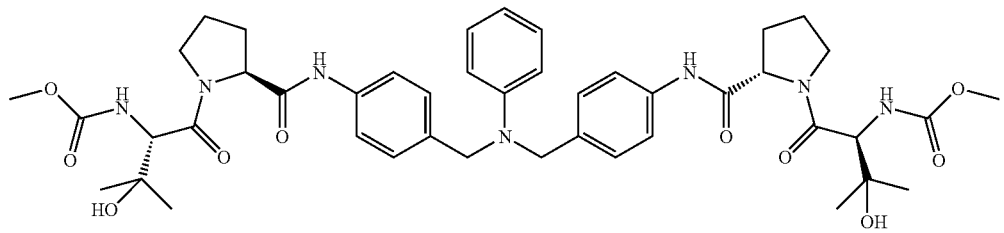

EXAMPLE 28 dimethyl [(phenylimino)bis{methanediylbenzene-4,1-diylcarbamoyl(2S)pyrrolidine-2,1-diyl[(2S)-3-hydroxy-3-methyl-1-oxobutane-1,2-diyl]}]biscarbamate

EXAMPLE 28B dimethyl [(phenylimino)bis{methanediylbenzene-4,1-diylcarbamoyl(2S)pyrrolidine-2,1-diyl[(2S)-3-hydroxy-3-methyl-1-oxobutane-1,2-diyl]}]biscarbamate The product from Example 28A (0.029 mg, 0.16 mmol) and the product from Example 1D (0.035 g, 0.07 mmol) were processed as in Example 25B to give 0.016 g (27%) of the title compound as a yellow solid. $^1$H NMR (500 MHz, DMSO-D6) δ ppm 1.14 (s, 6 H) 1.21 (s, 6 H) 1.84-1.97 (m, 6 H) 2.11-2.20 (m, 2 H) 3.54 (s, 6 H) 3.64-3.73 (m, 2 H) 3.84-3.93 (m, 2 H) 4.37 (d, J=8.70 Hz, 2 H) 4.46 (dd, J=8.62, 3.74 Hz, 2 H) 4.58 (s, 4 H) 5.09 (s, 2 H) 6.55 (t, J=7.25 Hz, 1 H) 6.63 (d, J=7.93 Hz, 2 H) 7.05 (dd, J=8.77, 7.25 Hz, 2 H) 7.14 (d, J=9.61 Hz, 2 H) 7.16 (d, J=8.70 Hz, 4 H) 7.51 (d, J=8.70 Hz, 4 H) 9.65 (s, 2 H); MS (TFA,ELSD+) m/z 844 (M+H)+.

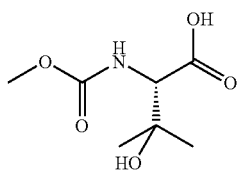

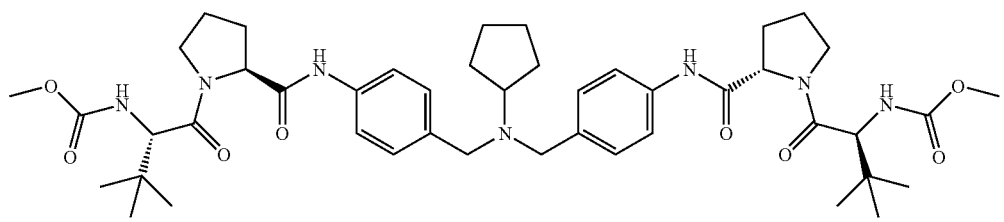

EXAMPLE 28A (S)-3-hydroxy-2-(methoxycarbonylamino)-3-methylbutanoic acid (S)-2-amino-3-hydroxy-3-methylbutanoic acid (0.52 g, 3.9 mmol) was processed as in Example 25A to give 0.55 g (74%) of the title compound as a waxy solid.

EXAMPLE 29 dimethyl[(cyclopentylimino)bis{methanediylbenzene-4,1-diylcarbamoyl(2S)pyrrolidine-2,1-diyl[(2S)-3,3-dimethyl-1-oxobutane-1,2-diyl]}]biscarbamate The product of Example 27D (50 mg, 0.102 mmol) was subjected to the procedure described in Example 24E, substituting (S)-2-(methoxycarbonylamino)-3,3-dimethylbutanoic acid for (S)-2-(methoxycarbonylamino)-3-methylbutanoic acid, to give the title compound as a TFA salt (9 mg). $^1$H NMR (500 MHz, DMSO-D6) δ ppm 0.81-0.89 (m, 2 H), 0.94-0.98 (m, 21 H), 1.49-1.57 (m, 2 H), 1.72 (d, J=3.2 Hz, 2 H), 1.84-1.93 (m, 5 H), 1.95-2.02 (m, 4 H), 2.14-2.21 (m, 2 H), 3.80 (d, J=8.9 Hz, 5 H), 4.15 (s, 3 H), 4.22 (d, J=8.7 Hz, 3 H), 4.28 (s, 1 H), 4.42-4.47 (m, 2 H), 7.09 (d, J=8.9 Hz, 2 H), 7.40 (dd, J=12.6, 8.6 Hz, 4 H), 7.65 (dd, J=8.7, 2.3 Hz, 4 H), 9.50 (s, 1 H), 10.22 (s, 2 H); MS (ESI) m/z 832.4 (M+H)$^+$.

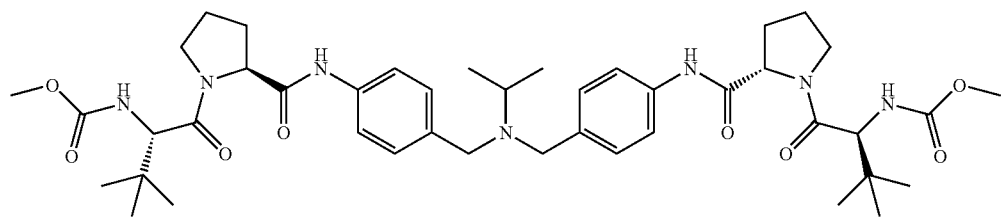

EXAMPLE 30 dimethyl ([[(1-methylethyl)imino]
bis{methanediylbenzene-4,1-diylcarbamoyl(2S)pyrrolidine-2,1-diyl[(2S)-3,3-dimethyl-1-oxobutane-1,2-diyl]})biscarbamate The product of Example 24D (60.0 mg, 0.129 mmol) was subjected to the procedure described in Example 24E, substituting (S)-2-(methoxycarbonylamino)-3,3-dimethylbutanoic acid for (S)-2-(methoxycarbonylamino)-3-methylbutanoic acid, to give the title compound as TFA salt (25 mg). $^1$H NMR (500 MHz, DMSO-D6) δ ppm 0.80-0.89 (m, 2 H), 0.91 (s, 1 H), 0.93-1.00 (m, 20 H), 1.22-1.30 (m, 2 H), 1.34 (d, J=6.6 Hz, 6 H), 1.83-1.92 (m, 4 H), 1.95-2.03 (m, 2 H), 2.13-2.22 (m, 2 H), 3.35 (s, 2 H), 4.06 (dd, J=13.4, 5.6 Hz, 4 H), 4.21 (d, J=8.9 Hz, 2 H), 4.34 (t, J=12.5 Hz, 2 H), 4.44 (d, J=6.6 Hz, 2 H), 7.09 (d, J=8.9 Hz, 2 H), 7.41 (dd, J=13.1, 8.7 Hz, 4 H), 7.64 (dd, J=8.7, 2.9 Hz, 4 H), 9.13 (s, 1 H), 10.22 (s, 2 H); MS (ESI) m/z 806.5 (M+H)$^+$.

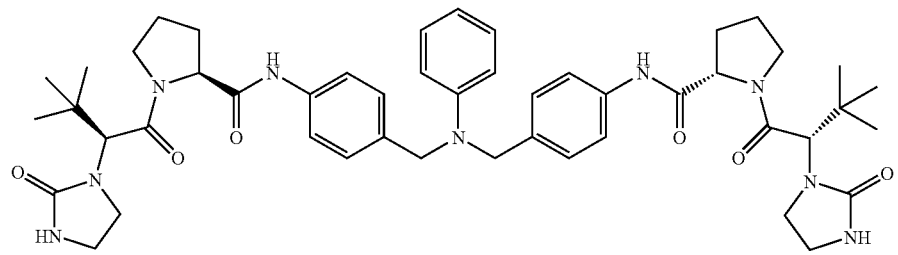 [SMILES: CC(C)(C)[C@@H](C(=O)N1CCC[C@H]1C(=O)Nc1ccc(CN(Cc2ccc(NC(=O)[C@@H]3CCCN3C(=O)[C@@H](N3CCNC3=O)C(C)(C)C)cc2)c2ccccc2)cc1)N1CCNC1=O]

EXAMPLE 31

(2S,2'S)-N,N'-[(phenylimino)bis(methanediylbenzene-4,1-diyl)]bis{1-[(2S)-3,3-dimethyl-2-(2-oxoimidazolidin-1-yl)butanoyl]pyrrolidine-2-carboxamide}

The product of Example 1D (32 mg, 0.064 mmol) and (S)-3,3-dimethyl-2-(2-oxoimidazolidin-1-yl)butanoic acid (39.6 mg, 0.193 mmol) were processed using the method described in Example 43 to afford 22 mg (40%) of the title compound. $^1$H NMR (500 MHz, DMSO-D6) δ ppm 10.01 (s, 2H), 7.58 (d, J=8.5 Hz, 4H), 7.24 (d, J=8.5 Hz, 4H), 7.13 (m, 2H), 6.73 (d, J=8.1 Hz, 2H), 6.63 (t, J=7.3 Hz, 1H), 6.47 (s, 2H), 4.65 (s, 4H), 4.53 (s, 2H), 4.46 (dd, J=8.4, 5.0 Hz, 2H), 3.67 (m, 6H), 3.55 (m, 2H), 3.24 (m, 4H), 2.21 (m, 2H), 2.03 (m, 2H), 1.91 (m, 4H), 1.06 (s, 18H).

EXAMPLE 32A 2-methoxy-N,N-bis(4-nitrobenzyl)ethanamine

To a solution of 2-methoxyethylamine (0.343 mL, 3.99 mmol) in DMF (20.0 mL) at room temperature was added potassium carbonate (0.964 mL, 15.98 mmol) followed by 4-nitrobenzyl bromide (1.812 g, 8.39 mmol). The reaction was stirred for 2 hours then quenched with water, extracted with EtOAc and concentrated. The residue was purified by chromatography (20% to 40% EtOAc-hexane) to provide the title compound. MS (DCI) m/z 346 (M+H)$^+$.

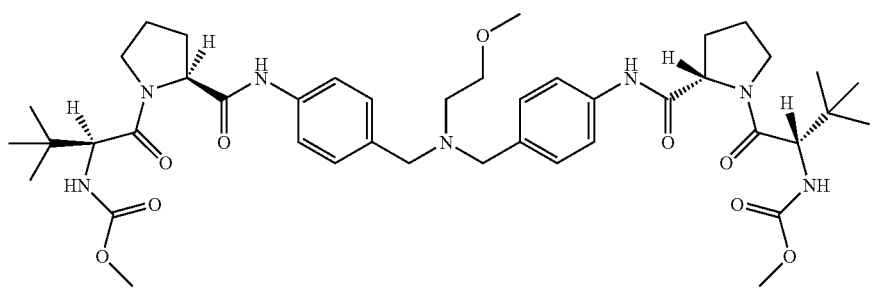 [SMILES: COCCN(Cc1ccc(NC(=O)[C@@H]2CCCN2C(=O)[C@@H](NC(=O)OC)C(C)(C)C)cc1)Cc1ccc(NC(=O)[C@@H]2CCCN2C(=O)[C@@H](NC(=O)OC)C(C)(C)C)cc1]

EXAMPLE 32 dimethyl ([[(2-methoxyethyl)imino]bis{methanediylbenzene-4,1-diylcarbamoyl(2S)pyrrolidine-2,1-diyl[(2S)-3,3-dimethyl-1-oxobutane-1,2-diyl]})biscarbamate

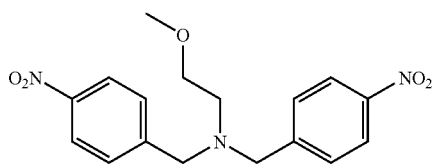 [SMILES: COCCN(Cc1ccc(N)cc1)Cc1ccc(N)cc1]

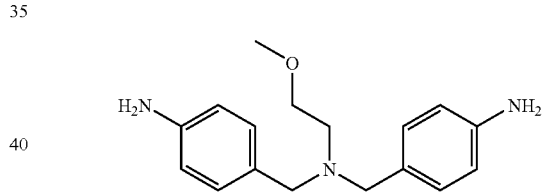

EXAMPLE 32B 4-(((4-aminobenzyl)(2-methoxyethyl)amino)methyl)aniline

The product from Example 32A was processed using the method described in Example 1B (Method A) to afford the title compound. MS (ESI) m/z 286 (M+H)$^+$.

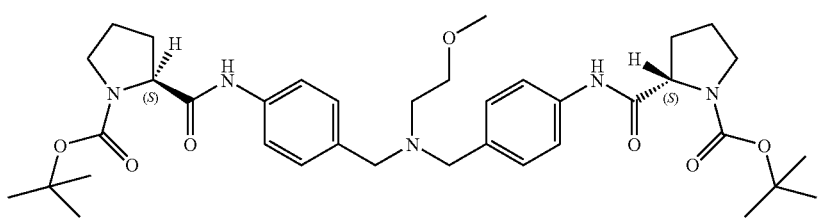

EXAMPLE 32C (2S,2'S)-tert-butyl 2,2'-(4,4'-(2-methoxyethyla-zanediyl)bis(methylene)bis(4,1-phenylene)bis(azanediyl))bis(oxomethylene)dipyrrolidine-1-carboxylate The product from Example 32B was processed using the method described in Example 1C replacing DMSO with dichloromethane to afford the title compound. MS (ESI) m/z 680 (M+H)⁺, 678 (M−H)⁺.

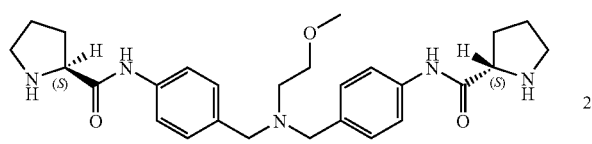

EXAMPLE 32D (2S,2'S)-N,N'-(4,4'-(2-methoxyethylazanediyl)bis(methylene)bis(4,1-phenylene))dipyrrolidine-2-carboxamide The product from Example 32C was processed using the method described in Example 1D to afford the title compound. MS (ESI) m/z 480 (M+H)⁺, 478 (M−H)⁺.

EXAMPLE 32E dimethyl ([(2-methoxyethyl)imino]bis{methanediylbenzene-4,1-diylcarbamoyl(2S)pyrrolidine-2,1-diyl[(2S)-3,3-dimethyl-1-oxobutane-1,2-diyl]})biscarbamate The product from Example 32D was processed using the method described in Example 6 replacing DMSO with dichloromethane and purified using flash chromatography (silica gel, MeOH/dichloromethane) to afford the title compound (7.5 mg, 3%). ¹H NMR (500 MHz, BENZENE-D6) δ 1.02 (s, 18H), 1.39-1.16 (m, 5H), 1.56-1.40 (m, 2H), 1.78-1.60 (m, 2H), 2.19-2.02 (m, 2H), 2.59 (t, J=5.9, 2H), 3.03 (s, 4H), 3.26-3.19 (m, 2H), 3.29 (t, J=5.9, 2H), 3.41-3.35 (m, 6H), 3.44 (s, 6H), 4.53 (d, J=9.7, 2H), 4.82-4.63 (m, 2H), 5.69 (d, J=8.6, 2H), 7.80 (d, J=7.8, 4H), 9.81 (s, 2H); MS (ESI) m/z 822 (M+H)⁺, 820 (M−H)⁺.

EXAMPLE 33 dimethyl[(isoxazol-3-ylimino)bis{methanediylbenzene-4,1-diylcarbamoyl(2S)pyrrolidine-2,1-diyl[(2S)-3,3-dimethyl-1-oxobutane-1,2-diyl]}]biscarbamate

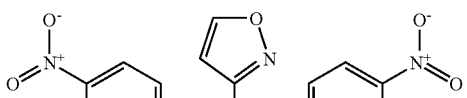

EXAMPLE 33A

N,N-bis(4-nitrobenzyl)isoxazol-3-amine

The title compound was prepared using the methods from Example 1A substituting isoxazol-3-amine for aniline to provide the title compound (0.49 g, 23% yield).

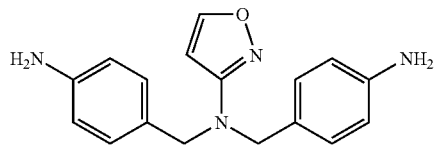

EXAMPLE 33B

N,N-bis(4-aminobenzyl)isoxazol-3-amine

The title compound was prepared using the methods from Example 1B substituting the product from Example 33A for the product from Example 1A to provide the title compound (0.32 g, 79% yield).

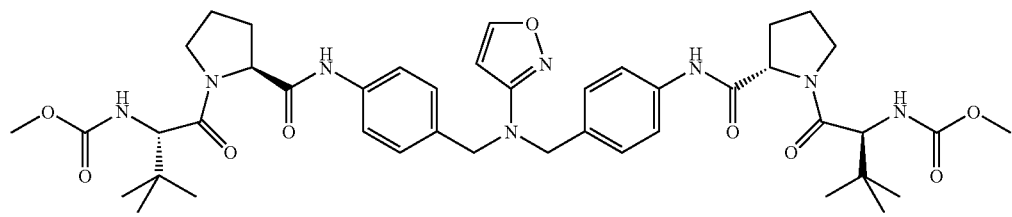

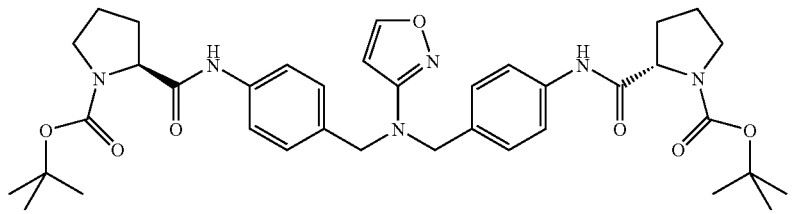 [SMILES: CC(C)(C)OC(=O)N1CCC[C@H]1C(=O)Nc1ccc(CN(Cc2ccc(NC(=O)[C@@H]3CCCN3C(=O)OC(C)(C)C)cc2)c2ccon2)cc1]

EXAMPLE 33C (2S,2'S)-tert-butyl 2,2'-(4,4'-(isoxazol-3-ylazanediyl)bis(methylene)bis(4,1-phenylene))bis(azanediyl)bis(oxomethylene)dipyrrolidine-1-carboxylate The title compound was prepared using the methods from Example 1C substituting the product from Example 33B for the product from Example 1B to provide the title compound (0.32 g, 43% yield).

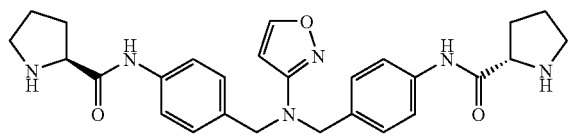 [SMILES: O=C(Nc1ccc(CN(Cc2ccc(NC(=O)[C@@H]3CCCN3)cc2)c2ccon2)cc1)[C@@H]1CCCN1]

EXAMPLE 33D (2S,2'S)-N,N'-(4,4'-(isoxazol-3-ylazanediyl)bis(methylene)bis(4,1-phenylene))dipyrrolidine-2-carboxamide The title compound was prepared using the methods from Example 1D substituting the product from Example 33C for the product from Example 1C to provide the title compound (0.14 g, 62% yield).

EXAMPLE 33E dimethyl[(isoxazol-3-ylimino)bis{methanediylbenzene-4,1-diylcarbamoyl(2S)pyrrolidine-2,1-diyl[(2S)-3,3-dimethyl-1-oxobutane-1,2-diyl]}]biscarbamate Example 33D and (S)-2-(methoxycarbonylamino)-3,3-dimethylbutanoic acid were reacted using the method from Example 1E and the product was purified by column chromatography eluting with 0-4% methanol in dichloromethane to provide the title compound (37 mg, 31% yield). $^1$H NMR (500 MHz, DMSO) δ 10.02 (s, 2H), 8.48 (d, J=1.8, 1H), 7.52 (d, J=8.5, 4H), 7.16 (d, J=8.5, 4H), 7.09 (d, J=8.8, 2H), 6.36 (d, J=1.8, 1H), 4.44 (dd, J=5.3, 8.1, 2H), 4.35 (s, 4H), 4.21 (d, J=8.8, 2H), 3.81-3.73 (m, 2H), 3.68-3.60 (m, 2H), 3.53 (d, J=10.5, 6H), 2.21-2.10 (m, 2H), 2.03-1.93 (m, 2H), 1.92-1.80 (m, 4H), 0.97 (s, 18H). MS (ESI; M+H) m/z=832.

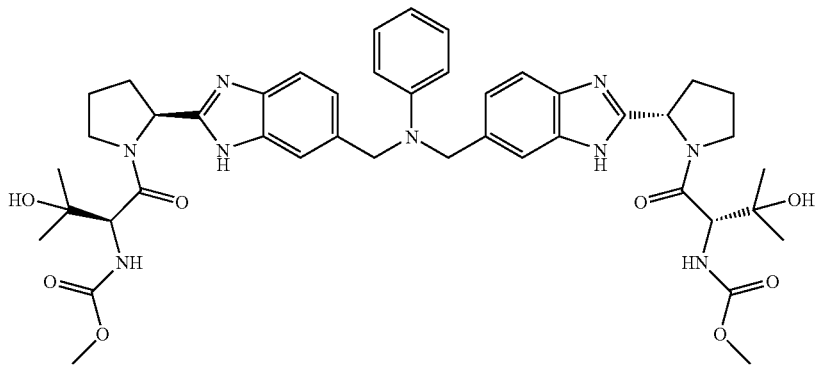 [SMILES: COC(=O)N[C@H](C(=O)N1CCC[C@H]1c1nc2ccc(CN(Cc3ccc4nc([C@@H]5CCCN5C(=O)[C@@H](NC(=O)OC)C(C)(C)O)[nH]c4c3)c3ccccc3)cc2[nH]1)C(C)(C)O]

EXAMPLE 34 methyl [(1S)-2-hydroxy-1-{[(2S)-2-(6-{[({2-[(2S)-1-{(2S)-3-hydroxy-2-[(methoxycarbonyl)amino]-3-methylbutanoyl}pyrrolidin-2-yl]-1H-benzimidazol-6-yl}methyl)(phenyl)amino]methyl}-1H-benzimidazol-2-yl)pyrrolidin-1-yl]carbonyl}-2-methylpropyl]carbamate The product of Example 7E (25 mg, 0.051 mmol) and (S)-3-hydroxy-2-(methoxycarbonylamino)-3-methylbutanoic acid (21.4 mg, 0.112 mmol) were processed using the method described in Example 7F and the HPLC fractions neutralized with saturated aqueous NaHCO₃ solution followed by extraction with a mixture of isopropyl alcohol/CH₂Cl₂ (1:3 ratio; 3×100 mL) and isolation to afford 32 mg (53%) of the title compound. $^1$H NMR (500 MHz, DMSO-$d_6$) δ ppm 1.02 (s, 6 H), 1.14 (s, 6 H), 1.91-2.16 (m, 6 H), 2.29-2.43 (m, 3 H), 2.53 (s, 2 H), 3.18 (s, 2 H), 3.55 (s, 6 H), 3.72-3.82 (m, 2 H), 3.97-4.06 (m, 2 H), 4.37 (d, J=8.70 Hz, 4 H), 4.88 (s, 4 H), 4.90 (d, J=10.99 Hz, 2 H), 5.26 (dd, J=8.24, 4.58 Hz, 2 H), 6.56-6.62 (m, 1 H), 6.72 (d, J=8.09 Hz, 2 H), 7.04-7.12 (m, 3 H), 7.18 (d, J=8.54 Hz, 2 H), 7.37 (d, J=8.39 Hz, 2 H), 7.52 (s, 2 H), 7.66 (d, J=8.24 Hz, 2 H). MS (ESI) m/z 838 (M+H)⁺.

EXAMPLE 35 methyl [(1S,2R)-2-hydroxy-1-{[(2S)-2-(6-{[({2-[(2S)-1-{(2S,3R)-3-hydroxy-2-[(methoxycarbonyl)amino]butanoyl}pyrrolidin-2-yl]-1H-benzimidazol-6-yl}methyl)(phenyl)amino]methyl}-1H-benzimidazol-2-yl)pyrrolidin-1-yl]carbonyl}propyl] carbamate The product of Example 7E (25 mg, 0.051 mmol) and (2S,3R)-3-hydroxy-2-(methoxycarbonylamino)butanoic acid (19.8 mg, 0.112 mmol) were processed using the method described in Example 7F and the HPLC fractions neutralized with saturated aqueous NaHCO₃ solution followed by extraction with a mixture of isopropyl alcohol/CH₂Cl₂ (1:3 ratio; 3×100 mL) and isolation to afford 25 mg (43%) of the title compound. $^1$H NMR (500 MHz, DMSO-$d_6$) δ ppm 1.00 (d, J=6.26 Hz, 6 H), 2.00-2.20 (m, 7 H), 2.34-2.44 (m, 4 H), 3.54 (s, 6 H), 3.87 (dt, J=12.40, 6.18 Hz, 2 H), 4.26 (dd, J=8.24, 5.34 Hz, 2 H), 4.90 (d, J=1.98 Hz, 4 H), 5.21 (dd, J=8.24, 5.34 Hz, 2 H), 6.60 (t, J=7.25 Hz, 1 H), 6.72 (d, J=8.09 Hz, 2 H), 6.99 (d, J=8.24 Hz, 2 H), 7.05-7.12 (m, 2 H), 7.41 (d, J=8.39 Hz, 2 H), 7.54 (s, 2 H), 7.71 (d, J=8.54 Hz, 2 H). MS (ESI) m/z 810 (M+H)⁺.

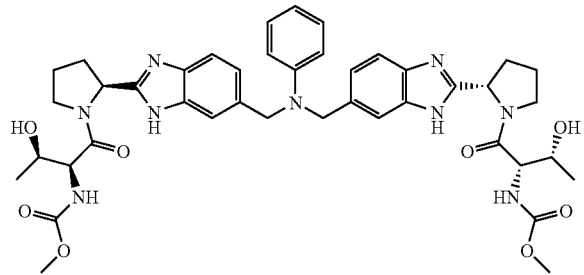 [SMILES: COC(=O)N[C@H](C(=O)N1CCC[C@H]1c1nc2ccc(CN(Cc3ccc4nc([C@@H]5CCCN5C(=O)[C@@H](NC(=O)OC)[C@@H](C)O)[nH]c4c3)c3ccccc3)cc2[nH]1)[C@@H](C)O]

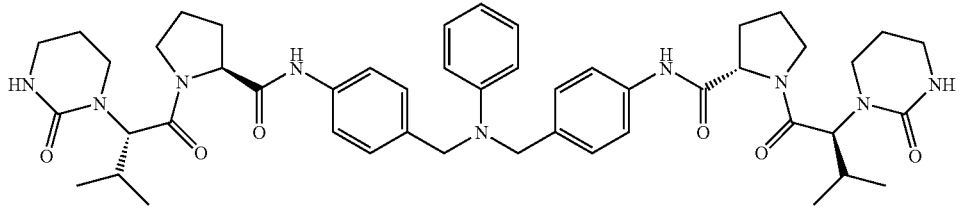 [SMILES: CC(C)[C@@H](C(=O)N1CCC[C@H]1C(=O)Nc1ccc(CN(Cc2ccc(NC(=O)[C@@H]3CCCN3C(=O)[C@H](C(C)C)N3CCCNC3=O)cc2)c2ccccc2)cc1)N1CCCNC1=O]

EXAMPLE 36

(2S,2'S)-N,N'-[(phenylimino)bis(methanediylbenzene-4,1-diyl)]bis {1-[(2S)-3-methyl-2-(2-oxotetrahydropyrimidin-1(2H)-yl)butanoyl]pyrrolidine-2-carboxamide}

The product of Example 1D (30 mg, 0.060 mmol) was subjected to the procedure described in Example 24E, substituting (S)-3-methyl-2-(2-oxotetrahydropyrimidin-1(2H)-yl)butanoic acid for (S)-2-(methoxycarbonylamino)-3-methylbutanoic acid, to give the title compound as a TFA salt (10 mg). $^1$H NMR (500 MHz, DMSO-D6) δ ppm 0.78-0.85 (m, 7 H), 0.88 (d, J=6.4 Hz, 6 H), 1.68-1.77 (m, 4 H), 1.79-1.88 (m, 4 H), 1.97 (d, J=6.0 Hz, 2 H), 2.06-2.16 (m, 4 H), 3.05-3.13 (m, 6 H), 3.54-3.63 (m, 2 H), 3.80-3.88 (m, 2 H), 4.36 (dd, J=8.2, 5.0 Hz, 2 H), 4.59 (s, 4 H), 4.78 (d, J=11.1 Hz, 2 H), 6.30 (s, 2 H), 6.56 (t, J=7.2 Hz, 1 H), 6.66 (d, J=8.2 Hz, 2 H), 7.07 (t, J=7.9 Hz, 2 H), 7.17 (d, J=8.4 Hz, 4 H), 7.51 (d, J=8.5 Hz, 4 H), 9.95 (s, 2 H); MS (ESI) m/z 862.5 (M+H)⁺.

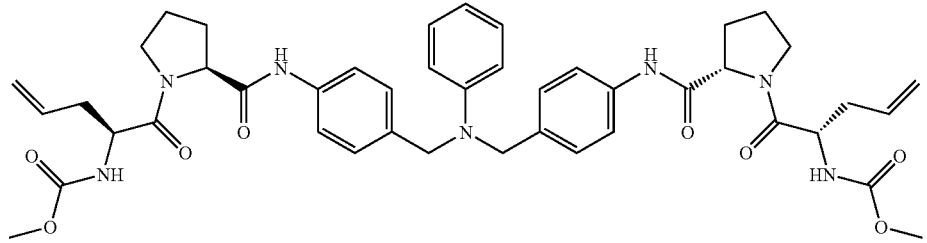

EXAMPLE 37 dimethyl [(phenylimino)bis{methanediylbenzene-4,
1-diylcarbamoyl(2S)pyrrolidine-2,1-diyl[(4S)-5-
oxopent-1-ene-5,4-diyl]}]biscarbamate

EXAMPLE 37A (S)-2-(methoxycarbonylamino)pent-4-enoic acid

A mixture of (S)-2-aminopent-4-enoic acid (1.0 g, 8.69 mmol) and $NaHCO_3$ (2.26 mg, 26.9 mmol) in $H_2O$ (40 mL) was cooled to 0° C. A mixture of methyl chloroformate (740 µL, 9.55 mmol) dissolved in $Et_2O$ (4 mL) was slowly added to the aqueous mixture and stirred for 20 hours coming to ambient temperature. Mixture was adjusted to pH 3.0 with HCl (conc). The mixture was extracted with EtOAc and then dried ($MgSO_4$), filtered and concentrated to afford 1.25 g (83%) of the title compound. MS (ESI) m/z 174 $(M+H)^+$.

EXAMPLE 37B dimethyl [(phenylimino)bis{methanediylbenzene-4,
1-diylcarbamoyl(2S)pyrrolidine-2,1-diyl[(4S)-5-
oxopent-1-ene-5,4-diyl]}]biscarbamate The product of Example 1D (50 mg, 0.100 mmol) and the product of Example 37A (34.8 mg, 0.201 mmol) were processed using the method described in Example 1E to afford 51 mg (53%) of the title compound as a TFA salt. $^1$H NMR (500 MHz, DMSO-$d_6$) δ ppm 1.81-1.93 (m, 3 H), 1.94-2.04 (m, 2 H), 2.08-2.17 (m, 2 H), 2.20-2.29 (m, 2 H), 2.33-2.42 (m, 2 H), 2.53 (s, 2 H), 3.50 (s, 6 H), 3.55-3.63 (m, 2 H), 3.64-3.72 (m, 2 H), 4.24-4.31 (m, 2 H), 4.42 (dd, J=8.09, 4.27 Hz, 2 H), 4.58 (s, 4 H), 5.03 (d, J=10.22 Hz, 2 H), 5.13 (d, J=16.48 Hz, 2 H), 5.75-5.86 (m, 2 H), 6.56 (t, J=6.71 Hz, 1 H), 6.65 (d, J=7.63 Hz, 2 H), 7.06 (t, J=7.78 Hz, 2 H), 7.16 (d, J=8.54 Hz, 4 H), 7.34 (d, J=7.93 Hz, 2 H), 7.49 (d, J=8.39 Hz, 4 H), 9.93 (s, 2 H). MS (ESI) m/z 808 $(M+H)^+$.

EXAMPLE 38 dimethyl [(phenylimino)bis{methanediylbenzene-4,
1-diylcarbamoyl(2S)pyrrolidine-2,1-diyl[(2S)-1-
oxobutane-1,2-diyl]}]biscarbamate

EXAMPLE 38A (S)-2-(methoxycarbonylamino)butanoic acid

The compound (S)-2-aminobutanoic acid (1.0 g, 9.70 mmol) was processed using the method described in Example 37A to afford 1.15 g (74%) of the title compound. MS (ESI) m/z 162 $(M+H)^+$.

EXAMPLE 38B dimethyl [(phenylimino)bis{methanediylbenzene-4,
1-diylcarbamoyl(2S)pyrrolidine-2,1-diyl[(2S)-1-
oxobutane-1,2-diyl]}]biscarbamate The product of Example 1D (50 mg, 0.100 mmol) and the product of Example 38A (32 mg, 0.201 mmol) were processed using the method described in Example 1E to afford 34 mg (38%) of the title compound as a TFA salt. $^1$H NMR (500 MHz, DMSO-$d_6$) δ ppm 0.89 (t, J=7.40 Hz, 6 H), 1.44-1.56 (m, 2 H), 1.58-1.70 (m, 2 H), 1.80-1.94 (m, 4 H), 1.94-2.04 (m, 2 H), 2.07-2.16 (m, 2 H), 3.50 (s, 6 H), 3.55-3.63 (m, 2 H), 3.67-3.77 (m, 2 H), 4.17 (dd, J=13.81, 7.55 Hz, 2 H), 4.41 (dd, J=8.09, 4.58 Hz, 2 H), 4.58 (s, 4 H), 6.56 (t, J=6.87 Hz, 1 H), 6.65 (d, J=7.78 Hz, 2 H), 7.06 (t, J=7.86 Hz, 2 H), 7.15 (d, J=8.54 Hz, 4 H), 7.30 (d, J=7.78 Hz, 2 H), 7.49 (d, J=8.39 Hz, 4 H), 9.94 (s, 2 H).

MS (ESI) m/z 784 $(M+H)^+$.

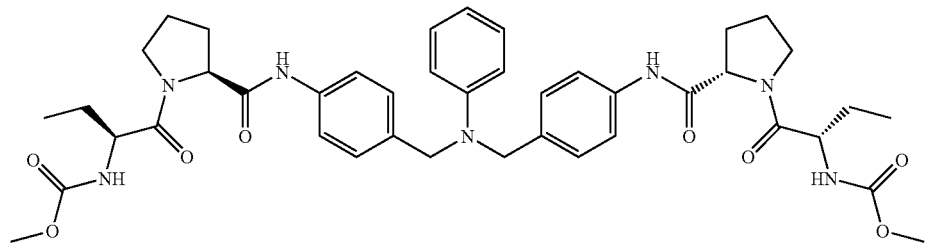

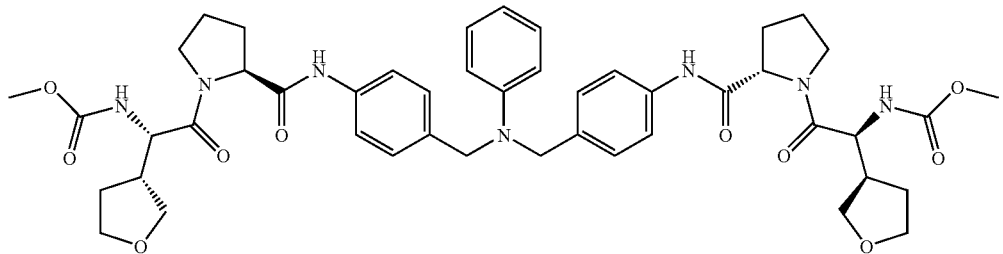

EXAMPLE 39 dimethyl {(phenylimino)bis[methanediylbenzene-4,1-diylcarbamoyl(2S)pyrrolidine-2,1-diyl{(1S)-2-oxo-1-[(3R)-tetrahydrofuran-3-yl]ethane-2,1-diyl}]}biscarbamate The product from Example 1D (0.05 g, 0.10 mmol) and (S)-2-(methoxycarbonylamino)-2-((R)-tetrahydrofuran-3-yl)acetic acid (0.045 g, 0.22 mmol) were processed as in Example 25B to give 0.039 g (45%) of the title compound as a yellow solid. $^1$H NMR (500 MHz, DMSO-D6) δ ppm 1.65-1.76 (m, 2 H) 1.82-1.91 (m, 6 H) 1.94-2.03 (m, 2H) 2.09-2.18 (m, 2 H) 3.43 (dd, J=8.47, 6.33 Hz, 2 H) 3.51-3.54 (m, 6 H) 3.57-3.70 (m, 7 H) 3.70-3.76 (m, 3 H) 3.80-3.87 (m, 2 H) 4.22 (t, J=8.85 Hz, 2 H) 4.42 (dd, J=8.09, 4.73 Hz, 2 H) 4.58 (s, 4 H) 6.55 (t, J=7.25 Hz, 1 H) 6.64 (d, J=8.24 Hz, 2 H) 7.05 (t, J=8.01 Hz, 2 H) 7.16 (d, J=8.54 Hz, 4 H) 7.50 (d, J=8.54 Hz, 4 H) 7.59 (d, J=7.93 Hz, 2 H) 9.97 (s, 2 H); MS ESI– m/z 866 (M–H)–.

EXAMPLE 40A (S)-2-(2-methoxyacetamido)-3,3-dimethylbutanoic acid (S)-2-amino-3,3-dimethylbutanoic acid (0.50 g, 3.8 mmol) and sodium bicarbonate (0.80 g, 9.5 mmol) were dissolved into water (20 mL) then cooled in an ice bath. Methoxyacetyl chloride (0.38 mL, 4.2 mmol) was dissolved in diethyl ether (5 mL) and added dropwise with vigorous stirring. The solution was stirred at ambient temperature for 5 hours then adjusted to pH 3 with concentrated hydrochloric acid and extracted into ethyl acetate. The organic solution was dried over sodium sulfate, filtered, and concentrated to give 0.16 g (21%) of the title compound as a waxy solid.

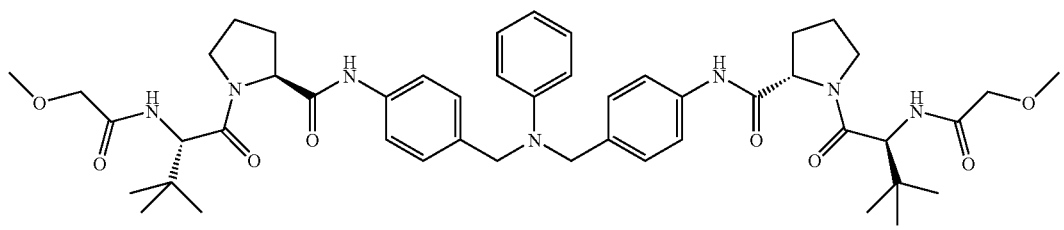

EXAMPLE 40

(2S,2'S)-N,N'-[(phenylimino)bis(methanediylbenzene-4,1-diyl)]bis(1-{(2S)-2-[(methoxyacetyl)amino]-3,3-dimethylbutanoyl}pyrrolidine-2-carboxamide)

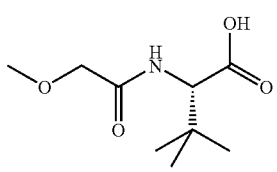

EXAMPLE 40B (2S,2'S)-N,N'-[(phenylimino)bis(methanediylbenzene-4,1-diyl)]bis(1-{(2S)-2-[(methoxyacetyl)amino]-3,3-dimethylbutanoyl}pyrrolidine-2-carboxamide)

The product from Example 1D (0.05 g, 0.10 mmol) and the product from Example 40A (0.045 g, 0.22 mmol) were processed as in Example 25B to give 0.006 g (7%) of the title compound as a yellow solid. $^1$H NMR (500 MHz, DMSO-D6) δ ppm 0.93 (s, 18 H) 1.85-1.93 (m, 4 H) 1.94-2.04 (m, 2 H) 2.08-2.17 (m, 2 H) 3.28 (s, 6 H) 3.63-3.76 (m, 4 H) 3.81-3.95 (m, 4 H) 4.38 (dd, J=8.54, 3.05 Hz, 2 H) 4.56-4.62 (m, 6 H) 6.55 (t, J=7.17 Hz, 1 H) 6.64 (d, J=8.09 Hz, 2 H) 7.03-7.08 (m, 2 H) 7.15 (d, J=8.54 Hz, 4 H) 7.38 (d, J=9.00 Hz, 2 H) 7.51 (d, J=8.54 Hz, 4 H) 9.82 (s, 2 H);
MS ESI– m/z 866 (M–H)–.

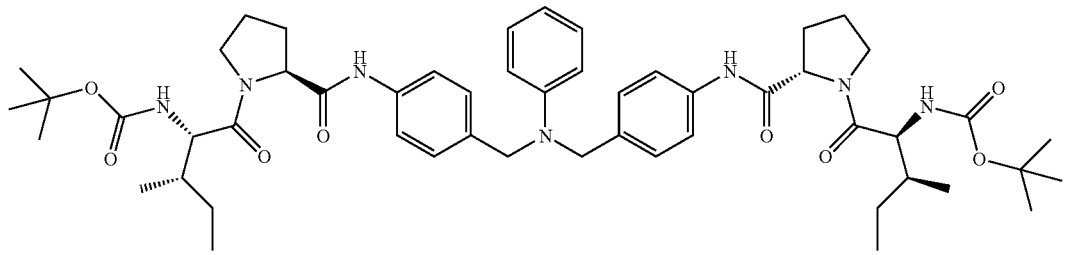 [SMILES: CC[C@H](C)[C@H](NC(=O)OC(C)(C)C)C(=O)N1CCC[C@H]1C(=O)Nc1ccc(CN(Cc2ccc(NC(=O)[C@@H]3CCCN3C(=O)[C@@H](NC(=O)OC(C)(C)C)[C@@H](C)CC)cc2)c2ccccc2)cc1]

EXAMPLE 41 di-tert-butyl[(phenylimino)bis{methanediylbenzene-4,1-diylcarbamoyl(2S)pyrrolidine-2,1-diyl[(2S,3S)-3-methyl-1-oxopentane-1,2-diyl]}]biscarbamate To a solution of the product from Example 1D (0.062 g, 0.125 mmol) in $CH_2Cl_2$ (5 mL) at rt was added (2S,3S)-2-(tert-butoxycarbonylamino)-3-methylpentanoic acid (Aldrich, 0.063 g, 0.274 mmol), N,N-disiopropylethylamine (0.100 mL) and HATU (0.104 g, 0.274 mmol). After 30 minutes, the reaction was washed with brine and the organic phase concentrated. The residue was purified by chromatography (1% gradient from 0 to 2% MeOH—$CH_2Cl_2$) to provide the 67 mg (58%) of the title compound. $^1$H NMR (500 MHz, DMSO-D6) δ 0.81 (t, J=7.02 Hz, 6 H) 0.85 (d, J=6.71 Hz, 6 H) 1.20-1.29 (m, 2 H) 1.37 (s, 18 H) 1.44-1.53 (m, 2 H) 1.65-1.75 (m, 2 H) 1.82-1.92 (m, 4 H) 1.95-2.04 (m, 2 H) 2.08-2.17 (m, 2 H) 3.56-3.64 (m, 2 H) 3.75-3.83 (m, 2 H) 4.04 (t, J=8.70 Hz, 2 H) 4.43 (dd, J=7.93, 4.88 Hz, 2 H) 4.59 (s, 4 H) 6.56 (m, 1 H) 6.65 (d, J=8.24 Hz, 2 H) 6.88 (d, J=8.39 Hz, 2 H) 7.07 (m, 2 H) 7.17 (d, J=8.54 Hz, 4 H) 7.51 (d, J=8.39 Hz, 4 H) 9.97 (s, 2 H).

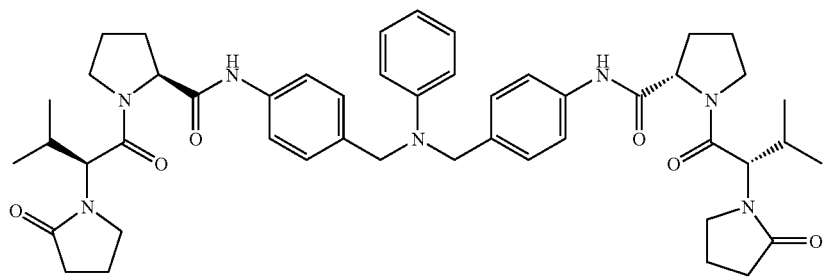 [SMILES: CC(C)[C@@H](C(=O)N1CCC[C@H]1C(=O)Nc1ccc(CN(Cc2ccc(NC(=O)[C@@H]3CCCN3C(=O)[C@H](C(C)C)N3CCCC3=O)cc2)c2ccccc2)cc1)N1CCCC1=O]

EXAMPLE 42

(2S,2'S)-N,N'-[(phenylimino)bis(methanediylbenzene-4,1-diyl)]bis{1-[(2S)-3-methyl-2-(2-oxopyrrolidin-1-yl)butanoyl]pyrrolidine-2-carboxamide}

The product of Example 1D (30 mg, 0.06 mmol) and (S)-3-methyl-2-(2-oxopyrrolidin-1-yl)butanoic acid (24.6 mg, 0.133 mmol) were processed using the method described in Example 43 to afford 21 mg (42%) of the title compound. $^1$H NMR (500 MHz, DMSO-D6) δ ppm 9.92 (s, 2H), 7.46 (d, J=8.6 Hz, 4H), 7.12 (d, J=8.5 Hz, 4H), 7.01 (m, 2H), 6.61 (d, J=8.1 Hz, 2H), 6.51 (t, J=7.2 Hz, 1H), 4.54 (s, 4H), 4.40 (d, J=11.0 Hz, 2H), 4.33 (m, 2H), 3.62 (m, 4H), 3.35 (m, 2H), 3.23 (m, 2H), 2.21 (m, 4H), 2.08 (m, 4H), 1.91 (m, 2H), 1.82 (s, 8H), 0.87 (d, J=6.6 Hz, 6H), 0.72 (d, J=6.6 Hz, 6H).

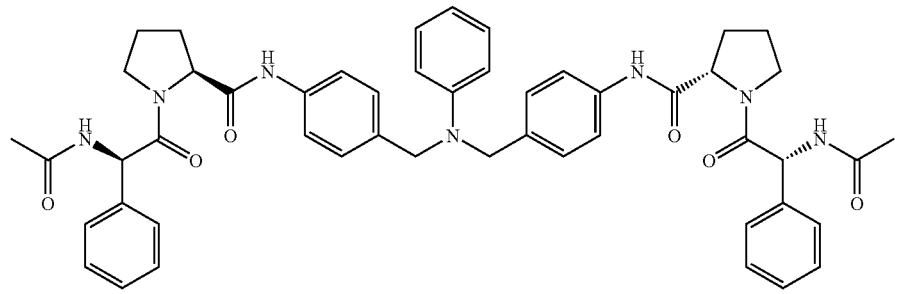 [SMILES: CC(=O)N[C@@H](C(=O)N1CCC[C@H]1C(=O)Nc1ccc(CN(Cc2ccc(NC(=O)[C@@H]3CCCN3C(=O)[C@H](NC(C)=O)c3ccccc3)cc2)c2ccccc2)cc1)c1ccccc1]

EXAMPLE 43

(2S,2'S)-N,N'-[(phenylimino)bis(methanediylbenzene-4,1-diyl)]bis{1-[(2R)-2-(acetylamino)-2-phenylacetyl]pyrrolidine-2-carboxamide}

The product of Example 1D (40 mg, 0.08 mmol), (R)-2-acetamido-2-phenylacetic acid (34.2 mg, 0.177 mmol) and HATU (67.2, 0.177 mmol) were dissolved in DMSO (3 mL) then added Hunig's base (0.07 mL, 0.402 mmol) and stirred the mixture at room temperature for 1 hour. The solution had dichloromethane added to it and the mixture extracted with water. The organic extract was then dried, filtered, concentrated and purified by chromatography (silica gel, 0-20% methanol in dichloromethane) to afford 8 mg (12%) of the title compound. $^1$H NMR (500 MHz, DMSO-D6) δ ppm 9.73 (s, 2H), 8.60 (d, J=7.9 Hz, 2H), 7.52 (m, 4H), 7.35 (m, 7H), 7.13 (m, 4H), 7.02 (m, 2H), 6.61 (d, J=8.2 Hz, 2H), 4.56 (m, 4H), 4.33 (m, 2H), 3.78 (m, 2H), 3.21 (m, 2H), 2.49 (s, 6H), 1.90 (m, 8H).

EXAMPLE 44 dimethyl ([(3R)-tetrahydrofuran-3-ylimino]bis{methanediylbenzene-4,1-diylcarbamoyl(2S)pyrrolidine-2,1-diyl[(2S)-3,3-dimethyl-1-oxobutane-1,2-diyl]})biscarbamate

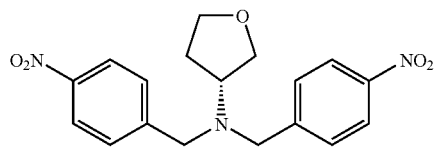

EXAMPLE 44A (R)-N,N-bis(4-nitrobenzyl)tetrahydrofuran-3-amine

The title compound was prepared using the methods from Example 1A substituting (R)-tetrahydrofuran-3-amine for aniline to provide the title compound (1.12 g, 59% yield).

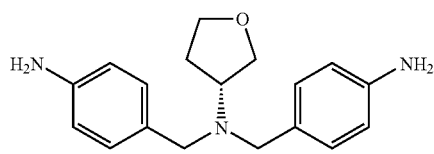

EXAMPLE 44B (R)-N,N-bis(4-aminobenzyl)tetrahydrofuran-3-amine

The title compound was prepared using the methods from Example 1B substituting the product from Example 44A for the product from Example 1A to provide the title compound (1.02 g, 109% yield).

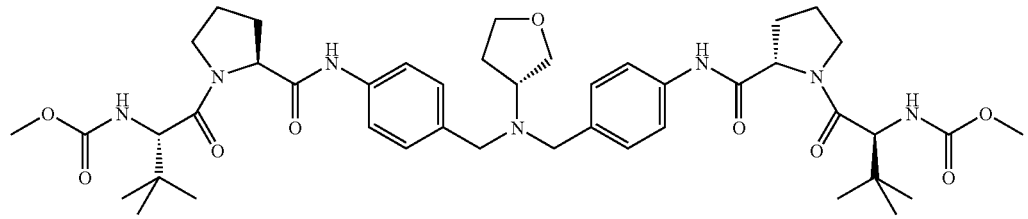

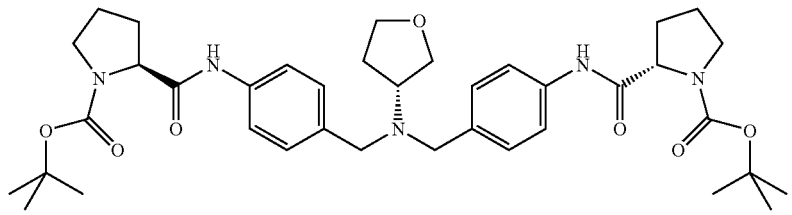 [SMILES: CC(C)(C)OC(=O)N1CCC[C@H]1C(=O)Nc1ccc(CN(Cc2ccc(NC(=O)[C@@H]3CCCN3C(=O)OC(C)(C)C)cc2)[C@@H]2CCOC2)cc1]

EXAMPLE 44C (2S,2'S)-tert-butyl 2,2'-(4,4'-(R)-tetrahydrofuran-3-ylazanediyl)bis(methylene)bis(4,1-phenylene))bis(azanediyl)bis(oxomethylene)dipyrrolidine-1-carboxylate The title compound was prepared using the methods from Example 1C substituting the product from Example 44B for the product from Example 1B to provide the title compound (0.78 g, 33% yield).

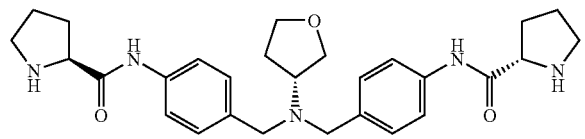

EXAMPLE 44D (2S,2'S)-N,N'-(4,4'-(R)-tetrahydrofuran-3-ylazanediyl)bis(methylene)bis(4,1-phenylene))dipyrrolidine-2-carboxamide The title compound was prepared using the methods from Example 1D substituting the product from Example 44C for the product from Example 1C to provide the title compound (0.39 g, 70% yield).

EXAMPLE 44E dimethyl ([(3R)-tetrahydrofuran-3-ylimino]bis{methanediylbenzene-4,1-diylcarbamoyl(2S)pyrrolidine-2,1-diyl[(2S)-3,3-dimethyl-1-oxobutane-1,2-diyl]})biscarbamate Example 44D and (S)-2-(methoxycarbonylamino)-3,3-dimethylbutanoic acid were reacted using the method from Example 1E and the product was purified by column chromatography eluting with ethyl acetate to provide the title compound (100 mg, 31% yield). $^1$H NMR (500 MHz, BENZENE-D6) δ 9.77 (bs, 2H), 7.74 (d, J=8.1, 4H), 6.99 (d, J=8.3, 4H), 5.50 (d, J=9.6, 2H), 4.73-4.66 (m, 2H), 4.50 (d, J=9.7, 2H), 3.77 (td, J=4.3, 8.4, 1H), 3.70 (dd, J=5.4, 9.0, 1H), 3.59-3.53 (m, 1H), 3.48-3.41 (m, 7H), 3.33 (d, J=12.9, 4H), 3.23-3.13 (m, 5H), 2.11 (td, J=6.1, 11.8, 2H), 1.71-1.53 (m, 4H), 1.52-1.42 (m, 2H), 1.26-1.16 (m, 2H), 0.99 (s, 18H). MS (ESI; M+H) m/z=835.

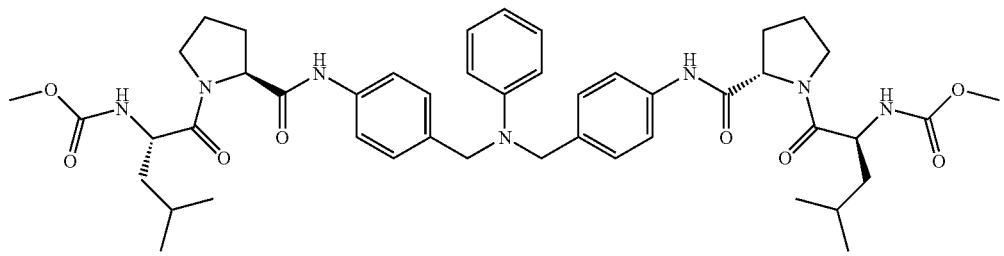

EXAMPLE 45 dimethyl [(phenylimino)bis{methanediylbenzene-4,1-diylcarbamoyl(2S)pyrrolidine-2,1-diyl[(2S)-4-methyl-1-oxopentane-1,2-diyl]}]biscarbamate The product of Example 1D (35 mg, 0.070 mmol) was subjected to the procedure described in Example 24E, substituting (S)-2-(methoxycarbonylamino)-4-methylpentanoic acid for (S)-2-(methoxycarbonylamino)-3-methylbutanoic acid to give the title compound as a TFA salt (18 mg). $^1$H NMR (500 MHz, DMSO-D6) δ ppm 0.85-0.92 (m, 15 H), 1.40 (dd, J=9.3, 4.1 Hz, 2 H), 1.42-1.46 (m, 2 H), 1.62-1.71 (m, 2 H), 1.86 (dt, J=11.6, 5.7 Hz, 2 H), 1.90-1.94 (m, 2 H), 1.96-2.05 (m, 2 H), 2.14 (td, J=7.6, 4.6 Hz, 2 H), 3.67-3.75 (m, 3 H), 4.23-4.31 (m, 2 H), 4.42 (dd, J=8.2, 4.7 Hz, 3 H), 4.59 (s, 5 H), 6.57 (s, 1 H), 6.66 (d, J=8.1 Hz, 2 H), 7.07 (t, J=7.9 Hz, 3 H), 7.17 (d, J=8.5 Hz, 5 H), 7.34 (d, J=8.1 Hz, 2 H), 7.50 (d, J=8.5 Hz, 5 H), 9.96 (s, 2 H); MS (ESI) m/z 840.5 (M+H)$^+$.

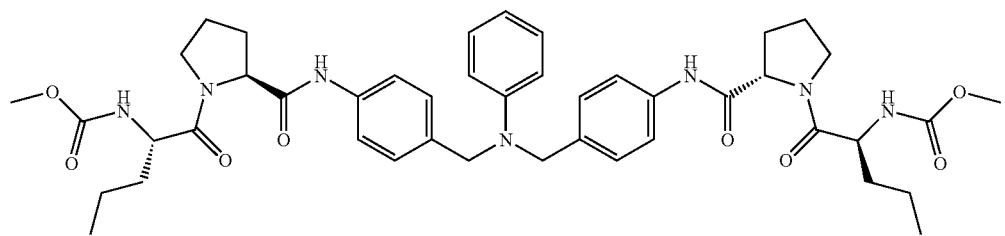

EXAMPLE 46 dimethyl [(phenylimino)bis{methanediylbenzene-4,1-diylcarbamoyl(2S)pyrrolidine-2,1-diyl[(2S)-1-oxopentane-1,2-diyl]}]biscarbamate The product of Example 1D (35 mg, 0.070 mmol) was subjected to the procedure described in Example 24E, substituting (S)-2-(methoxycarbonylamino)pentanoic acid for (S)-2-(methoxycarbonylamino)-3-methylbutanoic acid to give the title compound as a TFA salt (29 mg). $^1$H NMR (500 MHz, DMSO-D6) δ ppm 0.83-0.90 (m, 9 H), 1.22-1.30 (m, 3 H), 1.30-1.40 (m, 4 H), 1.43-1.52 (m, 3 H), 1.53-1.62 (m, 2 H), 1.83-1.93 (m, 4 H), 1.95-2.04 (m, 2 H), 2.08-2.17 (m, 2 H), 3.72 (dt, J=9.5, 6.8 Hz, 2 H), 4.24 (td, J=8.1, 5.4 Hz, 2 H), 4.42 (dd, J=8.2, 4.7 Hz, 2 H), 4.59 (s, 4 H), 6.57 (t, J=7.1 Hz, 1 H), 6.66 (d, J=8.1 Hz, 2 H), 7.07 (t, J=7.9 Hz, 2 H), 7.17 (d, J=8.5 Hz, 4 H), 7.32 (d, J=7.8 Hz, 2 H), 7.50 (d, J=8.5 Hz, 4 H), 9.95 (s, 2 H); MS (ESI) m/z 812.4 (M+H)$^+$.

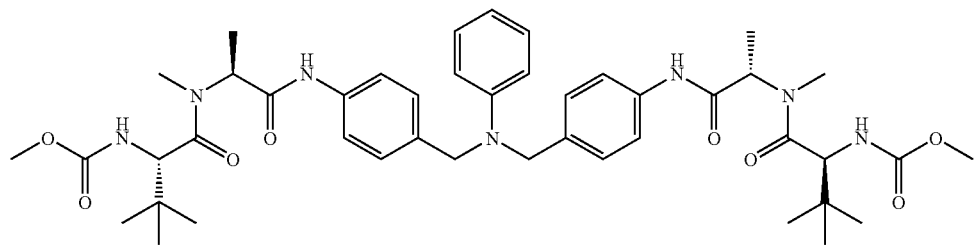

EXAMPLE 47 dimethyl[(phenylimino)bis{methanediylbenzene-4,
1-diylimino[(2S)-1-oxopropane-1,2-diyl](methylimino)[(2S)-3,3-dimethyl-1-oxobutane-1,2-diyl]}]
biscarbamate

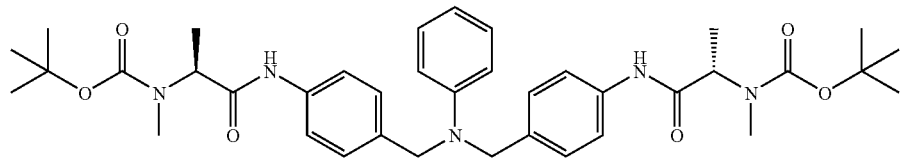 [SMILES: C[C@@H](C(=O)Nc1ccc(CN(Cc2ccc(NC(=O)[C@H](C)N(C)C(=O)OC(C)(C)C)cc2)c2ccccc2)cc1)N(C)C(=O)OC(C)(C)C]

EXAMPLE 47A tert-butyl (2S,2'S)-1,1'-(4,4'-(phenylazanediyl)bis(methylene)bis(4,1-phenylene)bis(azanediyl))bis(1-oxopropane-2,1-diyl)bis(methylcarbamate)

The product from Example 1B and (S)-2-(tert-butoxycarbonyl(methyl)amino)propanoic acid (Aldrich) were processed using the method described in Example 41. The crude residue was purified by silica gel chromatography (40% ethyl acetate-hexane) to provide the title compound. MS (ESI; M+H) m/z=674.

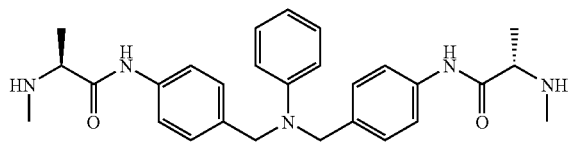 [SMILES: CN[C@@H](C)C(=O)Nc1ccc(CN(Cc2ccc(NC(=O)[C@H](C)NC)cc2)c2ccccc2)cc1]

EXAMPLE 47B (2S,2'S)-N,N'-(phenylazanediyl)bis(methylene)bis(4,1-phenylene))bis(2-(methylamino)propanamide)

A solution of the product from Example 47A (0.469 g, 0.696 mmol) in $CH_2Cl_2$ (10 mL) at rt was treated with TFA (5.00 mL) and stirring continued overnight. The reaction was concentrated and the residue partitioned between saturated $NaHCO_3$ and 25% IPA-$CHCl_3$. The organic phase was dried ($Na_2SO_4$) and concentrated to provide 210 mg (64%) of the title compound. MS (ESI; M+H) m/z=474.

EXAMPLE 47C dimethyl[(phenylimino)bis{methanediylbenzene-4,
1-diylimino[(2S)-1-oxopropane-1,2-diyl]methylimino)[(2S)-3,3-dimethyl-1-oxobutane-1,2-diyl]}]
biscarbamate The product from Example 47B and (S)-2-(methoxycarbonylamino)-3,3-dimethylbutanoic acid (DeGussa) were processed using the method described in Example 41. The crude residue was purified by silica gel chromatography (2% MeOH—$CH_2Cl_2$) to provide 122 mg (34%) of the title compound. NMR (500 MHz, DMSO-D6) δ 0.96 (m, 18 H) 1.33 (d, J=7.18 Hz, 6 H) 2.68 (m, 2 H) 3.09 (br s, 4 H) 3.53 (br s, 4 H) 3.58 (br s, 2 H) 4.45 (m, 2 H) 4.59 (m, 4 H) 5.03 (m, 2 H) 6.56 (t, J=7.25 Hz, 1 H) 6.65 (d, J=8.70 Hz, 2 H) 7.04-7.10 (m, 3 H) 7.15-7.21 (m, 4 H) 7.47-7.52 (m, 4 H) 7.62 (d, J=8.39 Hz, 1 H) 9.79 (s, 2 H).

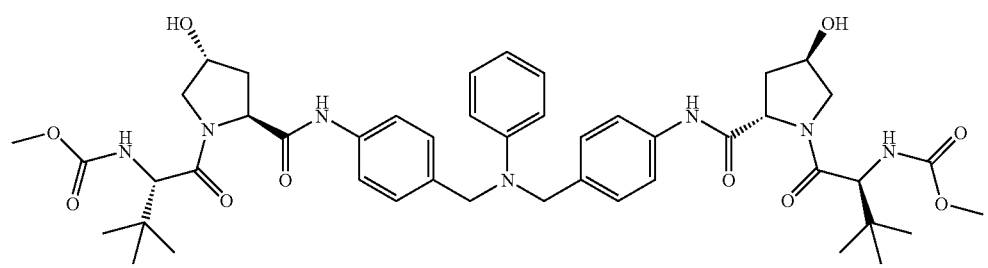

EXAMPLE 48 dimethyl [(phenylimino)bis{methanediylbenzene-4,1-diylcarbamoyl[(2S,4R)-4-hydroxypyrrolidine-2,1-diyl][(2S)-3,3-dimethyl-1-oxobutane-1,2-diyl]}] biscarbamate

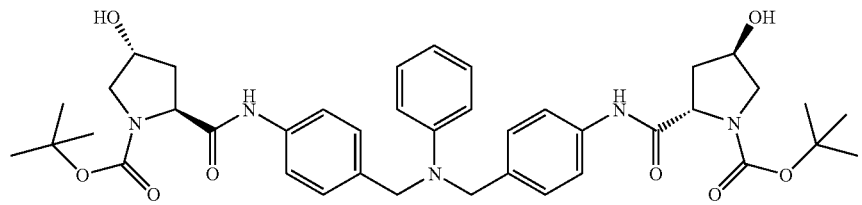 [SMILES: CC(C)(C)OC(=O)N1C[C@H](O)C[C@H]1C(=O)Nc1ccc(CN(Cc2ccc(NC(=O)[C@@H]3C[C@@H](O)CN3C(=O)OC(C)(C)C)cc2)c2ccccc2)cc1]

EXAMPLE 48A (3R,3'R,5S,5'S)-tert-butyl 5,5'-(4,4'-(phenylazanediyl)bis(methylene)bis(4,1-phenylene)bis(azanediyl))bis(oxomethylene)bis(3-hydroxypyrrolidine-1-carboxylate)

The product from Example 1B and (2S,4R)-1-(tert-butoxycarbonyl)-4-hydroxypyrrolidine-2-carboxylic acid (Chem-Impex) were processed using the method described in Example 41. The reaction was filtered, the solid washed with CH$_2$Cl$_2$ and dried in vacuum oven to provide 414 mg (69%) of the title compound. MS (DCI; M+H) m/z=730.

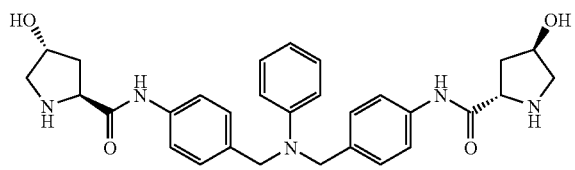 [SMILES: O=C(Nc1ccc(CN(Cc2ccc(NC(=O)[C@@H]3C[C@@H](O)CN3)cc2)c2ccccc2)cc1)[C@@H]1C[C@@H](O)CN1]

EXAMPLE 48B (2S,2'S,4R,4'R)-N,N'-(4,4'-(phenylazanediyl)bis(methylene)bis(4,1-phenylene))bis(4-hydroxypyrrolidine-2-carboxamide)

The product from Example 48A was processed using the method described in Example 47B to provide the title compound. MS (DCI; M+H) m/z=530.

EXAMPLE 48C dimethyl [(phenylimino)bis{methanediylbenzene-4,1-diylcarbamoyl[(2S,4R)-4-hydroxypyrrolidine-2,1-diyl][(2S)-3,3-dimethyl-1-oxobutane-1,2-diyl]}] biscarbamate The product from Example 48B and (S)-2-(methoxycarbonylamino)-3,3-dimethylbutanoic acid (DeGussa) were processed using the method described in Example 41. The crude residue was purified by silica gel chromatography (0% to 7% MeOH—CH$_2$Cl$_2$) to provide 60 mg (25%) of the title compound. $^1$H NMR (500 MHz, DMSO-D6) δ 0.94 (s, 18 H) 1.91 (ddd, J=12.86, 8.81, 4.43 Hz, 2 H) 2.04-2.12 (m, 2 H) 3.54 (s, 6 H) 3.62-3.71 (m, 4 H) 4.20 (d, J=9.31 Hz, 2 H) 4.36 (br s, 2 H) 4.49 (t, J=8.09 Hz, 2 H) 4.58 (s, 4 H) 5.18 (d, J=3.36 Hz, 2 H) 6.56 (t, J=7.25 Hz, 1 H) 6.65 (d, J=8.09 Hz, 2 H) 7.00-7.09 (m, 4 H) 7.17 (d, J=8.55 Hz, 4 H) 7.51 (d, J=8.54 Hz, 4 H) 10.03 (s, 2 H).

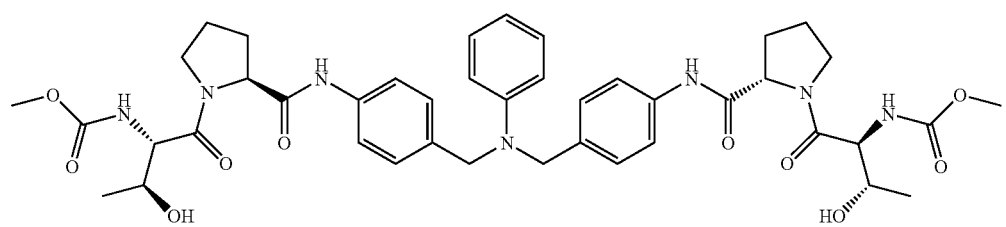

EXAMPLE 49 dimethyl [(phenylimino)bis{methanediylbenzene-4,1-diylcarbamoyl(2S)pyrrolidine-2,1-diyl[(2S,3S)-3-hydroxy-1-oxobutane-1,2-diyl]}]biscarbamate

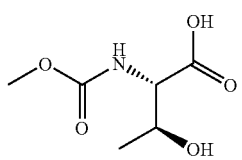

EXAMPLE 49A (2S,3S)-3-hydroxy-2-(methoxycarbonylamino)butanoic acid (2S,3S)-2-amino-3-hydroxybutanoic acid (0.54 g, 4.53 mmol) was processed as in Example 25A to give 0.139 g (17%) of the title compound as a waxy solid.

EXAMPLE 49B dimethyl [(phenylimino)bis{methanediylbenzene-4,1-diylcarbamoyl(2S)pyrrolidine-2,1-diyl[(2S,3S)-3-hydroxy-1-oxobutane-1,2-diyl]}]biscarbamate The product from Example 1D (0.05 g, 0.10 mmol) and the product from Example 49A (0.039 g, 0.22 mmol) were processed as in Example 25B to give 0.041 g (51%) of the title compound as an off-white solid. $^1$H NMR (500 MHz, DMSO-D6) δ ppm 1.16 (d, J=6.10 Hz, 6 H) 1.82-1.89 (m, 2 H) 1.90-2.00 (m, 4 H) 2.08-2.17 (m, 2 H) 3.52 (s, 6 H) 3.66-3.73 (m, 2 H) 3.77-3.87 (m, 4 H) 4.19 (t, J=8.39 Hz, 2 H) 4.46 (dd, J=8.39, 3.66 Hz, 2 H) 4.58 (s, 4 H) 5.29 (d, J=4.58 Hz, 2 H) 6.55 (t, J=7.17 Hz, 1 H) 6.63 (d, J=8.09 Hz, 2 H) 7.05 (dd, J=8.77, 7.25 Hz, 2 H) 7.16 (d, J=8.70 Hz, 4 H) 7.42 (d, J=8.24 Hz, 2 H) 7.47 (d, J=8.54 Hz, 4 H) 9.49 (s, 2 H); MS ESI+ m/z 816 (M+H)+; m/z 833 (M+NH4)+.

EXAMPLE 50 dimethyl[(phenylimino)bis{methanediylbenzene-4,1-diylcarbamoyl(2S)pyrrolidine-2,1-diyl[(2S,3R)-3-methyl-1-oxopentane-1,2-diyl]}]biscarbamate

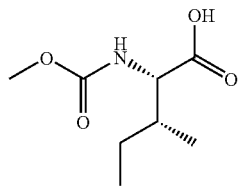

EXAMPLE 50A (2S,3R)-2-(methoxycarbonylamino)-3-methylpentanoic acid (2S,3R)-2-amino-3-methylpentanoic acid (0.965 g, 7.36 mmol) was processed as in Example 25A to give 1.16 g (83%) of the title compound as a waxy solid.

EXAMPLE 50B dimethyl[(phenylimino)bis{methanediylbenzene-4,1-diylcarbamoyl(2S)pyrrolidine-2,1-diyl[(2S,3R)-3-methyl-1-oxopentane-1,2-diyl]}]biscarbamate The product from Example 1D (0.05 g, 0.10 mmol) and the product from Example 50A (0.042 g, 0.22 mmol) were processed as in Example 25B to give 0.044 g (52%) of the title compound as an off-white solid. $^1$H NMR (500 MHz, DMSO-D6) δ ppm 0.80 (d, J=6.71 Hz, 6 H) 0.85 (t, J=7.32 Hz, 6 H) 1.06-1.15 (m, 2 H) 1.42-1.50 (m, 2 H) 1.73-1.79 (m, 2 H) 1.81-1.92 (m, 4 H) 1.95-2.03 (m, 2 H) 2.10-2.16 (m, 2 H) 3.23-3.30 (m, 2 H) 3.51 (s, 6 H) 3.54-3.63 (m, 1 H) 3.69-3.79 (m, 1 H) 4.19-4.24 (m, 2 H) 4.41 (dd, J=8.01, 5.26 Hz, 2 H) 4.57 (s, 4 H) 6.55 (t, J=7.25 Hz, 1 H) 6.64 (d, J=8.09 Hz, 2 H) 7.05 (dd, J=8.77, 7.25 Hz, 2 H) 7.12-7.19 (m, 6 H) 7.49 (d, J=8.54 Hz, 4 H) 9.95 (s, 2 H); MS ESI– m/z 838 (M–H)–.

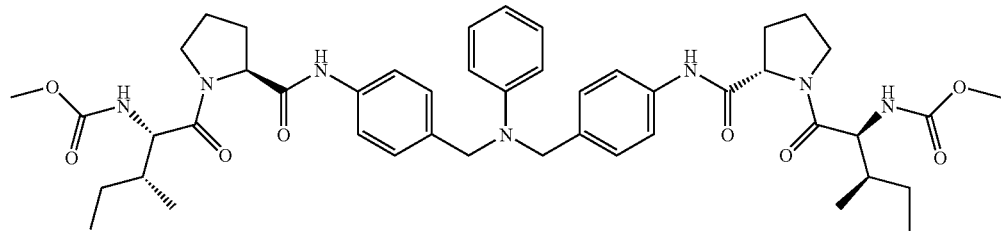

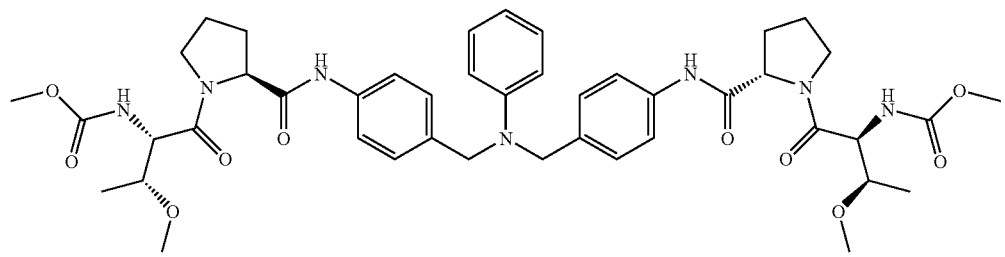

EXAMPLE 51 dimethyl[(phenylimino)bis{methanediylbenzene-4,1-diylcarbamoyl(2S)pyrrolidine-2,1-diyl[(2S,3R)-3-methoxy-1-oxobutane-1,2-diyl]}]biscarbamate

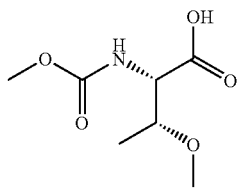

EXAMPLE 51A (2S,3R)-3-methoxy-2-(methoxycarbonylamino)butanoic acid (2S,3R)-2-amino-3-methoxybutanoic acid (1.0 g, 7.51 mmol) was processed as in Example 25A to give 0.28 g (20%) of the title compound as a waxy solid.

EXAMPLE 51B dimethyl[(phenylimino)bis{methanediylbenzene-4,1-diylcarbamoyl(2S)pyrrolidine-2,1-diyl[(2S,3R)-3-methoxy-1-oxobutane-1,2-diyl]}]biscarbamate The product from Example 1D (0.05 g, 0.10 mmol) and the product from Example 51A (0.042 g, 0.22 mmol) were processed as in Example 25B to give 0.060 g (71%) of the title compound as an off-white solid. $^1$H NMR (500 MHz, DMSO-D6) δ ppm 1.12 (d, J=6.26 Hz, 6 H) 1.82-1.90 (m, 4 H) 1.94-2.04 (m, 2 H) 2.10-2.18 (m, 2 H) 3.23 (s, 6 H) 3.42-3.48 (m, 2 H) 3.52 (s, 6 H) 3.62-3.70 (m, 2 H) 3.79-3.86 (m, 2 H) 4.25 (t, J=7.78 Hz, 2 H) 4.40 (dd, J=8.24, 5.04 Hz, 2 H) 4.57 (s, 4 H) 6.55 (t, J=7.25 Hz, 1 H) 6.64 (d, J=8.09 Hz, 2 H) 7.05 (dd, J=8.77, 7.25 Hz, 2 H) 7.16 (d, J=8.70 Hz, 4 H) 7.32 (d, J=7.93 Hz, 2 H) 7.49 (d, J=8.54 Hz, 4 H) 9.93 (s, 2 H); MS ESI– m/z 842 (M–H)–.

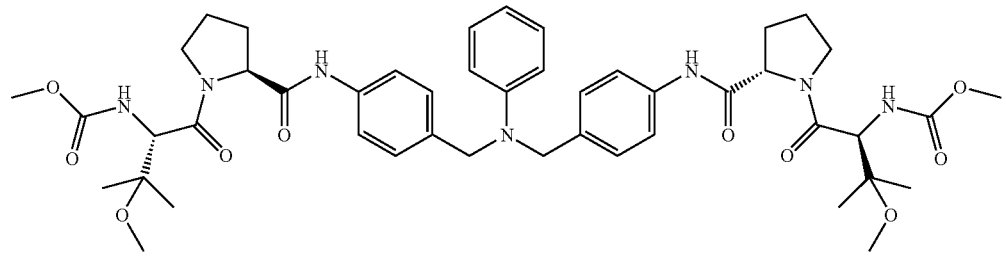

EXAMPLE 52 dimethyl [(phenylimino)bis{methanediylbenzene-4,1-diylcarbamoyl(2S)pyrrolidine-2,1-diyl[(2S)-3-methoxy-3-methyl-1-oxobutane-1,2-diyl]}]biscarbamate

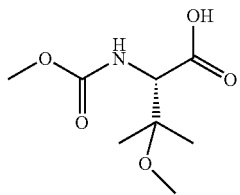

EXAMPLE 52A (S)-3-methoxy-2-(methoxycarbonylamino)-3-methylbutanoic acid (S)-2-amino-3-methoxy-3-methylbutanoic acid (0.55 g, 3.72 mmol) was processed as in Example 25A to give 0.18 g (24%) of the title compound as a waxy solid.

EXAMPLE 52B dimethyl[(phenylimino)bis{methanediylbenzene-4,1-diylcarbamoyl(2S)pyrrolidine-2,1-diyl[(2S)-3-methoxy-3-methyl-1-oxobutane-1,2-diyl]}]biscarbamate The product from Example 1D (0.05 g, 0.10 mmol) and the product from Example 52A (0.045 g, 0.22 mmol) were processed as in Example 25B to give 0.015 g (17%) the title compound as an off-white solid. $^1$H NMR (500 MHz, DMSO-D6) δ ppm 1.14 (s, 6 H) 1.83-1.92 (m, 4 H) 1.92-2.02 (m, 2 H) 2.10 (dd, J=20.52, 12.13 Hz, 2 H) 2.53 (s, 6 H) 3.11 (d, J=4.27 Hz, 6 H) 3.53 (s, 6 H) 3.63-3.81 (m, 4 H) 4.33-4.43 (m, 2 H) 4.50 (dd, J=13.12, 8.85 Hz, 2 H) 4.57 (s, 4 H) 6.55 (t, J=7.25 Hz, 1 H) 6.64 (d, J=8.39 Hz, 2 H) 7.05 (t, J=8.01 Hz, 2 H) 7.09-7.25 (m, 6 H) 7.48 (dd, J=17.85, 8.54 Hz, 4 H) 9.73 (d, J=7.02 Hz, 2 H); MS ESI- m/z 870.5 (M-H)-.

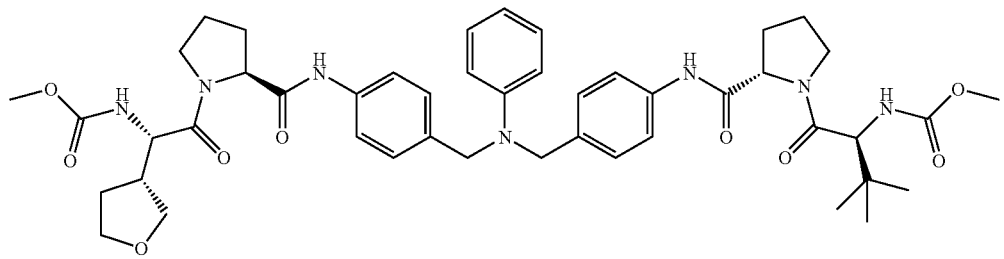

EXAMPLE 53

N-(methoxycarbonyl)-3-methyl-L-valyl-N-(4-{[{4-[(1-{(2S)-2-[(methoxycarbonyl)amino]-2-[(3R)-tetrahydrofuran-3-yl]acetyl}-L-prolyl)amino]benzyl}(phenyl)amino]methyl}phenyl)-L-prolinamide The product of Example 10A (0.035 g, 0.052 mmol) and (S)-2-(methoxycarbonylamino)-2-((R)-tetrahydrofuran-3-yl)acetic acid were processed as in Example 25B to give 0.030 g (67%) of the title compound as a thick oil. $^1$H NMR (500 MHz, DMSO-D6) δ ppm 0.91 (s, 9 H) 1.66 (ddd, J=20.03, 7.21, 7.10 Hz, 1 H) 1.77-1.88 (m, 6 H) 1.90-1.99 (m, 2 H) 2.06-2.14 (m, 2 H) 3.48 (s, 6 H) 3.54-3.65 (m, 4 H) 3.66-3.75 (m, 3 H) 3.78-3.85 (m, 1 H) 4.14-4.22 (m, 2 H) 4.38 (dd, J=8.09, 5.04 Hz, 2 H) 4.53 (s, 4 H) 6.51 (t, J=7.25 Hz, 1 H) 6.60 (d, J=8.09 Hz, 2 H) 6.99-7.06 (m, 3 H) 7.12 (d, J=7.48 Hz, 4 H) 7.45 (d, J=7.93 Hz, 4 H) 7.55 (d, J=7.93 Hz, 1 H) 9.93 (d, J=6.26 Hz, 2 H); MS ESI- m/z 852.5 (M-H)-.

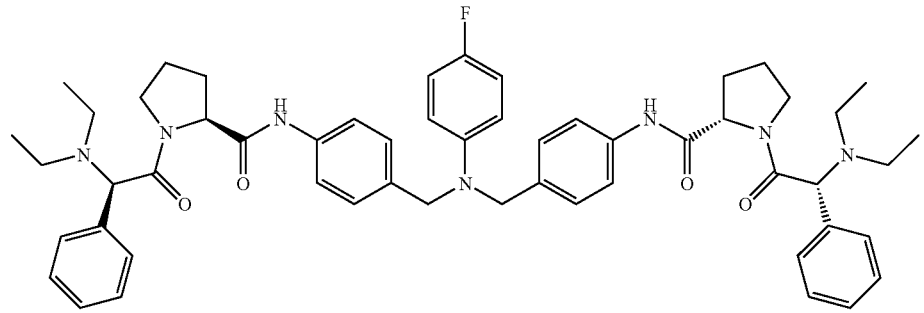 [SMILES: CCN(CC)[C@@H](C(=O)N1CCC[C@H]1C(=O)Nc1ccc(CN(Cc2ccc(NC(=O)[C@@H]3CCCN3C(=O)[C@@H](c3ccccc3)N(CC)CC)cc2)c2ccc(F)cc2)cc1)c1ccccc1]

EXAMPLE 54

(2S,2'S)-N,N-{[(4-fluorophenyl)imino]bis(methanediylbenzene-4,1-diyl)}bis{1-[(2R)-2-(diethylamino)-2-phenylacetyl]pyrrolidine-2-carboxamide}

The product from Example 13D (0.055 g, 0.107 mmol) and (R)-2-(diethylamino)-2-phenylacetic acid (0.048 g, 0.24 mmol) were processed as in Example 25B to give 0.046 g (48%) of the title compound as an off-white solid. MS (TFA, ELSD+) m/z 895 (M+H)+.

ate (2.103 g, 19.85 mmol) was added ethanol (40 mL) and the resultant mixture heated at 100° C. for 65 hours. After cooling, the resultant solid was removed by filtration and washed with ethanol. The filtrate was concentrated, and then dissolved in ethanol then a solution of 4N aqueous hydrochloric acid added until the pH of the solution was 3. The resultant solid was removed and discarded. The filtrate was concentrated and purified by reversed phase chromatography (C18), eluting with 10-100% acetonitrile in water (0.1% TFA) to give the title compound. MS (ESI) m/z 206 (M+H)+.

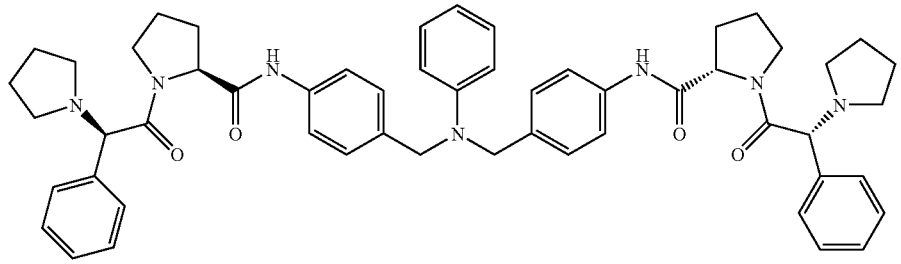 [SMILES: O=C(Nc1ccc(CN(Cc2ccc(NC(=O)[C@@H]3CCCN3C(=O)[C@@H](c3ccccc3)N3CCCC3)cc2)c2ccccc2)cc1)[C@@H]1CCCN1C(=O)[C@@H](c1ccccc1)N1CCCC1]

EXAMPLE 55

(2S,2'S)-N,N'-[(phenylimino)bis(methanediylbenzene-4,1-diyl)]bis{1-[(2R)-2-phenyl-2-pyrrolidin-1-ylacetyl]pyrrolidine-2-carboxamide}

EXAMPLE 55A (R)-2-phenyl-2-(pyrrolidin-1-yl)acetic acid

To (R)-2-amino-2-phenylacetic acid (1.0 g, 6.62 mmol), 1,4-dibromobutane (1.57 g, 0.727 mmol) and sodium carbon-

EXAMPLE 55B (2S,2'S)-N,N'-[(phenylimino)bis(methanediylbenzene-4,1-diyl)]bis{1-[(2R)-2-phenyl-2-pyrrolidin-1-ylacetyl]pyrrolidine-2-carboxamide}

The product of Example 1D (30 mg, 0.060 mmol) and the product of Example 55A (40.8 mg, 0.199 mmol) were processed using the method described in Example 43 to afford 34 mg (65%) of the title compound. $^1$H NMR (500 MHz, DMSO-D6) δ ppm 10.08 (bs, 2H), 7.55 (m, 4H), 7.49 (m, 10H), 7.16 (d, J=8.4 Hz, 4H), 7.03 (m, 2H), 6.61 (d, J=8.2 Hz, 2H), 6.53 (t, J=7.2 Hz, 1H), 5.50 (m, 2H), 4.57 (s, 4H), 4.38 (m, 2H), 3.84 (m, 2H), 3.50 (m, 2H), 3.10 (m, 6H), 3.86 (m, 2H), 3.75 (m, 2H), 2.02 (m, 4H), 1.90 (m, 8H), 1.76 (s, 4H).

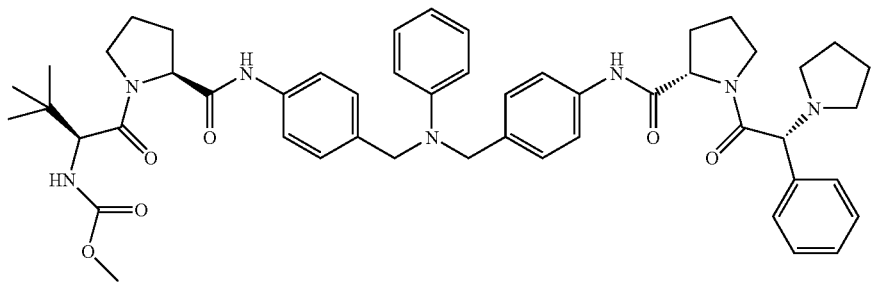 [SMILES: COC(=O)N[C@H](C(=O)N1CCC[C@H]1C(=O)Nc1ccc(CN(Cc2ccc(NC(=O)[C@@H]3CCCN3C(=O)[C@@H](c3ccccc3)N3CCCC3)cc2)c2ccccc2)cc1)C(C)(C)C]

EXAMPLE 56

N-(methoxycarbonyl)-3-methyl-L-valyl-N-[4-({phenyl[4-({1-[(2R)-2-phenyl-2-pyrrolidin-1-ylacetyl]-L-prolyl}amino)benzyl]amino}methyl)phenyl]-L-prolinamide The product from Example 10A (40 mg, 0.060 mmol) and the product of Example 55A (18.4 mg, 0.090 mmol) were processed using the method described in Example 43 to afford 31 mg (60%) of the title compound. $^1$H NMR (500 MHz, DMSO-D6) δ ppm 9.94 (bs, 1H), 9.90 (bs, 1H), 7.46 (m, 3H), 7.41 (m, 2H), 7.27 (m, 3H), 7.15 (m, 4H), 7.02 (m, 3H), 6.61 (d, J=8.2 Hz, 2H), 6.52 (t, J=7.3 Hz, 1H), 4.55 (bs, 4H), 4.38 (m, 1H), 4.27 (m, 1H), 4.17 (m, 2H), 3.79 (m, 1H), 3.72 (m, 1H), 3.58 (m, 1H), 3.49 (s, 3H), 3.40 (m, 1H), 2.43 (m, 3H), 2.29 (m, 2H), 2.09 (m, 1H), 1.95 (m, 3H), 1.89 (m, 4H), 1.57 (m, 3H), 0.91 (s, 9H).

filtrate was concentrated and purified by reversed phase chromatography (C18), eluting with 10-100% acetonitrile in water (0.1% TFA) to give the title compound. MS (ESI) m/z 222 (MA)$^+$.

EXAMPLE 57B (2S,2'S)-N,N'-[(phenylimino)bis(methanediylbenzene-4,1-diyl)]bis{1-[(2R)-2-morpholin-4-yl-2-phenylacetyl]pyrrolidine-2-carboxamide}

The product of Example 1D (30 mg, 0.060 mmol) and the product of Example 57A (44 mg, 0.199 mmol) were pro-

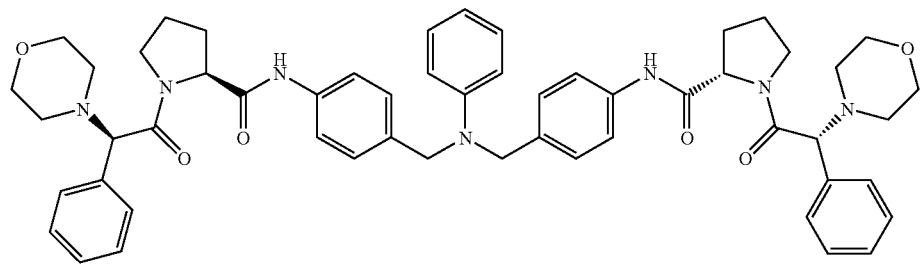 [SMILES: O=C(Nc1ccc(CN(Cc2ccc(NC(=O)[C@@H]3CCCN3C(=O)[C@@H](c3ccccc3)N3CCOCC3)cc2)c2ccccc2)cc1)[C@@H]1CCCN1C(=O)[C@@H](c1ccccc1)N1CCOCC1]

EXAMPLE 57

(2S,2'S)-N,N'-[(phenylimino)bis(methanediylbenzene-4,1-diyl)]bis{1-[(2R)-2-morpholin-4-yl-2-phenylacetyl]pyrrolidine-2-carboxamide}

EXAMPLE 57A (R)-2-morpholino-2-phenylacetic acid

To (R)-2-amino-2-phenylacetic acid (1.0 g, 6.62 mmol), 1-bromo-2-(2-bromoethoxy)ethane (1.686 g, 0.727 mmol)

cessed using the method described in Example 43 to afford 41 mg (75%) of the title compound. $^1$H NMR (500 MHz, DMSO-D6) δ ppm 9.93 (bs, 2H), 7.47 (d, J=8.4 Hz, 4H), 7.41 (d, J=7.0 Hz, 4H), 7.28 (m, 6H), 7.14 (m, 4H), 7.03 (m, 2H), 6.62 (d, J=8.1 Hz, 2H), 6.52 (t, J=7.2 Hz, 1H), 4.56 (bs, 4H), 4.24 (m, 4H), 3.81 (m, 2H), 3.45 (m, 8H), 3.40 (m, 2H), 2.63 (m, 8H), 2.39 (m, 4H), 2.29 (m, 4H), 1.95 (m, 4H), 1.77 (m, 4H).

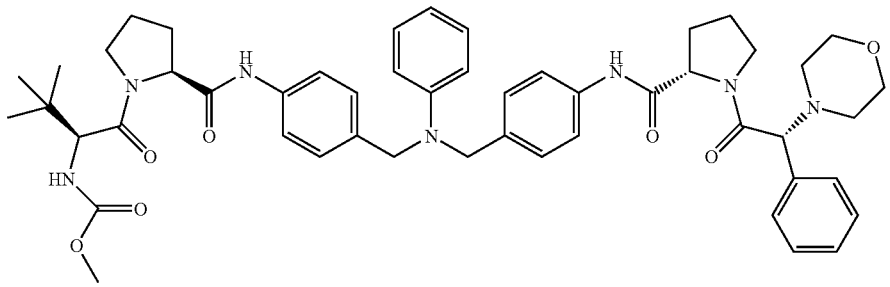 [SMILES: COC(=O)N[C@H](C(=O)N1CCC[C@H]1C(=O)Nc1ccc(CN(Cc2ccc(NC(=O)[C@@H]3CCCN3C(=O)[C@@H](c3ccccc3)N3CCOCC3)cc2)c2ccccc2)cc1)C(C)(C)C]

and sodium carbonate (2.103 g, 19.85 mmol) was added ethanol (40 mL) and the resultant mixture heated at 100° C. for 45 hours. After cooling, the resultant solid was removed by filtration and washed with ethanol. The filtrate was concentrated, and then dissolved in ethanol then a solution of 4N aqueous hydrochloric acid added until the pH of the solution was 3. The resultant solid was removed and discarded. The

EXAMPLE 58

N-(methoxycarbonyl)-3-methyl-L-valyl-N-[4-({[4-({1-[(2R)-2-morpholin-4-yl-2-phenylacetyl]-L-prolyl}amino)benzyl](phenyl)amino}methyl)phenyl]-L-prolinamide The product from Example 10A (40 mg, 0.060 mmol) and the product of Example 57A (19.9 mg, 0.090 mmol) were processed using the method described in Example 43 to afford 35 mg (67%) of the title compound. $^1$H NMR (500 MHz, DMSO-D6) δ ppm 9.80 (s, 1H), 9.78 (s, 1H), 7.35 (m, 3H), 7.28 (m, 2H), 7.14 (m, 3H), 6.97 (m, 4H), 6.88 (m, 3H), 6.46 (d, J=8.1 Hz, 2H), 6.37 (t, J=7.2 Hz, 1H), 4.40 (bs, 4H), 4.22 (m, 1H), 4.11 (m, 1H), 4.05 (m, 2H), 3.67 (m, 1H), 3.57 (m, 1H), 3.43 (m, 1H), 3.34 (s, 3H), 3.30 (m, 3H), 3.24 (m, 2H), 2.49 (s, 8H), 2.22 (m, 2H), 2.12 (m, 2H), 1.92 (m, 1H), 1.79 (m, 3H), 1.62 (m, 4H), 0.77 (s, 9H).

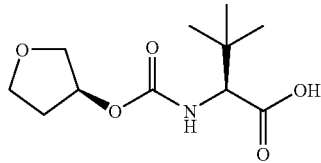

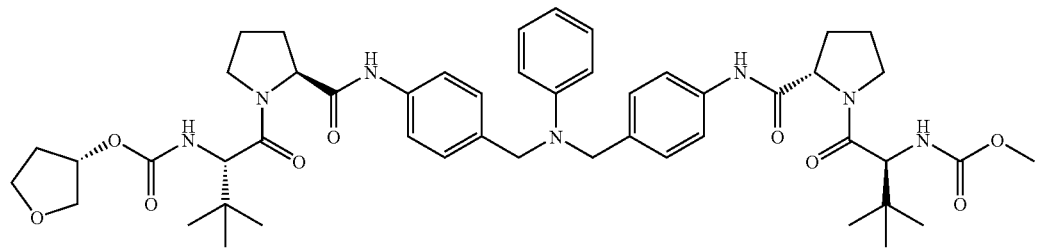 [SMILES: COC(=O)N[C@H](C(=O)N1CCC[C@H]1C(=O)Nc1ccc(CN(Cc2ccc(NC(=O)[C@@H]3CCCN3C(=O)[C@@H](NC(=O)O[C@H]3CCOC3)C(C)(C)C)cc2)c2ccccc2)cc1)C(C)(C)C]

EXAMPLE 59 methyl (3S)-tetrahydrofuran-3-yl[(phenylimino) bis{methanediylbenzene-4,1-diylcarbamoyl(2S)pyrrolidine-2,1-diyl[(2S)-3,3-dimethyl-1-oxobutane-1,2-diyl]}]biscarbamate

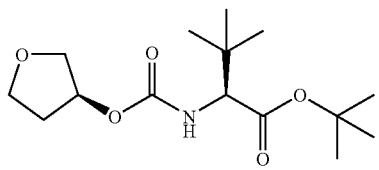 [SMILES: CC(C)(C)OC(=O)[C@@H](NC(=O)O[C@H]1CCOC1)C(C)(C)C]

EXAMPLE 59A (S)-tert-butyl 3,3-dimethyl-2-(((S)-tetrahydrofuran-3-yloxy)carbonylamino)butanoate A mixture of (S)-tert-butyl 2-amino-3,3-dimethylbutanoate hydrochloride (0.05 g, 0.223 mmol), (S)-2,5-dioxopyrrolidin-1-yl tetrahydrofuran-3-yl carbonate (0.056 g, 0.246 mmol) and Hunig's base (0.078 mL, 0.447 mmol) in THF (2.25 mL) was stirred at room temperature for 12 hours. The solvent was evaporated and the product was purified by chromatography on silica gel eluting with 0-15% ethyl acetate in dichloromethane to give the title compound (0.037 g, 55% yield).

EXAMPLE 59B (S)-3,3-dimethyl-2-(((S)-tetrahydrofuran-3-yloxy) carbonylamino)butanoic acid To a solution of the product from Example 59A (0.037 g, 0.123 mmol) in dichloromethane (1.2 mL) was added trifluoroacetic acid (1.2 mL) and the mixture was stirred at room temperature for 2 hours. The solvent was evaporated to give the title compound which was used without further purification.

EXAMPLE 59C methyl (3S)-tetrahydrofuran-3-yl[(phenylimino) bis{methanediylbenzene-4,1-diylcarbamoyl(2S)pyrrolidine-2,1-diyl[(2S)-3,3-dimethyl-1-oxobutane-1,2-diyl]}]biscarbamate To a solution of the product from Example 10A (0.025 g, 0.037 mmol) in DMSO (0.374 ml) at room temperature were added the product from Example 59B (0.011 g, 0.045 mmol), HATU (0.017 g, 0.045 mmol) and Hunig's base (0.033 mL, 0.187 mmol) and the mixture was stirred at room temperature for 1 hour. The reaction was diluted with ethyl acetate and washed with saturated NaHCO$_3$, water, and saturated NaCl. The organic was dried over MgSO$_4$, filtered and evaporated. The product was purified by reversed phase chromatography (C18), eluting with 10-100% acetonitrile in water (0.1% TFA) to give the title compound as a TFA salt (0.032 g). $^1$H NMR (500 MHz, DMSO-d$_6$) δ ppm 0.96 (s, 18 H) 1.80-1.92 (m, 5 H) 1.93-2.03 (m, 2 H) 2.05-2.21 (m, 3 H) 3.54 (s, 3 H) 3.58-3.85 (m, 7 H) 4.20 (dd, J=10.76, 9.08 Hz, 2 H) 4.43 (dd, J=8.09, 5.34 Hz, 2 H) 4.59 (s, 4 H) 5.10 (dd, J=5.87, 4.65 Hz, 1 H) 6.49-6.61 (m, 1 H) 6.66 (d, J=7.17 Hz, 2 H) 7.02-7.14 (m, 3 H) 7.17 (d, J=8.55 Hz, 4 H) 7.48-7.56 (m, 4 H) 9.99 (s, 2 H). MS (ESI) m/z 896.5 (M+H)+.

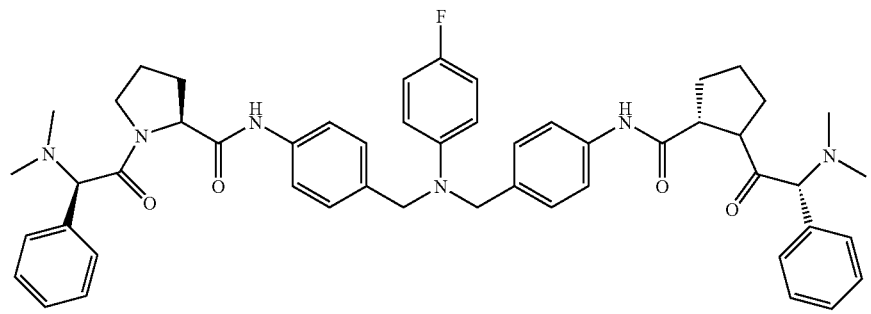

EXAMPLE 60

(2S,2')-N,N'-{[(4-fluorophenyl)imino]bis(methanediylbenzene-4,1-diyl)}bis{1-[(2R)-2-(dimethylamino)-2-phenylacetyl]pyrrolidine-2-carboxamide}

The title compound was prepared using the methods from Example 2 substituting the product from Example 13D for the product from Example 1D to provide the title compound (105 mg, 22% yield). $^1$H NMR (500 MHz, DMSO) δ 9.96 (s, 2H), 7.54-7.49 (m, 4H), 7.46-7.40 (m, 4H), 7.35-7.26 (m, 6H), 7.20-7.14 (m, 4H), 6.95-6.87 (m, 2H), 6.67-6.60 (m, 2H), 4.56 (s, 4H), 4.34-4.27 (m, 2H), 4.14 (s, 2H), 3.87-3.79 (m, 2H), 3.46-3.39 (m, 2H), 2.11 (s, 12H), 2.05-1.93 (m, 4H), 1.88-1.72 (m, 4H). MS (ESI; M+H) m/z=839.

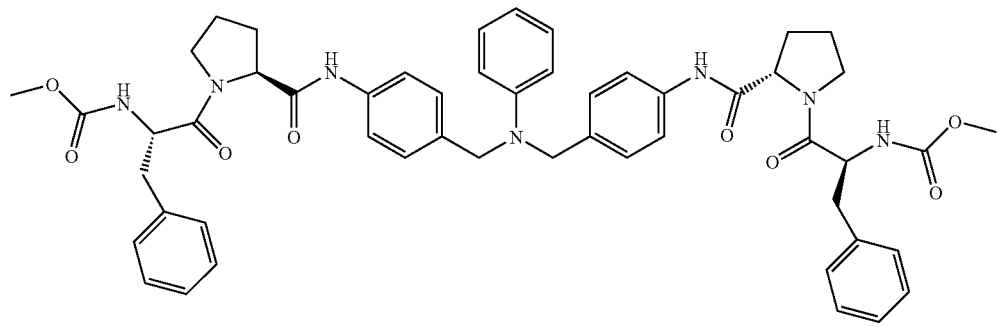

EXAMPLE 61 dimethyl [(phenylimino)bis{methanediylbenzene-4,
1-diylcarbamoyl(2S)pyrrolidine-2,1-diyl[(2S)-1-oxo-
3-phenylpropane-1,2-diyl]}]biscarbamate The product from Example 1D (0.030 g, 0.060 mmol) was subjected to the procedure described in Example 24E, substituting (S)-2-(methoxycarbonylamino)-3-phenylpropanoic acid for (S)-2-(methoxycarbonylamino)-3-methylbutanoic acid, to give the title compound as a TFA salt (16 mg). $^1$H NMR (500 MHz, DMSO-D6) δ ppm 1.85-2.06 (m, 8 H), 2.10-2.19 (m, 2 H), 2.74 (dd, J=14.0, 10.1 Hz, 2 H), 2.96 (dd, J=14.0, 3.7 Hz, 2 H), 3.44 (s, 6 H), 4.37-4.43 (m, 2 H), 4.46 (dd, J=8.2, 4.2 Hz, 2 H), 4.60 (s, 4 H), 6.57 (t, J=6.9 Hz, 1 H), 6.67 (d, J=8.1 Hz, 2 H), 7.07 (t, J=7.9 Hz, 2 H), 7.17-7.22 (m, 6 H), 7.26 (t, J=7.4 Hz, 4 H), 7.30-7.33 (m, 4 H), 7.48-7.55 (m, 6 H), 9.95 (s, 2 H); MS m/z 908.9 (M+H)$^+$.

EXAMPLE 62

N-(methoxycarbonyl)-3-methyl-L-valyl-N-(4-{[{4-
[(1-{(2S)-2-[(methoxycarbonyl)amino]butanoyl}-L-
prolyl)amino]benzyl}(phenyl)amino]
methyl}phenyl)-L-prolinamide The product from Example 10A (0.028 g, 0.054 mmol) was subjected to the procedure described in Example 10B, substituting (S)-2-(methoxycarbonylamino)butanoic acid for (R)-2-(dimethylamino)-2-phenylacetic acid, and the product purified using the HPLC conditions of Example 1E to give the title compound as a TFA salt (6.4 mg). $^1$H NMR (500 MHz, DMSO-D6) δ ppm 0.88-0.92 (m, 3 H), 0.96 (s, 9 H), 1.52 (dd, J=14.5, 6.9 Hz, 1 H), 1.65 (dd, J=14.0, 6.7 Hz, 1 H), 1.81-2.04 (m, 8 H), 2.09-2.18 (m, 2 H), 3.52 (s, 3 H), 3.54 (s, 3 H), 4.14-4.23 (m, 2 H), 4.40-4.46 (m, 2 H), 4.59 (s, 4 H), 6.57 (t, J=7.1 Hz, 1 H), 6.66 (d, J=8.1 Hz, 2 H), 7.04-7.11 (m, 2 H), 7.17 (d, J=8.5 Hz, 4 H), 7.50 (d, 4 H), 9.95 (s, 1 H), 9.99 (s, 1 H); MS m/z 812.1 (M+H)$^+$.

EXAMPLE 63 dimethyl [(phenylimino)bis{methanediylbenzene-4,1-diylcarbamoyl[(3S,6R,9aS)-5-oxooctahydro-1H-pyrrolo[1,2-a]azepine-3,6-diyl]}]biscarbamate

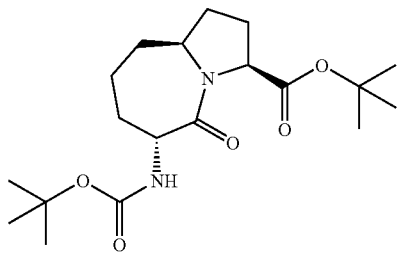 [SMILES: CC(C)(C)OC(=O)N[C@@H]1CCC[C@H]2CC[C@@H](C(=O)OC(C)(C)C)N2C1=O]

EXAMPLE 63A (3S,6R,9aS)-tert-butyl 6-(tert-butoxycarbonylamino)-5-oxooctahydro-1H-pyrrolo[1,2-a]azepine-3-carboxylate The title compound was prepared following the described procedures (Angiolini et al. *Eur. J. Org. Chem.* 2000, 2571-2581).

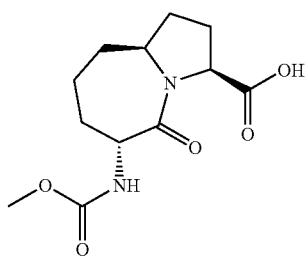 [SMILES: COC(=O)N[C@@H]1CCC[C@H]2CC[C@@H](C(=O)O)N2C1=O]

EXAMPLE 63B (3S,6R,9aS)-6-(methoxycarbonylamino)-5-oxooctahydro-1H-pyrrolo[1,2-a]azepine-3-carboxylic acid To a solution of the product from Example 63A (45 mg, 0.122 mmol) in 1,4-dioxane (0.2 mL) was added 2N HCl in 1,4-dioxane (0.3 mL, 1.2 mmol). The resulting solution was stirred at rt overnight and then concentrated in vacuo. The residue was dissolved in H$_2$O (0.4 mL), NaHCO$_3$ (33 mg, 0.39 mmol) was added, and the resulting mixture was stirred at 0° C. while a solution of methyl chloroformate (0.012 mL, 0.156 mmol) in Et$_2$O (0.100 mL) was added dropwise. The resulting mixture was stirred at rt for 3 h and then partitioned between 0.2 N aq. HCl and CH$_2$Cl$_2$. The organic layer was dried over Na$_2$SO$_4$, filtered and concentrated in vacuo to give the title compound as a solid (33 mg, quantitative).

EXAMPLE 63C dimethyl [(phenylimino)bis{methanediylbenzene-4,1-diylcarbamoyl[(3S,6R,9aS)-5-oxooctahydro-1H-pyrrolo[1,2-a]azepine-3,6-diyl]}]biscarbamate The product from Example 1B (10 mg, 0.033 mmol) was subjected to the conditions described in Example 24C, substituting the product from Example 63B (19 mg, 0.070 mmol) for N-(tert-butoxycarbonyl)-L-proline, to give the title compound as a TFA salt (10 mg). $^1$H NMR (500 MHz, DMSO-D6) δ ppm 1.51-1.86 (m, 14 H), 1.90-2.01 (m, 4 H), 2.02-2.11 (m, 2 H), 3.55 (s, 6 H), 3.96-4.04 (m, 2 H), 4.14 (t, J=5.95 Hz, 2 H), 4.44 (d, J=9.46 Hz, 2 H), 4.59 (s, 4 H), 6.57 (t, J=7.10 Hz, 1 H), 6.66 (d, J=7.93 Hz, 2 H), 7.07 (t, J=7.86 Hz, 2 H), 7.17 (d, J=8.54 Hz, 4 H), 7.44 (s, 2 H), 7.52 (d, J=8.55 Hz, 4 H), 9.99 (s, 2 H); MS m/z 809 (M+H)$^+$.

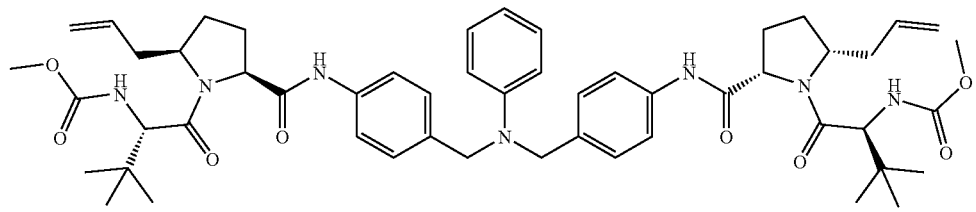 [SMILES: C=CC[C@H]1CC[C@@H](C(=O)Nc2ccc(CN(Cc3ccc(NC(=O)[C@@H]4CC[C@H](CC=C)N4C(=O)[C@@H](NC(=O)OC)C(C)(C)C)cc3)c3ccccc3)cc2)N1C(=O)[C@@H](NC(=O)OC)C(C)(C)C]

EXAMPLE 64 dimethyl [(phenylimino)bis{methanediylbenzene-4,1-diylcarbamoyl[(2S,5R)-5-prop-2-en-1-ylpyrrolidine-2,1-diyl][(2S)-3,3-dimethyl-1-oxobutane-1,2-diyl]}]biscarbamate

EXAMPLE 64A (2S,5R)-1-tert-butyl 2-ethyl 5-allylpyrrolidine-1,2-dicarboxylate The title compound was prepared following the described procedures (Zhang et al. *Org. Lett.* 2002, 4, 4029-4032).

EXAMPLE 64B (2S,5R)-5-allyl-1-(tert-butoxycarbonyl)pyrrolidine-2-carboxylic acid A solution of the product from Example 64A (0.35 g, 1.24 mmol) in MeOH (10 mL) was treated with a 3.0 M aq. solution of NaOH (2.06 mL, 6.18 mmol), and the resulting mixture was stirred at rt for 3 h. Added 1N HCl to adjust to pH 2, removed MeOH in vacuo, and extracted the aqueous layer with CH$_2$Cl$_2$ (2×). The combined organic layers were dried over Na$_2$SO$_4$, filtered and concentrated in vacuo to give the title compound.

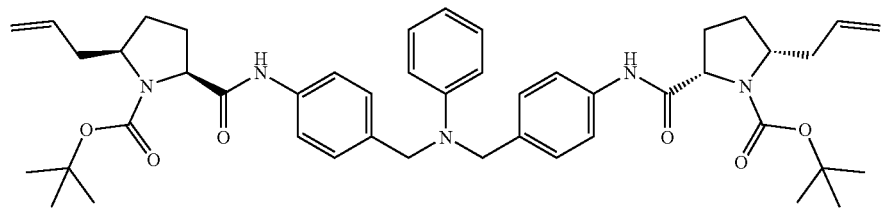 [SMILES: C=CC[C@H]1CC[C@@H](C(=O)Nc2ccc(CN(Cc3ccc(NC(=O)[C@@H]4CC[C@H](CC=C)N4C(=O)OC(C)(C)C)cc3)c3ccccc3)cc2)N1C(=O)OC(C)(C)C]

EXAMPLE 64C (2R,2'R,5S,5'S)-tert-butyl 5,5'-(4,4'-(phenylazanediyl)bis(methylene)bis(4,1-phenylene)bis(azanediyl))bis(oxomethylene)bis(2-allylpyrrolidine-1-carboxylate)

The product from Example 1B (119 mg, 0.392 mmol) was subjected to the procedure described in Example 24C, substituting the product from Example 64B (0.22 g, 0.862 mmol) for N-(tert-butoxycarbonyl)-L-proline to give the title compound (0.24 g, 79%).

EXAMPLE 64D (2S,2'S,5R,5'R)-N,N'-(4,4'-(phenylazanediyl)bis(methylene)bis(4,1-phenylene))bis(5-allylpyrrolidine-2-carboxamide)

The product from Example 64C (0.24 g, 0.31 mmol) was subjected to the conditions described in Example 1D to give the title compound (0.17 g, 95%).

EXAMPLE 64E dimethyl[(phenylimino)bis{methanediylbenzene-4,1-diylcarbamoyl[(2S,5R)-5-prop-2-en-1-ylpyrrolidine-2,1-diyl][(2S)-3,3-dimethyl-1-oxobutane-1,2-diyl]}]biscarbamate The product from Example 64D (20 mg, 0.035 mmol) was subjected to the conditions described in Example 24E, substituting (S)-2-(methoxycarbonylamino)-3,3-dimethylbutanoic acid for (S)-2-(methoxycarbonylamino)-3-methylbutanoic acid, to give the title compound as a TFA salt (17 mg). $^1$H NMR (500 MHz, DMSO-D6) δ ppm 0.89-1.01 (m, 18 H), 1.73-1.95 (m, 5 H), 2.02-2.28 (m, 3 H), 3.50-3.60 (m, 6 H), 3.97-4.13 (m, 1 H), 4.20 (d, J=9.46 Hz, 2 H), 4.26-4.45 (m, 3 H), 4.54-4.65 (m, 4 H), 4.95-5.21 (m, 4 H), 5.71-5.93 (m, 2 H), 6.57 (t, J=7.25 Hz, 1 H), 6.66 (d, J=8.24 Hz, 2 H), 6.88-6.96 (m, J=9.61 Hz, 1 H), 7.03-7.10 (m, 2 H), 7.13-7.23 (m, 4 H), 7.38 (d, J=9.46 Hz, 1 H), 7.47-7.56 (m, 4 H), 9.98 (s, 2 H); MS (ESI) m/z 920.5 (M+H)$^+$.

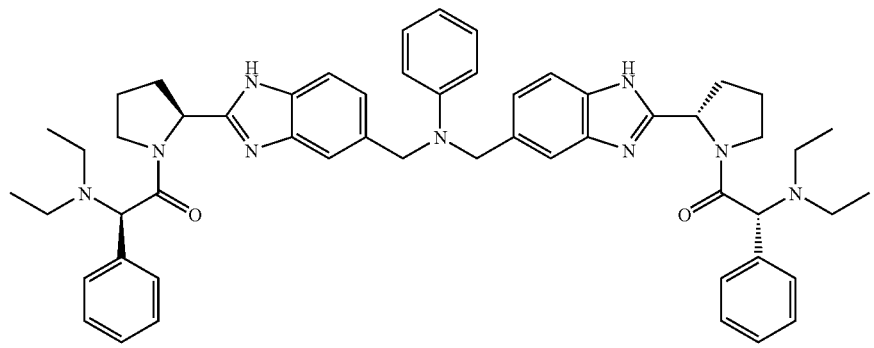 [SMILES: CCN(CC)[C@@H](C(=O)N1CCC[C@H]1c1nc2cc(CN(Cc3ccc4[nH]c([C@@H]5CCCN5C(=O)[C@@H](c5ccccc5)N(CC)CC)nc4c3)c3ccccc3)ccc2[nH]1)c1ccccc1]

EXAMPLE 65

N,N-bis[(2-{(2S)-1-[(2R)-2-(diethylamino)-2-phenylacetyl]pyrrolidin-2-yl}-1H-benzimidazol-5-yl)methyl]aniline The product from Example 7E (18 mg, 0.037 mmol) was subjected to the procedure described in Example 24E, substituting (R)-2-(diethylamino)-2-phenylacetic acid hydrochloride for (S)-2-(methoxycarbonylamino)-3-methylbutanoic acid, to give the title compound as a TFA salt (25 mg). $^1$H NMR (500 MHz, DMSO-D6) δ ppm 0.93-1.37 (m, 12 H), 1.84-2.14 (m, 8 H), 2.15-2.28 (m, 2 H), 2.77-3.40 (m, 10 H), 4.10-4.18 (m, 2 H), 4.79-4.95 (m, 4 H), 5.22 (dd, J=8.32, 2.37 Hz, 2 H), 5.45 (s, 2 H), 6.54-6.85 (m, 4 H), 6.99-7.18 (m, 3 H), 7.23-7.40 (m, 1 H), 9.64-9.86 (m, 2 H); MS (ESI) m/z 870.6 (M+H)$^+$.

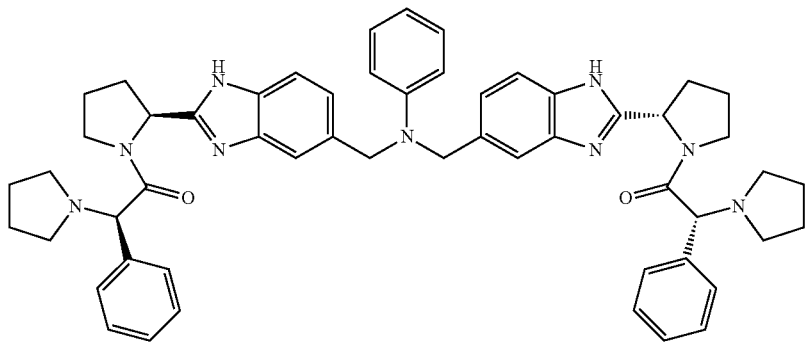 [SMILES: O=C([C@@H](c1ccccc1)N1CCCC1)N1CCC[C@H]1c1nc2cc(CN(Cc3ccc4[nH]c([C@@H]5CCCN5C(=O)[C@@H](c5ccccc5)N5CCCC5)nc4c3)c3ccccc3)ccc2[nH]1]

EXAMPLE 66

N,N-bis[(2-{(2S)-1-[(2R)-2-phenyl-2-pyrrolidin-1-ylacetyl]pyrrolidin-2-yl}-1H-benzimidazol-5-yl)methyl]aniline The product of Example 7E (20 mg, 0.041 mmol) was subjected to the procedure described in Example 24E, substituting (R)-2-phenyl-2-(pyrrolidin-1-yl)acetic acid for (S)-2-(methoxycarbonylamino)-3-methylbutanoic acid, to give the title compound as a TFA salt (14 mg). $^1$H NMR (500 MHz, DMSO-D6) δ ppm 1.22-1.29 (m, 3 H), 1.87-1.96 (m, 9 H), 1.99 (s, 2 H), 2.01-2.10 (m, 7 H), 2.18-2.28 (m, 3 H), 2.95-3.04 (m, 5 H), 4.03 (d, J=8.7 Hz, 5 H), 4.92 (s, 4 H), 5.49 (s, 3 H), 6.75 (d, J=8.1 Hz, 3 H), 7.08-7.17 (m, 3 H), 7.39 (d, J=8.4 Hz, 3 H), 7.57 (dd, J=6.9, 2.7 Hz, 8 H), 7.61-7.67 (m, 5 H), 7.70 (d, J=8.4 Hz, 3 H); MS (ESI) m/z 866.3 (M+H)$^+$.

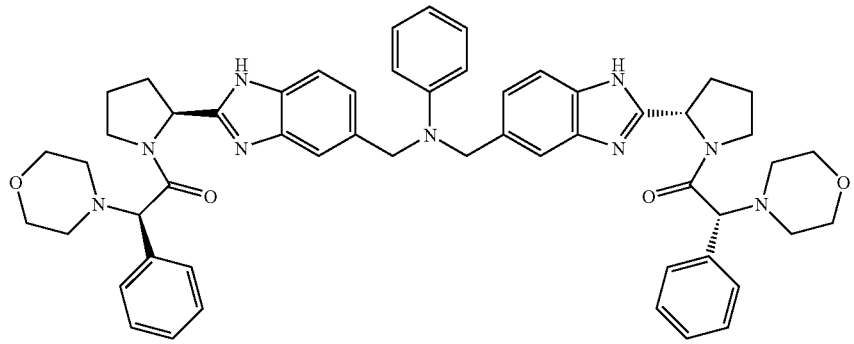 [SMILES: O=C([C@@H](c1ccccc1)N1CCOCC1)N1CCC[C@H]1c1nc2cc(CN(Cc3ccc4[nH]c([C@@H]5CCCN5C(=O)[C@@H](c5ccccc5)N5CCOCC5)nc4c3)c3ccccc3)ccc2[nH]1]

EXAMPLE 67

N,N-bis[(2-{(2S)-1-[(2R)-2-morpholin-4-yl-2-phenylacetyl]pyrrolidin-2-yl}-1H-benzimidazol-5-yl)methyl]aniline The product of Example 7E (20 mg, 0.041 mmol) was subjected to the procedure described in Example 24E, substituting (R)-2-morpholino-2-phenylacetic acid for (S)-2-(methoxycarbonylamino)-3-methylbutanoic acid, to give the title compound as a TFA salt (17 mg). $^1$H NMR (500 MHz, DMSO-D6) δ ppm 1.91 (d, J=2.6 Hz, 4 H), 2.02-2.11 (m, 7 H), 2.23 (d, J=6.6 Hz, 4 H), 3.04 (d, J=7.2 Hz, 6 H), 4.90 (s, 7 H), 5.30 (dd, J=8.4, 2.0 Hz, 3 H), 5.49 (s, 3 H), 6.61 (s, 2 H), 6.74 (d, J=8.2 Hz, 4 H), 7.07-7.14 (m, 3 H), 7.37 (d, J=8.2 Hz, 3 H), 7.53-7.59 (m, 11 H), 7.59-7.64 (m, 6 H), 7.68 (d, J=8.4 Hz, 3 H); MS (ESI) m/z 898.6 (M+H)$^+$.

EXAMPLE 68A

N,N-bis(4-nitrobenzyl)acetamide

To a solution of bis(4-nitrobenzyl)amine (500 mg, 1.741 mmol) in pyridine (9 mL) was slowly added acetic anhydride (0.18 mL, 1.92 mmol) via syringe. The resulting mixture was stirred at rt for 2 hours, and the reaction was concentrated in vacuo. The residue was dissolved in toluene and evaporated to dryness in vacuo. The residue was dissolved in 19:1 EtOAc:methanol, washed with water and brine, dried (Na$_2$SO$_4$), filtered and concentrated to afford the title compound (551 mg, 96%). MS (APCI) m/z 330.2 (M+H)$^+$.

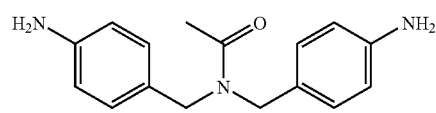

EXAMPLE 68 dimethyl [(acetylimino)bis{methanediylbenzene-4,1-diylcarbamoyl(2S)pyrrolidine-2,1-diyl[(2S)-3-methyl-1-oxobutane-1,2-diyl]}]biscarbamate

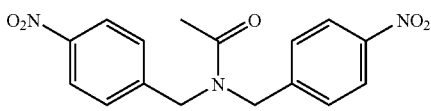

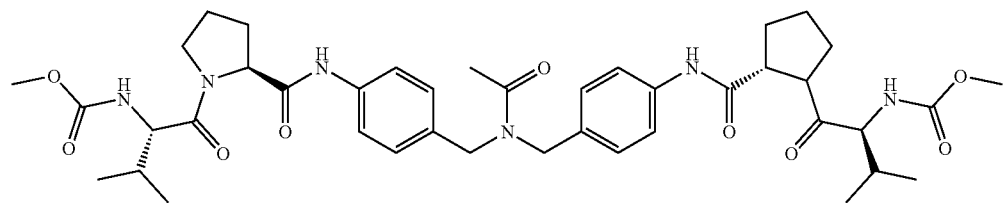

EXAMPLE 68B

N,N-bis(4-aminobenzyl)acetamide

A mixture of the product from Example 68A (250 mg, 0.759 mmol), iron powder (424 mg, 7.59 mmol), and ammonium chloride (203 mg, 3.80 mmol) in ethanol (1 mL), tetrahydrofuran (1 mL) and water (0.250 mL) was heated at 80° C. for 18 hours. The mixture was allowed to cool to rt, filtered, rinsed with methanol, and concentrated in vacuo. The residue was partitioned between EtOAc and H$_2$O, and the organic layer was dried (Na$_2$SO$_4$), filtered and concentrated in vacuo to afford the title compound (226 mg, 90%). MS (ESI) m/z 269.9 (M+H)$^+$

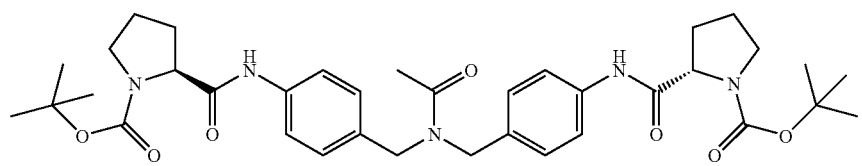 [SMILES: CC(=O)N(Cc1ccc(NC(=O)[C@@H]2CCCN2C(=O)OC(C)(C)C)cc1)Cc1ccc(NC(=O)[C@@H]2CCCN2C(=O)OC(C)(C)C)cc1]

EXAMPLE 68C (2S,2'S)-tert-butyl 2,2'-(4,4'-(acetylazanediyl)bis(methylene)bis(4,1-phenylene)bis(azanediyl))bis(oxomethylene)dipyrrolidine-1-carboxylate The product from Example 68B (264.4 mg, 0.982 mmol) was subjected to the procedure described in Example 24C to afford the title compound (684 mg, quant). MS (ESI) m/z 664.4 (M+H)$^+$.

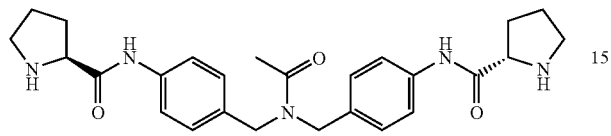

EXAMPLE 68D (S)-N-(4-((N-(4-((S)-pyrrolidine-2-carboxamido)benzyl)acetamido)methyl)phenyl)pyrrolidine-2-carboxamide The product from Example 68C (684 mg, 1.030 mmol) was subjected to the procedure described in Example 24D to afford the title compound (141 mg, 29%). MS (ESI) m/z 464.2 (M+H)$^+$.

EXAMPLE 68E dimethyl[(acetylimino)bis{methanediylbenzene-4,1-diylcarbamoyl(2S)pyrrolidine-2,1-diyl[(2S)-3-methyl-1-oxobutane-1,2-diyl]}]biscarbamate The product from Example 68D (35 mg, 0.076 mmol) was subjected to the procedure described in Example 2, substituting (S)-2-(methoxycarbonylamino)-3-methylbutanoic acid for (R)-2-(dimethylamino)-2-phenylacetic acid, to afford the title compound (22 mg, 37%). $^1$H NMR (500 MHz, DMSO-D6) δ ppm 0.88 (d, J=6.7 Hz, 6 H), 0.94 (d, J=6.9 Hz, 6 H), 1.85-1.94 (m, 6 H), 1.96-2.04 (m, 2 H), 2.10 (s, 3 H), 2.11-2.19 (m, 2 H), 3.50-3.56 (m, 6 H), 3.59-3.66 (m, 2 H), 3.78-3.85 (m, 2 H), 4.03 (t, J=8.5 Hz, 2 H), 4.38 (s, 4 H), 4.44 (dd, J=8.1, 4.9 Hz, 2 H), 7.10-7.16 (m, 4 H), 7.32 (d, J=8.4 Hz, 2 H), 7.50-7.59 (m, 4 H), 10.04 (d, J=20.0 Hz, 2 H); MS (ESI) m/z 778.4 (M+H)$^+$.

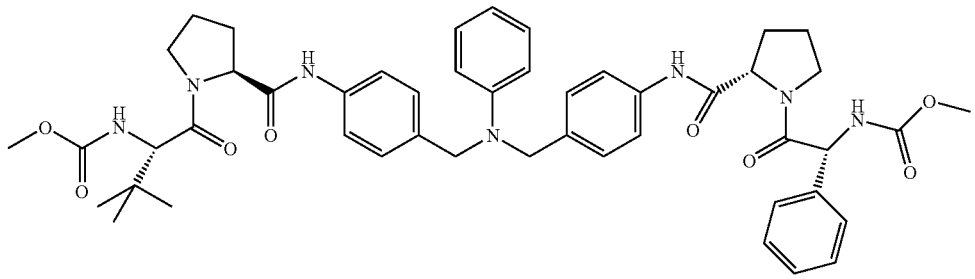

EXAMPLE 69

N-(methoxycarbonyl)-3-methyl-L-valyl-N-(4-{[{4-(1-{(2R)-2-[(methoxycarbonyl)amino]-2-phenylacetyl}-L-prolyl)amino]benzyl}(phenyl)amino]methyl}phenyl)-L-prolinamide

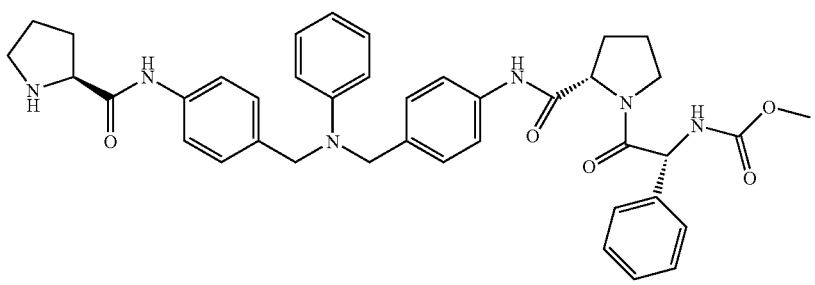 [SMILES: COC(=O)N[C@@H](C(=O)N1CCC[C@H]1C(=O)Nc1ccc(CN(Cc2ccc(NC(=O)[C@@H]3CCCN3)cc2)c2ccccc2)cc1)c1ccccc1]

EXAMPLE 69A

Methyl R-2-oxo-1-phenyl-2-((S)-2-(4-((phenyl(4-((S)-pyrrolidine-2-carboxamido)benzyl)amino)methyl)phenylcarbamoyl)pyrrolidin-1-yl)ethylcarbamate To a solution of product from Example 1D (1.198 g, 2.408 mmol) in DMSO (24 mL) was added R-2-(methoxycarbonylamino)-2-phenylacetic acid (0.403 g, 1.926 mmol), HATU (0.732 g, 1.926 mmol) and Hunig's base (0.673 mL, 3.85 mmol), and the resulting mixture was stirred at rt overnight. The mixture was poured into water to give a colorless precipitate that was filtered and washed with water. The solid was dissolved in CH$_2$Cl$_2$, dried over anhydrous sodium sulphate, filtered, and concentrated in vacuo. The crude product was purified by column chromatography on silica gel using a solvent gradient of 0-8% MeOH in CH$_2$Cl$_2$ to give the title compound (0.387 g, 24%).

EXAMPLE 69B

N-(methoxycarbonyl)-3-methyl-L-valyl-N-(4-{[{4-[(1-{(2R)-2-[(methoxycarbonyl)amino]-2-phenylacetyl}-L-prolyl)amino]benzyl}(phenyl)amino]methyl}phenyl)-L-prolinamide The product from Example 69A (0.031 g, 0.045 mmol) was subjected to the procedure described in Example 10B, substituting (S)-2-(methoxycarbonylamino)-3,3-dimethylbutanoic acid for (R)-2-(dimethylamino)-2-phenylacetic acid, to give the title compound (11 mg, 28%). $^1$H NMR (500 MHz, DMSO-D6) δ ppm 0.96 (s, 9 H), 1.80-2.05 (m, 8 H), 2.10-2.18 (m, 2 H), 3.53 (s, 3 H), 3.54 (s, 3 H), 3.60-3.68 (m, 1 H), 3.74-3.85 (m, 2 H), 4.21 (d, J=8.9 Hz, 2 H), 4.37 (dd, J=8.1, 3.4 Hz, 1 H), 4.44 (dd, J=8.2, 5.3 Hz, 1 H), 4.59 (s, 4 H), 6.57 (t, J=7.2 Hz, 1 H), 6.66 (d, J=8.1 Hz, 2 H), 7.04-7.11 (m, 2 H), 7.15-7.21 (m, 4 H), 7.29-7.42 (m, 5 H), 7.48-7.56 (m, 4 H), 7.69 (d, J=7.8 Hz, 1 H), 9.83 (s, 1 H), 9.99 (s, 1 H); MS m/z 860.8 (M+H)$^+$.

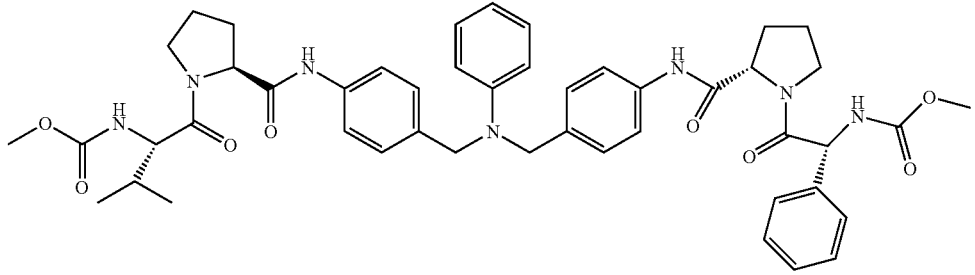

EXAMPLE 70

N-(methoxycarbonyl)-L-valyl-N-(4-{[{4-[(1-{(2R)-2-[(methoxycarbonyl)amino]-2-phenylacetyl}-L-prolyl)amino]benzyl}(phenyl)amino]methyl}phenyl)-L-prolinamide The product from Example 69A (0.031 g, 0.045 mmol) was subjected to the procedure described in Example 10B, substituting (S)-2-(methoxycarbonylamino)-3-methylbutanoic acid for (R)-2-(dimethylamino)-2-phenylacetic acid, to give the title compound (0.0135 g, 36%). $^1$H NMR (500 MHz, DMSO-D6) δ ppm 0.88 (d, J=6.7 Hz, 3 H), 0.93 (d, J=6.7 Hz, 3 H), 1.80-2.05 (m, 8 H), 2.09-2.20 (m, 2 H), 3.52 (s, 3 H), 3.53 (s, 3 H), 3.57-3.67 (m, 2 H), 3.76-3.86 (m, 2 H), 4.02 (t, J=8.5 Hz, 2 H), 4.37 (dd, J=8.1, 3.4 Hz, 1 H), 4.43 (dd, J=8.2, 4.8 Hz, 1 H), 4.59 (s, 4 H), 6.57 (t, J=7.2 Hz, 1 H), 6.66 (d, J=8.1 Hz, 2 H), 7.04-7.10 (m, 2 H), 7.15-7.21 (m, 4 H), 7.29-7.42 (m, 5 H), 7.48-7.57 (m, 4 H), 7.69 (d, J=7.9 Hz, 1 H), 9.83 (s, 1 H), 9.98 (s, 1 H); MS m/z 846.3 (M+H)$^+$.

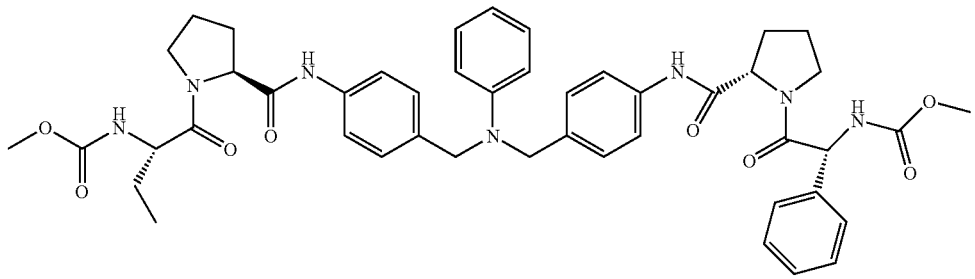

EXAMPLE 71 methyl {(1R)-2-[(2S)-2-{[4-({[4-({[(2S)-1-{(2S)-2-[(methoxycarbonyl)amino]butanoyl}pyrrolidin-2-yl]carbonyl}amino)benzyl](phenyl)amino}methyl)phenyl]carbamoyl}pyrrolidin-1-yl]-2-oxo-1-phenylethyl}carbamate The product from Example 69A (0.031 g, 0.045 mmol) was subjected to the procedure described in Example 10B, substituting (S)-2-(methoxycarbonylamino)butanoic acid for (R)-2-(dimethylamino)-2-phenylacetic acid, to give the title compound (0.0126 g, 34%). $^1$H NMR (500 MHz, DMSO-D6) δ ppm 0.90 (t, J=7.4 Hz, 3 H), 1.46-1.58 (m, 1 H), 1.61-1.71 (m, 1 H), 1.73-2.05 (m, 8 H), 2.07-2.20 (m, 2 H), 3.52 (s, 3 H), 3.53 (s, 3 H), 3.56-3.64 (m, 2 H), 3.69-3.76 (m, 1 H), 3.77-3.84 (m, 1 H), 4.14-4.21 (m, 1 H), 4.37 (dd, J=8.2, 3.4 Hz, 1 H), 4.43 (dd, J=8.1, 4.6 Hz, 1 H), 4.59 (s, 4 H), 6.57 (t, J=7.2 Hz, 1 H), 6.66 (d, J=8.1 Hz, 2 H), 7.04-7.11 (m, 2 H), 7.18 (dd, J=8.5, 5.9 Hz, 4 H), 7.29-7.42 (m, 5 H), 7.48-7.56 (m, 4 H), 7.69 (d, J=7.8 Hz, 1 H), 9.83 (s, 1 H), 9.95 (s, 1 H); MS m/z 832.2 (M+H)$^+$.

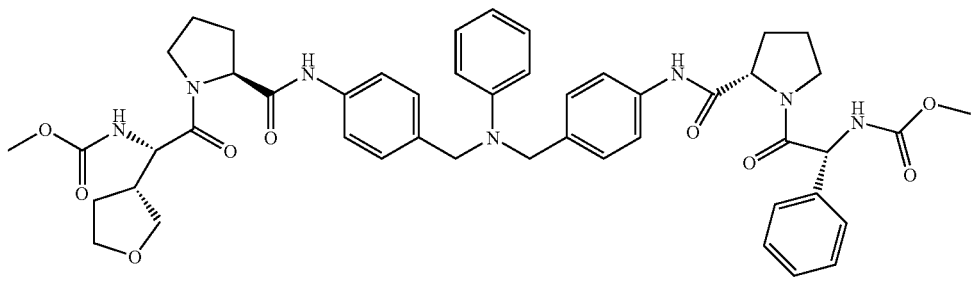

EXAMPLE 72 methyl {(1S)-2-[(2S)-2-{[4-({[4-({[(2S)-1-{(2R)-2-[(methoxycarbonyl)amino]-2-phenylacetyl}pyrrolidin-2-yl]carbonyl}amino)benzyl]phenyl)amino}methyl)phenyl]carbamoyl}pyrrolidin-1-yl]-2-oxo-1-[(3R)-tetrahydrofuran-3-yl]ethyl}carbamate The product from Example 69A (0.031 g, 0.045 mmol) was subjected to the procedure described in Example 10B, substituting (S)-2-(methoxycarbonylamino)-2-((R)-tetrahydrofuran-3-yl)acetic acid for (R)-2-(dimethylamino)-2-phenylacetic acid, to give the title compound (0.0219 g, 55%). $^1$H NMR (500 MHz, DMSO-D6) δ ppm 1.21-1.29 (m, 4 H), 1.69-1.80 (m, 2 H), 1.81-2.05 (m, 8 H), 2.11-2.20 (m, 2 H), 3.53 (s, 3 H), 3.53 (s, 3 H), 3.58-3.71 (m, 2 H), 3.71-3.89 (m, 2 H), 4.23 (t, J=8.9 Hz, 1 H), 4.37 (dd, J=8.1, 3.2 Hz, 1 H), 4.44 (dd, J=8.2, 4.7 Hz, 1 H), 4.60 (s, 4 H), 6.57 (t, J=7.2 Hz, 1 H), 6.66 (d, J=8.1 Hz, 2 H), 7.04-7.11 (m, 2 H), 7.18 (dd, J=8.6, 3.4 Hz, 3 H), 7.32-7.42 (m, 5 H), 7.53 (dd, J=13.5, 8.5 Hz, 4 H), 7.61 (d, J=7.9 Hz, 1 H), 7.69 (d, J=7.8 Hz, 1 H), 9.83 (s, 1 H), 9.98 (s, 1 H); MS m/z 874.3 (M+H)$^+$.

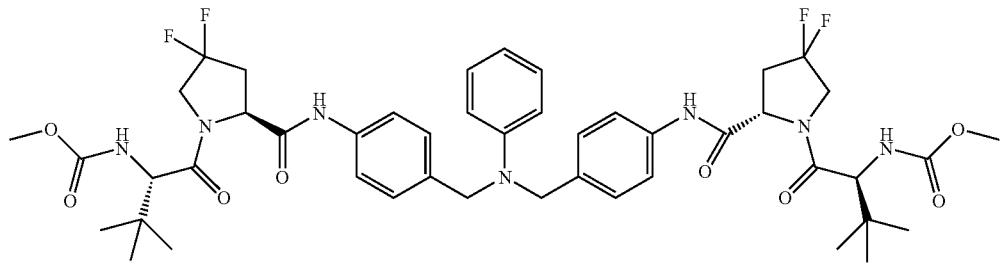

EXAMPLE 73 dimethyl[(phenylimino)bis{methanediylbenzene-4,1-diylcarbamoyl[(2S)-4,4-difluoropyrrolidine-2,1-diyl][(2S)-3,3-dimethyl-1-oxobutane-1,2-diyl]}]biscarbamate

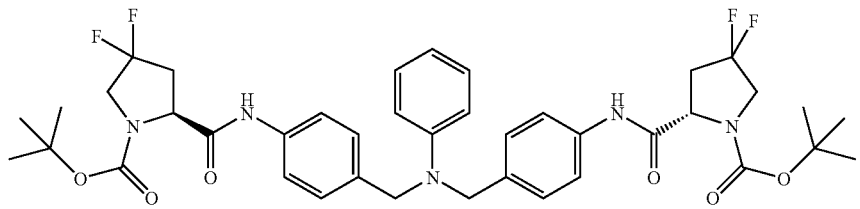 [SMILES: CC(C)(C)OC(=O)N1CC(F)(F)C[C@H]1C(=O)Nc1ccc(CN(Cc2ccc(NC(=O)[C@@H]3CC(F)(F)CN3C(=O)OC(C)(C)C)cc2)c2ccccc2)cc1]

EXAMPLE 73A (5S,5'S)-tert-butyl 5,5'-(4,4'-(phenylazanediyl)bis(methylene)bis(4,1-phenylene)bis(azanediyl))bis(oxomethylene)bis(3,3-difluoropyrrolidine-1-carboxylate)

The product from Example 1B and N-BOC-4,4-difluoro-L-proline (Aldrich) were processed using the method described in Example 41 to provide 457 mg (87%) of the title compound. MS (ESI; M+H) m/z=770.

EXAMPLE 73B (2S,2'S)-N,N'-(4,4'-(phenylazanediyl)bis(methylene)bis(4,1-phenylene))bis(4,4-difluoropyrrolidine-2-carboxamide)

The product from Example 73A was processed using the method described in Example 47B to provide 236 mg (70%) of the title compound. MS (DCI; M+H) m/z=570.

EXAMPLE 73C dimethyl[(phenylimino)bis{methanediylbenzene-4,1-diylcarbamoyl[(2S)-4,4-difluoropyrrolidine-2,1-diyl][(2S)-3,3-dimethyl-1-oxobutane-1,2-diyl]}]biscarbamate The product from Example 73B and (S)-2-(methoxycarbonylamino)-3,3-dimethylbutanoic acid (DeGussa) were processed using the method described in Example 41 to provide 35 mg (9%) of the title compound. $^1$H NMR (400 MHz, DMSO-D6) δ 0.97 (s, 18 H) 2.37-2.50 (m, 2 H) 2.78-2.85 (m, 2 H) 3.54 (s, 6 H) 4.00-4.20 (m, 4 H) 4.28-4.39 (m, 2 H) 4.59 (br s, 4 H) 4.64 (t, J=8.02 Hz, 2 H) 6.57 (t, J=7.21 Hz, 1 H) 6.65 (d, J=8.24 Hz, 2 H) 7.07 (t, J=7.92 Hz, 2 H) 7.19 (d, J=8.57 Hz, 4 H) 7.29 (d, J=8.13 Hz, 2 H) 7.50 (d, J=8.57 Hz, 4 H) 10.13 (s, 2 H).

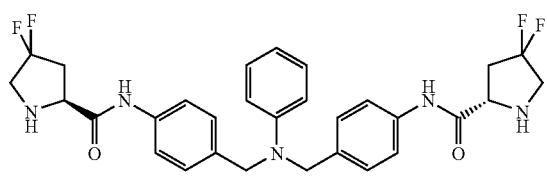 [SMILES: O=C(Nc1ccc(CN(Cc2ccc(NC(=O)[C@@H]3CC(F)(F)CN3)cc2)c2ccccc2)cc1)[C@@H]1CC(F)(F)CN1]

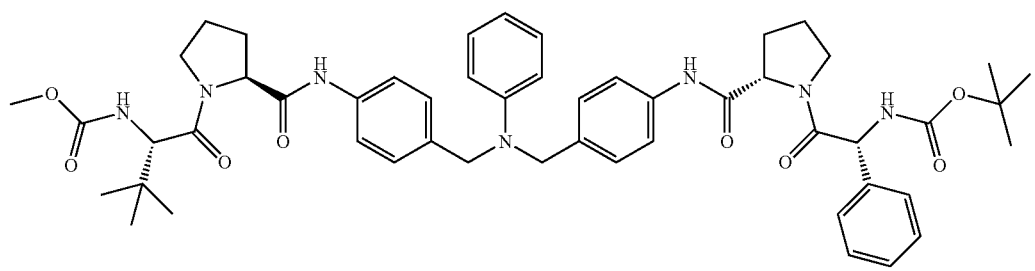 [SMILES: COC(=O)N[C@H](C(=O)N1CCC[C@H]1C(=O)Nc1ccc(CN(Cc2ccc(NC(=O)[C@@H]3CCCN3C(=O)[C@H](NC(=O)OC(C)(C)C)c3ccccc3)cc2)c2ccccc2)cc1)C(C)(C)C]

EXAMPLE 74

N-(methoxycarbonyl)-3-methyl-L-valyl-N-(4-{[{4-[(1-{(2R)-2-[(tert-butoxycarbonyl)amino]-2-phenylacetyl}-L-prolyl)amino]benzyl}(phenyl)amino]methyl}phenyl)-L-prolinamide The product of Example 10A (150 mg, 0.224 mmol) was subjected to the procedure described in Example 10B, substituting (R)-2-(tert-butoxycarbonylamino)-2-phenylacetic acid (62.0 mg, 0.247 mmol) for (R)-2-(dimethylamino)-2-phenylacetic acid to give the title compound (145 mg, 71%). $^1$H NMR (500 MHz, DMSO-D6) δ ppm 0.94-0.99 (m, 8 H), 1.32-1.38 (m, 9 H), 1.76 (d, J=4.1 Hz, 1 H), 1.82-1.91 (m, 3 H), 1.93-2.02 (m, 3 H), 2.11-2.20 (m, 1 H), 2.69 (s, 4 H), 3.17 (d, J=5.2 Hz, 2 H), 3.54 (s, 3 H), 3.63 (d, J=9.3 Hz, 1 H), 3.78 (dd, J=9.6, 6.4 Hz, 2 H), 4.11 (d, J=5.2 Hz, 1 H), 4.21 (d, J=9.0 Hz, 1 H), 4.37 (dd, J=7.9, 3.1 Hz, 1 H), 4.44 (dd, J=8.1, 5.3 Hz, 1 H), 4.59 (s, 4H), 6.57 (t, J=7.2 Hz, 1 H), 6.66 (d, J=8.1 Hz, 2 H), 7.04-7.11 (m, 3 H), 7.18 (dd, J=8.5, 3.2 Hz, 4 H), 7.34-7.40 (m, 4 H), 7.52 (dd, J=9.9, 8.7 Hz, 4 H), 10.00 (s, 1 H); MS (ESI) m/z 902.8 (M+H)$^+$.

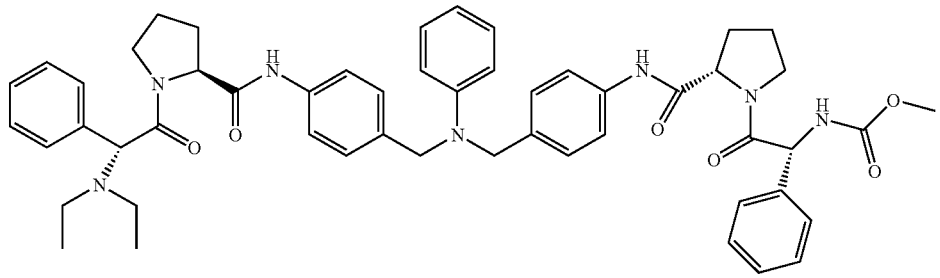 [SMILES: CCN(CC)[C@@H](C(=O)N1CCC[C@H]1C(=O)Nc1ccc(CN(Cc2ccc(NC(=O)[C@@H]3CCCN3C(=O)[C@H](NC(=O)OC)c3ccccc3)cc2)c2ccccc2)cc1)c1ccccc1]

EXAMPLE 75 methyl [(1R)-2-{(2S)-2-[(4-{[{-4-[({(2S)-1-[(2R)-2-(diethylamino)-2-phenylacetyl]pyrrolidin-2-yl}carbonyl)amino]benzyl}(phenyl)amino]methyl}phenyl)carbamoyl]pyrrolidin-1-yl}-2-oxo-1-phenylethyl]carbamate The product from Example 69A (0.033 g, 0.048 mmol) was subjected to the procedure described in Example 10B, substituting (R)-2-(diethylamino)-2-phenylacetic acid for (R)-2-(dimethylamino)-2-phenylacetic acid, to give the title compound (0.0238 g, 57%). $^1$H NMR (500 MHz, DMSO-D6) δ ppm 0.89 (t, J=6.9 Hz, 3 H), 1.07 (t, J=7.2 Hz, 3 H), 1.21-1.33 (m, 4 H), 1.74-2.03 (m, 8 H), 2.05-2.19 (m, 2 H), 3.53 (s, 3 H), 3.76-3.84 (m, 1 H), 3.97-4.04 (m, 1 H), 4.35-4.44 (m, 2 H), 4.61 (s, 4 H), 5.43-5.52 (m, 2 H), 6.58 (t, J=7.2 Hz, 1 H), 6.67 (d, J=8.1 Hz, 2 H), 7.05-7.11 (m, 2 H), 7.20 (t, J=8.3 Hz, 4 H), 7.33-7.42 (m, 6 H), 7.49-7.58 (m, 6 H), 7.66-7.71 (m, 2 H), 9.84 (s, 1 H), 10.16 (s, 1 H); MS m/z 878.3 (M+H)$^+$.

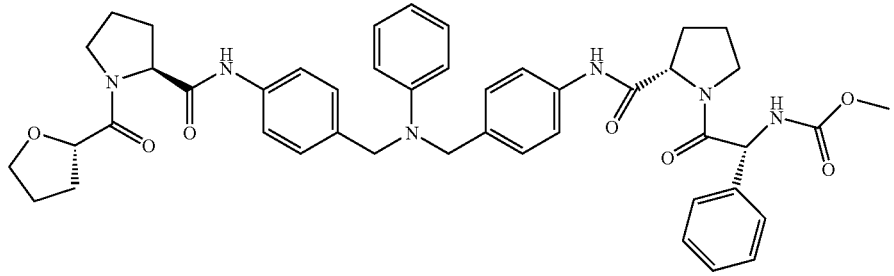 [SMILES: COC(=O)N[C@@H](C(=O)N1CCC[C@H]1C(=O)Nc1ccc(CN(Cc2ccc(NC(=O)[C@@H]3CCCN3C(=O)[C@@H]3CCCO3)cc2)c2ccccc2)cc1)c1ccccc1]

EXAMPLE 76 methyl {(1R)-2-oxo-1-phenyl-2-[(2S)-2-({4-[(phenyl{4-[({(2S)-1-[(2S)-tetrahydrofuran-2-ylcarbonyl]pyrrolidin-2-yl}carbonyl)amino]benzyl}amino)methyl]phenyl}carbamoyl)pyrrolidin-1-yl]ethyl}carbamate The product from Example 69A (0.032 g, 0.046 mmol) was subjected to the procedure described in Example 10B, substituting (S)-tetrahydrofuran-2-carboxylic acid for (R)-2-(dimethylamino)-2-phenylacetic acid, to give the title compound (0.0244 g, 66%). $^1$H NMR (400 MHz, DMSO-D6) δ ppm 1.72-2.16 (m, 12 H), 3.53 (s, 3 H), 3.58-3.84 (m, 4 H), 4.31-4.45 (m, 2 H), 6.57 (t, J=7.2 Hz, 1 H), 6.66 (d, J=8.2 Hz, 2 H), 7.03-7.12 (m, 2 H), 7.18 (dd, J=8.3, 4.6 Hz, 4 H), 7.32-7.42 (m, 5 H), 7.47-7.58 (m, 4 H), 7.68 (d, J=7.9 Hz, 1 H), 9.83 (s, 1 H), 9.96 (s, 1 H); MS m/z 787.2 $(M+H)^+$.

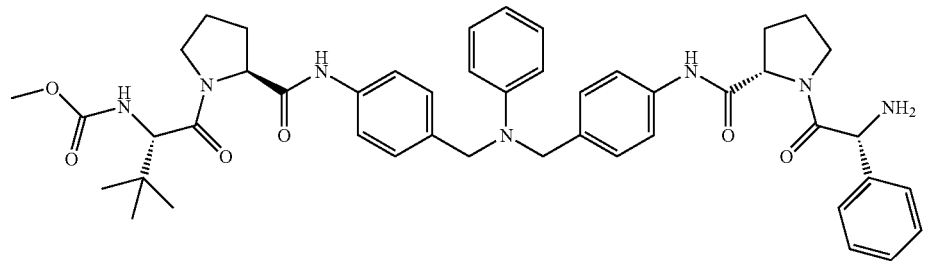 [SMILES: COC(=O)N[C@H](C(=O)N1CCC[C@H]1C(=O)Nc1ccc(CN(Cc2ccc(NC(=O)[C@@H]3CCCN3C(=O)[C@H](N)c3ccccc3)cc2)c2ccccc2)cc1)C(C)(C)C]

EXAMPLE 77

N-(methoxycarbonyl)-3-methyl-L-valyl-N-[4-({[4-({1-[(2R)-2-amino-2-phenylacetyl]-L-prolyl}amino)benzyl](phenyl)amino}methyl)phenyl]-L-prolinamide To a solution of the product from Example 74 (136.1 mg, 0.151 mmol) in $CH_2Cl_2$ (0.2 mL) was added trifluoroacetic acid (0.20 mL). The mixture was stirred at rt and concentrated in vacuo. The crude product was partitioned between $CH_2Cl_2$ and saturated aqueous $NaHCO_3$, and the organic layer was dried ($Na_2SO_4$), filtered and concentrated in vacuo to afford the title compound (115 mg, 94%). $^1$H NMR (400 MHz, DMSO-D6) δ ppm 0.96 (s, 8 H), 1.53 (s, 1 H), 1.74 (s, 1 H), 1.82-1.91 (m, 3 H), 1.99 (s, 2 H), 2.15 (s, 1 H), 2.69 (s, 2 H), 2.84 (s, 1 H), 3.54 (s, 3 H), 3.63 (s, 1 H), 3.79 (s, 2 H), 4.21 (d, J=8.9 Hz, 1 H), 4.41-4.47 (m, 2 H), 4.60 (s, 4 H), 5.29 (s, 1 H), 6.57 (t, J=7.2 Hz, 1 H), 6.66 (d, J=8.2 Hz, 2 H), 7.05-7.11 (m, 3 H), 7.19 (t, J=8.3 Hz, 4 H), 7.42-7.49 (m, 4 H), 7.53 (dd, J=12.8, 8.5 Hz, 5 H), 10.00 (s, 1 H), 10.09 (s, 1 H); MS (ESI) m/z 802.5 $(M+H)^+$.

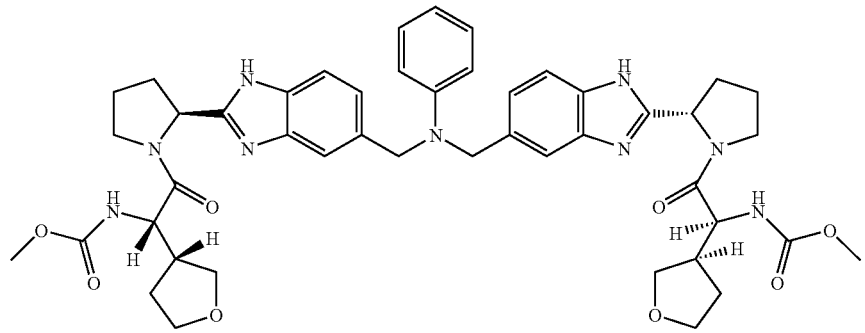

EXAMPLE 78 dimethyl {(phenylimino)bis[methanediyl-1H-benz-imidazole-5,2-diyl(2S)pyrrolidine-2,1-diyl{(1S)-2-oxo-1-[(3R)-tetrahydrofuran-3-yl]ethane-2,1-diyl}]}biscarbamate The product from Example 7E (17 mg, 0.035 mmol) was subjected to the procedure described in Example 2, substituting (S)-2-(methoxycarbonylamino)-2-((R)-tetrahydrofuran-3-yl)acetic acid (14.75 mg, 0.073 mmol) for (R)-2-(dimethylamino)-2-phenylacetic acid, to afford the title compound (10 mg, 34%). $^1$H NMR (400 MHz, DMSO-D6) δ ppm 0.80-0.87 (m, 1 H), 1.19-1.30 (m, 6 H), 1.63 (s, 2 H), 1.73 (d, J=12.9 Hz, 2 H), 1.96 (s, 3 H), 2.10 (s, 2 H), 2.17 (s, 1 H), 3.39-3.47 (m, 3 H), 3.52-3.57 (m, 7 H), 3.61 (t, J=7.9 Hz, 2 H), 3.70 (d, J=8.0 Hz, 2 H), 3.81 (s, 3 H), 4.29 (s, 2 H), 4.75 (d, J=10.1 Hz, 3 H), 5.12 (s, 2 H), 6.54 (s, 1 H), 6.72 (d, J=8.3 Hz, 2 H), 7.01-7.09 (m, 4 H), 7.26 (s, 1 H), 7.34-7.38 (m, 2 H), 7.44 (d, J=8.2 Hz, 1 H), 7.57 (s, 1 H), 12.00 (s, 2 H); MS (ESI) m/z 862.4 (M+H)$^+$.

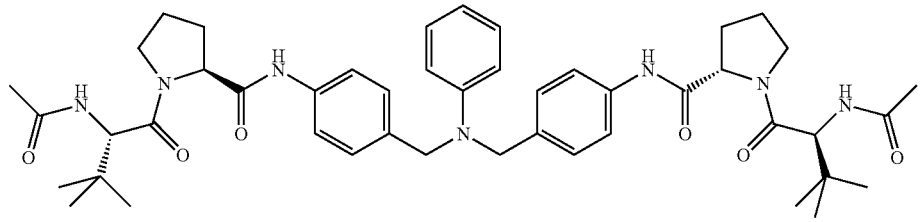 [SMILES: CC(=O)N[C@H](C(=O)N1CCC[C@H]1C(=O)Nc1ccc(CN(Cc2ccc(NC(=O)[C@@H]3CCCN3C(=O)[C@@H](NC(C)=O)C(C)(C)C)cc2)c2ccccc2)cc1)C(C)(C)C]

EXAMPLE 79

(2S,2'S)-N,N'-[(phenylimino)bis(methanediylbenzene-4,1-diyl)]bis{1-[(2S)-2-(acetylamino)-3,3-dimethylbutanoyl]pyrrolidine-2-carboxamide}

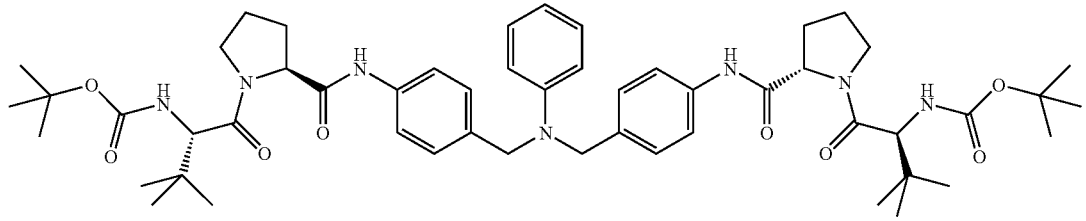 [SMILES: CC(C)(C)OC(=O)N[C@H](C(=O)N1CCC[C@H]1C(=O)Nc1ccc(CN(Cc2ccc(NC(=O)[C@@H]3CCCN3C(=O)[C@@H](NC(=O)OC(C)(C)C)C(C)(C)C)cc2)c2ccccc2)cc1)C(C)(C)C]

EXAMPLE 79A tert-butyl (2S,2'S)-1,1'-((2S,2'S)-2,2'-(4,4'-(phenylazanediyl)bis(methylene)bis(4,1-phenylene)bis(azanediyl))bis(oxomethylene)bis(pyrrolidine-2,1-diyl))bis(3,3-dimethyl-1-oxobutane-2,1-diyl)dicarbamate The product of Example 1D (1.0 g, 2.01 mmol) and (S)-2-(tert-butoxycarbonylamino)-3,3-dimethylbutanoic acid (1.02 g, 4.42 mmol) were processed as in Example 25B to give 1.46 g (76%) of the title compound as an off-white solid.

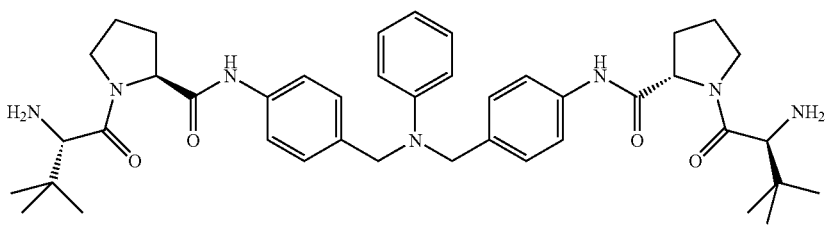 [SMILES: CC(C)(C)[C@H](N)C(=O)N1CCC[C@H]1C(=O)Nc1ccc(CN(Cc2ccc(NC(=O)[C@@H]3CCCN3C(=O)[C@@H](N)C(C)(C)C)cc2)c2ccccc2)cc1]

EXAMPLE 79B (S,2S,2'S)-N,N'-(4,4'-(phenylazanediyl)bis(methylene)bis(4,1-phenylene))bis(1-((S)-2-amino-3,3-dimethylbutanoyl)pyrrolidine-2-carboxamide)

The product from Example 79A (1.44 g, 1.56 mmol) was dissolved in dichloromethane (10 mL) at ambient temperature and treated with trifluoroacetic acid (5 mL). After 3 hours, the solution was concentrated, taken up into 25% isopropanol in chloroform and washed with 10% sodium bicarbonate solution. The organic was dried over sodium sulfate, filtered, and concentrated to dryness to give the title compound as a white solid.

EXAMPLE 79C (2S,2'S)-N,N'-[(phenylimino)bis(methanediylbenzene-4,1-diyl)]bis{1-[(2S)-2-(acetylamino)-3,3-dimethylbutanoyl]pyrrolidine-2-carboxamide}

The product from Example 79B (0.03 g, 0.041 mmol) was dissolved dichloromethane (1.5 mL) at ambient temperature and was treated with DMAP (0.012 g, 0.10 mmol), followed by acetic anhydride (0.009 mL, 0.091 mmol) and stirred for 2 hours. The solution was concentrated and purified by combi-flash 12 g column, eluting with 0-4% methanol in dichloromethane to give 0.025 g (75%) of the title compound as a white solid. $^1$H NMR (500 MHz, DMSO-D6) δ ppm 0.95 (s, 18 H) 1.79-1.90 (m, 10 H) 1.90-2.00 (m, 2 H) 2.07-2.19 (m, 2 H) 3.59-3.67 (m, 2 H) 3.73-3.82 (m, 2 H) 4.41 (dd, J=8.32, 5.26 Hz, 2 H) 4.51 (d, J=9.00 Hz, 2 H) 4.57 (s, 4 H) 6.55 (t, J=7.25 Hz, 1 H) 6.64 (d, J=8.09 Hz, 2 H) 7.03-7.10 (m, 2 H) 7.16 (d, J=8.54 Hz, 4 H) 7.50 (d, J=8.54 Hz, 4 H) 7.87 (d, J=9.00 Hz, 2 H) 9.97 (s, 2 H); MS ESI– m/z 806.6.

EXAMPLE 80

(2S,2'S)-N,N'-[(phenylimino)bis(methanediylbenzene-4,1-diyl)]bis(1-{(2S)-2-[(dimethylcarbamoyl)amino]-3,3-dimethylbutanoyl}pyrrolidine-2-carboxamide)

The product from Example 79B (0.045 g, (0.062 mmol) was dissolved in dichloromethane (2 mL) at ambient temperature and treated with diisopropylamine (0.065 mL, 0.37 mmol), followed by dimethylcarbamoyl chloride (0.013 mL, 0.14 mmol) and stirred for 3 days. The solution was concentrated at dryness and purified by combi-flash 12 g silica column, eluting with 0-10% methanol in dichloromethane to give 0.031 g (58%) of the title compound as a white solid. NMR (400 MHz, DMSO-D6) δ ppm 0.95 (s, 18 H) 1.79-1.90 (m, 4 H) 1.92-2.04 (m, 2 H) 2.08-2.18 (m, 2 H) 2.79 (s, 12 H) 3.55-3.66 (m, 2 H) 3.77-3.86 (m, 2 H) 4.35 (d, J=9.11 Hz, 2 H) 4.40 (dd, J=8.08, 5.69 Hz, 2 H) 4.57 (s, 4 H) 5.36 (d, J=9.11 Hz, 2 H) 6.55 (t, J=7.26 Hz, 1 H) 6.64 (d, J=8.35 Hz, 2 H) 7.05 (t, J=7.92 Hz, 2 H) 7.16 (d, J=8.46 Hz, 4 H) 7.49 (d, J=8.46 Hz, 4 H) 9.98 (s, 2 H); MS ESI– m/z 864.6.

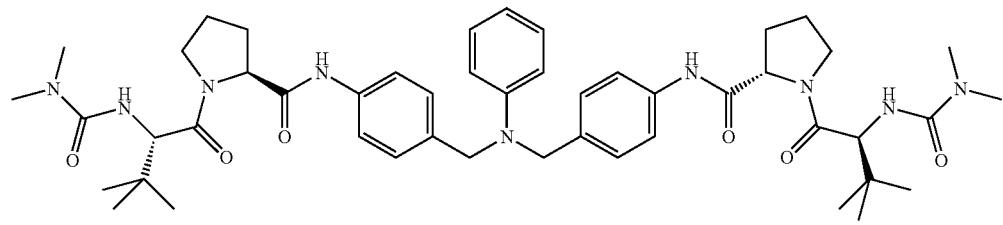

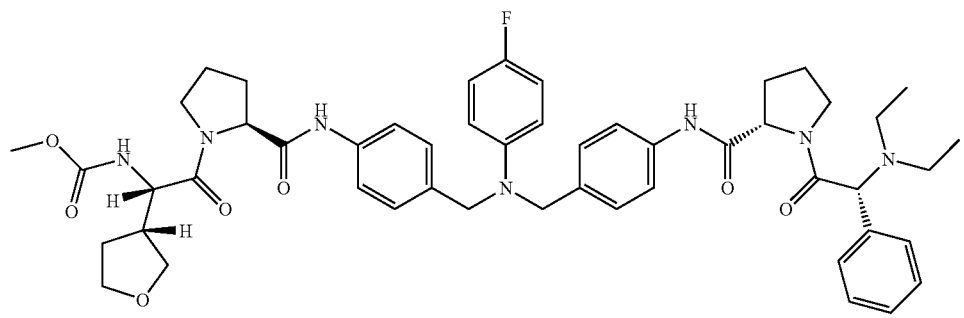 [SMILES: CCN(CC)[C@@H](C(=O)N1CCC[C@H]1C(=O)Nc1ccc(CN(Cc2ccc(NC(=O)[C@@H]3CCCN3C(=O)[C@@H](NC(=O)OC)[C@H]3CCOC3)cc2)c2ccc(F)cc2)cc1)c1ccccc1]

EXAMPLE 81 methyl {(1S)-2-{(2S)-2-[(4-{[{4-[({(2S)-1-[(2R)-2-(diethylamino)-2-phenylacetyl]pyrrolidin-2-yl}carbonyl)amino]benzy}(4-fluorophenyl)amino]methyl}phenyl)carbamoyl]pyrrolidin-1-yl}-2-oxo-1-[(3R)-tetrahydrofuran-3-yl]ethyl}carbamate mmol) were combined in dimethylsulfoxide (8 mL) at ambient temperature and treated with diisopropylethylamine (0.26 mL, 1.49 mmol), followed by HATU (0.252 g, 0.664 mmol). After one hour, the solution was diluted with water and the product filtered off and purified by combi-flash 24 g column, eluting with 0-10% methanol in dichloromethane to give 0.159 g (27%) of the title compound as a white solid.

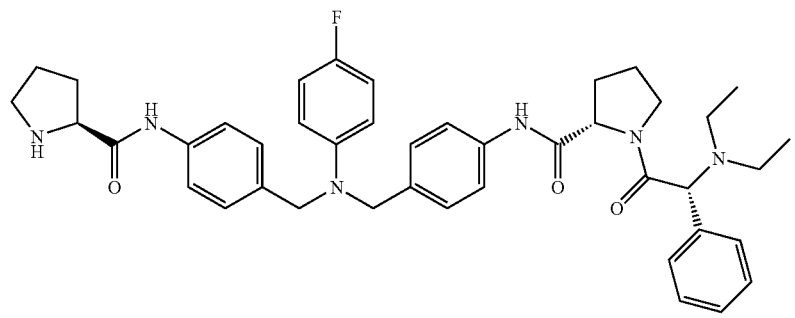 [SMILES: CCN(CC)[C@@H](C(=O)N1CCC[C@H]1C(=O)Nc1ccc(CN(Cc2ccc(NC(=O)[C@@H]3CCCN3)cc2)c2ccc(F)cc2)cc1)c1ccccc1]

EXAMPLE 81A (S)-1-((R)-2-(diethylamino)-2-phenylacetyl)-N-(4-(((4-fluorophenyl)(4-((S)-pyrrolidine-2-carboxamido)benzyl)amino)methyl)phenyl)pyrrolidine-2-carboxamide The product from Example 13D (0.428 g, 0.83 mmol) and (R)-2-(diethylamino)-2-phenylacetic acid (0.138 g, 0.664

EXAMPLE 81B methyl {(1S)-2-{(2S)-2-[(4-{[{-4-[({(2S)-1-[(2R)-2-(diethylamino)-2-phenylacetyl]pyrrolidin-2-yl}carbonyl)amino]benzyl}(4-fluorophenyl)amino]methyl}phenyl)carbamoyl]pyrrolidin-1-yl}-2-oxo-1-[(3R)-tetrahydrofuran-3-yl]ethyl}carbamate The product from Example 81A (0.042 g, 0.060 mmol) and (S)-2-(methoxycarbonylamino)-2-((R)-tetrahydrofuran-3-yl)acetic acid (0.013 g, 0.066 mmol) were processed as in Example 81A to give 0.033 g (62%) of the title compound as an off-white solid. MS (AA, ELSD+) m/z 890 (M+H)+.

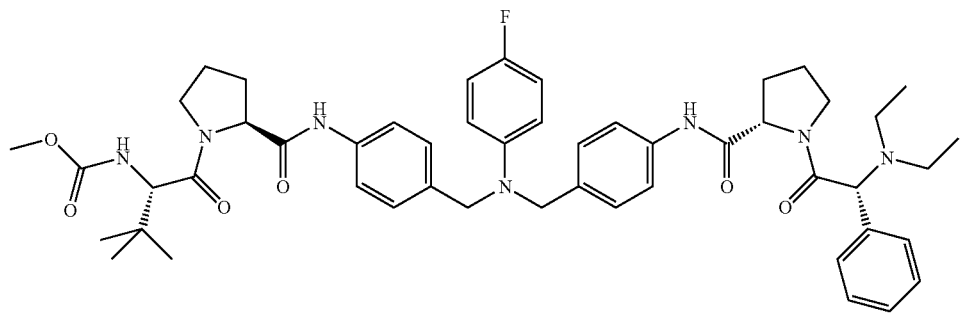 [SMILES: CCN(CC)[C@@H](C(=O)N1CCC[C@H]1C(=O)Nc1ccc(CN(Cc2ccc(NC(=O)[C@@H]3CCCN3C(=O)[C@@H](NC(=O)OC)C(C)(C)C)cc2)c2ccc(F)cc2)cc1)c1ccccc1]

EXAMPLE 82

N-(methoxycarbonyl)-3-methyl-L-valyl-N-[4-({[4-({1-[(2R)-2-(diethylamino)-2-phenylacetyl]-L-prolyl}amino)benzyl](4-fluorophenyl)amino}methyl)phenyl]-L-prolinamide The product from Example 81A (0.042 g, 0.060 mmol) and (S)-2-(methoxycarbonylamino)-3,3-dimethylbutanoic acid (0.013 g, 0.066 mmol) were processed as in Example 81A to give 0.031 g (59%) of the title compound as an off-white solid. ¹H NMR (500 MHz, DMSO-D6) δ ppm 0.88 (t, J=7.10 Hz, 6 H) 0.95 (s, 9 H) 1.76-1.89 (m, 4 H) 1.93-2.00 (m, 2 H) 2.02-2.10 (m, 1 H) 2.10-2.18 (m, 1 H) 2.40-2.47 (m, 2 H) 2.56-2.65 (m, 2 H) 3.52 (s, 3 H) 3.61 (dd, J=17.24, 7.48 Hz, 2 H) 3.73-3.80 (m, 2 H) 4.20 (d, J=9.00 Hz, 1 H) 4.37 (dd, J=7.93, 4.27 Hz, 1 H) 4.42 (dd, J=7.78, 5.19 Hz, 1 H) 4.54 (s, 4 H) 4.66 (s, 1 H) 6.63 (dd, J=9.31, 4.43 Hz, 2 H) 6.90 (t, J=8.85 Hz, 2 H) 7.07 (d, J=8.85 Hz, 1 H) 7.17 (dd, J=8.47, 3.89 Hz, 4 H) 7.26 (t, J=7.17 Hz, 1 H) 7.32 (t, J=7.40 Hz, 2 H) 7.39 (d, J=7.17 Hz, 2 H) 7.50 (dd, J=8.39, 6.10 Hz, 4 H) 9.95 (s, 1 H) 9.99 (s, 1 H); MS ESI+ m/z 876.5.

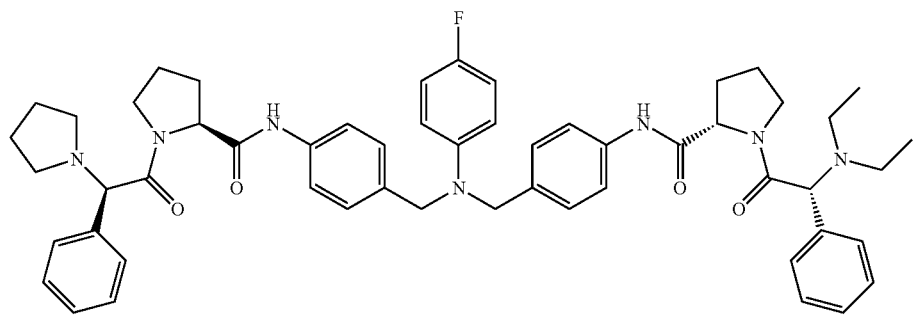 [SMILES: CCN(CC)[C@@H](C(=O)N1CCC[C@H]1C(=O)Nc1ccc(CN(Cc2ccc(NC(=O)[C@@H]3CCCN3C(=O)[C@@H](c3ccccc3)N3CCCC3)cc2)c2ccc(F)cc2)cc1)c1ccccc1]

EXAMPLE 83

(2S)-1-[(2R)-2-(diethylamino)-2-phenylacetyl]-N-(4-{[(4-fluorophenyl){4-[({(2S)-1-[(2R)-2-phenyl-2-pyrrolidin-1-ylacetyl]pyrrolidin-2-yl}carbonyl)amino]benzyl}amino]methyl}phenyl)pyrrolidine-2-carboxamide The product from Example 81A (0.032 g, 0.045 mmol) and (R)-2-phenyl-2-(pyrrolidin-1-yl)acetic acid (0.010 g, 0.05 mmol) were processed as in Example 81A to give 0.015 g (37%) of the title compound as an off-white solid. ¹H NMR (500 MHz, DMSO-D6) δ ppm 0.89 (t, J=7.10 Hz, 6 H) 1.56-1.66 (m, 4 H) 1.74-1.88 (m, 4 H) 1.94-2.09 (m, 4 H) 2.29-2.34 (m, 2 H) 2.57-2.62 (m, 4 H) 3.36-3.50 (m, 4 H) 3.75-3.88 (m, 2 H) 4.21 (s, 1 H) 4.31 (dd, J=7.93, 4.27 Hz, 1 H) 4.38 (dd, J=8.16, 4.50 Hz, 1 H) 4.57 (s, 4 H) 4.68 (s, 1 H) 6.65 (dd, J=9.31, 4.43 Hz, 2 H) 6.92 (t, J=8.93 Hz, 2 H) 7.19 (d, J=8.24 Hz, 4 H) 7.26-7.30 (m, 2 H) 7.31-7.36 (m, 4 H) 7.40 (d, J=7.17 Hz, 2 H) 7.46 (d, J=6.87 Hz, 2 H) 7.53 (d, J=8.24 Hz, 4H) 9.96 (d, J=5.34 Hz, 2 H); MS ESI− m/z 890.5.

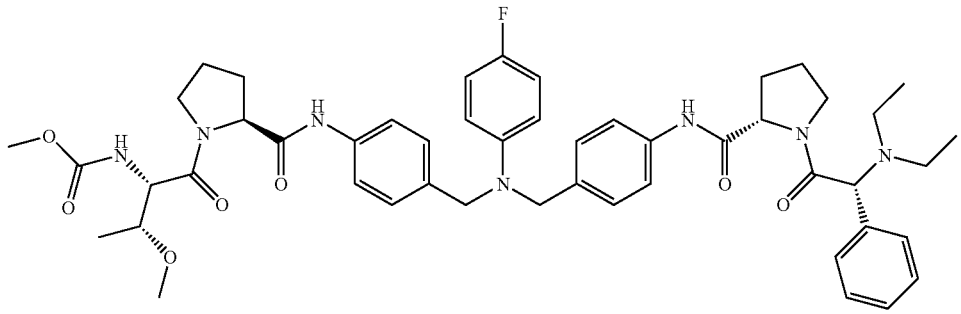 [SMILES: CCN(CC)[C@@H](C(=O)N1CCC[C@H]1C(=O)Nc1ccc(CN(Cc2ccc(NC(=O)[C@@H]3CCCN3C(=O)[C@@H](NC(=O)OC)[C@@H](C)OC)cc2)c2ccc(F)cc2)cc1)c1ccccc1]

EXAMPLE 84

N-(methoxycarbonyl)-O-methyl-L-threonyl-N-[4-({[4-({1-[(2R)-2-(diethylamino)-2-phenylacetyl]-L-prolyl}amino)benzyl](4-fluorophenyl)amino}methyl)phenyl]-L-prolinamide The product from Example 81A (0.038 g, 0.054 mmol) and (2S,3R)-3-methoxy-2-(methoxycarbonylamino)butanoic acid (0.011 g, 0.059 mmol) were processed as in Example 81A to give 0.019 g (40%) of the title compound as an off-white solid. $^1$H NMR (500 MHz, DMSO-D6) δ ppm 0.89 (t, J=7.10 Hz, 3 H) 1.07 (t, J=7.17 Hz, 2 H) 1.13 (d, J=6.26 Hz, 3 H) 1.28 (t, J=7.25 Hz, 1 H) 1.76-1.92 (m, 4 H) 1.94-2.05 (m, 2 H) 2.07-2.23 (m, 2 H) 2.39-2.46 (m, 2 H) 2.57-2.63 (m, 2 H) 3.24 (s, 3 H) 3.34-3.42 (m, 1 H) 3.43-3.50 (m, 1 H) 3.53 (s, 3 H) 3.63-3.70 (m, 1 H) 3.75-3.87 (m, 2 H) 3.97-4.03 (m, 1 H) 4.26 (t, J=7.78 Hz, 1 H) 4.36-4.46 (m, 2 H) 4.56 (s, 4 H) 4.67 (s, 1 H) 6.64 (dd, J=9.31, 4.43 Hz, 2 H) 6.89-6.95 (m, 2 H) 7.16-7.22 (m, 4 H) 7.28 (t, J=7.17 Hz, 1 H) 7.33 (t, J=7.40 Hz, 2 H) 7.40 (d, J=7.17 Hz, 1 H) 7.49-7.57 (m, 4 H) 7.66-7.70 (m, 1 H) 9.96 (d, J=7.02 Hz, 2 H); MS ESI– m/z 876.5.

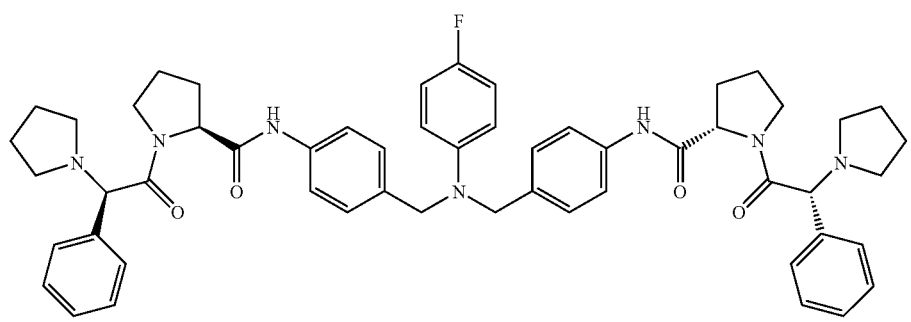 [SMILES: O=C(Nc1ccc(CN(Cc2ccc(NC(=O)[C@@H]3CCCN3C(=O)[C@@H](c3ccccc3)N3CCCC3)cc2)c2ccc(F)cc2)cc1)[C@@H]1CCCN1C(=O)[C@@H](c1ccccc1)N1CCCC1]

EXAMPLE 85

(2S,2'S)-N,N'-{[(4-fluorophenyl)imino]bis(methanediylbenzene-4,1-diyl)}bis{1-[(2R)-2-phenyl-2-pyrrolidin-1-ylacetyl]pyrrolidine-2-carboxamide}

The product from Example 13D (0.10 g, 0.19 mmol) and (R)-2-phenyl-2-(pyrrolidin-1-yl)acetic acid (0.088 g, 0.43 mmol) were processed as in Example 25B to give 0.098 g (57%) of the title compound as an off-white solid. $^1$H NMR (500 MHz, DMSO-D6) δ ppm 1.62 (s, 8 H) 1.76-1.86 (m, 6 H) 1.94-2.06 (m, 6 H) 2.28-2.43 (m, 4 H) 3.42-3.49 (m, 2 H) 3.81-3.89 (m, 2 H) 4.21 (s, 2 H) 4.31 (dd, J=7.86, 4.20 Hz, 2 H) 4.57 (s, 4 H) 6.65 (dd, J=9.31, 4.43 Hz, 2 H) 6.92 (t, J=8.85 Hz, 2 H) 7.19 (d, J=8.54 Hz, 4 H) 7.26-7.37 (m, 6 H) 7.46 (d, J=7.02 Hz, 4 H) 7.52 (d, J=8.54 Hz, 4H) 9.96 (s, 2 H); MS ESI– m/z 888.6 (M–H)–.

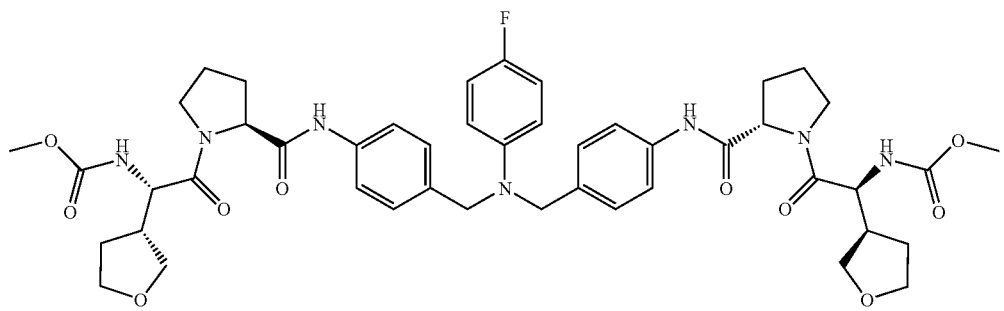

EXAMPLE 86 dimethyl {[(4-fluorophenyl)imino]bis[methanediyl-benzene-4,1-diylcarbamoyl(2 S)pyrrolidine-2,1-diyl{(1S)-2-oxo-1-[(3R)-tetrahydrofuran-3-yl]ethane-2,1-diyl}]}biscarbamate The product from Example 13D (0.03 g, 0.058 mmol) and (S)-2-(methoxycarbonylamino)-2-((R)-tetrahydrofuran-3-yl)acetic acid (0.026 g, 0.128 mmol) were processed as in Example 25B to give 0.040 g (78%) of the title compound as an off-white solid. $^1$H NMR (500 MHz, DMSO-D6) δ ppm 1.71 (dt, J=20.07, 7.21 Hz, 2 H) 1.82-1.94 (m, 6 H) 1.96-2.05 (m, 2 H) 2.10-2.21 (m, 2 H) 2.37-2.45 (m, 2 H) 3.41-3.47 (m, 2 H) 3.53 (s, 6 H) 3.58-3.70 (m, 6 H) 3.71-3.79 (m, 2 H) 3.85 (ddd, J=9.57, 6.71, 6.60 Hz, 2 H) 4.20-4.26 (m, 2 H) 4.43 (dd, J=8.16, 4.65 Hz, 2 H) 4.55 (s, 4 H) 6.63 (dd, J=9.31, 4.43 Hz, 2 H) 6.91 (t, J=8.93 Hz, 2 H) 7.17 (d, J=8.70 Hz, 4 H) 7.51 (d, J=8.54 Hz, 4 H) 7.61 (d, J=7.93 Hz, 2 H) 9.98 (s, 2 H); MS ESI– m/z 884 (M–H)–.

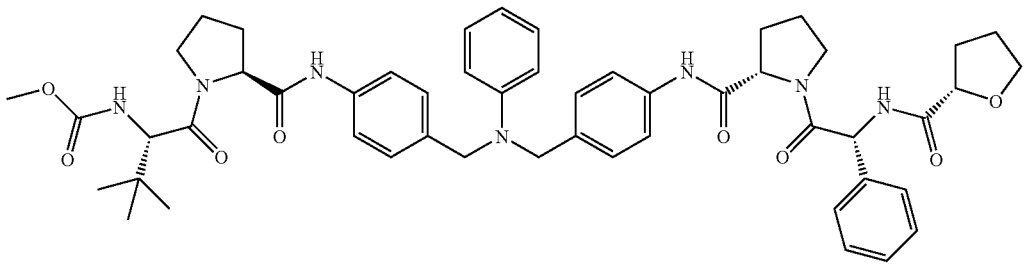

EXAMPLE 87

N-(methoxycarbonyl)-3-methyl-L-valyl-N-[4-({phenyl[4-({1-[(2R)-2-phenyl-2-{[(2S)-tetrahydrofuran-2-ylcarbonyl]amino}acetyl]-L-prolyl}amino)benzyl]amino}methyl)phenyl]-L-prolinamide The product from Example 77 (20 mg, 0.025 mmol) was subjected to the procedure described in Example 10B, substituting (S)-(–)-2-tetrahydrofuroic acid (3 μL, 0.031 mmol) for (R)-2-(dimethylamino)-2-phenylacetic acid, to give the title compound (21 mg, 94%). $^1$H NMR (500 MHz, DMSO-D6) δ ppm 0.96 (s, 8 H), 1.22-1.27 (m, 3 H), 1.73-1.82 (m, 3 H), 1.82-1.90 (m, 3 H), 1.94-2.03 (m, 2 H), 2.09 (s, 2 H), 2.69 (s, 3 H), 3.54 (s, 3 H), 3.71-3.80 (m, 2 H), 3.82-3.89 (m, 2 H), 4.19-4.25 (m, 2 H), 4.38 (dd, J=8.5, 3.1 Hz, 1 H), 4.44 (dd, J=8.0, 5.3 Hz, 1 H), 4.60 (s, 4 H), 5.65 (d, J=7.2 Hz, 1 H), 6.57 (t, J=7.2 Hz, 1 H), 6.66 (d, J=8.1 Hz, 2 H), 7.05-7.11 (m, 3 H), 7.18 (dd, J=8.5, 5.2 Hz, 4 H), 7.33 (dd, J=5.7, 3.0 Hz, 1 H), 7.37-7.41 (m, 3 H), 7.49-7.56 (m, 4 H), 8.08 (d, J=7.3 Hz, 1 H), 8.31 (s, 1 H), 9.88 (s, 1 H), 10.00 (s, 1 H); MS (ESI) m/z 900.4 (M+H)$^+$.

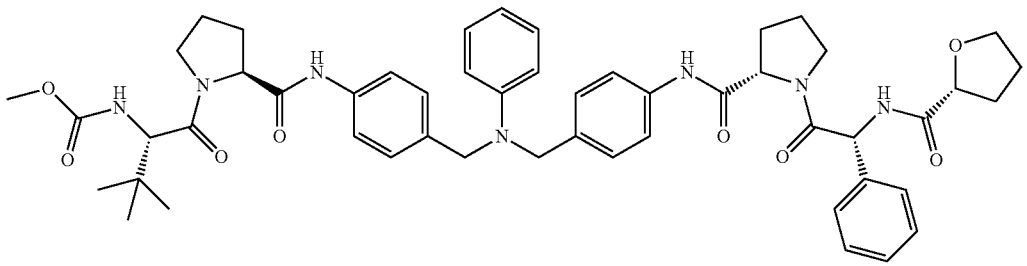 [SMILES: COC(=O)N[C@H](C(=O)N1CCC[C@H]1C(=O)Nc1ccc(CN(Cc2ccc(NC(=O)[C@@H]3CCCN3C(=O)[C@H](NC(=O)[C@H]3CCCO3)c3ccccc3)cc2)c2ccccc2)cc1)C(C)(C)C]

EXAMPLE 88

N-(methoxycarbonyl)-3-methyl-L-valyl-N-[4-({phe-nyl[4-({1-[(2R)-2-phenyl-2-{[(2R)-tetrahydrofuran-2-ylcarbonyl]amino}acetyl]-L-prolyl}amino)benzyl]amino}methyl)phenyl]-L-prolinamide The product from Example 77 (20 mg, 0.025 mmol) was subjected to the procedure described in Example 10B, substituting (R)-(+)-2-tetrahydrofuroic acid (2.6 μL, 0.027 mmol) for (R)-2-(dimethylamino)-2-phenylacetic acid, to afford the title compound (17 mg, 76%). $^1$H NMR (500 MHz, DMSO-D6) δ ppm 0.96 (s, 9 H), 1.24 (s, 4 H), 1.66 (s, 2 H), 1.74 (s, 1 H), 1.78 (s, 1 H), 1.86 (dd, J=5.6, 2.8 Hz, 3 H), 1.99 (s, 2 H), 2.06 (s, 1 H), 2.14 (s, 1 H), 2.69 (s, 3 H), 3.54 (s, 3 H), 3.72-3.79 (m, 2 H), 3.82 (d, J=7.9 Hz, 2 H), 4.21 (d, J=9.0 Hz, 1 H), 4.27 (dd, J=8.2, 5.1 Hz, 1 H), 4.37 (s, 1 H), 4.44 (s, 1 H), 4.60 (s, 4 H), 5.64 (d, J=7.0 Hz, 1 H), 6.57 (s, 1 H), 6.66 (d, J=8.1 Hz, 2 H), 7.04-7.10 (m, 3 H), 7.18 (dd, J=8.5, 5.0 Hz, 4 H), 7.37-7.40 (m, 3 H), 7.49-7.55 (m, 4 H), 8.14 (d, J=7.0 Hz, 1 H), 9.90 (s, 1 H), 10.00 (s, 1 H); MS (ESI) m/z 900.5 (M+H)$^+$.

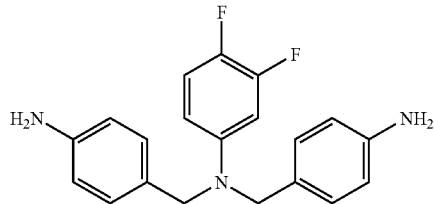

EXAMPLE 89B

N,N-bis(4-aminobenzyl)-3,4-difluoroaniline

The product from Example 89A was processed using the method described in Example 1B to afford the title compound.

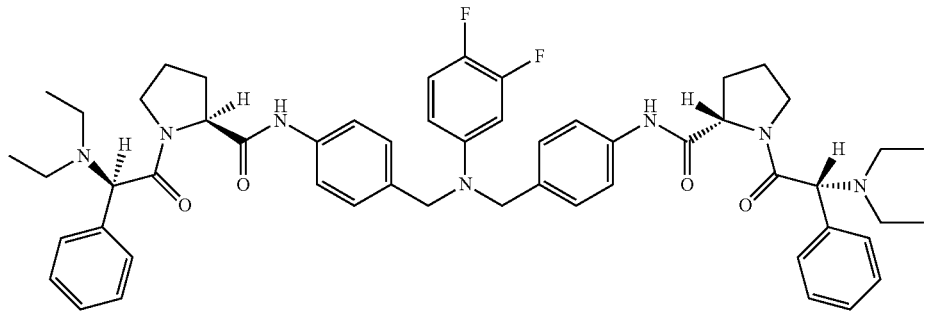 [SMILES: CCN(CC)[C@@H](C(=O)N1CCC[C@H]1C(=O)Nc1ccc(CN(Cc2ccc(NC(=O)[C@@H]3CCCN3C(=O)[C@@H](c3ccccc3)N(CC)CC)cc2)c2ccc(F)c(F)c2)cc1)c1ccccc1]

EXAMPLE 89

(2S,2'S)-N,N'-{[(3,4-difluorophenyl)imino]bis(methanediylbenzene-4,1-diyl)}bis{1-[(2R)-2-(diethylamino)-2-phenylacetyl]pyrrolidine-2-carboxamide}

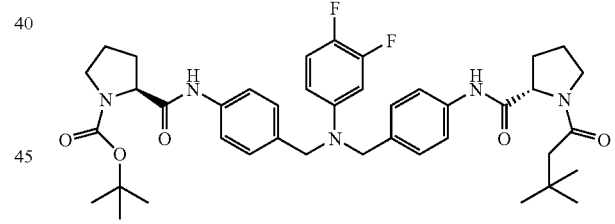

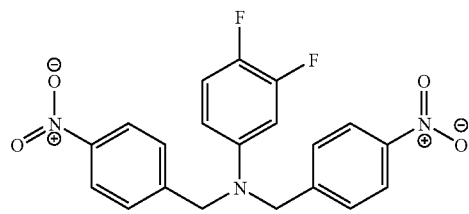 [SMILES: O=[N+]([O-])c1ccc(CN(Cc2ccc([N+](=O)[O-])cc2)c2ccc(F)c(F)c2)cc1]

EXAMPLE 89A 3,4-difluoro-N,N-bis(4-nitrobenzyl)aniline 3,4-Difluoroaniline and 4-nitrobenzyl bromide were processed using the method described in Example 32A to afford the title compound. LC/MS Rt 2.15 m/z 400 (M+H)$^+$.

EXAMPLE 89C (2S,2'S)-tert-butyl 2,2'-(4,4'-(3,4-difluorophenylazanediyl)bis(methylene)bis(4,1-phenylene)bis(azanediyl))bis(oxomethylene)dipyrrolidine-1-carboxylate The product from Example 89B was processed using the method described in Example 1C replacing DMSO with dichloromethane to afford the title compound. $^1$H NMR (400 MHz, DMSO) δ 0.89-0.80 (m, 1H), 1.26 (s, 12H), 1.39 (s, 6H), 1.93-1.74 (m, 6H), 2.23-2.08 (m, 2H), 3.41 (m, J=9.6, 8.9, 6.4, 3H), 4.17 (dd, J=8.0, 4.4, 1H), 4.24 (dd, J=8.1, 2.6, 1H), 4.60 (s, 4H), 6.41 (d, J=9.4, 1H), 6.68-6.55 (m, 1H), 7.11 (dd, J=19.7, 9.7, 1H), 7.18 (d, J=8.0, 4H), 7.54 (d, J=8.5, 4H), 9.94 (s, 2H). MS (ESI) m/z 734 (M+H)$^+$, 732 (M–H)$^+$.

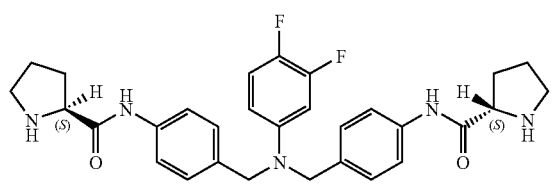

EXAMPLE 89D (2S,2'S)-N,N'-(4,4'-(3,4-difluorophenylazanediyl)bis(methylene)bis(4,1-phenylene))dipyrrolidine-2-carboxamide The product from Example 89C was processed using the method described in Example 1D to afford the title compound. MS (ESI) m/z 534 (M+H$^+$, 60%), 532 (M–H)$^+$.

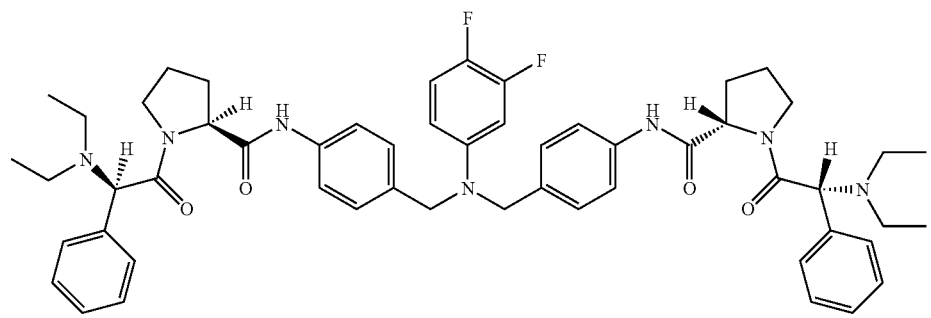 [SMILES: CCN(CC)[C@@H](C(=O)N1CCC[C@H]1C(=O)Nc1ccc(CN(Cc2ccc(NC(=O)[C@@H]3CCCN3C(=O)[C@@H](c3ccccc3)N(CC)CC)cc2)c2ccc(F)c(F)c2)cc1)c1ccccc1]

EXAMPLE 89E (2S,2'S)-N,N'-{[(3,4-difluorophenyl)imino]bis(methanediylbenzene-4,1-diyl)}bis{1-[(2R)-2-(diethylamino)-2-phenylacetyl]pyrrolidine-2-carboxamide}

The product from Example 89D was processed using the method described in Example 12 replacing DMSO with dichloromethane to afford the title compound (68.5 mg, 52%). $^1$H NMR (500 MHz, DMSO) δ 0.95-0.83 (m, 14H), 1.23 (s, 2H), 1.81 (m, 5H), 2.10-1.91 (m, 5H), 2.61 (dt, J=14.1, 3.5, 3H), 3.84-3.73 (m, 2H), 4.39 (dd, J=8.2, 4.5, 2H), 4.60 (s, 4H), 4.68 (s, 2H), 6.46-6.36 (m, 1H), 6.64 (ddd, J=17.5, 6.8, 3.0, 1H), 7.16-7.06 (m, 2H), 7.19 (d, J=8.6, 4H), 7.30-7.25 (m, 2H), 7.33 (t, J=7.4, 4H), 7.40 (d, J=7.1, 4H), 7.54 (d, J=8.5, 4H), 9.98 (s, 2H). MS (ESI) m/z 912 (M+H$^+$, 40%) 457 (0.5M+H$^+$, 100%), 910 (M–H)$^+$.

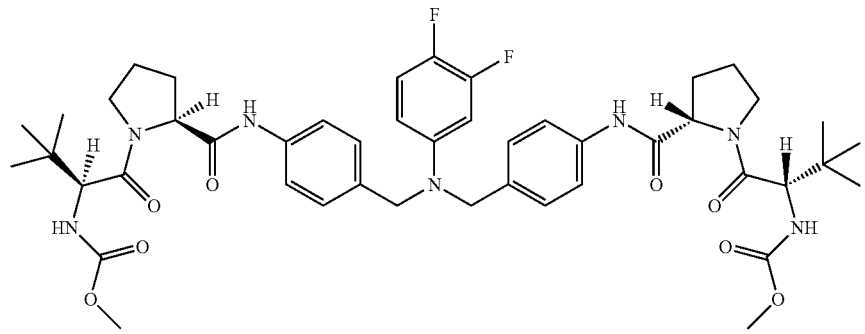 [SMILES: COC(=O)N[C@H](C(=O)N1CCC[C@H]1C(=O)Nc1ccc(CN(Cc2ccc(NC(=O)[C@@H]3CCCN3C(=O)[C@@H](NC(=O)OC)C(C)(C)C)cc2)c2ccc(F)c(F)c2)cc1)C(C)(C)C]

EXAMPLE 90 dimethyl ([(3,4-difluorophenyl)imino]
bis{methanediylbenzene-4,1-diylcarbamoyl(2S)pyr-
rolidine-2,1-diyl[(2S)-3,3-dimethyl-1-oxobutane-1,2-
diyl]})biscarbamate The product from Example 89D was processed using the method described in Example 6 replacing DMSO with dichloromethane and purified using flash chromatography (silica gel, MeOH/dichloromethane) to afford the title compound (0.14 g, 35%). $^1$H NMR (500 MHz, DMSO) δ 0.96 (s, 18H), 1.93-1.75 (m, 4H), 2.05-1.93 (m, 2H), 2.22-2.08 (m, 2H), 3.54 (s, 6H), 3.63 (dd, J=16.0, 6.8, 2H), 3.84-3.71 (m, 2H), 4.21 (d, J=8.9, 2H), 4.44 (dd, J=7.9, 5.3, 2H), 4.58 (s, 4H), 6.40 (d, J=9.1, 1H), 6.62 (ddd, J=14.5, 6.8, 3.0, 1H), 7.10 (m, 3H), 7.17 (d, J=8.5, 4H), 7.52 (d, J=8.5, 4H), 10.00 (s, 2H). MS (ESI) m/z 876 (M+H)$^+$, 874 (M−H)$^+$.

EXAMPLE 91A (S)-2-(methoxycarbonylamino)-4-phenylbutanoic acid (S)-2-amino-4-phenylbutanoic acid (0.50 g, 2.8 mmol) was suspended in 1M Na$_2$CO$_3$ (8.4 mL, 8.4 mmol) and then a solution of methyl chloroformate (0.32 mL, 4.2 mmol) in THF (4.0 mL) was added and the mixture was stirred vigorously at room temperature for 4 hours. The mixture was then concentrated under reduced pressure and the residue was dissolved in water and made acidic with 0.1N HCl. The mixture was extracted with ethyl acetate, dried over Na$_2$SO$_4$, filtered and concentrated under reduced pressure to provide the title compound (0.64 g, 97% yield).

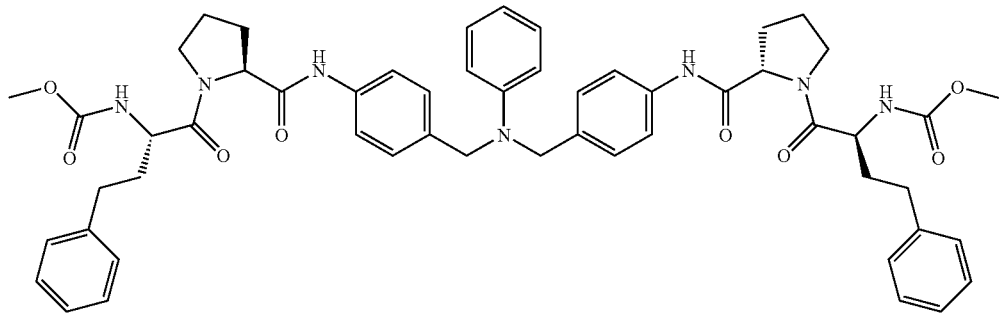

EXAMPLE 91 dimethyl[(phenylimino)bis{methanediylbenzene-4,
1-diylcarbamoyl(2S)pyrrolidine-2,1-diyl[(2S)-1-oxo-
4-phenylbutane-1,2-diyl]}]biscarbamate

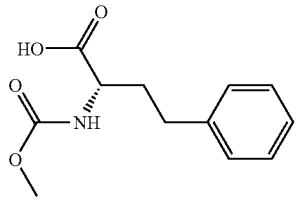 [SMILES: COC(=O)N[C@@H](CCc1ccccc1)C(=O)O]

EXAMPLE 91B dimethyl [(phenylimino)bis{methanediylbenzene-4,
1-diylcarbamoyl(2S)pyrrolidine-2,1-diyl[(2S)-1-oxo-
4-phenylbutane-1,2-diyl]}]biscarbamate The title compound was prepared using the methods from Example 2 substituting the product from Example 91A for (R)-2-(dimethylamino)-2-phenylacetic acid to provide the title compound (103 mg, 55% yield). $^1$H NMR (500 MHz, DMSO) δ 9.97 (s, 2H), 7.53-7.46 (m, 6H), 7.31-7.26 (m, 4H), 7.23 (d, J=7.0, 4H), 7.18 (t, J=7.3, 2H), 7.15 (d, J=8.6, 4H), 7.05 (dd, J=7.3, 8.7, 2H), 6.64 (d, J=8.1, 2H), 6.56 (t, J=7.2, 1H), 4.58 (s, 4H), 4.42 (dd, J=4.5, 8.3, 2H), 4.22 (dd, J=8.1, 13.5, 2H), 3.61-3.54 (m, 2H), 3.54 (s, 6H), 3.45-3.37 (m, 2H), 2.73-2.57 (m, 4H), 2.18-2.06 (m, 2H), 1.99-1.74 (m, 10H). MS (ESI; M+H) m/z=937.

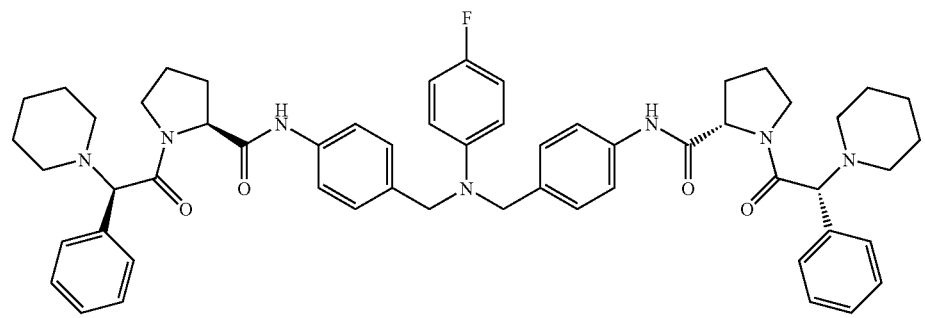 [SMILES: O=C(Nc1ccc(CN(Cc2ccc(NC(=O)[C@@H]3CCCN3C(=O)[C@@H](c3ccccc3)N3CCCCC3)cc2)c2ccc(F)cc2)cc1)[C@@H]1CCCN1C(=O)[C@@H](c1ccccc1)N1CCCCC1]

EXAMPLE 92

(2S,2'S)-N,N'-{[(4-fluorophenyl)imino]bis(methanediylbenzene-4,1-diyl)}bis{1-[(2R)-2-phenyl-2-piperidin-1-ylacetyl]pyrrolidine-2-carboxamide}

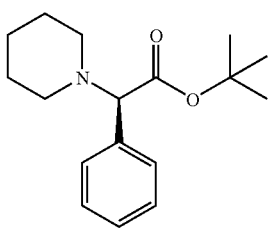 [SMILES: CC(C)(C)OC(=O)[C@@H](c1ccccc1)N1CCCCC1]

EXAMPLE 92A (R)-tert-butyl 2-phenyl-2-(piperidin-1-yl)acetate

To a slurry of (R)-tert-butyl 2-amino-2-phenylacetate HCL (Chem-Impex, 0.200 g, 0.821 mmol), MP-cyanoborohydride (2.44 mmol/g; 500 mg) and acetic acid (0.141 mL, 2.462 mmol) in MeOH (2.00 mL) and CH$_2$Cl$_2$ (2 mL) at rt was added glutaraldehyde (0.155 mL, 0.821 mmol) as a 50% solution in water. The reaction was stirred for 30 min., the reaction filtered, washed with MeOH and concentrated. The residue was taken up in CH$_2$Cl$_2$, washed with saturated NaHCO$_3$, dried (Na$_2$SO$_4$) and concentrated to give the title compound. MS (DCI; M+H) m/z=276.

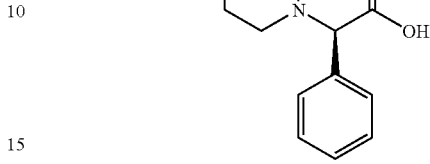

EXAMPLE 92B (R)-2-phenyl-2-(piperidin-1-yl)acetic acid

The product from Example 92A was treated with TFA (1.5 mL) at rt for 3 h. The volatiles were removed under vacuum, the residue concentrated from toluene (×2) and dried in a vacuum oven to give title compound which was used without further purification. MS (DCI; M+H) m/z=220.

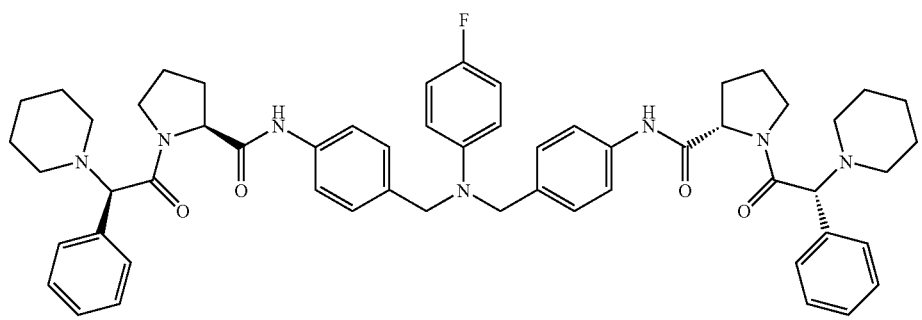 [SMILES: O=C(Nc1ccc(CN(Cc2ccc(NC(=O)[C@@H]3CCCN3C(=O)[C@@H](c3ccccc3)N3CCCCC3)cc2)c2ccc(F)cc2)cc1)[C@@H]1CCCN1C(=O)[C@@H](c1ccccc1)N1CCCCC1]

EXAMPLE 92C (2S,2'S)-N,N'-{[(4-fluorophenyl)imino]bis(methanediylbenzene-4,1-diyl)}bis{1-[(2R)-2-phenyl-2-piperidin-1-ylacetyl]pyrrolidine-2-carboxamide}

The product from Example 13D and the product from 92B were processed using the method described in Example 41 to provide 30 mg (11%) of the title compound. $^1$H NMR (500 MHz, methanol-D4) δ 1.40-1.45 (m, 4 H) 1.50-1.58 (m, 8 H) 1.79-1.88 (m, 2 H) 1.92-2.02 (m, 2 H) 2.05-2.14 (m, 4 H) 2.30-2.40 (m, 4 H) 2.35-2.48 (m, 4 H) 3.43-3.51 (m, 2 H) 3.87-3.93 (m, 2 H) 4.15 (m, 2 H) 4.42 (dd, J=7.78, 4.43 Hz, 2 H) 4.54 (s, 4H) 6.69-6.75 (m, 2 H) 6.81-6.88 (m, 2 H) 7.17-7.23 (m, 4 H) 7.30-7.38 (m, 8 H) 7.46-7.53 (m, 8 H).

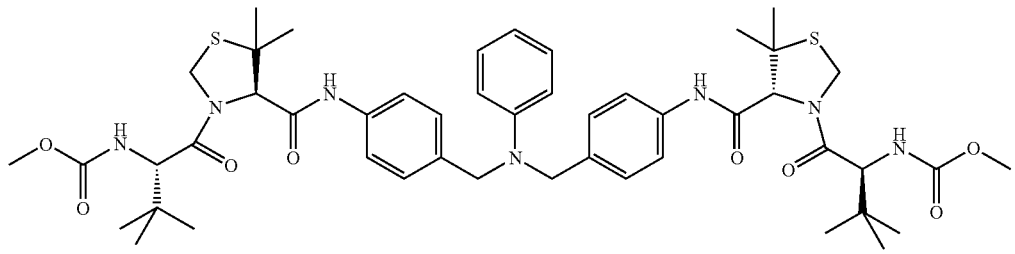

EXAMPLE 93 methyl [(1S)-1-{[(4R)-4-{[4-({[4-({[(4R)-3-{(2S)-2-[(methoxycarbonyl)amino]-3,3-dimethylbutanoyl}-5,5-dimethyl-1,3-thiazolidin-4-yl]carbonyl}amino)benzyl](phenyl)amino}methyl)phenyl]carbamoyl}-5,5-dimethyl-1,3-thiazolidin-3-yl]carbonyl}-2,2-dimethylpropyl]carbamate

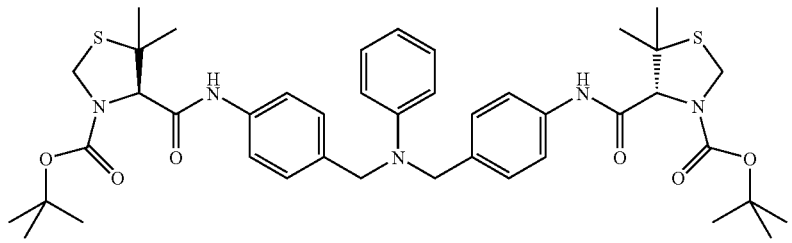 [SMILES: CC(C)(C)OC(=O)N1CSC(C)(C)[C@H]1C(=O)Nc1ccc(CN(Cc2ccc(NC(=O)[C@H]3N(C(=O)OC(C)(C)C)CSC3(C)C)cc2)c2ccccc2)cc1]

EXAMPLE 93A (4R,4'R)-tert-butyl 4,4'-(4,4'-(phenylazanediyl)bis(methylene)bis(4,1-phenylene)bis(azanediyl))bis(oxomethylene)bis(5,5-dimethylthiazolidine-3-carboxylate)

The title compound was prepared using the methods from Example 1C substituting (R)-3-(tert-butoxycarbonyl)-5,5-dimethylthiazolidine-4-carboxylic acid for N-(tert-butoxycarbonyl)-L-proline to provide the title compound (0.32 g, 61% yield).

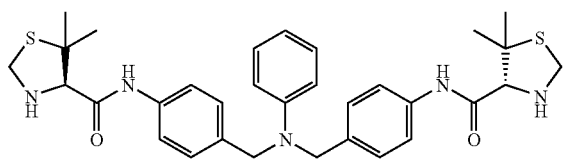 [SMILES: CC1(C)SCN[C@@H]1C(=O)Nc1ccc(CN(Cc2ccc(NC(=O)[C@H]3NCSC3(C)C)cc2)c2ccccc2)cc1]

EXAMPLE 93B (4R,4'R)-N,N'-(4,4'-(phenylazanediyl)bis(methylene)bis(4,1-phenylene))bis(5,5-dimethylthiazolidine-4-carboxamide)

The title compound was prepared using the methods from Example 1D substituting the product from Example 93A for the product from Example 1C to provide the title compound (0.23 g, 97% yield).

EXAMPLE 93C methyl [(1S)-1-{[(4R)-4-{[4-({[4-({[(4R)-3-{(2S)-2-[(methoxycarbonyl)amino]-3,3-dimethylbutanoyl}-5,5-dimethyl-1,3-thiazolidin-4-yl]carbonyl}amino)benzyl](phenyl)amino}methyl)phenyl]carbamoyl}-5,5-dimethyl-1,3-thiazolidin-3-yl]carbonyl}-2,2-dimethylpropyl]carbamate The title compound was prepared using the methods from Example 13E substituting the product from Example 93B for the product from Example 13D to provide the title compound. $^1$H NMR (500 MHz, DMSO) δ 10.02 (s, 2H), 7.51 (d, J=8.6, 4H), 7.28 (d, J=8.1, 2H), 7.19 (d, J=8.6, 4H), 7.08 (dd, J=7.3, 8.7, 2H), 6.66 (d, J=8.1, 2H), 6.57 (t, J=7.2, 1H), 5.07 (d, J=8.6, 2H), 4.85 (d, J=8.6, 2H), 4.65-4.56 (m, 6H), 4.22 (d, J=8.0, 2H), 3.55 (s, 6H), 1.50 (s, 6H), 1.36 (s, 6H), 0.97 (s, 18H). MS (ESI; M+H) m/z=933.

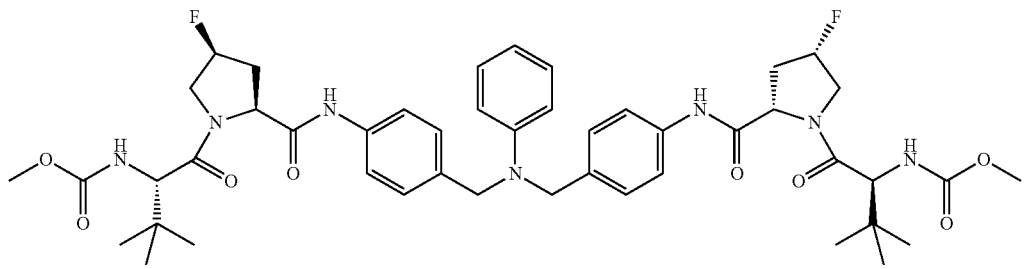

EXAMPLE 94 dimethyl [(phenylimino)bis{methanediylbenzene-4,1-diylcarbamoyl[(2S,4S)-4-fluoropyrrolidine-2,1-diyl][(2S)-3,3-dimethyl-1-oxobutane-1,2-diyl]}] biscarbamate

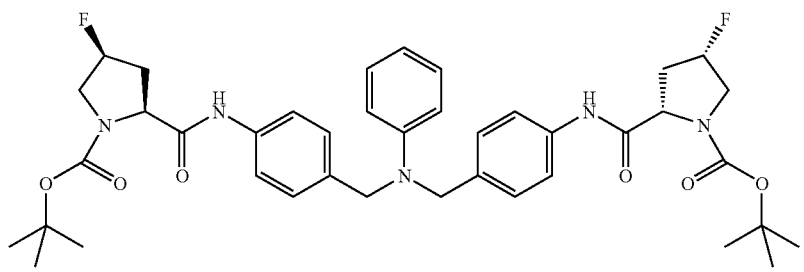 [SMILES: CC(C)(C)OC(=O)N1C[C@@H](F)C[C@H]1C(=O)Nc1ccc(CN(Cc2ccc(NC(=O)[C@@H]3C[C@H](F)CN3C(=O)OC(C)(C)C)cc2)c2ccccc2)cc1]

EXAMPLE 94A (3S,3'S,5S,5'S)-tert-butyl 5,5'-(4,4'-(phenylazanediyl)bis(methylene)bis(4,1-phenylene)bis(azanediyl))bis(oxomethylene)bis(3-fluoropyrrolidine-1-carboxylate)

The title compound was prepared using the methods from Example 1C substituting (2S,4S)-1-(tert-butoxycarbonyl)-4-fluoropyrrolidine-2-carboxylic acid for N-(tert-butoxycarbonyl)-L-proline to provide the title compound (0.42 g, 87% yield).

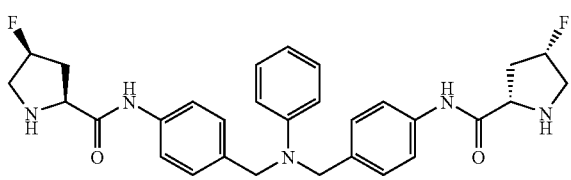 [SMILES: O=C(Nc1ccc(CN(Cc2ccc(NC(=O)[C@@H]3C[C@H](F)CN3)cc2)c2ccccc2)cc1)[C@@H]1C[C@H](F)CN1]

EXAMPLE 94B (2S,2'S,4S,4'S)-N,N'-(4,4'-(phenylazanediyl)bis(methylene)bis(4,1-phenylene))bis(4-fluoropyrrolidine-2-carboxamide)

The title compound was prepared using the methods from Example 1D substituting the product from Example 94A for the product from Example 1C to provide the title compound (0.29 g, 93% yield).

EXAMPLE 94C dimethyl [(phenylimino)bis{methanediylbenzene-4,1-diylcarbamoyl[(2S,4S)-4-fluoropyrrolidine-2,1-diyl][(2S)-3,3-dimethyl-1-oxobutane-1,2-diyl]}] biscarbamate The title compound was prepared using the methods from Example 13E substituting the product from Example 94B for the product from Example 13D to provide the title compound (89 mg, 57% yield). $^1$H NMR (500 MHz, DMSO) δ 9.88 (s, 2H), 7.49 (d, J=8.5, 4H), 7.22-7.14 (m, 6H), 7.06 (dd, J=7.3, 8.7, 2H), 6.65 (d, J=8.1, 2H), 6.56 (t, J=7.2, 1H), 5.36 (d, J=53.5, 2H), 4.65 (dd, J=2.1, 10.0, 2H), 4.59 (s, 4H), 4.16 (d, J=8.7, 2H), 4.12-4.04 (m, 1H), 4.04-3.86 (m, 3H), 3.54 (s, 6H), 2.29-2.19 (m, 2H), 0.98 (s, 18H). MS (ESI; M+H) m/z=877.

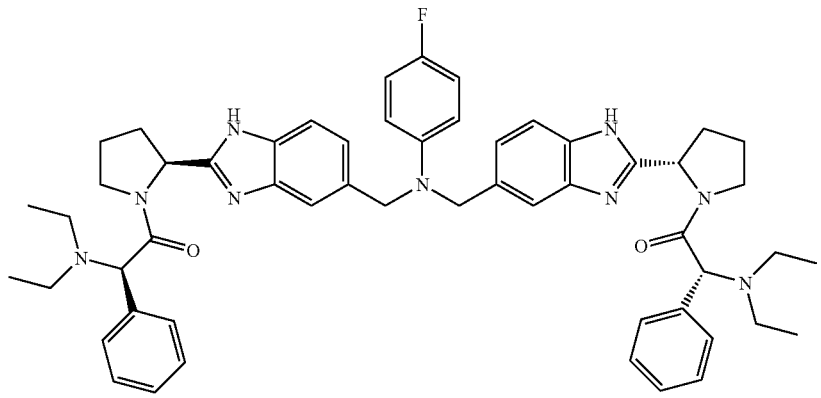 [SMILES: CCN(CC)[C@@H](C(=O)N1CCC[C@H]1c1nc2cc(CN(Cc3ccc4[nH]c([C@@H]5CCCN5C(=O)[C@@H](c5ccccc5)N(CC)CC)nc4c3)c3ccc(F)cc3)ccc2[nH]1)c1ccccc1]

EXAMPLE 95

N,N-bis[(2-{(2S)-1-[(2R)-2-(diethylamino)-2-phenylacetyl]pyrrolidin-2-yl}-1H-benzimidazol-5-yl)methyl]-4-fluoroaniline

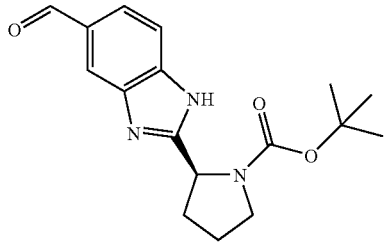 [SMILES: CC(C)(C)OC(=O)N1CCC[C@H]1c1nc2cc(C=O)ccc2[nH]1]

EXAMPLE 95A (S)-tert-butyl 2-(5-formyl-1H-benzo[d]imidazol-2-yl)pyrrolidine-1-carboxylate The product of Example 7B (1.0 g, 3.15 mmol) and MnO$_2$ (1.37 g, 15.75 mmol) in tetrahydrofuran (20 mL) were heated to reflux for 24 hours. The mixture was filtered and concentrated to afford the title compound (0.99 g, 100%). MS (ESI) m/z 316 (M+H)$^+$.

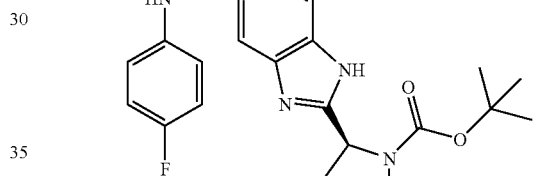

EXAMPLE 95B (S)-tert-butyl 2-(5-((4-fluorophenylamino)methyl)-1H-benzo[d]imidazol-2-yl)pyrrolidine-1-carboxylate To a mixture of the product from Example 95A (1.0 g, 3.17 mmol), 4-fluoroaniline (304 µL, 3.17 mmol) and AcOH (150 µL) in MeOH (30 mL) was added sodium cyanoborohydride (199 mg, 3.17 mmol). The mixture was stirred at rt overnight, and was then quenched with aqueous 1N HCl followed by stirring for 5 minutes. A few drops of aqueous NH$_4$OH were added, and the mixture was diluted with EtOAc and washed with saturated aq. NaHCO$_3$, H$_2$O, and brine. The organic layer was dried (MgSO$_4$), filtered and concentrated to afford the title compound (1.3 g, 100%). MS (ESI) m/z 411 (M+H)$^+$.

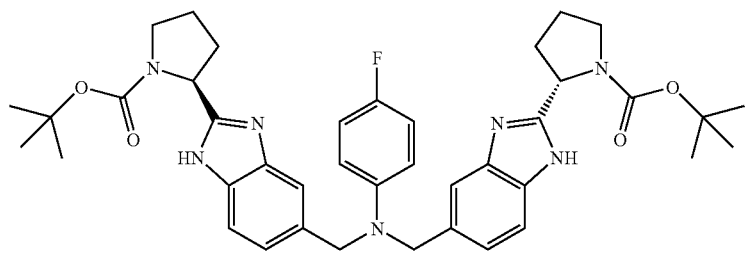 [SMILES: CC(C)(C)OC(=O)N1CCC[C@H]1c1nc2cc(CN(Cc3ccc4[nH]c([C@@H]5CCCN5C(=O)OC(C)(C)C)nc4c3)c3ccc(F)cc3)ccc2[nH]1]

EXAMPLE 95C (2S,2'S)-tert-butyl 2,2'-(5,5'-(4-fluorophenyla-zanediyl)bis(methylene)bis(1H-benzo[d]imidazole-5,2-diyl))dipyrrolidine-1-carboxylate The product of Example 95B (1.29 g, 3.14 mmol), Example 7C (1.2 g, 3.14 mmol) and $K_2CO_3$ (1.3 g, 9.43 mmol) in dimethylformamide (25 mL) were processed using the method described in Example 7D to afford the title compound (1.3 g, 58%). MS (ESI) m/z 710 $(M+H)^+$.

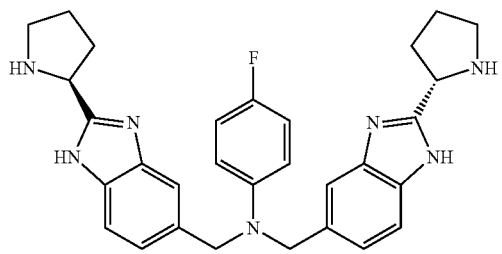 [SMILES: Fc1ccc(N(Cc2ccc3[nH]c([C@@H]4CCCN4)nc3c2)Cc2ccc3[nH]c([C@@H]4CCCN4)nc3c2)cc1]

EXAMPLE 95D 4-fluoro-N,N-bis((2-((S)-pyrrolidin-2-yl)-1H-benzo[d]imidazol-5-yl)methyl)aniline The product of Example 95C (1.3 g, 1.83 mmol) was processed using the method described in Example 7E to afford the title compound (0.46 g, 50%). MS (ESI) m/z 510 $(M+H)^+$.

EXAMPLE 95E

N,N-bis[(2-{(2S)-1-[(2R)-2-(diethylamino)-2-phenylacetyl]pyrrolidin-2-yl}-1H-benzimidazol-5-yl)methyl]-4-fluoroaniline The product from Example 95D (20 mg, 0.039 mmol) was subjected to the procedure described in Example 7F, substituting (R)-2-(diethylamino)-2-phenylacetic acid hydrochloride (23.9 mg, 0.098 mmol) for (S)-2-(methoxycarbonylamino)-3,3-dimethylbutanoic acid to afford the title compound as a TFA salt (8.5 mg). $^1$H NMR (500 MHz, DMSO-D6) δ ppm 0.76 (t, J=7.0 Hz, 1 H), 0.99 (t, J=7.0 Hz, 2 H), 1.07-1.16 (m, 11 H), 1.22-1.31 (m, 4 H), 1.91 (s, 3 H), 1.99-2.08 (m, 5 H), 2.17-2.25 (m, 3 H), 3.05-3.15 (m, 10 H), 4.11-4.18 (m, 2 H), 4.83 (s, 3 H), 5.21 (dd, J=8.5, 2.7 Hz, 2 H), 5.45 (s, 2 H), 6.68-6.77 (m, 2 H), 6.93 (t, J=8.9 Hz, 2 H), 7.27 (d, J=8.2 Hz, 2 H), 7.47 (s, 2 H), 7.52-7.61 (m, 8 H), 7.63-7.70 (m, 4 H); MS (ESI) m/z 888.6 $(M+H)^+$.

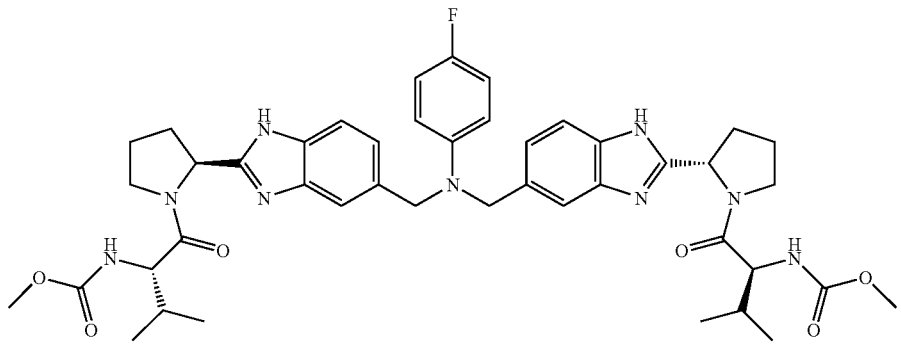

EXAMPLE 96 methyl [(1S)-1-{[(2S)-2-(5-{[(4-fluorophenyl)({2-[(2S)-1-{(2S)-2-[(methoxycarbonyl)amino]-3-methylbutanoyl}pyrrolidin-2-yl]-1H-benzimidazol-5-yl}methyl)amino]methyl}-1H-benzimidazol-2-yl)pyrrolidin-1-yl]carbonyl}-2-methylpropyl]carbamate The product from Example 95D (20 mg, 0.039 mmol) was subjected to the procedure described in Example 7F, substituting (S)-2-(methoxycarbonylamino)-3-methylbutanoic acid (17.2 mg, 0.098 mmol) for (S)-2-(methoxycarbonylamino)-3,3-dimethylbutanoic acid to afford the title compound as a TFA salt (8 mg). $^1$H NMR (500 MHz, DMSO-D6) δ ppm 0.75-0.84 (m, 11 H), 1.20-1.28 (m, 2 H), 1.97 (dd, J=13.8, 6.8 Hz, 3 H), 2.05-2.14 (m, 4 H), 2.18 (dd, J=11.9, 6.4 Hz, 2 H), 3.54 (s, 14 H), 3.81-3.90 (m, 4 H), 4.12 (t, J=7.9 Hz, 2 H), 4.87 (s, 3 H), 5.20 (dd, J=7.9, 5.5 Hz, 2 H), 6.69-6.75 (m, 2 H), 6.94 (t, J=8.9 Hz, 2 H), 7.33 (d, J=8.4 Hz, 2 H), 7.41 (d, J=8.4 Hz, 2 H), 7.55 (s, 2 H), 7.71 (d, J=8.4 Hz, 2 H); MS (ESI) m/z 824.4 $(M+H)^+$.

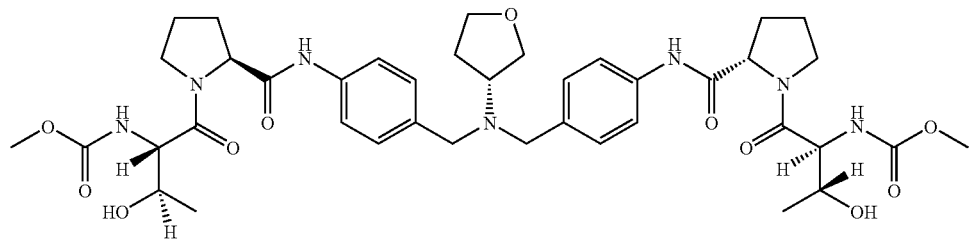

EXAMPLE 97 dimethyl ([(3R)-tetrahydrofuran-3-ylimino]
bis{methanediylbenzene-4,1-diylcarbamoyl(2S)pyr-
rolidine-2,1-diyl[(2S,3R)-3-hydroxy-1-oxobutane-1,
2-diyl]})biscarbamate To a solution of the product from Example 44D (0.05 g, 0.102 mmol) in DMSO (1.0 ml) at room temperature were added the product from Example 25A (0.040 g, 0.224 mmol), HATU (0.085 g, 0.244 mmol) and Hunig's base (0.089 mL, 0.509 mmol), and the mixture was stirred at room temperature for 1 hour. The reaction was diluted with ethyl acetate and washed with saturated $NaHCO_3$, water, and saturated NaCl. The organic was dried over $MgSO_4$, filtered and evaporated. The product was purified by chromatography on silica gel to give the title compound. $^1H$ NMR (400 MHz, DMSO-$d_6$) δ ppm 1.14 (d, J=6.40 Hz, 6 H) 1.80-2.03 (m, 8 H) 2.10-2.22 (m, 2 H) 3.33-3.44 (m, 3 H) 3.47-3.53 (m, 2 H) 3.53 (s, 6 H) 3.56-3.64 (m, 2 H) 3.66-3.75 (m, 2 H) 3.76-3.87 (m, 4 H) 4.21 (t, J=7.37 Hz, 2 H) 4.43 (dd, J=8.29, 4.72 Hz, 2 H) 4.81 (d, J=5.64 Hz, 2 H) 7.09 (d, J=7.48 Hz, 2 H) 7.24 (d, J=8.46 Hz, 4 H) 7.52 (d, J=8.46 Hz, 4 H) 9.83 (s, 2 H). MS (ESI) m/z 810.4 $(M+H)^+$.

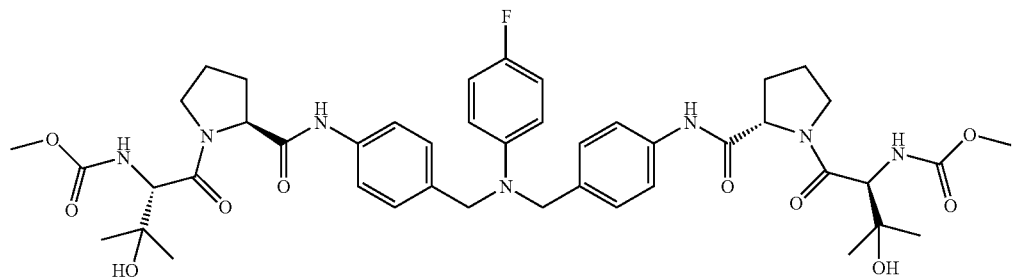

EXAMPLE 98 dimethyl ([(4-fluorophenyl)imino]
bis{methanediylbenzene-4,1-diylcarbamoyl(2S)pyr-
rolidine-2,1-diyl[(2S)-3-hydroxy-3-methyl-1-oxobu-
tane-1,2-diyl]})biscarbamate The product from Example 13D (0.03 g, 0.058 mmol) and (S)-3-hydroxy-2-(methoxycarbonylamino)-3-methylbutanoic acid (0.025 g, 0.128 mmol) were processed as in Example 25B to give 0.010 g (82%) of the title compound as an off-white solid. $^1$H NMR (400 MHz, DMSO -D6) δ ppm 1.15 (s, 6 H) 1.22 (s, 6 H) 1.86-1.98 (m, 6 H) 2.11-2.23 (m, 2 H) 3.55 (s, 6 H) 3.65-3.74 (m, 2 H) 3.83-3.94 (m, 2 H) 4.38 (d, J=8.67 Hz, 2 H) 4.44-4.51 (m, 2 H) 4.56 (s, 4 H) 5.09 (s, 2 H) 6.63 (dd, J=9.22, 4.45 Hz, 2 H) 6.91 (t, J=8.89 Hz, 2 H) 7.11-7.21 (m, 6 H) 7.52 (d, J=8.46 Hz, 4 H) 9.66 (s, 2 H); MS ESI+ m/z 862 (M+H)+; m/z 879 (M+NH4)+.

EXAMPLE 99A (S)-tert-butyl 2-(5-formyl-1H-benzo[d]imidazol-2-yl)pyrrolidine-1-carboxylate The product from Example 7B (0.50 g, 1.58 mmol) was dissolved in tetrahydrofuran (8 mL), heated to 70° C. and treated with manganese dioxide, adding an amount (0.27 g, 3.5 mmol) every two hours till the reaction was complete for a total of 10 eq. The solution was filtered through celite and concentrated to dryness to give the title compound.

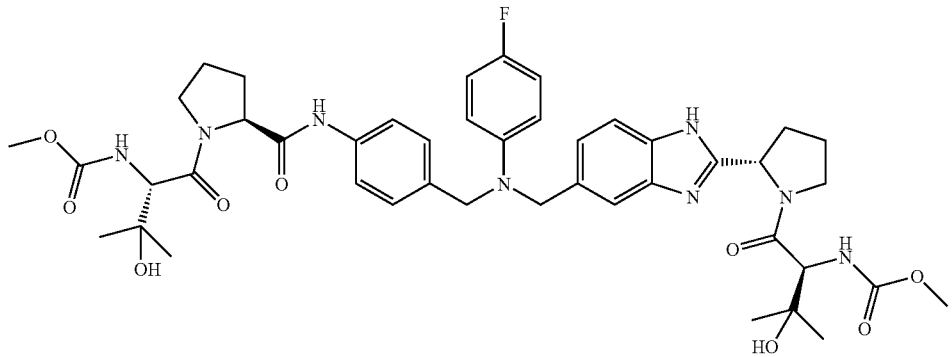

EXAMPLE 99

3-hydroxy-N-(methoxycarbonyl)-L-valyl-N-[4-({(4-fluorophenyl)[(2-{(2S)-1-[3-hydroxy-N-(methoxy-carbonyl)-L-valyl]pyrrolidin-2-yl}-1H-benzimida-zol-5-yl)methyl]amino}methyl)phenyl]-L-prolinamide

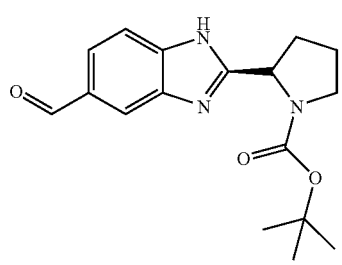

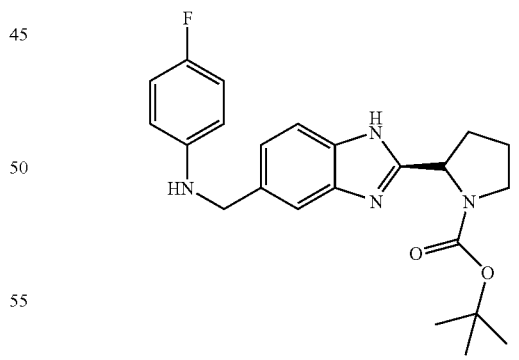

EXAMPLE 99B (S)-tert-butyl 2-(5-((4-fluorophenylamino)methyl)-1H-benzo[d]imidazol-2-yl)pyrrolidine-1-carboxylate The product from Example 99A (0.50 g, 1.59 mmol), 4-fluoroaniline (0.15 g, 1.59 mmol), and acetic acid (0.09 mL, 1.59 mmol) were combined at ambient temperature in methanol (15 mL) and treated with sodium cyanoborohydride (0.10 g, 1.59 mmol) and stirred 17 hours. The mixture was poured into water, extracted into ethyl acetate, dried over sodium sulfate, filtered, and concentrated to give 0.65 g (100%) of the title compound.

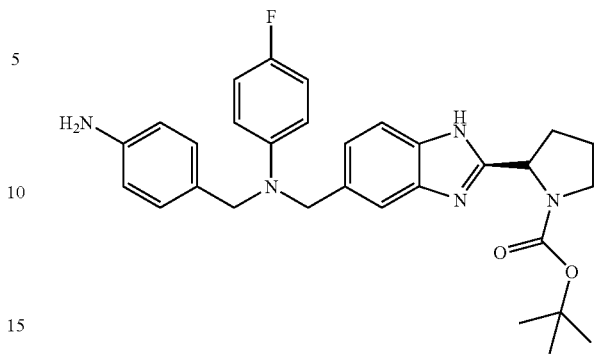

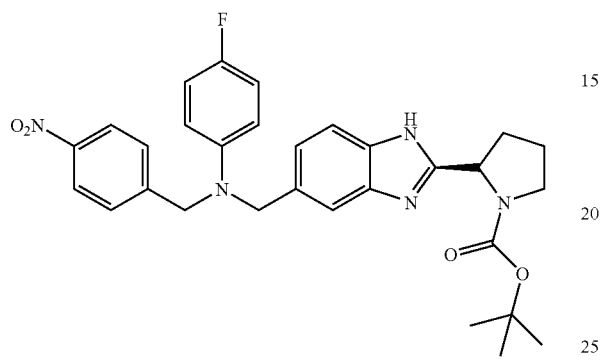

EXAMPLE 99C (S)-tert-butyl 2-(5-(((4-fluorophenyl)(4-nitrobenzyl)amino)methyl)-1H-benzo[d]imidazol-2-yl)pyrrolidine-1-carboxylate The product from Example 99B (0.65 g, 1.58 mmol), 1-(bromomethyl)-4-nitrobenzene (0.479 g, 2.22 mmol), and potassium carbonate (0.547 g, 3.96 mmol) were combined in dimethyl formamide (15 mL) and heated at 40° C. for 3 hours then diluted with water and filtered. The product was purified by combi-flash 24 g silica column, eluting with 0-5% methanol in dichloromethane to give 0.805 g (93%) of the title compound.

EXAMPLE 99D (S)-tert-butyl 2-(5-(((4-aminobenzyl)(4-fluorophenyl)amino)methyl)-1H-benzo[d]imidazol-2-yl)pyrrolidine-1-carboxylate The product from Example 99C (0.67 g, 1.23 mmol) was dissolved in ethanol (15 mL) and cooled in an ice bath. Bismuth trichloride (0.245 mL, 3.68 mmol) was added and a slurry formed to which was added sodium borohydride (0.743 g, 19.7 mmol) portionwise causing a black precipitate to form. This mixture was stirred at ambient temperature for 20 minutes, then re-cooled and quenched with methanol (2 mL), stirring for 10 min before filtering through celite. The filtrated was concentrated to give the title compound.

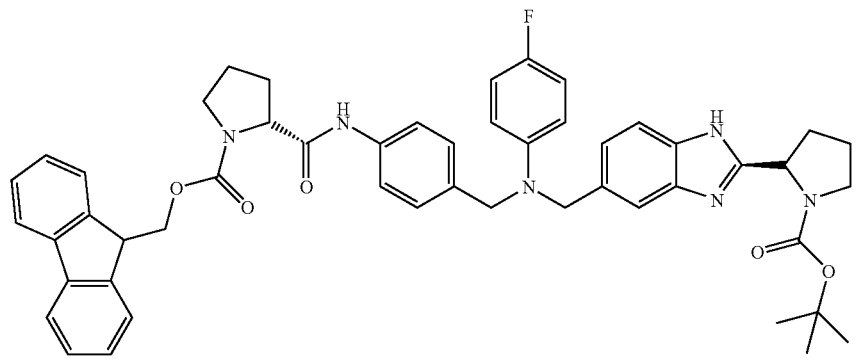

EXAMPLE 99E (R)-(9H-fluoren-9-yl)methyl 2-(4-((((2-((S)-1-(tert-butoxycarbonyl)pyrrolidin-2-yl)-1H-benzo[d]imidazol-5-yl)methyl)(4-fluorophenyl)amino)methyl)phenylcarbamoyl)pyrrolidine-1-carboxylate The product from Example 99D (0.251 g, 0.75 mmol), FMOC-PRO-OH (0.32 g, 0.621 mmol), and diisopropylethylamine (0.27 mL, 1.55 mmol) were combined in dimethyl sulfoxide (8 mL) at ambient temperature and treated with HATU (0.26 g, 0.683 mmol). The solution was stirred for 40 min then diluted with water, filtered, and purified by combi-flash 24 g silica column, eluting with 0-5% methanol in dichloromethane to give 0.38 g (55%) of the title compound.

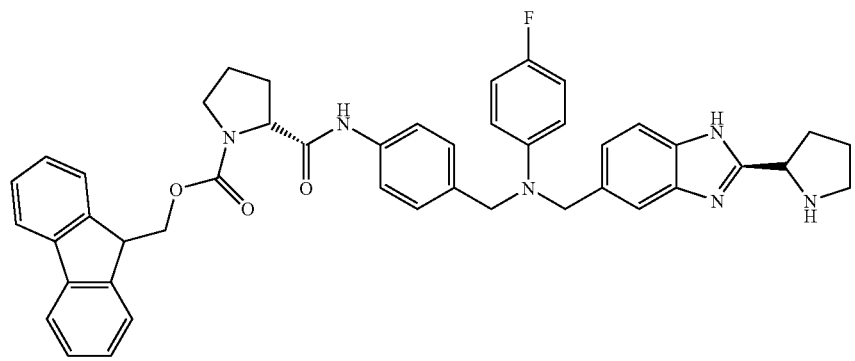

EXAMPLE 99F (R)-(9H-fluoren-9-yl)methyl 2-(4-(((4-fluorophenyl)((2-((S)-pyrrolidin-2-yl)-1H-benzo[d]imidazol-5-yl)methyl)amino)methyl)phenylcarbamoyl)pyrrolidine-1-carboxylate The product from Example 99E (0.38 g, 0.455 mmol) was dissolved in dichloromethane (4 mL) and treated with trifluoroacetic acid (3 mL) at ambient temperature for 3 hours, then concentrated to dryness, taken up in ethyl acetate and washed with sodium bicarbonate solution. The organic was dried over sodium sulfate, filtered, and concentrated to give 0.092 g (28%) of the title compound.

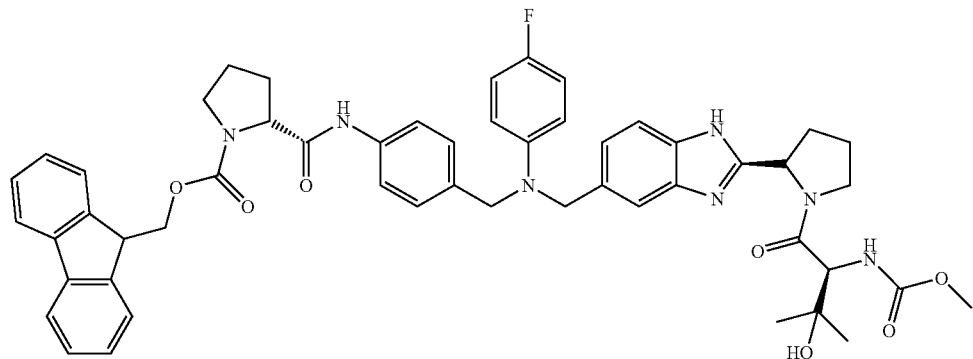

EXAMPLE 99G (R)-(9H-fluoren-9-yl)methyl 2-(4-(((4-fluorophenyl)((2-((S)-1-((S)-3-hydroxy-2-(methoxycarbonylamino)-3-methylbutanoyl)pyrrolidin-2-yl)-1H-benzo[d]imidazol-5-yl)methyl)amino)methyl)phenylcarbamoyl)pyrrolidine-1-carboxylate The product from Example 99F (0.092 g, 0.125 mmol), (S)-3-hydroxy-2-(methoxycarbonylamino)-3-methylbutanoic acid (0.029 g, 0.15 mmol) was processed as in Example 99E to give 0.115 g (100%) of the title compound.

EXAMPLE 99I 3-hydroxy-N-(methoxycarbonyl)-L-valyl-N-[4-({(4-fluorophenyl)[(2-{(2S)-1-[3-hydroxy-N-(methoxycarbonyl)-L-valyl]pyrrolidin-2-yl}-1H-benzimidazol-5-yl)methyl]amino}methyl)phenyl]-L-prolinamide The product from Example 99H (0.087 g, (0.127) was processed as in Example 99G to give 0.048 g (44%) of ancon-centrated to dryness to give the crude title compound.off-white solid. ¹H NMR (400 MHz, DMSO-D6) δ ppm 1.06 (d,

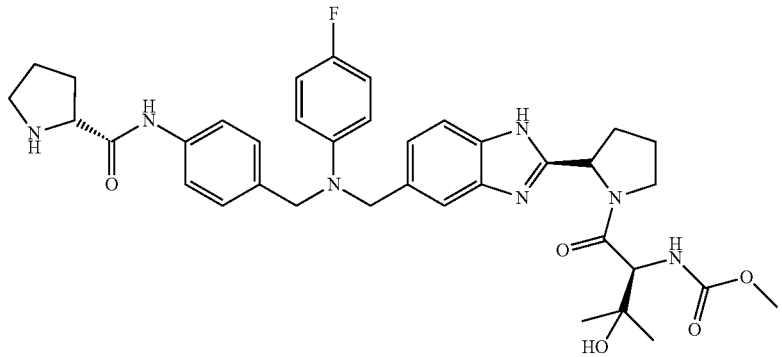

EXAMPLE 99H methyl (S)-1-((S)-2-(5-(((4-fluorophenyl)(4-((R)-pyrrolidine-2-carboxamido)benzyl)amino)methyl)-1H-benzo[d]imidazol-2-yl)pyrrolidin-1-yl)-3-hydroxy-3-methyl-1-oxobutan-2-ylcarbamate The product from Example 99G (0.115 g, 0.127 mmol) was dissolved in acetonitrile (2 mL) at ambient temperature and treated with diethylamine (1 mL) for 1 hour. The solution was J=7.05 Hz, 3 H) 1.15 (s, 3 H) 1.17 (s, 3 H) 1.23 (s, 3 H) 1.87-2.05 (m, 6 H) 2.13-2.20 (m, 1 H) 2.23-2.30 (m, 1 H) 3.55 (s, 6 H) 3.69 (ddd, J=16.13, 8.00, 7.86 Hz, 2 H) 3.84-3.92 (m, 1 H) 4.08-4.15 (m, 1 H) 4.40 (dd, J=14.42, 8.78 Hz, 2 H) 4.47 (dd, J=8.35, 3.36 Hz, 1 H) 4.59 (d, J=2.93 Hz, 2 H) 4.70 (d, J=8.67 Hz, 2 H) 5.09 (d, J=2.49 Hz, 1 H) 5.22-5.28 (m, 1 H) 5.84 (d, J=5.64 Hz, 1 H) 6.64-6.70 (m, 2 H) 6.90 (td, J=8.84, 4.77 Hz, 2 H) 7.03-7.09 (m, 2 H) 7.14 (d, J=8.67 Hz, 1 H) 7.19 (d, J=7.59 Hz, 2 H) 7.30 (d, J=20.28 Hz, 1 H) 7.39 (dd, J=11.66, 8.29 Hz, 1 H) 7.52 (dd, J=8.51, 1.57 Hz, 2 H) 9.67 (d, J=2.39 Hz, 1 H) 12.11 (d, J=13.34 Hz, 1 H); MS ESI+ m/z 859 (M+H)+.

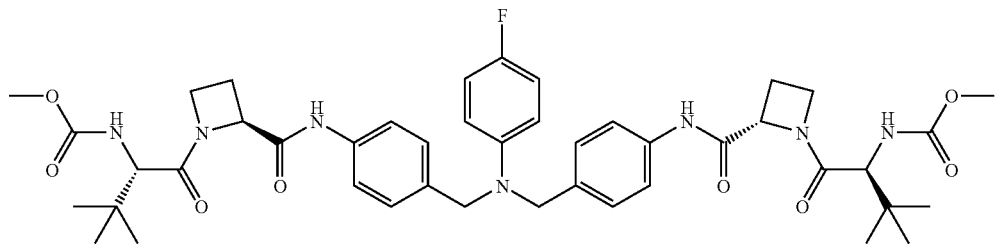

EXAMPLE 100 methyl [(1S)-1-{[(2S)-2-{[4-({(4-fluorophenyl)[4-({[(2S)-1-{(2S)-2-[(methoxycarbonyl)amino]-3,3-dimethylbutanoyl}azetidin-2-yl]carbonyl}amino)benzyl]amino}methyl)phenyl]carbamoyl}azetidin-1-yl]carbonyl}-2,2-dimethylpropyl]carbamate

EXAMPLE 100B (2S,2'S)-N,N'-(4,4'-(4-fluorophenylazanediyl)bis(methylene)bis(4,1-phenylene))diazetidine-2-carboxamide The product from Example 100A was processed using the method described in Example 1D to afford the title compound. MS (ESI) m/z 488 (M+H)$^+$, 486 (M−H)$^+$.

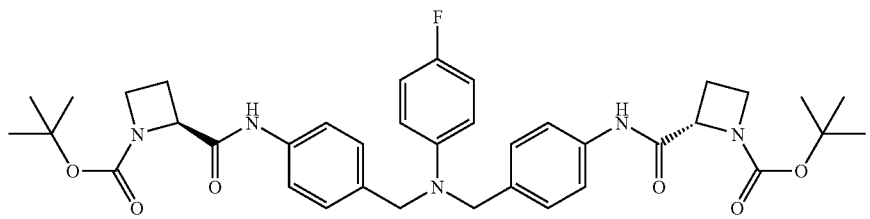 [SMILES: CC(C)(C)OC(=O)N1CC[C@H]1C(=O)Nc1ccc(CN(Cc2ccc(NC(=O)[C@@H]3CCN3C(=O)OC(C)(C)C)cc2)c2ccc(F)cc2)cc1]

EXAMPLE 100A (2S,2'S)-tert-butyl 2,2'-(4,4'-(4-fluorophenylazanediyl)bis(methylene)bis(4,1-phenylene)bis(azanediyl))bis(oxomethylene)diazetidine-1-carboxylate The product of Example 13B and (S)-N-Boc-azetidine carboxylic acid were processed using the method described in Example 1C replacing DMSO with dichloromethane to afford the title compound. LC/MS Rt 2.04 m/z 688 (M+H)$^+$.

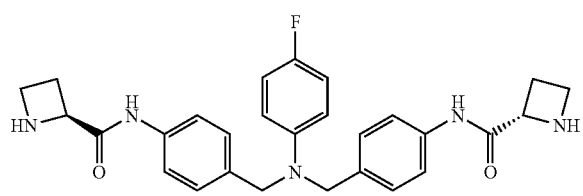 [SMILES: O=C(Nc1ccc(CN(Cc2ccc(NC(=O)[C@@H]3CCN3)cc2)c2ccc(F)cc2)cc1)[C@@H]1CCN1]

EXAMPLE 100C methyl [(1S)-1-{[(2S)-2-{[4-({(4-fluorophenyl)[4-({[(2S)-1-{(2S)-2-[(methoxycarbonyl)amino]-3,3-dimethylbutanoyl}azetidin-2-yl]carbonyl}amino)benzyl]amino}methyl)phenyl]carbamoyl}azetidin-1-yl]carbonyl}-2,2-dimethylpropyl]carbamate The product from Example 100B was processed using the method described in Example 13E to afford the title compound (93.9 mg, 21%). $^1$H NMR (400 MHz, DMSO) δ 0.96 (s, 18H), 2.28-2.11 (m, 2H), 2.48-2.36 (m, 2H), 3.55 (s, 6H), 3.85 (d, J=8.6, 2H), 4.30-4.14 (m, 4H), 4.57 (s, 4H), 4.79 (dd, J=8.9, 5.7, 2H), 6.64 (dd, J=9.2, 4.4, 2H), 6.91 (t, J=8.9, 2H), 7.20 (t, J=7.9, 6H), 7.53 (d, J=8.4, 4H), 10.05 (s, 2H). MS (ESI) m/z 830 (M+H)$^+$, 828 (M−H)$^+$.

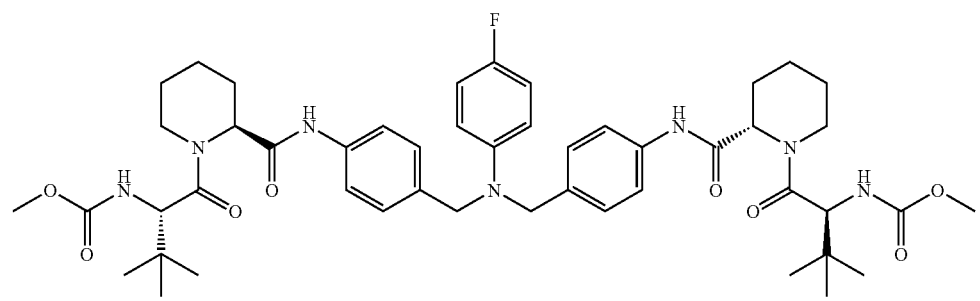

EXAMPLE 101 methyl [(1S)-1-{[(2S)-2-{[4-({(4-fluorophenyl)[4-({[(2S)-1-{(2S)-2-[(methoxycarbonyl)amino]-3,3-dimethylbutanoyl}piperidin-2-yl]carbonyl}amino)benzyl]amino}methyl)phenyl]carbamoyl}piperidin-1-yl]carbonyl}-2,2-dimethylpropyl]carbamate

EXAMPLE 101A (2S,2'S)-tert-butyl 2,2'-(4,4'-(4-fluorophenylazanediyl)bis(methylene)bis(4,1-phenylene)bis(azanediyl))bis(oxomethylene)dipiperidine-1-carboxylate

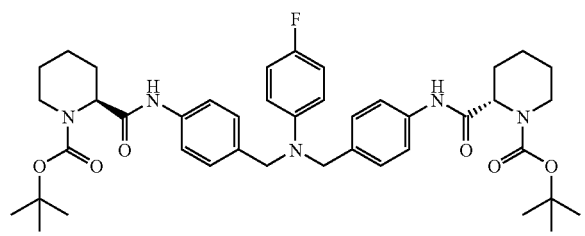 [SMILES: CC(C)(C)OC(=O)N1CCCC[C@H]1C(=O)Nc1ccc(CN(Cc2ccc(NC(=O)[C@@H]3CCCCN3C(=O)OC(C)(C)C)cc2)c2ccc(F)cc2)cc1]

The product from 13B and Boc-L-pipecolic acid were processed using the method described in Example 1C replacing DMSO with dichloromethane to afford the title compound. LC/MS Rt 2.31 m/z 744 (M+H)+ present.

EXAMPLE 101B

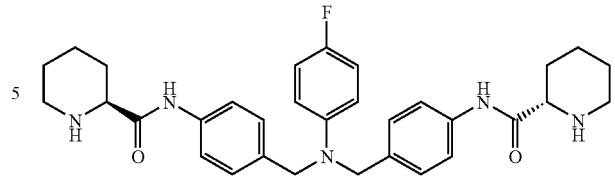

(2S,2'S)-N,N'-(4,4'-(4-fluorophenylazanediyl)bis(methylene)bis(4,1-phenylene))dipiperidine-2-carboxamide The product from Example 101A was processed using the method described in Example 1D to afford the title compound. MS (DCI) m/z 544 (M+H)+.

EXAMPLE 101C methyl [(1S)-1-{[(2S)-2-{[4-({(4-fluorophenyl)[4-({[(2S)-1-{(2S)-2-[(methoxycarbonyl)amino]-3,3-dimethylbutanoyl}piperidin-2-yl]carbonyl}amino)benzyl]amino}methyl)phenyl]carbamoyl}piperidin-1-yl]carbonyl}-2,2-dimethylpropyl]carbamate The product from Example 101B was processed using the method described in Example 13E replacing DMF with dichloromethane to afford the title compound (0.23 g, 57%). ¹H NMR (400 MHz, DMSO) δ 0.95 (s, 13H), 0.97 (d, J=10.6, 5H), 1.80-1.08 (m, 12H), 2.10 (d, J=13.1, 0.51H), 2.27 (d, J=10.5, 0.5H), 3.54 (s, 6H), 4.03 (d, J=12.2, 1H), 4.44 (dd, J=12.9, 6.5, 1H), 4.56 (d, J=5.9, 6H), 5.10 (s, 0.5H), 5.20 (s, 1.5H), 6.64 (dd, J=9.1, 4.4, 2H), 6.91 (t, J=8.9, 2H), 7.05 (d, J=9.1, 1H), 7.20 (dd, J=18.9, 9.9, 5H), 7.50 (d, J=8.5, 3H), 7.60 (d, J=8.3, 1H), 9.83 (s, 0.5H), 9.88 (s, 1.5H). MS (ESI) m/z 886 (M+H+, 20%) 944 (M+CH₃CN+NH₄, 100%), 884 (M−H)+.

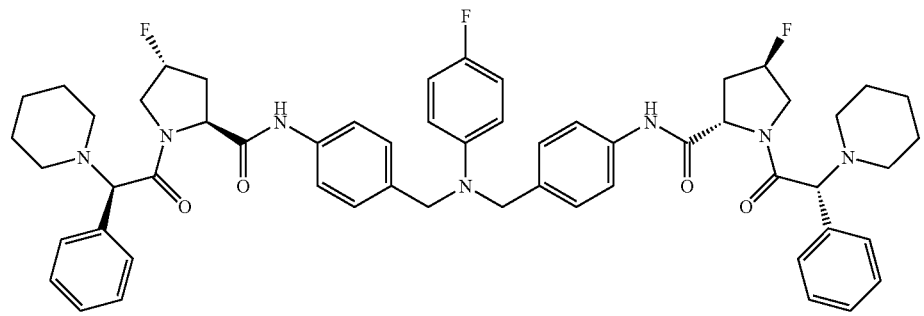 [SMILES: O=C(Nc1ccc(CN(Cc2ccc(NC(=O)[C@@H]3C[C@@H](F)CN3C(=O)[C@@H](c3ccccc3)N3CCCCC3)cc2)c2ccc(F)cc2)cc1)[C@@H]1C[C@@H](F)CN1C(=O)[C@@H](c1ccccc1)N1CCCCC1]

EXAMPLE 102

(2S,4R,2'S,4'R)-N,N'-{[(4-fluorophenyl)imino]bis(methanediylbenzene-4,1-diyl)}bis{4-fluoro-1-[(2R)-2-phenyl-2-piperidin-1-ylacetyl]pyrrolidine-2-carboxamide}

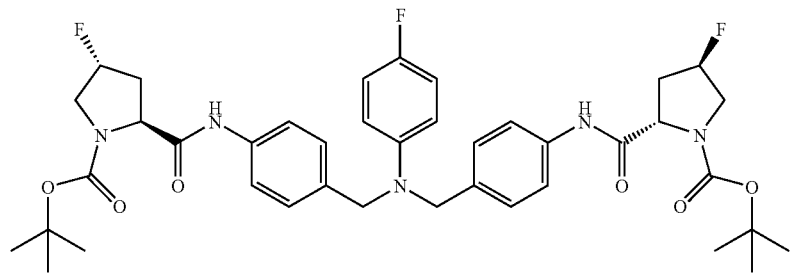 [SMILES: CC(C)(C)OC(=O)N1C[C@H](F)C[C@H]1C(=O)Nc1ccc(CN(Cc2ccc(NC(=O)[C@@H]3C[C@@H](F)CN3C(=O)OC(C)(C)C)cc2)c2ccc(F)cc2)cc1]

EXAMPLE 102A (3R,3'R,5S,5'S)-tert-butyl 5,5'-(4,4'-(4-fluorophenylazanediyl)bis(methylene)bis(4,1-phenylene)bis(azanediyl))bis(oxomethylene)bis(3-fluoropyrrolidine-1-carboxylate)

The product from Example 13D and (2S,4R)-1-(tert-butoxycarbonyl)-4-fluoropyrrolidine-2-carboxylic acid (Aldrich) were processed using the method described in Example 41 to provide 1.05 g (90%) of the title compound. MS (DCI; M+H) m/z=752.

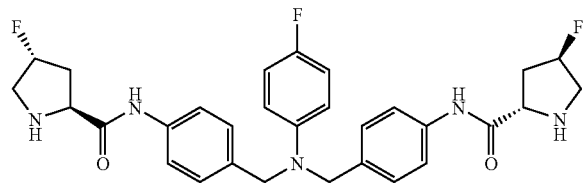 [SMILES: O=C(Nc1ccc(CN(Cc2ccc(NC(=O)[C@@H]3C[C@@H](F)CN3)cc2)c2ccc(F)cc2)cc1)[C@@H]1C[C@@H](F)CN1]

EXAMPLE 102B (2S,2'S,4R,4'R)-N,N'-(4,4'-(4-fluorophenylazanediyl)bis(methylene)bis(4,1-phenylene))bis(4-fluoropyrrolidine-2-carboxamide)

The product from Example 102A was processed using the method described in Example 47B to provide 540 mg (70%) of the title compound. MS (ESI; M+H) m/z=552.

EXAMPLE 102C (2S,4R,2'S,4'R)-N,N'-{[(4-fluorophenyl)imino]bis(methanediylbenzene-4,1-diyl)}bis{4-fluoro-1-[(2R)-2-phenyl-2-piperidin-1-ylacetyl]pyrrolidine-2-carboxamide}

The product from Example 102B and the product from 92B were processed using the method described in Example 41 to provide 25 mg (8%) of the title compound. $^1$H NMR (400 MHz, methanol-D4) δ 1.45-1.55 (m, 4 H) 1.58-1.70 (m, 8 H) 2.09-2.27 (m, 2 H) 2.39-2.90 (m, 10 H) 3.75-4.04 (m, 4 H) 4.22-4.70 (m, 4 H) 4.55 (s, 4 H) 5.22 (s, 1 H) 5.35 (s, 1 H) 6.69-6.76 (m, 2 H) 6.81-6.89 (m, 2 H) 7.22 (d, J=8.46 Hz, 4 H) 7.42 (s, 6 H) 7.50 (d, J=8.46 Hz, 4 H) 7.54 (d, J=4.23 Hz, 4 H).

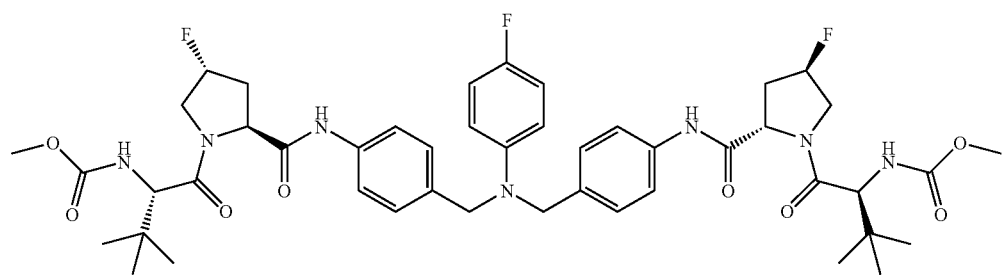

EXAMPLE 103 dimethyl ([(4-fluorophenyl)imino]
bis{methanediylbenzene-4,1-diylcarbamoyl[(2S,
4R)-4-fluoropyrrolidine-2,1-diyl][(2S)-3,3-dimethyl-
1-oxobutane-1,2-diyl]})biscarbamate

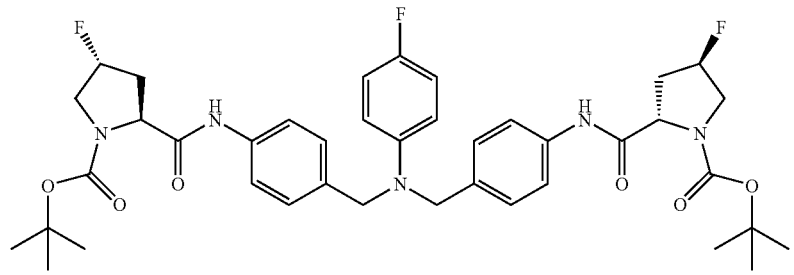 [SMILES: CC(C)(C)OC(=O)N1C[C@H](F)C[C@H]1C(=O)Nc1ccc(CN(Cc2ccc(NC(=O)[C@@H]3C[C@@H](F)CN3C(=O)OC(C)(C)C)cc2)c2ccc(F)cc2)cc1]

EXAMPLE 103A (3S,3'S,5S,5'S)-tert-butyl 5,5'-(4,4'-(4-fluorophenyla-
zanediyl)bis(methylene)bis(4,1-phenylene)bis
(azanediyl))bis(oxomethylene)bis(3-fluoropyrroli-
dine-1-carboxylate)

The title compound was prepared using the methods from Example 13C substituting (2S,4R)-1-(tert-butoxycarbonyl)-4-fluoropyrrolidine-2-carboxylic acid for N-(tert-butoxycarbonyl)-L-proline to provide the title compound (0.29 g, 83% yield).

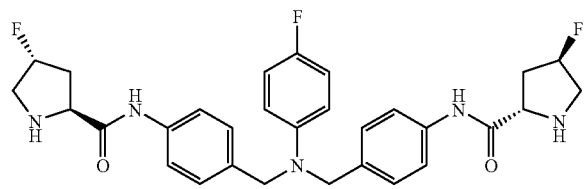 [SMILES: O=C(Nc1ccc(CN(Cc2ccc(NC(=O)[C@@H]3C[C@@H](F)CN3)cc2)c2ccc(F)cc2)cc1)[C@@H]1C[C@@H](F)CN1]

EXAMPLE 103B (2S,2'S,4S,4'S)-N,N'-(4,4'-(4-fluorophenylazanediyl)
bis(methylene)bis(4,1-phenylene))bis(4-fluoropyrro-
lidine-2-carboxamide)

The title compound was prepared using the methods from Example 13D substituting the product from Example 103A for the product from Example 13C to provide the title compound.

EXAMPLE 103C dimethyl ([(4-fluorophenyl)imino]
bis{methanediylbenzene-4,1-diylcarbamoyl[(2S,
4R)-4-fluoropyrrolidine-2,1-diyl][(2S)-3,3-dimethyl-
1-oxobutane-1,2-diyl]})biscarbamate The title compound was prepared using the methods from Example 13E substituting the product from Example 103B for the product from Example 13D to provide the title compound (89 mg, 57% yield). $^1$H NMR (400 MHz, DMSO) δ10.11 (bs, 2H), 7.51 (d, J=8.5, 4H), 7.21-7.15 (m, 6H), 6.91 (t, J=8.9, 2H), 6.64 (dd, J=4.4, 9.1, 2H), 5.46 (bs, 1H), 5.32 (bs, 1H), 4.57-4.48 (m, 6H), 4.20-4.06 (m, 4H), 3.88-3.71 (m, 2H), 3.54 (s, 6H), 3.17 (d, J=5.2, 2H), 2.21-1.97 (m, 2H), 0.96 (s, 18H). MS (ESI; M+H) m/z=895.

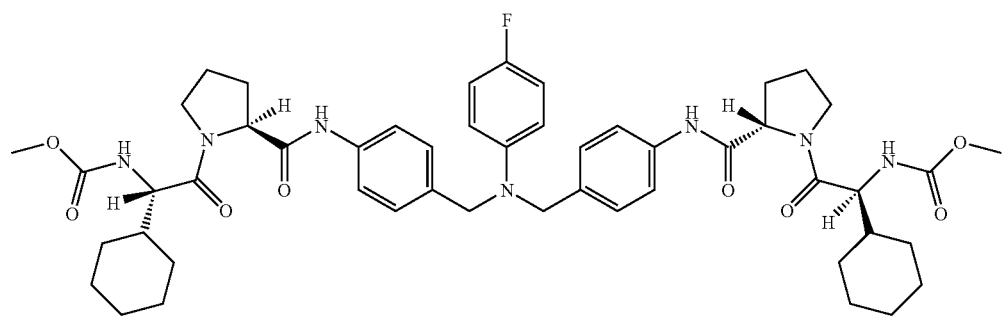

EXAMPLE 104 dimethyl ([(4-fluorophenyl)imino]
bis{methanediylbenzene-4,1-diylcarbamoyl(2S)pyr-
rolidine-2,1-diyl[(1S)-1-cyclohexyl-2-oxoethane-2,
1-diyl]})biscarbamate The product from Example 13D and (S)-2-cyclohexyl-2-(methoxycarbonylamino)acetic acid were processed using the method described in Example 13E replacing DMF with dichloromethane to afford the title compound (74.4 mg, 16%). $^1$H NMR (400 MHz, DMSO) δ 1.29-0.83 (m, 10H), 1.69 (dd, J=14.2, 61.5, 12H), 1.93-1.81 (m, 4H), 2.06-1.93 (m, 2H), 2.19-2.06 (m, 2H), 3.51 (s, 6H), 3.66-3.55 (m, 2H), 3.88-3.73 (m, 2H), 4.07 (t, J=8.6, 2H), 4.41 (dd, J=4.8, 8.1, 2H), 4.55 (s, 4H), 6.69-6.56 (m, 2H), 6.97-6.83 (m, 2H), 7.17 (d, J=8.5, 4H), 7.30 (d, J=8.4, 2H), 7.50 (d, J=8.5, 4H), 9.96 (s, 2H). MS (ESI) m/z 910 (M+H)$^+$, 908 (M−H)$^+$.

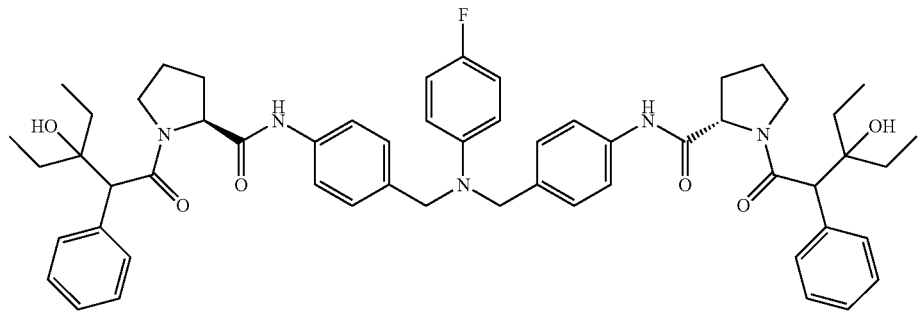 [SMILES: CCC(O)(CC)C(C(=O)N1CCC[C@H]1C(=O)Nc1ccc(CN(Cc2ccc(NC(=O)[C@@H]3CCCN3C(=O)C(c3ccccc3)C(O)(CC)CC)cc2)c2ccc(F)cc2)cc1)c1ccccc1]

EXAMPLE 105

(2S,2'S)-N,N'-{[(4-fluorophenyl)imino]bis(methanediylbenzene-4,1-diyl)}bis[1-(3-ethyl-3-hydroxy-2-phenylpentanoyl)pyrrolidine-2-carboxamide]

The product from Example 13D (30 mg, 0.058 mmol) was subjected to the procedure described in Example 24E, substituting 3-ethyl-3-hydroxy-2-phenylpentanoic acid (27 mg, 0.122 mmol) for (S)-2-(methoxycarbonylamino)-3-methylbutanoic acid to afford the title compound as a TFA salt (11 mg). $^1$H NMR (400 MHz, DMSO-D6) δ ppm 0.66-0.74 (m, 7 H), 0.84 (t, J=7.4 Hz, 6 H), 1.00 (d, J=7.9 Hz, 4 H), 1.52-1.63 (m, 3 H), 1.86 (d, J=7.3 Hz, 4 H), 2.05 (d, J=16.6 Hz, 2 H), 3.30 (s, 2 H), 3.34-3.42 (m, 2 H), 3.83 (d, J=13.3 Hz, 3 H), 4.32-4.39 (m, 1 H), 4.50 (s, 1 H), 4.53-4.61 (m, 5 H), 6.65 (ddd, J=9.3, 4.9, 4.7 Hz, 2 H), 6.88-6.96 (m, 3 H), 7.14-7.22 (m, 4 H), 7.24-7.33 (m, 7 H), 7.39 (d, J=6.7 Hz, 2 H), 7.42-7.50 (m, 5 H), 7.55 (ddd, J=15.8, 8.6, 2.3 Hz, 3 H), 9.94 (s, 1 H), 10.00 (s, 1 H); MS (ESI) m/z 924.5 (M+H)$^+$.

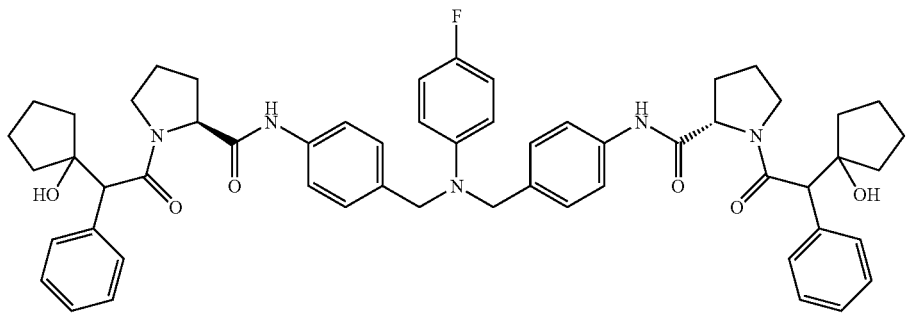 [SMILES: O=C(Nc1ccc(CN(Cc2ccc(NC(=O)[C@@H]3CCCN3C(=O)C(c3ccccc3)C3(O)CCCC3)cc2)c2ccc(F)cc2)cc1)[C@@H]1CCCN1C(=O)C(c1ccccc1)C1(O)CCCC1]

EXAMPLE 106

(2S,2'S)-N,N'-{[(4-fluorophenyl)imino]bis(methanediylbenzene-4,1-diyl)}bis{1-[(1-hydroxycyclopentyl)(phenyl)acetyl]pyrrolidine-2-carboxamide}

The product from Example 13D (30 mg, 0.058 mmol) was subjected to the procedure described in Example 24E, substituting 2-(1-hydroxycyclopentyl)-2-phenylacetic acid (27 mg, 0.122 mmol) for (S)-2-(methoxycarbonylamino)-3-methylbutanoic acid to afford the title compound as a TFA salt (13 mg). $^1$H NMR (400 MHz, DMSO-D6) δ ppm 1.09 (s, 2 H), 1.50 (d, J=5.9 Hz, 6 H), 1.61 (s, 4 H), 1.67 (d, J=4.7 Hz, 6 H), 1.77 (s, 1 H), 1.81-1.87 (m, 3 H), 1.91 (s, 1 H), 2.02 (s, 1 H), 2.07 (s, 1 H), 3.14 (s, 1 H), 3.22 (d, J=10.0 Hz, 1 H), 3.71 (d, J=10.1 Hz, 2 H), 3.80 (s, 1 H), 3.91 (d, J=12.8 Hz, 2 H), 4.38 (dd, J=8.2, 4.1 Hz, 1 H), 4.49 (d, J=3.8 Hz, 1 H), 4.57 (d, J=2.9 Hz, 4 H), 6.62-6.69 (m, J=4.6, 2.3 Hz, 2 H), 6.92 (t, J=8.8 Hz, 2 H), 7.16-7.22 (m, 4 H), 7.24-7.31 (m, 6 H), 7.34-7.37 (m, 2 H), 7.47 (dd, J=16.2, 7.6 Hz, 4 H), 7.54 (d, J=8.3 Hz, 3 H), 9.97 (d, J=1.7 Hz, 2 H); MS (ESI) m/z 920.2 (M+H)$^+$.

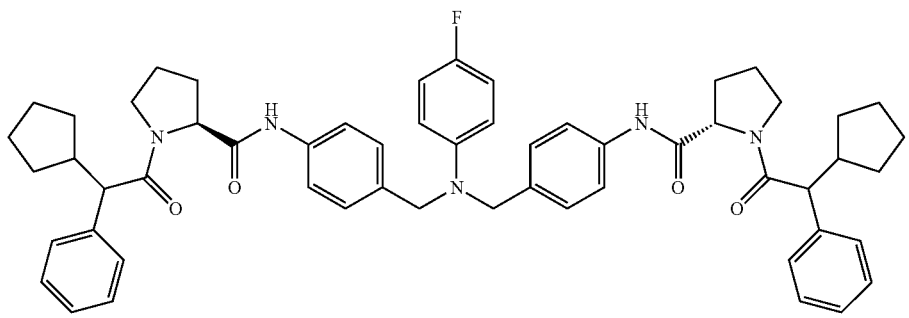 [SMILES: O=C(Nc1ccc(CN(Cc2ccc(NC(=O)[C@@H]3CCCN3C(=O)C(c3ccccc3)C3CCCC3)cc2)c2ccc(F)cc2)cc1)[C@@H]1CCCN1C(=O)C(c1ccccc1)C1CCCC1]

EXAMPLE 107

(2S,2'S)-N,N'-{[(4-fluorophenyl)imino]bis(methanediylbenzene-4,1-diyl)}bis{1-[cyclopentyl(phenyl)acetyl]pyrrolidine-2-carboxamide}

The product from Example 13D (30 mg, 0.058 mmol) was subjected to the procedure described in Example 24E, substituting 2-cyclopentyl-2-phenylacetic acid (25 mg, 0.122 mmol) for (S)-2-(methoxycarbonylamino)-3-methylbutanoic acid to afford the title compound as a TFA salt (12 mg). $^1$H NMR (400 MHz, DMSO-D6) δ ppm 1.03 (s, 2 H), 1.16 (d, J=4.2 Hz, 3 H), 1.25 (d, J=13.1 Hz, 3 H), 1.38 (d, J=3.3 Hz, 3 H), 1.48-1.60 (m, 4 H), 1.74 (s, 2 H), 1.79 (s, 2 H), 1.81-1.91 (m, 4 H), 1.99 (s, 2 H), 2.07 (s, 1 H), 3.32 (d, J=9.7 Hz, 2 H), 3.42 (s, 1 H), 3.70 (s, 2 H), 3.81 (s, 1 H), 4.29-4.35 (m, 1 H), 4.45 (dd, J=8.2, 3.6 Hz, 1 H), 4.52-4.62 (m, 4 H), 6.60-6.70 (m, 2 H), 6.88-6.98 (m, 2 H), 7.14-7.26 (m, 6 H), 7.27-7.38 (m, 8 H), 7.44 (dd, J=8.6, 2.6 Hz, 2 H), 7.51-7.56 (m, 2 H), 7.58 (dd, J=8.6, 2.6 Hz, 1 H), 9.88 (s, 1 H), 9.93 (s, 1 H); MS (ESI) m/z 888.3 (M+H)$^+$.

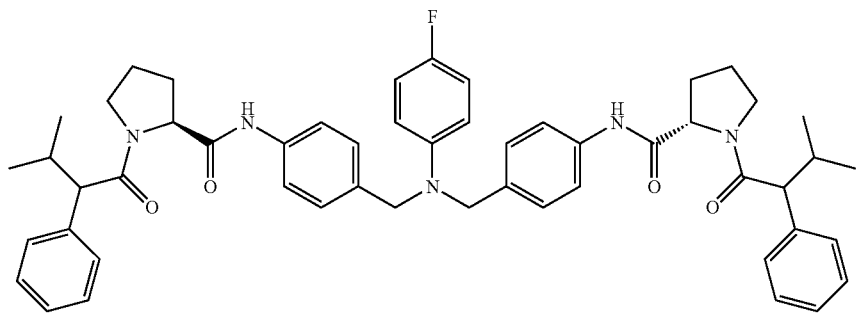 [SMILES: CC(C)C(C(=O)N1CCC[C@H]1C(=O)Nc1ccc(CN(Cc2ccc(NC(=O)[C@@H]3CCCN3C(=O)C(c3ccccc3)C(C)C)cc2)c2ccc(F)cc2)cc1)c1ccccc1]

EXAMPLE 108

(2S,2'S)-N,N'-{[(4-fluorophenyl)imino]bis(methanediylbenzene-4,1-diyl)}bis[1-(3-methyl-2-phenylbutanoyl)pyrrolidine-2-carboxamide]

The product from Example 13D (30 mg, 0.058 mmol) was subjected to the procedure described in Example 24E, substituting 3-methyl-2-phenylbutanoic acid (22 mg, 0.122 mmol) for (S)-2-(methoxycarbonylamino)-3-methylbutanoic acid to afford the title compound as a TFA salt (24 mg). $^1$H NMR (400 MHz, DMSO-D6) δ ppm 0.41 (dd, J=6.7, 1.5 Hz, 2 H), 0.56 (dd, J=6.6, 4.5 Hz, 4 H), 0.75-0.84 (m, 2 H), 0.94 (dd, J=8.4, 6.7 Hz, 4 H), 1.20 (s, 3 H), 1.73-1.88 (m, 5 H), 1.96 (s, 3 H), 2.10-2.24 (m, 4 H), 3.37 (d, J=10.2 Hz, 2 H), 4.27 (d, J=7.7 Hz, 1 H), 4.43 (dd, J=8.3, 3.4 Hz, 2 H), 4.53 (dd, J=16.5, 8.3 Hz, 4 H), 6.61 (s, 3 H), 6.83-6.93 (m, 3 H), 7.08-7.34 (m, 11 H), 7.35-7.44 (m, 2 H), 7.46-7.53 (m, 2 H), 7.53-7.59 (m, 1 H), 9.84 (s, 1 H), 9.92 (s, 1 H); MS (ESI) m/z 836.8 (M+H)$^+$.

EXAMPLE 109A (1S,1'S,2S,2'S,5R,5'R)-tert-butyl 2,2'-(4,4'-(4-fluorophenylazanediyl)bis(methylene)bis(4,1-phenylene)bis(azanediyl))bis(oxomethylene)bis(3-azabicyclo[3.1.0]hexane-3-carboxylate)

The product from Example 13D and (1S,2S,5R)-3-(tert-butoxycarbonyl)-3-azabicyclo[3.1.0]hexane-2-carboxylic acid (Tensiid) were processed using the method described in Example 41 to provide 685 mg (96%) of the title compound. MS (ESI; M+H) m/z=740.

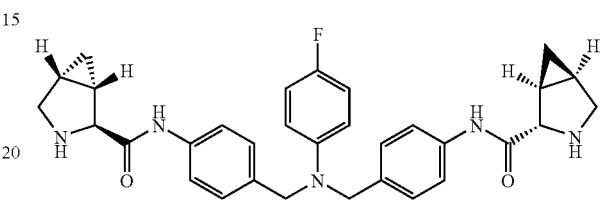

EXAMPLE 109 methyl [(1S)-1-{[(1S,2S,5R)-2-{[4-({(4-fluorophenyl)[4-({[(1S,2S,5R)-3-{(2S)-2-[(methoxycarbonyl)amino]-3,3-dimethylbutanoyl}-3-azabicyclo[3.1.0]hex-2-yl]carbonyl}amino)benzyl]amino}methyl)phenyl]carbamoyl}-3-azabicyclo[3.1.0]hex-3-yl]carbonyl}-2,2-dimethylpropyl]carbamate

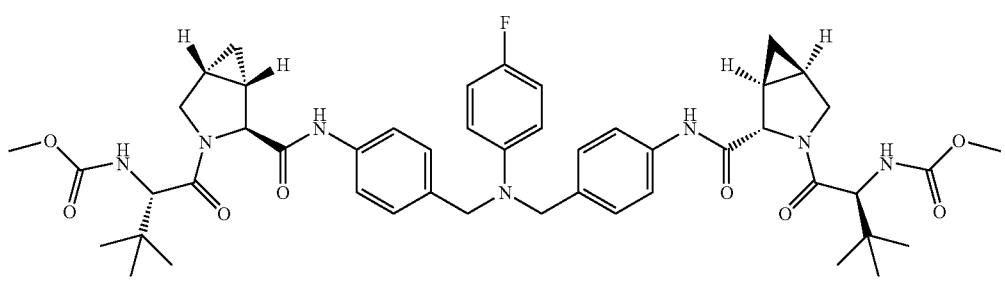

EXAMPLE 109B (1S,1'S,2S,2'S,5R,5'R)-N,N'-(4,4'-(4-fluorophenylazanediyl)bis(methylene)bis(4,1-phenylene))bis(3-azabicyclo[3.1.0]hexane-2-carboxamide)

The product from Example 109A was processed using the method described in Example 47B to provide 458 mg (92%) of the title compound. MS (ESI; M+H) m/z=540.

EXAMPLE 109C methyl [(1S)-1-{[(1S,2S,5R)-2-{[4-({(4-fluorophenyl)[4-({[(1S,2S,5R)-3-{(2S)-2-[(methoxycarbonyl)amino]-3,3-dimethylbutanoyl}-3-azabicyclo[3.1.0]hex-2-yl]carbonyl}amino)benzyl]amino}methyl)phenyl]carbamoyl}-3-azabicyclo[3.1.0]hex-3-yl]carbonyl}-2,2-dimethylpropyl]carbamate The product from Example 109B and (S)-2-(methoxycarbonylamino)-3,3-dimethylbutanoic acid were processed using the method described in Example 41 to provide 237 mg

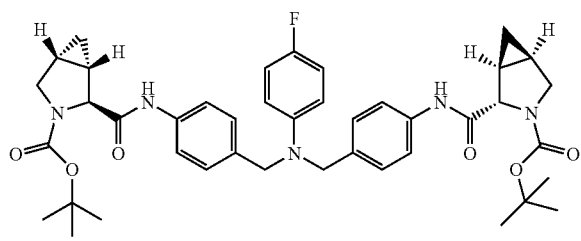 [SMILES: CC(C)(C)OC(=O)N1C[C@@H]2C[C@@H]2[C@H]1C(=O)Nc1ccc(CN(Cc2ccc(NC(=O)[C@@H]3[C@H]4C[C@H]4CN3C(=O)OC(C)(C)C)cc2)c2ccc(F)cc2)cc1]

(73%) of the title compound. ¹H NMR (400 MHz, methanol-D4) δ 0.20-0.30 (m, 2 H) 0.81-0.91 (m, 2 H) 0.92-1.03 (m, 18 H) 1.67-1.79 (m, 4 H) 3.64 (s, 6 H) 3.72 (m, 2 H) 3.92 (dd, J=9.81, 4.07 Hz, 2 H) 4.03-4.13 (m, 2 H) 4.21 (s, 2 H) 4.53 (s, 4 H) 4.72 (s, 2 H) 6.67-6.73 (m, 2 H) 6.79-6.86 (m, 2 H) 7.20 (d, J=8.46 Hz, 4 H) 7.48 (d, J=8.46 Hz, 4 H).

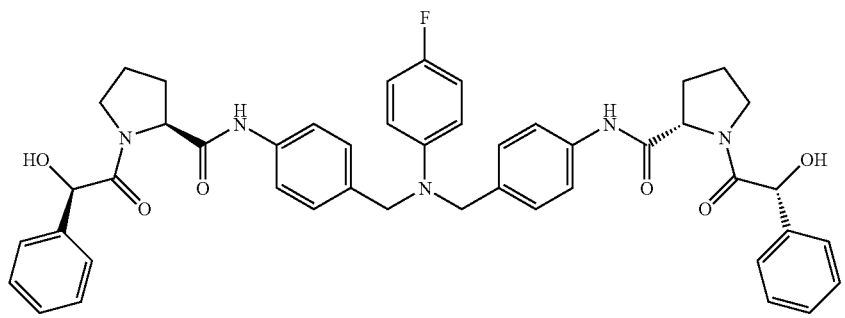 [SMILES: O=C(Nc1ccc(CN(Cc2ccc(NC(=O)[C@@H]3CCCN3C(=O)[C@H](O)c3ccccc3)cc2)c2ccc(F)cc2)cc1)[C@@H]1CCCN1C(=O)[C@H](O)c1ccccc1]

EXAMPLE 110

(2S,2'S)-N,N'-{[(4-fluorophenyl)imino]bis(methanediylbenzene-4,1-diyl)}bis{1-[(2R)-2-hydroxy-2-phenylacetyl]pyrrolidine-2-carboxamide}

The product from Example 13D (0.045 g, 0.087 mmol) and (R)-2-hydroxy-2-phenylacetic acid (0.095 g, 0.192 mmol) were processed as in Example 25B to give the title compound as an off-white solid. ¹H NMR (400 MHz, DMSO-D6) δ ppm 1.71-1.88 (m, 4 H) 1.88-2.06 (m, 4 H) 3.09-3.18 (m, 2 H) 3.62-3.73 (m, 2 H) 4.40 (dd, J=8.13, 3.25 Hz, 2 H) 4.57 (s, 4 H) 5.26 (d, J=3.58 Hz, 2 H) 5.50 (d, J=5.64 Hz, 2 H) 6.65 (dd, J=9.27, 4.39 Hz, 2 H) 6.92 (t, J=8.89 Hz, 2 H) 7.13-7.23 (m, 6 H) 7.27-7.33 (m, 2 H) 7.33-7.42 (m, 6 H) 7.53 (d, J=8.57 Hz, 4 H) 10.00 (s, 2 H); MS ESI– m/z 782 (M–H)–.

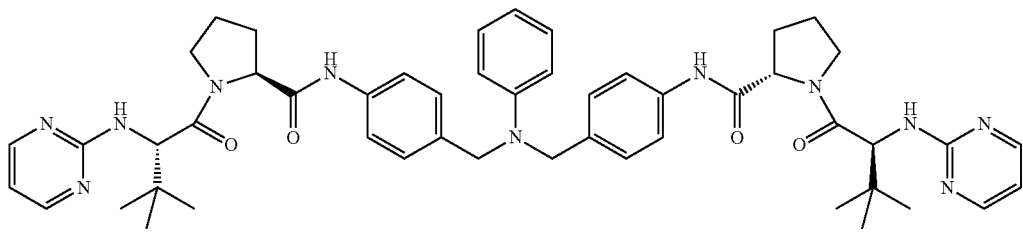 [SMILES: CC(C)(C)[C@H](Nc1ncccn1)C(=O)N1CCC[C@H]1C(=O)Nc1ccc(CN(Cc2ccc(NC(=O)[C@@H]3CCCN3C(=O)[C@@H](Nc3ncccn3)C(C)(C)C)cc2)c2ccccc2)cc1]

EXAMPLE 111

(2S,2'S)-N,N'-[(phenylimino)bis(methanediylbenzene-4,1-diyl)]bis{1-[(2S)-3,3-dimethyl-2-(pyrimidin-2-ylamino)butanoyl]pyrrolidine-2-carboxamide}

The product from Example 79B (0.05 g, 0.069 mmol) and 2-bromopyrimidine (0.066 g, 0.414 mmol) were dissolved in dimethylsulfoxide (1.5 mL), treated with diisopropylethylamine (0.072 mL, 0.414 mmol) and heated at 100° C. in a sealed tube in a microwave reactor for 1.5 hours. The solution was poured into water, extracted into ethyl acetate, concentrated, and purified by combi-flash 12 g column, eluting with 0-5% methanol in dichloromethane to give 0.004 g (7%) of the title compound as an off-white solid. $^1$H NMR (400 MHz, DMSO-D6) δ ppm 1.04 (s, 18 H) 1.81-1.94 (m, 4 H) 1.97-2.07 (m, 2 H) 2.07-2.18 (m, 2 H) 3.63-3.72 (m, 2 H) 3.96-4.04 (m, 2 H) 4.40 (dd, J=7.92, 5.75 Hz, 2 H) 4.59 (s, 4 H) 4.68 (d, J=9.00 Hz, 2 H) 6.51 (d, J=9.00 Hz, 2 H) 6.57 (t, J=7.16 Hz, 1 H) 6.62 (t, J=4.77 Hz, 2 H) 6.66 (d, J=8.13 Hz, 2 H) 7.04-7.11 (m, 2 H) 7.17 (d, J=8.57 Hz, 4 H) 7.51 (d, J=8.57 Hz, 4 H) 8.29 (d, J=4.77 Hz, 4 H) 9.98 (s, 2 H); MS ESI– m/z 878.6 (M–H)–.

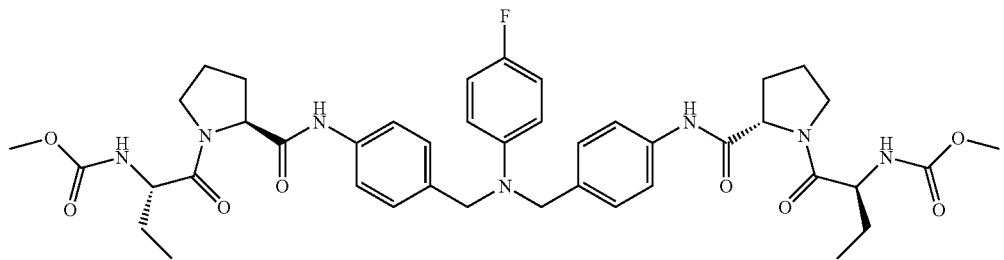

EXAMPLE 112 dimethyl ([(4-fluorophenyl)imino]bis{methanediylbenzene-4,1-diylcarbamoyl(2S)pyrrolidine-2,1-diyl[(2S)-1-oxobutane-1,2-diyl]})biscarbamate The product from Example 13D (0.030 g, 0.058 mmol) and (S)-2-(methoxycarbonylamino)butanoic acid (0.021 g, 0.128 mmol) were processed as in Example 25B to give the title compound as an off-white solid. NMR (400 MHz, DMSO-D6) δ ppm 0.90 (t, J=7.37 Hz, 6 H) 1.52 (td, J=14.07, 6.89 Hz, 2 H) 1.65 (td, J=13.61, 6.61 Hz, 2 H) 1.81-1.93 (m, 4 H) 1.95-2.05 (m, 2 H) 2.08-2.20 (m, 2 H) 3.52 (s, 6 H) 3.56-3.67 (m, 2 H) 3.68-3.81 (m, 2 H) 4.12-4.23 (m, 2 H) 4.42 (dd, J=8.02, 4.55 Hz, 2 H) 4.55 (s, 4 H) 6.63 (dd, J=9.22, 4.45 Hz, 2 H) 6.91 (t, J=8.89 Hz, 2 H) 7.16 (d, J=8.46 Hz, 4 H) 7.30 (d, J=7.70 Hz, 2 H) 7.50 (d, J=8.46 Hz, 4 H) 9.94 (s, 2 H); MS ESI– m/z 800 (M–H)–.

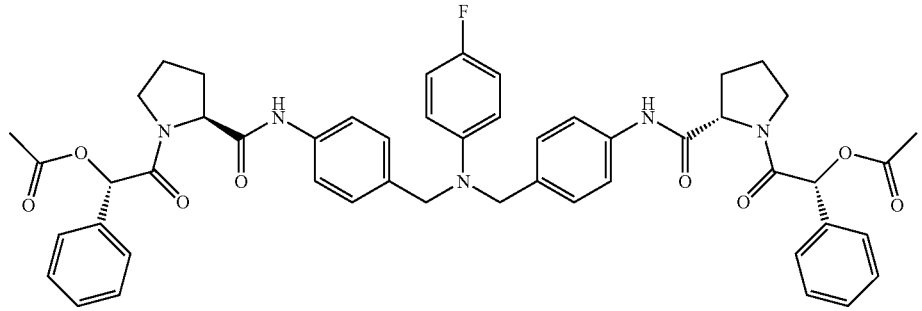 [SMILES: CC(=O)O[C@H](C(=O)N1CCC[C@H]1C(=O)Nc1ccc(CN(Cc2ccc(NC(=O)[C@@H]3CCCN3C(=O)[C@H](OC(C)=O)c3ccccc3)cc2)c2ccc(F)cc2)cc1)c1ccccc1]

EXAMPLE 113

[(4-fluorophenyl)imino]bis[methanediylbenzene-4,1-diylcarbamoyl(2S)pyrrolidine-2,1-diyl(1R)-2-oxo-1-phenylethane-2,1-diyl]diacetate The product from Example 13D (0.030 g, 0.058 mmol) and (R)-2-acetoxy-2-phenylacetic acid (0.025 g, 0.128 mmol) were processed as in Example 25B to give the title compound as an off-white solid. $^1$H NMR (400 MHz, DMSO-D6) d ppm 1.74-2.01 (m, 8 H) 2.02-2.09 (m, 6 H) 3.07-3.15 (m, 2 H) 3.79-3.88 (m, 2 H) 4.38 (dd, J=7.75, 2.87 Hz, 2 H) 4.57 (s, 4 H) 5.98-6.23 (m, 2 H) 6.65 (ddd, J=9.30, 4.36, 2.49 Hz, 2 H) 6.92 (td, J=8.95, 3.04 Hz, 2 H) 7.11-7.23 (m, 6 H) 7.28-7.36 (m, 2 H) 7.40-7.47 (m, 6 H) 7.48-7.52 (m, 2 H) 7.54 (d, J=8.57 Hz, 2 H) 9.73-10.02 (m, 2 H); MS ESI– m/z 866 (M–H)–.

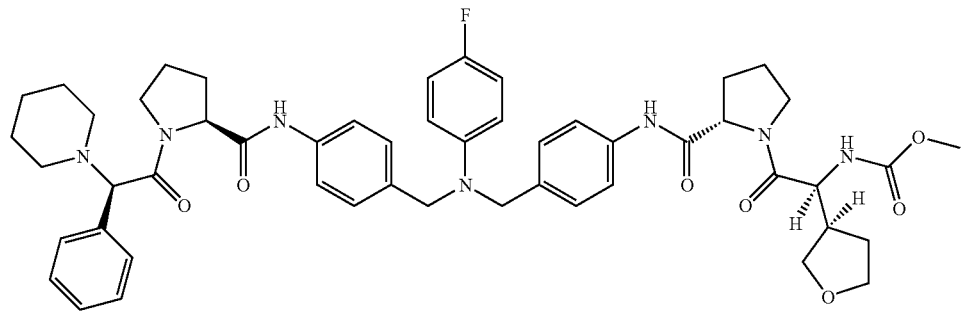 [SMILES: COC(=O)N[C@H](C(=O)N1CCC[C@H]1C(=O)Nc1ccc(CN(Cc2ccc(NC(=O)[C@@H]3CCCN3C(=O)[C@@H](c3ccccc3)N3CCCCC3)cc2)c2ccc(F)cc2)cc1)[C@H]1CCOC1]

EXAMPLE 114 methyl {(1S)-2-{(2S)-2-[(4-{[(4-fluorophenyl){4-[({(2S)-1-[(2R)-2-phenyl-2-piperidin-1-ylacetyl]pyrrolidin-2-yl}carbonyl)amino]benzyl}amino]methyl}phenyl)carbamoyl]pyrrolidin-1-yl}-2-oxo-1-[(3R)-tetrahydrofuran-3-yl]ethyl}carbamate

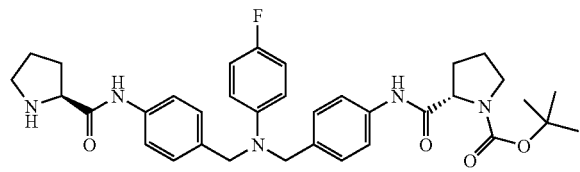 [SMILES: CC(C)(C)OC(=O)N1CCC[C@H]1C(=O)Nc1ccc(CN(Cc2ccc(NC(=O)[C@@H]3CCCN3)cc2)c2ccc(F)cc2)cc1]

EXAMPLE 114A (S)-tert-butyl 2-(4-(((4-fluorophenyl)(4-((S)-pyrrolidine-2-carboxamido)benzyl)amino)methyl)phenylcarbamoyl)pyrrolidine-1-carboxylate A solution of Example 13C (2.25 g, 3.14 mmol) in dichloromethane (20 mL) was treated trifluoroacetic acid at ambient temperature, adding 1 mL every 30 min for a total of 4 mL. The reaction was monitored closely to achieve a good distribution of bis-boc, mono-boc, and unreacted compounds. The mixture was washed with sodium bicarbonate solution, extracted into dichloromethane, concentrated, and purified by combi-flash 40 g silica column with 0-40% methanol in dichloromethane to give 0.632 g (33%) of the title compound containing a single Boc group.

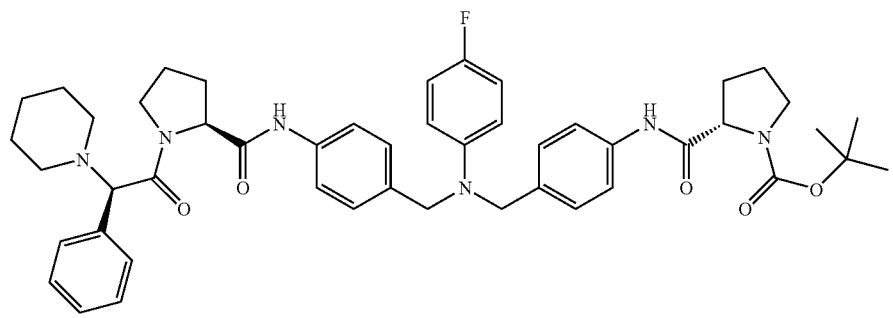 [SMILES: CC(C)(C)OC(=O)N1CCC[C@H]1C(=O)Nc1ccc(CN(Cc2ccc(NC(=O)[C@@H]3CCCN3C(=O)[C@@H](c3ccccc3)N3CCCCC3)cc2)c2ccc(F)cc2)cc1]

EXAMPLE 114B (S)-tert-butyl 2-(4-(((4-fluorophenyl)(4-((S)-1-((R)-2-phenyl-2-(piperidin-1-yl)acetyl)pyrrolidine-2-carboxamido)benzyl)amino)methyl)phenylcarbamoyl) pyrrolidine-1-carboxylate The product from Example 114A (0.26 g, 0.42 mmol) and (R)-2-phenyl-2-(piperidin-1-yl)acetic acid (0.12 g, 0.55 mmol) was processed as in Example 81A to give 0.20 g (58%) of the title compound as a white solid.

EXAMPLE 114C (S)-N-(4-(((4-fluorophenyl)(4-((S)-pyrrolidine-2-carboxamido)benzyl)amino)methyl)phenyl)-1-((R)-2-phenyl-2-(piperidin-1-yl)acetyl)pyrrolidine-2-carboxamide The product from Example 114B (0.20 g, 0.24 mmol) was dissolved in dichloromethane (3 mL) and treated with trifluoroacetic acid (2 mL) at ambient temperature for 2 hours. The solution was concentrated, taken up in 25% isopropanol in chloroform, washed with sodium bicarbonate solution, dried over sodium sulfate, filtered and concentrated to give 0.16 g (91%) of the title compound.

EXAMPLE 114D methyl {(1S)-2-{(2S)-2-[(4-{[(4-fluorophenyl){4-[({(2S)-1-[(2R)-2-phenyl-2-piperidin-1-ylacetyl]pyrrolidin-2-yl}carbonyl)amino]benzyl}amino] methyl}phenyl)carbamoyl]pyrrolidin-1-yl}-2-oxo-1-[(3R)-tetrahydrofuran-3-yl]ethyl}carbamate The product from Example 114C (0.040 g, 0.056 mmol) and (S)-2-(methoxycarbonylamino)-2-((R)-tetrahydrofuran-

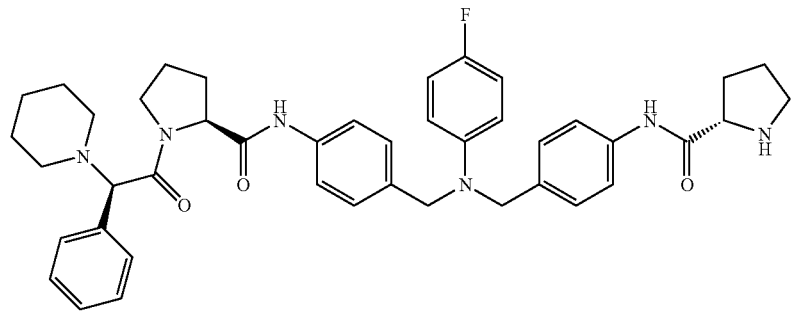 [SMILES: O=C(Nc1ccc(CN(Cc2ccc(NC(=O)[C@@H]3CCCN3C(=O)[C@@H](c3ccccc3)N3CCCCC3)cc2)c2ccc(F)cc2)cc1)[C@@H]1CCCN1]

3-yl)acetic acid (0.014 g, 0.067 mmol) were processed as in Example 81A to give the title compound. $^1$H NMR (400 MHz, DMSO-D6) δ ppm 1.29-1.38 (m, 2 H) 1.39-1.47 (m, 4 H) 1.68-1.78 (m, 1 H) 1.79-1.90 (m, 4 H) 1.93-2.06 (m, 4 H) 2.10-2.22 (m, 1 H) 3.14-3.25 (m, 1 H) 3.41-3.50 (m, 4 H) 3.53 (s, 3 H) 3.58-3.70 (m, 4 H) 3.71-3.79 (m, 2 H) 3.80-3.90 (m, 2 H) 4.20-4.28 (m, 2 H) 4.31 (dd, J=7.64, 4.07 Hz, 1 H) 4.44 (dd, J=7.97, 4.93 Hz, 1 H) 4.56 (s, 4 H) 6.64 (dd, J=9.22, 4.34 Hz, 2 H) 6.91 (t, J=8.95 Hz, 2 H) 7.18 (d, J=8.13 Hz, 4 H) 7.25-7.37 (m, 3 H) 7.42 (d, J=6.83 Hz, 2 H) 7.51 (dd, J=8.57, 1.84 Hz, 4 H) 7.60 (d, J=8.02 Hz, 1 H) 9.96 (s, 1 H) 9.98 (s, 1 H); MS ESI– m/z 900.6 (M–H)–.

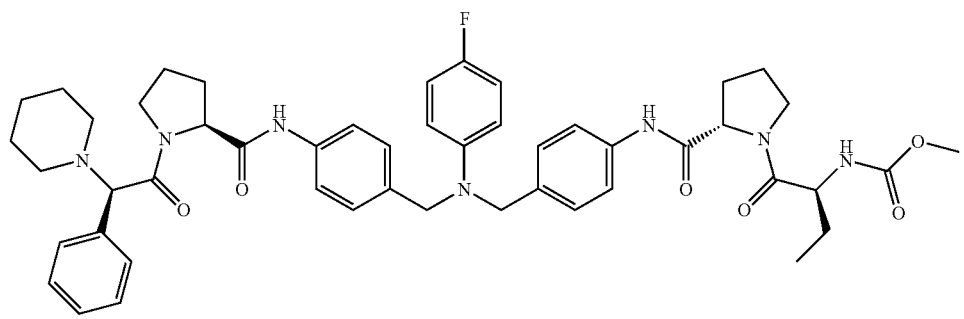 [SMILES: CC[C@H](NC(=O)OC)C(=O)N1CCC[C@H]1C(=O)Nc1ccc(CN(Cc2ccc(NC(=O)[C@@H]3CCCN3C(=O)[C@@H](c3ccccc3)N3CCCCC3)cc2)c2ccc(F)cc2)cc1]

EXAMPLE 115 methyl [(1S)-1-({(2S)-2-[(4-{[(4-fluorophenyl){4-[({(2S)-1-[(2R)-2-phenyl-2-piperidin-1-ylacetyl]pyrrolidin-2-yl}carbonyl)amino]benzyl}amino]methyl}phenyl)carbamoyl]pyrrolidin-1-yl}carbonyl)propyl]carbamate The product from Example 114C (0.040 g, 0.056 mmol) and (S)-2-(methoxycarbonylamino)butanoic acid (0.011 g, 0.067 mmol) were processed as in Example 81A to give the title compound. $^1$H NMR (400 MHz, DMSO-D6) δ ppm 0.90 (t, J=7.37 Hz, 3 H) 1.29-1.37 (m, 2 H) 1.39-1.47 (m, 4 H) 1.47-1.58 (m, 1 H) 1.61-1.72 (m, 1 H) 1.75-2.06 (m, 6 H) 2.08-2.20 (m, 1 H) 3.39-3.50 (m, 1 H) 3.52 (s, 3 H) 3.56-3.64 (m, 1 H) 3.69-3.77 (m, 1 H) 3.79-3.90 (m, 1 H) 4.14-4.21 (m, 1 H) 4.24 (s, 1 H) 4.31 (dd, J=7.81, 4.23 Hz, 1 H) 4.43 (dd, J=7.92, 4.34 Hz, 1 H) 4.56 (s, 4 H) 6.64 (dd, J=9.27, 4.39 Hz, 2 H) 6.91 (t, J=8.89 Hz, 2 H) 7.17 (dd, J=8.51, 2.55 Hz, 4 H) 7.27-7.36 (m, 3 H) 7.42 (d, J=6.94 Hz, 2 H) 7.51 (dd, J=8.51, 3.74 Hz, 4 H) 9.95 (d, J=2.93 Hz, 2 H); MS ESI– m/z 858.6 (M–H)–.

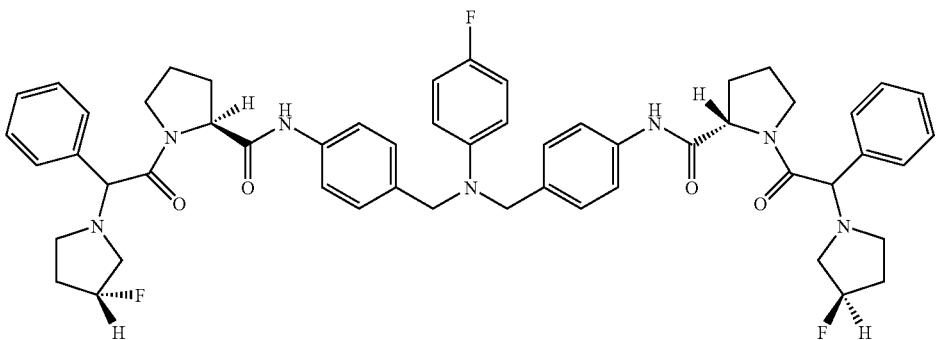 [SMILES: O=C(Nc1ccc(CN(Cc2ccc(NC(=O)[C@@H]3CCCN3C(=O)C(c3ccccc3)N3CC[C@@H](F)C3)cc2)c2ccc(F)cc2)cc1)[C@@H]1CCCN1C(=O)C(c1ccccc1)N1CC[C@@H](F)C1]

EXAMPLE 116

(2S,2'S)-N,N'-{[(4-fluorophenyl)imino]bis(methanediylbenzene-4,1-diyl)}bis(1-{[(3R)-3-fluoropyrrolidin-1-yl](phenyl)acetyl}pyrrolidine-2-carboxamide)

The product from Example 13D and 2-((R)-3-fluoropyrrolidin-1-yl)-2-phenylacetic acid were processed using the method described in Example 13E replacing DMT with dichloromethane to afford a mixture of three stereoisomers. The title compound of Example 116 was the first isomer to elute from the chromatography. $^1$H NMR (400 MHz, DMSO) S1.90-1.68 (m, 6H), 2.15-1.90 (m, 6H), 2.45-2.35 (m, 2H), 2.65-2.58 (m, 3H), 2.70 (dd, J=4.1, 10.7, 1H), 2.77 (d, J=11.2, 1H), 2.84 (d, J=11.4, 1H), 3.45-3.34 (m, 2H), 3.90-3.76 (m, 2H), 4.36-4.29 (m, 2H), 4.38 (s, 2H), 4.57 (s, 4H), 5.07 (t, J=5.6, 1H), 5.21 (t, J=5.6, 1H), 6.70-6.60 (m, 2H), 6.96-6.87 (m, 2H), 7.19 (d, J=8.5, 4H), 7.38-7.27 (m, 6H), 7.46 (d, J=6.8, 4H), 7.53 (d, J=8.5, 4H), 9.97 (s, 2H). MS (ESI) m/z 926 (M+H)$^+$, 924 (M–H)$^+$.

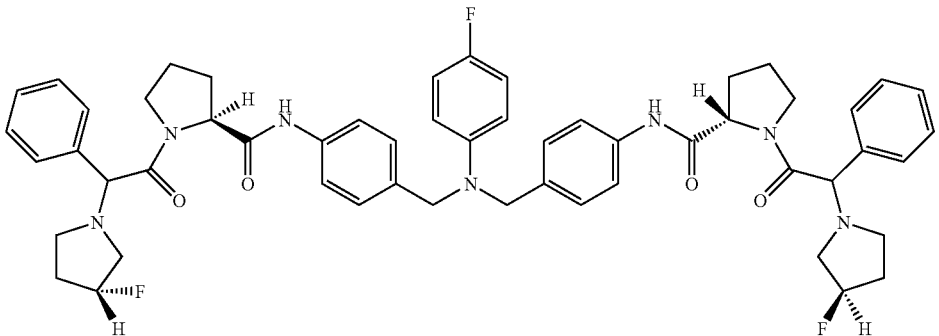 [SMILES: O=C(Nc1ccc(CN(Cc2ccc(NC(=O)[C@@H]3CCCN3C(=O)C(c3ccccc3)N3CC[C@@H](F)C3)cc2)c2ccc(F)cc2)cc1)[C@@H]1CCCN1C(=O)C(c1ccccc1)N1CC[C@@H](F)C1]

EXAMPLE 117

(2S,2'S)-N,N'-{[(4-fluorophenyl)imino]bis(methanediylbenzene-4,1-diyl)}bis(1-{[(3R)-3-fluoropyrrolidin-1-yl](phenyl)acetyl}pyrrolidine-2-carboxamide)

The title compound of Example 117 was isolated from the purification of Example 116 as the second eluting isomer. $^1$H NMR (400 MHz, DMSO) δ 1.91-1.70 (m, 7H), 2.14-1.93 (m, 6H), 2.46-2.35 (m, 3H), 2.66-2.57 (m, 2H), 2.88-2.69 (m, 4H), 3.39 (dd, J=8.4, 17.4, 1H), 3.68 (td, J=5.5, 9.6, 1H), 3.86-3.78 (m, 1H), 4.36-4.30 (m, 1H), 4.38 (s, 1H), 4.46 (dd, J=4.3, 8.4, 1H), 4.49 (s, 1H), 4.57 (d, J=10.2, 3H), 5.07 (t, J=5.5, 1H), 5.21 (t, J=5.3, 1H), 6.65 (dt, J=4.4, 9.2, 2H), 6.92 (td, J=2.8, 9.1, 2H), 7.26-7.13 (m, 4H), 7.39-7.26 (m, 6H), 7.59-7.39 (m, 8H), 10.34-9.87 (m, 2H). MS (ESI) m/z 926 (M+H)$^+$, 924 (M−H)$^+$.

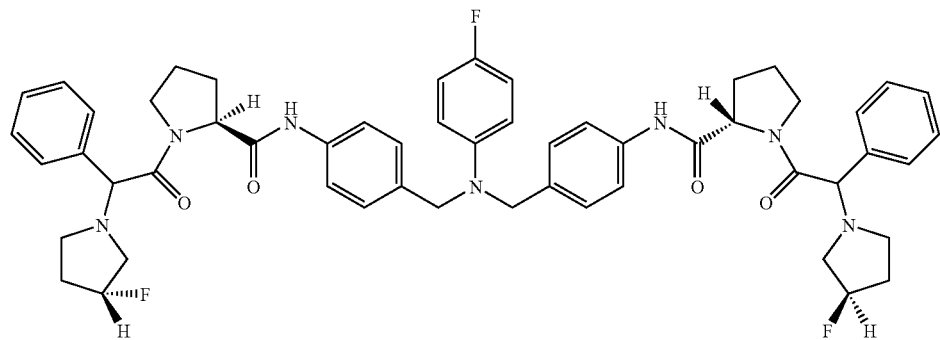 [SMILES: O=C(Nc1ccc(CN(Cc2ccc(NC(=O)[C@@H]3CCCN3C(=O)C(c3ccccc3)N3CC[C@@H](F)C3)cc2)c2ccc(F)cc2)cc1)[C@@H]1CCCN1C(=O)C(c1ccccc1)N1CC[C@@H](F)C1]

EXAMPLE 118

(2S,2'S)-N,N'-{[(4-fluorophenyl)imino]bis(methanediylbenzene-4,1-diyl)}bis(1-{[(3R)-3-fluoropyrrolidin-1-yl](phenyl)acetyl}pyrrolidine-2-carboxamide)

The title compound of Example 118 was isolated from the purification of Example 116 as the third eluting isomer. $^1$H NMR (400 MHz, DMSO) δ 1.00-0.77 (m, 8H), 1.94-1.69 (m, 6H), 2.15-1.94 (m, 6H), 2.87-2.69 (m, 2H), 3.73-3.52 (m, 2H), 4.61-4.40 (m, 7H), 5.06 (t, J=5.5, 1H), 5.21 (t, J=5.3, 1H), 6.64 (dt, J=4.4, 8.9, 2H), 6.91 (td, J=2.9, 8.9, 2H), 7.60-7.12 (m, 19H), 10.31-9.90 (m, 2H). MS (ESI) m/z 926 (M+H)$^+$, 924 (M−H)$^+$.

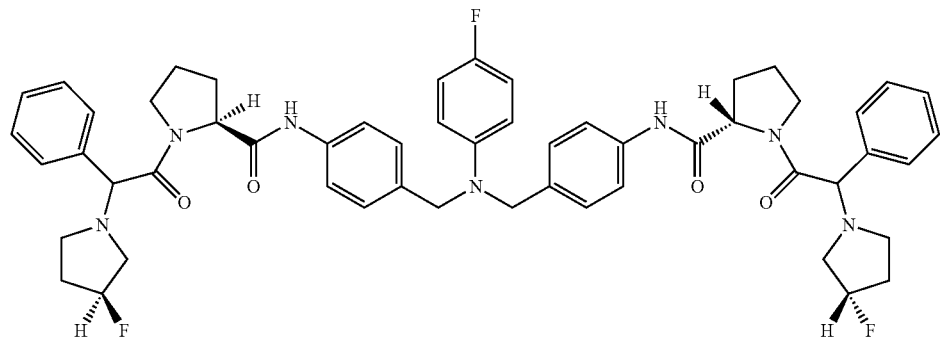 [SMILES: O=C(Nc1ccc(CN(Cc2ccc(NC(=O)[C@@H]3CCCN3C(=O)C(c3ccccc3)N3CC[C@H](F)C3)cc2)c2ccc(F)cc2)cc1)[C@@H]1CCCN1C(=O)C(c1ccccc1)N1CC[C@H](F)C1]

EXAMPLE 119

(2S,2'S)-N,N'-{[(4-fluorophenyl)imino]bis(methanediylbenzene-4,1-diyl)}bis(1-{[(3S)-3-fluoropyrrolidin-1-yl](phenyl)acetyl}pyrrolidine-2-carboxamide)

The product from Example 13D and 2-((S)-3-fluoropyrrolidin-1-yl)-2-phenylacetic acid were processed using the method described in Example 13E replacing DMT with dichloromethane to afford a mixture of stereoisomers. The title compound of Example 119 was the first isomer to elute from the chromatography. $^1$H NMR (400 MHz, DMSO) δ 2.15-1.70 (m, 13H), 2.66-2.57 (m, 2H), 2.81-2.71 (m, 3H), 3.43-3.34 (m, 2H), 3.90-3.78 (m, 2H), 4.32 (dd, J=4.2, 7.9, 2H), 4.36 (s, 2H), 4.57 (s, 4H), 5.06 (s, 1H), 5.20 (s, 1H), 6.70-6.60 (m, 2H), 6.97-6.86 (m, 2H), 7.19 (d, J=8.5, 5H), 7.39-7.24 (m, 7H), 7.46 (d, J=6.9, 4H), 7.53 (d, J=8.5, 4H), 9.96 (s, 2H). MS (ESI) m/z 925 (M+H)$^+$.

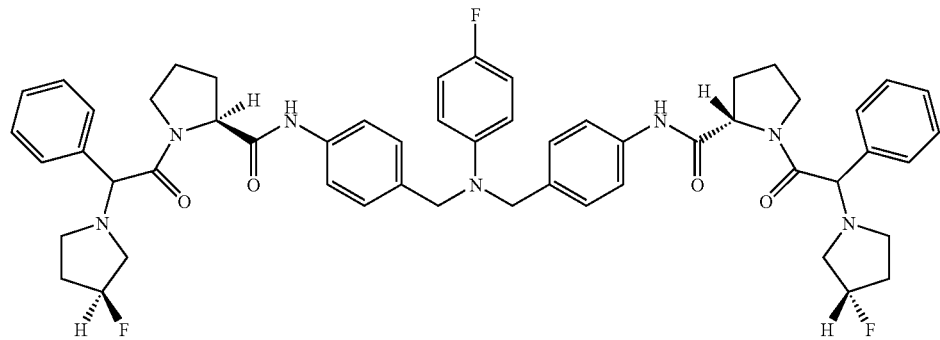 [SMILES: O=C(Nc1ccc(CN(Cc2ccc(NC(=O)[C@@H]3CCCN3C(=O)C(c3ccccc3)N3CC[C@H](F)C3)cc2)c2ccc(F)cc2)cc1)[C@@H]1CCCN1C(=O)C(c1ccccc1)N1CC[C@H](F)C1]

EXAMPLE 120

(2S,2'S)-N,N'-{[(4-fluorophenyl)imino]bis(methanediylbenzene-4,1-diyl)}bis(1-{[(3S)-3-fluoropyrrolidin-1-yl](phenyl)acetyl}pyrrolidine-2-carboxamide)

The title compound of Example 120 was isolated from the purification of Example 119 as the second eluting isomer. $^1$H NMR (400 MHz, DMSO) δ 2.16-1.67 (m, 12H), 2.39 (dd, J=11.8, 19.9, 2H), 2.65-2.55 (m, 2H), 2.91-2.70 (m, 4H), 3.44-3.33 (m, 2H), 3.66 (dt, J=6.1, 14.0, 1H), 3.92-3.78 (m, 1H), 4.32 (dd, J=4.2, 7.9, 1H), 4.36 (s, 1H), 4.45 (dd, J=3.9, 8.2, 1H), 4.49 (s, 1H), 4.57 (d, J=10.0, 4H), 5.06 (dd, J=3.5, 9.6, 1H), 5.25-5.15 (m, 1H), 6.65 (dt, J=4.4, 9.2, 2H), 6.92 (td, J=2.9, 9.1, 2H), 7.59-7.12 (m, 18H), 10.32-9.86 (m, 2H). MS (ESI) m/z 926 (M+H)$^+$, 924 (M−H)$^+$.

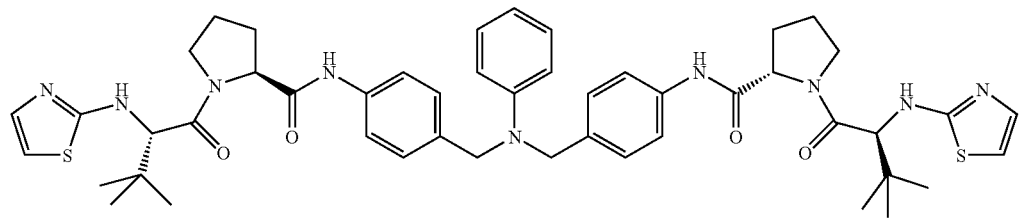 [SMILES: CC(C)(C)[C@H](Nc1nccs1)C(=O)N1CCC[C@H]1C(=O)Nc1ccc(CN(Cc2ccc(NC(=O)[C@@H]3CCCN3C(=O)[C@@H](Nc3nccs3)C(C)(C)C)cc2)c2ccccc2)cc1]

EXAMPLE 121

(2S,2'S)-N,N'-[(phenylimino)bis(methanediylbenzene-4,1-diyl)]bis{1-[(2S)-3,3-dimethyl-2-(1,3-thiazol-2-ylamino)butanoyl]pyrrolidine-2-carboxamide}

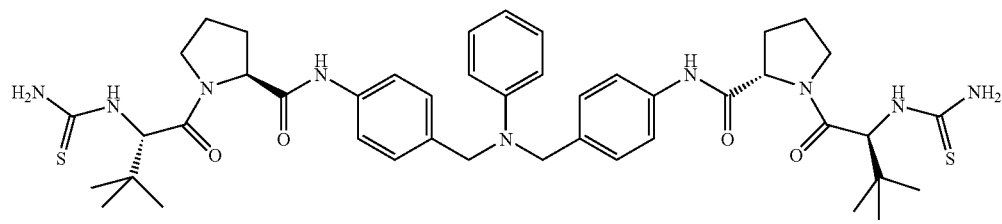 [SMILES: CC(C)(C)[C@H](NC(N)=S)C(=O)N1CCC[C@H]1C(=O)Nc1ccc(CN(Cc2ccc(NC(=O)[C@@H]3CCCN3C(=O)[C@@H](NC(N)=S)C(C)(C)C)cc2)c2ccccc2)cc1]

EXAMPLE 121A (S,2S,2'S)-N,N'-(4,4'-(phenylazanediyl)bis(methylene)bis(4,1-phenylene))bis(1-((S)-3,3-dimethyl-2-thioureidobutanoyl)pyrrolidine-2-carboxamide)

The product from Example 79B (0.075 g, 0.104 mmol) was dissolved in dichloromethane (2 mL) at ambient temperature and treated with fluorenylmethoxycarbonyl isothiocyanate (0.061 g, 0.218 mmol) and stirred for 4 hours. Diethylamine (0.50 mL) was added dropwise and the resulting solution was stirred for 1 hour, then concentrated to dryness to give the title compound.

EXAMPLE 121B (2S,2'S)-N,N'-[(phenylimino)bis(methanediylbenzene-4,1-diyl)]bis{1-[(2S)-3,3-dimethyl-2-(1,3-thiazol-2-ylamino)butanoyl]pyrrolidine-2-carboxamide}

The product from Example 121A (0.087 g, 0.103 mmol) was dissolved in ethanol (1 mL) and treated with chloroacetaldehyde (0.040 mL, 0.310 mmol) and the solution was heated at 70° C. for 18 hours at which time another 0.04 mL of chloroacetaldehyde was added to push the reaction to completion. The solution was concentrated and purified by combi-flash 12 g silica column, eluting with 0-5% methanol in dichloromethane, followed by a second column, eluting with 0-15% ethyl acetate in dichloromethane to give 3.5 mg of the title compound. $^1$H NMR (400 MHz, DMSO-D6) δ ppm 1.02 (s, 18 H) 1.46-1.65 (m, 4 H) 1.67-1.77 (m, 1 H) 1.79-1.91 (m, 4 H) 2.08-2.20 (m, 1 H) 3.63-3.71 (m, 2 H) 4.43 (dd, J=7.92, 5.64 Hz, 2 H) 4.56-4.63 (m, 6 H) 6.54-6.61 (m, 3 H) 6.66 (d, J=8.24 Hz, 2 H) 6.96 (d, J=3.69 Hz, 2 H) 7.07 (t, J=7.97 Hz, 2 H) 7.17 (d, J=8.46 Hz, 4 H) 7.51 (d, J=8.57 Hz, 4 H) 7.64 (d, J=9.11 Hz, 2 H) 9.99 (s, 2 H); MS ESI– m/z 888.5 (M–H)–.

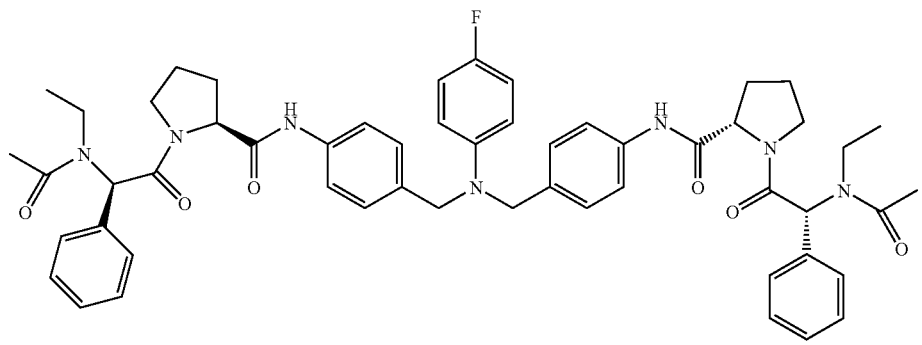 [SMILES: CCN(C(C)=O)[C@@H](C(=O)N1CCC[C@H]1C(=O)Nc1ccc(CN(Cc2ccc(NC(=O)[C@@H]3CCCN3C(=O)[C@@H](c3ccccc3)N(CC)C(C)=O)cc2)c2ccc(F)cc2)cc1)c1ccccc1]

EXAMPLE 122

(2S,2'S)-N,N'-{[(4-fluorophenyl)imino]bis(methanediylbenzene-4,1-diyl)}bis(1-{(2R)-2-[acetyl(ethyl)amino]-2-phenylacetyl}pyrrolidine-2-carboxamide)

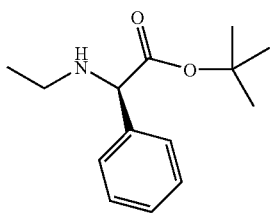 [SMILES: CCN[C@@H](C(=O)OC(C)(C)C)c1ccccc1]

EXAMPLE 122A (R)-tert-butyl 2-(ethylamino)-2-phenylacetate

To a solution of (R)-tert-butyl 2-amino-2-phenylacetate hydrochloride (0.25 g, 1.026 mmol) in MeOH (10.26 mL) was added 10% Pd/C (0.080 g, 1.026 mmol). The resulting mixture was cooled to 0° C., and acetaldehyde (0.576 mL, 10.26 mmol) was added. The resulting mixture was stirred at 0° C. for 10-15 mins, the ice bath was removed, and the mixture was placed under a hydrogen balloon and stirred at rt for 45 mins. The mixture was filtered through celite, washed with methanol, and the filtrate was concentrated in vacuo to give the title compound (0.267 g).

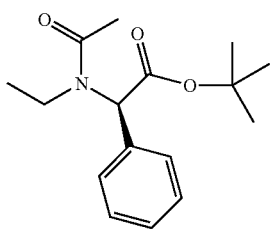 [SMILES: CCN(C(C)=O)[C@@H](C(=O)OC(C)(C)C)c1ccccc1]

EXAMPLE 122B (R)-tert-butyl 2-(N-ethylacetamido)-2-phenylacetate

A solution of product from Example 122A (0.267 g, 1.135 mmol) in acetic anhydride (1.073 mL, 11.35 mmol) and pyridine (0.918 mL, 11.35 mmol) was stirred at 98° C. for 2 hrs. The mixture was partitioned between $CH_2Cl_2$ and 1N HCl solution, and the organic extract was separated, dried over anhydrous sodium sulphate, filtered, and concentrated in vacuo. The crude product was purified by column chromatography on silica gel using a solvent gradient of 1-35% ethyl acetate in hexane to give the title compound (0.083 g, 27%).

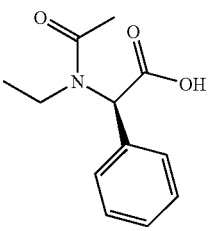 [SMILES: CCN(C(C)=O)[C@@H](C(=O)O)c1ccccc1]

EXAMPLE 122C (R)-2-(N-ethylacetamido)-2-phenylacetic acid

To a solution of product from example 122B (81 mg, 0.293 mmol) in $CH_2Cl_2$ (3 mL) was added 2,2,2-trifluoroacetic acid (1.5 mL, 0.293 mmol), and the resulting mixture was stirred at rt for 1 hr. The mixture was concentrated in vacuo to give the title compound (50 mg, 77%).

EXAMPLE 122D (2S,2'S)-N,N'-{[(4-fluorophenyl)imino]bis(methanediylbenzene-4,1-diyl)}bis(1-{(2R)-2-[acetyl(ethyl)amino]-2-phenylacetyl}pyrrolidine-2-carboxamide)

The product from Example 13D (0.024 g, 0.047 mmol) was subjected to the procedure described in Example 24E, substituting the product from Example 122C for (S)-2-(methoxycarbonylamino)-3-methylbutanoic acid, to give the title compound as a TFA salt (7 mg). $^1$H NMR (400 MHz, DMSO-D6) δ ppm 0.49-0.63 (m, 4 H), 0.69-0.78 (m, 2 H), 1.24 (s, 2 H), 1.70-2.04 (m, 8 H), 2.05-2.16 (m, 4 H), 2.84-3.27 (m, 4 H), 3.42-3.69 (m, 3 H), 4.42-4.48 (m, 2 H), 4.58 (s, 4 H), 6.63-6.68 (m, 2 H), 6.92 (t, J=8.9 Hz, 2 H), 7.20 (dd, J=8.3, 3.8 Hz, 4 H), 7.31-7.50 (m, 11 H), 7.51-7.64 (m, 6 H), 9.62 (s, 1 H), 10.05 (s, 1 H); MS m/z 923.6 (M+H)$^+$.

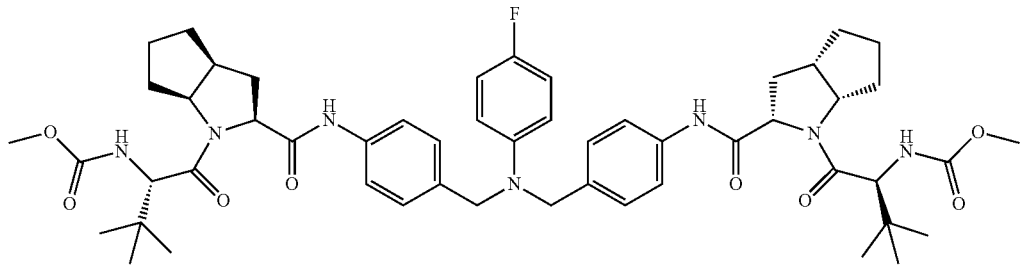

EXAMPLE 123 dimethyl ([[(4-fluorophenyl)imino]
bis{methanediylbenzene-4,1-diylcarbamoyl(2S,3aS,
6aS)hexahydrocyclopenta[b]pyrrole-2,1(2H)-diyl
[(2S)-3,3-dimethyl-1-oxobutane-1,2-diyl]})
biscarbamate

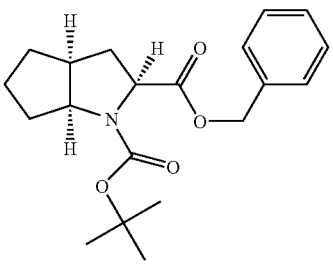 [SMILES: CC(C)(C)OC(=O)N1[C@H](C(=O)OCc2ccccc2)C[C@@H]2CCC[C@@H]21]

EXAMPLE 123A (2S,3aS,6aS)-2-benzyl 1-tert-butyl hexahydrocyclo-
penta[b]pyrrole-1,2(2H)-dicarboxylate To a solution of (S,S,S)-2-azabicyclo[3,3,0]-octane-3-carboxylic acid benzyl ester hydrochloride (0.50 g, 1.8 mmol) in CH$_2$Cl$_2$ (8.9 mL) at room temperature was added di-tert-butyl dicarbonate (0.45 mL, 2.0 mmol) and Hunig's base (0.77 mL, 4.4 mmol) to give a tan solution. The mixture was stirred for 2 hours at room temperature then diluted with CH$_2$Cl$_2$, washed with saturated sodium bicarbonate solution, and brine. The organic layer was dried over Na$_2$SO$_4$, filtered, and concentrated under reduced pressure to provide the title compound (0.56 g, 91% yield).

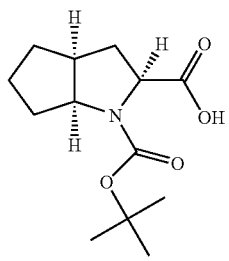 [SMILES: CC(C)(C)OC(=O)N1[C@H](C(=O)O)C[C@@H]2CCC[C@@H]21]

EXAMPLE 123B (2S,3aS,6aS)-1-(tert-butoxycarbonyl)octahydrocy-
clopenta[b]pyrrole-2-carboxylic acid To a solution of the product from Example 123A (0.56 g, 1.6 mmol) in MeOH (8.0 mL) was added Pd(OH)$_2$/carbon. The mixture was evacuated and a H$_2$ atmosphere was introduced via a balloon. The mixture was stirred overnight then filtered and the solvent was removed under reduced pressure to provide the title compound (0.42 g, 102% yield).

EXAMPLE 123C (2S,2'S,3aS,3a'S,6aS,6a'S)-tert-butyl 2,2'-(4,4'-(4-
fluorophenylazanediyl)bis(methylene)bis(4,1-phe-
nylene)bis(azanediyl))bis(oxomethylene)bis(hexahy-
drocyclopenta[b]pyrrole-1(2H)-carboxylate)

The title compound was prepared using the methods from Example 13C substituting the product from Example 123B for N-(tert-butoxycarbonyl)-L-proline to provide the title compound (0.95 g, 100% yield).

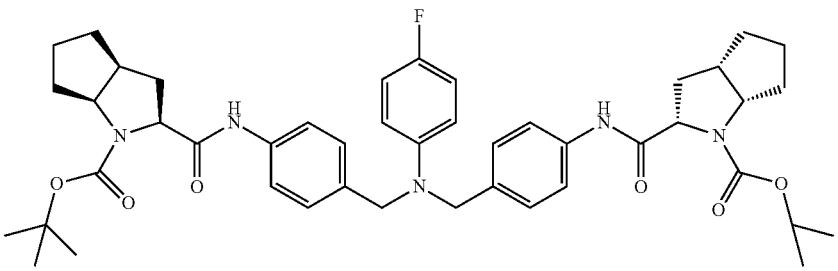 [SMILES: CC(C)OC(=O)N1[C@H](C(=O)Nc2ccc(CN(Cc3ccc(NC(=O)[C@@H]4C[C@@H]5CCC[C@@H]5N4C(=O)OC(C)(C)C)cc3)c3ccc(F)cc3)cc2)C[C@@H]2CCC[C@@H]21]

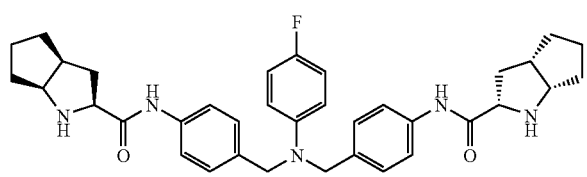 [SMILES: O=C(Nc1ccc(CN(Cc2ccc(NC(=O)[C@@H]3C[C@@H]4CCC[C@@H]4N3)cc2)c2ccc(F)cc2)cc1)[C@@H]1C[C@@H]2CCC[C@@H]2N1]

EXAMPLE 123D (2S,2'S,3aS,3a'S,6aS,6a'S)-N,N'-(4,4'-(4-fluorophe-
nylazanediyl)bis(methylene)bis(4,1-phenylene))bis
(octahydrocyclopenta[b]pyrrole-2-carboxamide)

Title compound was prepared using the methods from Example 13D substituting the product from Example 123C for the product from Example 13C to provide the title compound O (0.17 g, 81%).

EXAMPLE 123E dimethyl ([[(4-fluorophenyl)imino]
bis{methanediylbenzene-4,1-diylcarbamoyl(2S,3aS,
6aS)hexahydrocyclopenta[b]pyrrole-2,1 (2H)-diyl
[(2S)-3,3-dimethyl-1-oxobutane-1,2-diyl]})
biscarbamate The title compound was prepared using the methods from Example 13E substituting the product from Example 123D for the product from Example 13D to provide the title compound (75 mg, 41% yield). $^1$H NMR (400 MHz, METHANOL-D4) δ 7.52-7.43 (m, 4H), 7.22-7.15 (m, 4H), 6.83 (t, J=8.6, 2H), 6.74-6.67 (m, 2H), 4.73-4.65 (m, 2H), 4.59-4.50 (m, 6H), 4.39 (bs, 2H), 3.65 (s, 6H), 2.85-2.74 (m, 2H), 2.39 (m, 2H), 2.19 (d, J=8.0, 2H), 2.09-1.90 (m, 4H), 1.89-1.56 (m, 8H), 1.03 (s, 18H). MS (ESI; M+H) m/z=939.

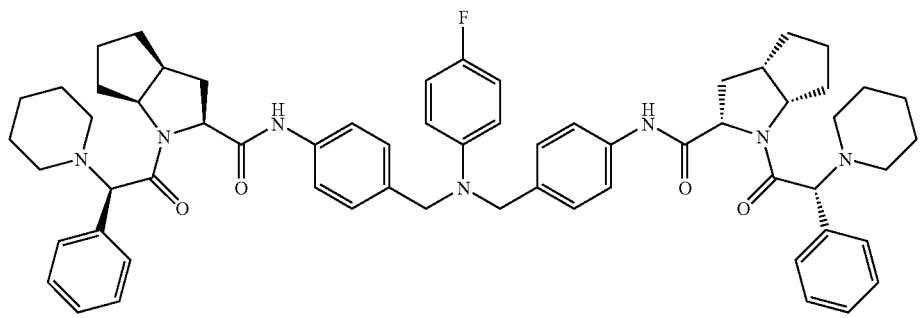 [SMILES: O=C(Nc1ccc(CN(Cc2ccc(NC(=O)[C@@H]3C[C@@H]4CCC[C@@H]4N3C(=O)[C@@H](c3ccccc3)N3CCCCC3)cc2)c2ccc(F)cc2)cc1)[C@@H]1C[C@@H]2CCC[C@@H]2N1C(=O)[C@@H](c1ccccc1)N1CCCCC1]

EXAMPLE 124

(2S,3aS,6aS,2'S,3a'S,6a'S)-N,N'-{[(4-fluorophenyl)
imino]bis(methanediylbenzene-4,1-diyl)}bis{1-
[(2R)-2-phenyl-2-piperidin-1-ylacetyl]octahydrocy-
clopenta[b]pyrrole-2-carboxamide}

To a mixture of the product from Example 123D (0.17 g, 0.29 mmol), (R)-2-phenyl-2-(piperidin-1-yl)acetic acid-TFA salt (0.21 g, 0.67 mmol), and HATU (0.24 g, 0.64 mmol) in CH$_2$Cl$_2$ (2.9 mL) was added Hunig's base (0.41 mL, 2.3 mmol), and the reaction was stirred at room temperature for 1 hour. The mixture was then concentrated under reduced pressure and purified by column chromatography eluting with 30-70% ethyl acetate in hexanes to provide the title compound (39 mg, 13% yield). $^1$H NMR (400 MHz, METHANOL-D4) δ 7.54-7.43 (m, 8H), 7.38-7.30 (m, 6H), 7.23-7.17 (m, 4H), 6.84 (t, J=8.6, 2H), 6.72 (dd, J=4.2, 9.2, 2H), 4.54 (bs, 4H), 4.46 (t, J=8.3, 2H), 4.31 (dd, J=8.1, 13.9, 2H), 4.12 (s, 2H), 2.73-2.60 (m, 2H), 2.53-2.44 (m, 3H), 2.42-2.24 (m, 8H), 2.17-2.04 (m, 2H), 2.03-1.88 (m, 2H), 1.83-1.64 (m, 7H), 1.55 (s, 10H), 1.43 (s, 4H). MS (ESI; M+H) m/z=999.

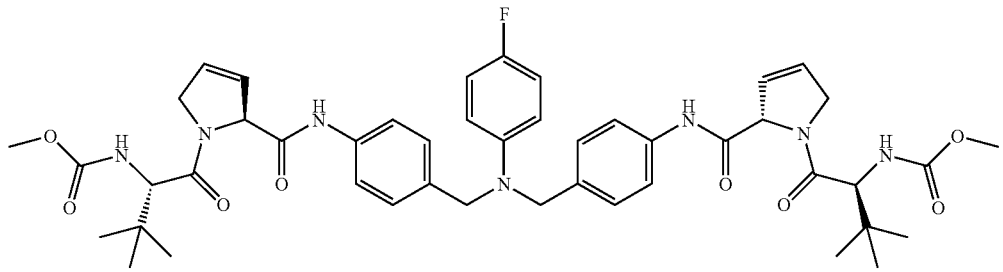

EXAMPLE 125 methyl [(1S)-1-{[(2S)-2-{[4-({(4- fluorophenyl)[4-({[(2S)-1-{(2S)-2-[(methoxycarbonyl)amino]-3,3-dimethylbutanoyl}-2,5-dihydro-1H-pyrrol-2-yl]carbonyl}amino)benzyl]amino}methyl)phenyl]carbamoyl}-2,5-dihydro-1H-pyrrol-1-yl]carbonyl}-2,2-dimethylpropyl]carbamate

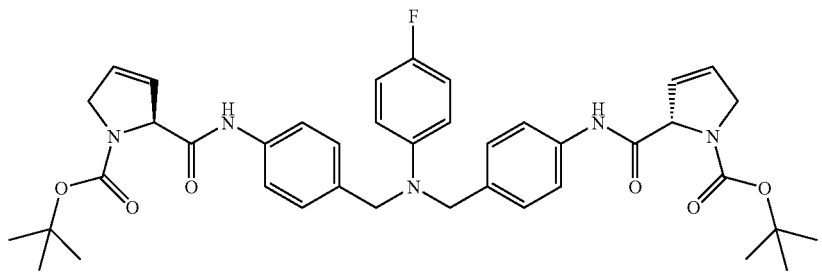 [SMILES: CC(C)(C)OC(=O)N1CC=C[C@H]1C(=O)Nc1ccc(CN(Cc2ccc(NC(=O)[C@@H]3C=CCN3C(=O)OC(C)(C)C)cc2)c2ccc(F)cc2)cc1]

EXAMPLE 125A (2S,2'S)-tert-butyl 2,2'-(4,4'-(4-fluorophenylazanediyl)bis(methylene)bis(4,1-phenylene)bis(azanediyl))bis(oxomethylene)bis(2,5-dihydro-1H-pyrrole-1-carboxylate)

The title compound was prepared using the methods from Example 13C substituting (S)-1-(tert-butoxycarbonyl)-2,5-dihydro-1H-pyrrole-2-carboxylic acid for N-(tert-butoxycarbonyl)-L-proline to provide the title compound (0.64 g, 96% yield).

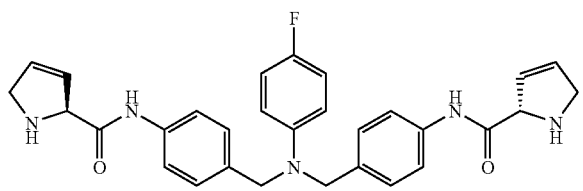 [SMILES: O=C(Nc1ccc(CN(Cc2ccc(NC(=O)[C@@H]3C=CCN3)cc2)c2ccc(F)cc2)cc1)[C@@H]1C=CCN1]

EXAMPLE 125B (2S ,2'S)-N,N'-(4,4'-(4-fluorophenylazanediyl)bis(methylene)bis(4,1-phenylene))bis(2,5-dihydro-1H-pyrrole-2-carboxamide)

The title compound was prepared using the methods from Example 13D substituting the product from Example 125A for the product from Example 13C to provide the title compound (0.50 g, 109% yield).

EXAMPLE 125C methyl [(1S)-1-{[(2S)-2-{[4-({(4-fluorophenyl)[4-({[(2S)-1-{(2S)-2-[(methoxycarbonyl)amino]-3,3-dimethylbutanoyl}-2,5-dihydro-1H-pyrrol-2-yl]carbonyl}amino)benzyl]amino}methyl)phenyl]carbamoyl}-2,5-dihydro-1H-pyrrol-1-yl]carbonyl}-2,2-dimethylpropyl]carbamate The title compound was prepared using the methods from Example 13E substituting the product from Example 125B for the product from Example 13D to provide the title compound (0.15 g, 45% yield). $^1$H NMR (400 MHz, DMSO) δ 10.13 (s, 2H), 7.51 (d, J=8.5, 4H), 7.23 (d, J=8.7, 2H), 7.18 (d, J=8.5, 4H), 6.91 (t, J=8.9, 2H), 6.63 (dd, J=9.2, 4.4, 2H), 6.06 (dd, J=6.3, 1.8, 2H), 5.88 (dd, J=6.2, 2.1, 2H), 5.20-5.13 (m, 2H), 4.61-4.51 (m, 6H), 4.49-4.39 (m, 2H), 4.15 (d, J=8.7, 2H), 3.54 (s, 6H), 0.99 (s, 18H). MS (ESI; M+H) m/z=855.

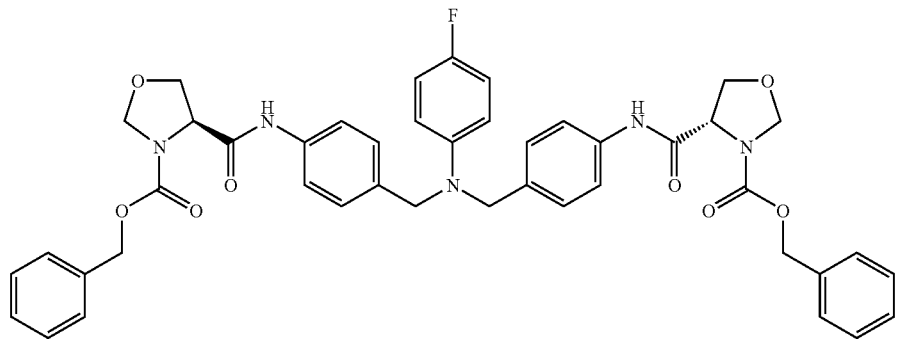 [SMILES: O=C(Nc1ccc(CN(Cc2ccc(NC(=O)[C@@H]3COCN3C(=O)OCc3ccccc3)cc2)c2ccc(F)cc2)cc1)[C@@H]1COCN1C(=O)OCc1ccccc1]

EXAMPLE 126 dibenzyl (4S,4'S)-4,4'-{[(4-fluorophenyl)imino]bis(methanediylbenzene-4,1-diylcarbamoyl)}bis(1,3-oxazolidine-3-carboxylate)

The product from Example 13B (100 mg, 0.311 mmol) and (S)-3-(benzyloxycarbonyl)oxazolidine-4-carboxylic acid (195 mg, 0.778 mmol) were processed using the method described in Example 43 to afford 215 mg (88%) of the title compound. $^1$H NMR (400 MHz, DMSO-D6) δ ppm 10.09 (s, 2H), 7.51 (d, J=7.1 Hz, 4H), 7.36 (m, 4H), 7.18 (m, 10H), 6.91 (d, J=8.9 Hz, 2H), 6.64 (m, 2H), 5.13 (m, 2H), 5.03 (m, 2H), 4.93 (m, 4H), 4.58 (bs, 4H), 4.48 (m, 2H), 4.28 (m, 2H), 4.01 (m, 2H).

temperature overnight. The mixture then had water (425 mL) added and the solution was extracted with EtOAc and the organic extract concentrated to a residue that was dissolved in 25% EtOAc and 75% hexanes then extracted with brine and the organic extract concentrated to a solid. The resultant solid was dissolved in methanol (65 mL) and water (85 mL) then lithium hydroxide monohydrate (1.93 g, 46 mmol) added and the solution stirred at room temperature for 2 h. Afterwards water (106 mL) and a solution of 1N aqueous hydrochloric acid was added until a pH of 2 was reached. The mixture was then extracted with a mixture of 25% EtOAc and 75% hexanes, the organic extract dried, filtered and concentrated to give the title compound as a colorless solid. MS (ESI) m/z 346 (M+H)+.

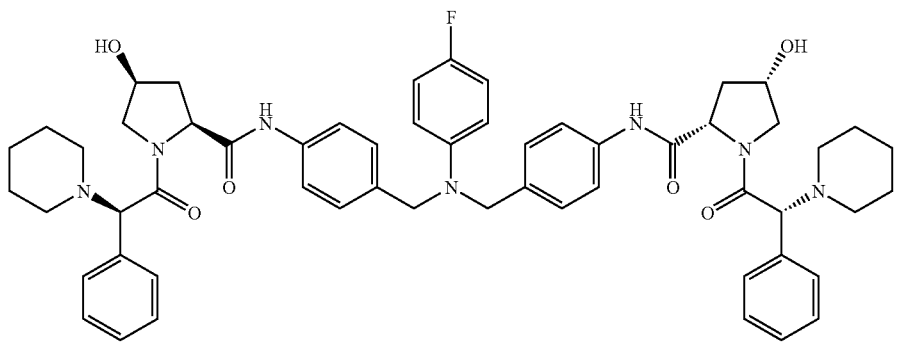 [SMILES: O=C(Nc1ccc(CN(Cc2ccc(NC(=O)[C@@H]3C[C@H](O)CN3C(=O)[C@@H](c3ccccc3)N3CCCCC3)cc2)c2ccc(F)cc2)cc1)[C@@H]1C[C@H](O)CN1C(=O)[C@@H](c1ccccc1)N1CCCCC1]

EXAMPLE 127

(2S,4S,2'S,4'S)-N,N'-{[(4-fluorophenyl)imino]bis(methanediylbenzene-4,1-diyl)}bis{4-hydroxy-1-[(2R)-2-phenyl-2-piperidin-1-ylacetyl]pyrrolidine-2-carboxamide}

EXAMPLE 127A (2S,4S)-1-(tert-butoxycarbonyl)-4-hydroxypyrrolidine-2-carboxylic acid To a solution of (2S,4S)-4-hydroxypyrrolidine-2-carboxylic acid (3.9 g, 29.7 mmol) in THF (26.7 mL) and water (13.3 mL) was added di-tert-butyl dicarbonate (7.14 g, 32.7 mmol) and sodium hydroxide (2.0 N, 22.9 mL, 45.8 mmol) and the mixture stirred at room temperature overnight. The mixture then had 10% citric acid (50 mL) added followed by EtOAc and extraction with water and brine. The organic extract was dried, filtered and concentrated to afford 5.31 g (77%) of the title compound. MS (ESI) m/z 232 (M+H)+.

EXAMPLE 127B (2S,4S)-1-(tert-butoxycarbonyl)-4-(tert-butyldimethylsilyloxy)pyrrolidine-2-carboxylic acid To a solution of Example 127A (5.31 g, 22.96 mmol) and imidazole (7.82 g, 115 mmol) in dichloromethane (106 mL) and DMF (21.3 mL) was added tert-butyldimethylsilyl chloride (7.61 g, 50.5 mmol) and the mixture stirred at room

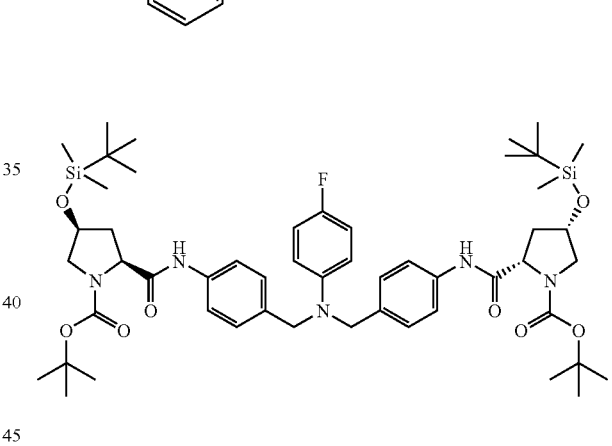

EXAMPLE 127C (3S,3'S,5S,5'S)-tert-butyl 5,5'-(4,4'-(4-fluorophenylazanediyl)bis(methylene)bis(4,1-phenylene)bis(azanediyl))bis(oxomethylene)bis(3-(tert-butyldimethylsilyloxy)pyrrolidine-1-carboxylate)

The product of Example 127B (161 mg, 0.467 mmol) and the product from Example 13B (50 mg, 0.156 mmol) were processed using the method described in Example 43 to afford 110 mg (72%) of the title compound. MS (ESI) m/z 977 (M+H)+.

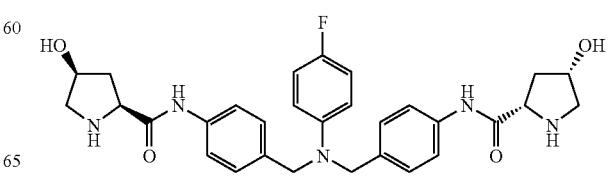

EXAMPLE 127D (2S,2'S,4S,4'S)-N,N'-(4,4'-(4-fluorophenylazanediyl)bis(methylene)bis(4,1-phenylene))bis(4-hydroxypyrrolidine-2-carboxamide)

The product of Example 127C (110 mg, 0.113 mmol) was dissolved in trifluoroacetic acid (6 mL), water (0.2 mL) and dichloromethane (0.3 mL) and the mixture stirred at room temperature for 2 hours. Afterwards the mixture was concentrated to an oil which was dissolved in 75% $CHCl_3$ and 25% isopropyl alcohol then extracted with a saturated aqueous sodium bicarbonate solution, the organic extract separated, dried, filtered and concentrated to give the title compound as a colorless solid. MS (ESI) m/z 548 (M+H)+.

EXAMPLE 127E (2S,4S,2'S,4'S)-N,N'-{[(4-fluorophenyl)imino]bis(methanediylbenzene-4,1-diyl)}bis{4-hydroxy-1-[(2R)-2-phenyl-2-piperidin-1-ylacetyl]pyrrolidine-2-carboxamide}

The product from Example 127D (30 mg, 0.055 mmol) and (R)-2-phenyl-2-(piperidin-1-yl)acetic acid (36 mg, 0.164 mmol) were processed using the method described in Example 43 to afford 8 mg (15%) of the title compound. $^1$H NMR (400 MHz, DMSO-D6) δ ppm 9.97 (s, 2H), 7.51 (d, J=8.4 Hz, 4H), 7.40 (m, 4H), 7.30 (m, 6H), 7.19 (d, J=8.6 Hz, 4H), 6.91 (d, J=9.0 Hz, 2H), 6.63 (m, 2H), 5.27 (d, J=6.6 Hz, 2H), 4.56 (bs, 4H), 4.24 (m, 2H), 4.07 (m, 2H), 3.68 (m, 2H), 3.61 (m, 2H), 3.32 (m, 8H), 1.74 (m, 2H), 1.42 (m, 8H), 1.35 (m, 4H).

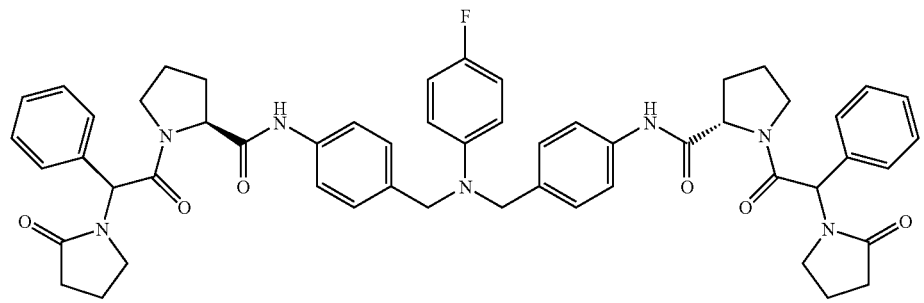 [SMILES: O=C(Nc1ccc(CN(Cc2ccc(NC(=O)[C@@H]3CCCN3C(=O)C(c3ccccc3)N3CCCC3=O)cc2)c2ccc(F)cc2)cc1)[C@@H]1CCCN1C(=O)C(c1ccccc1)N1CCCC1=O]

EXAMPLE 128

(2S,2'S)-N,N'-{[(4-fluorophenyl)imino]bis(methanediylbenzene-4,1-diyl)}bis{1-[(2-oxopyrrolidin-1-yl)(phenyl)acetyl]pyrrolidine-2-carboxamide}

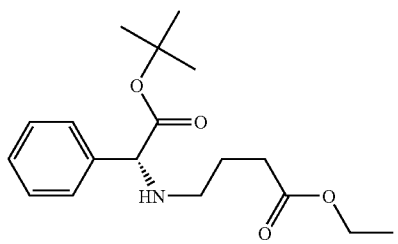 [SMILES: CCOC(=O)CCCN[C@@H](C(=O)OC(C)(C)C)c1ccccc1]

EXAMPLE 128A (R)-ethyl 4-(2-tert-butoxy-2-oxo-1-phenylethylamino)butanoate

A mixture of (R)-tert-butyl 2-amino-2-phenylacetate hydrochloride (0.5 g, 2.051 mmol), ethyl 4-bromobutanoate (0.44 g, 2.26 mmol), and $K_2CO_3$ (1.13 g, 8.21 mmol) in $CH_3CN$ (10 mL) was heated to 50° C. for 40 hours. The mixture was diluted with EtOAc and then washed with $H_2O$ and brine. The organic was then dried ($MgSO_4$), filtered and concentrated. Purification by chromatography (silica gel, 40% EtOAc in Hexanes) afforded 486 mg (74%) of the title compound. MS (ESI) m/z 322 (M+H)$^+$.

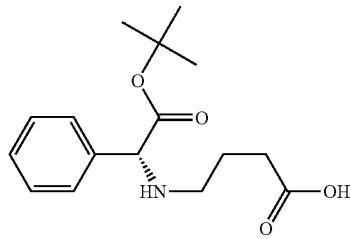 [SMILES: CC(C)(C)OC(=O)[C@H](NCCCC(=O)O)c1ccccc1]

EXAMPLE 128B (R)-4-(2-tert-butoxy-2-oxo-1-phenylethylamino)butanoic Acid

The product of example 128A (480 mg, 1.49 mmol) and NaOH (299 mg, 7.47 mmol) in MeOH (10 mL) was stirred at ambient temperature for 1 hour. The mixture had HCl (1M) added and was extracted with EtOAc. The organic was washed with brine, dried ($MgSO_4$), filtered and concentrated to afford 310 mg (71%) of the title compound. MS (ESI) m/z 294 (M+H)$^+$.

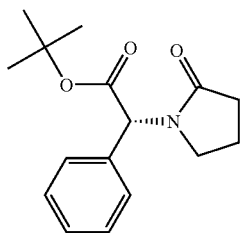 [SMILES: CC(C)(C)OC(=O)[C@@H](c1ccccc1)N1CCCC1=O]

EXAMPLE 128C (R)-tert-butyl 2-(2-oxopyrrolidin-1-yl)-2-phenylacetate

The product of example 128B (307 mg, 1.05 mmol) and N1-((ethylimino)methylene)-N3,N3-dimethylpropane-1,3-diamine hydrochloride (602 mg, 3.14 mmol) in pyridine (5 mL) and dimethylformamide (5 mL) was stirred at ambient temperature for 16 hours. The mixture was diluted with EtOAc and washed with H$_2$O and brine. The organic was dried (MgSO$_4$), filtered and concentrated. Purification by chromatography (silica gel, 60% EtOAc in Hexanes) afforded 249 mg (86%) of the title compound. MS (ESI) m/z 276 (M+H)$^+$.

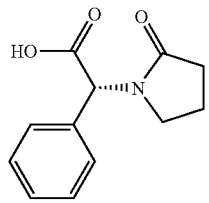 [SMILES: O=C(O)[C@@H](c1ccccc1)N1CCCC1=O]

EXAMPLE 128D (R)-2-(2-oxopyrrolidin-1-yl)-2-phenylacetic acid

The product of example 128C (245 mg, 0.89 mmol) in trifluoroacetic acid (5 mL) was stirred at ambient temperature for 2 hours. The mixture was concentrated to afford 201 mg (100%) of the title compound. MS (ESI) m/z 276 (M+H)$^+$.

EXAMPLE 128E (2S ,2'S)-N,N'-{[(4-fluorophenyl)imino]bis(methanediylbenzene-4,1-diyl)}bis{1-[(2S)-2-(2-oxopyrrolidin-1-yl)-2-phenylacetyl]pyrrolidine-2-carboxamide}

The product of Example 128D (42.5 mg, 0.194 mmol) and Example 13E (50 mg, 0.087 mmol) were processed using the method described in Example 7F to afford three stereoisomers. The title compound was the first eluting isomer and the HPLC fractions were neutralized with saturated aqueous NaHCO$_3$ solution followed by extraction with a mixture of isopropyl alcohol/CH$_2$Cl$_2$ (1:3 ratio; 3×100 mL) and isolation of the title compound. The title compound of Example 129 eluted second and the title compound of Example 130 eluted third. $^1$H NMR (400 MHz, DMSO-d$_6$) δ ppm 1.72-2.00 (m, 5 H), 2.03-2.14 (m, 2 H), 2.27-2.34 (m, 6 H), 2.94 (td, J=8.81, 5.80 Hz, 2 H), 3.16 (s, 6 H), 3.50-3.58 (m, 2 H), 3.65 (td, J=8.67, 6.07 Hz, 2 H), 4.08 (s, 2 H), 4.44 (dd, J=8.29, 4.39 Hz, 2 H), 4.55 (s, 4 H), 6.59-6.65 (m, 2 H), 6.90 (t, J=8.89 Hz, 2 H), 7.17 (d, J=8.57 Hz, 4 H), 7.23 (d, J=6.94 Hz, 4 H), 7.30-7.41 (m, 6 H), 7.53 (d, J=8.46 Hz, 4 H), 9.94 (s, 2 H). MS (ESI) m/z 919 (M+H)$^-$.

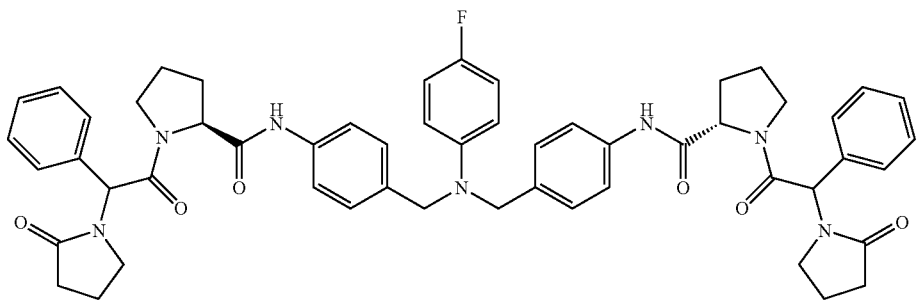 [SMILES: O=C(Nc1ccc(CN(Cc2ccc(NC(=O)[C@@H]3CCCN3C(=O)C(c3ccccc3)N3CCCC3=O)cc2)c2ccc(F)cc2)cc1)[C@@H]1CCCN1C(=O)C(c1ccccc1)N1CCCC1=O]

EXAMPLE 129

(2S ,2'S)-N,N'-{[(4-fluorophenyl)imino]bis(methanediylbenzene-4,1-diyl)}bis{1-[(2-oxopyrrolidin-1-yl)(phenyl)acetyl]pyrrolidine-2-carboxamide}

The title compound, Example 129, was the second eluting compound described in the procedures for Example 128E. Neutralization of the HPLC fractions with saturated aqueous NaHCO$_3$ solution followed by extraction with a mixture of isopropyl alcohol/CH$_2$Cl$_2$ (1:3 ratio; 3×100 mL) and isolation afforded 26 mg (25%) of the title compound. $^1$H NMR (400 MHz, DMSO-d$_6$) δ ppm 1.73-2.00 (m, 10 H), 2.04-2.21 (m, 2 H), 2.23-2.36 (m, 4 H), 2.63-2.70 (m, 2 H), 2.90-3.03 (m, 2 H), 3.16 (s, 6 H), 3.47-3.61 (m, 4 H), 3.60-3.72 (m, 1 H), 4.09 (s, 2 H), 4.46 (td, J=8.13, 4.88 Hz, 2 H), 4.56 (s, 4 H), 5.94 (d, J=3.04 Hz, 2 H), 6.64 (dd, J=9.27, 4.39 Hz, 2 H), 6.91 (t, J=8.89 Hz, 2 H), 7.18 (dd, J=8.40, 5.15 Hz, 6 H), 7.23 (d, J=6.94 Hz, 1 H), 7.32-7.43 (m, 8 H), 7.54 (d, J=8.46 Hz, 4 H), 9.94 (s, 1 H), 10.08 (s, 1 H). MS (ESI) m/z 919 (M+H)$^+$.

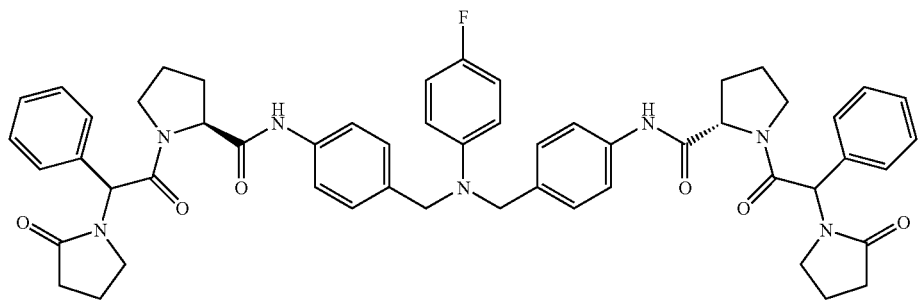 [SMILES: O=C(Nc1ccc(CN(Cc2ccc(NC(=O)[C@@H]3CCCN3C(=O)C(c3ccccc3)N3CCCC3=O)cc2)c2ccc(F)cc2)cc1)[C@@H]1CCCN1C(=O)C(c1ccccc1)N1CCCC1=O]

EXAMPLE 130

(2S,2'S)-N,N'-{[(4-fluorophenyl)imino]bis(methanediylbenzene-4,1-diyl)}bis{1-[(2-oxopyrrolidin-1-yl)(phenyl)acetyl]pyrrolidine-2-carboxamide}

The title compound, Example 130, was the third eluting compound described in the procedures for Example 128E. Neutralization of the HPLC fractions with saturated aqueous NaHCO$_3$ solution followed by extraction with a mixture of isopropyl alcohol/CH$_2$Cl$_2$ (1:3 ratio; 3×100 mL) and isolation afforded 13 mg (12%) of the title compound. $^1$H NMR (400 MHz, DMSO-d$_6$) δ ppm 1.73-1.92 (m, 10 H), 2.11-2.34 (m, 7 H), 2.64-2.72 (m, 4 H), 2.95-3.04 (m, 2 H), 3.47-3.63 (m, 6 H), 4.43-4.51 (m, 2 H), 4.57 (s, 4 H), 5.94 (s, 2 H), 6.65 (dd, J=9.22, 4.45 Hz, 2 H), 6.91 (t, J=8.89 Hz, 2 H), 7.20 (d, J=8.57 Hz, 4 H), 7.34-7.43 (m, 10 H), 7.55 (d, J=8.46 Hz, 4 H), 10.09 (s, 2 H). MS (ESI) m/z 919 (M+H)$^+$.

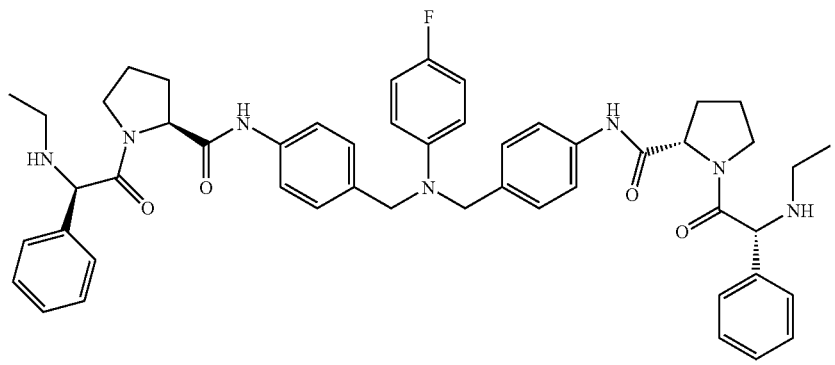 [SMILES: CCN[C@@H](C(=O)N1CCC[C@H]1C(=O)Nc1ccc(CN(Cc2ccc(NC(=O)[C@@H]3CCCN3C(=O)[C@H](NCC)c3ccccc3)cc2)c2ccc(F)cc2)cc1)c1ccccc1]

EXAMPLE 131

(2S,2'S)-N,N'-{[(4-fluorophenyl)imino]bis(methanediylbenzene-4,1-diyl)}bis{1-[(2R)-2-(ethylamino)-2-phenylacetyl]pyrrolidine-2-carboxamide}

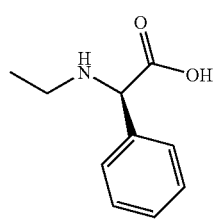

EXAMPLE 131A (R)-2-(ethylamino)-2-phenylacetic Acid

The product from Example 122A was subjected to the procedure described in Example 122C to give the title compound.

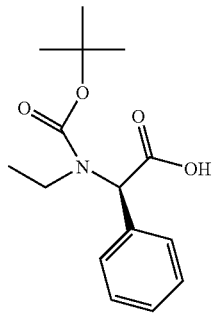 [SMILES: CCN(C(=O)OC(C)(C)C)[C@@H](C(=O)O)c1ccccc1]

EXAMPLE 131B (R)-2-(tert-butoxycarbonyl(ethyl)amino)-2-phenylacetic Acid

To a solution of product from Example 131A (0.23 g, 1.28 mmol) in MeOH (5 mL) was added Hunig's base (0.90 mL, 5.13 mmol) and di-tert-butyl dicarbonate (0.56 g, 2.57 mmol). The mixture was stirred at rt for 22 hrs and was partitioned between CH$_2$Cl$_2$ and 1N HCl solution. The organic layer was dried over anhydrous sodium sulphate, filtered, and concentrated in vacuo. The crude product was purified by column chromatography on silica gel using a solvent gradient of 0-4% MeOH in CH$_2$Cl$_2$ to give the title compound (0.086 g, 24%).

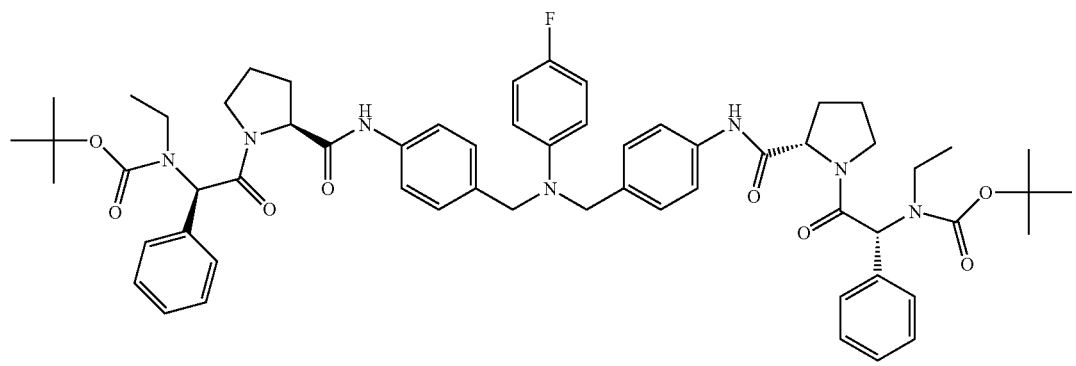 [SMILES: CCN(C(=O)OC(C)(C)C)[C@@H](C(=O)N1CCC[C@H]1C(=O)Nc1ccc(CN(Cc2ccc(NC(=O)[C@@H]3CCCN3C(=O)[C@@H](c3ccccc3)N(CC)C(=O)OC(C)(C)C)cc2)c2ccc(F)cc2)cc1)c1ccccc1]

EXAMPLE 131C tert-butyl (1R,1'R)-2,2'-((2S,2'S)-2,2'-(4,4'-(4-fluo-rophenylazanediyl)bis(methylene)bis(4,1-phenylene)bis(azanediyl))bis(oxomethylene)bis(pyrrolidine-2,1-diyl))bis(2-oxo-1-phenylethane-2,1-diyl)bis(ethylcarbamate)

The product from Example 13D (0.062 g, 0.120 mmol) was subjected to the procedure described in Example 2, substituting the product from Example 131B for (S)-2-(methoxycarbonylamino)-3-methylbutanoic acid, to give the title compound (0.0427 g, 34%).

EXAMPLE 131D (2S,2'S)-N,N'-{[(4-fluorophenyl)imino]bis(methanediylbenzene-4,1-diyl)}bis{1-[(2R)-2-(ethylamino)-2-phenylacetyl]pyrrolidine-2-carboxamide}

To a solution of the product from Example 131C (0.043 g, 0.041 mmol) in CH$_2$Cl$_2$ (1.5 mL) was added 2,2,2-trifluoroacetic acid (0.75 mL, 0.041 mmol), and the solution was stirred at rt for 45 mins. The mixture was partitioned between CH$_2$Cl$_2$ and saturated aq. NaHCO$_3$, and the organic layer was dried over anhydrous sodium sulphate. The drying agent was filtered off, and the solvent was removed in vacuo to give the title compound (18 mg, 51%). $^1$H NMR (400 MHz, DMSO-D6) δ ppm 0.98 (q, J=6.9 Hz, 6 H), 1.70-2.26 (m, 10 H), 3.18-3.27 (m, 2 H), 3.82 (s, 2 H), 4.37 (dd, J=7.9, 3.7 Hz, 2 H), 4.56 (d, J=3.9 Hz, 4 H), 6.61-6.69 (m, 2 H), 6.88-6.96 (m, 2 H), 7.14-7.22 (m, 4 H), 7.24-7.42 (m, 10 H), 7.46-7.58 (m, 4 H), 9.97 (d, J=9.7 Hz, 2 H); MS m/z 838.3 (M+H)$^+$.

EXAMPLE 132

(2S,2'S)-N,N'-{[(4-fluorophenyl)imino]bis(methanediylbenzene-4,1-diyl)}bis(1-{(2R)-2-[ethyl(1-methylethyl)amino]-2-phenylacetyl}pyrrolidine-2-carboxamide)

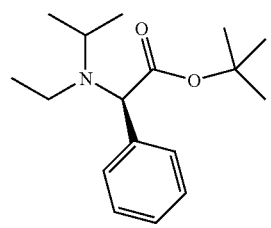

EXAMPLE 132A (R)-tert-butyl 2-(ethyl(isopropyl)amino)-2-phenylacetate

To a solution of product from example 122A (0.098 g, 0.416 mmol) in EtOH (5 mL) was added acetone (0.031 mL, 0.416 mmol), acetic acid (0.024 mL, 0.416 mmol), and sodium cyanoborohydride (0.039 g, 0.625 mmol), and the resulting mixture and stirred at rt for 8 hrs. The mixture was partitioned between CH$_2$Cl$_2$ and saturated aq. NaHCO$_3$, and the organic layer was dried over anhydrous sodium sulphate, filtered, and concentrated in vacuo. The crude product was purified by column chromatography on silica gel using a solvent gradient of 0-1% MeOH in CH$_2$Cl$_2$ to give the title compound (0.0352 g, 31%).

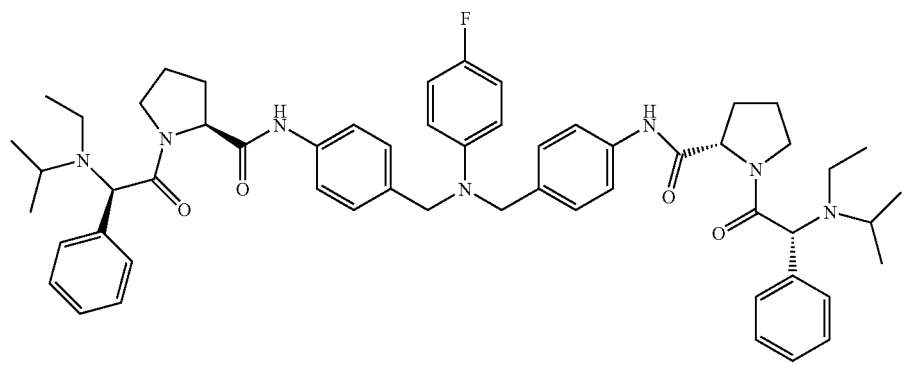 [SMILES: CCN(C(C)C)[C@@H](C(=O)N1CCC[C@H]1C(=O)Nc1ccc(CN(Cc2ccc(NC(=O)[C@@H]3CCCN3C(=O)[C@@H](c3ccccc3)N(CC)C(C)C)cc2)c2ccc(F)cc2)cc1)c1ccccc1]

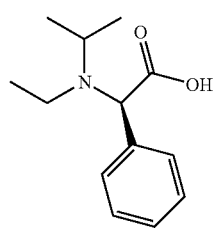 [SMILES: CCN(C(C)C)[C@@H](C(=O)O)c1ccccc1]

EXAMPLE 132B (R)-2-(ethyl(isopropyl)amino)-2-phenylacetic Acid

The product from Example 132A (0.035 g, 0.13 mmol) was subjected to the procedure described in Example 122C to give the title compound (0.027 g).

EXAMPLE 132C (2S,2'S)-N,N'-{[(4-fluorophenyl)imino]bis(methanediylbenzene-4,1-diyl)}bis(1-{(2R)-2-[ethyl(1-methylethyl)amino]-2-phenylacetyl}pyrrolidine-2-carboxamide)

The product from Example 13D (0.030 g, 0.058 mmol) was subjected to the procedure described in Example 13E, substituting the product from Example 132B for (S)-2-(methoxycarbonylamino)-3,3-dimethylbutanoic acid, to give the title compound (0.011 g, 21%). $^1$H NMR (400 MHz, DMSO-D6) δ ppm 0.78-1.02 (m, 6 H), 1.14 (d, J=6.4 Hz, 2 H), 1.21-1.35 (m, 12 H), 1.39 (d, J=6.4 Hz, 4 H), 1.73-2.18 (m, 8 H), 2.74-3.21 (m, 6 H), 4.41 (dd, J=8.3, 3.4 Hz, 2 H), 4.59 (s, 4 H), 5.43-5.52 (m, 2 H), 6.59-6.69 (m, 2 H), 6.92 (t, J=8.8 Hz, 2 H), 7.21 (d, J=8.3 Hz, 4 H), 7.47-7.82 (m, 12 H), 9.32 (s, 1 H), 10.14 (s, 1 H); MS m/z=922.6 (M+H)$^+$.

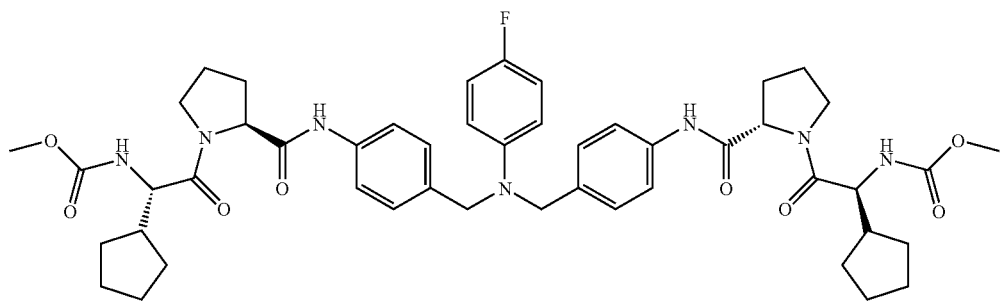

EXAMPLE 133 dimethyl ([[(4-fluorophenyl)imino]
bis{methanediylbenzene-4,1-diylcarbamoyl(2S)pyrrolidine-2,1-diyl[(1S)-1-cyclopentyl-2-oxoethane-2,1-diyl]})biscarbamate The product from Example 13D (0.035 g, 0.068 mmol) and (S)-2-cyclopentyl-2-(methoxycarbonylamino)acetic acid (0.030 g, 0.149 mmol) were processed as in Example 25B to give the title compound as an off-white solid. $^1$H NMR (400 MHz, DMSO-D6) δ ppm 1.20-1.36 (m, 4 H) 1.41-1.50 (m, 4 H) 1.51-1.74 (m, 8 H) 1.82-1.92 (m, 4 H) 1.95-2.04 (m, 2 H) 2.08-2.19 (m, 4 H) 3.52 (s, 6 H) 3.57-3.65 (m, 2 H) 3.79-3.89 (m, 2 H) 4.10 (t, J=8.73 Hz, 2 H) 4.42 (dd, J=8.13, 4.77 Hz, 2 H) 4.55 (s, 4 H) 6.64 (dd, J=9.22, 4.45 Hz, 2 H) 6.91 (t, J=8.84 Hz, 2 H) 7.17 (d, J=8.46 Hz, 4 H) 7.41 (d, J=7.92 Hz, 2 H) 7.51 (d, J=8.57 Hz, 4 H) 9.95 (s, 2 H)
MS ESI− m/z 880.6 (M−H)−.

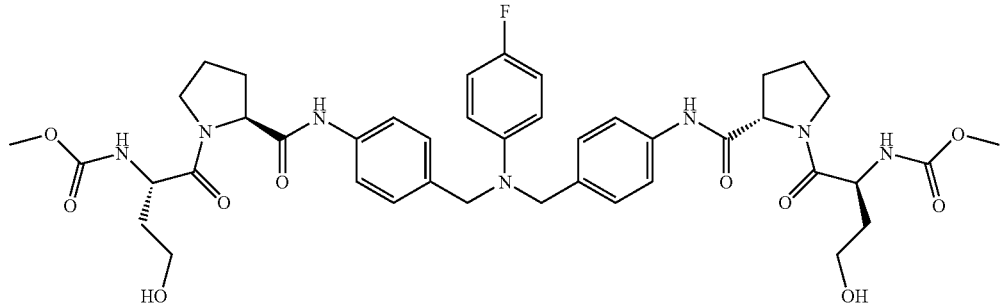

EXAMPLE 134 dimethyl ([(4-fluorophenyl)imino]
bis{methanediylbenzene-4,1-diylcarbamoyl(2S)pyr-
rolidine-2,1-diyl[(2S)-4-hydroxy-1-oxobutane-1,2-
diyl]})biscarbamate The product from Example 13D (0.035 g, 0.068 mmol) and (S)-4-hydroxy-2-(methoxycarbonylamino)butanoic acid (0.027 g, 0.149 mmol) were processed as in Example 25B to give the title compound as an off-white solid. $^1$H NMR (400 MHz, DMSO-D6) δ ppm 1.58-1.70 (m, 2 H) 1.75-1.82 (m, 2 H) 1.84-2.04 (m, 6 H) 2.07-2.17 (m, 2 H) 3.42-3.50 (m, 4 H) 3.50-3.54 (m, 6 H) 3.68 (t, J=6.45 Hz, 4 H) 4.37-4.47 (m, 4 H) 4.55 (s, 4 H) 4.61 (t, J=4.93 Hz, 2 H) 6.63 (dd, J=9.22, 4.34 Hz, 2 H) 6.91 (t, J=8.89 Hz, 2 H) 7.16 (d, J=8.46 Hz, 4 H) 7.34 (d, J=7.70 Hz, 2 H) 7.50 (d, J=8.46 Hz, 4 H) 9.94 (s, 2 H); MS ESI+ m/z 834.4 (M+H)$^+$.

EXAMPLE 135A (S)-3-ethyl-2-(methoxycarbonylamino)pentanoic Acid (S)-2-amino-3-ethylpentanoic acid (1.0 g, 6.89 mmol) was processed as in Example 25A to give 1.02 g (73%) of the title compound as a waxy solid.

EXAMPLE 135B dimethyl ([(4-fluorophenyl)imino]
bis{methanediylbenzene-4,1-diylcarbamoyl(2S)pyr-
rolidine-2,1-diyl[(2S)-3-ethyl-1-oxopentane-1,2-
diyl]}) biscarbamate The product from Example 13D (0.040 g, 0.078 mmol) and the product from Example 135A (0.035 g, 0.171 mmol) were

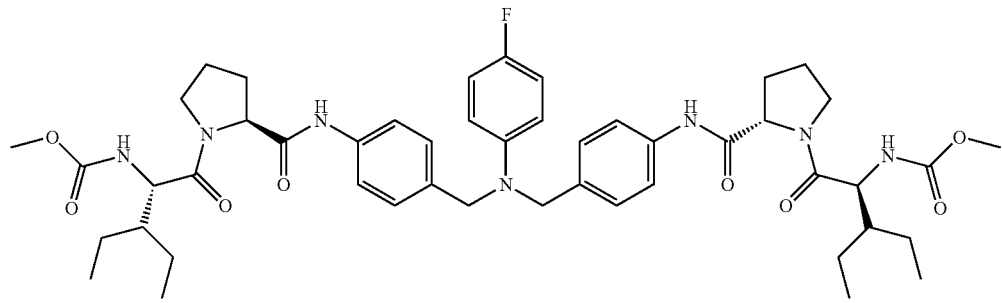

EXAMPLE 135 dimethyl ([(4-fluorophenyl)imino]
bis{methanediylbenzene-4,1-diylcarbamoyl(2S)pyr-
rolidine-2,1-diyl[(2S)-3-ethyl-1-oxopentane-1,2-
diyl]}) biscarbamate

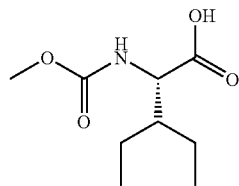

processed as in Example 25B to give the title compound as an off-white solid. $^1$H NMR (400 MHz, DMSO-D6) δ ppm 0.59-0.93 (m, 12 H) 1.05-1.36 (m, 6 H) 1.37-1.50 (m, 2 H) 1.54-1.70 (m, 2 H) 1.78-1.97 (m, 3 H) 2.08-2.21 (m, 2 H) 3.41-3.49 (m, 2 H) 3.51-3.64 (m, 9 H) 3.74-3.85 (m, 2 H) 4.27-4.48 (m, 4 H) 4.55 (s, 4 H) 6.63 (dd, J=9.22, 4.34 Hz, 2 H) 6.90 (t, J=8.89 Hz, 2 H) 7.17 (d, J=8.24 Hz, 4 H) 7.20-7.38 (m, 2 H) 7.47-7.55 (m, 4 H) 9.71-10.24 (m, 2 H); MS ESI− m/z 884.6 (M−H)−.

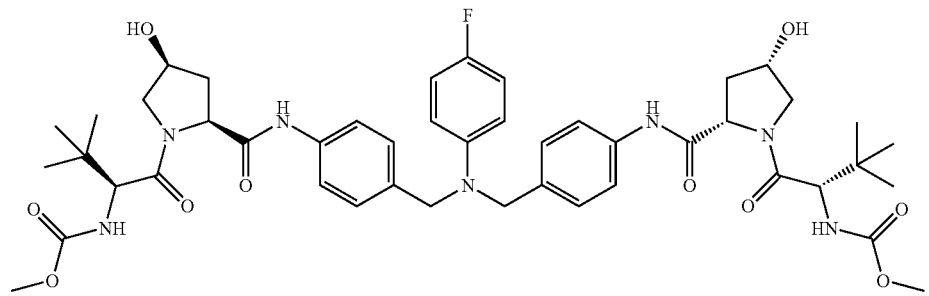

EXAMPLE 136 dimethyl ([[(4-fluorophenyl)imino]
bis{methanediylbenzene-4,1-diylcarbamoyl[(2S,4S)-
4-hydroxypyrrolidine-2,1-diyl][(2S)-3,3-dimethyl-1-
oxobutane-1,2-diyl]})biscarbamate The product from Example 127D (30 mg, 0.057 mmol) and (S)-2-(methoxycarbonylamino)-3,3-dimethylbutanoic acid (26.8 mg, 0.142 mmol) were processed using the method described in Example 43 to afford 8.5 mg (15%) of the title compound. $^1$H NMR (400 MHz, DMSO-D6) δ ppm 9.97 (s, 2H), 7.49 (d, J=7.6 Hz, 4H), 7.17 (d, J=7.6 Hz, 4H), 7.10 (m, 2H), 6.90 (m, 4H), 6.62 (m, 2H), 5.29 (d, J=5.5 Hz, 2H), 4.54 (bs, 4H), 4.38 (m, 2H), 4.22 (m, 2H), 4.15 (m, 2H), 3.96 (m, 2H), 3.52 (s, 6H), 2.53 (s, 4H), 2.38 (m, 2H), 1.65 (m, 2H), 0.95 (s, 18H).

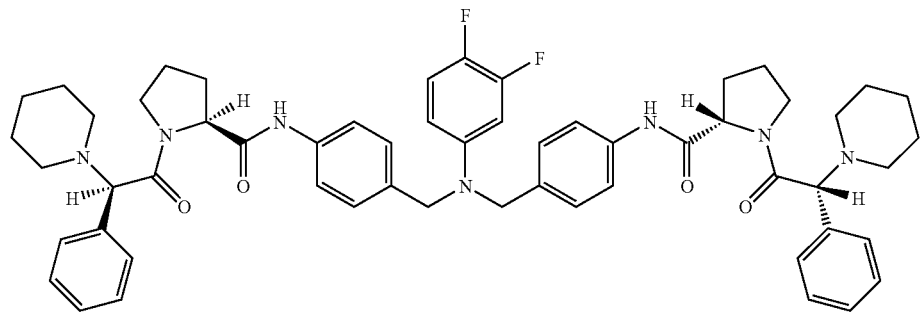 [SMILES: O=C(Nc1ccc(CN(Cc2ccc(NC(=O)[C@@H]3CCCN3C(=O)[C@@H](c3ccccc3)N3CCCCC3)cc2)c2ccc(F)c(F)c2)cc1)[C@@H]1CCCN1C(=O)[C@@H](c1ccccc1)N1CCCCC1]

EXAMPLE 137

(2S,2'S)-N,N'-{[(3,4-difluorophenyl)imino]bis(methanediylbenzene-4,1-diyl)}bis{1-[(2R)-2-phenyl-2-piperidin-1-ylacetyl]pyrrolidine-2-carboxamide}

The product from Example 89D and (R)-2-phenyl-2-(piperidin-1-yl)acetic acid hydrochloride were processed using the method described in Example 13E replacing DMF with dichloromethane to afford the title compound (55.5 mg, 25%). $^1$H NMR (400 MHz, DMSO) δ 1.51-1.20 (m, 14H), 1.90-1.74 (m, 5H), 2.10-1.91 (m, 5H), 2.40-2.34 (m, 4H), 3.54-3.41 (m, 2H), 3.90-3.78 (m, 2H), 4.24 (s, 2H), 4.36-4.29 (m, 2H), 4.60 (s, 4H), 6.46-6.37 (m, 1H), 6.68-6.57 (m, 1H), 7.14-7.07 (m, 2H), 7.19 (d, J=8.4, 4H), 7.36-7.25 (m, 5H), 7.42 (d, J=7.2, 4H), 7.53 (d, J=8.5, 4H), 9.97 (s, 2H). MS (ESI) m/z 936 (M+H$^+$, 30%) 469 (0.5M+H$^+$, 100%).

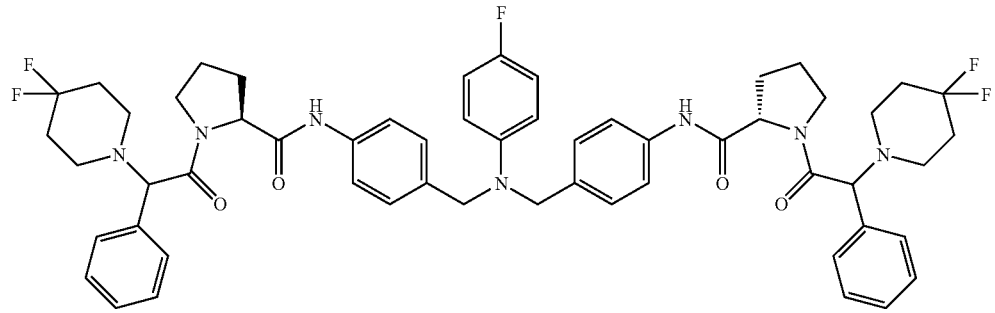 [SMILES: O=C(Nc1ccc(CN(Cc2ccc(NC(=O)[C@@H]3CCCN3C(=O)C(c3ccccc3)N3CCC(F)(F)CC3)cc2)c2ccc(F)cc2)cc1)[C@@H]1CCCN1C(=O)C(c1ccccc1)N1CCC(F)(F)CC1]

EXAMPLE 138

(2S,2'S)-N,N'-{[(4-fluorophenyl)imino]bis(methanediylbenzene-4,1-diyl)}bis{1-[(4,4-difluoropiperidin-1-yl)(phenyl)acetyl]pyrrolidine-2-carboxamide}

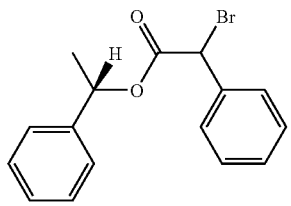 [SMILES: C[C@H](OC(=O)C(Br)c1ccccc1)c1ccccc1]

EXAMPLE 138A (S)-1-phenylethyl 2-bromo-2-phenylacetate

To a mixture of α-bromophenylacetic acid (11.20 g, 52.1 mmol), (S)-(−)-1-phenylethanol (8.2 mL, 67.9 mmol) and DMAP (0.63 g, 5.2 mmol) in $CH_2Cl_2$ (100 mL). was added EDAC (13.80 g, 72.0 mmol). The resulting mixture was stirred at room temperature for 3 hours then diluted with ethyl acetate (200 mL), washed with water (2×100 mL) and brine (100 mL). The organic layer was dried ($MgSO_4$), filtered, and concentrated then purified by column chromatography to provide the title compound (12.6 g, 76% yield).

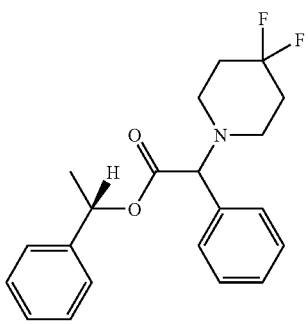 [SMILES: C[C@H](OC(=O)C(c1ccccc1)N1CCC(F)(F)CC1)c1ccccc1]

EXAMPLE 138B (S)-1-phenylethyl 2-(4,4-difluoropiperidin-1-yl)-2-phenylacetate To a solution of the product from Example 138A (1.00 g, 3.13 mmol) in tetrahydrofuran (20 mL) at room temperature was added triethylamine (1.75 mL, 12.5 mmol) and tetrabutylammonium iodide (0.46 g, 1.25 mmol). The mixture was stirred for 5 minutes and then 4,4-difluoropiperidine hydrochloride (0.74 g, 4.70 mmol) was added as the free base in THF. The mixture was stirred for 1 hour at room temperature and then heated to 55° C. overnight. The cooled mixture was washed with brine, concentrated, then purified by column chromatography (EtOAc-hexane) to provide the title compound (1.04 g, 92% yield).

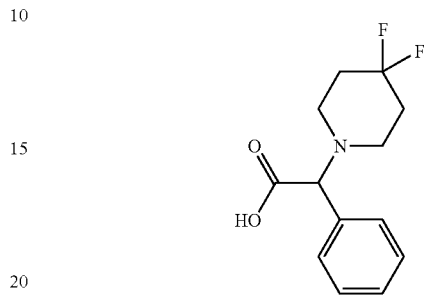

EXAMPLE 138C 2-(4,4-difluoropiperidin-1-yl)-2-phenylacetic Acid

To a solution of the product from Example 138B (1.04 g, 2.89 mmol) in $CH_2Cl_2$ (6 mL) at room temperature was added trifluoroacetic acid (2.0 mL) and the mixture was stirred for 48 hours. The mixture was concentrated under reduced pressure and the residue was taken up in toluene. The mixture was concentrated under reduced pressure and dried in vacuum oven at 50° C. to provide the title compound (as the TFA salt) as a light yellow solid (1.07 g, 100%).

EXAMPLE 138D (2S,2'S)-N,N'-{[(4-fluorophenyl)imino]bis(methanediylbenzene-4,1-diyl)}bis{1-[(4,4-difluoropiperidin-1-yl)(phenyl)acetyl]pyrrolidine-2-carboxamide}

Title compound was prepared using the methods from Example 13E substituting the product from Example 138C for (S)-2-(methoxycarbonylamino)-3,3-dimethylbutanoic acid to provide a mixture of three diastereomers. The title compound (176 mg, 31% yield) was isolated by column chromatography as the first eluting diastereomer. $^1$H NMR (400 MHz, METHANOL-D4) δ 7.52-7.46 (m, 8H), 7.41-7.31 (m, 6H), 7.21 (d, J=8.4, 4H), 6.85 (t, J=8.8, 2H), 6.72 (dd, J=9.2, 4.3, 2H), 4.54 (s, 4H), 4.42 (dd, J=7.8, 4.8, 2H), 4.31 (s, 2H), 3.94-3.85 (m, 2H), 3.52-3.40 (m, 2H), 2.66-2.44 (m, 8H), 2.19-1.79 (m, 161-1). MS (ESI; M+H) m/z=990.

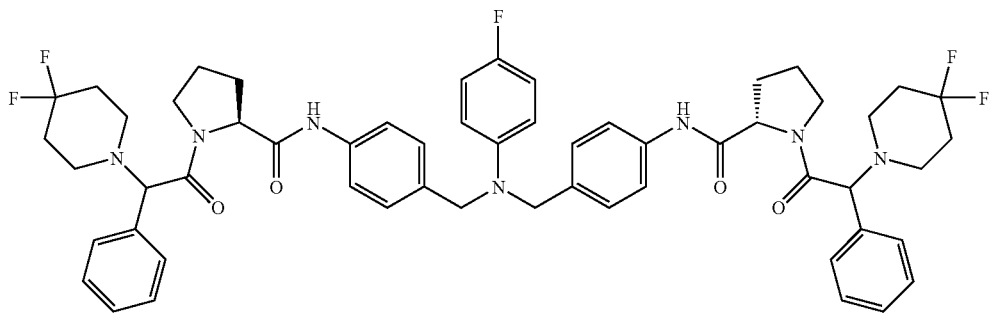 [SMILES: O=C(Nc1ccc(CN(Cc2ccc(NC(=O)[C@@H]3CCCN3C(=O)C(c3ccccc3)N3CCC(F)(F)CC3)cc2)c2ccc(F)cc2)cc1)[C@@H]1CCCN1C(=O)C(c1ccccc1)N1CCC(F)(F)CC1]

EXAMPLE 139

(2S,2'S)-N,N'-{[(4-fluorophenyl)imino]bis(methanediylbenzene-4,1-diyl)}bis{1-[(4,4-difluoropiperidin-1-yl)(phenyl)acetyl]pyrrolidine-2-carboxamide}

The title compound (77 mg, 14% yield) was isolated from the column chromatography of Example 138D as the second eluting diastereomer. $^1$H NMR (400 MHz, METHANOL-D4) δ 7.57-7.44 (m, 6H), 7.43-7.30 (m, 8H), 7.28-7.15 (m, 4H), 6.88-6.81 (m, 2H), 6.77-6.68 (m, 2H), 4.63-4.51 (m, 5H), 4.48 (s, 1H), 4.42 (dd, J=7.4, 4.6, 1H), 4.31 (s, 1H), 3.94-3.86 (m, 1H), 3.81-3.71 (m, 1H), 3.54-3.39 (m, 2H), 2.69-2.35 (m, 8H), 2.23-1.77 (m, 16H). MS (ESI; M+H) m/z=990.

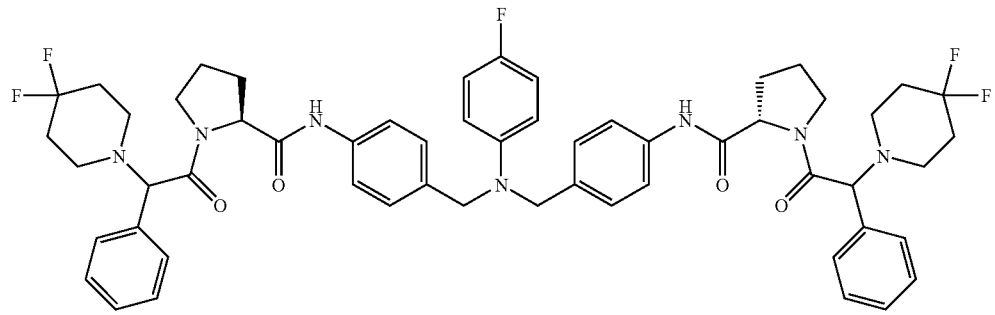 [SMILES: O=C(Nc1ccc(CN(Cc2ccc(NC(=O)[C@@H]3CCCN3C(=O)C(c3ccccc3)N3CCC(F)(F)CC3)cc2)c2ccc(F)cc2)cc1)[C@@H]1CCCN1C(=O)C(c1ccccc1)N1CCC(F)(F)CC1]

EXAMPLE 140

(2S,2'S)-N,N'-{[(4-fluorophenyl)imino]bis(methanediylbenzene-4,1-diyl)}bis{1-[(4,4-difluoropiperidin-1-yl)(phenyl)acetyl]pyrrolidine-2-carboxamide}

The title compound (49 mg, 9% yield) was isolated from the column chromatography of Example 138D eluting as the third eluting diastereomer. $^1$H NMR (400 MHz, METHANOL-D4) δ 7.57-7.15 (m, 18H), 6.88-6.81 (m, 2H), 6.76-6.68 (m, 2H), 4.62-4.51 (m, 4H), 4.50-4.40 (m, 2H), 3.81-3.67 (m, 2H), 3.53-3.33 (m, 2H), 2.70-2.35 (m, 8H), 2.29-1.81 (m, 18H). MS (ESI; M+H) m/z=990.

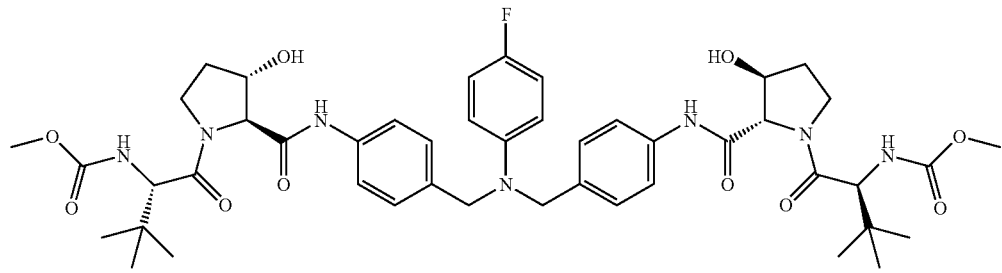

EXAMPLE 141 dimethyl ([[(4-fluorophenyl)imino]bis{methanediyl (6-methoxybenzene-3,1-diyl)carbamoyl(2S)pyrrolidine-2,1-diyl[(2S)-3,3-dimethyl-1-oxobutane-1,2-diyl]})biscarbamate dimethyl ([[(4-fluorophenyl)imino]bis{methanediylbenzene-4,1-diylcarbamoyl[(2S,3S)-3-hydroxypyrrolidine-2,1-diyl][(2S)-3,3-dimethyl-1-oxobutane-1,2-diyl]})biscarbamate

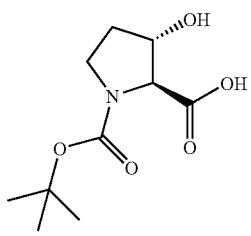 [SMILES: CC(C)(C)OC(=O)N1CC[C@H](O)[C@H]1C(=O)O]

EXAMPLE 141A (2S,3S)-1-(tert-butoxycarbonyl)-3-hydroxypyrrolidine-2-carboxylic Acid To a solution of (2S,3S)-3-hydroxypyrrolidine-2-carboxylic acid (0.50 g, 3.8 mmol) in $CH_2Cl_2$ (19 mL) at room temperature was added di-tert-butyl dicarbonate (0.96 mL, 4.2 mmol) and Hunig's base (1.32 mL, 7.6 mmol) to give a tan solution. The reaction was stirred overnight at room temperature and then diluted with $CH_2Cl_2$ and washed with saturated sodium bicarbonate solution. The aqueous layer was concentrated under reduced pressure and then suspended in methanol and filtered. The solvent was then removed under reduced pressure to prodive the title compound (0.91 g, 103% yield).

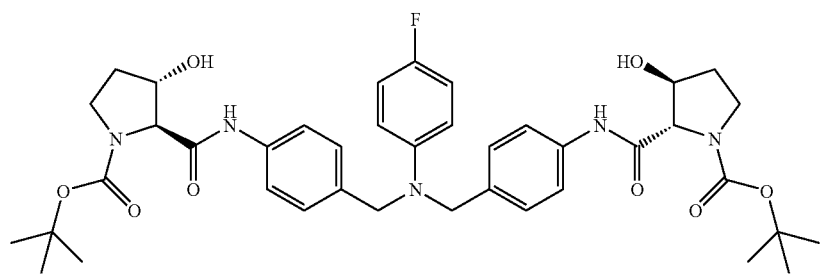 [SMILES: CC(C)(C)OC(=O)N1CC[C@H](O)[C@H]1C(=O)Nc1ccc(CN(Cc2ccc(NC(=O)[C@@H]3[C@@H](O)CCN3C(=O)OC(C)(C)C)cc2)c2ccc(F)cc2)cc1]

EXAMPLE 141B (2S,2'S,3S,3'S)-tert-butyl 2,2'-(4,4'-(4-fluorophenylazanediyl)bis(methylene)bis(4,1-phenylene)bis(azanediyl))bis(oxomethylene)bis(3-hydroxypyrrolidine-1-carboxylate)

The title compound was prepared using the methods from Example 13C substituting the product from Example 141A for N-(tert-butoxycarbonyl)-L-proline to provide the title compound (0.51 g, 77% yield).

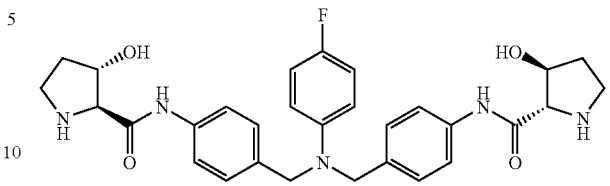

EXAMPLE 141C (2S,2'S,3S,3'S)-N,N'-(4,4'-(4-fluorophenylazanediyl)bis(methylene)bis(4,1-phenylene))bis(3-hydroxypyrrolidine-2-carboxamide)

The title compound was prepared using the methods from Example 13D substituting the product from Example 141B for the product from Example 13C to provide the title compound (0.28 g, 76% yield).

EXAMPLE 141D dimethyl ([[(4-fluorophenyl)imino]bis{methanediyl (6-methoxybenzene-3,1-diyl)carbamoyl(2S)pyrrolidine-2,1-diyl[(2S)-3,3-dimethyl-1-oxobutane-1,2-diyl]})biscarbamate dimethyl ([[(4-fluorophenyl)imino]bis{methanediylbenzene-4,1-diylcarbamoyl[(2S,3S)-3-hydroxypyrrolidine-2,1-diyl][(2S)-3,3-dimethyl-1-oxobutane-1,2-diyl]})biscarbamate The title compound was prepared using the methods from Example 13E substituting the product from Example 141C for the product from Example 13D to provide the title compound (0.15 g, 45% yield). $^1$H NMR (400 MHz, DMSO) δ 10.14 (s, 2H), 7.52 (d, J=8.5, 4H), 7.15 (d, J=8.5, 4H), 7.08 (d, J=9.3, 2H), 6.89 (t, J=8.6, 2H), 6.62 (dd, J=4.4, 9.2, 2H), 5.39 (s, 2H), 4.53 (bs, 4H), 4.30-4.16 (m, 6H), 3.82-3.69 (m, 4H), 3.53 (s, 6H), 2.15-2.02 (m, 2H), 1.88-1.78 (m, 2H), 0.96-0.88 (m, 18H). MS (ESI; M+H) m/z=891.

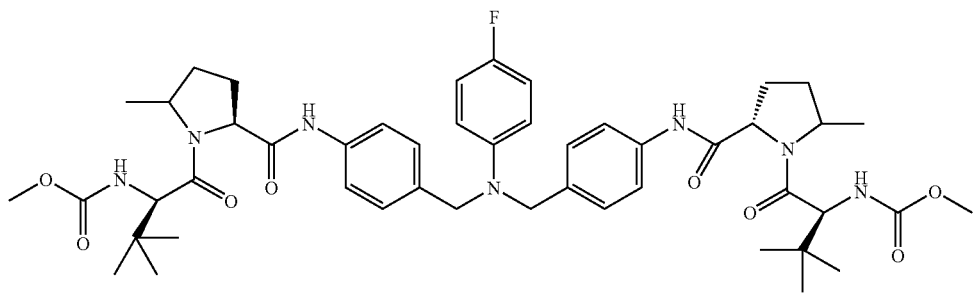

EXAMPLE 142 methyl[(1R)-1-{[(2S)-2-{[4-({(4-fluorophenyl)[4-({[(2S)-1-{(2S)-2-[(methoxycarbonyl)amino]-3,3-dimethylbutanoyl}-5-methylpyrrolidin-2-yl]carbonyl}amino)benzyl]amino}methyl)phenyl]carbamoyl}-5-methylpyrrolidin-1-yl]carbonyl}-2,2-dimethylpropyl]carbamate

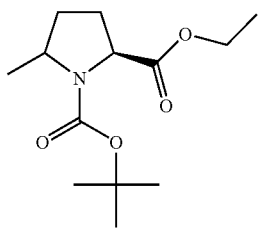 [SMILES: CCOC(=O)[C@@H]1CCC(C)N1C(=O)OC(C)(C)C]

EXAMPLE 142A (2S)-1-tert-butyl-2-ethyl-5-methylpyrrolidine-1,2-dicarboxylate The title compound was prepared from (2S)-1-tert-butyl 2-ethyl 5-hydroxy pyrrolidine-1,2-dicarboxylate following the method described by Collado et al. J. Org. Chem. 1995, 60, 5011-5015.

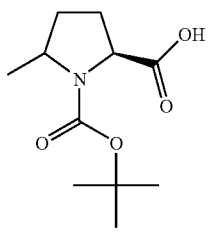 [SMILES: CC1CC[C@@H](C(=O)O)N1C(=O)OC(C)(C)C]

EXAMPLE 142B (2S)-1-(tert-butoxycarbonyl)-5-methylpyrrolidine-2-carboxylic Acid To a solution of product from Example 142A (0.068 g, 0.264 mmol) in MeOH (2.64 mL) was added NaOH (10.57 mg, 0.264 mmol), and the resulting mixture was stirred at rt overnight. The mixture was partitioned between $CH_2Cl_2$ and aq.1N HCl solution, and the organic layer was separated and dried over anhydrous sodium sulphate. The drying agent was filtered off, and solvent was removed in vacuo to give the title compound (0.050 g, 83%).

EXAMPLE 142C methyl [(1R)-1-{[(2S)-2-{[4-({(4-fluorophenyl)[4-({[(2S)-1-{(2S)-2-[(methoxycarbonyl)amino]-3,3-dimethylbutanoyl}-5-methylpyrrolidin-2-yl]carbonyl}amino)benzyl]amino}methyl)phenyl]carbamoyl}-5-methylpyrrolidin-1-yl]carbonyl}-2,2-dimethylpropyl]carbamate The title compound was prepared from the product from Example 13B using the procedures described in Examples 1C-1E, substituting the product from Example 142B for N-(tert-butoxycarbonyl)-L-proline, and substituting (S)-2-(methoxycarbonylamino)-3,3-dimethylbutanoic acid for (S)-2-(methoxycarbonylamino)-3-methylbutanoic acid, and the final product purified by silica gel chromatography gradient eluting with 0-3% methanol in dichloromethane. $^1$H NMR (400 MHz, DMSO-D6) δ ppm 0.96 (s, 18 H), 1.25 (d, J=6.0 Hz, 6 H), 1.61 (dd, J=11.4, 6.1 Hz, 2 H), 1.78-2.30 (m, 6 H), 3.53 (s, 6 H), 3.58-3.67 (m, 2 H), 4.27-4.38 (m, 3 H), 4.43 (d, J=9.4 Hz, 2 H), 4.54 (s, 4 H), 6.60-6.67 (m, 2 H), 6.85-6.95 (m, 2 H), 7.16 (d, J=8.5 Hz, 4 H), 7.49 (d, J=8.6 Hz, 4 H), 9.97 (s, 2 H); MS m/z 886.7 (M+H)$^+$.

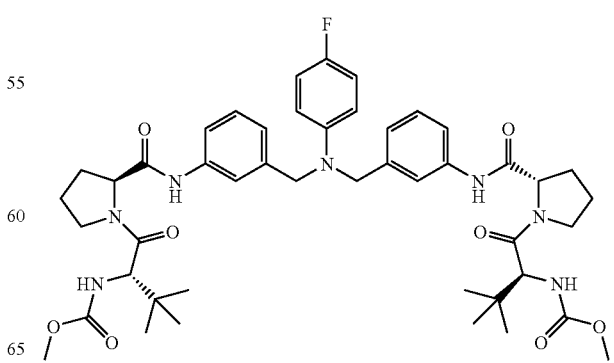

EXAMPLE 143 dimethyl ([(4-fluorophenyl)imino]
bis{methanediylbenzene-3,1-diylcarbamoyl(2S)pyr-
rolidine-2,1-diyl[(2S)-3,3-dimethyl-1-oxobutane-1,2-
diyl]})biscarbamate

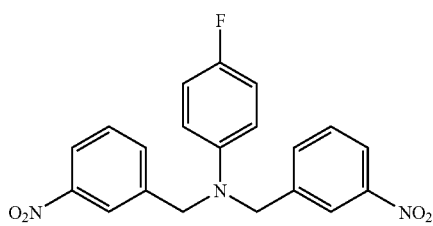

Example 143A 4-fluoro-N,N-bis(3-nitrobenzyl)aniline

4-Fluoroaniline and 3-nitrobenzyl bromide were processed using the method described in Example 1A to provide 1.46 g (87%) of the title compound. $^1$H NMR (400 MHz, DMSO-D6) δ 4.88 (s, 4 H) 6.69-6.75 (m, 2 H) 6.97 (t, J=8.89 Hz, 2 H) 7.64 (t, J=7.81 Hz, 2 H) 7.70-7.74 (m, 2 H) 8.08-8.13 (m, 4 H).

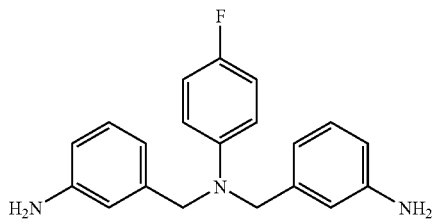 [SMILES: Nc1cccc(CN(Cc2cccc(N)c2)c2ccc(F)cc2)c1]

EXAMPLE 143B

N,N-bis(3-aminobenzyl)-4-fluoroaniline

To a slurry of the product from Example 143A (0.450 g, 1.180 mmol) in THF (4 mL), ethanol (1.00 mL) and water (4.00 mL) at rt was added ammonium chloride (0.189 g, 3.54 mmol) followed by iron (0.329 g, 5.90 mmol) and the mixture heated to 80° C. After 3 h, the mixture was filtered through Celite, concentrated and the residue partitioned between water and 25% isopropyl alcohol-CHCl₃. The organic phase was dried (Na₂SO₄) and concentrated. The solid was dried in a vacuum oven to provide 321 mg (85%) of the title compound. MS (ESI; M+H) m/z=322.

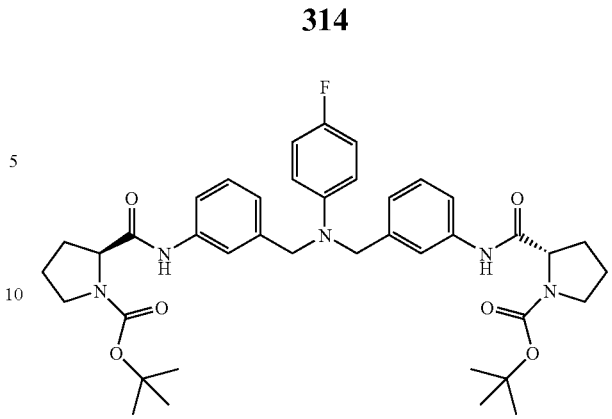

EXAMPLE 143C (2S,2'S)-tert-butyl 2,2'-(3,3'-(4-fluorophenyla-
zanediyl)bis(methylene)bis(3,1-phenylene)bis
(azanediyl))bis(oxomethylene)dipyrrolidine-1-car-
boxylate The product from Example 143B and (S)-1-(tert-butoxycarbonyl)pyrrolidine-2-carboxylic acid (Aldrich) were processed using the method described in Example 41 to provide 495 mg (69%) of the title compound. MS (ESI; M+H) m/z=716.

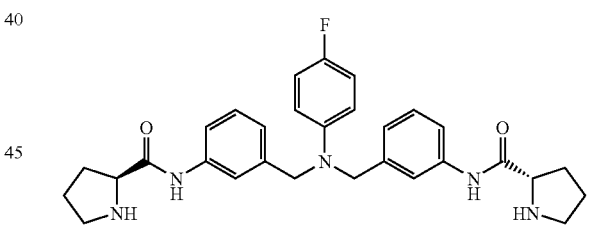

EXAMPLE 143D (2S,2'S)-N,N'-(3,3'-(4-fluorophenylazanediyl)bis
(methylene)bis(3,1-phenylene))dipyrrolidine-2-car-
boxamide The product from Example 143C was processed using the method described in Example 47B to provide 341 mg (96%) of the title compound. $^1$H NMR (400 MHz, DMSO-D6) δ 1.60-1.68 (m, 4 H) 1.71-1.80 (m, 2 H) 1.98-2.08 (m, 2 H) 2.69 (s, 6 H) 2.88 (t, J=6.56 Hz, 4 H) 3.67 (dd, J=8.73, 5.69 Hz, 2 H) 4.63 (s, 4 H) 6.61 (dd, J=9.27, 4.39 Hz, 2 H) 6.89-6.97 (m, 4 H) 7.25 (dd, J=7.81 Hz, 2 H) 7.55 (s, 4 H) 9.92 (s, 2 H).

EXAMPLE 143E dimethyl ([[(4-fluorophenyl)imino]
bis{methanediylbenzene-3,1-diylcarbamoyl(2 S)pyr-
rolidine-2,1-diyl[(2S)-3,3-dimethyl-1-oxobutane-1,2-
diyl]})biscarbamate The product from Example 143D and (S)-2-(methoxycarbonylamino)-3,3-dimethylbutanoic acid were processed using the method described in Example 41 to provide 460 mg (81%) of the title compound. $^1$H NMR (400 MHz, DMSO-D6) δ 0.96 (s, 18 H) 1.80-1.90 (m, 4 H) 1.93-2.03 (m, 2 H) 2.09-2.19 (m, 2 H) 3.54 (s, 6 H) 3.60-3.68 (m, 2 H) 3.71-3.82 (m, 2 H) 4.21 (d, J=8.89 Hz, 2 H) 4.43 (dd, J=8.02, 5.31 Hz, 2 H) 4.63 (s, 4 H) 6.57-6.66 (m, 2 H) 6.89-6.96 (m, 4 H) 7.08 (d, J=8.78 Hz, 2 H) 7.24 (t, J=7.86 Hz, 2 H) 7.38 (s, 2 H) 7.59 (d, J=8.13 Hz, 2 H) 10.00 (s, 2 H).

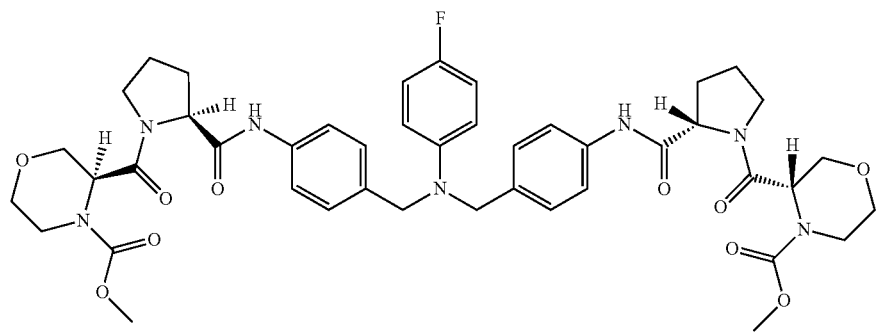 [SMILES: COC(=O)N1CCOC[C@H]1C(=O)N1CCC[C@H]1C(=O)Nc1ccc(CN(Cc2ccc(NC(=O)[C@@H]3CCCN3C(=O)[C@@H]3COCCN3C(=O)OC)cc2)c2ccc(F)cc2)cc1]

EXAMPLE 144 dimethyl (3S,3'S)-3,3'-{[(4-fluorophenyl)imino]bis
[methanediylbenzene-4,1-diylcarbamoyl(2S)pyrroli-
dine-2,1-diylcarbonyl]}dimorpholine-4-carboxylate The product from Example 13D and (S)-4-(methoxycarbonyl)morpholine-3-carboxylic acid were processed using the method described in Example 13E replacing DMF with dichloromethane to afford the title compound (0.21 g, 52%). $^1$H NMR (400 MHz, DMSO) δ 1.95-1.76 (m, 4H), 2.08-1.95 (m, 2H), 2.23-2.08 (m, 2H), 3.90-3.36 (m, 20H), 4.15 (d, J=11.6, 2H), 4.50-4.38 (m, 2H), 4.55 (s, 6H), 6.63 (dd, J=9.2, 4.4, 2H), 6.91 (t, J=8.9, 2H), 7.17 (d, J=8.5, 4H), 7.51 (d, J=8.4, 4H), 9.90 (s, 2H). MS (ESI) m/z 858 (M+H)$^+$.

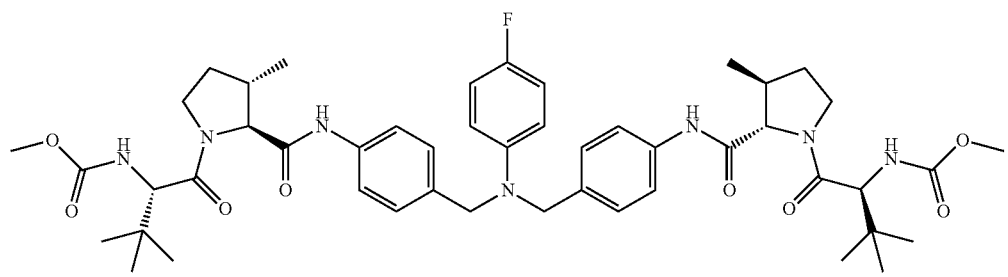

EXAMPLE 145 dimethyl ([(4-fluorophenyl)imino]
bis{methanediylbenzene-4,1-diylcarbamoyl[(2S,3S)-
3-methylpyrrolidine-2,1-diyl][(2S)-3,3-dimethyl-1-
oxobutane-1,2-diyl]})biscarbamate

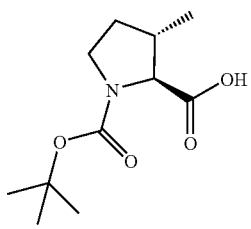 [SMILES: C[C@H]1CCN(C(=O)OC(C)(C)C)[C@@H]1C(=O)O]

EXAMPLE 145A (2S,3S)-1-(tert-butoxycarbonyl)-3-methylpyrrolidine-2-carboxylic Acid The title compound was prepared using the methods from Example 141A substituting the (2S,3S)-3-methylpyrrolidine-2-carboxylic acid for (2S,3S)-3-hydroxypyrrolidine-2-carboxylic acid to provide the title compound (0.31 g, 74% yield).

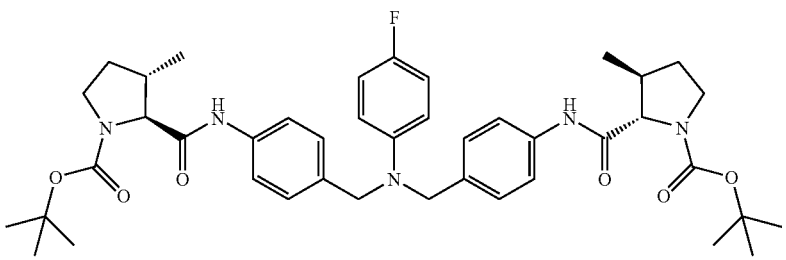 [SMILES: C[C@H]1CCN(C(=O)OC(C)(C)C)[C@@H]1C(=O)Nc1ccc(CN(Cc2ccc(NC(=O)[C@@H]3[C@@H](C)CCN3C(=O)OC(C)(C)C)cc2)c2ccc(F)cc2)cc1]

EXAMPLE 145B (2S,2'S,3S,3'S)-tert-butyl 2,2'-(4,4'-(4-fluorophenylazanediyl)bis(methylene)bis(4,1-phenylene)bis(azanediyl))bis(oxomethylene)bis(3-methylpyrrolidine-1-carboxylate)

The title compound was prepared using the methods from Example 13C substituting the product from Example 145A for N-(tert-butoxycarbonyl)-L-proline to provide the title compound (0.32 g, 70% yield).

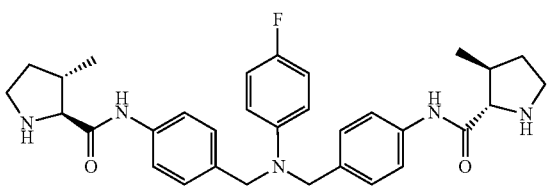 [SMILES: C[C@H]1CCN[C@@H]1C(=O)Nc1ccc(CN(Cc2ccc(NC(=O)[C@H]3NCC[C@@H]3C)cc2)c2ccc(F)cc2)cc1]

EXAMPLE 145C (2S,2'S,3S,3'S)-N,N'-(4,4'-(4-fluorophenylazanediyl)bis(methylene)bis(4,1-phenylene))bis(3-methylpyrrolidine-2-carboxamide)

The title compound was prepared using the methods from Example 13D substituting the product from Example 145B for the product from Example 13C to provide the title compound (0.20 g, 86% yield).

EXAMPLE 145D dimethyl ([(4-fluorophenyl)imino]bis{methanediyl
(6-methoxybenzene-3,1-diyl)carbamoyl(2S)pyrrolidine-2,1-diyl[(2S)-3,3-dimethyl-1-oxobutane-1,2-
diyl]})biscarbamate dimethyl([(4-fluorophenyl)
imino]bis{methanediylbenzene-4,1-diylcarbamoyl
[(2S,3S)-3-hydroxypyrrolidine-2,1-diyl][(2S)-3,3-
dimethyl-1-oxobutane-1,2-diyl]})biscarbamate The title compound was prepared using the methods from Example 13E substituting the product from Example 145C for the product from Example 13D to provide the title compound (55 mg, 33% yield). $^1$H NMR (400 MHz, DMSO)δ 10.01 (bs, 2H), 7.53 (d, J=8.5, 4H), 7.17 (d, J=8.5, 5H), 7.07 (d, J=8.6, 2H), 6.91 (t, J=8.7, 2H), 6.64 (dd, J=4.4, 9.2, 2H), 4.55 (bs, 4H), 4.16 (d, J=8.5, 2H), 3.97 (d, J=6.8, 2H), 3.90 (s, 2H), 3.62-3.55 (m, 2H), 3.54 (s, 6H), 2.28-2.16 (m, 2H), 2.15-2.03 (m, 2H), 1.62-1.49 (m, 2H), 1.09 (d, J=6.7, 6H), 0.95 (s, 18H). MS (ESI; M+H) m/z=887.

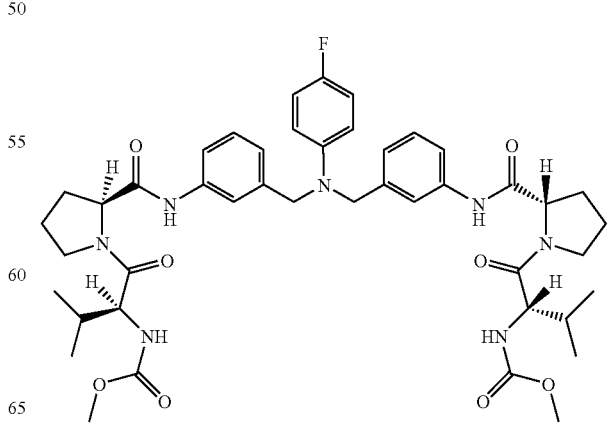

EXAMPLE 146 dimethyl ([[(4-fluorophenyl)imino]
bis{methanediylbenzene-3,1-diylcarbamoyl(2S)pyr-
rolidine-2,1-diyl[(2S)-3-methyl-1-oxobutane-1,2-
diyl]})biscarbamate

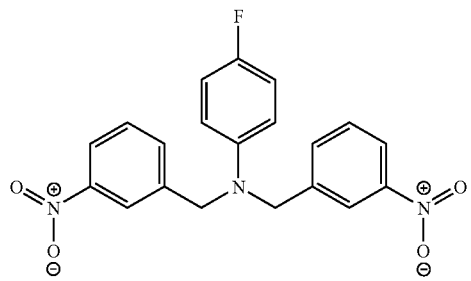 [SMILES: O=[N+]([O-])c1cccc(CN(Cc2cccc([N+](=O)[O-])c2)c2ccc(F)cc2)c1]

EXAMPLE 146B

N,N-bis(3-aminobenzyl)-4-fluoroaniline

The product from Example 146A (1 g, 2.62 mmol), ammonium chloride (0.4965 g, 9.28 mmol) and iron (0.7849 g, 14.05 mmol) were combined in THF (12 mL)/Ethanol (12.00 mL)/Water (3.00 mL) and warmed to 80° C. After 18 hours additional ammonium chloride (0.5162 g, 9.65 mmol) and iron (0.8541 g, 15.29 mmol) were added and heating continued for 3 days. The reaction mixture was filtered through a celite plug and concentrated. The residue was taken up in EtOAc and washed with water (2×), brine (1×), dried (MgSO4), and concentrated. The title compound was used without purification. MS (DCI) m/z 322 (M+H)$^+$.

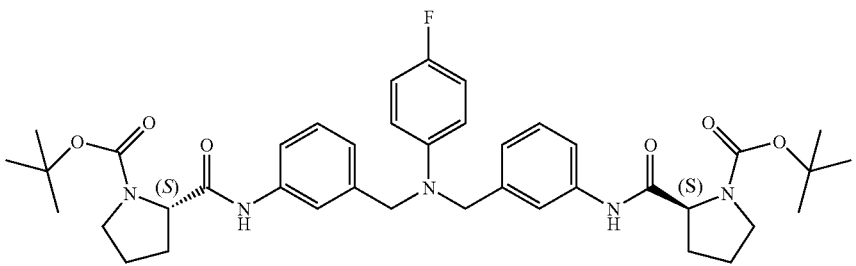

EXAMPLE 146A 4-fluoro-N,N-bis(3-nitrobenzyl)aniline

4-Fluoroaniline and 3-nitrobenzyl bromide were processed using the method described in Example 32A to afford the title compound. LC/MS Rt 2.15 m/z 423 (M+CH$_3$CN)$^+$.

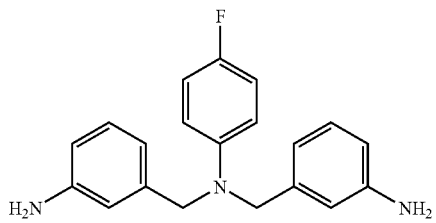

EXAMPLE 146C (2S,2'S)-tert-butyl 2,2'-(3,3'-(4-fluorophenyla-
zanediyl)bis(methylene)bis(3,1-phenylene)bis
(azanediyl))bis(oxomethylene)dipyrrolidine-1-car-
boxylate The product from Example 146B was processed using the method described in Example 1C replacing DMSO with dichloromethane to afford the title compound (1.34 g, 71%). MS (ESI) m/z 716 (M+H)$^+$.

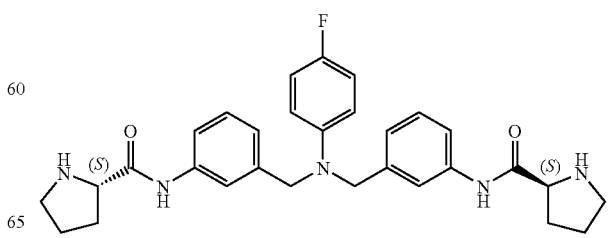

EXAMPLE 146D (2S,2'S)-N,N'-(3,3'-(4-fluorophenylazanediyl)bis(methylene)bis(3,1-phenylene))dipyrrolidine-2-carboxamide The product from Example 146C was processed using the method described in Example 1D to afford the title compound. LC/MS Rt 1.26 m/z 516 (M+H)+.

EXAMPLE 146E dimethyl([[(4-fluorophenyl)imino]bis{methanediylbenzene-3,1-diylcarbamoyl(2 S)pyrrolidine-2,1-diyl[(2S)-3-methyl-1-oxobutane-1,2-diyl]})biscarbamate The product from Example 146D was processed using the method described in Example 1E and purified using flash chromatography (silica gel, MeOH/dichloromethane) to afford the title compound. ¹H NMR (400 MHz, DMSO) δ 0.97-0.82 (m, 12H), 2.19-1.79 (m, 10H), 3.52 (s, 6H), 3.67-3.57 (m, 2H), 3.85-3.75 (m, 2H), 4.02 (t, J=8.5, 2H), 4.43 (dd, J=4.7, 8.1, 2H), 4.63 (s, 4H), 6.63-6.56 (m, 2H), 6.92 (dd, J=5.6, 12.0, 4H), 7.24 (t, J=7.9, 2H), 7.31 (d, J=8.4, 2H), 7.40 (s, 2H), 7.58 (d, J=8.1, 2H), 10.00 (s, 2H). MS (ESI) m/z 831 (M+H)+, 828 (M−H)+.

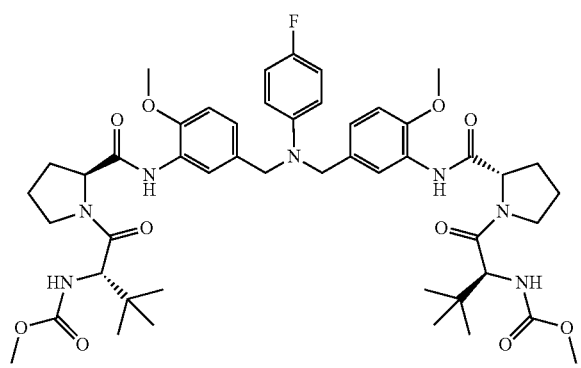

EXAMPLE 147 dimethyl ([[(4-fluorophenyl)imino]bis{methanediyl(6-methoxybenzene-3,1-diyl)carbamoyl(2S)pyrrolidine-2,1-diyl[(2S)-3,3-dimethyl-1-oxobutane-1,2-diyl]})biscarbamate

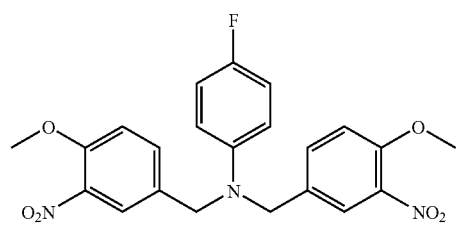

EXAMPLE 147A 4-fluoro-N,N-bis(4-methoxy-3-nitrobenzyl)aniline

4-Fluoroaniline and 4-methoxy-3-nitrobenzyl bromide were processed using the method described in Example 1A to provide 2.33 g (91%) of the title compound. MS (ESI; M+H) m/z=442.

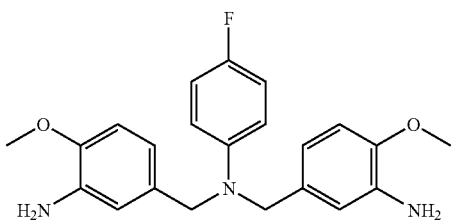

EXAMPLE 147B

N,N-bis(3-amino-4-methoxybenzyl)-4-fluoroaniline

The product from Example 147A was processed using the method described in Example 143B to provide 1.64 g (81%) of the title compound. MS (ESI; M+H) m/z=382.

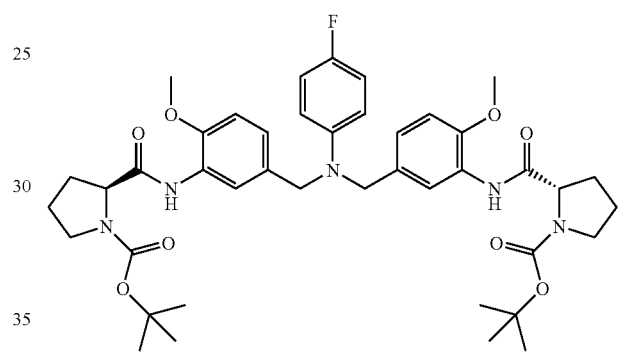

EXAMPLE 147C (2S,2'S)-tert-butyl 2,2'-(5,5'-(4-fluorophenylazanediyl)bis(methylene)bis(2-methoxy-5,1-phenylene))bis(azanediyl)bis(oxomethylene)dipyrrolidine-1-carboxylate The product from Example 147B and (S)-1-(tert-butoxycarbonyl)pyrrolidine-2-carboxylic acid (Aldrich) were processed using the method described in Example 41 to provide 2.49 g (75%) of the title compound. MS (ESI; M+H) m/z=776.

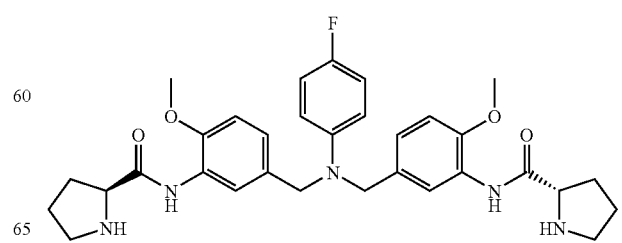

EXAMPLE 147D (2S,2'S)-N,N'-(5,5'-(4-fluorophenylazanediyl)bis(methylene)bis(2-methoxy-5,1-phenylene))dipyrrolidine-2-carboxamide The product from Example 147C was processed using the method described in Example 47B to provide 1.82 g (99%) of the title compound. LC/MS (M+H) m/z=576; retention time 1.13 minutes.

EXAMPLE 147E dimethyl ([[(4-fluorophenyl)imino]bis{methanediyl(6-methoxybenzene-3,1-diyl)carbamoyl(2S)pyrrolidine-2,1-diyl[(2S)-3,3-dimethyl-1-oxobutane-1,2-diyl]})biscarbamate The product from Example 147D and (S)-2-(methoxycarbonylamino)-3,3-dimethylbutanoic acid were processed using the method described in Example 41 to provide 250 mg (48%) of the title compound. $^1$H NMR (400 MHz, DMSO-D6) δ 0.97 (s, 18 H) 1.88-1.95-2.03 (m, 8 H) 3.54 (s, 6 H) 3.61-3.67 (m, 2 H) 3.73-3.82 (m, 2 H) 3.79 (s, 6 H) 4.21 (d, J=8.78 Hz, 2 H) 4.51 (s, 4 H) 4.67 (dd, J=6.89, 5.15 Hz, 2 H) 6.58-6.68 (m, 2 H) 6.86-6.96 (m, 6 H) 7.16 (d, J=8.67 Hz, 2 H) 8.05 (br s, 2 H) 9.20 (br s, 2 H).

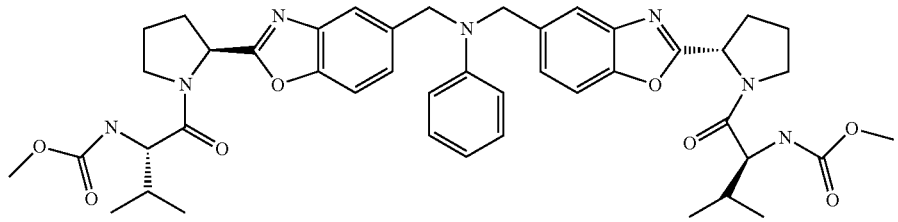

EXAMPLE 148 methyl [(1S)-1-{[(2S)-2-(5-{[({2-[(2S)-1-{(2S)-2-[(methoxycarbonyl)amino]-3-methylbutanoyl}pyrrolidin-2-yl]-1,3-benzoxazol-5-yl}methyl)(phenyl)amino]methyl}-1,3-benzoxazol-2-yl)pyrrolidin-1-yl]carbonyl}-2-methylpropyl]carbamate

EXAMPLE 148AA 4-(bromomethyl)-1-chloro-2-nitrobenzene

To a solution of (4-chloro-3-nitrophenyl)methanol (5.0 g, 26.6 mmol) in toluene (100 mL) was added phosphorus tribromide (0.879 mL, 9.32 mmol) at 40° C. The reaction mixture was stirred at 100° C. for 15 mins and partitioned between water and ethyl acetate. The organic layer was dried over Na$_2$SO$_4$, filtered, and concentrated in vacuo to give the title compound.

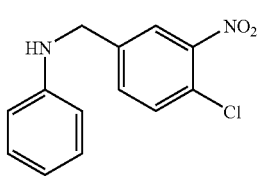 [SMILES: O=[N+]([O-])c1cc(CNc2ccccc2)ccc1Cl]

EXAMPLE 148BB

N-(4-chloro-3-nitrobenzyl)aniline

To a solution of 4-chloro-3-nitrobenzaldehyde (10.0 g, 53.9 mmol) and aniline (2.34 mL, 25.7 mmol) in ethanol (200 mL) was added acetic acid (7.35 mL, 128 mmol), followed by the portion-wise addition of sodium cyanoborohydride (4.84 g, 77 mmol). The resulting mixture was stirred at rt for 2.5 hrs and concentrated to vacuo. The residue was partitioned between ethyl acetate and saturated aq. NaHCO$_3$, and the organic layer was dried over anhydrous Na$_2$SO$_4$. The drying agent was filtered off, and solvent was removed in vacuo to give a crude product that was purified by column chromatography on silica gel using a solvent gradient of 0-1% methanol in dichloromethane to give the title compound (5.7 g, 85%).

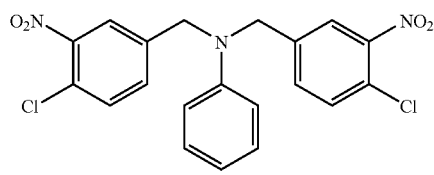 [SMILES: Nc1cc(CN(Cc2ccc(Cl)c(N)c2)c2ccccc2)ccc1Cl]

EXAMPLE 148C

N,N-bis(4-chloro-3-nitrobenzyl)aniline

To a solution of product from Example 148A (4.0 g, 15.23 mmol) and the product from Example 148B (7.63 g, 30.5 mmol) in DMF (150 mL) was added Hunig's base (8.0 mL, 45.7 mmol), and the resulting mixture was stirred at 90° C. overnight. The mixture was cooled to rt and partitioned between CH$_2$Cl$_2$ and H$_2$O, and the organic layer was dried over anhydrous Na$_2$SO$_4$. The drying agent was filtered off, and solvent was removed in vacuo to give a crude product that was purified by column chromatography on silica gel using a solvent gradient 0-5% methanol in dichloromethane to give the title compound.

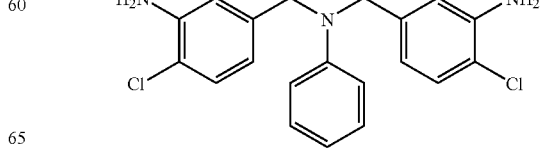

EXAMPLE 148D

N,N-bis(3-amino-4-chlorobenzyl)aniline

To a solution of product from Example 148C (0.304 g, 0.703 mmol) in EtOH (10 mL), THF (10 mL) and H$_2$O (2.5 mL) was added iron powder (0.393 g, 7.03 mmol), followed by addition of ammonium chloride (0.188 g, 3.52 mmol). The resulting mixture was stirred at 90° C. for 2 hrs and then filtered through celite and washed with ethanol. The filtrate was concentrated in vacuo, and the residue was partitioned between CH$_2$Cl$_2$ and H$_2$O, and the organic layer was dried over anhydrous Na$_2$SO$_4$. The drying agent was filtered off, and solvent was removed in vacuo to give a crude product that was purified by column chromatography on silica gel using a solvent gradient 0-0.1% MeOH in CH$_2$Cl$_2$ to afford the title compound (0.259 gm, 99%).

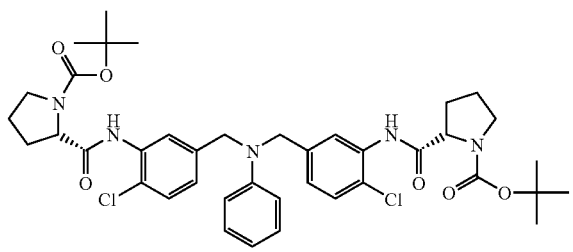

EXAMPLE 148E

(2S,2'S)-tert-butyl 2,2'-(5,5'-(phenylazanediyl)bis (methylene)bis(2-chloro-5,1-phenylene))bis (azanediyl)bis(oxomethylene)dipyrrolidine-1-carboxylate To a solution of the product from Example 148D (0.50 g, 1.343 mmol) in DMF (6.7 mL) and pyridine (6.7 mL) was added (S)-1-(tert-butoxycarbonyl)pyrrolidine-2-carboxylic acid (0.723 g, 3.36 mmol) and 1-[3-(dimethylamino-propyl]-3-ethylcarbodiimide hydrochloride (2.57 g, 13.43 mmol). The resulting mixture was stirred at rt overnight, and then partitioned between ethyl acetate and 1N aq. HCl. The organic layer was dried over anhydrous sodium sulphate, filtered, and concentrated in vacuo to give a crude product that was purified by column chromatography on silica gel using a solvent gradient of 0-2% MeOH in CH$_2$Cl$_2$ to afford the title compound (0.875 g, 85%).

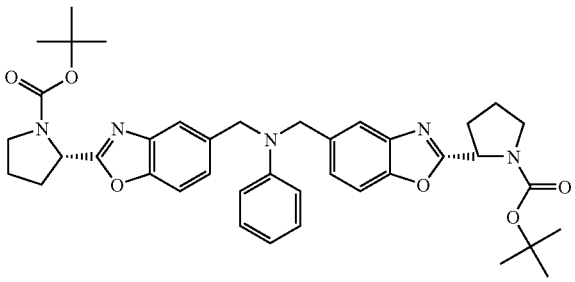

EXAMPLE 148F

(2S,2'S)-tert-butyl 2,2'-(5,5'-(phenylazanediyl)bis (methylene)bis(benzo[d]oxazole-5,2-diyl))dipyrrolidine-1-carboxylate To a solution of product from Example 148E (0.366 g, 0.477 mmol) in 1,4-dioxane (5 mL) was added 1,10-phenanthroline (0.086 g, 0.477 mmol), cesium carbonate (0.933 g, 2.86 mmol) and copper(I) iodide (0.045 g, 0.239 mmol). The resulting mixture was stirred at 110° C. for 3.5 days. The cooled mixture was partitioned between CH$_2$Cl$_2$ and H$_2$O, and the organic layer was dried over anhydrous sodium sulphate. The drying agent was filtered off, and solvent was removed in vacuo to give a crude product that was purified by column chromatography on silica gel using a solvent gradient 0-5% MeOH in CH$_2$Cl$_2$ to give the title compound (0.150 g, 45%).

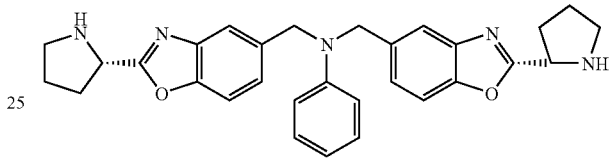

EXAMPLE 148G

N,N-bis((2-((S)-pyrrolidin-2-yl)benzo[d]oxazol-5-yl)methyl)aniline

To a solution of the product from Example 148F (0.150 g, 0.216 mmol) in CH$_3$Cl$_2$ (2 mL) was added 2,2,2-trifluoroacetic acid (1 mL, 0.216 mmol). The resulting mixture was stirred at rt for 30 mins and concentrated in vacuo. The mixture was partitioned between CH$_2$Cl$_2$ and saturated aq. NaHCO$_3$, and the organic layer was dried over anhydrous sodium sulphate. The drying agent was filtered off, and solvent was removed in vacuo to give a crude product that was purified by column chromatography on silica gel using a solvent gradient 0-14% MeOH in CH$_2$Cl$_2$ to give the title compound (44.3 mg, 42%).

EXAMPLE 148H methyl [(1S)-1-{[(2S)-2-(5-{[({2-[(2S)-1-{(2S)-2-[(methoxycarbonyl)amino]-3-methylbutanoyl}pyrrolidin-2-yl]-1,3-benzoxazol-5-yl}methyl)(phenyl)amino]methyl}-1,3-benzoxazol-2-yl)pyrrolidin-1-yl]carbonyl}-2-methylpropyl] carbamate The product from Example 148G (0.019 g, 0.038 mmol) was subjected to the procedure described in Example 24E to give the title compound as a TFA salt (6 mg). $^1$H NMR (500 MHz, DMSO-D6) δ ppm 0.84-0.93 (m, 12 H), 1.85-2.34 (m, 12 H), 3.53 (s, 6 H), 3.87-3.97 (m, 3 H), 4.05-4.14 (m, 2 H), 4.79-4.86 (m, 4 H), 5.12 (dd, 1 H), 5.16 (dd, J=7.7, 3.1 Hz, 1 H), 6.58 (t, J=7.2 Hz, 1 H), 6.71 (d, J=8.1 Hz, 2 H), 7.04-7.11 (m, 2 H), 7.28 (d, J=8.5 Hz, 2 H), 7.32-7.39 (m, 1 H), 7.50 (s, 2 H), 7.56-7.64 (m, 2 H); MS m/z 808.3 (M+H)$^+$.

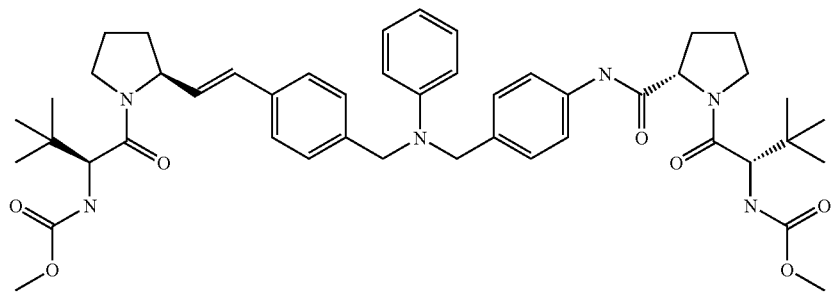 [SMILES: COC(=O)N[C@H](C(=O)N1CCC[C@H]1/C=C/c1ccc(CN(Cc2ccc(NC(=O)[C@@H]3CCCN3C(=O)[C@@H](NC(=O)OC)C(C)(C)C)cc2)c2ccccc2)cc1)C(C)(C)C]

EXAMPLE 149

N-(methoxycarbonyl)-3-methyl-L-valyl-N-(4-{[{4-[(E)-2-{(23)-1-[N-(methoxycarbonyl)-3-methyl-L-valyl]pyrrolidin-2-yl}ethenyl]benzyl}(phenyl)amino]methyl}phenyl)-L-prolinamide

EXAMPLE 149A methyl 4-((diethoxyphosphoryl)methyl)benzoate

A solution of methyl 4-(bromomethyl)benzoate (12.5 g, 54.6 mmol) in triethyl phosphite (20 mL, 114 mmol) was heated at 150° C. for 2 hours. After cooling, the solution was concentrated under vacuum. Purification by chromatography (silica gel, 0-2% methanol in dichloromethane) afforded the title compound. MS (ESI) m/z 287 (M+H)+.

EXAMPLE 149B (S,E)-tert-butyl 2-(4-(methoxycarbonyl)styryl)pyrrolidine-1-carboxylate To a solution of the product of Example 149A (4.02 g, 14.05 mmol) dissolved in THF (50 mL) and cooled to −78° C. was added lithium bis(trimethylsilyl)amide (1.0M in THF, 12.05 mL, 12.05 mmol) dropwise and the resultant solution stirred at −78° C. for 1 additional hour. Afterwards a solution of (S)-tert-butyl 2-formylpyrrolidine-1-carboxylate (2.0 g, 10.04 mmol) in THF (20 mL) was added dropwise, the cooling bath was then removed and after the reaction reached room temperature it was maintained at this temperature for an additional 3 hours. The solution had EtOAc added to it and the mixture extracted with water. The organic extract was then dried, filtered, concentrated and purified by chromatography (silica gel, 10-50% EtOAc in hexanes) to afford 2.05 g (62%) of the title compound. MS (ESI) m/z 332 (M+H)+.

EXAMPLE 149C (S,E)-tert-butyl 2-(4-(hydroxymethyl)styryl)pyrrolidine-1-carboxylate To a solution of the product of Example 149B (1.0 g, 3.02 mmol) dissolved in dichloromethane (20 mL) and cooled to −78° C. was added diisobutylaluminum hydride (1.0M in dichloromethane, 10.56 mL, 10.56 mmol) dropwise and the resultant solution stirred at −78° C. for 10 minutes, the cooling bath was then removed and after the reaction reached room temperature it was maintained at this temperature for an additional 1 hour. The solution had acetone (1 mL) added then EtOAc added to it and the mixture extracted with aqueous sodium potassium tartrate solution. The organic extract was then dried, filtered, and concentrated to afford 0.9 g (98%) of the title compound.

MS (ESI) m/z 304 (M+H)+.

EXAMPLE 149D (S,E)-tert-butyl 2-(4-(bromomethyl)styryl)pyrrolidine-1-carboxylate To a solution of the product of Example 149C (0.9 g, 2.97 mmol) dissolved in THF (50 mL) was added resin bound triphenylphosphine (5.93 mmol) and carbon tetrabromide (1.48 g, 4.45 mmol) and the resultant solution stirred at room temperature for 2 hours. The resin was then filtered off, washed with THF and the combined filtrate was then dried, filtered, and concentrated to afford the title compound. m/z 368 (M+H)+.

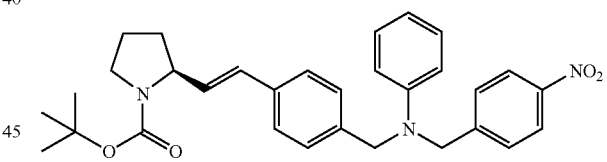

EXAMPLE 149E (S,E)-tert-butyl 2-(4-(((4-nitrobenzyl)(phenyl)amino)methyl)styryl)pyrrolidine-1-carboxylate To a solution of the product of Example 149D (1.09 g, 2.97 mmol) and N-(4-nitrobenzyl)aniline (0.677 g, 2.97 mmol) dissolved in DMF (10 mL) was added potassium carbonate (1.23 g, 8.9 mmol) and the mixture heated at 50° C. for 1 hour. After cooling, the solution had dichloromethane added to it and the mixture extracted with water. The organic extract was then dried, filtered, concentrated and purified by chromatography (silica gel, 0-2% methanol in dichloromethane) to afford 0.85 g (56%) of the title compound. MS (ESI) m/z 514 (M+H)+.

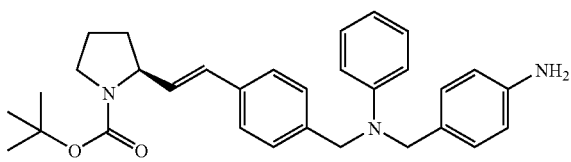 [SMILES: CC(C)(C)OC(=O)N1CCC[C@H]1/C=C/c1ccc(CN(Cc2ccc([N+](=O)[O-])cc2)c2ccccc2)cc1]

EXAMPLE 149F (S,E)-tert-butyl 2-(4-(((4-aminobenzyl)(phenyl)amino)methyl)styryl)pyrrolidine-1-carboxylate To a solution of the product of Example 149E (0.8 g, 1.56 mmol) dissolved in ethanol (20 mL) was cooled in an ice bath to 0° C., then bismuth(III) chloride (1.47 g, 4.67 mmol) was added followed by the portionwise addition of sodium borohydride (943 mg, 24.92 mmol) and warming the solution to room temperature for 20 minutes. The methanol was added and the solid removed by filtration, the filtrate concentrated to an oil, which was redissolved with dichloromethane and extracted with aqueous sodium bicarbonate. The organic solution was then dried, filtered, and concentrated to afford the title compound. m/z 484 (M+H)⁺.

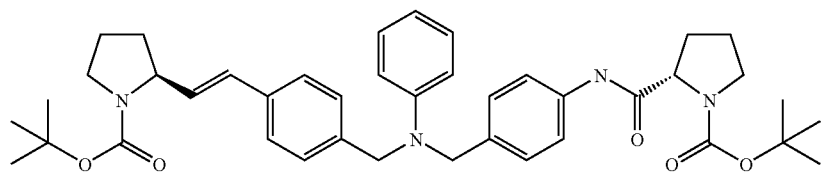 [SMILES: CC(C)(C)OC(=O)N1CCC[C@H]1/C=C/c1ccc(CN(Cc2ccc(NC(=O)[C@@H]3CCCN3C(=O)OC(C)(C)C)cc2)c2ccccc2)cc1]

EXAMPLE 149G (S)-tert-butyl 2-(4-(((4-((E)-2-((S)-1-(tert-butoxycarbonyl)pyrrolidin-2-yl)vinyl)benzyl)(phenyl)amino)methyl)phenylcarbamoyl)pyrrolidine-1-carboxylate The product from Example 149F (700 mg, 1.45 mmol) and (S)-1-(tert-butoxycarbonyl)pyrrolidine-2-carboxylic acid (374 mg, 1.74 mmol) were processed using the method described in Example 43 to afford 240 mg (23%) of the title compound. ¹H NMR (500 MHz, DMSO-D6) δ ppm 9.92 (s, 1H), 7.52 (d, J=8.4 Hz, 2H), 7.34 (d, J=7.9 Hz, 2H), 7.18 (m, 4H), 7.07 (m, 2H), 6.64 (d, J=8.1 Hz, 2H), 6.55 (t, J=7.7 Hz, 1H), 6.31 (d, J=15.6 Hz, 1H), 6.14 (dd, J=15.5, 6.5 Hz, 1H), 4.63 (s, 2H), 4.60 (s, 2H), 4.22 (m, 1H), 4.17 (m, 1H), 3.38 (m, 2H), 3.28 (m, 2H), 1.85 (m, 8H), 1.38 (s, 9H), 1.30 (s, 9H).

EXAMPLE 149H (S)-N-(4-((phenyl(4-((E)-2-((S)-pyrrolidin-2-yl)vinyl)benzyl)amino)methyl)phenyl)pyrrolidine-2-carboxamide To a solution of the product of Example 149G (50 mg, 0.073 mmol) dissolved in dichloromethane (0.3 mL) was added trifluoroacetic acid (2.7 mL) and the resultant solution stirred at room temperature for 20 minutes. The solution was then concentrated under vacuum, the residue dissolved in a chloroform/isopropanol mixture and extracted with aqueous sodium bicarbonate, the organic solution was then dried, filtered, and concentrated to afford the title compound. m/z 481 (M+H)⁺.

EXAMPLE 149I

N-(methoxycarbonyl)-3-methyl-L-valyl-N-(4-{[{4-[(E)-2-{(2S)-1-[N-(methoxycarbonyl)-3-methyl-L-valyl]pyrrolidin-2-yl}ethenyl]benzyl}(phenyl)amino]methyl}phenyl)-L-prolinamide The product from Example 149H (35 mg, 0.73 mmol) and (S)-2-(methoxycarbonylamino)-3,3-dimethylbutanoic acid (33.1 mg, 0.175 mmol) were processed using the method described in Example 43 to afford 33 mg (55%) of the title compound. ¹H NMR (500 MHz, DMSO-D6) δ ppm 9.98 (s, 1H), 7.50 (d, J=8.4 Hz, 2H), 7.28 (d, J=8.3 Hz, 2H), 7.17 (m, 4H), 7.06 (m, 3H), 6.63 (m, 2H), 6.55 (t, J=7.3 Hz, 1H), 6.37 (d, J=15.7 Hz, 1H), 6.22 (m, 1H), 6.17 (dd, J=16.0, 6.3 Hz, 1H), 4.63 (m, 1H), 4.61 (s, 2H), 4.58 (s, 2H), 4.42 (m, 1H), 4.19 (m, 2H), 3.77 (m, 1H), 3.70 (m, 1H), 3.63 (m, 2H), 3.52 (s, 6H), 2.16 (m, 2H), 1.96 (m, 2H), 1.84 (m, 4H), 0.95 (s, 9H), 0.93 (s, 9H).

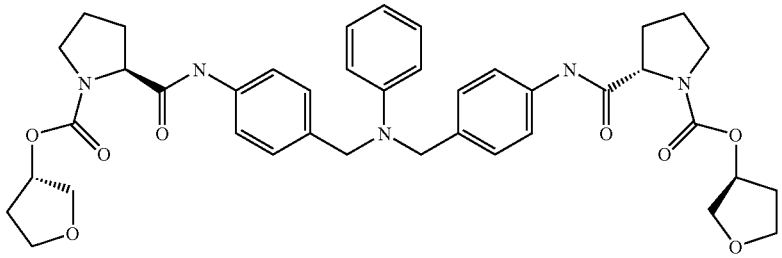 [SMILES: O=C(Nc1ccc(CN(Cc2ccc(NC(=O)[C@@H]3CCCN3C(=O)O[C@H]3CCOC3)cc2)c2ccccc2)cc1)[C@@H]1CCCN1C(=O)O[C@H]1CCOC1]

EXAMPLE 150 di[(3S)-tetrahydrofuran-3-yl](2S,2'S)-2,2'-[(phenylimino)bis(methanediylbenzene-4,1-diylcarbamoyl)]dipyrrolidine-1-carboxylate The product of Example 1D (25 mg, 0.050 mmol), and (S)-2,5-dioxopyrrolidin-1-yl tetrahydrofuran-3-yl carbonate (25.3 mg, 0.111 mmol) were dissolved in dichloromethane (3 mL) then added Hunig's base (0.026 mL, 0.151 mmol) and stirred the mixture at room temperature for 18 hours. The solution had dichloromethane added to it and the mixture extracted with water. The organic extract was then dried, filtered, concentrated and purified by chromatography (silica gel, 0-10% methanol in dichloromethane) to afford 28 mg (77%) of the title compound. $^1$H NMR (500 MHz, DMSO-D6) δ ppm: 9.96 (s, 2H), 7.48 (d, J=8.4 Hz, 4H), 7.17 (d, J=8.1 Hz, 4H), 7.06 (t, J=8.0 Hz, 2H), 6.64 (d, J=8.4 Hz, 2H), 6.55 (t, J=7.3 Hz, 1H), 5.05 (m, 2H), 4.59 (s, 4H), 4.24 (m, 2H), 3.73 (m, 8H), 3.40 (m, 6H), 2.15 (m, 4H), 1.95 (m, 2H), 1.83 (m, 4H).

The title compounds of Examples 1, 2, 3, 6, 7, 9, 10, 11, 12, 13, 14, 17, 18, 20, 21, 22, 23, 28, 31, 34, 35, 39, 42, 43, 50, 53, 54, 55, 56, 57, 58, 60, 64, 65, 66, 67, 69, 70, 71, 72, 73, 74, 75, 76, 77, 78, 81, 82, 83, 84, 85, 86, 87, 88, 89, 90, 92, 95, 96, 98, 99, 101, 102, 103, 104, 105, 106, 110, 113, 114, 115, 116, 117, 119, 120, 121, 123, 124, 125, 127, 128, 131, 132, 133, 136, 137, 138, 142, 143, and 145 showed an EC50 of less than 1 nM in HCV 1b-Con-1 replicon assay; the title compounds of Examples 8, 15, 24, 25, 33, 36, 37, 38, 45, 46, 47, 48, 49, 51, 52, 61, 62, 91, 93, 94, 100, 108, 111, 112, 118, 129, 130, 134, 135, 139, 140, and 146 showed an EC50 of from 1 nM to 10 nM in HCV 1b-Con-1 replicon assay; the title compounds of Examples 4, 5, 16, 19, 26, 27, 40, 41, 44, 59, 63, 79, 80, 107, 109, 122, 126, 141, 149, and 150 showed an EC50 of from 10 nM to 100 nM in HCV 1b-Con-1 replicon assay; and the title compounds of Examples 29, 30, 32, 68, 97, 144, 147, and 148 showed an EC50 of from 100 nM to 250 nM in HCV 1b-Con-1 replicon assay. Each compound's anti-HCV activity was determined by measuring the activity of the luciferase reporter gene in the replicon in the presence of 5% FBS. The luciferase reporter gene was placed under the translational control of the poliovirus IRES instead of the HCV IRES, and HuH-7 cells were used to support the replication of the replicon.

The following compounds were similarly prepared according to the above-described Schemes and Examples:

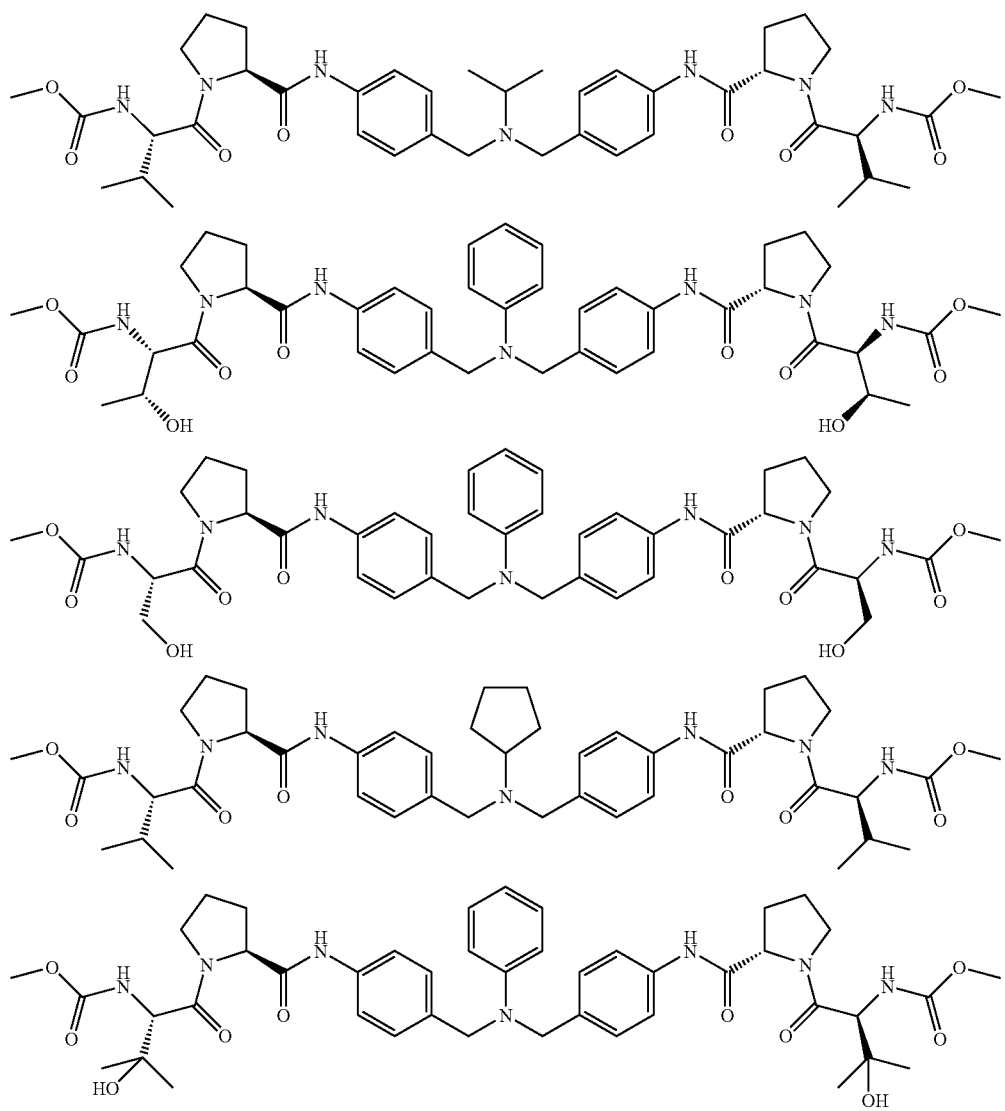

-continued
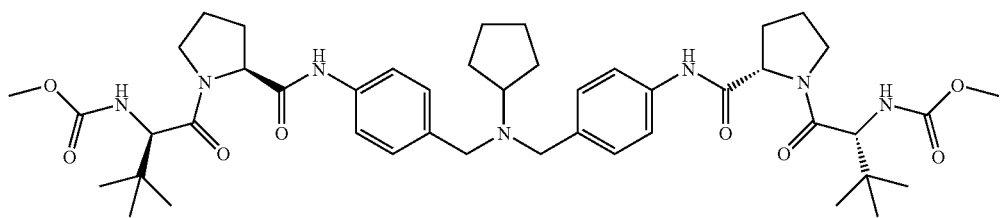
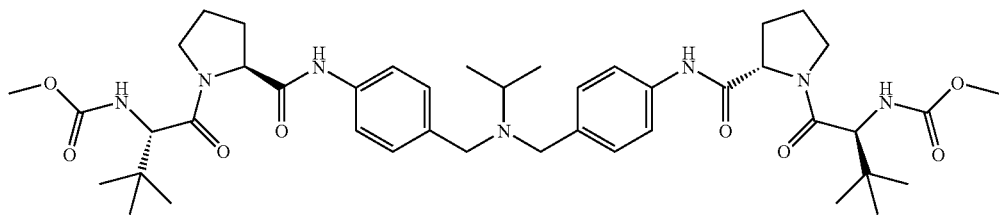
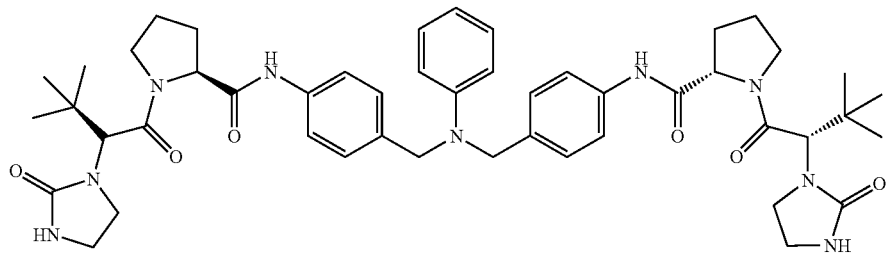
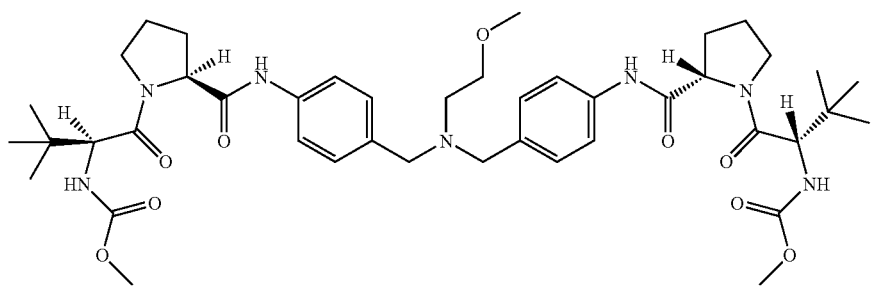
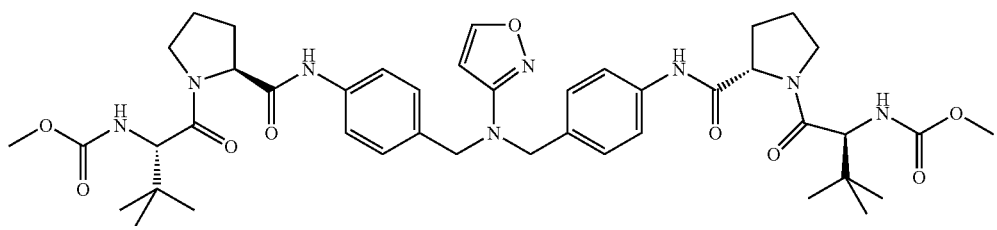
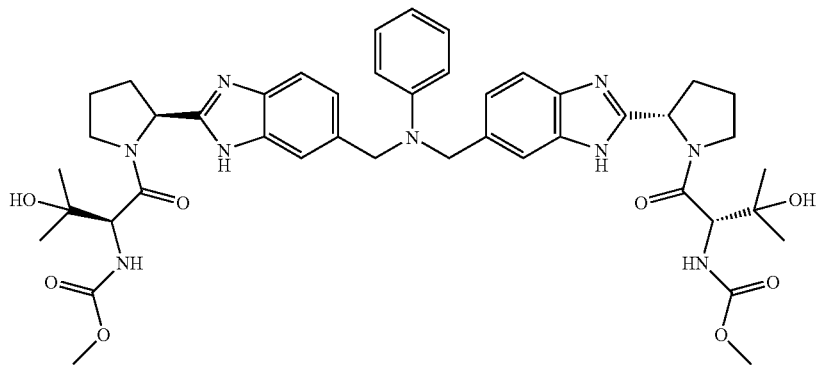

-continued
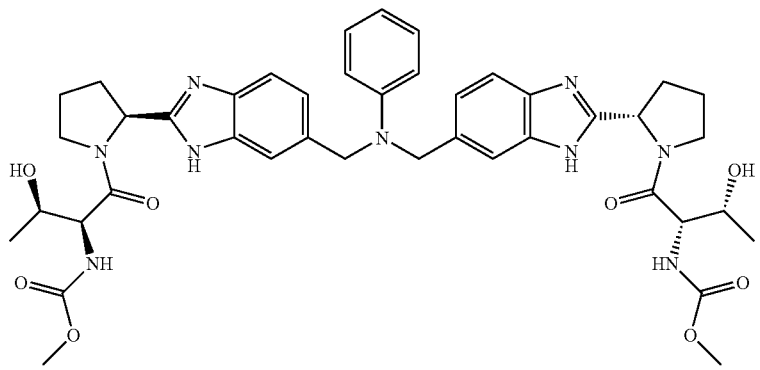
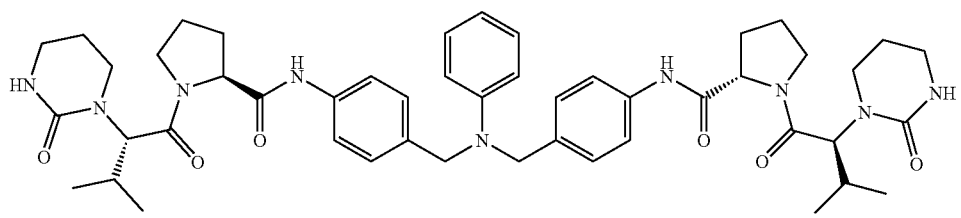
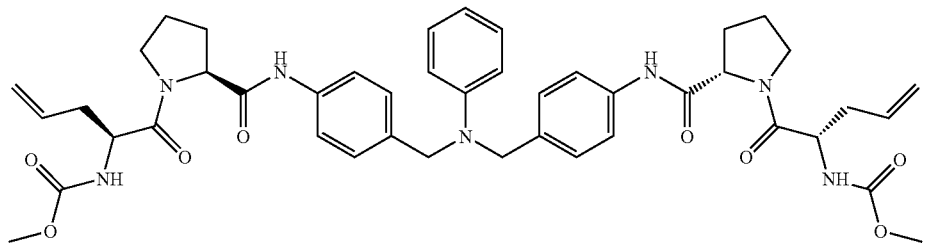
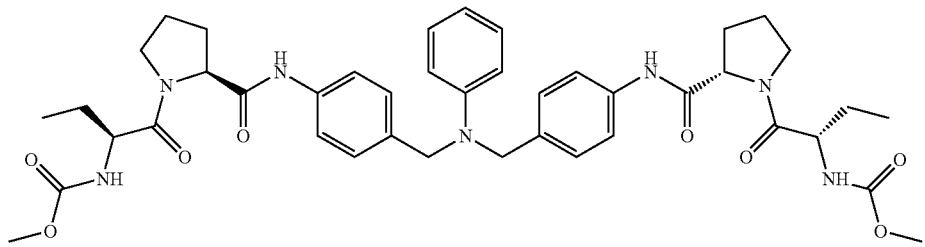
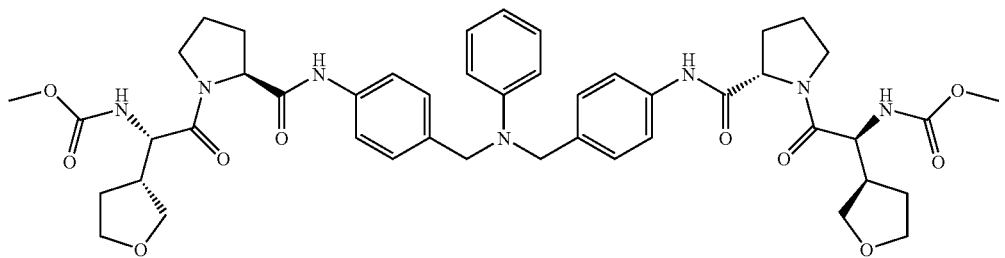
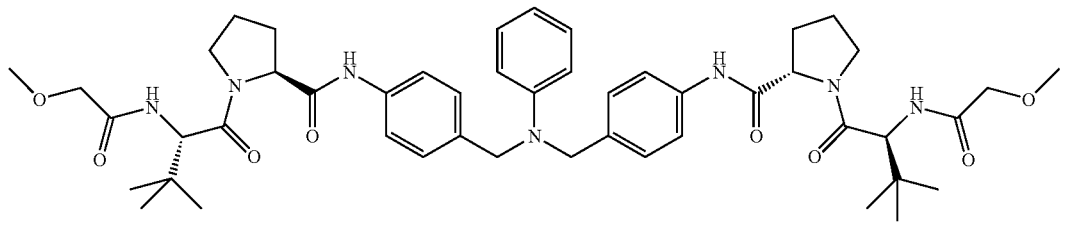

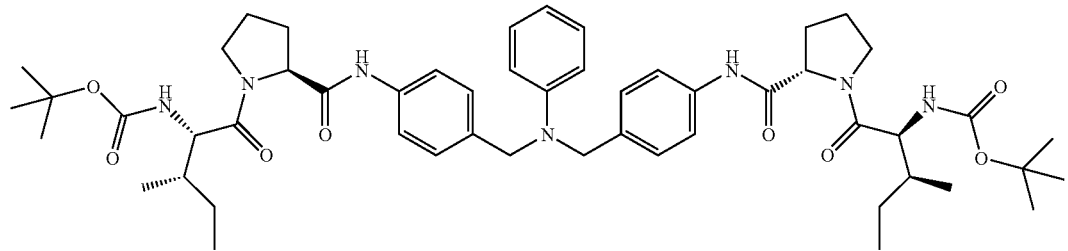
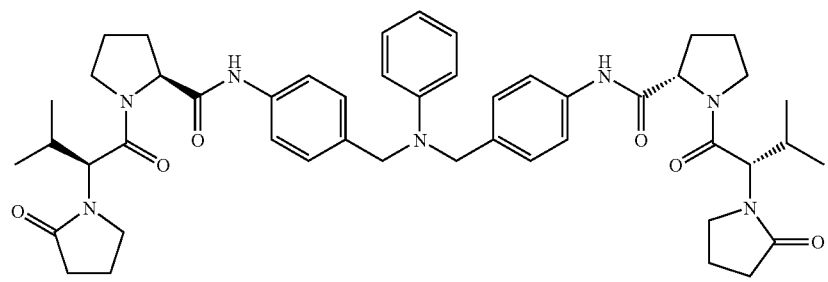
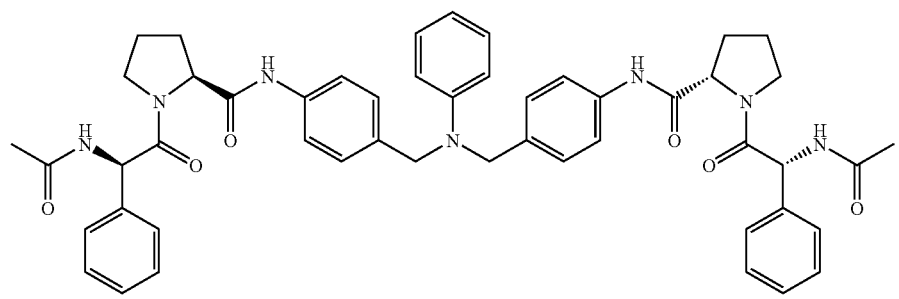
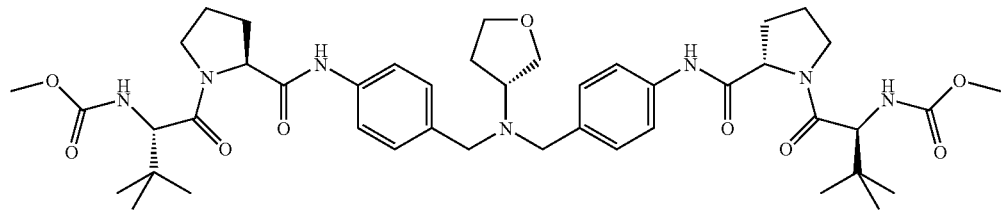
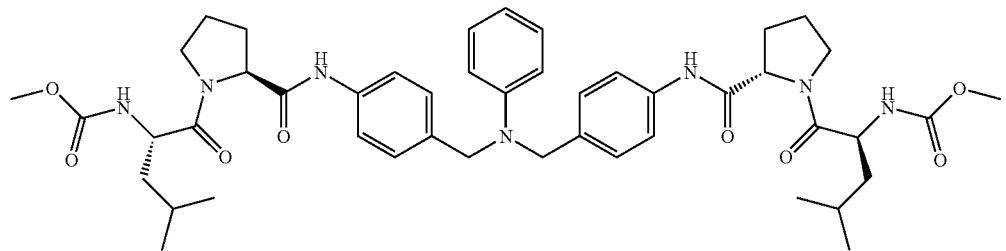
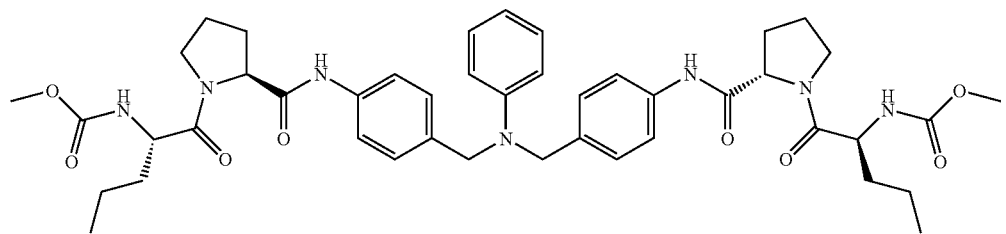

-continued
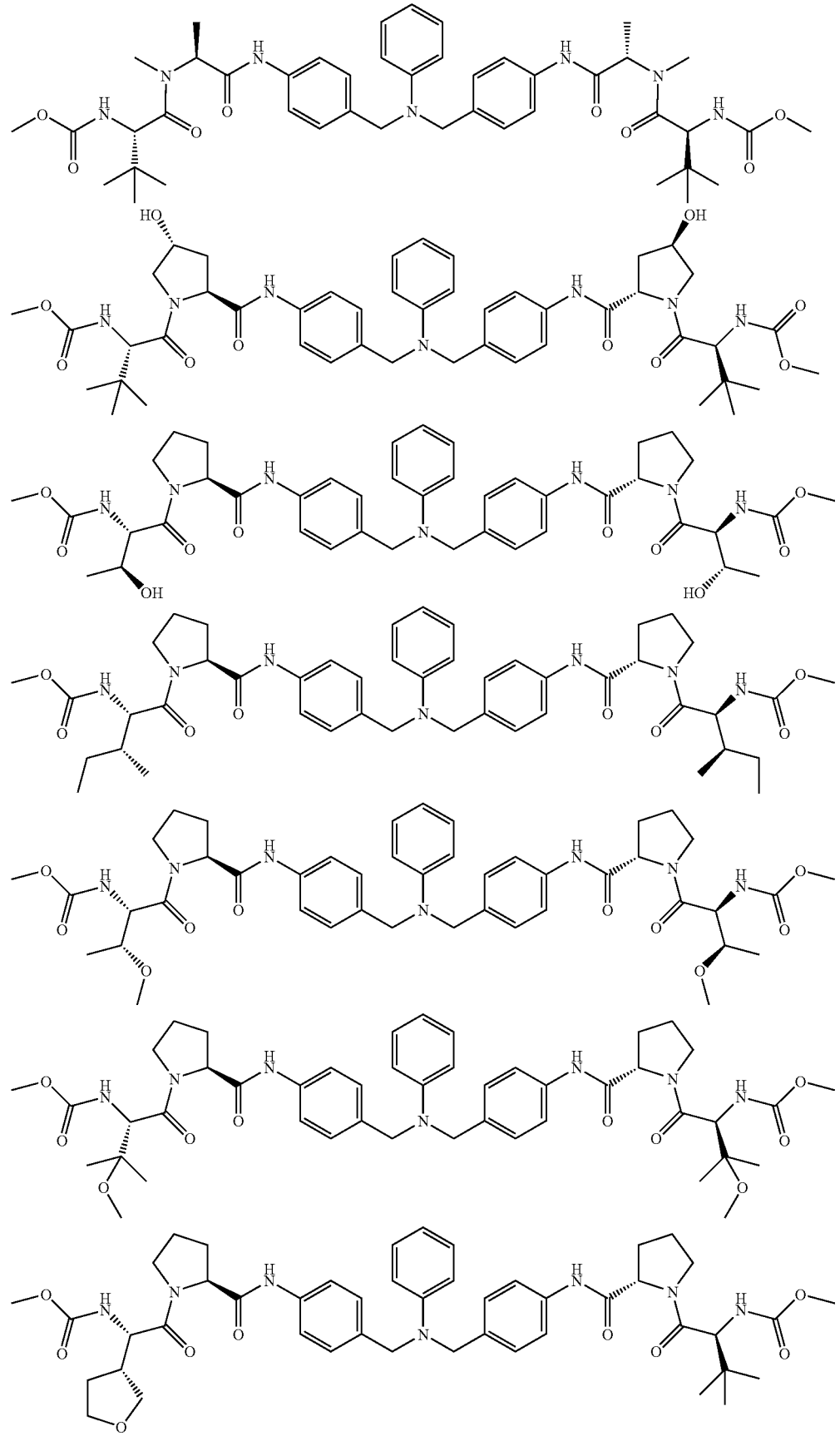

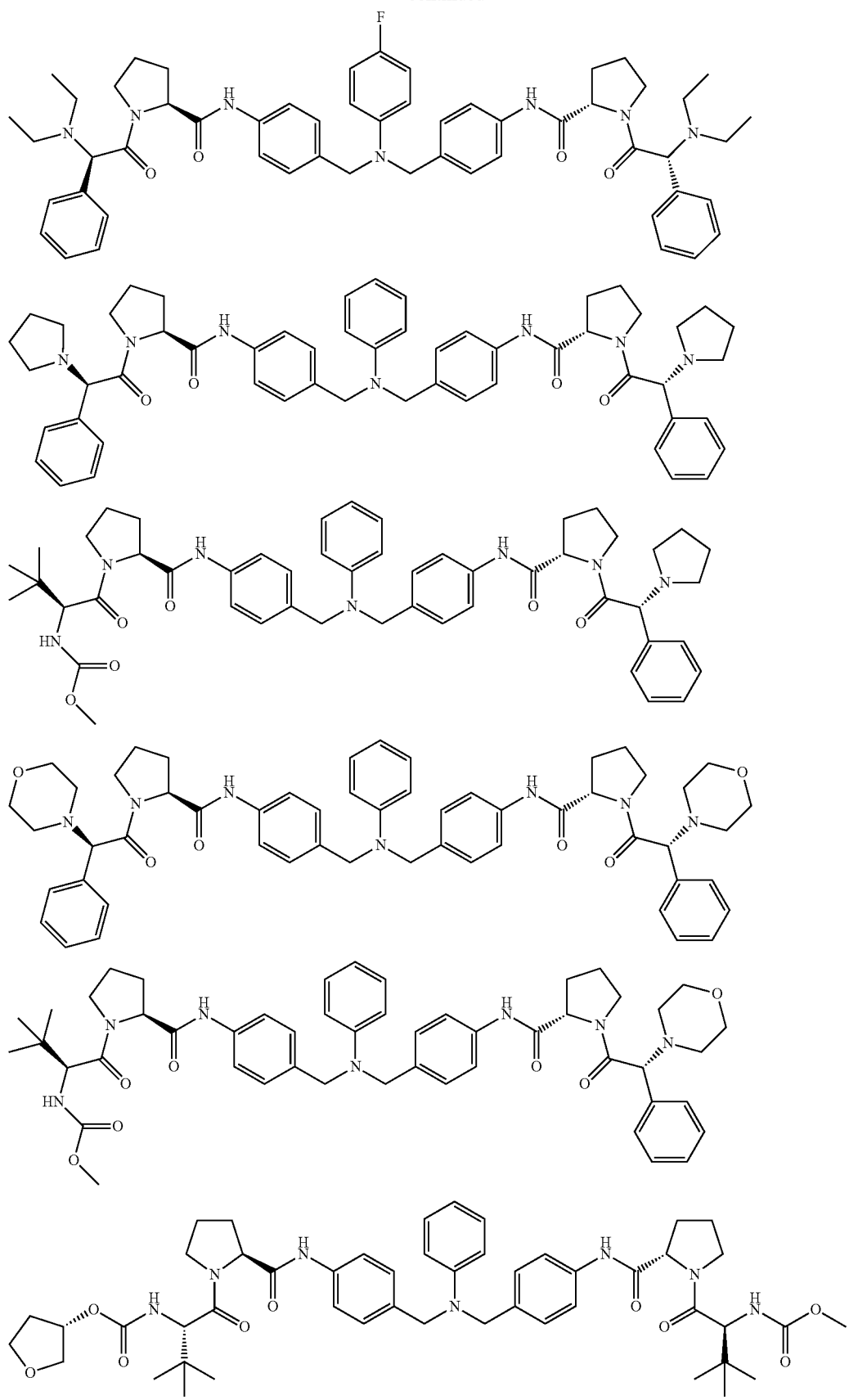

-continued
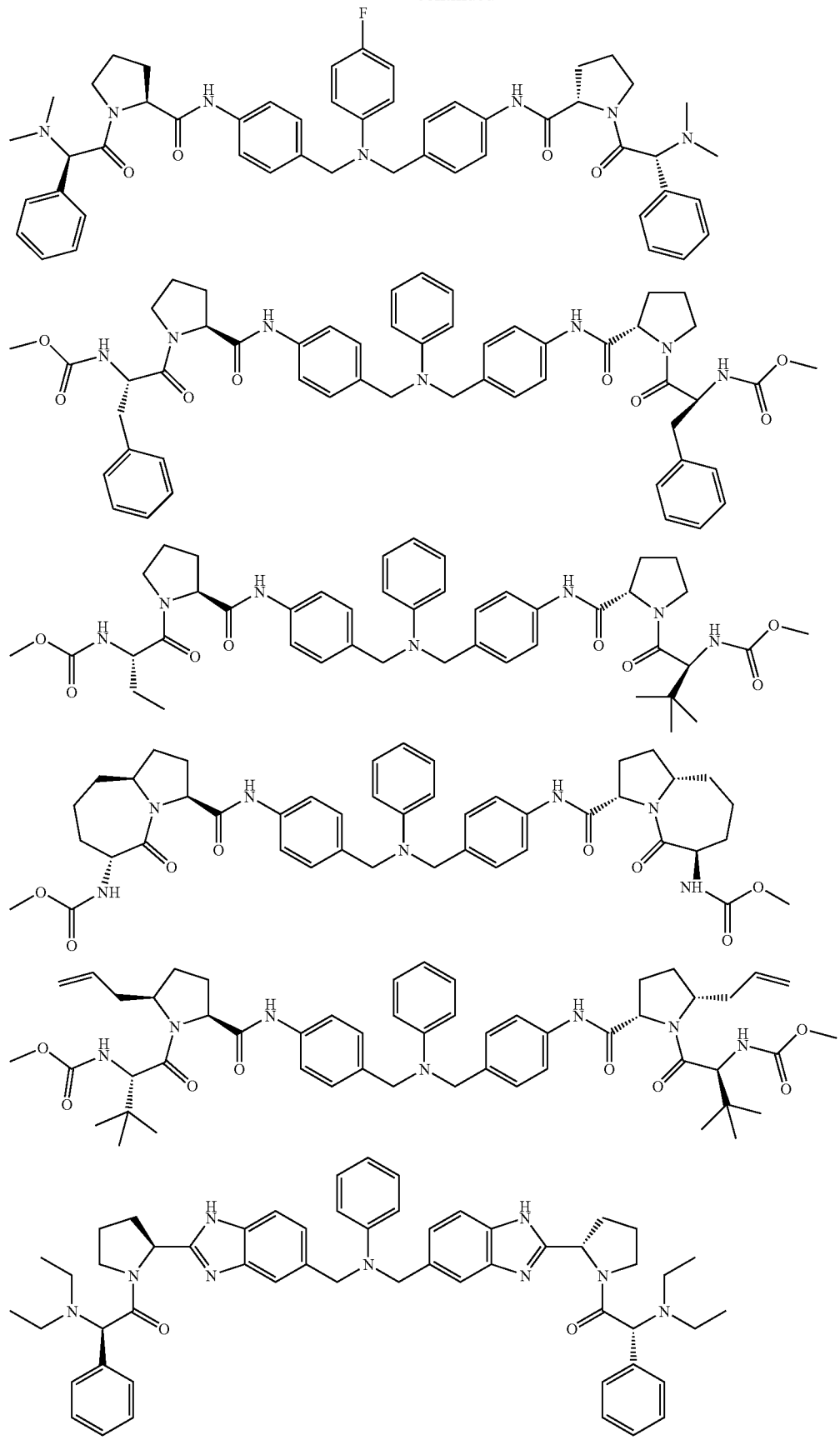

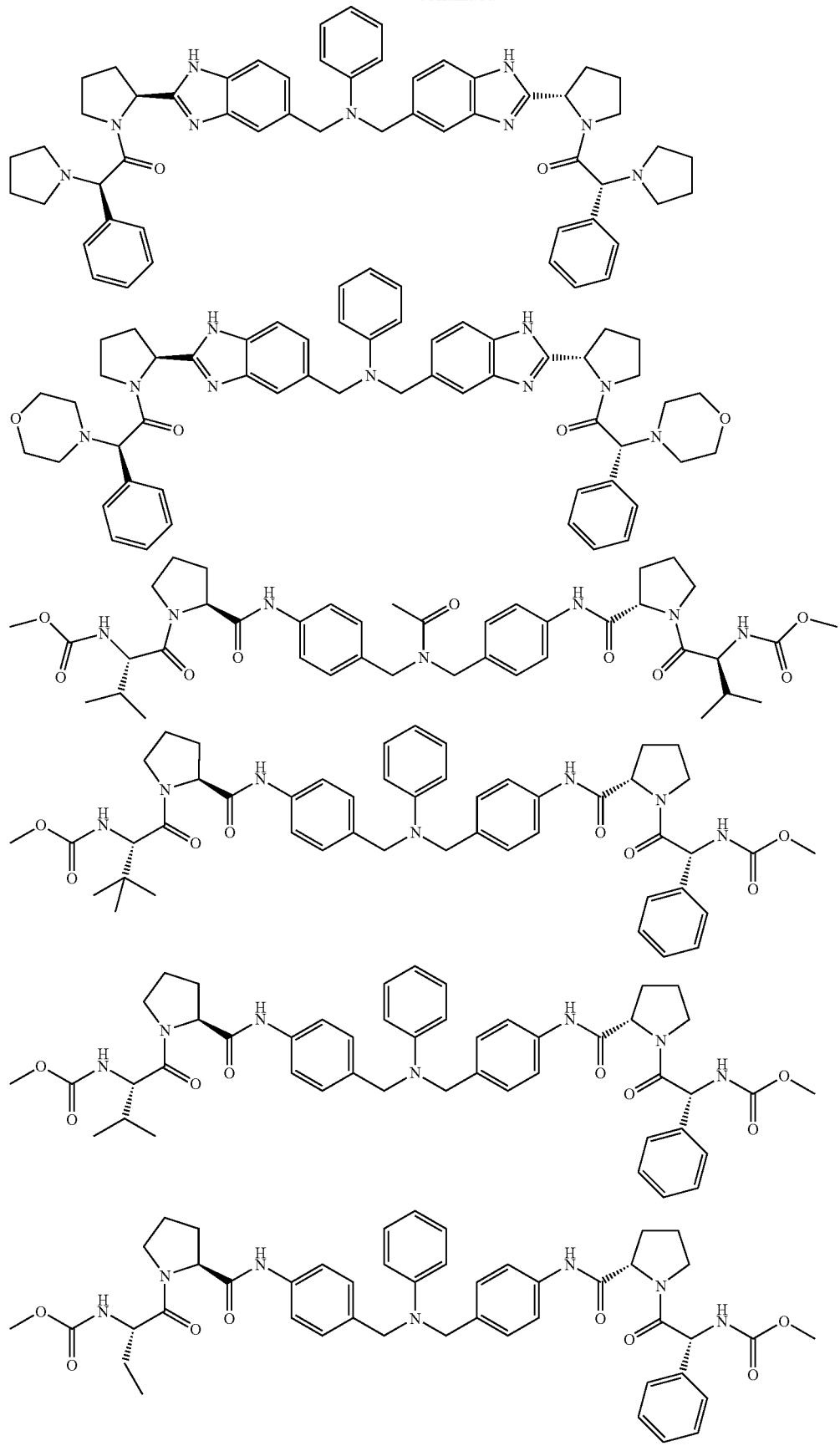

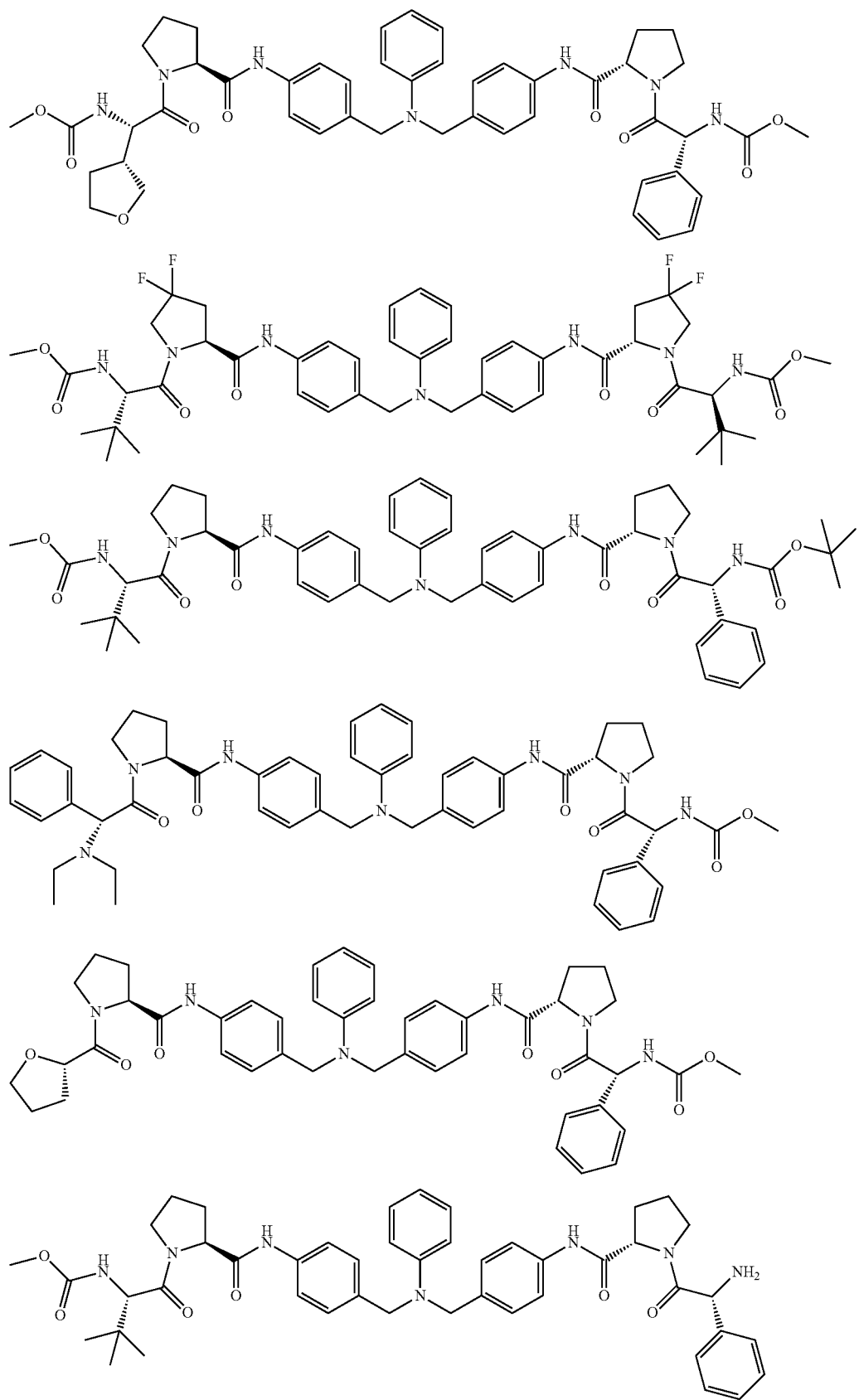

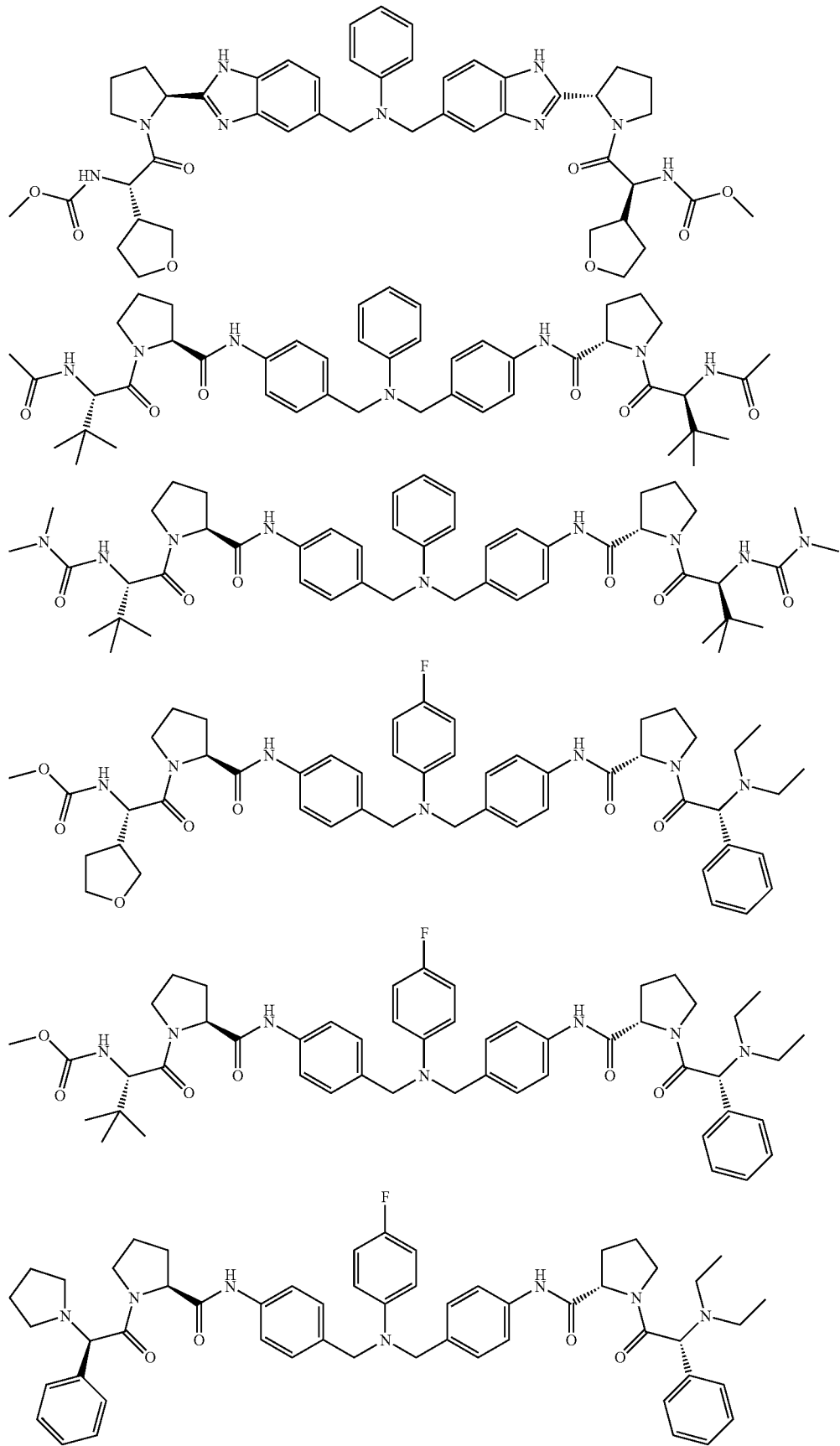

-continued
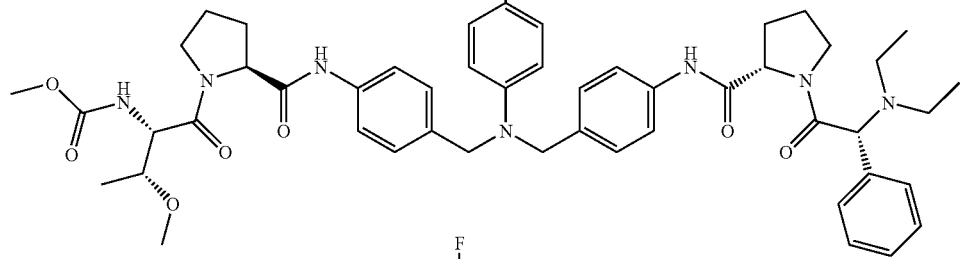
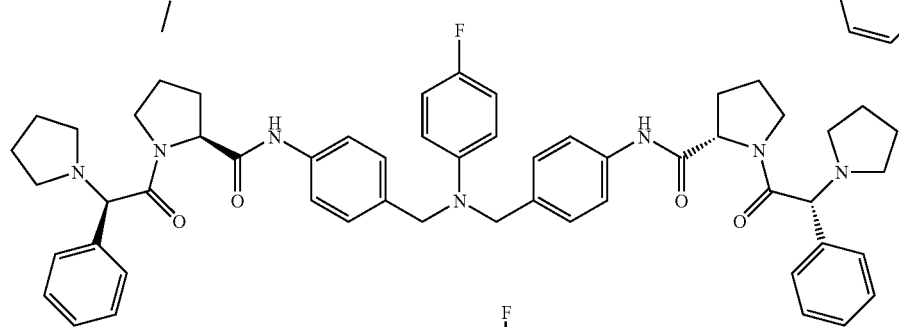
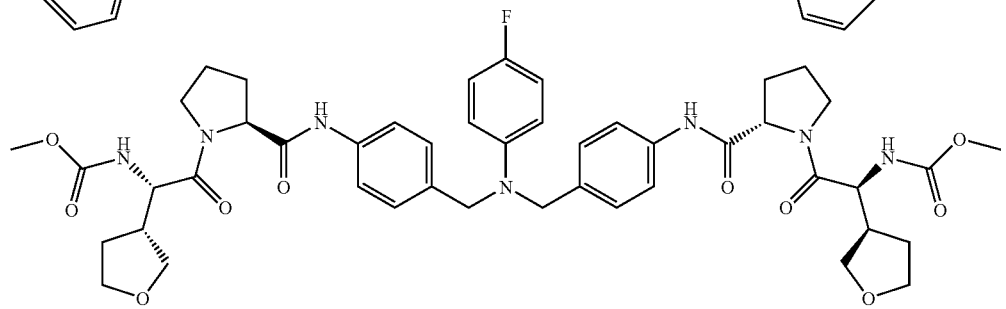
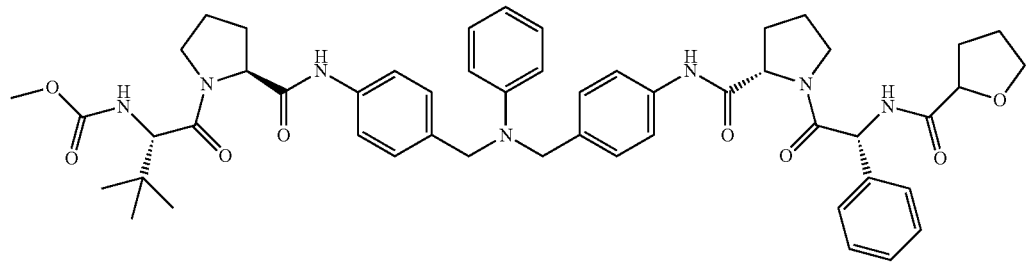
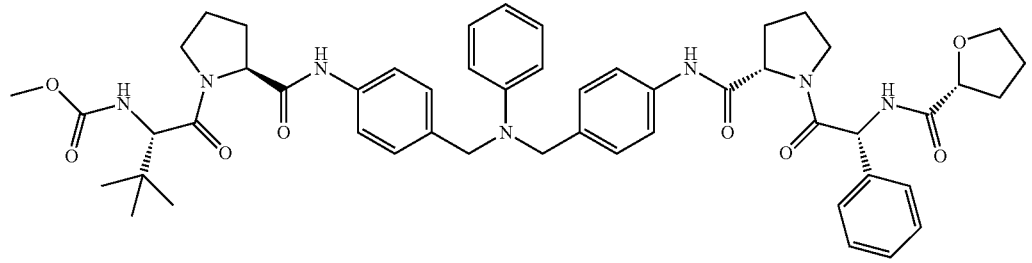
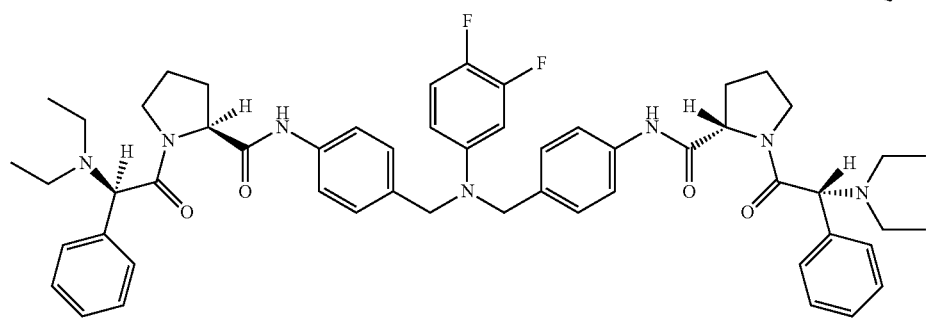

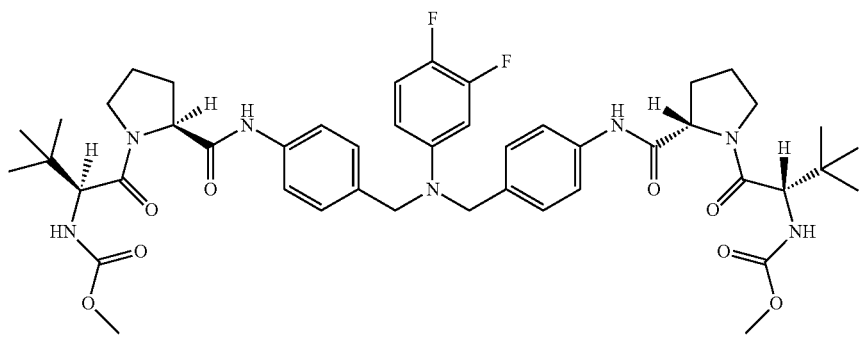
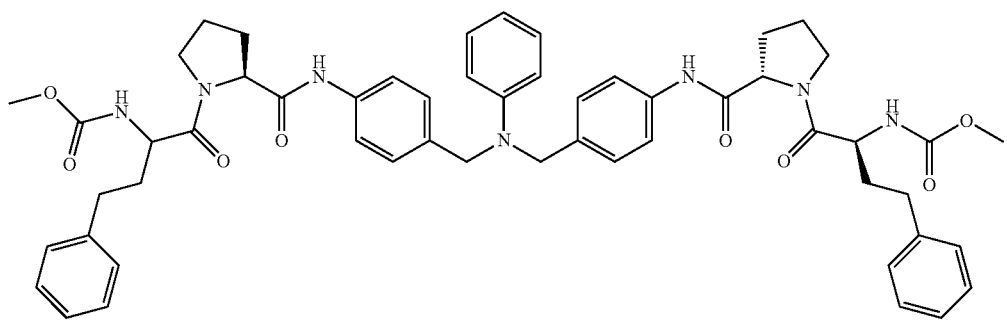
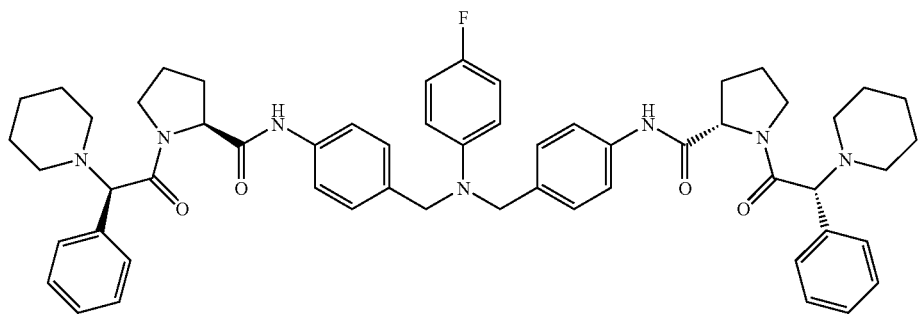
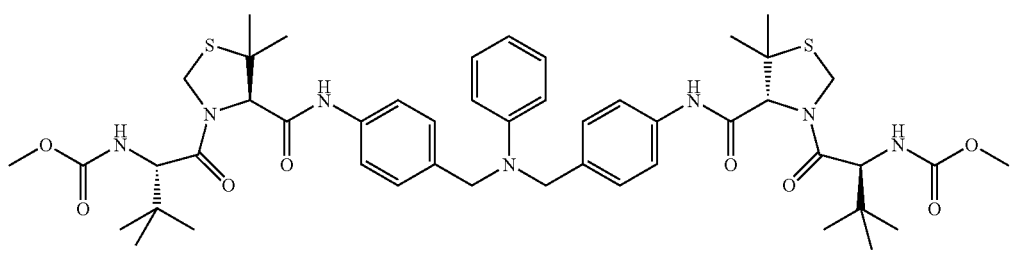
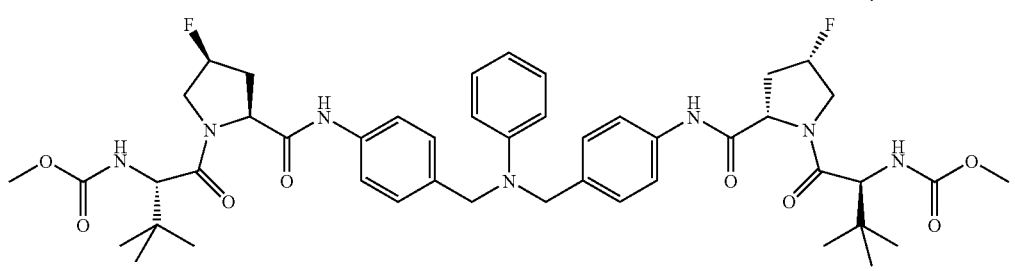

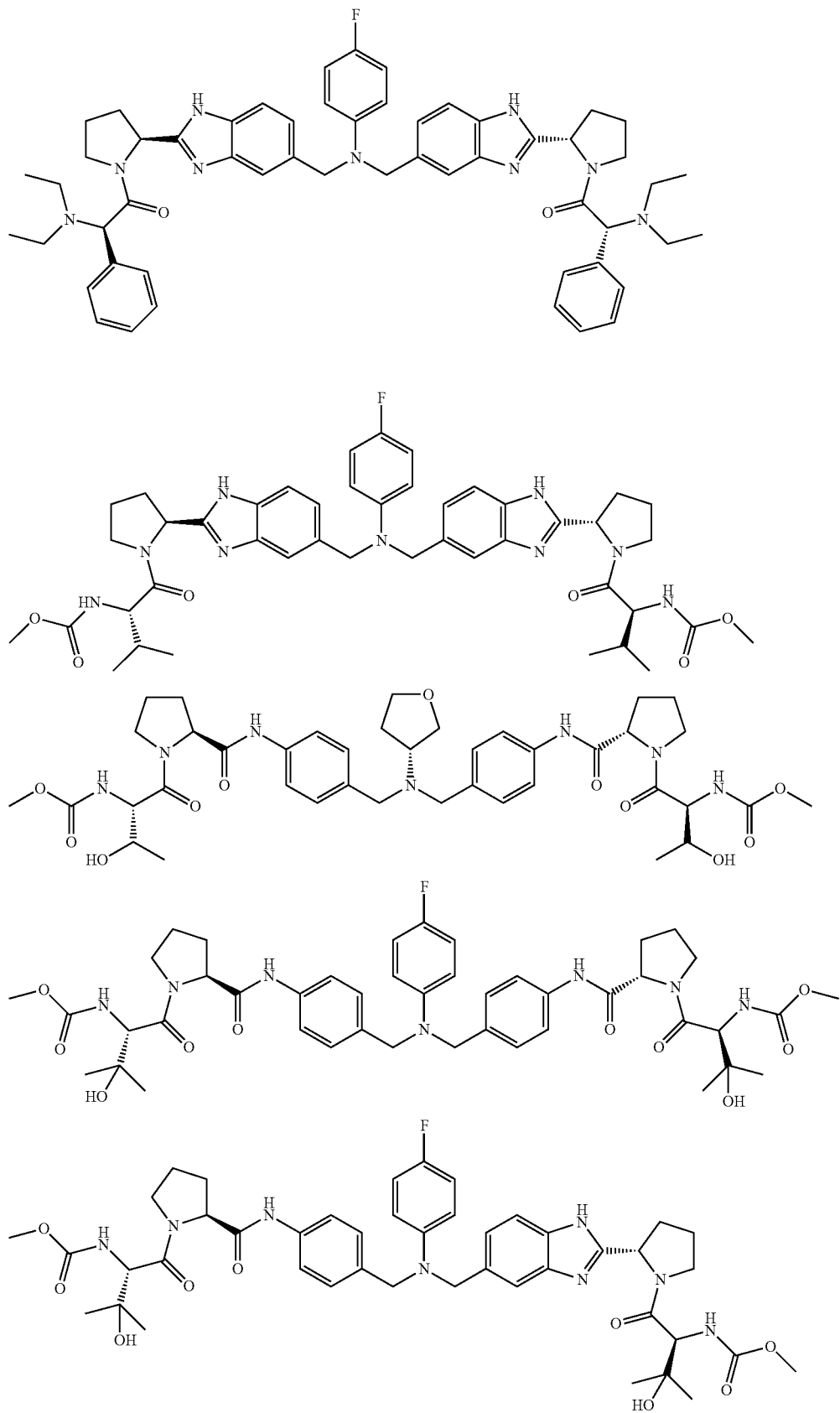

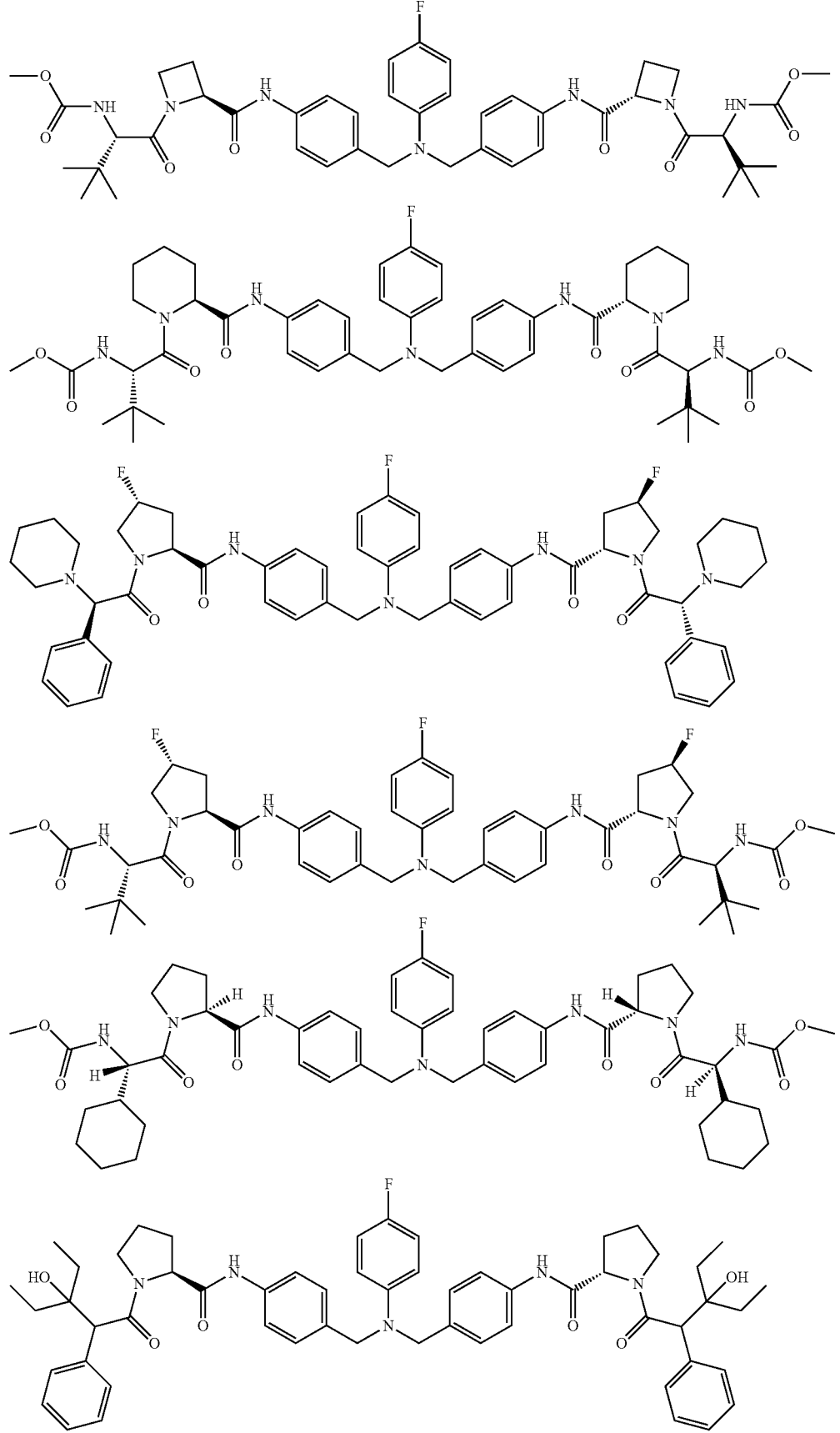

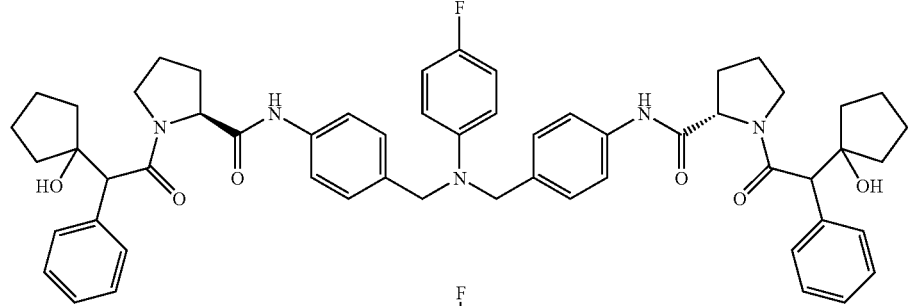
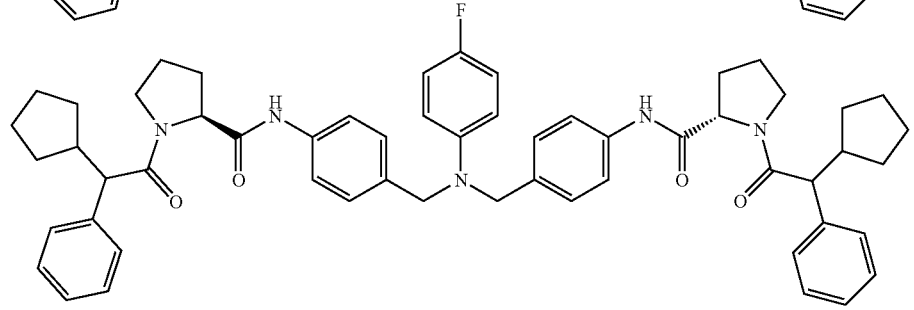
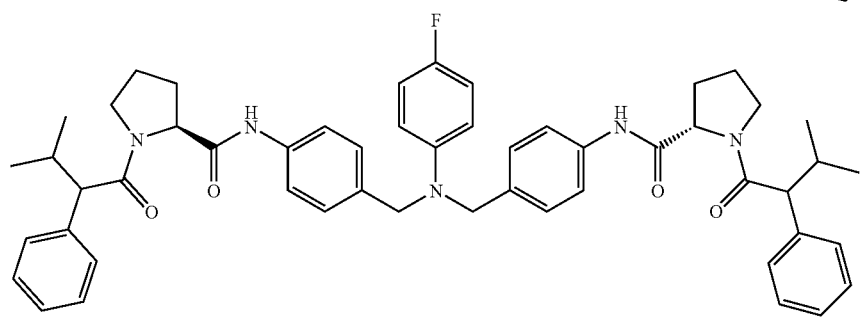
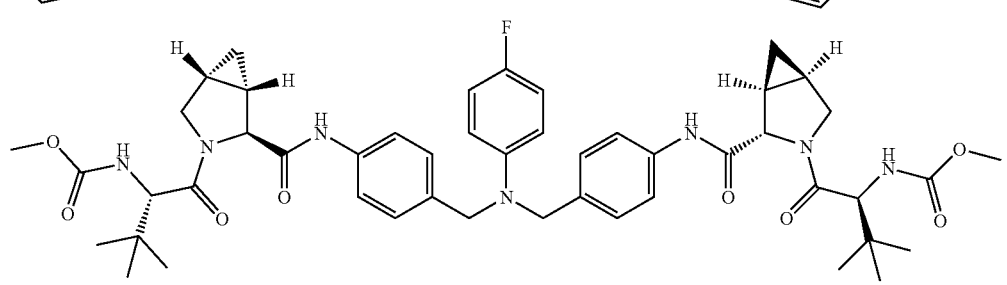
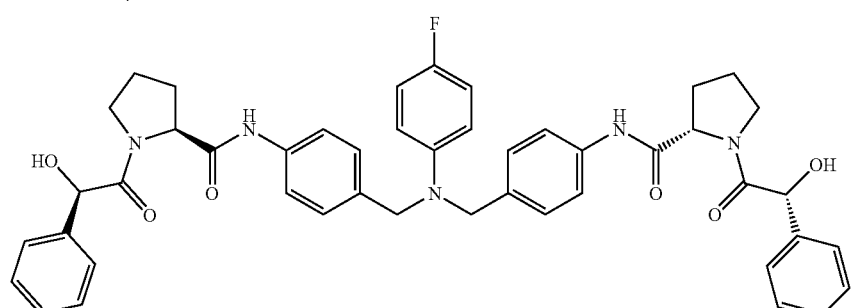
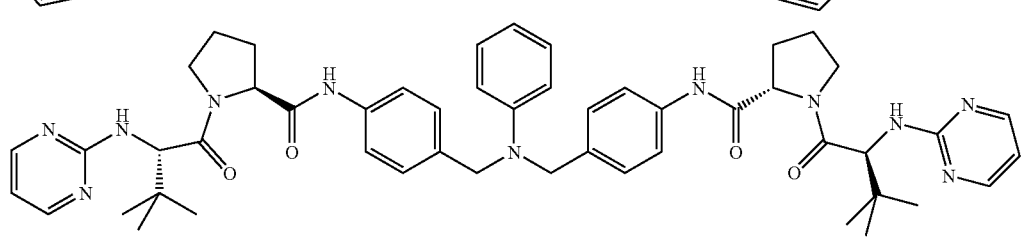

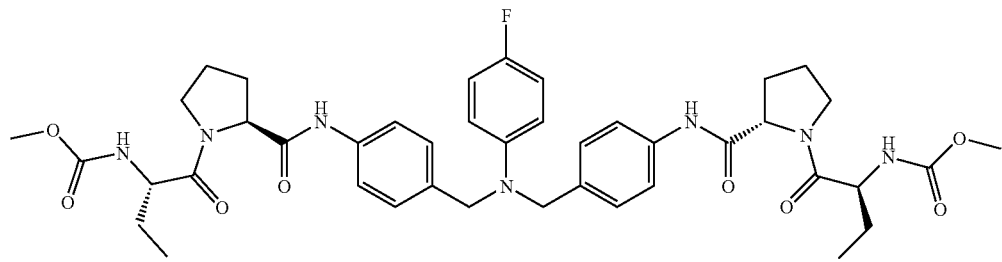
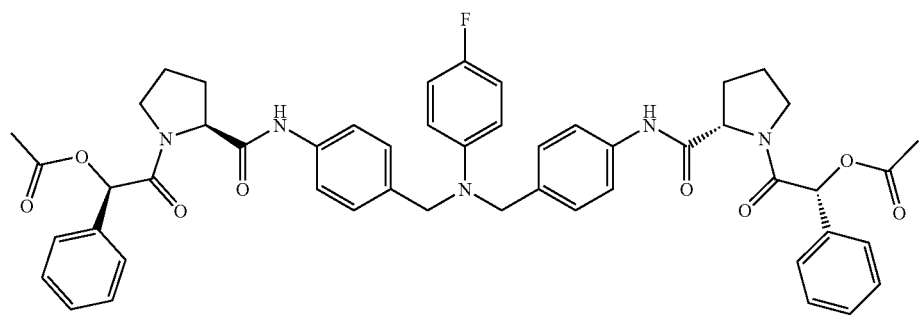
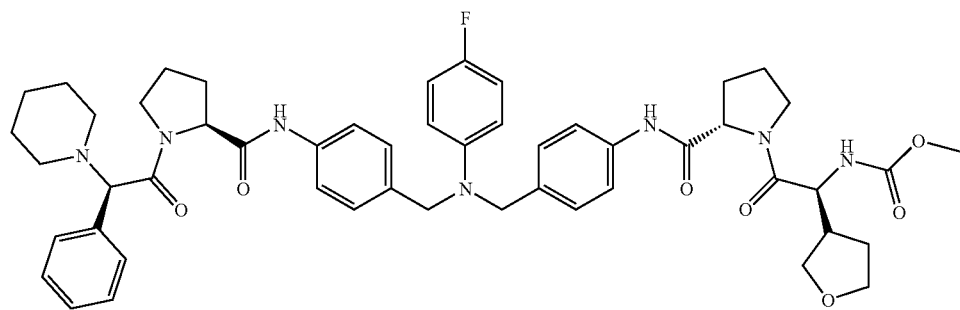
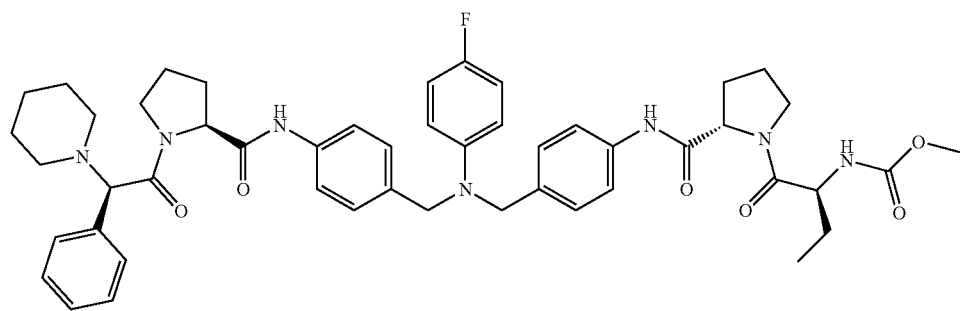
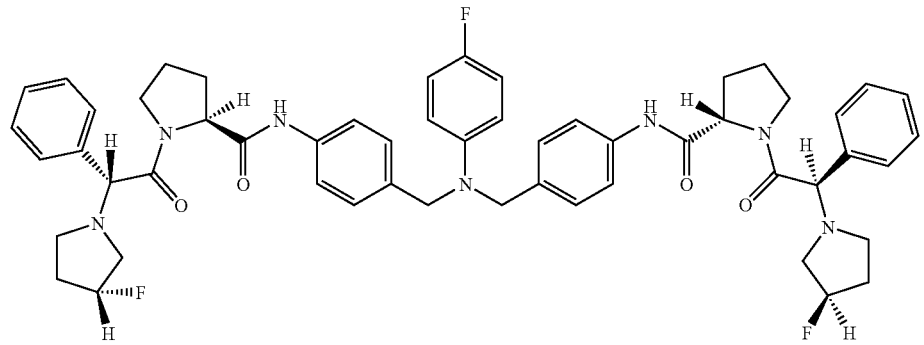

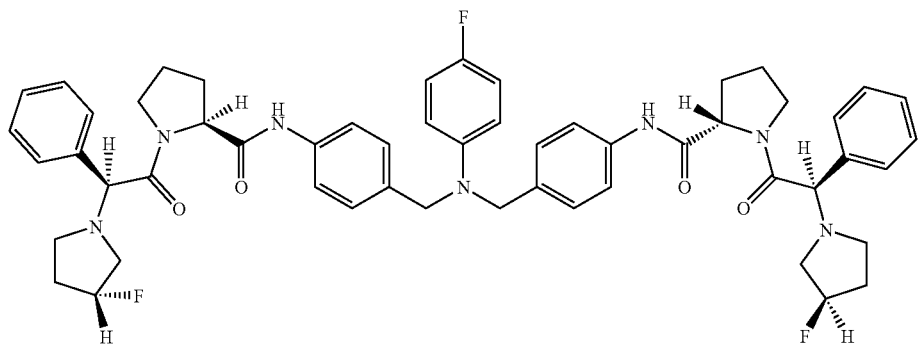
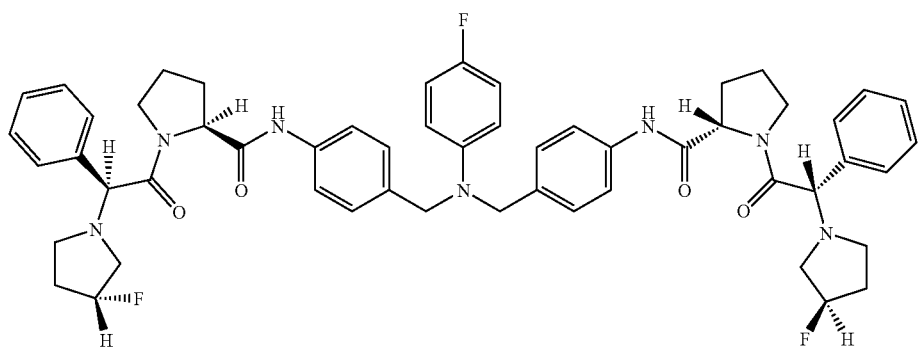
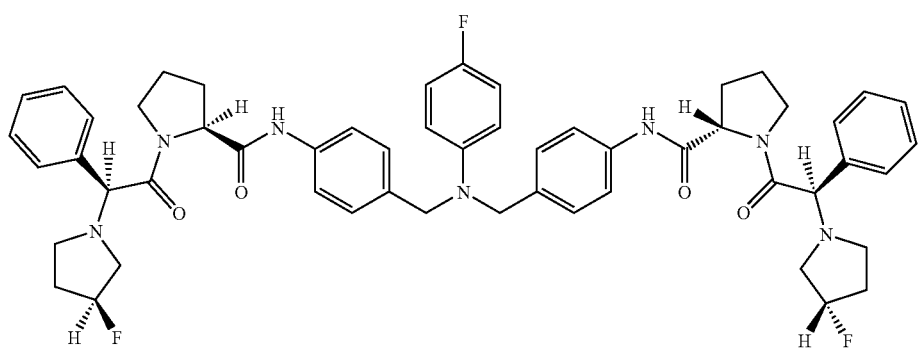
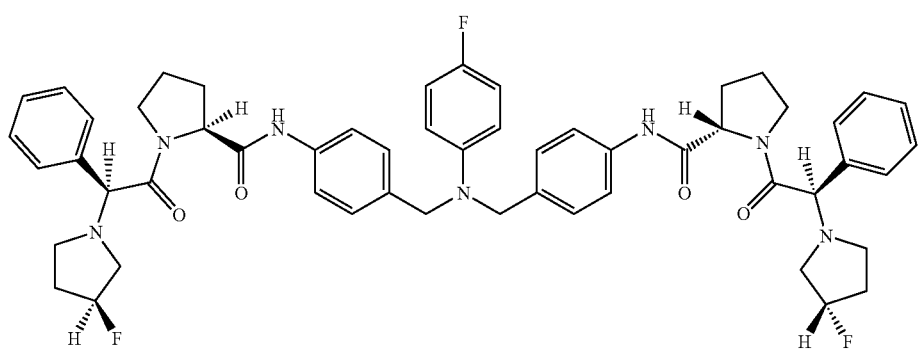
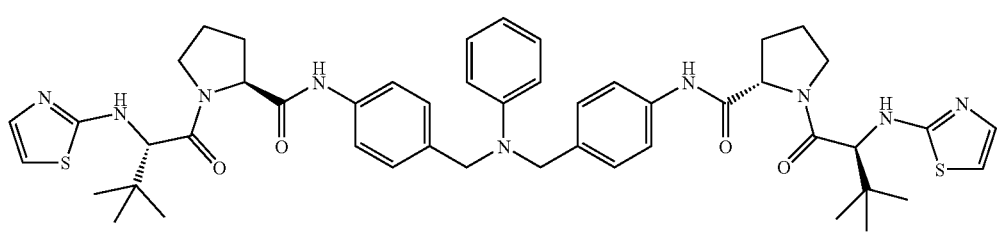

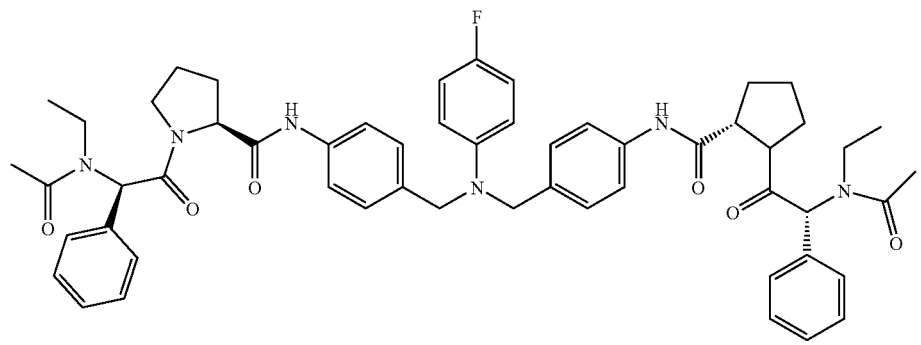
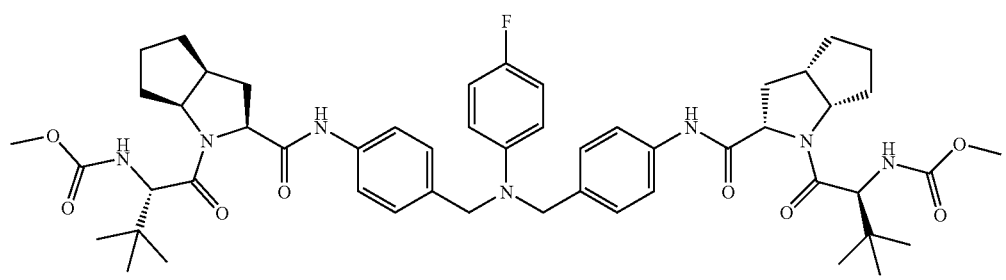
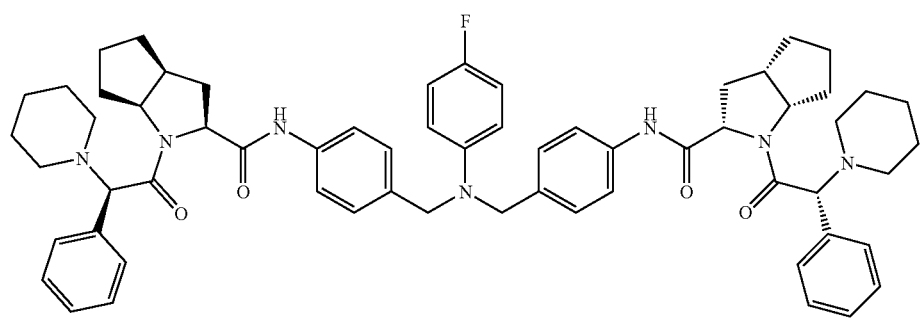
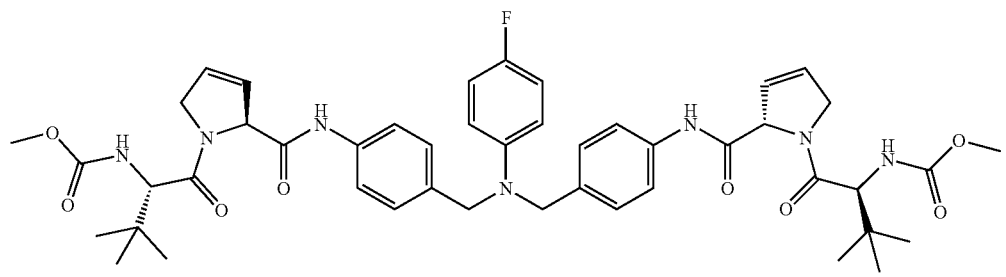
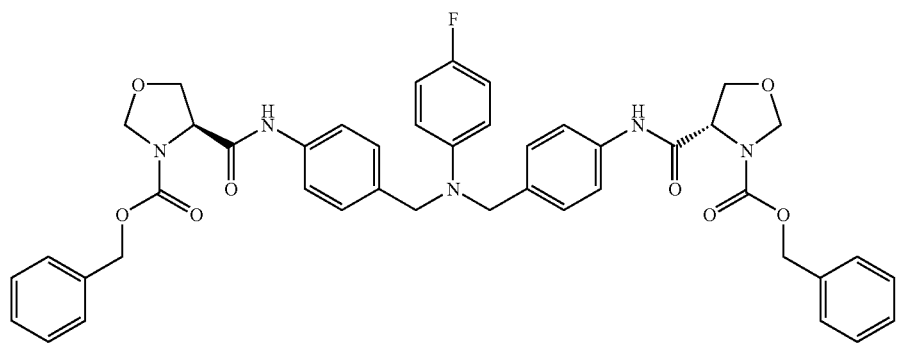

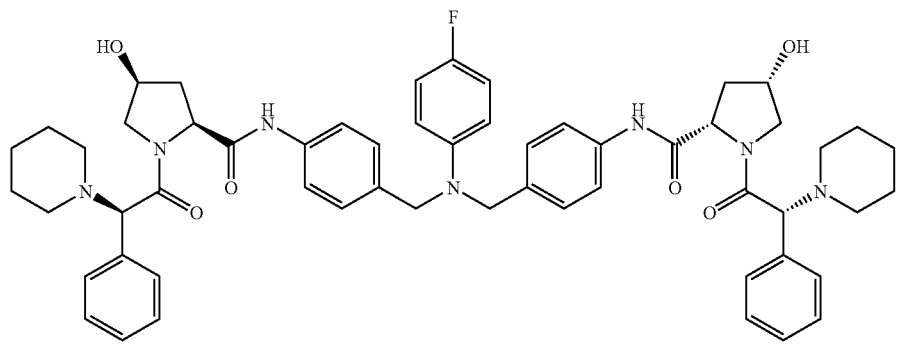
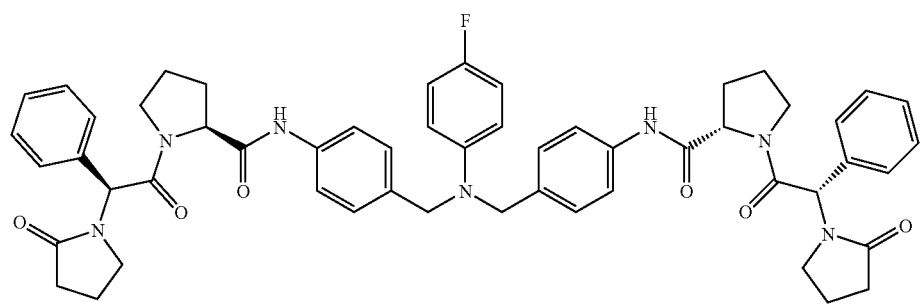
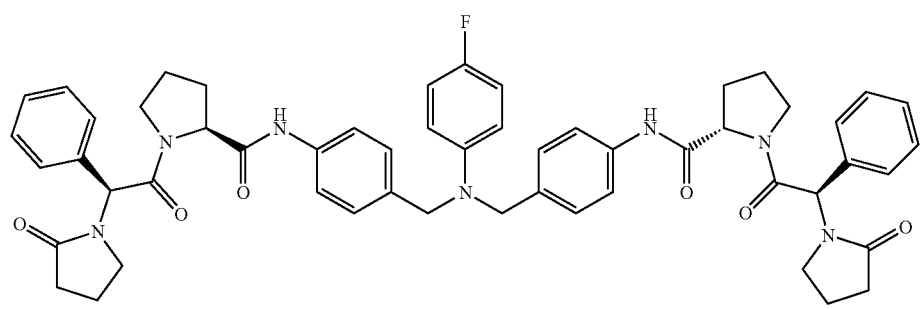
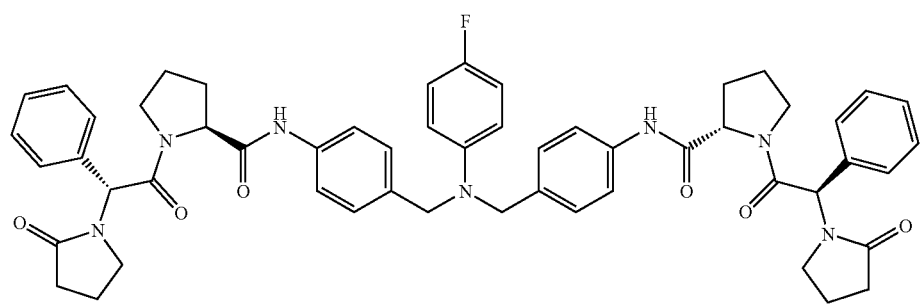
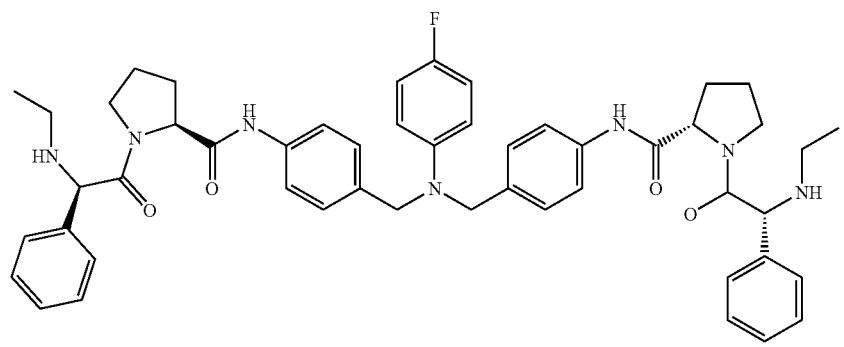

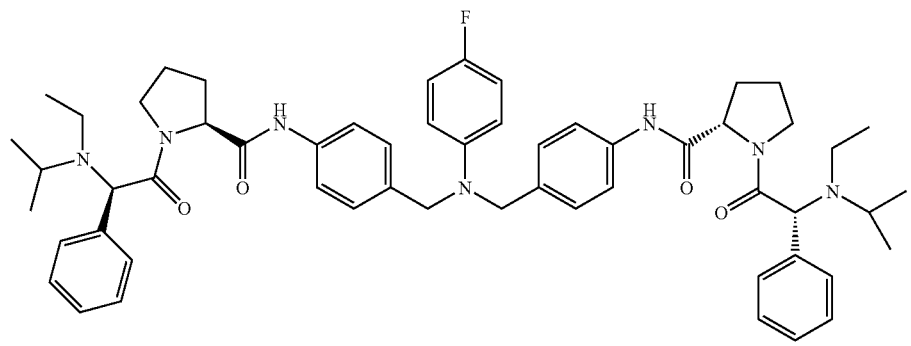
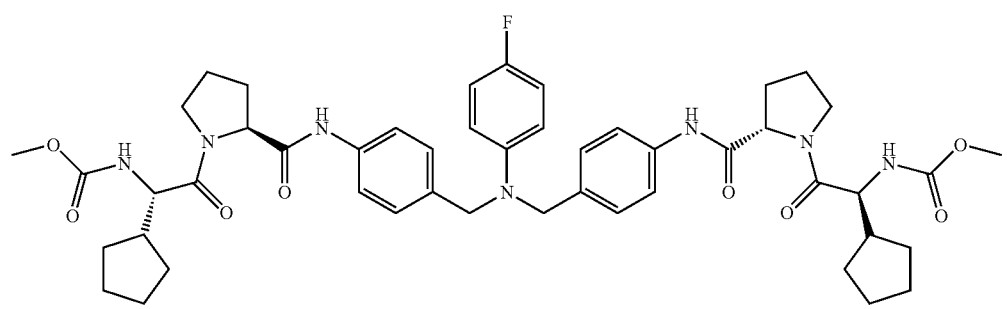
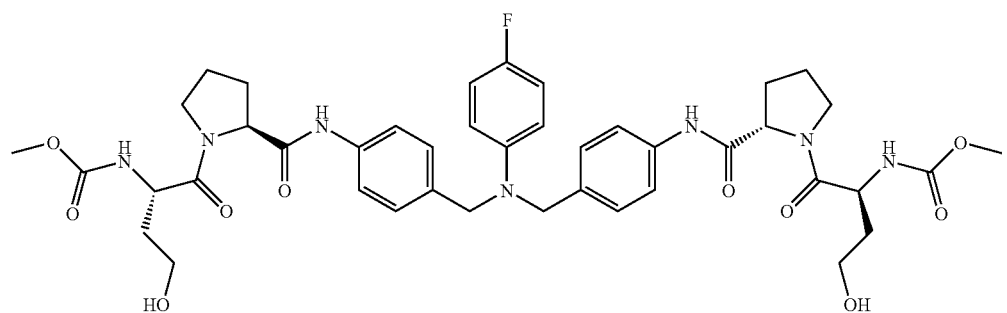
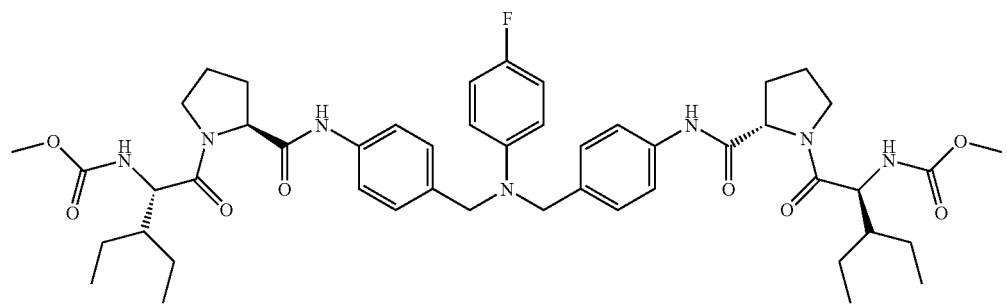
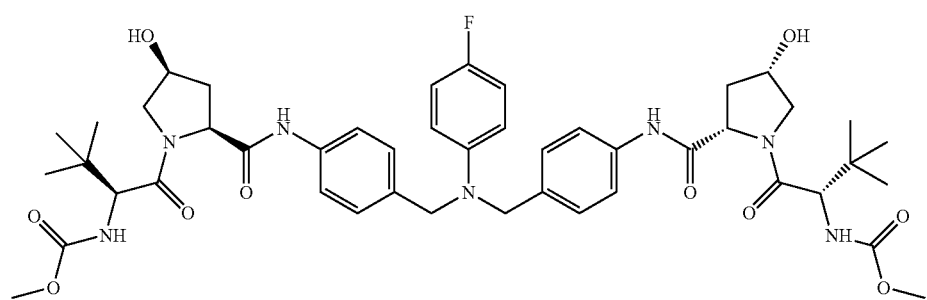

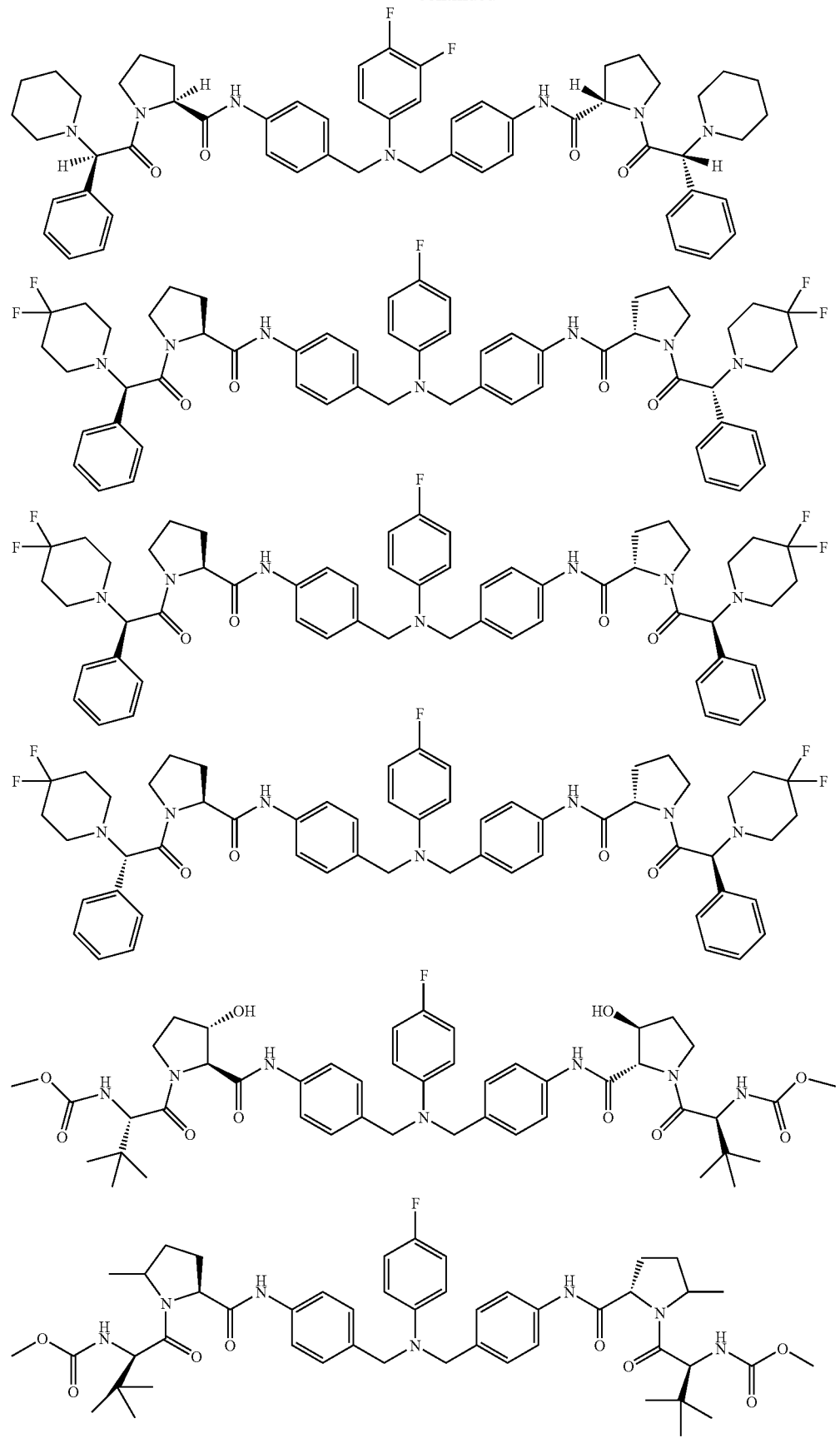

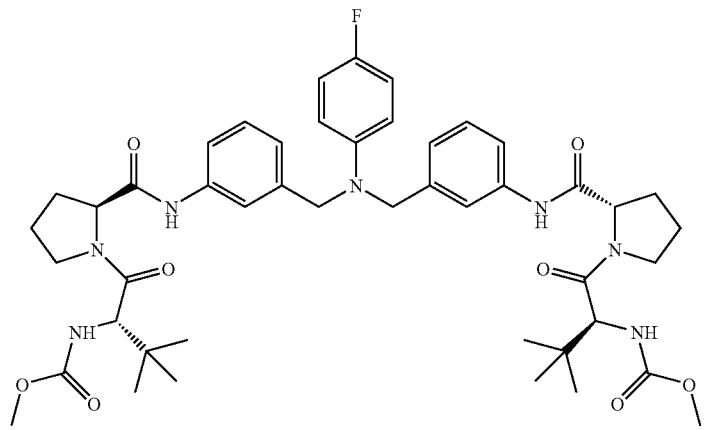
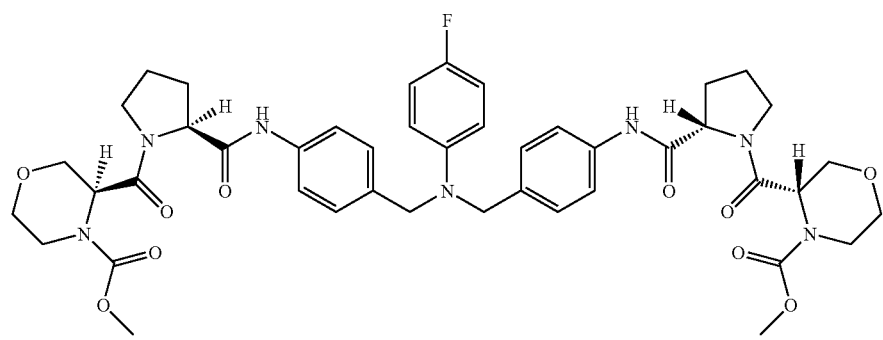
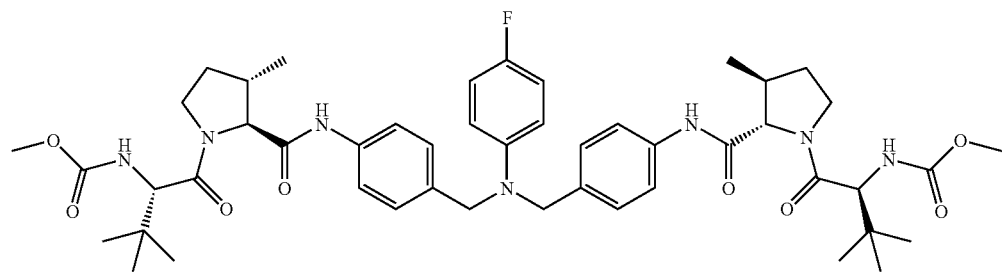
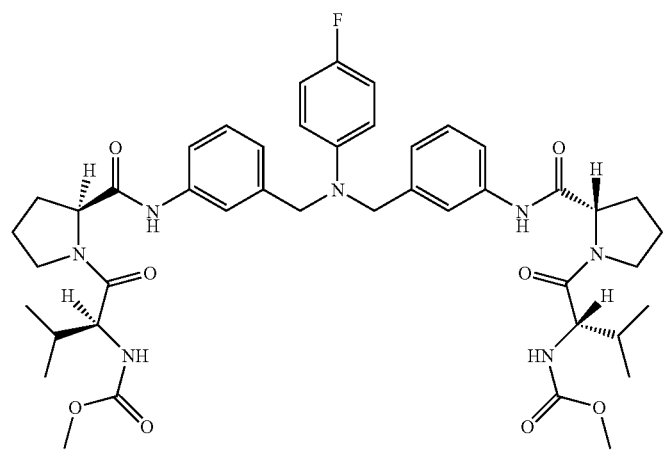

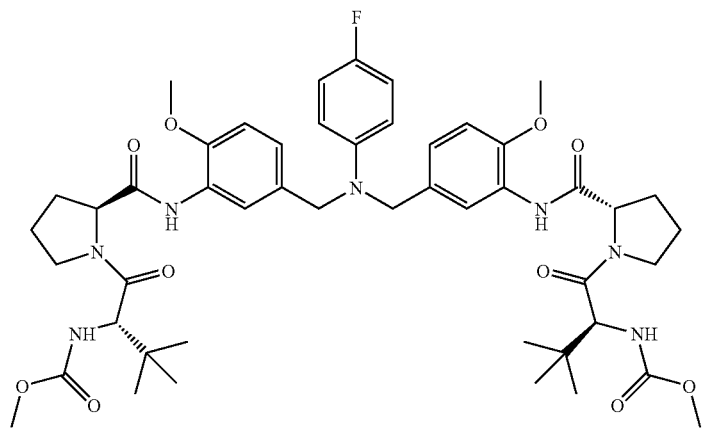

Moreover, the following compounds of Formula I can be similarly prepared according to the present invention,

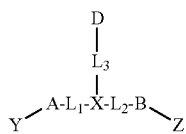

I wherein A is selected from Table 1a, B is selected from Table 1b, D is selected from Tablet 2, Y and Z are each independently selected from Table 3, and A, B, and D are each independently optionally substituted with one or more $R_A$, and wherein X, $L_1$, $L_2$, $L_3$ and $R_A$ are as described above. Preferably, X is N, $L_1$ and $L_2$ are each independently $C_1$-$C_6$alkylene (e.g., —(CH$_2$)—), and $L_3$ is a bond, wherein $L_1$ and $L_2$ are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano, and $R_T$, $R_S$, and $R_S'$ are as defined above.

TABLE 1a

A

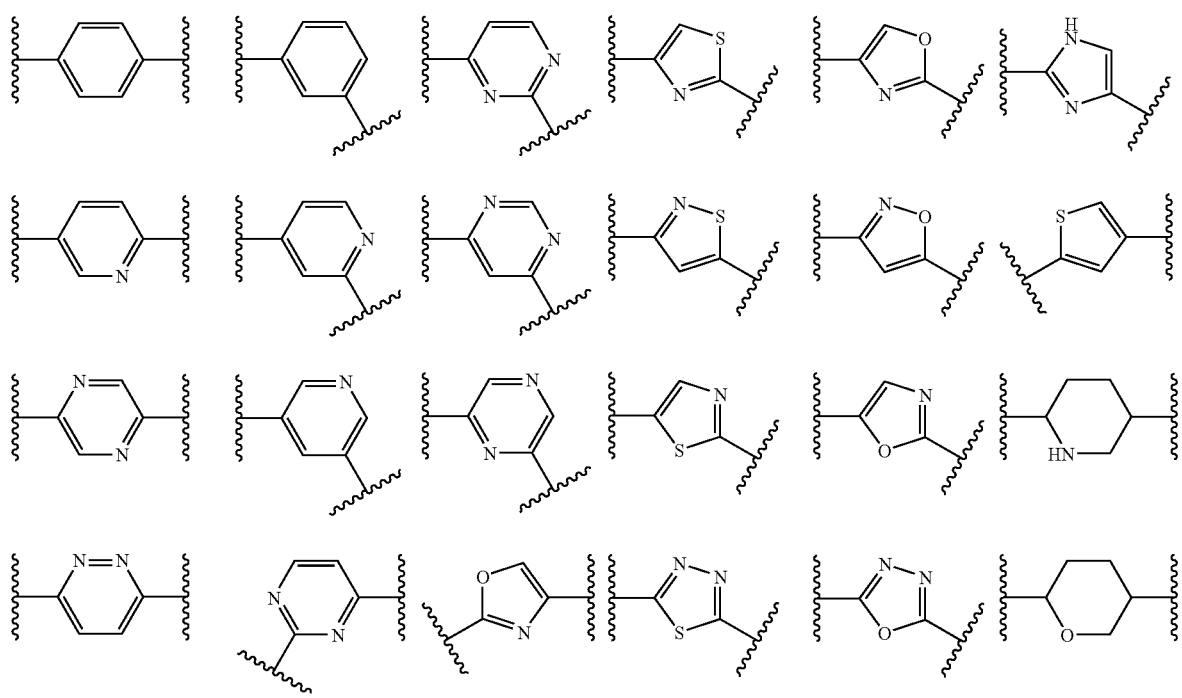

TABLE 1a-continued
A
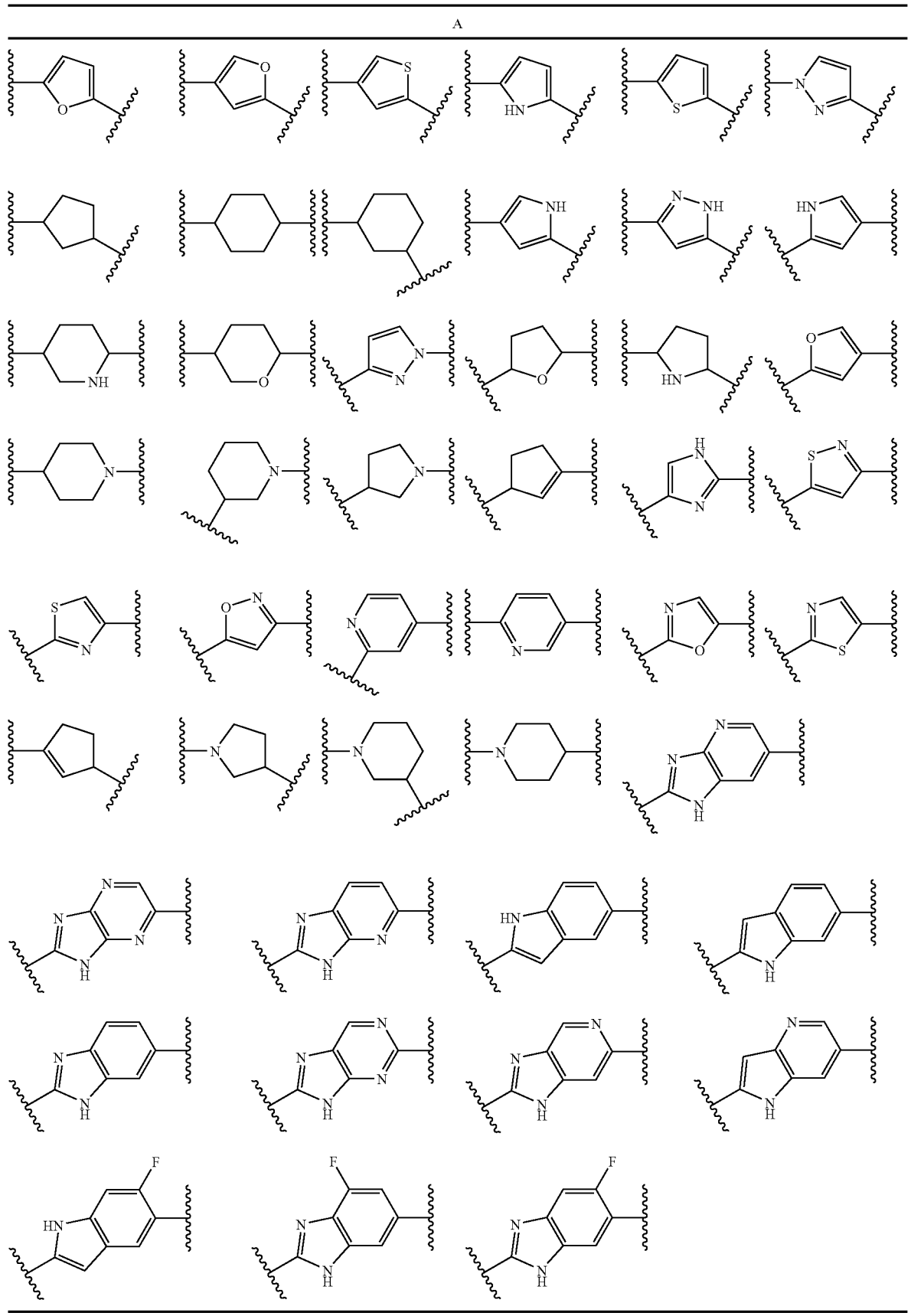

TABLE 1b
B
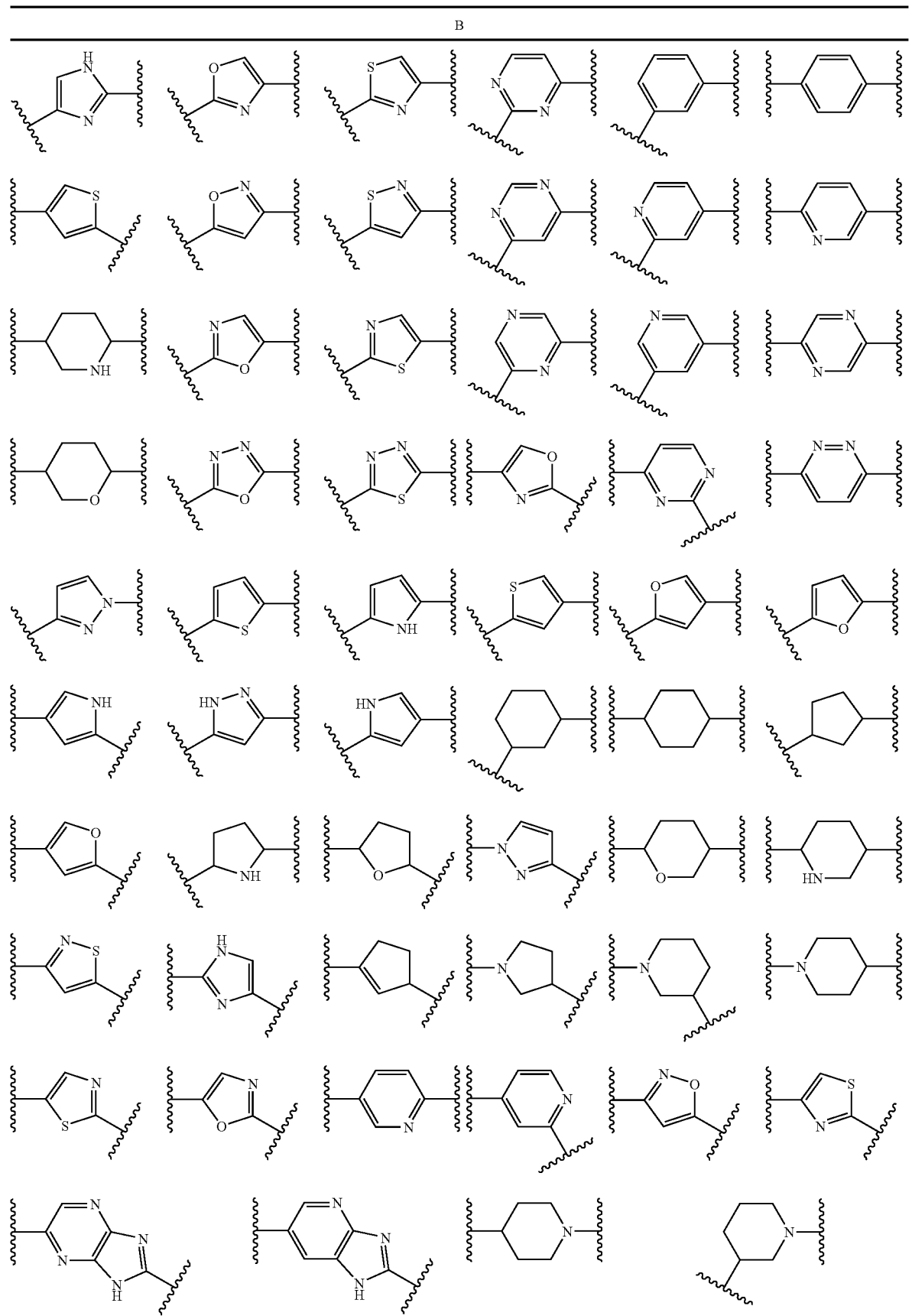

TABLE 1b-continued
B
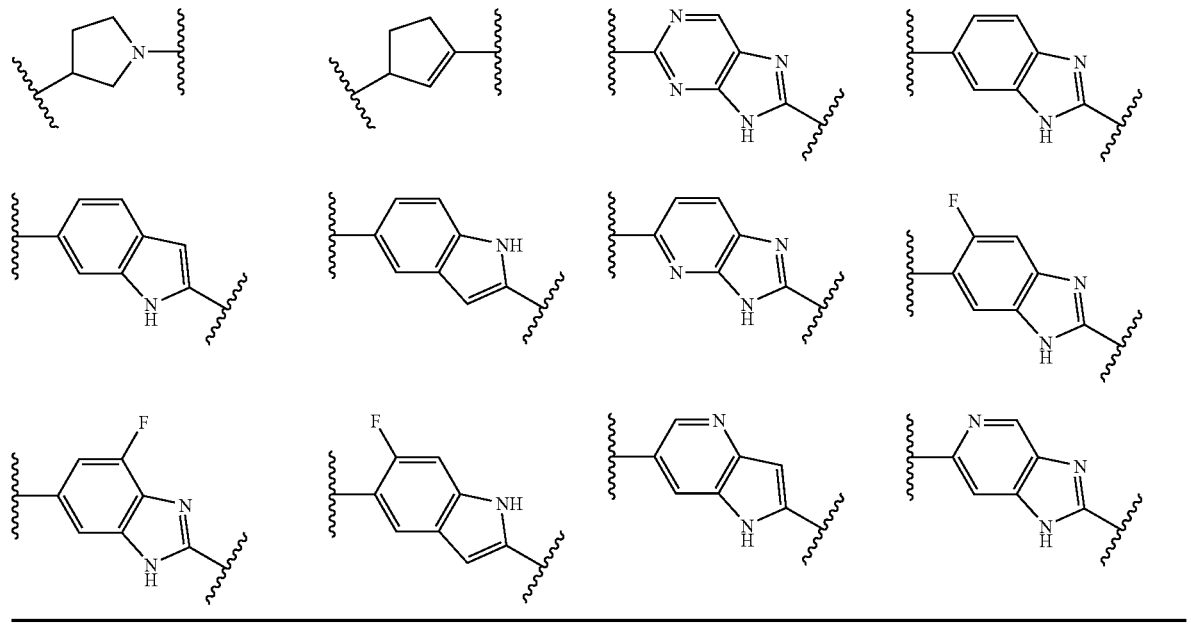
TABLE 2
D
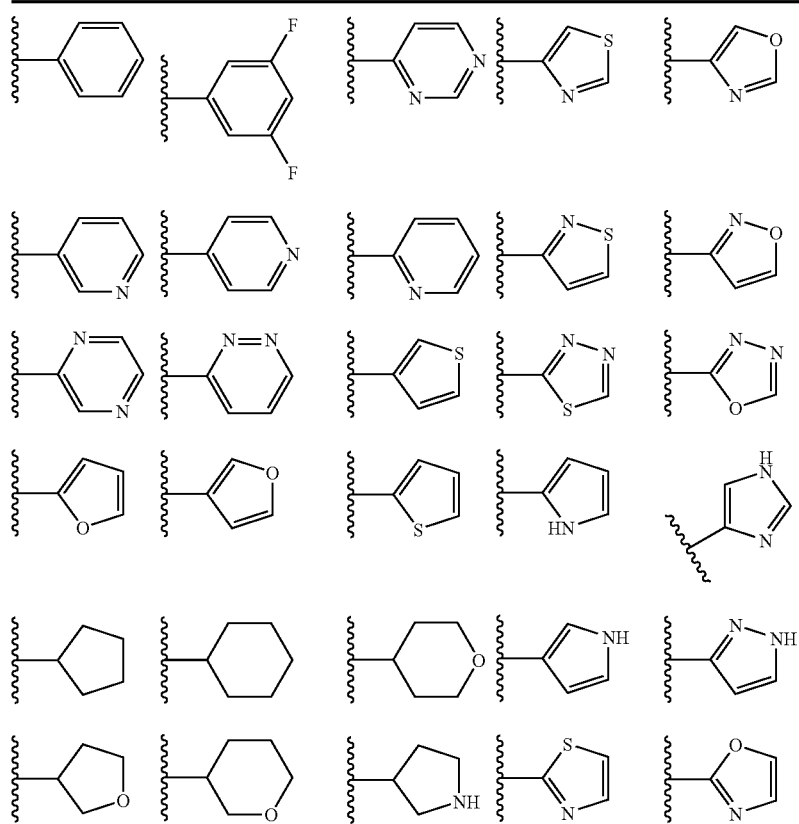

TABLE 2-continued
D
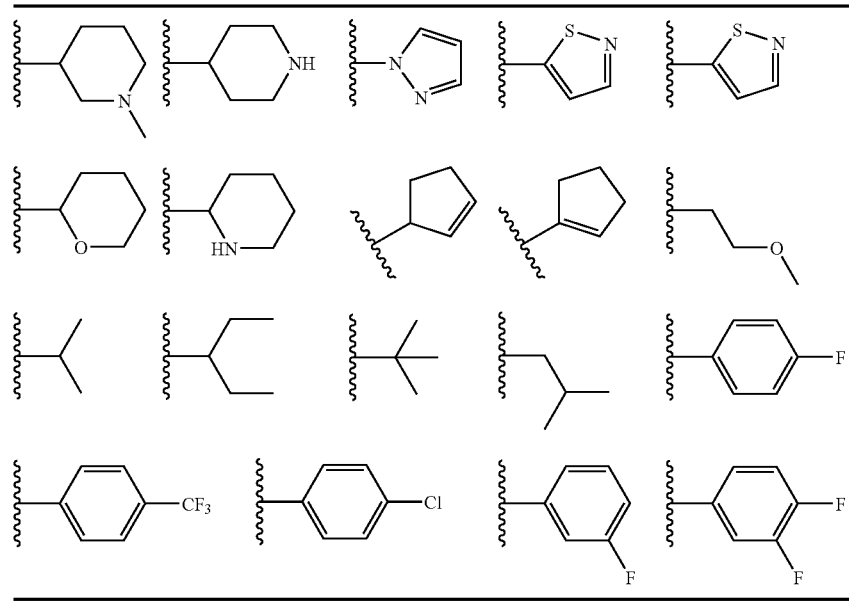
TABLE 3
Y and Z
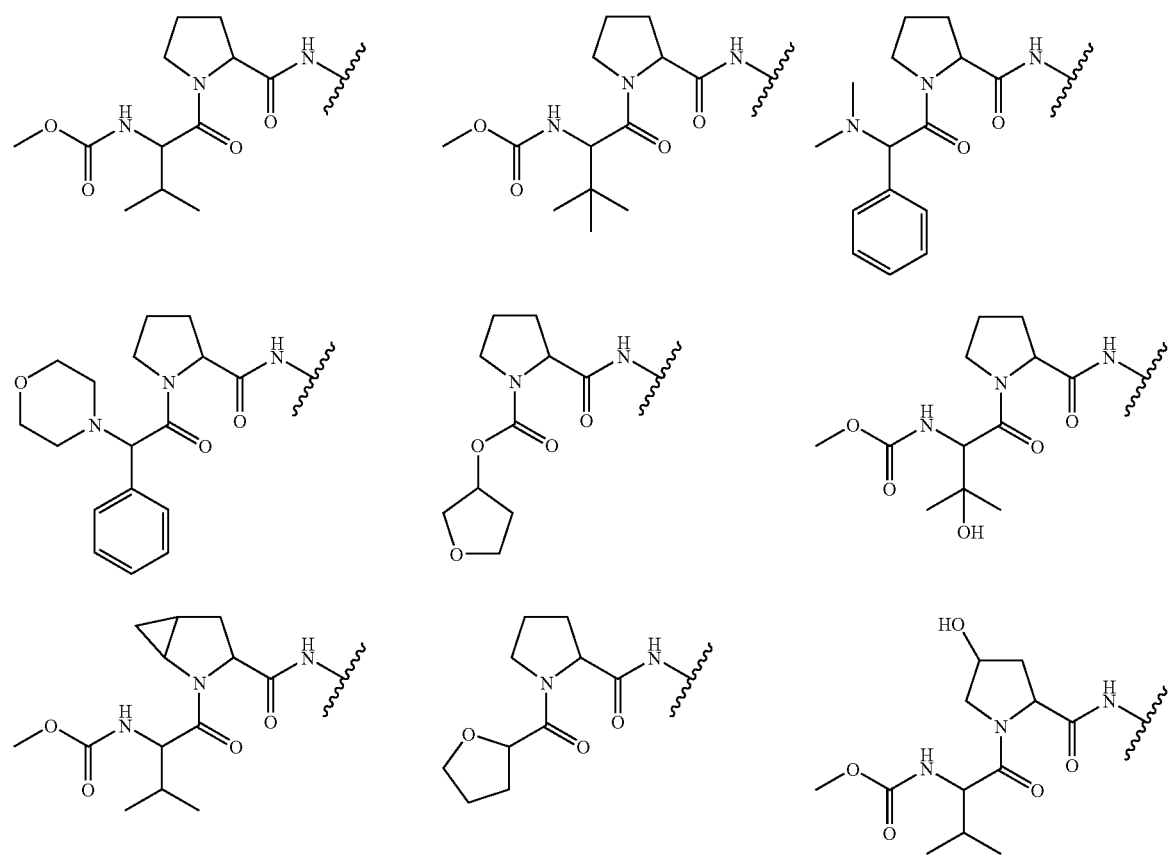

TABLE 3-continued
Y and Z
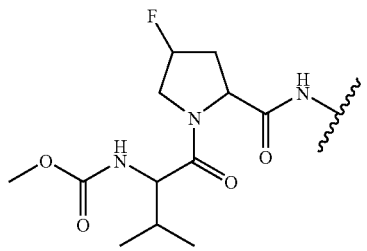 [SMILES: *NC(=O)C1CC(O)CN1C(=O)C(NC(=O)OC)C(C)C] 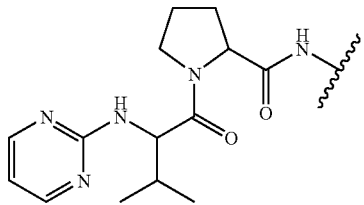 [SMILES: *NC(=O)C1CCCN1C(=O)C(Nc1ncccn1)C(C)C] 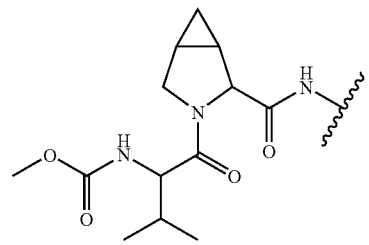 [SMILES: *NC(=O)C1C2CC2CN1C(=O)C(NC(=O)OC)C(C)C]
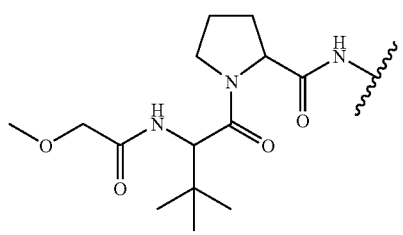 [SMILES: *NC(=O)C1CCCN1C(=O)C(NC(=O)COC)C(C)(C)C] 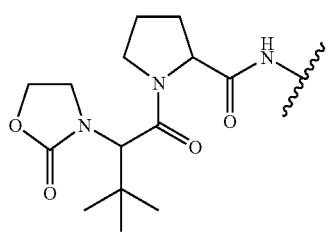 [SMILES: *NC(=O)C1CCCN1C(=O)C(N1CCOC1=O)C(C)(C)C] 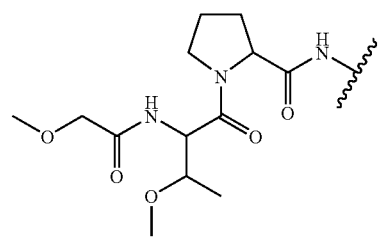 [SMILES: *NC(=O)C1CCCN1C(=O)C(NC(=O)COC)C(C)OC]
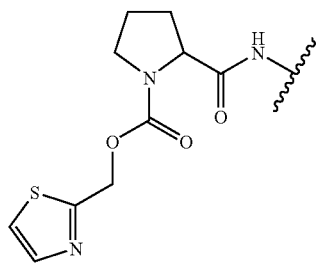 [SMILES: *NC(=O)C1CCCN1C(=O)OCc1nccs1] 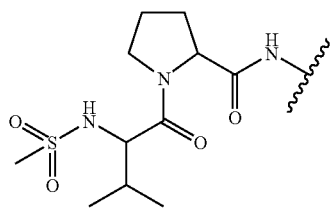 [SMILES: *NC(=O)C1CCCN1C(=O)C(NS(C)(=O)=O)C(C)C] 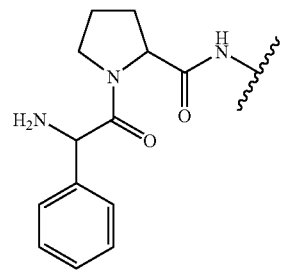 [SMILES: *NC(=O)C1CCCN1C(=O)C(N)c1ccccc1]
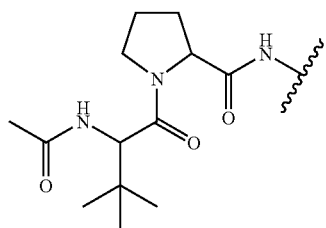 [SMILES: *NC(=O)C1CCCN1C(=O)C(NC(C)=O)C(C)(C)C] 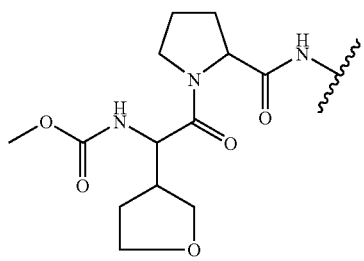 [SMILES: *NC(=O)C1CCCN1C(=O)C(NC(=O)OC)C1CCOC1] 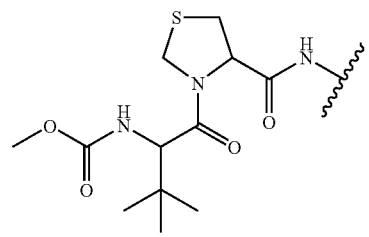 [SMILES: *NC(=O)C1CSCN1C(=O)C(NC(=O)OC)C(C)(C)C]
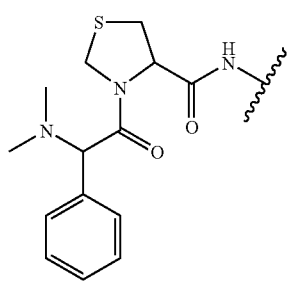 [SMILES: *NC(=O)C1CSCN1C(=O)C(c1ccccc1)N(C)C] 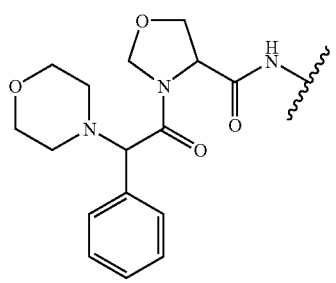 [SMILES: *NC(=O)C1COCN1C(=O)C(c1ccccc1)N1CCOCC1] 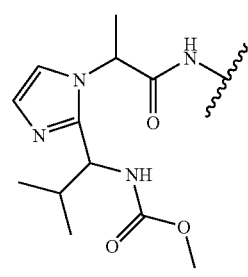 [SMILES: *NC(=O)C(C)n1ccnc1C(NC(=O)OC)C(C)C]

TABLE 3-continued
Y and Z
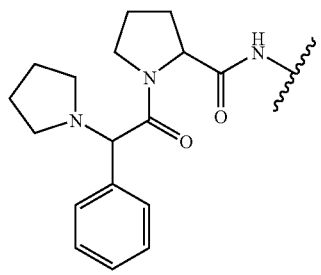 [SMILES: *NC(=O)C1CCCN1C(=O)C(c1ccccc1)N1CCCC1] 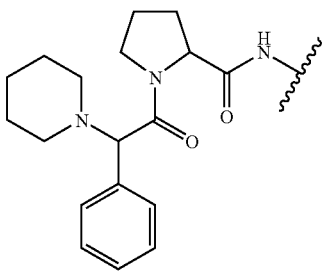 [SMILES: *NC(=O)C1CCCN1C(=O)C(c1ccccc1)N1CCCCC1] 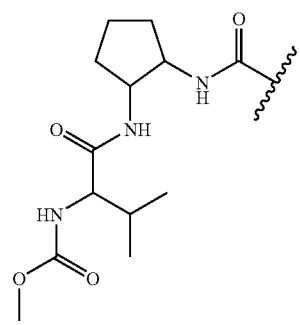 [SMILES: *C(=O)NC1CCCC1NC(=O)C(NC(=O)OC)C(C)C]
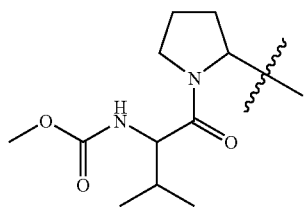 [SMILES: *C1CCCN1C(=O)C(NC(=O)OC)C(C)C] 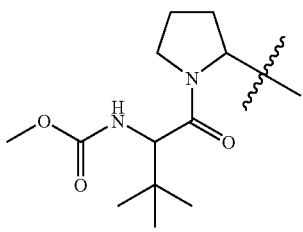 [SMILES: *C1CCCN1C(=O)C(NC(=O)OC)C(C)(C)C] 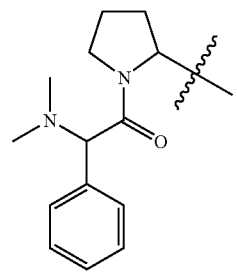 [SMILES: *C1CCCN1C(=O)C(c1ccccc1)N(C)C]
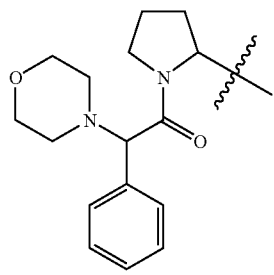 [SMILES: *C1CCCN1C(=O)C(c1ccccc1)N1CCOCC1] 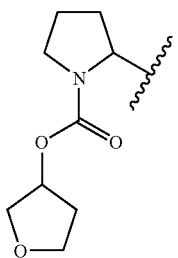 [SMILES: *C1CCCN1C(=O)OC1CCOC1] 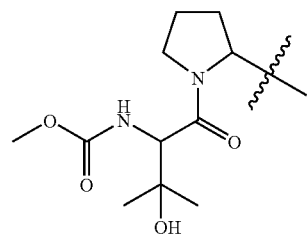 [SMILES: *C1CCCN1C(=O)C(NC(=O)OC)C(C)(C)O]
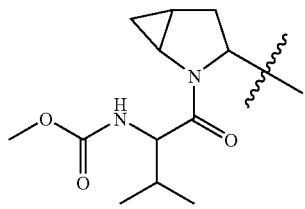 [SMILES: *C1CC2CC2N1C(=O)C(NC(=O)OC)C(C)C] 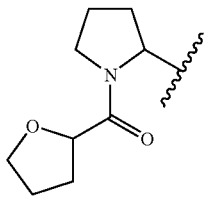 [SMILES: *C1CCCN1C(=O)C1CCCO1] 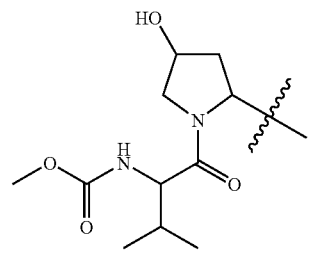 [SMILES: *C1CC(O)CN1C(=O)C(NC(=O)OC)C(C)C]
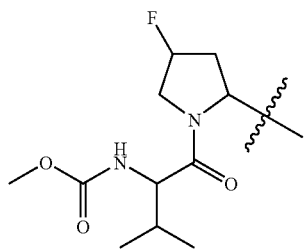 [SMILES: *C1CC(F)CN1C(=O)C(NC(=O)OC)C(C)C] 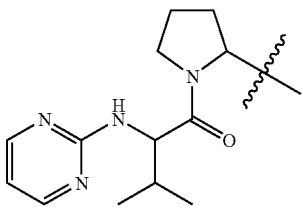 [SMILES: *C1CCCN1C(=O)C(Nc1ncccn1)C(C)C] 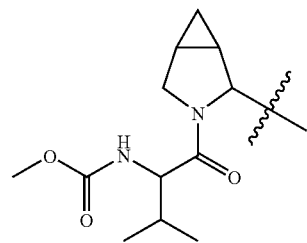 [SMILES: *C1C2CC2CN1C(=O)C(NC(=O)OC)C(C)C]

TABLE 3-continued
Y and Z
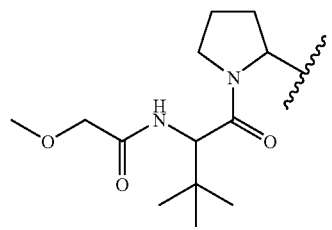 [SMILES: *C1CCCN1C(=O)C(NC(=O)COC)C(C)(C)C] 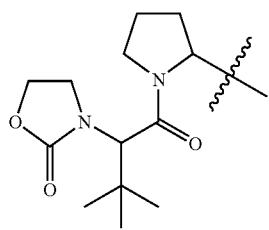 [SMILES: *C1CCCN1C(=O)C(N1CCOC1=O)C(C)(C)C] 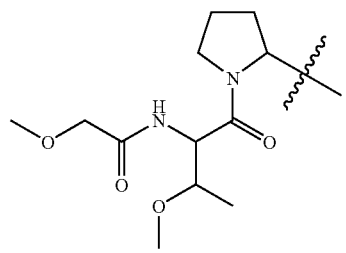 [SMILES: *C1CCCN1C(=O)C(NC(=O)COC)C(C)OC]
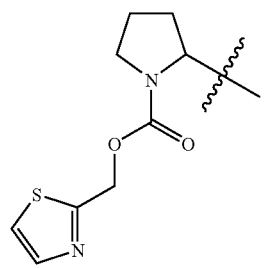 [SMILES: *C1CCCN1C(=O)OCc1nccs1] 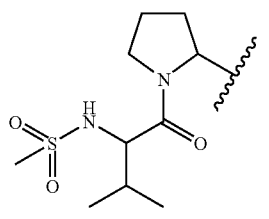 [SMILES: *C1CCCN1C(=O)C(NS(C)(=O)=O)C(C)C] 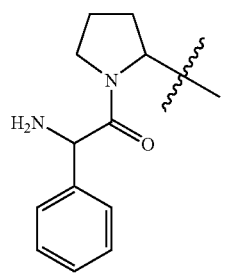 [SMILES: *C1CCCN1C(=O)C(N)c1ccccc1]
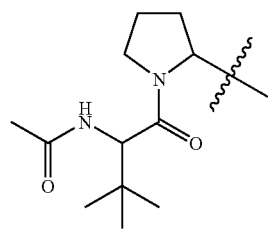 [SMILES: *C1CCCN1C(=O)C(NC(C)=O)C(C)(C)C] 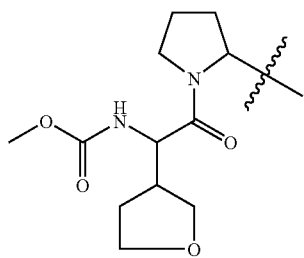 [SMILES: *C1CCCN1C(=O)C(NC(=O)OC)C1CCOC1] 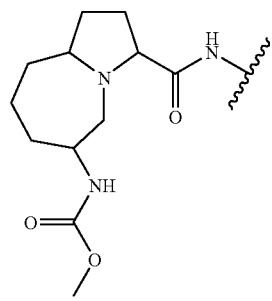 [SMILES: *NC(=O)C1CCC2CCCC(NC(=O)OC)CN21]
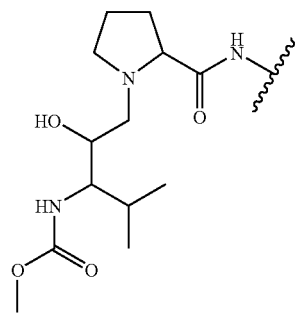 [SMILES: *NC(=O)C1CCCN1CC(O)C(NC(=O)OC)C(C)C] 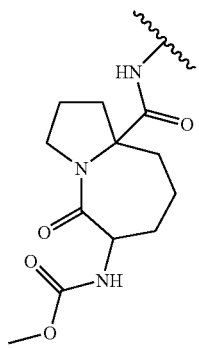 [SMILES: *NC(=O)C12CCCC(NC(=O)OC)C(=O)N1CCC2] 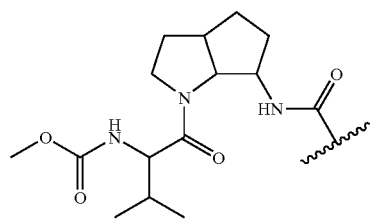 [SMILES: *C(=O)NC1CCC2CCN(C(=O)C(NC(=O)OC)C(C)C)C21]
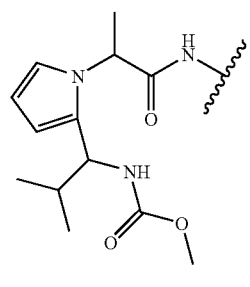 [SMILES: *NC(=O)C(C)n1cccc1C(NC(=O)OC)C(C)C] 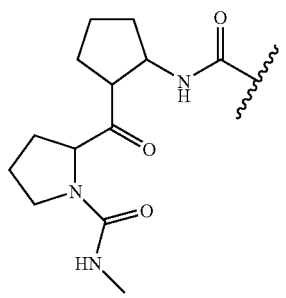 [SMILES: *C(=O)NC1CCCC1C(=O)C1CCCN1C(=O)NC] 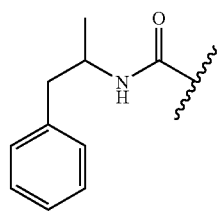 [SMILES: *C(=O)NC(C)Cc1ccccc1]

TABLE 3-continued

Y and Z

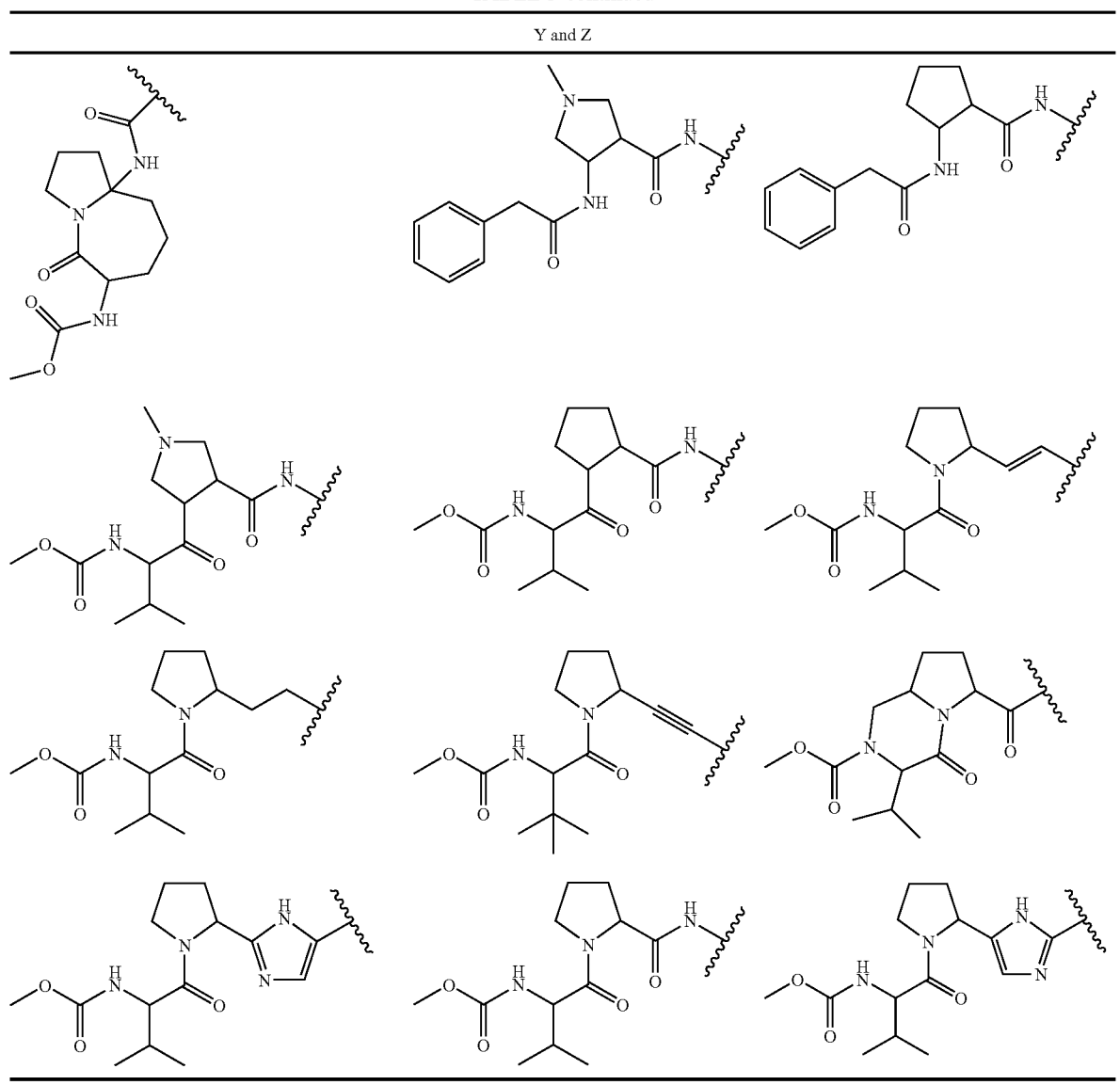

The inhibitory activities of the compounds of the present invention can be evaluated using a variety of assays known in the art. For instance, two stable subgenomic replicon cell lines can be used for compound characterization in cell culture: one derived from genotype 1a-H77 and the other derived from genotype 1b-Con1, obtained from University of Texas Medical Branch (Galveston, Tex.) and Apath, LLC (St. Louis, Mo.), respectively. The replicon constructs can be bicistronic subgenomic replicons. The genotype 1a replicon construct contains NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K 1691R, K2040R and S2204I. The 1b-Con1 replicon construct is identical to the 1a-H77 replicon, except that HCV 5' UTR, 3' UTR, and the NS3-NS5B coding region are derived from the 1b-Con1 strain, and the adaptive mutations are K1609E, K1846T and Y3005C. In addition, the 1b-Coni replicon construct contains a poliovirus IRES between the HCV IRES and the luciferase gene. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can be determined by measuring activity of the luciferase reporter gene. For example, replicon-containing cells can be seeded into 96 well plates at a density of 5000 cells per well in 100 µl DMEM containing 5% FBS. The following day compounds can be diluted in dimethyl sulfoxide (DMSO) to generate a 200× stock in a series of eight half-log dilutions. The dilution series can then be further diluted 100-fold in the medium containing 5% FBS. Medium with the inhibitor is added to the overnight cell culture plates already containing 100 µl of DMEM with 5% FBS. In assays measuring inhibitory activity in the presence of human plasma, the medium from the overnight cell culture plates can be replaced with DMEM containing 40% human plasma and 5% FBS. The cells can be incubated for three days in the tissue culture incubators after which time 30 μl of Passive Lysis buffer (Promega) can be added to each well, and then the plates are incubated for 15 minutes with rocking to lyse the cells. Luciferin solution (100 μl, Promega) can be added to each well, and luciferase activity can be measured with a Victor II luminometer (Perkin-Elmer). The percent inhibition of HCV RNA replication can be calculated for each compound concentration and the $EC_{50}$ value can be calculated using nonlinear regression curve fitting to the 4-parameter logistic equation and GraphPad Prism 4 software. Using the above-described assays or similar cell-based replicon assays, representative compounds of the present invention showed significantly inhibitory activities against HCV replication.

The present invention also features pharmaceutical compositions comprising the compounds of the invention. A pharmaceutical composition of the present invention can comprise one or more compounds of the invention, each of which has Formula I (or $I_A$, $I_B$ or $I_C$).

In addition, the present invention features pharmaceutical compositions comprising pharmaceutically acceptable salts, solvates, or prodrugs of the compounds of the invention. Without limitation, pharmaceutically acceptable salts can be zwitterions or derived from pharmaceutically acceptable inorganic or organic acids or bases. Preferably, a pharmaceutically acceptable salt retains the biological effectiveness of the free acid or base of the compound without undue toxicity, irritation, or allergic response, has a reasonable benefit/risk ratio, is effective for the intended use, and is not biologically or otherwise undesirable.

The present invention further features pharmaceutical compositions comprising a compound of the invention (or a salt, solvate or prodrug thereof) and another therapeutic agent. By way of illustration not limitation, these other therapeutic agents can be selected from antiviral agents (e.g., anti-HIV agents, anti-HBV agents, or other anti-HCV agents such as HCV protease inhibitors, HCV polymerase inhibitors, HCV helicase inhibitors, IRES inhibitors or NS5A inhibitors), anti-bacterial agents, anti-fungal agents, immunomodulators, anti-cancer or chemotherapeutic agents, anti-inflammation agents, antisense RNA, siRNA, antibodies, or agents for treating cirrhosis or inflammation of the liver. Specific examples of these other therapeutic agents include, but are not limited to, ribavirin, α-interferon, β-interferon, pegylated interferon-α, pegylated interferon-lambda, ribavirin, viramidine, R-5158, nitazoxanide, amantadine, Debio-025, NIM-811, R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728, GL60667, BMS-790052, BMS-791325, BMS-650032, GS-9132, ACH-1095, AP-H005, A-831, A-689, AZD2836, telaprevir, boceprevir, ITMN-191, BI-201335, VBY-376, VX-500 (Vertex), PHX-B, ACH-1625, IDX136, IDX316, VX-813 (Vertex), SCH 900518 (Schering-Plough), TMC-435 (Tibotec), ITMN-191 (Intermune, Roche), MK-7009 (Merck), IDX-PI (Novartis), BI-201335 (Boehringer Ingelheim), R7128 (Roche), PSI-7851 (Pharmasset), MK-3281 (Merck), PF-868554 (Pfizer), IDX-184 (Novartis), IDX-375 (Pharmasset), BILB-1941 (Boehringer Ingelheim), GS-9190 (Gilead), BMS-790052 (BMS), Albuferon (Novartis), ritonavir, another cytochrome P450 monooxygenase inhibitor, or any combination thereof.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. For example, a pharmaceutical composition of the present invention can comprise a compound(s) of the present invention having Formula I, $I_A$, $I_B$ or $I_C$ (or a salt, solvate or prodrug thereof), and an agent selected from HCV polymerase inhibitors (including nucleoside or non-nucleoside type of polymerase inhibitors), HCV protease inhibitors, HCV helicase inhibitors, CD81 inhibitors, cyclophilin inhibitors, IRES inhibitors, or NS5A inhibitors.

In yet another embodiment, a pharmaceutical composition of the present invention comprises one or more compounds of the present invention (or salts, solvates or prodrugs thereof), and one or more other antiviral agents, such as anti-HBV, anti-HIV agents, or anti-hepatitis A, anti-hepatitis D, anti-hepatitis E or anti-hepatitis G agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, or other HIV protease, reverse transcriptase, integrase or fusion inhibitors. Any other desirable antiviral agents can also be included in a pharmaceutical composition of the present invention, as appreciated by those skilled in the art.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

Any compound described herein, or a pharmaceutically acceptable salt thereof, can be used to prepared pharmaceutical compositions of the present invention.

The present invention further features methods of using the compounds of the present invention (or salts, solvates or prodrugs thereof) to inhibit HCV replication. The methods comprise contacting cells infected with HCV virus with an effective amount of a compound of the present invention (or a salt, solvate or prodrug thereof), thereby inhibiting the replication of HCV virus in the cells. As used herein, "inhibiting" means significantly reducing, or abolishing, the activity being inhibited (e.g., viral replication). In many cases, representative compounds of the present invention can reduce the replication of HCV virus (e.g., in an HCV replicon assay as described above) by at least 10%, 20%, 30%, 40%, 50%, 60%, 70%, 80%, 90%, 95% or more.

The compounds of the present invention may inhibit one or more HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c or 3a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. The methods typically comprise administering a therapeutic effective amount of a compound of the present invention (or a salt, solvate or prodrug thereof), or a pharmaceutical composition comprising the same, to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof), or a pharmaceutical composition comprising the same, to an HCV patient, thereby reducing the HCV viral level in the blood or liver of the patient.

A compound of the present invention (or a salt, solvate or prodrug thereof) can be administered as the sole active pharmaceutical agent, or in combination with another desired drug, such as other anti-HCV agents, anti-HIV agents, anti-HBV agents, anti-hepatitis A agents, anti-hepatitis D agents, anti-hepatitis E agents, anti-hepatitis G agents, or other antiviral drugs. Any compound described herein, or a pharmaceutically acceptable salt thereof, can be employed in the methods of the present invention.

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The present invention further features methods of using the pharmaceutical compositions of the present invention to treat HCV infection. The methods typically comprise administering a pharmaceutical composition of the present invention to an HCV patient, thereby reducing the HCV viral level in the blood or liver of the patient. Any pharmaceutical composition described herein can be used in the methods of the present invention.

In addition, the present invention features use of the compounds or salts of the present invention for the manufacture of medicaments for the treatment of HCV infection. Any compound described herein, or a pharmaceutically acceptable salt thereof, can be used to make medicaments of the present invention.

The compounds of the present invention can also be isotopically substituted. Preferred isotopic substitution include substitutions with stable or nonradioactive isotopes such as deuterium, $^{13}C$, $^{15}N$ or $^{18}O$. Incorporation of a heavy atom, such as substitution of deuterium for hydrogen, can give rise to an isotope effect that could alter the pharmacokinetics of the drug. In one example, at least 10 mol % of hydrogen in a compound of the present invention is substituted with deuterium. In another example, at least 25 mole % of hydrogen in a compound of the present invention is substituted with deuterium. In a further example, at least 50, 60, 70, 80 or 90 mole % of hydrogen in a compound of the present invention is substituted with deuterium. The natural abundance of deuterium is about 0.015%. Deuterium substitution or enrichment can be achieved, without limitation, by either exchanging protons with deuterium or by synthesizing the molecule with enriched or substituted starting materials. Other methods known in the art can also be used for isotopic substitutions.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound of Formula I, or a pharmaceutically acceptable salt thereof,

I

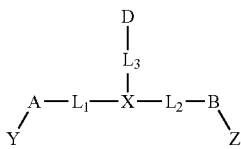

wherein:
A is

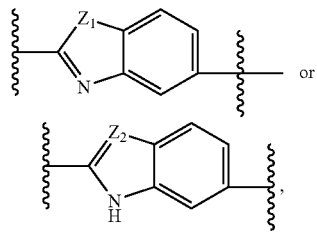 or

B is

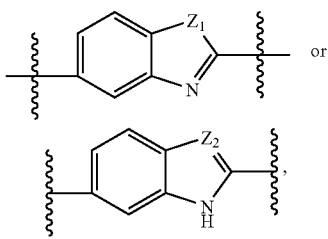, $Z_1$ is independently selected at each occurrence from O, S, NH or $CH_2$, $Z_2$ is independently selected at each occurrence from N or CH, wherein A and B are each independently optionally substituted with one or more $R_A$;

D is $C_3$-$C_{10}$carbocycle or 3- to 10-membered heterocycle, and is optionally substituted with one or more $R_A$; or D is selected from $C_1$-$C_6$alkyl, $C_2$-$C_6$alkenyl or $C_2$-$C_6$alkynyl, and is optionally substituted with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano;

X is N;

$L_1$ and $L_2$ are —($CH_2$)—, and are each independently optionally substituted with one or more substituents selected from halogen, $R_T$, —O—$R_S$, —S—$R_S$, —N($R_S R_S'$), —OC(O)$R_S$, —C(O)O$R_S$, nitro, oxo, phosphonoxy, phosphono, thioxo, formyl or cyano;

$L_3$ is bond;

Y is selected from —C($R_1 R_2$)N($R_5$)-T-$R_D$ or —C($R_3 R_4$)C($R_6 R_7$)-T-$R_D$;

$R_1$ is $R_C$, and $R_2$ and $R_5$, taken together with the atoms to which they are attached, form a 3- to 8-membered heterocyclic ring which is optionally substituted with one or more $R_A$;

$R_3$ and $R_6$ are each independently $R_C$, and $R_4$ and $R_7$, taken together with the atoms to which they are attached, form a 3- to 8-membered carbocyclic or heterocyclic ring which is optionally substituted with one or more $R_A$;

Z is selected from —C($R_8 R_9$)N($R_{12}$)-T-$R_D$ or —C($R_{10} R_{11}$)C($R_{13} R_{14}$)-T-$R_D$;

$R_8$ is $R_C$, and $R_9$ and $R_{12}$, taken together with the atoms to which they are attached, form a 3- to 8-membered heterocyclic ring which is optionally substituted with one or more $R_A$;

$R_{10}$ and $R_{13}$ are each independently $R_C$, and $R_{11}$ and $R_{14}$, taken together with the atoms to which they are attached, form a 3- to 8-membered carbocyclic or heterocyclic ring which is optionally substituted with one or more $R_A$;

T is each independently selected at each occurrence from a bond, -$L_S$-, -$L_S$-M-$L_S'$-, -$L_S$-M-$L_S'$-M'-$L_S''$-, wherein M and M' are each independently selected at each occurrence from a bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B'$)—, N($R_B$)SO$_2$N($R_B'$)—, —N($R_B$)S(O)N($R_B'$)—, $C_3$-$C_{10}$carbocycle, or 3- to 10-membered heterocycle, and wherein said $C_3$-$C_{10}$carbocycle and 3- to 10-membered heterocycle are each independently optionally substituted at each occurrence with one or more $R_A$;

$R_A$ is independently selected at each occurrence from halogen, hydroxy, mercapto, amino, carboxy, nitro, oxo, phosphonoxy, phosphono, thioxo, formyl, cyano, -$L_A$, or -$L_S$-$R_E$;

$R_B$ and $R_B'$ are each independently selected at each occurrence from hydrogen or $R_F$;

$R_C$ is independently selected at each occurrence from hydrogen, halogen, hydroxy, mercapto, amino, carboxy, nitro, oxo, phosphonoxy, phosphono, thioxo, formyl, cyano, or $R_F$;

$R_D$ is each independently selected at each occurrence from hydrogen or $R_A$;

$R_E$ is independently selected at each occurrence from —O—$R_S$, —S—$R_S$, —C(O)$R_S$, —OC(O)$R_S$, —C(O)O$R_S$, —N($R_S R_S'$),—S(O)$R_S$, —SO$_2 R_S$, —C(O)N($R_S R_S'$), —N($R_S$)C(O)$R_S'$,—N($R_S$)C(O)N($R_S' R_S''$), —N($R_S$)SO$_2 R_S'$, —SO$_2$N($R_S R_S'$), —N($R_S$)SO$_2$N($R_S' R_S''$), —N($R_S$)S(O)N($R_S' R_S''$), —OS(O)—$R_S$, —OS(O)$_2$—$R_S$, —S(O)$_2$O$R_S$, —S(O)$_2$O$R_S$, —OC(O)O$R_S$,—N($R_S$)C(O)O$R_S'$, —OC(O)N($R_S R_S'$),—N($R_S$)S(O)—$R_S'$, —S(O)N($R_S R_S'$), —C(O)N($R_S$)C(O)—$R_S'$, $C_3$-$C_{10}$carbocyclyl, or 3- to 10-membered heterocyclyl, wherein said $C_3$-$C_{10}$carbocyclyl and 3- to 10-membered heterocyclyl are each independently optionally substituted at each occurrence with one or more substituents selected from halogen, $R_T$, —O—$R_B$, —S—$R_B$, —N($R_B R_B'$),—OC(O)$R_B$, —C(O)O$R_B$, nitro, phosphonoxy, phosphono, oxo, thioxo, formyl or cyano;

$R_F$ is independently selected at each occurrence from $C_1$-$C_6$alkyl, $C_2$-$C_6$alkenyl, $C_2$-$C_6$alkynyl, $C_3$-$C_6$carbocyclyl, $C_3$-$C_6$carbocyclylC$_1$-$C_6$alkyl, 3- to 6-membered heterocyclyl or (3- or 6-membered heterocyclyl)$C_1$-$C_6$alkyl, each of which is independently optionally substituted at each occurrence with one or more substituents selected from halogen, hydroxy, mercapto, amino, carboxy, nitro, oxo, phosphonoxy, phosphono, thioxo, formyl or cyano;

$L_A$ is independently selected at each occurrence from $C_1$-$C_6$alkyl, $C_2$-$C_6$alkenyl, or $C_2$-$C_6$alkynyl, each of which is independently optionally substituted at each occurrence with one or more substituents selected from halogen, $R_T$, —O—$R_S$, —S—$R_S$, —N($R_S R_S'$), —OC(O)$R_S$, —C(O)O$R_S$, nitro, phosphonoxy, phosphono, oxo, thioxo, formyl or cyano;

$L_S$, $L_S'$ and $L_S''$ are each independently selected at each occurrence from a bond; or $C_1$-$C_6$alkylene, $C_2$-$C_6$alkenylene, or $C_2$-$C_6$alkynylene, each of which is independently optionally substituted at each occurrence with one or more substituents selected from halogen, $R_T$, —O—$R_S$, —S—$R_S$, —N($R_S R_S'$), —OC(O)$R_S$, —C(O)OR$_S$, nitro, phosphonoxy, phosphono, oxo, thioxo, formyl or cyano;

$R_S$, $R_S'$ and $R_S''$ are each independently selected at each occurrence from hydrogen or $R_T$;

$R_T$ is independently selected at each occurrence from $C_1$-$C_6$alkyl, $C_2$-$C_6$alkenyl, $C_2$-$C_6$alkynyl, $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from halogen, $R_F$, —O—$R_B$, —S—$R_B$, —N($R_B R_B'$), —OC(O)$R_B$, —C(O)OR$_B$, nitro, oxo, phosphonoxy, phosphono, thioxo, formyl or cyano.

2. The compound or salt of claim 1, wherein:

$Z_1$ is NH, and $Z_2$ is N;

T is independently selected at each occurrence from —C(O)-$L_S'$-M'-$L_S''$- or —N($R_B$)C(O)-$L_S'$-M'-$L_S''$-; and $L_S'$ is independently $C_1$-$C_6$alkylene, and is independently optionally substituted at each occurrence with one or more substituents selected from halogen, $R_T$, —O—$R_S$, —S—$R_S$, —N($R_S R_S'$), —OC(O)$R_S$, —C(O)OR$_S$, nitro, phosphonoxy, phosphono, oxo, thioxo, formyl or cyano.

3. The compound or salt of claim 1, wherein:

$Z_1$ is NH, and $Z_2$ is N;

Y is 13 C($R_1 R_2$)N($R_5$)-T-$R_D$;

Z is —C($R_8 R_9$)N($R_{12}$)-T-$R_D$;

T is independently selected at each occurrence from —C(O)-$L_S'$-M'-$L_S''$-; and D is $C_5$-$C_6$carbocycle, 5- to 6-membered heterocycle, or 6- to 10-membered bicycles, and is substituted with one or more $R_M$, where $R_M$ is halogen, nitro, oxo, phosphonoxy, phosphono, thioxo, cyano, or -$L_S$-$R_E$.

4. The compound or salt of claim 3, wherein T is independently selected at each occurrence from —C(O)-$L_S'$-N($R_B$)C(O)-$L_S''$- or —C(O)-$L_S'$- N($R_B$)C(O)O-$L_S''$-.

5. The compound or salt of claim 3, wherein $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

\* \* \* \* \*